US006924313B1

(12) United States Patent
Sikorski et al.

(10) Patent No.: US 6,924,313 B1
(45) Date of Patent: *Aug. 2, 2005

(54) SUBSTITUTED TERTIARY-HETEROALKYLAMINES USEFUL FOR INHIBITING CHOLESTERYL ESTER TRANSFER PROTEIN ACTIVITY

(75) Inventors: James A. Sikorski, Des Peres, MO (US); Richard C. Durley, Chesterfield, MO (US); Melvin L. Rueppel, St. Louis, MO (US); Deborah A. Mischke, Defiance, MO (US); Barry L. Parnas, University City, MO (US)

(73) Assignee: Pfizer Inc., New York, NY (US)

( * ) Notice: Subject to any disclaimer, the term of this patent is extended or adjusted under 35 U.S.C. 154(b) by 173 days.

This patent is subject to a terminal disclaimer.

(21) Appl. No.: 10/326,035

(22) Filed: Dec. 23, 2002

Related U.S. Application Data

(63) Continuation of application No. 09/716,728, filed on Nov. 21, 2000, now abandoned, which is a continuation of application No. 09/404,638, filed on Sep. 23, 1999, now abandoned.

(51) Int. Cl.$^7$ ............... A61K 31/135; A61K 31/136; A61K 31/137
(52) U.S. Cl. ............... 514/645; 514/649; 514/654; 514/655; 514/658
(58) Field of Search ................ 514/645, 649, 514/654, 655, 658

(56) References Cited

U.S. PATENT DOCUMENTS

| | | | |
|---|---|---|---|
| 3,334,017 A | 8/1967 | Biel | 167/65 |
| 3,359,316 A | 12/1967 | Biel | 260/570.8 |
| 3,711,543 A | 1/1973 | Bollag et al. | 260/553 |
| 5,306,718 A | 4/1994 | Lauffer et al. | 514/230.8 |
| 5,519,001 A | 5/1996 | Kushwaha et al. | 514/12 |
| 6,063,788 A | 5/2000 | Brandes et al. | 514/290 |
| 6,448,295 B1 * | 9/2002 | Sikorski et al. | 514/654 |
| 6,451,823 B1 * | 9/2002 | Sikorski et al. | 514/351 |
| 6,451,830 B1 * | 9/2002 | Sikorski et al. | 514/378 |
| 6,455,519 B1 * | 9/2002 | Sikorski et al. | 514/211.09 |
| 6,458,803 B1 * | 10/2002 | Sikorski et al. | 514/311 |
| 6,458,849 B1 * | 10/2002 | Sikorski et al. | 514/649 |
| 6,458,852 B1 * | 10/2002 | Sikorski et al. | 514/658 |
| 6,462,092 B1 | 10/2002 | Sikorski et al. | 514/655 |
| 6,476,057 B1 * | 11/2002 | Sikorski et al. | 514/351 |
| 6,476,075 B1 * | 11/2002 | Sikorski et al. | 514/574 |
| 6,479,552 B2 * | 11/2002 | Sikorski et al. | 514/649 |
| 6,482,862 B1 * | 11/2002 | Sikorski et al. | 514/654 |
| 6,521,607 B1 * | 2/2003 | Sikorski et al. | 514/150 |
| 6,544,974 B2 * | 4/2003 | Sikorski et al. | 514/183 |
| 6,583,183 B2 * | 6/2003 | Sikorski et al. | 514/654 |
| 6,586,433 B2 * | 7/2003 | Sikorski et al. | 514/242 |
| 6,605,624 B1 * | 8/2003 | Lee et al. | 514/332 |
| 6,677,341 B2 * | 1/2004 | Sikorski et al. | 514/245 |
| 6,677,353 B2 | 1/2004 | Sikorski et al. | 514/311 |
| 6,677,375 B2 | 1/2004 | Sikorski et al. | 514/574 |
| 6,677,379 B2 | 1/2004 | Sikorski et al. | 514/649 |
| 6,677,380 B2 | 1/2004 | Sikorski et al. | 514/649 |
| 6,683,099 B2 | 1/2004 | Sikorski et al. | 514/351 |
| 6,683,113 B2 * | 1/2004 | Sikorski et al. | 514/649 |
| 6,688,382 B2 | 2/2004 | Sikorski et al. | 514/658 |
| 6,696,472 B2 | 2/2004 | Sikorski et al. | 514/351 |
| 6,699,898 B2 | 3/2004 | Sikorski et al. | 514/378 |
| 6,710,089 B2 | 3/2004 | Sikorski et al. | 514/654 |
| 6,723,752 B2 * | 4/2004 | Sikorski et al. | 514/649 |
| 6,723,753 B2 * | 4/2004 | Sikorski et al. | 514/649 |
| 6,765,023 B2 * | 7/2004 | Sikorski et al. | 514/655 |
| 6,787,570 B2 * | 9/2004 | Sikorski et al. | 514/645 |
| 6,794,396 B2 * | 9/2004 | Lee et al. | 514/333 |
| 6,803,388 B2 | 10/2004 | Sikorski et al. | 514/658 |

FOREIGN PATENT DOCUMENTS

| | | |
|---|---|---|
| CH | 441366 | 1/1968 |
| DE | 9627430 | 1/1998 |
| EP | 0442172 | 8/1991 |
| EP | 0314435 | 9/1993 |
| EP | 0801060 | 10/1997 |
| EP | 0796846 | 7/2000 |
| EP | 0818197 | 11/2003 |
| EP | 0818448 | 11/2003 |
| GB | 2305665 | 4/1997 |
| JP | 5320117 | 12/1993 |
| WO | WO9001874 | 3/1990 |
| WO | WO9002113 | 3/1990 |
| WO | WO9738973 | 10/1997 |

OTHER PUBLICATIONS

Barter, P. J., et al. High density lipoproteins and coronary heart disease, *Atherosclerosis*, vol. 121, pp. 1–12 (1996).

Tall, A. R., Plasma cholesteryl ester transfer protein, *Journal of Lipid Research*, vol. 34, pp. 1255–1274 (1993).

Sirtori, C. R., New Targets for Lipid Lowering and Atherosclerosis Prevention, *Pharmac. Ther.*, vol. 67, No. 3, pp. 433–447 (1995).

Swenson, T. L., et al., Mechanism of Cholesteryl Ester Transfer Protein Inhibition by a Neutralizing Monoclonal Antibody and Mapping of the Monoclonal Antibody Epitope, *Journal of Biological Chemistry*, vol. 264, No. 24, pp. 14318–14326 (1989).

Morton, R. E., et al., Regulation of lipid transfer between lipoproteins by an endogenous plasma protein: selective inhibition among lipoprotein classes, *Journal of Lipid Research*, vol. 35, pp. 836–847, (1994).

Pietzonka, T., et al., Phosphonate–containing Analogs of Cholesteryl Ester as Novel Inhibitors of Cholesteryl Ester Transfer Protein, *Bioorganic & Medicinal Chemistry Letters*, vol. 6, No. 16, PP. 1951–9154 (1996).

(Continued)

Primary Examiner—Richard L. Raymond
(74) Attorney, Agent, or Firm—Peter C. Richardson; Gregg C. Benson; Lisa A. Samuels

(57) ABSTRACT

The invention relates to substituted tertiary-heteroalkylamine compounds useful as inhibitors of cholesteryl ester transfer protein (CETP; plasma lipid trans: protein-I) and compounds, compositions and methods for treating atherosclerosis and other coronary artery disease.

8 Claims, No Drawings

OTHER PUBLICATIONS

Coval, S. J., et al., Wiedendiol–A and –B Cholesteryl Ester Transfer Protein Inhibitors from the Marin Sponge *Xestospongia Wiedenmayeri*, *Bioorganic & Medicinal Chemistry Letters*, vol. 5, No. 6, pp. 605–610 (1995).

Connolly, D. T., et al., Inactivation of Cholesteryl Ester Transfer Protein by Cysteine Modification, *Biochemical & Biophysical Research Communications*, vol. 223, pp. 42–47 (1996).

Xia, Y., et al., Substituted 1,3,5–Triazines as Cholesteryl Ester Transfer Protein Inhibitors, *Bioorganic & Medicinal Chemistry Letters*, vol. 6, No. 7, pp. 919–922 (1996).

Wagaw, S., et al. The Synthesis of Aminopyridines: A Method Employing Palladium–Catalyzed Carbon–Nitrogen Bond Formation, *J. Org. Chem.*, vol. 61, pp. 7240–7241, (1996).

Wolfe, J. P., et al., Improved Functional Group Compatibility in the Palladium–Catalyzed Amination of Aryl Bromides, *Tetrahedron Letters*, vol. 38, No. 36, pp. 6359–6362 (1997).

Sternbach, D. D., et al., Reduction of O–Acyl Oximes, *Tetrahedron Letters*, vol. 22, No. 35, pp. 3331–3334, (1981).

Ramachandran, P. V., et al., Chiral Synthesis via Organoboranes. 40. Selective Reductions. 55. A Simple One–Pot Synthesis of the Enantiomers of (Trifluoromethyl)oxirane. A General Synthesis in High Optical Purities of α–Trifluoromethyl Secondary Alcohols via the Ring–Cleavage Reactions of the Epoxide, *J. Org. Chem.* vol. 60, pp. 41–46, (1995).

Kuo, M. S., et al., Discovery, Isolation, Structure Elucidation, and Biosynthesis of U–106305, a Cholesteryl Ester Transfer Protein Inhibitor from UC 11136, *J. Am. Chem. Soc.*, vol. 117, pp.10629–10634, (1995).

Barrett, A. G. M., et al., Total Synthesis and Stereochemical Assignment of the Quinquecyclopropane–Containing Cholesteryl Ester Transfer Protein Inhibitor U–106305, *J. Am. Chem. Soc.*, vol. 118, pp. 7863–7864 (1996).

McCarthy, P. A., et al., New Approaches to Atherosclerosis: An Overview, *Medicinal Research Reviews*, vol. 13, No. 2, pp. 139–159, (1993).

Son, Y. C., et a., Purification and Characterization of Human Plasma Proteins that Inhibit Lipid Transfer Activities, *Biochimica et Biophysica Acta*, vol. 795, pp. 473–480, (1984).

Tollefson, J. H., et al., Regulation of plasma lipid transfer by the high–density lipoproteins, *American Physiological Society*, pp. E894–E902, (1988).

Lee, J. C., et al., A Cholesteryl Ester Transfer Protein Inhibitor from an Insect–associated Fungus, *The Journal of Antibiotics*, vol. 49, No. 7, pp. 693–696, (1996).

Busch, S. J., et al., Cholesteryl Ester Analogs Inhibit Cholesteryl Ester but not Triglyceride Transfer Catalyzed by the Plasma Cholesteryl Ester–Triglyceride Transfer Protein, *Lipids*, vol. 25, No. 4, pp. 216–220 (1990).

Bisgaier, C. L., et al., Cholesteryl Ester Transfer Protein Inhibition by PD 140195, *Lipids*, vol. 29, No. 12, pp. 811–818, (1994).

Marcoux, J. F., er al., A General Copper–Catalyzed Synthesis of Diaryl Ethers, *J. Am. Chem. Soc.*, vol. 119, pp. 10539–10540, (1997).

Wolfe, J. P., et al., An Improved Catalyst System for Aromatic Carbon–Nitrogen Bond Formation: The Possible Involvement of Bis(Phosphine) Palladium Complexes as Key Intermediates, *J. Am. Chem. Soc.*, vol. 118, pp. 7215–7216, (1996).

Sheradsky, T., et al., Studies on the Preparation of N–Alky-1–O–phenylhydroxylamines, *J. Chem. Soc. Perkin Trans.*, vol. 12, pp. 2781–2781, (1980).

*The Systematic Identification of Organic Compounds: A Laboratory Manual*, Shriner/Fuson/Curtin, Fifth Edition, copyright 1956 and 1964, John Wiley & Sons, Inc.

*Reagents for Organic Synthesis*, Feiser & Feiser, vol. 1, copyright 1967, John Wiley & Sons, Inc.

*Vogel's Textbook of Practical Organic Chemistry*, Fifth Edition, copyright 1989, John Wiley & Sons, Inc., pp. 902–905.

*English language equivalent of CH 441366, 1968.
**English language equivalent of DE 19627430, 1998.
***English language equivalent of JP 05320117, 1993.

* cited by examiner

US 6,924,313 B1

SUBSTITUTED TERTIARY-HETEROALKYLAMINES USEFUL FOR INHIBITING CHOLESTERYL ESTER TRANSFER PROTEIN ACTIVITY

This is a continuation of application Ser. No. 09/716,728, filed Nov. 21, 2000, now abandoned, which is a continuation of application Ser. No. 09/404,638, filed Sep. 23, 1999, now abandoned.

FIELD OF THE INVENTION

This invention is in the field of treating cardiovascular disease, and specifically relates to compounds, compositions and methods for treating atherosclerosis and other coronary artery disease. More particularly, the invention relates to substituted tertiary-heteroalkylamine compounds that inhibit cholesteryl ester transfer protein (CETP), also known as plasma lipid transfer protein-I.

BACKGROUND OF THE INVENTION

Numerous studies have demonstrated that a low plasma concentration of high density lipoprotein (HDL) cholesterol is a powerful risk factor for the development of atherosclerosis (Barter and Rye, *Atherosclerosis*, 121, 1–12 (1996)). HDL is one of the major classes of lipoproteins that function in the transport of lipids through the blood. The major lipids found associated with HDL include cholesterol, cholesteryl ester, triglycerides, phospholipids and fatty acids. The other classes of lipoproteins found in the blood are low density lipoprotein (LDL) and very low density lipoprotein (VLDL). Since low levels of HDL cholesterol increase the risk of atherosclerosis, methods for elevating plasma HDL cholesterol would be therapeutically beneficial for the treatment of atherosclerosis and other diseases associated with accumulation of lipid in the blood vessels. These diseases include, but are not limited to, coronary heart disease, peripheral vascular disease, and stroke.

Atherosclerosis underlies most coronary artery disease (CAD), a major cause of morbidity and mortality in modern society. High LDL cholesterol (above 180 mg/dl) and low HDL cholesterol (below 35 mg/dl) have been shown to be important contributors to the development of atherosclerosis. Other diseases, such as peripheral vascular disease, stroke, and hypercholesterolaemia subject compounds is shown to effectively modify plasma HDL/LDL ratios, and to check the progress and/or formation of these diseases:

CETP is a plasma protein that facilitates the movement of cholesteryl esters and triglycerides between the various lipoproteins in the blood (Tall, *J. Lipid Res.*, 34, 1255–74 (1993)). The movement of cholesteryl ester from HDL to LDL by CETP has the effect of lowering HDL cholesterol. It therefore follows that inhibition of CETP should lead to elevation of plasma HDL cholesterol and lowering of plasma LDL cholesterol, thereby providing a therapeutically beneficial plasma lipid profile (McCarthy, *Medicinal Res. Revs.*, 13, 139–59 (1993); Sitori, *Pharmac. Ther.*, 67,443–47 (1995)). This exact phenomenon was first demonstrated by Swenson et al., (*J. Biol. Chem.*, 264, 14318 (1989)) with the use of a monoclonal antibody that specifically inhibited CETP. In rabbits, the antibody caused an elevation of the plasma HDL cholesterol and a decrease in LDL cholesterol. Son et al. (*Biochim. Biophys. Acta* 795, 743–480 (1984)), Morton et al. (*J. Lipid Res.* 35, 836–847 (1994)) and Tollefson et al. (*Am. J. Physiol.*, 255, (Endocrinol. Metab. 18, E894–E902 (1988))) describe proteins from human plasma that inhibit CETP. U.S. Pat. No. 5,519,001, issued to Kushwaha et al., describes a 36 amino acid peptide derived from baboon apo C-1 that inhibits CETP activity.

There have been several reports of non-peptidic compounds that act as CETP inhibitors. Barrett et al. (*J. Am. Chem. Soc.*, 188, 7863–63 (1996)) and Kuo et al. (*J. Am. Chem. Soc.*, 117, 10629–34 (1995)) describe cyclopropane-containing CETP inhibitors. Pietzonka et al. (*Bioorg. Med. Chem. Lett*, 6, 1951–54 (1996)) describe phosphonate-containing analogs of cholesteryl ester as CETP inhibitors. Coval et al. (*Bioorg. Med. Chem. Lett.*, 5, 605–610 (1995)) describe Wiedendiol-A and -B, and related sesquiterpene compounds as CETP inhibitors. Lee et al. (*J. Antibiotics*, 49, 693–96 (1996)) describe CETP inhibitors derived from an insect fungus. Busch et al. (*Lipids*, 25, 216–220, (1990)) describe cholesteryl acetyl bromide as a CETP inhibitor. Morton and Zilversmit (*J. Lipid Res.*, 35, 836–47 (1982)) describe that p-chloromercuriphenyl sulfonate, p-hydroxymercuribenzoate and ethyl mercurithiosalicylate inhibit CETP. Connolly et al. (*Biochem. Biophys. Res. Comm.* 223, 42–47 (1996)) describe other cysteine modification reagents as CETP inhibitors. Xia et al. describe 1,3,5-triazines as CETP inhibitors (Bioorg. Med. Chem. Lett., 6, 919–22 (1996)). Bisgaier et al. (*Lipids*, 29, 811–8 (1994)) describe 4-phenyl-5-tridecyl-4H-1,2,4-triazole-thiol as a CETP inhibitor.

Some substituted heteroalkylamine compounds are known. In European Patent Application No. 796846, Schmidt et al. describe 2-aryl-substituted pyridines as cholesterol ester transfer protein inhibitors useful as cardiovascular agents. One substitutent at C3 of the pyridine ring can be an hydroxyalkyl group. In European Patent Application No. 801060, Dow and Wright describe heterocyclic derivatives substituted with an aldehyde addition product of an alkylamine to afford 1-hydroxy-1-amines. These are reported to be β3-adrenergic receptor agonists useful for treating diabetes and other disorders. In Great Britain Patent Application No. 2305665, Fisher et al. disclose 3-agonist secondary amino alcohol substituted pyridine derivatives useful for treating several disorders including cholesterol levels and artherosclerotic diseases. In European Patent Application No 818448, Schmidt et al. describe tetrahydroquinoline derivatives as chlolesterol ester transfer protein inhibitors. European Patent Application No. 818197, Schmek et al. describe pyridines with fused heterocycles as chlolesterol ester transfer protein inhibitors. Brandes et al. in German Patent Application No. 19627430 describe bicyclic condensed pyridine derivatives as cholesterol ester transfer protein inhibitors.

DESCRIPTION OF THE INVENTION

The present invention relates to a class of compounds comprising substituted tertiary-heteroalkylamines which are beneficial in the therapeutic and prophylactic treatment of coronary artery disease as given in Formula I (also referred to herein as generic tertiary omegaheteroalkylamine):

$$R_1 \wedge\!\!\wedge\!\!\wedge \underset{\underset{R_{16}-X}{|}}{\overset{R_2}{\underset{|}{C}}} - (CH)_n - \underset{|}{\overset{R_{19}}{\underset{|}{(CH)_m}}} - \underset{\underset{R_{14}}{|}}{\overset{\overset{A}{\underset{|}{R_{15}-Z}}}{N}} - Y - Q \quad (I)$$

wherein m=0 to 5; n=1 to 6; m+n=1 to 6; and a terminal carbon atom of the $CH_n(R_3)$ moiety is directly bonded by a covalent bond to the nitrogen when m=0;

wherein $R_1$ is selected independently from:

(a) hydrido, alkyl, aryl, aralkyl, alkylsulfinylalkyl, alkylsulfonylalkyl, haloalkylsulfinylalkyl, haloalkylsulfonylalkyl, haloalkyl, haloalkenyl, halocycloalkyl, halocycloalkenyl, haloalkoxy, haloalkoxyalkyl, haloalkenyloxyalkyl, halocycloalkoxy, perhaloaryl, perhaloaralkyl, perhaloaryloxyalkyl, heteroaryl, heteroaralkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, heteroaralkylsulfonylalkyl, heteroaralkylsulfinyl, heteroaralkylsulfonyl, heteroaralkylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_1+R_2$ represents a spacer group selected from a moiety having a chain length of 2 to 7 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboxylalkyl, hydroxy, hydroxyalkyl, and halo groups;

(c) or $R_1+R_3$ represents a spacer group selected from a covalent bond or a moiety having a chain length of 2 to 7 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_1+R_{19}$ represents a spacer group selected from a covalent bond or a moiety having a chain length of 2 to 7 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein $R_2$ is independently selected from:

(a) hydrido, hydroxy, hydroxyalkyl, amino, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_2+R_1$ represents a spacer group selected from a moiety having a chain length of 2 to 7 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboxylalkyl, hydroxy, hydroxyalkyl, and halo groups;

(c) or $R_2+R_3$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_2+R_{14}$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_2+R_{15}$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_2$ represents a spacer group selected from a covalent bond or a moiety having a chain length of 1 to 4 atoms connected to a point of bonding on A or Q to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein $R_3$ is selected from:

(a) hydrido, hydroxy, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, beteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl:

(b) or $R_3+R_1$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_3+R_2$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_3+R_{14}$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_3+R_{15}$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_3$ represents a spacer group selected from a covalent bond or a linear moiety having a chain length of 1 to 6 atoms connected to a point of bonding on A or Q to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_3+R_{19}$ represents a spacer group selected from a covalent bond or a linear moiety having a chain length of 1 to 5 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein X is selected from —H, —F, —O—, —S—, —S(O)—, —S(O)$_2$—, —S(O)$_2$(NH)—, —NH—, —N(OH)—, —N(NH$_2$)—, —N(NHCH$_3$)—, —N(alkyl)-, —N(alkoxy)-, —N(aryloxy)-, —N(heteroaryloxy)-, —N(acyloxy)-, —N(aroyloxy)-, —N(cycloalkyl), —N(aralkoxy)-, and —N(aryl)-;

wherein $R_{16}$ is selected from:

(a) hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocyanoalkyl, dicyanoalkyl, carboalkoxycyanoalkyl, acyl, aroyl, heteroaroyl, heteroaryloxyalkyl, dialkoxyphosphonoalkyl or absent:

(b) or a spacer group selected from a covalent bond or a moiety having a chain length of 1 to 5 atoms connected to A or Q to form a C5 to C10 saturated heterocyclyl or a C5 to C10 partially saturated heterocyclyl ring substituted independently and optionally with, for example, one to three alkyl, haloalkyl, aryl, hydroxyl, thiol, amino, alkylamino, heteroaryl, alkoxyalkyl, alkoxy, haloalkoxy, carboxy, aryloxy, heteroaryloxy, cyano, carboalkoxy, hydroxy, hydroxyalkyl, and halo groups;

(c) or $R_{16}+R_{14}$ represents a spacer group selected from a covalent bond or a moiety having a chain length of 1 to 5 atoms connected to form a C5 to C10 saturated heterocyclyl or a C5 to C10 partially saturated heterocyclyl ring substituted independently and optionally with, for example, one to three alkyl, haloalkyl, aryl, hydroxyl, thiol, amino, alkylamino, heteroaryl, alkoxyalkyl, alkoxy, haloalkoxy, carboxy, aryloxy, heteroaryloxy, cyano, carboalkoxy, hydroxy, hydroxyalkyl, and halo groups;

wherein Y is a (—C($R_{14}$)$_y$—)$_n$ where n=1 to 4 and y=0 to 2 or (—CH($R_{14}$)$_y$—)$_n$—W—(—CH($R_{14}$)$_y$—)$_n$ where n=1 to 2 and y=0 to 1 and $R_{14}$ is independently selected from:

(a) hydrido, hydroxy, cyano, aryloxy, amino, alkylamino, dialkylamino hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{14}+R_2$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{14}+R_3$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{14}+R_{15}$ represents a spacer group selected from a moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{14}$ represents a spacer group selected from a moiety having a chain length of 3 to 6 atoms connected to Q to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{14}$ represents a spacer group selected from a moiety having a chain length of 2 to 5 atoms connected to point of bonding on A to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_{14}+R_{14}$ represents a covalent bond, an alkylene, a haloalkylene, alkylenedioxy, haloalkylenedioxy, or a spacer group selected from a moiety having a chain length of 2 to 5 atoms connected to form a C5 to C8 saturated cycloalkyl, a C5 to C8 partially saturated cycloalkyl, a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_{14}+R_{14}$ represents, when bonded to the same atom, an oxo, an alkylene, a haloalkylene, alkylenedioxy, haloalkylenedioxy, or a spacer group selected from a moiety having a chain length of 3 to 7 atoms connected to form a C4 to C8 saturated cycloalkyl, a C4 to C8 partially saturated cycloalkyl, a C4 to C8 saturated heterocyclyl or a C4 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein W is selected from —O—, —S—, —S(O)—, —S(O)$_2$—, —S(O)$_2$(NH)—, —NH—, —N(OH)—, —N(NH$_2$)—, —N(NHCH$_3$)—, —N(alkyl)-, —N(alkoxy)-, —N(aryloxy)-, —N(heteroaryloxy)-, —N(acyloxy)-, —N(aroyloxy)-, —N(cycloalkyl), —N(aralkoxy)-, and —N(aryl)-;

wherein Z is independently selected from a covalent bond, (—C(R$_{15}$)$_y$—)$_n$ wherein n=1 to 4 and y=0 to 2, (—CH(R$_{15}$)$_y$—)$_n$—W—(—CH(R$_{15}$)$_y$—)$_n$ wherein n=1 to 2 and y=0 to 2, —N—, —N(OH)—, —N(alkyl)-, —N(alkoxy)-, —N(aryloxy)-, —N(aralkoxy), —N(cycloalkyl)-, —N(aryl)-, oxygen radical (—O—), —OCH$_2$—, or —OCH(R$_{15}$)$_y$— where y=0 to 1;

wherein, when Z is (—C(R$_{15}$)$_y$—)$_n$ where n=1 to 4 and y=0 to 2 or (—CH(R$_{15}$)$_y$—)$_n$—W—(—CH(R$_{15}$)$_y$—)$_n$ wherein n=1 to 2 and y=0 to 2, R$_{15}$ is independently selected from:

(a) hydrido, hydroxy, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinylalkyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroaryl sulfonyl heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{15}+R_2$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{14}+R_{15}$ represents a spacer group selected from a moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}$ represents a spacer group selected from a moiety having a chain length of 3 to 6 atoms connected to Q to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{15}$ represents a spacer group selected from a moiety having a chain length of 2 to 5 atoms connected to point of bonding on A to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups; (g) or $R_{15}+R_{15}$ represents a covalent bond, an alkylene, a haloalkylene, alkylenedioxy, haloalkylenedioxy, or a spacer group selected from a moiety having a chain length of 2 to 5 atoms connected to form a C5 to C8 saturated cycloalkyl, a C5 to C8 partially saturated cycloalkyl, a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_{15}+R_{15}$ represents, when bonded to the same atom, an oxo, an alkylene, a haloalkylene, alkylenedioxy, haloalkylenedioxy, or a spacer group selected from a moiety having a chain length of 3 to 7 atoms connected to form a C4 to C8 saturated cycloalkyl, a C4 to C8 partially saturated cycloalkyl, a C4 to C8 saturated heterocyclyl or a C4 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is N, $R_{15}$ is independently selected from:

(a) hydrido, hydroxyalkyl, aryloxy, aminoalkyl, alkylaminoalkyl, dialkylaminoalkyl, acyl, aroyl, heteroaroyl, heteroaryloxyalcyl, acylamido, alkyl, alkenyl, alkynyl, aryl, aralkyl, aryloxyalkyl, aralkoxyalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, aralkylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl;

(b) or $R_{15}+R_2$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{15}+R_{14}$ represents a spacer group selected from a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}$ represents a spacer group selected from a linear moiety having a chain length of 3 to 6 atoms connected to A to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{15}$ represents a spacer group selected from a linear moiety having a chain length of 2 to 5 atoms connected to Q to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is $(-CH(R_{15})_y-)_n-W-(-CH(R_{15})_y-)_n$ wherein n=1 to 2 and y=0 to 2 or $-OCH(R_{15})_y-$ wherein y=0 to 1, $R_{15}$ is independently selected from:

(a) aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl;

(b) or $R_{15}+R_2$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{15}+R_{14}$ represents a spacer group selected from a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}$ represents a spacer group selected from a linear moiety having a chain length of 3 to 6 atoms connected to A to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{15}$ represents a spacer group selected from a linear moiety having a chain length of 2 to 5 atoms connected to Q to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is a covalent bond, —N(OH)—, —N(alkyl)-, —N(alkoxy)-, —N(aryloxy)-, —N(cycloalkyl)-, —N(aryl)-, —N(aralkoxy)-, oxygen radical (—O—), or —OCH$_2$—, an $R_{15}$ substituent is not attached to Z;

wherein $R_{19}$ is selected from:

(a) hydrido, hydroxyalkyl, acyl, sulfhydryl, acylamido, alkoxy, alkylthio, arylthio, alkyl, alkenyl, alkynyl, aryl, aralkyl, aryloxyalkyl, heteroarylthio, aralkylthio, aroyl, aralkanoyl, heteroaroyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{19}+R_1$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{19}+R_2$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{19}+R_3$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{19}+R_{14}$ represents a spacer group selected from a covalent bond or a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{19}+R_{15}$ represents a spacer group selected from a covalent bond or a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups; (g) or $R_{19}$ represents a spacer group selected from a covalent bond or a linear moiety having a chain length of 2 to 5 atoms connected to a point of bonding on A or Q to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein A and Q are independently selected from alkyl, alkenyl, alkynyl, aryl, hydroxyalkyl, saturated heterocyclyl, partially saturated heterocyclyl, heteroaryl, aralkyl, cycloalkyl, cycloalkylalkyl, cycloalkenyl, cycloalkenylalkyl, cycloalkylalkenyl, aryloxyalkyl, alkoxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaralkyl, heteroaryloxyalkyl, carboxyalkyl, carboalkoxyalkyl, carboxamidoalkyl, cyanoalkyl, dialkoxyphosphonoalkyl, N-arylcarboxamidoalkyl, or N-heteroarylcarboxamidoalkyl, provided one of A and Q must be aryl, aryloxyalkyl, heteroaryl, perhaloaryloxyalkyl, aralkyl, or heteroaralkyl;

or a pharmaceutically-acceptable salt thereof.

Alternatively, compounds of the present invention consist of quaternary ammonium salt compounds of Formula II (also referred to herein as Generic Tertiary OmegaHeteroalkylamineammonium salt):

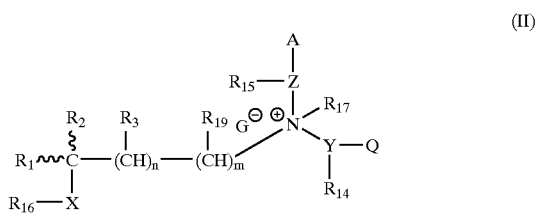

(II)

wherein m=0 to 5; n=1 to 6; m+n=1 to 6; and a terminal carbon atom of the $CH(R_3)$ moiety is directly connected by a covalent bond to the nitrogen when m=0;

wherein $R_{17}$ is selected from alkyl, alkenyl, alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl;

wherein G is selected from chloro, bromo, iodo, fluoride, trifluoroacetate, perhaloalkylcarboxylates, arylcarboxylates, formate, monoalkylsulfates, arylsulfonates, diarylsulfonylimide anion, benzenesulfonate, tosylate, brosylate, alkylphosphates, arylphosphates, mixed alkyl aryl phosphates, perhaloalkylsulfonates, betylates, perchlorate, mesylate, and pharmaceutically acceptable salts as disclosed herein;

wherein $R_1$, $R_2$, $R_3$, $R_{14}$, $R_{15}$, $R_{16}$, $R_{19}$, A, Q, X, Y, and Z are substituents selected from those disclosed for the compounds of Formula I:

or a pharmaceutically-acceptable salt thereof.

The compounds of this invention can be used to inhibit cholesteryl ester transfer protein (CETP) activity, thereby decreasing the concentrations of low density lipoprotein (LDL) and raising the level of high density lipoprotein (HDL), resulting in a therapeutically beneficial plasma lipid profile. The compounds also can be used to treat dyslipidemia (hypoalphalipoproteinemia), hyperlipoproteinaemia (chylomicronemia and hyperapobetalipoproteinemia), peripheral vascular disease, hypercholesterolaemia, atherosclerosis, coronary artery disease and other CETP-mediated disorders. The compounds can also be used in prophylactic treatment of subjects who are at risk of developing such disorders. The compounds can be used to lower the risk of atherosclerosis. The compounds of Formula I and Formula II would be also useful in prevention of cerebral vascular accident (CVA) or stroke.

Besides being useful for human treatment, these compounds are also useful for veterinary treatment of companion animals, exotic animals and farm animals, including mammals, rodents, and the like. More preferred animals include horses, dogs, and cats.

In one embodiment, the compounds correspond to Formula I wherein m=0 and n=1. Compounds of Formula I wherein m=0 and n=1 have the $CH(R_3)$ moiety directly connected by a covalent bond to the nitrogen and correspond to Formula III (also referred to herein as generic tertiary 2-heteroalkylamine):

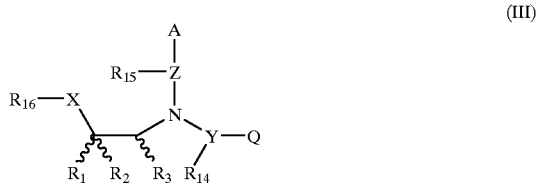

(III)

wherein $R_1$, $R_2$, $R_3$, $R_{14}$, $R_{15}$, $R_{16}$, A, Q, X, Y, and Z are as defined above for the compounds of Formula I;

or a pharmaceutically-acceptable salt thereof.

Alternatively, compounds of the present invention consist of quaternary ammonium salt compounds of Formula IV (also referred to herein as generic tertiary 2-heteroalkylammonium salt):

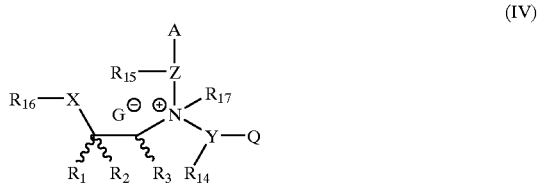

(IV)

wherein m=0 and n=1 have the terminal carbon atom of the $CH(R_3)$ moiety directly connected by a covalent bond to the nitrogen;

wherein $R_1$, $R_2$, $R_3$, $R_{14}$, $R_{15}$, $R_{16}$, A, Q, X, Y, and Z are as defined above for the compounds of Formula II;

wherein $R_{17}$ is selected from alkyl, alkenyl, alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl;

wherein G is selected from chloro, bromo, iodo, fluoride, trifluoroacetate, perhaloalkylcarboxylates, arylcarboxylates, formate, monoalkylsulfates, arylsulfonates, diarylsulfonylimide anion, benzenesulfonate, tosylate, brosylate, alkylphosphates, arylphosphates, mixed alkyl aryl phosphates, perhaloalkylsulfonates, betylates, perchlorate, mesylate, and pharmaceutically acceptable salts as disclosed herein;

or a pharmaceutically-acceptable salt thereof.

In another embodiment, the compounds correspond to Formula I wherein m=0 to 5; n=1 to 5; m+n=1 to 6, A=aryl or heteroaryl substituted independently at one or more meta and para positions with substituents independently selected from alkoxy, aralkoxy, heteroaralkoxy, haloalkoxy, haloalkenyloxy, aryloxy, haloaryloxy, heteroaryloxy, aryl, arylthio, heteroaryl, heteroarylthio, arylamino, heteroarylamino, aroyl, heteroaroyl, and haloheteroaryloxy groups; Q=aryl or heteroaryl substituted independently at one or more meta and para positions with substituents independently selected from alkoxy, aralkoxy, heteroaralkoxy, haloalkoxy, haloalkenyloxy, aryloxy, haloaryloxy, heteroaryloxy, aryl, arylthio, heteroaryl, heteroarylthio, arylamino, heteroarylamino, aroyl, heteroaroyl, and haloheteroaryloxy groups; and a terminal carbon atom of the $CH(R_3)$ moiety is directly connected by a covalent bond to the nitrogen when m=0. Compounds of Formula I wherein m=0 to 5; n=1 to 5; m+n=1 to 6, A=aryl or heteroaryl substituted independently at one or more meta and para positions with substituents independently selected from alkoxy, aralkoxy, heteroaralkoxy, haloalkoxy, haloalkenyloxy, aryloxy, haloaryloxy, heteroaryloxy, and haloheteroaryloxy groups, and Q=aryl or heteroaryl substituted independently at one or more meta and para positions with substituents independently selected from alkoxy, aralkoxy, heteroaralkoxy, haloalkoxy, haloalkenyloxy, aryloxy, haloaryloxy, heteroaryloxy, and haloheteroaryloxy groups have the $CH(R_3)$ moiety directly connected by a covalent bond to the nitrogen when m=0 and correspond to Formula I-I (also referred to herein as generic aromatic tertiary omegaheteroalkylamines):

$$(I\text{-}I)$$

$$R_1 \mathord{\sim}\!\!\!\!\overset{R_2}{\underset{R_{16}-X}{\overset{R_3}{\mathrm{C}}}}\!\!-(CH)_n-(CH)_m\!\!\overset{\overset{A}{|}}{\underset{R_{14}}{\overset{R_{15}-Z}{\mathrm{N}}}}\!\!-Y-Q$$

wherein $R_1$, $R_2$, $R_3$, $R_{14}$, $R_{15}$, $R_{16}$, $R_{19}$, X, Y, and Z are as defined for the compounds of Formula I;

wherein A and Q are independently selected from aryl or heteroaryl, provided that at least one of A or Q must be substituted at one or more meta and para positions with substituents independently selected from alkoxy, aralkoxy, heteroaralkoxy, haloalkoxy, haloalkenyloxy, aryloxy, haloaryloxy, heteroaryloxy, aryl, arylthio, heteroaryl, heteroarylthio, arylamino, heteroarylamino, aroyl, heteroaroyl, and haloheteroaryloxy groups, and provided that A and Q may additionally both be substituted optionally and independently at one or more meta and para positions with substituents independently selected from haloalkenyloxy, haloaryloxy, haloheteroaryloxy heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydroxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, N-aryl-N-cycloalkylamino, N-cycloalkylamino, N-alkenylamino, N-cycloalkenylamino, cycloalkenyloxy, N-heteroarylalkyl, arylalkenyl, heteroarylalkenyl, carboalkoxy, carboaralkoxy, cyano, and carbohaloalkoxy groups;

wherein A and Q are not linked together by a covalent bond or a spacer group to form a C5 to C10 partially saturated heterocyclyl ring or a C5 to C6 heteroaryl substituted independently and optionally with, for example, one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

or a pharmaceutically-acceptable salt thereof.

Alternatively, compounds of the present invention consist of quaternary ammonium salt compounds of Formula II-II (also referred to herein as generic aromatic tertiary omega-heteroalkylammonium salt):

$$(II\text{-}II)$$

$$R_1 \mathord{\sim}\!\!\!\!\overset{R_2}{\underset{R_{16}-X}{\overset{R_3}{\mathrm{C}}}}\!\!-(CH)_n-(CH)_m\!\!\overset{\overset{A}{|}}{\underset{R_{14}}{\overset{R_{15}-Z}{\underset{R_{19}\;G^{\ominus}\,\oplus}{\mathrm{N}}}}}\!\!\overset{R_{17}}{\underset{}{\diagdown}}\!\!Y-Q$$

wherein m=0 to 5; n=1 to 5; m+n=1 to 6;

wherein the $CH(R_3)$ moiety is directly connected when m=0 by a covalent bond to the nitrogen;

wherein $R_1$, $R_2$, $R_3$, $R_{14}$, $R_{15}$, $R_{16}$, $R_{19}$, A, Q, X, Y, and Z are as defined above for the compounds of Formula I-I;

wherein $R_{17}$ is selected from alkyl, alkenyl, alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl;

wherein G is selected from chloro, bromo, iodo, fluoride, trifluoroacetate, perhaloalkylcarboxylates, arylcarboxylates, formate, monoalkylsulfates, arylsulfonates, diarylsulfonylimide anion, benzenesulfonate, tosylate, brosylate, alkylphosphates, arylphosphates, mixed alkyl aryl phosphates, perhaloalkylsulfonates, betylates, perchlorate, mesylate, and pharmaceutically acceptable salts as disclosed herein;

or a pharmaceutically-acceptable salt thereof.

In another embodiment, the compounds correspond to Formula I wherein m=0 to 5; n=1 to 5; m+n=1 to 6; A=aryl or heteroaryl substituted independently at one or more meta and para positions with substituents independently selected from alkoxy, aralkoxy, heteroaralkoxy, haloalkoxy, haloalkenyloxy, aryloxy, haloaryloxy, heteroaryloxy, aryl, arylthio, heteroaryl, heteroarylthio, arylamino, heteroarylamino, aroyl, heteroaroyl, and haloheteroaryloxy groups; Q=aryl or heteroaryl substituted independently at one or more meta and para positions with substituents independently selected from alkoxy, aralkoxy, heteroaralkoxy, haloalkoxy, haloalkenyloxy, aryloxy, haloaryloxy, heteroaryloxy, aryl, arylthio, heteroaryl, heteroarylthio, arylamino, heteroarylamino, aroyl, heteroaroyl, and haloheteroaryloxy groups; and a terminal carbon atom of the $CH(R_3)$ moiety is directly connected by a covalent bond to the nitrogen when m=0. Compounds of Formula I wherein m=0 to 5; n=1 to 5; m+n=1 to 6, A=aryl or heteroaryl substituted independently at one or more meta and para positions with substituents independently selected from alkoxy, aralkoxy, heteroaralkoxy, haloalkoxy, haloalkenyloxy, aryloxy, haloaryloxy, heteroaryloxy, and haloheteroaryloxy groups, and Q=aryl or heteroaryl substituted independently at one or more meta and para positions with substituents independently selected from alkoxy, aralkoxy, heteroaralkoxy, haloalkoxy, haloalkenyloxy, aryloxy, haloaryloxy, heteroaryloxy, and haloheteroaryloxy groups have the CH(R$_3$) moiety directly connected by a covalent bond to the nitrogen when m=0 and correspond to Formula I-IA (also referred to herein as generic aromatic tertiary omegaheteroalkylamines):

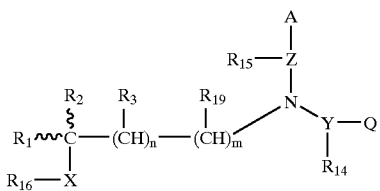

(I-IA)

wherein R$_1$, R$_2$, R$_3$, R$_{14}$, R$_{15}$, R$_{16}$, R$_{19}$, X, Y, and Z are as defined for the compounds of Formula I;

wherein A and Q are independently selected from aryl or heteroaryl, provided that at least one of A or Q must be substituted at one or more meta and para positions with substituents independently selected from alkoxy, aralkoxy, heteroaralkoxy, haloalkoxy, haloalkenyloxy, aryloxy, haloaryloxy, heteroaryloxy, aryl, arylthio, heteroaryl, heteroarylthio, arylamino, heteroarylamino, aroyl, heteroaroyl, and haloheteroaryloxy groups, and provided that A and Q may additionally both be substituted optionally and independently at one or more meta and para positions with substituents independently selected from haloalkenyloxy, haloaryloxy, haloheteroaryloxy heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydroxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, N-aryl-N-cycloalkylamino, N-cycloalkylamino, N-alkenylamino, N-cycloalkenylamino, cycloalkenyloxy, N-heteroarylalkyl, arylalkenyl, heteroarylalkenyl, carboalkoxy, carboaralkoxy, cyano, and carbohaloalkoxy groups;

wherein A and Q may optionally be linked together by a covalent bond or a spacer group to form a C5 to C10 partially saturated heterocyclyl ring or a C5 to C6 heteroaryl substituted independently and optionally with, for example, one to three alkyl, haloalkyl, aryl, heteroaryl, aryloxy, alkoxyalkyl, alkoxy, haloalkoxy, hydroxy, hydroxyalkyl, cyano, carboalkoxy, and halo groups;

or a pharmaceutically-acceptable salt thereof.

Alternatively, compounds of the present invention consist of quaternary ammonium salt compounds of Formula II-IIA (also referred to herein as generic aromatic tertiary omegaheteroalkylammonium salt):

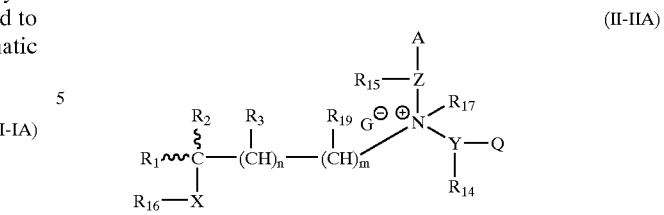

(II-IIA)

wherein m=0 to 5; n=1 to 5; m+n=1 to 6;

wherein the CH(R$_3$) moiety is directly connected by a covalent bond to the nitrogen when m=0;

wherein R$_1$, R$_2$, R$_3$, R$_{14}$, R$_{15}$, R$_{16}$, R$_{19}$, A, Q, X, Y, and Z are as defined above for the compounds of Formula I-I;

wherein R$_{17}$ is selected from alkyl, alkenyl, alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl;

wherein G is selected from chloro, bromo, iodo, fluoride, trifluoroacetate, perhaloalkylcarboxylates, arylcarboxylates, formate, monoalkylsulfates, arylsulfonates, diarylsulfonylimide anion, benzenesulfonate, tosylate, brosylate, alkylphosphates, arylphosphates, mixed alkyl aryl phosphates, perhaloalkylsulfonates, betylates, perchlorate, mesylate, and pharmaceutically acceptable salts as disclosed herein;

or a pharmaceutically-acceptable salt thereof.

In another embodiment, the compounds correspond to Formula I wherein m=0; n=1; A=alkyl, haloalkyl, alkylene, haloalkylene, cycloalkyl, halocycloalkyl, cycloalkenyl, halocycloalkenyl, aryl, aralkyl, heterocyclyl, aryloxyalkyl, heteroaryloxyalkyl, heteroaralkyl, or heteroaryl provided that, when Q=alkyl, haloalkyl, alkylene, haloalkylene, cycloalkyl, halocycloalkyl, cycloalkenyl, halocycloalkenyl, A must be aryl, aralkyl, heterocyclyl, aryloxyalkyl, heteroaryloxyalkyl, heteroaralkyl, or heteroaryl; Q=alkyl, haloalkyl, alkylene, haloalkylene, cycloalkyl, halocycloalkyl, cycloalkenyl, halocycloalkenyl, aryl, aralkyl, heterocyclyl, aryloxyalkyl, heteroaryloxyalkyl, heteroaralkyl, or heteroaryl provided that, when A=alkyl, haloalkyl, alkylene, haloalkylene, cycloalkyl, halocycloalkyl, cycloalkenyl, halocycloalkenyl, Q must be aryl, aralkyl, heterocyclyl, aryloxyalkyl, heteroaryloxyalkyl, heteroaralkyl, or heteroaryl; and a terminal carbon atom of the CH(R$_3$) moiety is directly connected by a covalent bond to the nitrogen when m=0. Compounds of Formula I wherein m=0; n=1; A=alkyl, haloalkyl, alkylene, haloalkylene, cycloalkyl, halocycloalkyl, cycloalkenyl, halocycloalkenyl, aryl, aralkyl, heterocyclyl, aryloxyalkyl, heteroaryloxyalkyl, heteroaralkyl, or heteroaryl provided that, when Q=alkyl, haloalkyl, alkylene, haloalkylene, cycloalkyl, halocycloalkyl, cycloalkenyl, halocycloalkenyl. A must be aryl, aralkyl, heterocyclyl, aryloxyalkyl, heteroaryloxyalkyl, heteroaralkyl, or heteroaryl; Q=alkyl, haloalkyl, alkylene, haloalkylene, cycloalkyl, halocycloalkyl, cycloalkenyl, halocycloalkenyl, aryl, aralkyl, heterocyclyl, aryloxyalkyl, heteroaryloxyalkyl, heteroaralkyl, or heteroaryl provided that, when A=alkyl, haloalkyl, alkylene, haloalkylene, cycloalkyl, halocycloalkyl, cycloalkenyl, halocycloalkenyl, Q must be aryl, aralkyl, heterocyclyl, aryloxyalkyl, heteroaryloxyalkyl, heteroaralkyl, or heteroaryl; and a terminal carbon atom of the CH(R$_3$) moiety is directly connected by a covalent bond to the nitrogen when m=0 correspond to Formula III-III (also referred to herein as generic aromatic tertiary 2-heteroalkylamines):

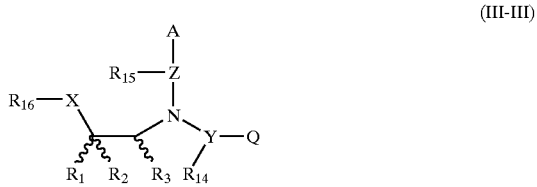

(III-III)

wherein $R_1$ is as defined for the compounds of Formula I or $R_1$ is hydrido;

wherein $R_2$, $R_3$, $R_{14}$, $R_{15}$, $R_{16}$, X, Y, and Z are as defined for the compounds of Formula I;

wherein A is independently selected from alkyl, haloalkyl, alkylene, haloalkylene, cycloalkyl, halocycloalkyl, cycloalkenyl, halocycloalkenyl, hydroxyhaloalkyl, aryloxyhydroxyalkyl, aryl, aralkyl, heterocyclyl, aryloxyalkyl, heteroaryloxyalkyl, heteroaralkyl, or heteroaryl provided that, when Q is alkyl, haloalkyl, alkylene, haloalkylene, cycloalkyl, halocycloalkyl, cycloalkenyl, halocycloalkenyl, hydroxyhaloalkyl, or aryloxyhydroxyalkyl, A must be aryl, aralkyl, heterocyclyl, aryloxyalkyl, heteroaryloxyalkyl, heteroaralkyl, or heteroaryl;

wherein Q is independently selected from alkyl, haloalkyl, alkylene, haloalkylene, cycloalkyl, halocycloalkyl, cycloalkenyl, halocycloalkenyl, hydroxyhaloalkyl, aryloxyhydroxyalkyl, aryl, aralkyl, heterocyclyl, aryloxyalkyl, heteroaryloxyalkyl, heteroaralkyl, or heteroaryl provided that, when A is alkyl, haloalkyl, alkylene, haloalkylene, cycloalkyl, halocycloalkyl, cycloalkenyl, halocycloalkenyl, hydroxyhaloalkyl, or aryloxyhydroxyalkyl, Q must be aryl, aralkyl, heterocyclyl, aryloxyalkyl, heteroaryloxyalkyl, heteroaralkyl, or heteroaryl;

wherein A and Q are not linked together by a covalent bond or a spacer group to form a C5 to C10 partially saturated heterocyclyl ring or a C5 to C6 heteroaryl substituted independently and optionally with, for example, one to three alkyl, haloalkyl, aryl, heteroaryl, aryloxy, alkoxyalkyl, alkoxy, haloalkoxy, hydroxy, hydroxyalkyl, cyano, carboalkoxy, and halo groups;

or a pharmaceutically-acceptable salt thereof.

Alternatively, compounds of the present invention consist of quaternary ammonium salt compounds of Formula IV-IV (also referred to herein as generic aromatic tertiary 2-heteroalkylammonium salt):

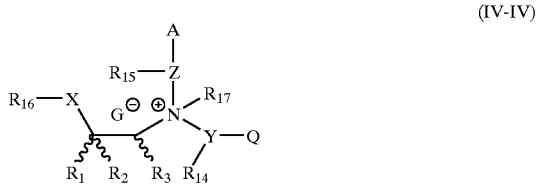

(IV-IV)

wherein $R_1$, $R_2$, $R_3$, $R_{14}$, $R_{15}$, $R_{16}$, A, Q, X, Y, and Z are as defined for the compounds of Formula III-III;

wherein $R_{17}$ is selected from alkyl, alkenyl, alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl:

wherein G is selected from chloro, bromo, iodo, fluoride, trifluoroacetate, perhaloalkylcarboxylates, arylcarboxylates, formate, monoalkylsulfates, arylsulfonates, diarylsulfonylimide anion, benzenesulfonate, tosylate, brosylate, alkylphosphates, arylphosphates, mixed alkyl aryl phosphates, perhaloalkylsulfonates, betylates, perchlorate, mesylate, and pharmaceutically acceptable salts as disclosed herein;

or a pharmaceutically-acceptable salt thereof.

In another embodiment, the compounds correspond to Formula I wherein m=0; n=1; A=alkyl, haloalkyl, alkylene, haloalkylene, cycloalkyl, halocycloalkyl, cycloalkenyl, halocycloalkenyl, hydroxyhaloalkyl, aryloxyhydroxyalkyl, aryl, aralkyl, heterocyclyl, aryloxyalkyl, heteroaryloxyalkyl, heteroaralkyl, or heteroaryl provided that, when Q=alkyl, haloalkyl, alkylene, haloalkylene, cycloalkyl, halocycloalkyl, cycloalkenyl, halocycloalkenyl, hydroxyhaloalkyl, or aryloxyhydroxyalkyl, A must be aryl, aralkyl, heterocyclyl, aryloxyalkyl, heteroaryloxyalkyl, heteroaralkyl, or heteroaryl; Q=alkyl, haloalkyl, alkylene, haloalkylene, cycloalkyl, halocycloalkyl, cycloalkenyl, halocycloalkenyl, hydroxyhaloalkyl, aryloxyhydroxyalkyl, aryl, aralkyl, heterocyclyl, aryloxyalkyl, heteroaryloxyalkyl, heteroaralkyl, or heteroaryl provided that, when A=alkyl, haloalkyl, alkylene, haloalkylene, cycloalkyl, halocycloalkyl, cycloalkenyl, halocycloalkenyl, hydroxyhaloalkyl, or aryloxyhydroxyalkyl, Q must be aryl, aralkyl, heterocyclyl, aryloxyalkyl, heteroaryloxyalkyl, heteroaralkyl, or heteroaryl; and a terminal carbon atom of the $CH(R_3)$ moiety is directly connected by a covalent bond to the nitrogen when m=0. Compounds of Formula I wherein m=0; n=1; A=alkyl, haloalkyl, alkylene, haloalkylene, cycloalkyl, halocycloalkyl, cycloalkenyl, halocycloalkenyl, hydroxyhaloalkyl, aryloxyhydroxyalkyl, aryl, aralkyl, heterocyclyl, aryloxyalkyl, heteroaryloxyalkyl, heteroaralkyl, or heteroaryl provided that, when Q=alkyl, haloalkyl, alkylene, haloalkylene, cycloalkyl, halocycloalkyl, cycloalkenyl, halocycloalkenyl, hydroxyhaloalkyl, or aryloxyhydroxyalkyl. A must be aryl, aralkyl, heterocyclyl, aryloxyalkyl, heteroaryloxyalkyl, heteroaralkyl, or heteroaryl; Q=alkyl, haloalkyl, alkylene, haloalkylene, cycloalkyl, halocycloalkyl, cycloalkenyl, halocycloalkenyl, hydroxyhaloalkyl, aryloxyhydroxyalkyl, aryl, aralkyl, heterocyclyl, aryloxyalkyl, heteroaryloxyalkyl, heteroaralkyl, or heteroaryl provided that, when A=alkyl, haloalkyl, alkylene, haloalkylene, cycloalkyl, halocycloalkyl, cycloalkenyl, halocycloalkenyl, hydroxyhaloalkyl, or aryloxyhydroxyalkyl, Q must be aryl, aralkyl, heterocyclyl, aryloxyalkyl, heteroaryloxyalkyl, heteroaralkyl, or heteroaryl; and a terminal carbon atom of the $CH(R_3)$ moiety is directly connected by a covalent bond to the nitrogen when m=0 correspond to Formula III-IIIA (also referred to herein as generic aromatic tertiary 2-heteroalkylamines):

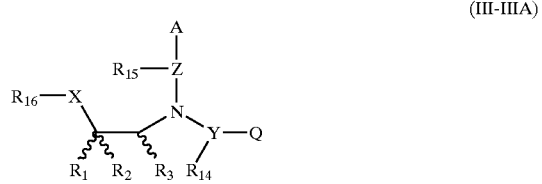

(III-IIIA)

wherein $R_1$ is as defined for the compounds of Formula I or $R_1$ is hydrido;

wherein $R_2$, $R_3$, $R_{14}$, $R_{15}$, $R_{16}$, X, Y, and Z are as defined for the compounds of Formula I;

wherein A is independently selected from alkyl, haloalkyl, alkylene, haloalkylene, cycloalkyl, halocycloalkyl, cycloalkenyl, halocycloalkenyl, hydroxyhaloalkyl, aryloxyhydroxyalkyl, aryl, aralkyl, heterocyclyl, aryloxyalkyl, heteroaryloxyalkyl, heteroaralkyl, or heteroaryl provided that, when Q is alkyl, haloalkyl, alkylene, haloalkylene, cycloalkyl, halocycloalkyl, cycloalkenyl, halocycloalkenyl, hydroxyhaloalkyl, or aryloxyhydroxyalkyl. A must be aryl, aralkyl, heterocyclyl, aryloxyalkyl, heteroaryloxyalkyl, heteroaralkyl, or heteroaryl;

wherein Q is independently selected from alkyl, haloalkyl, alkylene, haloalkylene, cycloalkyl, halocycloalkyl, cycloalkenyl, halocycloalkenyl, hydroxyhaloalkyl, aryloxyhydroxyalkyl, aryl, aralkyl, heterocyclyl, aryloxyalkyl, heteroaryloxyalkyl, heteroaralkyl, or heteroaryl provided that, when A is alkyl, haloalkyl, alkylene, haloalkylene, cycloalkyl, halocycloalkyl, cycloalkenyl, halocycloalkenyl, hydroxyhaloalkyl, or aryloxyhydroxyalkyl, Q must be aryl, aralkyl, heterocyclyl, aryloxyalkyl, heteroaryloxyalkyl, heteroaralkyl, or heteroaryl;

wherein A and Q may optionally be linked together by a covalent bond or a spacer group to form a C5 to C10 partially saturated heterocyclyl ring or a C5 to C6 heteroaryl substituted independently and optionally with, for example, one to three alkyl, haloalkyl, aryl, heteroaryl, aryloxy, alkoxyalkyl, alkoxy, haloalkoxy, hydroxy, hydroxyalkyl, cyano, carboalkoxy, and halo groups;

or a pharmaceutically-acceptable salt thereof.

Alternatively, compounds of the present invention consist of quaternary ammonium salt compounds of Formula IV-IVA (also referred to herein as generic aromatic tertiary 2-heteroalkylammonium salt):

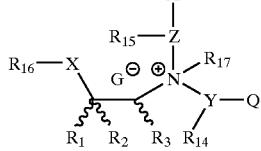

(IV-IVA)

wherein $R_1$, $R_2$, $R_3$, $R_{14}$, $R_{15}$, $R_{16}$, A, Q, X, Y, and Z are as defined for the compounds of Formula III-IIIA;

wherein $R_{17}$ is selected from alkyl, alkenyl, alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl;

wherein G is selected from chloro, bromo, iodo, fluoride, trifluoroacetate, perhaloalkylcarboxylates, arylcarboxylates, formate, monoalkylsulfates, arylsulfonates, diarylsulfonylimide anion, benzenesulfonate, tosylate, brosylate, alkylphosphates, arylphosphates, mixed alkyl aryl phosphates, perhaloalkylsulfonates, betylates, perchlorate, mesylate, and pharmaceutically acceptable salts as disclosed herein;

or a pharmaceutically-acceptable salt thereof.

In another embodiment, the compounds correspond to Formula I wherein m=0 to 5; n=1 to 5; m+n=1 to 6; A=aryl or heteroaryl; Q=aryl or heteroaryl; and a terminal carbon atom of the CH($R_3$) moiety is directly connected by a covalent bond to the nitrogen when m=0. Compounds of Formula I wherein m=0 to 5; n=1 to 5; m+n=1 to 6; A=aryl or heteroaryl; and Q=aryl or heteroaryl have the CH($R_3$) moiety directly connected by a covalent bond to the nitrogen when m=0 and correspond to Formula V-H (also referred to herein as generic heteroaryl tertiary omegaheteroalkylamines):

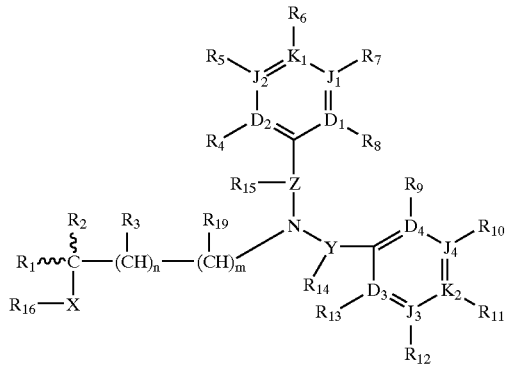

(V-H)

wherein $R_1$ is haloalkyl, haloalkenyl, haloalkoxyalkyl, or haloalkenyloxyalkyl;

wherein X is oxy;

wherein $R_{16}$ is selected from:

(a) hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocyanoalkyl, dicyanoalkyl, carboalkoxycyanoalkyl, acyl, aroyl, heteroaroyl, heteroaryloxyalkyl, dialkoxyphosphonoalkyl;

(b) or a spacer group selected from a covalent bond or a linear moiety having a chain length of 1 to 4 atoms linked to the point of bonding of $R_4$, $R_8$, $R_9$, $R_{13}$, $R_{14}$, or $R_{15}$ to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein one or more spacer groups selected from a covalent bond or a linear moiety having a chain length of 1 to 6 atoms is present between any two points of bonding of any two of $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, or $R_{19}$;

wherein $D_1$, $D_2$, $J_1$, $J_2$ and $K_1$ are independently selected from C, N, O, S and a covalent bond provided that:

(a) no more than one can be a covalent bond, (b) only one of $D_1$, $D_2$, $J_1$, $J_2$ and $K_1$ can be O, (c) only one of $D_1$, $D_2$, $J_1$, $J_2$ and $K_1$ can be S, (d) only two of $D_1$, $D_2$, $J_1$, $J_2$ and $K_1$ can be O and S, (e) when two of $D_1$, $D_2$, $J_1$, $J_2$ and $K_1$ are O or S, one of $D_1$, $D_2$, $J_1$, $J_2$ and $K_1$ must be a covalent bond, (f) only four of $D_1$, $D_2$, $J_1$, $J_2$ and $K_1$ can be N, (g) one of $D_1$, $D_2$, $J_1$, $J_2$ and $K_1$ must be N, O, or S unless one of $D_3$, $D_4$, $J_3$, $J_4$ and $K_2$ is N, O, or S;

wherein $D_3$, $D_4$, $J_3$, $J_4$ and $K_2$ are independently selected from C, N, O, S and a covalent bond provided that:

(a) no more than one can be a covalent bond, (b) only one of $D_3$, $D_4$, $J_3$, $J_4$ and $K_2$ can be O, (c) only one of $D_3$, $D_4$, $J_3$, $J_4$ and $K_2$ can be S, (d) only two of $D_3$, $D_4$, $J_3$, $J_4$ and $K_2$ can be O and S, (e) when two of $D_3$, $D_4$, $J_3$, $J_4$ and $K_2$ are O or S, one of $D_3$, $D_4$, $J_3$, $J_4$ and $K_2$ must be a covalent bond, (f) only four of $D_3$, $D_4$, $J_3$, $J_4$ and $K_2$ can be N, (g) one of $D_3$, $D_4$, $J_3$, $J_4$ and $K_2$ must be N, O, or S unless one of $D_1$, $D_2$, $J_1$, $J_2$ and $K_1$ is N, O, or S;

wherein $R_2$ is independently selected from:

(a) hydrido, hydroxy, hydroxyalkyl, amino, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_2+R_3$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_2+R_{14}$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_2+R_{15}$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_2+R_4$ represents a spacer group selected from a covalent bond or a linear moiety having a chain length of 1 to 4 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_2+R_8$ represents a spacer group selected from a covalent bond or a linear moiety having a chain length of 1 to 4 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_2+R_9$ represents a spacer group selected from a covalent bond or a linear moiety having a chain length of 1 to 4 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_2+R_{13}$ represents a spacer group selected from a covalent bond or a linear moiety having a chain length of 1 to 4 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein $R_3$ is selected from:

(a) hydrido, hydroxy, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_3+R_2$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_3+R_{14}$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_3+R_{15}$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_3+R_4$ represents a spacer group selected from a covalent bond or a linear moiety having a chain length of 1 to 6 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_3+R_8$ represents a spacer group selected from a covalent bond or a linear moiety having a chain length of 1 to 6 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_3+R_9$ represents a spacer group selected from a covalent bond or a linear moiety having a chain length of 1 to 6 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_3+R_{13}$ represents a spacer group selected from a covalent bond or a linear moiety having a chain length of 1 to 6 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(i) or $R_3+R_{19}$ represents a spacer group selected from a covalent bond or a linear moiety having a chain length of 1 to 5 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups, wherein Y is a $(-C(R_{14})_y-)_n$ where n=1 to 4 and y=0 to 2 or $(-CH(R_{14})_y-)_n-W-(-CH(R_{14})_y-)_n$ where n=1 to 2 and y=0 to 1 and $R_{14}$ is independently selected from:

(a) hydrido, hydroxy, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{14}+R_2$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{14}+R_3$ represents a spacer group selected from a covalent bond or a moiety having, a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{14}+R_{15}$ represents a spacer group selected from a moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{14}$ represents a spacer group selected from a moiety having a chain length of 3 to 6 atoms connected to the point of bonding of $R_9$ or $R_{13}$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{14}$ represents a spacer group selected from a moiety having a chain length of 2 to 5 atoms connected to the point of bonding of $R_4$ or $R_8$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_{14}+R_{14}$ represents a covalent bond, an alkylene, a haloalkylene, alkylenedioxy, haloalkylenedioxy, or a spacer group selected from a moiety having a chain length of 2 to 5 atoms connected to form a C5 to C8 saturated cycloalkyl, a C5 to C8 partially saturated cycloalkyl, a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_{14}+R_{14}$ represents, when bonded to the same atom, an oxo, an alkylene, a haloalkylene, alkylenedioxy, haloalkylenedioxy, or a spacer group selected from a moiety having a chain length of 3 to 7 atoms connected to form a C4 to C8 saturated cycloalkyl, a C4 to C8 partially saturated cycloalkyl, a C4 to C8 saturated heterocyclyl or a C4 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein W is selected from —O—, —S—, —S(O)—, —S(O)$_2$—, —S(O)$_2$(NH)—, —NH—, —N(OH)—, —N(NH$_2$)—, —N(NHCH$_3$)—, —N(alkyl)-, —N(alkoxy)-, —N(aryloxy)-, —N(heteroaryloxy)-, —N(acyloxy)-, —N(aroyloxy)-, —N(cycloalkyl), —N(aralkoxy)-, and —N(aryl)-;

wherein Z is independently selected from a covalent bond, (—C(R$_{15}$)$_y$—)$_n$ wherein n=1 to 4 and y=0 to 2, (—CH(R$_{15}$)$_y$—)$_n$—W—(—CH(R$_{15}$)$_y$—)$_n$ wherein n=1 to 2 and y=0 to 2, —N—, —N(OH)—, —N(alkyl)-, —N(alkoxy)-, —N(aryloxy)-, —N(aralkoxy), —N(cycloalkyl)-, —N(aryl)-, oxygen radical (—O—), —OCH$_2$—, or —OCH(R$_{15}$)$_y$— where y=0 to 1;

wherein, when Z is (—C(R$_{15}$)$_y$—)$_n$ where n=1 to 4 and y=0 to 2 or (—CH(R$_{15}$)$_y$—)$_n$—W—(—CH(R$_{15}$)$_y$—)$_n$ wherein n=1 to 2 and y=0 to 2, R$_{15}$ is independently selected from:

(a) hydrido, hydroxy, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{15}+R_2$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{14}+R_{15}$ represents a spacer group selected from a moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}$ represents a spacer group selected from a moiety having a chain length of 3 to 6 atoms connected to the point of bonding of $R_4$ or $R_8$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{15}$ represents a spacer group selected from a moiety having a chain length of 2 to 5 atoms connected to the point of bonding of $R_9$ or $R_{13}$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_{15}+R_{15}$ represents a covalent bond, an alkylene, a haloalkylene, alkylenedioxy, haloalkylenedioxy, or a spacer group selected from a moiety having a chain length of 2 to 5 atoms connected to form a C5 to C8 saturated cycloalkyl, a C5 to C8 partially saturated cycloalkyl, a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_{15}+R_{15}$ represents, when bonded to the same atom, an oxo, an alkylene, a haloalkylene, alkylenedioxy, haloalkylenedioxy, or a spacer group selected from a moiety having a chain length of 3 to 7 atoms connected to form a C4 to C8 saturated cycloalkyl, a C4 to C8 partially saturated cycloalkyl, a C4 to C8 saturated heterocyclyl or a C4 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is N, $R_{15}$ is independently selected from:

(a) hydrido, hydroxyalkyl, aryloxy, aminoalkyl, alkylaminoalkyl, dialkylaminoalkyl, acyl, aroyl, heteroaroyl, heteroaryloxyalkyl, acylamido, alkyl, alkenyl, alkynyl, aryl, aralkyl, aryloxyalkyl, aralkoxyalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, heteroaryl, heteroarylalkyl, heteroarylthioalkyl, aralkylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl;

(b) or $R_{15}+R_2$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{15}+R_{14}$ represents a spacer group selected from a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}$ represents a spacer group selected from a linear moiety having a chain length of 3 to 6 atoms connected to the point of bonding of $R_4$ or $R_8$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{15}$ represents a spacer group selected from a linear moiety having a chain length of 2 to 5 atoms connected to the point of bonding of $R_9$ or $R_{13}$ form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is $(-CH(R_{15})_y-)_n-W-(-CH(R_{15})_y-)_n$ wherein n=1 to 2 and y=0 to 2 or $-OCH(R_{15})_y-$ wherein y=0 to 1, $R_{15}$ is independently selected from:

(a) aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl;

(b) or $R_{15}+R_2$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{15}+R_{14}$ represents a spacer group selected from a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}$ represents a spacer group selected from a linear moiety having a chain length of 3 to 6 atoms connected to the point of bonding of $R_4$ or $R_8$ to form a C5 to C8 saturated heterocyclyl or a C5 to C8 partially saturated heterocyclyl substituted independently and optionally with, for ex ample, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{15}$ represents a spacer group selected from a linear moiety having a chain length of 2 to 5 atoms connected to the point of bonding of $R_9$ or $R_{13}$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is a covalent bond, —N(OH)—, —N(alkyl)-, —N(alkoxy)-, —N(aryloxy)-, —N(cycloalkyl)-, —N(aryl)-, —N(aralkoxy)-, oxygen radical (—O—), or —OCH$_2$—, an $R_{15}$ substituent is not attached to Z;

wherein $R_4$, $R_5$, $R_6$, $R_7$, $R_8$, $R_9$, $R_{10}$, $R_{11}$, $R_{12}$ and $R_{13}$ are independently selected from hydrido, heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, aralkylamino, alkylthio, alkylthioalkyl, arylamino, arylthio, alkylsulfinyl, alkylsulfonyl, arylsulfinyl, arylsulfonyl, heteroarylthio, heteroarylsulfinyl, heteroarylsulfonyl, hydroxyhaloalkyl, halolakanoyl, heteroarylthio, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, alkanoyl, alkenoyl, aroyl, heteroaroyl, alkyl, alkenyl, alkynyl, cycloalkyl, cycloalkenyl, cycloalkylalkyl, cycloalkenylalkyl, halo, haloalkyl, haloalkoxy, haloalkoxyalkyl, aryl, aralkyl, aryloxy, aralkoxy, aryloxyalkyl, saturated heterocyclyl, partially saturated heterocyclyl, heteroaryl, heteroarylamino, heteroarylalkylamino, heteroaryloxy, heteroarylalkyl, heteroaryloxyalkyl, arylalkenyl, heteroarylalkenyl, carboalkoxy, carboaryloxy, carboaralkoxy, cyano, and carbohaloalkoxy;

wherein $R_4+R_5$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_5+R_6$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_6+R_7$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_7+R_8$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_9+R_{10}$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{10}+R_{11}$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{11}+R_{12}$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{12}+R_{13}$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_{14}$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_{14}$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_{15}$ represents a spacer group selected from a covalent bond or a linear moiety having a chain length of 2 to 5 atoms to form a C5 to C8 cycloalkenyl, a C6 to C8 partially saturated heterocyclyl, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_{15}$ represents a spacer group selected from a covalent bond or a linear moiety having a chain length of 2 to 5 atoms to form a C5 to C8 cycloalkenyl, a C6 to C8 partially saturated heterocyclyl, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_9+R_{15}$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{13}+R_{15}$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_9+R_{14}$ represents a spacer group selected from a covalent bond or a linear moiety having a chain length of 2 to 5 atoms to form a C5 to C8 cycloalkenyl, a C6 to C8 partially saturated heterocyclyl, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{13}+R_{14}$ represents a spacer group selected from a covalent bond or a linear moiety having a chain length of 2 to 5 atoms to form a C5 to C8 cycloalkenyl, a C6 to C8 partially saturated heterocyclyl, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_2$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_3$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_2$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_3$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_9+R_2$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_9+R_3$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{13}+R_2$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{13}+R_3$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_9$ represents a spacer group to form a C5 to C8 partially saturated heterocyclyl ring or a C5 to C6 heteroaryl substituted independently and optionally with, for example, one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_{13}$ represents a spacer group to form a C5 to C8 partially saturated heterocyclyl ring or a C5 to C6 heteroaryl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_9$ represents a spacer group to form a C5 to C8 partially saturated heterocyclyl ring or a C5 to C6 heteroaryl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_{13}$ represents a spacer group to form a C5 to C8 partially saturated heterocyclyl ring or a C5 to C6 heteroaryl substituted independently and optionally with, for example, one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

provided that there are no more than three non-hydrido ring substituents $R_4$, $R_5$, $R_6$, $R_7$, and $R_8$, that there are no more than three non-hydrido ring substituents $R_9$, $R_{10}$, $R_{11}$, $R_{12}$, and $R_{13}$, and $R_4$, $R_5$, $R_6$, $R_7$, $R_8$, $R_9$, $R_{10}$, $R_{11}$, $R_{12}$, and $R_{13}$ are each independently selected to maintain the tetravalent nature of carbon, trivalent nature of nitrogen, the divalent nature of sulfur, and the divalent nature of oxygen;

wherein $R_{19}$ is selected from:

(a) hydrido, hydroxyalkyl, acyl, sulfhydryl, acylamido, alkoxy, alkylthio, arylthio, alkyl, alkenyl, alkynyl, aryl, aralkyl, aryloxyalkyl, aralkanoyl, heteroarylthio, aralkylthio, aroyl, heteroaroyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{19}+R_2$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{19}+R_3$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{19}+R_{14}$ represents a spacer group selected from a covalent bond or a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{19}+R_{15}$ represents a spacer group selected from a covalent bond or a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_{19}$ represents a spacer group selected from a covalent bond or a linear moiety having a chain length of 2 to 5 atoms connected to the point of bonding of $R_4$, $R_8$, $R_9$, or $R_{13}$ to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

or a pharmaceutically-acceptable salt thereof.

Alternatively, compounds of the present invention consist of quaternary ammonium salt compounds of Formula VI-H (also referred to herein as generic heteroaryl tertiary omegaheteroalkylammonium salt):

(VI-H)

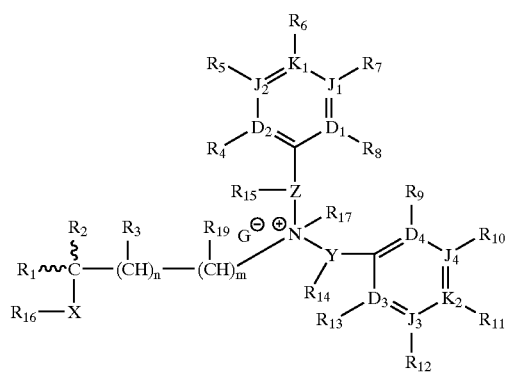

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula V-H;

wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$, $R_{19}+R_2$, $R_{19}+R_3$, $R_{19}+R_{14}$, $R_{19}+R_{15}$ are as defined for the compounds of Formula V-H;

wherein $R_{17}$ is selected from alkyl, alkenyl, alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl;

wherein G is selected from chloro, bromo, iodo, fluoride, trifluoroacetate, perhaloalkylcarboxylates, arylcarboxylates, formate, monoalkylsulfates, arylsulfonates, diarylsulfonylimide anion, benzenesulfonate, tosylate, brosylate, alkylphosphates, arylphosphates, mixed alkyl aryl phosphates, perhaloalkylsulfonates, betylates, perchlorate, mesylate, and pharmaceutically acceptable salts as disclosed herein;

or a pharmaceutically-acceptable salt thereof.

In another embodiment, the compounds correspond to Formula V-H wherein m=0 to 5; n=1 to 5; m+n=1 to 6; $D_1$, $D_2$, $D_3$, $D_4$, $J_1$, $J_2$, $J_3$, $J_4$, $K_1$, and $K_2$ are each a carbon atom; and a terminal carbon atom of the $CH(R_3)$ moiety is directly connected by a covalent bond to the nitrogen when m=0. Compounds of Formula V-H wherein m=0 to S, n=1 to 5, m+n=1 to 6, and $D_1$, $D_2$, $D_3$, $D_4$, $J_1$, $J_2$, $J_3$, $J_4$, $K_1$, and $K_2$ are each a carbon atom, have the $CH(R_3)$ moiety directly connected by a covalent bond to the nitrogen when m=0 and correspond to Formula V (also referred to herein as generic phenyl tertiary omegaheteroalkylamines):

(V)

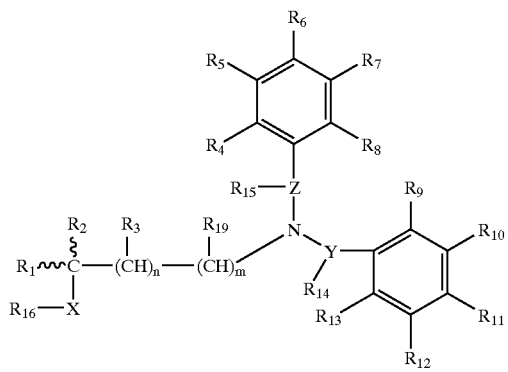

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula V-H;

wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$, $R_{19}+R_2$, $R_{19}+R_3$, $R_{19}+R_{14}$, $R_{19}+R_{15}$ are as defined for the compounds of Formula V-H;

or a pharmaceutically-acceptable salt thereof.

Alternatively, compounds of the present invention consist of quaternary ammonium salt compounds of Formula VI (also referred to herein as generic phenyl tertiary omega-heteroalkylammonium salt):

(VI)

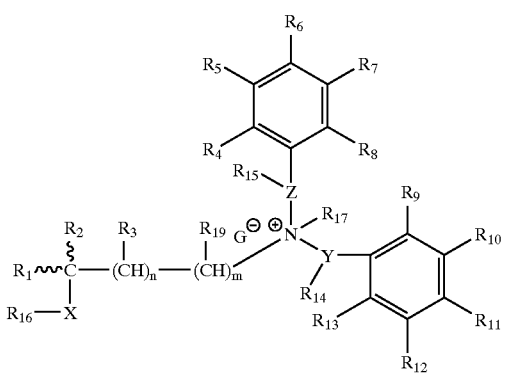

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula V;

wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$, $R_{19}+R_2$, $R_{19}+R_3$, $R_{19}+R_{14}$, $R_{19}+R_{15}$ are as defined for the compounds of Formula V;

wherein $R_{17}$ and G as defined for the compounds of Formula VI-H;

or a pharmaceutically-acceptable salt thereof.

In another embodiment, the compounds correspond to Formula V, wherein m=0, n=1, and a terminal carbon atom of the $CH(R_3)$ moiety is directly connected by a covalent bond to the nitrogen when m=0. Compounds of Formula V, wherein m=0, n=1, and a terminal carbon atom of the $CH(R_3)$ moiety is directly connected by a covalent bond to the nitrogen correspond to Formula VII (also referred to herein as generic phenyl tertiary 2-heteroalkylamines):

(VII)

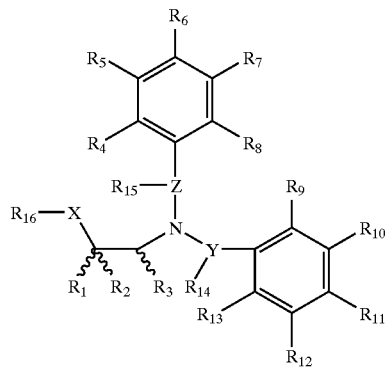

wherein $R_1$, $R_2$, $R_3$, $R_{14}$, $R_{15}$, $R_{16}$, X, Y, and Z are as defined for the compounds of Formula V;

wherein $R_4$, $R_5$, $R_6$, $R_7$, $R_8$, $R_9$, $R_{10}$, $R_{11}$, $R_{12}$, and $R_{13}$ are as defined for Formula V;

wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$ are as defined for the compounds of Formula V;

wherein $R_{19}$, $R_{19}+_{R2}$, $R_{19}+R_3$, $R_{19}+R_{14}$, $R_{19}+R_{15}$, $R_{19}+R_2$, $R_{19}+R_3$, $R_{19}+R_{14}$, $R_{19}+R_{15}$ substitutents are absent;

or a pharmaceutically-acceptable salt thereof.

Alternatively, compounds of the present invention consist of quaternary ammonium salt compounds of Formula VIII (also referred to herein as generic phenyl tertiary 2-heteroalkylammonium salt):

(VIII)

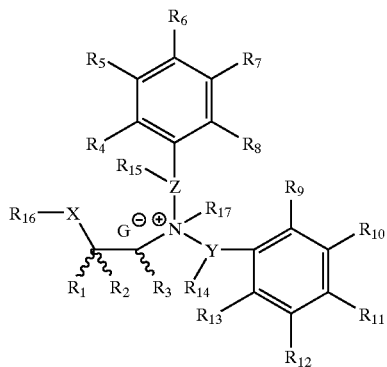

wherein $R_1$, $R_2$, $R_3$, $R_{14}$, $R_{15}$, $R_{16}$, X, Y, and Z are as defined for the compounds of Formula VII;

wherein $R_4$, $R_5$, $R_6$, $R_7$, $R_8$, $R_9$, $R_{10}$, $R_{11}$, $R_{12}$, and $R_{13}$ are as defined for Formula VII;

wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$ are as defined for the compounds of Formula VII;

wherein $R_{17}$ and G as defined for the compounds of Formula VI;

or a pharmaceutically-acceptable salt thereof.

In another embodiment, the compounds correspond to Formula V-H wherein m=0 to 5; n=1 to 5; m+n=1 to 6; A=aryl or heteroaryl; Q=aryl or heteroaryl; wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$ spacers are absent; and a terminal carbon atom of the $CH(R_3)$ moiety is directly connected by a covalent bond to the nitrogen when m=0. Compounds of Formula V-H wherein m=0 to 5; n=1 to 5; m+n=1 to 6; A=aryl or heteroaryl; and Q=aryl or heteroaryl; wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$ spacers are absent; have the $CH(R_3)$ moiety directly connected by a covalent bond to the nitrogen when m=0 and correspond to Formula V-HA (also referred to herein as generic heteroaryl tertiary omegaheteroalkylamines):

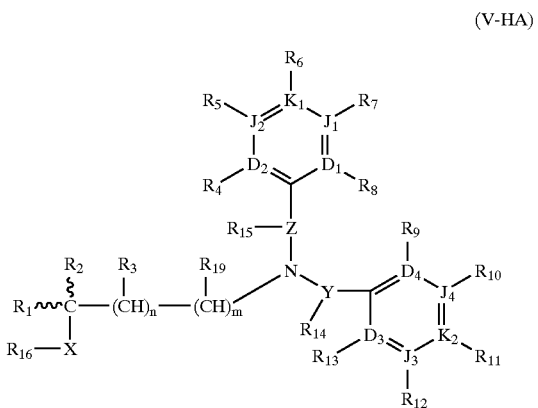

(V-HA)

wherein $R_1$ is haloalkyl, haloalkenyl, haloalkoxyalkyl, or haloalkenyloxyalkyl;

wherein X is oxy;

wherein $R_{16}$ is selected from hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocyanoalkyl, dicyanoalkyl, carboalkoxycyanoalkyl, acyl, aroyl, heteroaroyl, heteroaryloxyalkyl, or dialkoxyphosphonoalkyl;

wherein $D_1$, $D_2$, $J_1$, $J_2$ and $K_1$ are independently selected from C, N, O, S and a covalent bond provided that:

(a) no more than one can be a covalent bond, (b) only one of $D_1$, $D_2$, $J_1$, $J_2$ and $K_1$ can be O, (c) only one of $D_1$, $D_2$, $J_1$, $J_2$ and $K_1$ can be S, (d) only two of $D_1$, $D_2$, $J_1$, $J_2$ and $K_1$ can be O and S, (e) when two of $D_1$, $D_2$, $J_1$, $J_2$ and $K_1$ are O or S, one of $D_1$, $D_2$, $J_1$, $J_2$ and $K_1$ must be a covalent, (f) only four of $D_1$, $D_2$, $J_1$, $J_2$ and $K_1$ can be N, (g) one of $D_1$, $D_2$, $J_1$, $J_2$ and $K_1$ must be N, O, or S unless one of $D_3$, $D_4$, $J_3$, $J_4$ and $K_2$ is N, O, or S;

wherein $D_3$, $D_4$, $J_3$, $J_4$ and $K_2$ are independently selected from C, N, O, S and a covalent bond provided that:

(a) no more than one can be a covalent bond, (b) only one of $D_3$, $D_4$, $J_3$, $J_4$ and $K_2$ can be O, (c) only one of $D_3$, $D_4$, $J_3$, $J_4$ and $K_2$ can be S, (d) only two of $D_3$, $D_4$, $J_3$, $J_4$ and $K_2$ can be O and S, (e) when two of $D_3$, $D_4$, $J_3$, $J_4$ and $K_2$ are O or S, one of $D_3$, $D_4$, $J_3$, $J_4$ and $K_2$ must be a covalent bond, (f) only four of $D_3$, $D_4$, $J_3$, $J_4$ and $K_2$ can be N, (g) one of $D_3$, $D_4$, $J_3$, $J_4$ and $K_2$ must be N, O, or S unless one of $D_1$, $D_2$, $J_1$, $J_2$ and $K_1$ is N, O, or S;

wherein $R_2$ is independently selected from:

(a) hydrido, hydroxy, hydroxyalkyl, amino, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_2+R_3$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_2+R_{14}$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_2+R_{15}$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein $R_3$ is selected from:

(a) hydrido, hydroxy, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_3+R_2$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_3+R_{14}$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_3+R_{15}$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_3+R_{19}$ represents a spacer group selected from a covalent bond or a linear moiety having a chain length of 1 to 5 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein Y is a $(-C(R_{14})_y-)_n$ where n=1 to 4 and y=0 to 2 or $(-CH(R_{14})_y-)_n-W-(-CH(R_{14})_y-)_n$ where n=1 to 2 and y=0 to 1 and $R_{14}$ is independently selected from:

(a) hydrido, hydroxy, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{14}+R_2$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{14}+R_3$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{14}+R_{15}$ represents a spacer group selected from a moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{14}+R_{14}$ represents a covalent bond, an alkylene, a haloalkylene, alkylenedioxy, haloalkylenedioxy, or a spacer group selected from a moiety having a chain length of 2 to 5 atoms connected to form a C5 to C8 saturated cycloalkyl, a C5 to C8 partially saturated cycloalkyl, a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{14}+R_{14}$ represents, when bonded to the same atom, an oxo, an alkylene, a haloalkylene, alkylenedioxy, haloalkylenedioxy, or a spacer group selected from a moiety having a chain length of 3 to 7 atoms connected to form a C4 to C8 saturated cycloalkyl, a C4 to C8 partially saturated cycloalkyl, a C4 to C8 saturated heterocyclyl or a C4 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein W is selected from —O—, —S—, —S(O)—, —S(O)2—, —S(O)$_2$(NH)—, —NH—, —N(OH)—, —N(NH$_2$)—, —N(NHCH$_3$)—, —N(alkyl)-, —N(alkoxy)-, —N(aryloxy)-, —N(heteroaryloxy)-, —N(acyloxy)-, —N(aroyloxy)-, —N(cycloalkyl), —N(aralkoxy)-, and —N(aryl)-;

wherein Z is independently selected from a covalent bond, $(-C(R_{15})_y-)_n$ wherein n=1 to 4 and y=0 to 2, $(-CH(R_{15})_y-)_n-W-(-CH(R_{15})_y-)_n$ wherein n=1 to 2 and y=0 to 2, —N—, —N(OH)—, —N(alkyl)-, —N(alkoxy)-, —N(aryloxy)-, —N(aralkoxy), —N(cycloalkyl)-, —N(aryl)-, oxygen radical (—O—), —OCH$_2$—, or —OCH(R$_{15}$)$_y$— where y=0 to 1;

wherein, when Z is $(-C(R_{15})_y-)_n$ where n=1 to 4 and y=0 to 2 or $(-CH(R_{15})_y-)_n-W-(-CH(R_{15})_y-)_n$ wherein n=1 to 2 and y=0 to 2, $R_{15}$ is independently selected from:

(a) hydrido, hydroxy, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{15}+R_2$, represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{14}+R_{15}$ represents a spacer group selected from a moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}+R_{15}$ represents a covalent bond, an alkylene, a haloalkylene, alkylenedioxy, haloalkylenedioxy, or a spacer group selected from a moiety having a chain length of 2 to 5 atoms connected to form a C5 to C8 saturated cycloalkyl, a C5 to C8 partially saturated cycloalkyl, a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{15}+R_{15}$ represents, when bonded to the same atom, an oxo, an alkylene, a haloalkylene, alkylenedioxy, haloalkylenedioxy, or a spacer group selected from a moiety having a chain length of 3 to 7 atoms connected to form a C4 to C8 saturated cycloalkyl, a C4 to C8 partially saturated cycloalkyl, a C4 to C8 saturated heterocyclyl or a C4 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is N, $R_{15}$ is independently selected from:

(a) hydrido, hydroxyalkyl, aryloxy, aminoalkyl, alkylaminoalkyl, dialkylaminoalkyl, acyl, aroyl, heteroaroyl, heteroaryloxyalkyl, acylamido, alkyl, alkenyl, alkynyl, aryl, aralkyl, aryloxyalkyl, aralkoxyalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, aralkylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl;

(b) or $R_{15}+R_2$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{15}+R_{14}$ represents a spacer group selected from a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is $(-CH(R_{15})_y-)_n-W-(-CH(R_{15})_y-)_n$ wherein n=1 to 2 and y=0 to 2 or $-OCH(R_{15})_y-$ wherein y=0 to 1, $R_{15}$ is independently selected from:

(a) aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl;

(b) or $R_{15}+R_2$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{15}+R_{14}$ represents a spacer group selected from a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is a covalent bond, —N(OH)—, —N(alkyl)-, —N(alkoxy)-, —N(aryloxy)-, —N(cycloalkyl)-, —N(aryl)-, —N(aralkoxy)-, oxygen radical (—O—), or —OCH$_2$—, an $R_{15}$ substituent is not attached to Z;

wherein $R_4$, $R_5$, $R_6$, $R_7$, $R_8$, $R_9$, $R_{10}$, $R_{11}$, $R_{12}$, and $R_{13}$ are independently selected from hydrido, heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, aralkylamino, alkylthio, alkylthioalkyl, arylamino, arylaminoalkyl, arylsulfonyl, arylsulfinyl, heteroarylthio, heteroarylsulfinyl, heteroarylsulfonyl, hydroxyhaloalkyl, haloalkanoyl, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, alkanoyl, alkenoyl, aroyl, heteroaroyl, alkyl, alkenyl, alkynyl, cycloalkyl, cycloalkenyl, cycloalkylalkyl, cycloalkenylalkyl, halo, haloalkyl, haloalkoxy, haloalkoxyalkyl, aryl, aralkyl, aryloxy, aralkoxy, aryloxyalkyl, saturated heterocyclyl, partially saturated heterocyclyl, heteroaryl, heteroarylamino, heteroarylalkyl amino, heteroaryloxy, heteroarylalkyl, heteroaryloxyalkyl, arylalkenyl, heteroarylalkenyl, carboalkoxy, carboaryloxy, carboaralkoxy, cyano, and carbohaloalkoxy;

provided that there are no more than three non-hydrido ring substituents $R_4$, $R_5$, $R_6$, $R_7$, and $R_8$, that there are no more than three non-hydrido ring substituents $R_9$, $R_{10}$, $R_{11}$, $R_{12}$, and $R_{13}$, and $R_4$, $R_5$, $R_6$, $R_7$, $R_8$, $R_9$, $R_{10}$, $R_{11}$, $R_{12}$, and $R_{13}$ are each independently selected to maintain the tetravalent nature of carbon, trivalent nature of nitrogen, the divalent nature of sulfur, and the divalent nature of oxygen;

wherein $R_{19}$ is selected from:

(a) hydrido, carboxyl, hydroxyalkyl, acyl, sulfhydryl, acylamido, alkoxy, alkylthio, arylthio, alkyl, alkenyl, alkynyl, aryl, aralkyl, aryloxyalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylthio, aralkylthio, aroyl, aralkanoyl, heteroaroyl, aralkoxyalkyl, alkylsulfinylalkyl, alkylsulfonylalkyl, aralkylthioalkyl, heteroaralkylthioalkyl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{19}+R_2$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{19}+R_3$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{19}+R_{14}$ represents a spacer group selected from a covalent bond or a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{19}+R_{15}$ represents a spacer group selected from a covalent bond or a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

or a pharmaceutically-acceptable salt thereof.

Alternatively, compounds of the present invention consist of quaternary ammonium salt compounds of Formula VI-HA (also referred to herein as generic heteroaryl tertiary omegaheteroalkylammonium salt):

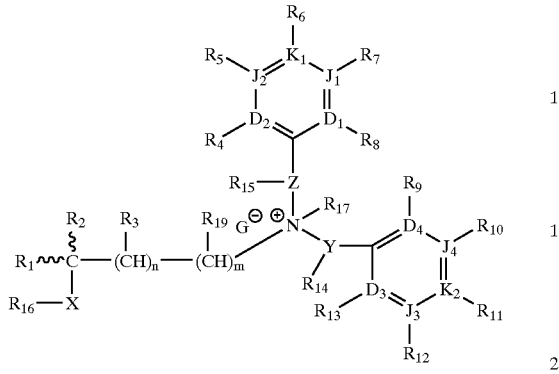

(VI-HA)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula V-HA;

wherein $R_{17}$ is selected from alkyl, alkenyl, alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylkyl, heteroaryloxyalkyl, heteroarylthioalkyl, and heteroarylalkenyl;

wherein G is selected from chloro, bromo, iodo, fluoride, trifluoroacetate, perhaloalkylcarboxylates, arylcarboxylates, formate, monoalkylsulfates, arylsulfonates, diarylsulfonylimide anion, benzenesulfonate, tosylate, brosylate, alkylphosphates, arylphosphates, mixed alkyl aryl phosphates, perhaloalkylsulfonates, betylates, perchlorate, mesylate, and pharmaceutically acceptable salts as disclosed herein;

or a pharmaceutically-acceptable salt thereof.

In another embodiment, the compounds correspond to Formula V-HA wherein m=0 to 5; n=1 to 5; m+n=1 to 6; $D_1$, $D_2$, $D_3$, $D_4$, $J_1$, $J_2$, $J_3$, $J_4$, $K_1$, and $K_2$ are each a carbon atom; and a terminal carbon atom of the CH($R_3$) moiety is directly connected by a covalent bond to the nitrogen when m=0. Compounds of Formula V-HA wherein m=0 to 5, n=1 to 5, m+n=1 to 6, and $D_1$, $D_2$, $D_3$, $D_4$, $J_1$, $J_2$, $J_3$, $J_4$, $K_1$, and $K_2$ are each a carbon atom, have the CH($R_3$) moiety directly connected by a covalent bond to the nitrogen when m=0 and correspond to Formula VA (also referred to herein as generic phenyl tertiary omegaheteroalkylamines):

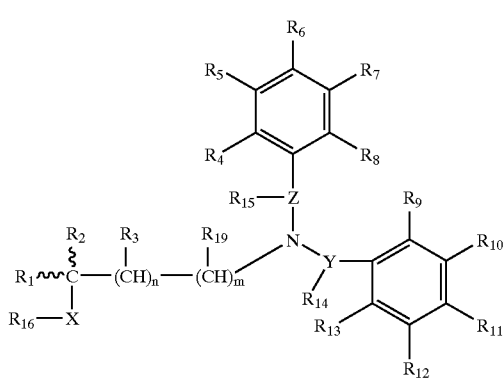

(VA)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula V-HA;

or a pharmaceutically-acceptable salt thereof.

Alternatively, compounds of the present invention consist of quaternary ammonium salt compounds of Formula VIA (also referred to herein as generic phenyl tertiary omega-heteroalkylammonium salt):

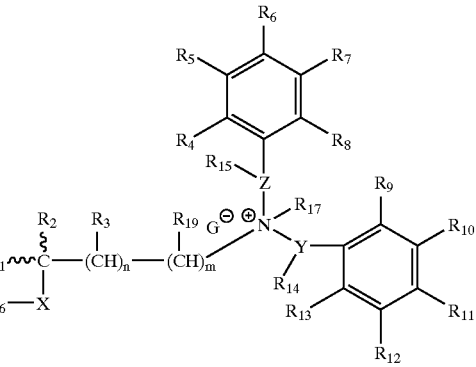

(VIA)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula VA;

wherein $R_{17}$ and G as defined for the compounds of Formula VI-HA;

or a pharmaceutically-acceptable salt thereof.

In another embodiment, the compounds correspond to Formula VA, wherein m=0, n=1, and a terminal carbon atom of the CH($R_3$) moiety is directly connected by a covalent bond to the nitrogen when m=0. Compounds of Formula VA, wherein m=0, n=1, and a terminal carbon atom of the CH($R_3$) moiety is directly connected by a covalent bond to the nitrogen correspond to Formula VIIA (also referred to herein as generic phenyl tertiary 2-heteroalkylamines):

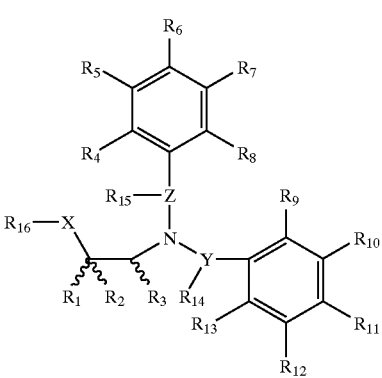

(VIIA)

wherein $R_1$, $R_2$, $R_3$, $R_{14}$, $R_{15}$, $R_{16}$, X, Y, and Z are as defined for the compounds of Formula VA;

wherein $R_4$, $R_5$, $R_6$, $R_7$, $R_8$, $R_9$, $R_{10}$, $R_{11}$, $R_{12}$, and $R_{13}$ are as defined for Formula VA;

wherein $R_{19}$, $R_{19}+R_2$, $R_{19}+R_3$, $R_{19}+R_{14}$, $R_{19}+R_{15}$, $R_{19}+R_2$, $R_{19}+R_3$, $R_{19}+R_{14}$, $R_{19}+R_{15}$ substitutents are absent;

or a pharmaceutically-acceptable salt thereof.

Alternatively, compounds of the present invention consist of quaternary ammonium salt compounds of Formula VIIIA (also referred to herein as generic phenyl tertiary 2-heteroalkylammonium salt):

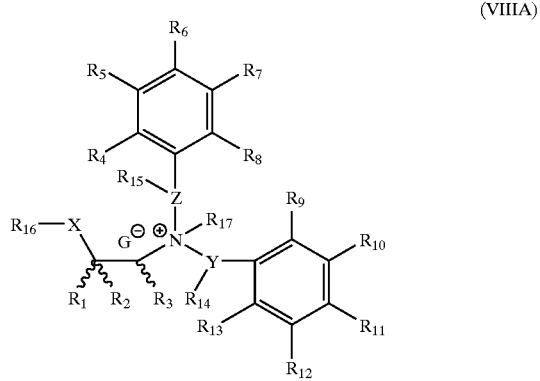

(VIIIA)

wherein $R_1$, $R_2$, $R_3$, $R_{14}$, $R_{15}$, $R_{16}$, X, Y, and Z are as defined for the compounds of Formula VIIA;

wherein $R_4$, $R_5$, $R_6$, $R_7$, $R_8$, $R_9$, $R_{10}$, $R_{11}$, $R_{12}$, and $R_{13}$ are as defined for Formula VIIA;

wherein $R_{17}$ and G as defined for the compounds of Formula VIA;

or a pharmaceutically-acceptable salt thereof.

In another embodiment, the compounds correspond to Formula I wherein m=0 to 5; n=1 to 5; m+n=1 to 6; A=aryl or heteroaryl; Q=aryl or heteroaryl; and a terminal carbon atom of the $CH(R_3)$ moiety is directly connected by a covalent bond to the nitrogen when m=0. Compounds of Formula I wherein m=0 to 5; n=1 to 5; m+n=1 to 6; A=aryl or heteroaryl; and Q=aryl or heteroaryl have the $CH(R_3)$ moiety directly connected by a covalent bond to the nitrogen when m=0 and correspond to Formula V-HX (also referred to herein as generic heteroaryl tertiary omegaheteroalkylamines):

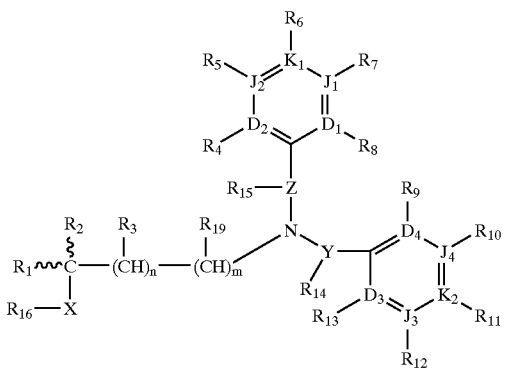

(V-HX)

wherein $R_1$ is haloalkyl, haloalkenyl, haloalkoxyalkyl, or haloalkenyloxyalkyl;

wherein X is selected from H, F, —S—, —S(O)—, —S(O)$_2$—, —S(O)$_2$(NH)—, —NH—, —N(OH)—, —N(NH$_2$)—, —N(NHCH$_3$)—, —N(alkyl)-, or —N(alkoxy)-;

wherein $R_{16}$ is selected from:

(a) hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, mononocyanoalkyl, dicyanoalkyl, carboalkoxycyanoalkyl, acyl, aroyl, heteroaroyl, heteroaryloxyalkyl, dialkoxyphosphonoalkyl;

(b) or a spacer group selected from a covalent bond or a linear moiety having a chain length of 1 to 4 atoms linked to the point of bonding of $R_4$, $R_8$, $R_9$, $R_{13}$, $R_{14}$, or $R_{15}$ to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or absent when X is H or F;

wherein one or more spacer groups selected from a covalent bond or a linear moiety having a chain length of 1 to 6 atoms is present between any two points of bonding of any two of $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, or $R_{19}$;

wherein $D_1$, $D_2$, $J_1$, $J_2$ and $K_1$ are independently selected from C, N, O, S and a covalent bond provided that:

(a) no more than one can be a covalent bond, (b) only one of $D_1$, $D_2$, $J_1$, $J_2$ and $K_1$, can be O, (c) only one of $D_1$, $D_2$, $J_1$, $J_2$ and $K_1$, can be S, (d) only two of $D_1$, $D_2$, $J_1$, $J_2$ and $K_1$ can be O and S, (e) when two of $D_1$, $D_2$, $J_1$, $J_2$ and $K_1$ are O or S, one of $D_1$, $D_2$, $J_1$, $J_2$ and $K_1$, must be a covalent bond, (f) only four of $D_1$, $D_2$, $J_1$, $J_2$ and $K_1$ can be N, (g) one of $D_1$, $D_2$, $J_1$, $J_2$ and $K_1$ must be N, O, or S unless one of $D_3$, $D_4$, $J_3$, $J_4$ and $K_2$ is N, O, or S;

wherein $D_3$, $D_4$, $J_3$, $J_4$ and $K_2$ are independently selected from C, N, O, S and a covalent bond provided that:

(a) no more than one can be a covalent bond, (b) only one of $D_3$, $D_4$, $J_3$, $J_4$ and $K_2$, can be O, (c) only one of $D_3$, $D_4$, $J_3$, $J_4$ and $K_2$, can be S, (d) only two of $D_3$, $D_4$, $J_3$, $J_4$ and $K_2$ can be O and S, (e) when two of $D_3$, $D_4$, $J_3$, $J_4$ and $K_2$ are O or S, one of $D_3$, $D_4$, $J_3$, $J_4$ and $K_2$, must be a covalent bond, (f) only four of $D_3$, $D_4$, $J_3$, $J_4$ and $K_2$ can be N, (g) one of $D_3$, $D_4$, $J_3$, $J_4$ and $K_2$ must be N, O, or S unless one of $D_1$, $D_2$, $J_1$, $J_2$ and $K_1$ is N, O, or S;

wherein $R_2$ is independently selected from:

(a) hydrido, hydroxy, hydroxyalkyl, amino, alkylamino, dialkylamino, alkyl alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_2+R_3$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_2+R_{14}$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_2+R_{15}$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_2+R_4$ represents a spacer group selected from a covalent bond or a linear moiety having a chain length of 1 to 4 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_2+R_8$ represents a spacer group selected from a covalent bond or a linear moiety having a chain length of 1 to 4 atoms to form a C5 to C 10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_2+R_9$ represents a spacer group selected from a covalent bond or a linear moiety having a chain length of 1 to 4 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_2+R_{13}$ represents a spacer group selected from a covalent bond or a linear moiety having a chain length of 1 to 4 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein $R_3$ is selected from:

(a) hydrido, hydroxy, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_3+R_2$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_3+R_{14}$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_3+R_{15}$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_3+R_4$ represents a spacer group selected from a covalent bond or a linear moiety having a chain length of 1 to 6 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_3+R_8$ represents a spacer group selected from a covalent bond or a linear moiety having a chain length of 1 to 6 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_3+R_9$ represents a spacer group selected from a covalent bond or a linear moiety having a chain length of 1 to 6 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_3+R_{13}$ represents a spacer group selected from a covalent bond or a linear moiety having a chain length of 1 to 6 atoms to form a C5 to C10 saturated heterocyclyl or a C5 to C10 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(i) or $R_3+R_{19}$ represents a spacer group selected from a covalent bond or a linear moiety having a chain length of 1 to 5 atoms to form a C3 to C8 cycloalkyl, a C5 to C8 cycloalkenyl, a C4 to C8 saturated heterocyclyl, or a C8 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein Y is a $(-C(R_{14})_y-)_n$ where n=1 to 4 and y=0 to 2 or $(-CH(R_{14})_y-)_n-W-(-CH(R_{14})_y-)_n$ where n=1 to 2 and y=0 to 1 and $R_{14}$ is independently selected from:

(a) hydrido, hydroxy, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalcyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{14}+R_2$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{14}+R_3$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{14}+R_{15}$ represents a spacer group selected from a moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{14}$ represents a spacer group selected from a moiety having a chain length of 3 to 6 atoms connected to the point of bonding of $R_9$ or $R_{13}$ to form a C5 to C8 saturated heterocyclyl or a C5 to C8 partially saturated heterocyclyl substituted independently and optionally with, for example; one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{14}$ represents a spacer group selected from a moiety having a chain length of 2 to 5 atoms connected to the point of bonding of $R_4$ or $R_8$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_{14}+R_{14}$ represents a covalent bond, an alkylene, a haloalkylene, alkylenedioxy, haloalkylenedioxy, or a spacer group selected from a moiety having a chain length of 2 to 5 atoms connected to form a C5 to C8 saturated cycloalkyl, a C5 to C8 partially saturated cycloalkyl, a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_{14}+R_{14}$ represents, when bonded to the same atom, an oxo, an alkylene, a haloalkylene, alkylenedioxy, haloalkylenedioxy, or a spacer group selected from a moiety having a chain length of 3 to 7 atoms connected to form a C4 to C8 saturated cycloalkyl, a C4 to C8 partially saturated cycloalkyl, a C4 to C8 saturated heterocyclyl or a C4 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein W is selected from —O—, —S—, —S(O)—, —S(O)$_2$—, —S(O)$_2$(NH)—, —NH—, —N(OH)—, —N(NH$_2$)—, —N(NHCH$_3$)—, —N(alkyl)-, —N(alkoxy)-, —N(aryloxy)-, —N(heteroaryloxy)-, —N(acyloxy)-, —N(aroyloxy)-, —N(cycloalkyl), —N(aralkoxy)-, and —N(aryl)-;

wherein Z is independently selected from a covalent bond, $(-C(R_{15})_y-)_n$ wherein n=1 to 4 and y=0 to 2, $(-CH(R_{15})_y-)_n-W-(-CH(R_{15})_y-)_n$ wherein n=1 to 2 and y=0 to 2, —N—, —N(OH)—, —N(alkyl)-, —N(alkoxy), —N(aryloxy)-, —N(aralkoxy), —N(cycloalkyl)-, —N(aryl)-, oxygen radical (—O—), —OCH$_2$—, or —OCH(R$_{15}$)$_y$— where y=0 to 1;

wherein, when Z is $(-C(R_{15})_y-)_n$ where n=1 to 4 and y=0 to 2 or $(-CH(R_{15})_y-)_n-W-(-CH(R_{15})_y-)_n$ wherein n=1 to 2 and y=0 to 2, $R_{15}$ is independently selected from:

(a) hydrido, hydroxy, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{15}+R_2$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{14}+R_{15}$ represents a spacer group selected from a moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}$ represents a spacer group selected from a moiety having a chain length of 3 to 6 atoms connected to the point of bonding of $R_4$ or $R_8$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{15}$ represents a spacer group selected from a moiety having a chain length of 2 to 5 atoms connected to the point of bonding of $R_9$ or $R_{13}$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_{15}+R_{15}$ represents a covalent bond, an alkylene, a haloalkylene, alkylenedioxy, haloalkylenedioxy, or a spacer group selected from a moiety having a chain length of 2 to 5 atoms connected to form a C5 to C8 saturated cycloalkyl, a C5 to C8 partially saturated cycloalkyl, a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_{15}+R_{15}$ represents, when bonded to the same atom, an oxo, an alkylene, a haloalkylene, alkylenedioxy, haloalkylenedioxy, or a spacer group selected from a moiety having a chain length of 3 to 7 atoms connected to form a C4 to C8 saturated cycloalkyl, a C4 to C8 partially saturated cycloalkyl, a C4 to C8 saturated heterocyclyl or a C4 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is N, $R_{15}$ is independently selected from:

(a) hydrido, hydroxyalkyl, aryloxy, aminoalkyl, alkylaminoalkyl, dialkylaminoalkyl, acyl, aroyl, heteroaroyl, heteroaryloxyalkyl, acylamido, alkyl, alkenyl, alkynyl, aryl, aralkyl, aryloxyalkyl, aralkoxyalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, aralkylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, akylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl;

(b) or $R_{15}+R_2$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{15}+R_{14}$ represents a spacer group selected from a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}$ represents a spacer group selected from a linear moiety having a chain length of 3 to 6 atoms connected to the point of bonding of $R_4$ or $R_8$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{15}$ represents a spacer group selected from a linear moiety having a chain length of 2 to 5 atoms connected to the point of bonding of $R_9$ or $R_{13}$ form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is $(-CH(R_{15})_y-)_n-W-(-CH(R_{15})_y-)_n$ wherein n=1 to 2 and y=0 to 2 or $-OCH(R_{15})_y-$ wherein y=0 to 1, $R_{15}$ is independently selected from:

(a) aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl;

(b) or $R_{15}+R_2$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{15}+R_{14}$ represents a spacer group selected from a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}$ represents a spacer group selected from a linear moiety having a chain length of 3 to 6 atoms connected to the point of bonding of $R_4$ or $R_8$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{15}$ represents a spacer group selected from a linear moiety having a chain length of 2 to 5 atoms connected to the point of bonding of $R_9$ or $R_{13}$ to form a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is a covalent bond, —N(OH)—, —N(alkyl)-, —N(alkoxy)-, —N(aryloxy)-, —N(cycloalkyl)-, —N(aryl)-, —N(aralkoxy)-, oxygen radical (—O—), or —OCH$_2$—, an $R_{15}$ substituent is not attached to Z;

wherein $R_4$, $R_5$, $R_6$, $R_7$, $R_8$, $R_9$, $R_{10}$, $R_{11}$, $R_{12}$, and $R_{13}$ are independently selected from hydrido, heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, aralkylamino, alkylthio, alkylthioalkyl, arylamino, arylalkylamino, arylsulfinyl, arylsulfonyl, heteroarylthio, heteroarylsulfinyl, heteroarylsulfonyl, hydroxyhaloalkyl, haloalkanoyl, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, alkanoyl, alkenoyl, aroyl, heteroaroyl, alkyl, alkenyl, alkynyl, cycloalkyl, cycloalkenyl, cycloalkylalkyl, cycloalkenylalkyl, halo, haloalkyl, haloalkoxy, haloalkoxyalkyl, aryl, aralkyl, aryloxy, aralkoxy, aryloxyalkyl, saturated heterocyclyl, partially saturated heterocyclyl, heteroaryl, heteroarylamino, heteroarylalkylamino, heteroaryloxy, heteroarylalkyl, heteroaryloxyalkyl, arylalkenyl, heteroarylalkenyl, carboalkoxy, carboaryloxy, carboaralkoxy, cyano, and carbohaloalkoxy;

wherein $R_4+R_5$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_5+R_6$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_6+R_7$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_7+R_8$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_9+R_{10}$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{10}+R_{11}$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{11}+R_{12}$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{12}+R_{13}$ represents a spacer group selected from a linear moiety having a chain length of 3 to 6 atoms connected to form a C5 to C8 cycloalkenyl, a C6 to C8 partially saturated heterocyclyl ring, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_{14}$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl aryloxy, alkoxyalkyl, alkoxy, haloalkoxy, cyano, carboalkoxy, hydroxy, hydroxyalkyl, and halo groups;

wherein $R_8+R_{14}$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_{15}$ represents a spacer group selected from a covalent bond or a linear moiety having a chain length of 2 to 5 atoms to form a C5 to C8 cycloalkenyl, a C6 to C8 partially saturated heterocyclyl, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_{15}$ represents a spacer group selected from a covalent bond or a linear moiety having a chain length of 2 to 5 atoms to form a C5 to C8 cycloalkenyl, a C6 to C8 partially saturated heterocyclyl, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_9+R_{15}$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{13}+R_{15}$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_9+R_{14}$ represents a spacer group selected from a covalent bond or a linear moiety having a chain length of 2 to 5 atoms to form a C5 to C8 cycloalkenyl, a C6 to C8 partially saturated heterocyclyl, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{13}+R_{14}$ represents a spacer group selected from a covalent bond or a linear moiety having a chain length of 2 to 5 atoms to form a C5 to C8 cycloalkenyl, a C6 to C8 partially saturated heterocyclyl, a C5 to C6 heteroaryl, an aryl, an aryl-C5 to C6-cycloalkyl, or an aryl-C5 to C6-cycloalkoxy substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_2$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_3$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_2$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_3$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_9+R_2$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_9+R_3$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{13}+R_2$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_{13}+R_3$ represents a spacer group selected from a covalent bond or a linear moiety having a chain length of 1 to 4 atoms to form a C5 to C8 partially saturated heterocyclyl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_9$ represents a spacer group to form a C5 to C8 partially saturated heterocyclyl ring or a C5 to C6 heteroaryl substituted independently and optionally with, for example, one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_4+R_{13}$ represents a spacer group to form a C5 to C8 partially saturated heterocyclyl ring or a C5 to C6 heteroaryl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_9$ represents a spacer group to form a C5 to C8 partially saturated heterocyclyl ring or a C5 to C6 heteroaryl substituted independently and optionally, for example, with one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

wherein $R_8+R_{13}$ represents a spacer group to form a C5 to C8 partially saturated heterocyclyl ring or a C5 to C6 heteroaryl substituted independently and optionally with, for example, one to three alkyl, haloalkyl, aryl, heteroaryl, aryloxy, alkoxyalkyl, alkoxy, haloalkoxy, cyano, carboalkoxy, hydroxy, hydroxyalkyl, and halo groups;

provided that there are no more than three non-hydrido ring substituents $R_4$, $R_5$, $R_6$, $R_7$, and $R_8$, that there are no more than three non-hydrido ring substituents $R_9$, $R_{10}$, $R_{11}$, $R_{12}$, and $R_{13}$, and $R_4$, $R_5$, $R_6$, $R_7$, $R_8$, $R_9$, $R_{10}$, $R_{11}$, $R_{12}$, and $R_{13}$ are each independently selected to maintain the tetravalent nature of carbon, trivalent nature of nitrogen, the divalent nature of sulfur, and the divalent nature of oxygen;

wherein $R_{19}$ is selected from:

(a) hydrido, carboxyl, hydroxyalkyl, acyl, sulfhydryl acylamido, alkoxy, alkylthio, arylthio, alkyl, alkenyl, alkynyl, aryl, aralkyl, aryloxyalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylthio, aralkylthio, aroyl, aralkanoyl, heteroaroyl, aralkoxyalkyl, alkylsulfinylalkyl, alkylsulfonylalkyl, aralkylthioalkyl, heteroaralkylthioalkyl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{19}+R_2$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{19}+R_3$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{19}+R_{14}$ represents a spacer group selected from a covalent bond or a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{19}+R_{15}$ represents a spacer group selected from a covalent bond or a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(g) or $R_{19}$ represents a spacer group selected from a covalent bond or a linear moiety having a chain length of 2 to 5 atoms connected to the point of bonding of $R_4$, $R_8$, $R_9$, or $R_{13}$ to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

or a pharmaceutically-acceptable salt thereof.

Alternatively, compounds of the present invention consist of quaternary ammonium salt compounds of Formula VI-HX (also referred to herein as generic heteroaryl tertiary omegaheteroalkylammonium salt):

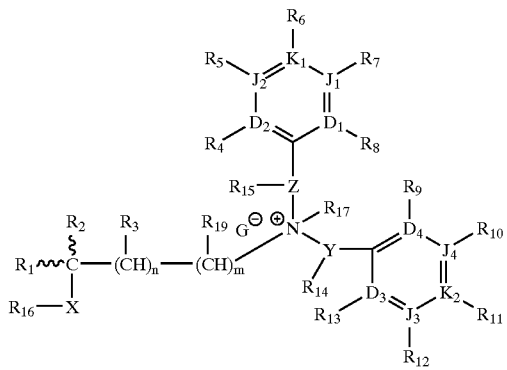

(VI-HX)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula V-HX;

wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$, $R_{19}+R_2$, $R_{19}+R_3$, $R_{19}+R_{14}$, $R_{19}+R_{15}$ are as defined for the compounds of Formula V-HX;

wherein $R_{17}$ is selected from alkyl, alkenyl, alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl;

wherein G is selected from chloro, bromo, iodo, fluoride, trifluoroacetate, perhaloalkylcarboxylates, arylcarboxylates, formate, monoalkylsulfates, arylsulfonates, diarylsulfonylimide anion, benzenesulfonate, tosylate, brosylate, alkylphosphates, arylphosphates, mixed alkyl aryl phosphates, perhaloalkylsulfonates, betylates, perchlorate, mesylate, and pharmaceutically acceptable salts as disclosed herein;

or a pharmaceutically-acceptable salt thereof.

In another embodiment, the compounds correspond to Formula V-HX wherein m=0 to 5; n=1 to 5; m+n=1 to 6; $D_1$, $D_2$, $D_3$, $D_4$, $J_1$, $J_2$, $J_3$, $J_4$, $K_1$, and $K_2$ are each a carbon atom; and a terminal carbon atom of the $CH(R_3)$ moiety is directly connected by a covalent bond to the nitrogen when m=0. Compounds of Formula V-HX wherein m=0 to 5, n=1 to 5, m+n=1 to 6, and $D_1$, $D_2$, $D_3$, $D_4$, $J_1$, $J_2$, $J_3$, $J_4$, $K_1$, and $K_2$ are each a carbon atom, have the $CH(R_3)$ moiety directly connected by a covalent bond to the nitrogen when m=0 and correspond to Formula VX (also referred to herein as generic phenyl tertiary omegaheteroalkylamines):

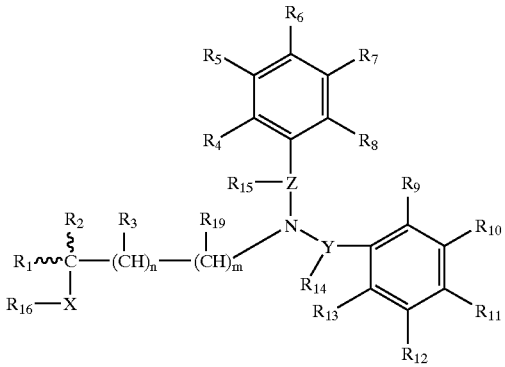

(VX)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula V-HX;

wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$, $R_{19}+R_2$, $R_{19}+R_3$, $R_{19}+R_{14}$, $R_{19}+R_{15}$ are as defined for the compounds of Formula V-HX;

or a pharmaceutically-acceptable salt thereof.

Alternatively, compounds of the present invention consist of quaternary ammonium salt compounds of Formula VIX (also referred to herein as generic phenyl tertiary omega-heteroalkylammonium salt):

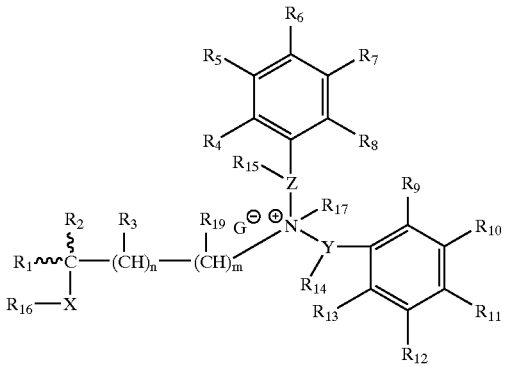

(VIX)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula VX;

wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$, $R_{19}+R_2$, $R_{19}+R_3$, $R_{19}+R_{14}$, $R_{19}+R_{15}$ are as defined for the compounds of Formula VX;

wherein $R_{17}$ and G as defined for the compounds of Formula VI-HX;

or a pharmaceutically-acceptable salt thereof.

In another embodiment, the compounds correspond to Formula VX, wherein m=0, n=1, and a terminal carbon atom of the $CH(R_3)$ moiety is directly connected by a covalent bond to the nitrogen when m=0. Compounds of Formula VX, wherein m=0, n=1, and a terminal carbon atom of the $CH(R_3)$ moiety is directly connected by a covalent bond to the nitrogen correspond to Formula VIIX (also referred to herein as generic phenyl tertiary 2-heteroalkylamines):

(VIIX)

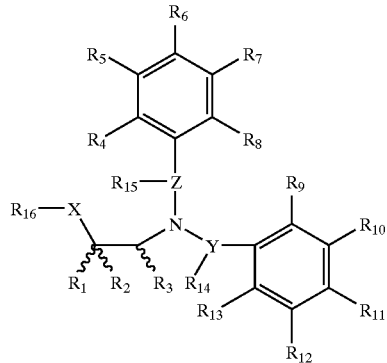

wherein $R_1$, $R_2$, $R_3$, $R_{14}$, $R_{15}$, $R_{16}$, X, Y, and Z are as defined for the compounds of Formula VX;

wherein $R_4$, $R_5$, $R_6$, $R_7$, $R_8$, $R_9$, $R_{10}$, $R_{11}$, $R_{12}$, and $R_{13}$ are as defined for Formula VX;

wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$ are as defined for the compounds of Formula VX;

wherein $R_{19}$, $R_{19}+R_2$, $R_{19}+R_3$, $R_{19}+R_{14}$, $R_{19}+R_{15}$, $R_{19}+R_2$, $R_{19}+R_3$, $R_{19}+R_{14}$, $R_{19}+R_{15}$ substitutents are absent;

or a pharmaceutically-acceptable salt thereof.

Alternatively, compounds of the present invention consist of quaternary ammonium salt compounds of Formula VIIIX (also referred to herein as generic phenyl tertiary 2-heteroalkylammonium salt):

(VIIIX)

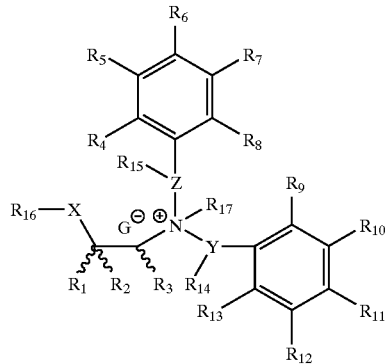

wherein $R_1$, $R_2$, $R_3$, $R_{14}$, $R_{15}$, $R_{16}$, X, Y, and Z are as defined for the compounds of Formula VIIX:

wherein $R_4$, $R_5$, $R_6$, $R_7$, $R_8$, $R_9$, $R_{10}$, $R_{11}$, $R_{12}$, and $R_{13}$ are as defined for Formula VIIX;

wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4R+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, $R_8+R_{13}$ are as defined for the compounds of Formula VIIX;

wherein $R_{17}$ and G as defined for the compounds of Formula VIX;

or a pharmaceutically-acceptable salt thereof.

In another embodiment, the compounds correspond to Formula I wherein m=0 to 5; n=1 to 5; m+n=1 to 6; A=aryl or heteroaryl; Q=aryl or heteroaryl; wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2$, $R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, and $R_8+R_{13}$ spacers are absent; and a terminal carbon atom of the $CH(R_3)$ moiety is directly connected by a covalent bond to the nitrogen when m=0. Compounds of Formula I wherein m=0 to 5; n=1 to 5; m+n=1 to 6; A=aryl or heteroaryl; and Q=aryl or heteroaryl; wherein $R_4+R_5$, $R_5+R_6$, $R_6+R_7$, $R_7+R_8$, $R_9+R_{10}$, $R_{10}+R_{11}$, $R_{11}+R_{12}$, $R_{12}+R_{13}$, $R_4+R_{14}$, $R_8+R_{14}$, $R_4+R_{15}$, $R_8+R_{15}$, $R_9+R_{15}$, $R_{13}+R_{15}$, $R_9+R_{14}$, $R_{13}+R_{14}$, $R_4+R_2R_4+R_3$, $R_8+R_2$, $R_8+R_3$, $R_9+R_2$, $R_9+R_3$, $R_{13}+R_2$, $R_{13}+R_3$, $R_4+R_9$, $R_4+R_{13}$, $R_8+R_9$, and $R_8+R_{13}$ spacers are absent; have the $CH(R_3)$ moiety directly connected by a covalent bond to the nitrogen when m=0 and correspond to Formula V-HAX (also referred to herein as generic heteroaryl tertiary omegaheteroalkylamines):

(V-HAX)

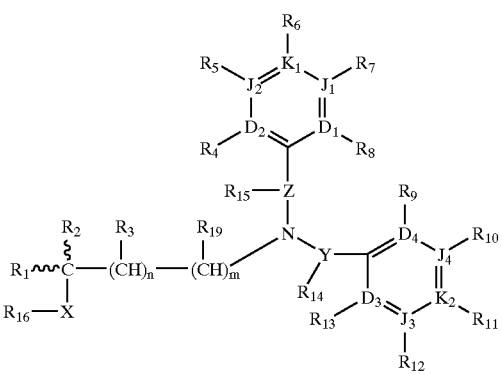

wherein $R_1$ is haloalkyl, haloalkenyl, haloalkoxyalkyl, or haloalkenyloxyalkyl;

wherein X is selected from H, F, —S—, —S(O)—, —S(O)$_2$—, —S(O)$_2$(NH)—, —NH—, —N(OH)—, —N(NH$_2$)—, —N(NHCH$_3$)—, —N(alkyl)-, or —N(alkoxy)-;

wherein $R_{16}$ is selected from:

(a) hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocyanoalkyl, dicyanoalkyl, carboalkoxycyanoalkyl, acyl, aroyl, heteroaroyl, heteroaryloxyalkyl, dialkoxyphosphonoalkyl;

(b) or absent when X is H or F;

wherein $D_1$, $D_2$, $J_1$, $J_2$ and $K_1$ are independently selected from C, N, O, S and a covalent bond provided that:

(a) no more than one can be a covalent bond, (b) only one of $D_1$, $D_2$, $J_1$, $J_2$ and $K_1$ can be O, (c) only one of D, $D_2$, $J_1$, $J_2$ and $K_1$, can be S, (d) only two of $D_1$, $D_2$, $J_1$, $J_2$ and $K_1$ can be O and S, (e) when two of $D_1$, $D_2$, $J_1$, $J_2$ and $K_1$ are O or S, one of $D_1$, $D_2$, $J_1$, $J_2$ and $K_1$ must be a covalent bond, (f) only four of $D_1$, $D_2$, $J_1$, $J_2$ and $K_1$ can be N, (g) one of $D_1$, $D_2$, $J_1$, $J_2$ and $K_1$ must be N, O, or S unless one of $D_3$, $D_4$, $J_3$, $J_4$ and $K_2$ is N, O, or S;

wherein $D_3$, $D_4$, $J_3$, $J_4$ and $K_2$ are independently selected from C, N, O, S and a covalent bond provided that:

(a) no more than one can be a covalent bond, (b) only one of $D_3$, $D_4$, $J_3$, $J_4$ and $K_2$ can be O, (c) only one of $D_3$, $D_4$, $J_3$, $J_4$ and $K_2$ can be S, (d) only two of $D_3$, $D_4$, $J_3$, $J_4$ and $K_2$ can be O and S, (e) when two of $D_3$, $D_4$, $J_3$, $J_4$ and $K_2$ are O or S, one of $D_3$, $D_4$, $J_3$, $J_4$ and $K_2$ must be a covalent bond, (f) only four of $D_3$, $D_4$, $J_3$, $J_4$ and $K_2$ can be N, (g) one of $D_3$, $D_4$, $J_3$, $J_4$ and $K_2$ must be N, O, or S unless one of $D_1$, $D_2$, $J_1$, $J_2$ and $K_1$ is N, O, or S;

wherein $R_2$ is independently selected from:

(a) hydrido, hydroxy, hydroxyalkyl, amino, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_2+R_3$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_2+R_{14}$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_2+R_{15}$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein $R_3$ is selected from:

(a) hydrido, hydroxy, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_3+R_2$ represents a spacer group selected from a covalent bond or a moiety having a chain length of 1 to 6 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_3+R_{14}$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_3+R_{15}$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_3+R_{19}$ represents a spacer group selected from a covalent bond or a linear moiety having a chain length of 1 to 5 atoms to form a C3 to C8 cycloalkyl, a C5 to C8 cycloalkenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein Y is a $(-C(R_{14})_y-)_n$ where n=1 to 4 and y=0 to 2 or $(-CH(R_{14})_y-)_n-W-(-CH(R_{14})_y-)_n$ where n=1 to 2 and y=0 to 1 and $R_{14}$ is independently selected from:

(a) hydrido, hydroxy, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfonyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoakyl, diaralkoxyphosphonoalkyl;

(b) or $R_{14}+R_2$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{14}+R_3$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{14}+R_{15}$ represents a spacer group selected from a moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{14}+R_{14}$ represents a covalent bond, an alkylene, a haloalkylene, alkylenedioxy, haloalkylenedioxy, or a spacer group selected from a moiety having a chain length of 2 to 5 atoms connected to form a C5 to C8 saturated cycloalkyl, a C5 to C8 partially saturated cycloalkyl, a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_{14}+R_{14}$ represents, when bonded to the same atom, an oxo, an alkylene, a haloalkylene, alkylenedioxy, haloalkylenedioxy, or a spacer group selected from a moiety having a chain length of 3 to 7 atoms connected to form a C4 to C8 saturated cycloalkyl, a C4 to C8 partially saturated cycloalkyl, a C4 to C8 saturated heterocyclyl or a C4 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein W is selected from —O—, —S—, —S(O)—, —S(O)$_2$—, —S(O)$_2$(NH)—, —NH—, —N(OH)—, —N(NH$_2$)—, —N(NHCH$_3$)—, —N(alkyl)-, —N(alkoxy)-, —N(aryloxy)-, —N(heteroaryloxy)-, —N(acyloxy)-, —N(aroyloxy)-, —N(cycloalkyl), —N(aralkoxy)-, and —N(aryl)-;

wherein Z is independently selected from a covalent bond, (—C(R$_{15}$)$_y$—)$_n$ wherein n=1 to 4 and y=0 to 2, (—CH(R$_{15}$)$_y$—)$_n$—W—(—CH(R$_{15}$)$_y$—)$_n$ wherein n=1 to 2 and y=0 to 2, —N—, —N(OH)—, —N(alkyl)-, —N(alkoxy)-, —N(aryloxy)-, —N(aralkoxy), —N(cycloalkyl)-, —N(aryl)-, oxygen radical (—O—), —OCH$_2$—, or —OCH(R$_{15}$)$_y$— where y=0 to 1;

wherein, when Z is (—C(R$_{15}$)$_y$—)$_n$ where n=1 to 4 and y=0 to 2 or (—CH(R$_{15}$)$_y$—)$_n$—W—(—CH(R$_{15}$)$_y$—)$_n$ wherein n=1 to 2 and y=0 to 2, R$_{15}$ is independently selected from:

(a) hydrido, hydroxy, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{15}+R_2$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl alkoxy, haloalkoxy, cyano, carboalkoxy, hydroxy, hydroxyalkyl, and halo groups;

(c) or $R_{15}+R_3$ represents a spacer group selected from a covalent bond or a moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{14}+R_{15}$ represents a spacer group selected from a moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{15}+R_{15}$ represents a covalent bond an alkylene, a haloalkylene, alkylenedioxy, haloalkylenedioxy, or a spacer group selected from a moiety having a chain length of 2 to 5 atoms connected to form a C5 to C8 saturated cycloalkyl, a C5 to C8 partially saturated cycloalkyl, a C5 to C8 saturated heterocyclyl or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(h) or $R_{15}+R_{15}$ represents, when bonded to the same atom, an oxo, an alkylene, a haloalkylene, alkylenedioxy, haloalkylenedioxy, or a spacer group selected from a moiety having a chain length of 3 to 7 atoms connected to form a C4 to C8 saturated cycloalkyl, a C4 to C8 partially saturated cycloalkyl, a C4 to C8 saturated heterocyclyl or a C4 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is N, $R_{15}$ is independently selected from:

(a) hydrido, hydroxyalkyl, aryloxy, aminoalkyl, alkylaminoalkyl, dialkylaminoalkyl, acyl, aroyl, heteroaroyl, heteroaryloxyalkyl, acylamido, alkyl, alkenyl, alkynyl, aryl, aralkyl, aryloxyalkyl, aralkoxyalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, aralkylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl;

(b) or $R_{15}+R_2$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{15}+R_{14}$ represents a spacer group selected from a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is $(-CH(R_{15})_y-)_n-W-(-CH(R_{15})_y-)_n$ wherein n=1 to 2 and y=0 to 2 or $-OCH(R_{15})_y-$ wherein y=0 to 1, $R_{15}$ is independently selected from:

(a) aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl;

(b) or $R_{15}+R_2$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(c) or $R_{15}+R_3$ represents a spacer group selected from a covalent bond or a linear moiety having a chain length of 1 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{15}+R_{14}$ represents a spacer group selected from a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

wherein, when Z is a covalent bond, —N(OH)—, —N(alkyl)-, —N(alkoxy)-, —N(aryloxy)-, —N(cycloalkyl)-, —N(aryl)-, —N(aralkoxy)-, oxygen radical (—O—), or —OCH$_2$—, an $R_{15}$ substituent is not attached to Z;

wherein $R_4$, $R_5$, $R_6$, $R_7$, $R_8$, $R_9$, $R_{10}$, $R_{11}$, $R_{12}$, and $R_{13}$ are independently selected from hydrido, heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, aralkylamino, alkylthio, alkylthioalkyl, arylamino, arylaminoalkyl, arylsulfonyl, arylsulfinyl, heteroarylthio, heteroarylsulfinyl, heteroarylsulfonyl, hydroxyhaloalkyl, haloalkanoyl, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, alkanoyl, alkenoyl, aroyl, heteroaroyl, alkyl, alkenyl, alkynyl, cycloalkyl, cycloalkenyl, cycloalkylalkyl, cycloalkenylalkyl, halo, haloalkyl, haloalkoxy, haloalkoxyalkyl, aryl, aralkyl, aryloxy, aralkoxy, aryloxyalkyl, saturated heterocyclyl, partially saturated heterocyclyl, heteroaryl, heteroarylamino, heteroarylalkylamino, heteroaryloxy, heteroarylalkyl, heteroaryloxyalkyl, arylalkenyl, heteroarylalkenyl, carboalkoxy, carboaryloxy, carboaralkoxy, cyano, and carbohaloalkoxy;

provided that there are no more than three non-hydrido ring substituents $R_4$, $R_5$, $R_6$, $R_7$, and $R_8$, a that there are no more than three non-hydrido ring substituents $R_9$, $R_{10}$, $R_{11}$, $R_{12}$, and $R_{13}$, and $R_4$, $R_5$, $R_6$, $R_7$, $R_8$, $R_9$, $R_{10}$, $R_{11}$, $R_{12}$, and $R_{13}$ are each independently selected to maintain the tetravalent nature of carbon, trivalent nature of nitrogen, the divalent nature of sulfur, and the divalent nature of oxygen;

wherein $R_{19}$ is selected from:

(a) hydrido, carboxyl, hydroxyalkyl, acyl, sulfhydryl, acylamido, alkoxy, alkylthio, arylthio, alkyl, alkenyl, alkynyl, aryl, aralkyl, aryloxyalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylthio, aralkylthio, aroyl, aralkanoyl, heteroaroyl, aralkoxyalkyl, alkylsulfinylalkyl, alkylsulfonylalkyl, aralkylthioalkyl, heteroaralkylthioalkyl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

(b) or $R_{19}+R_2$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(d) or $R_{19}+R_3$ represents a spacer group selected from a covalent bond or a linear moiety having a chain length of 1 to 5 atoms to form a C3 to C8 cycloalkyl, a C5 to C8 cycloalkylenyl, a C4 to C8 saturated heterocyclyl, or a C5 to C8 partially saturated heterocyclyl substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(e) or $R_{19}+R_{14}$ represents a spacer group selected from a covalent bond or a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

(f) or $R_{19}+R_{15}$ represents a spacer group selected from a covalent bond or a linear moiety having a chain length of 2 to 5 atoms to form a C5 to C8 saturated heterocyclyl or a C5 to C8 partially saturated heterocyclyl ring substituted independently and optionally with, for example, one to three alkyl, haloalkyl, aryl, heteroaryl, alkoxyalkyl, alkoxy, haloalkoxy, cyano, carboalkoxy, hydroxy, hydroxyalkyl, and halo groups;

or a pharmaceutically-acceptable salt thereof.

Alternatively, compounds of the present invention consist of quaternary ammonium salt compounds of Formula VI-HAX (also referred to herein as generic heteroaryl tertiary omegaheteroalkylammonium salt):

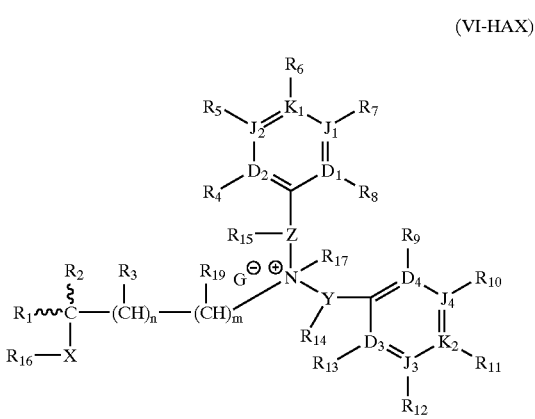

(VI-HAX)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula V-HAX;

wherein $R_{17}$ is selected from alkyl, alkenyl, alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl;

wherein G is selected from chloro, bromo, iodo, fluoride, trifluoroacetate, perhaloalkylcarboxylates, arylcarboxylates, formate, monoalkylsulfates, arylsulfonates, diarylsulfonylimide anion, benzenesulfonate, tosylate, brosylate, alkylphosphates, arylphosphates, mixed alkyl aryl phosphates, perhaloalkylsulfonates, betylates, perchlorate, mesylate, and pharmaceutically acceptable salts as disclosed herein;

or a pharmaceutically-acceptable salt thereof.

In another embodiment, the compounds correspond to Formula V-HAX wherein m=0 to 5; n=1 to 5; m+n=1 to 6;

$D_1$, $D_2$, $D_3$, $D_4$, $J_1$, $J_2$, $J_3$, $J_4$, $K_1$, and $K_2$ are each a carbon atom; and a terminal carbon atom of the $CH(R_3)$ moiety is directly connected by a covalent bond to the nitrogen when m=0. Compounds of Formula V-HAX wherein m=0 to 5, n=1 to 5, m+n=1 to 6, and $D_1$, $D_2$, $D_3$, $D_4$, $J_1$, $J_2$, $J_3$, $J_4$, $K_1$, and $K_2$ are each a carbon atom, have the $CH(R_3)$ moiety directly connected by a covalent bond to the nitrogen when m=0 and correspond to Formula VIAX (also referred to herein as generic phenyl tertiary omegaheteroalkylamines):

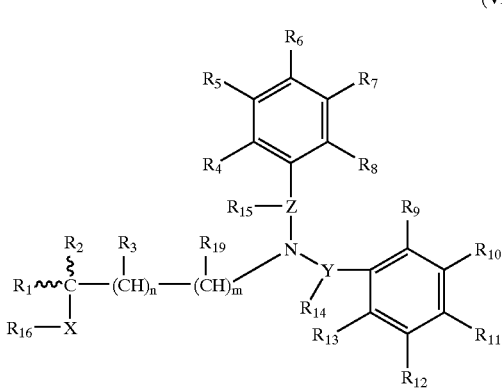

(VAX)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula V-HAX;

or a pharmaceutically-acceptable salt thereof.

Alternatively, compounds of the present invention consist of quaternary ammonium salt compounds of Formula VIAX (also referred to herein as generic phenyl tertiary omega-heteroalkylammonium salt):

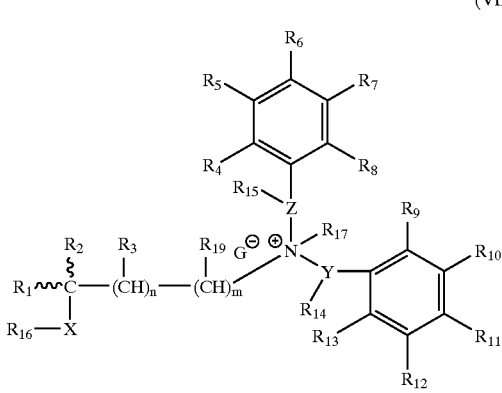

(VIAX)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{19}$, X, Y, and Z are as defined for the compounds of Formula VAX;

wherein $R_{17}$ and G as defined for the compounds of Formula VI-HAX;

or a pharmaceutically-acceptable salt thereof.

In another embodiment, the compounds correspond to Formula VAX, wherein m=0, n=1, and a terminal carbon atom of the $CH(R_3)$ moiety is directly connected by a covalent bond to the nitrogen when m=0. Compounds of Formula VAX, wherein m=0, n=1, and a terminal carbon atom of the $CH(R_3)$ moiety is directly connected by a covalent bond to the nitrogen correspond to Formula VIIAX (also referred to herein as generic phenyl tertiary 2-heteroalkylamines):

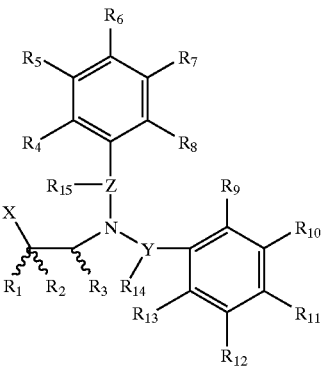

(VIIAX)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, X, Y, and Z are as defined for the compounds of Formula VAX;

wherein $R_{19}$, $R_{19}+R_2$, $R_{19}+R_3$, $R_{19}+R_{14}$, $R_{19}+R_{15}$, $R_{19}+R_2$, $R_{19}+R_3$, $R_{19}+R_{14}$, $R_{19}+R_{15}$ substitutents are absent;

or a pharmaceutically-acceptable salt thereof.

Alternatively, compounds of the present invention consist of quaternary ammonium salt compounds of Formula VII-IAX (also referred to herein as generic phenyl tertiary 2-heteroalkylammonium salt):

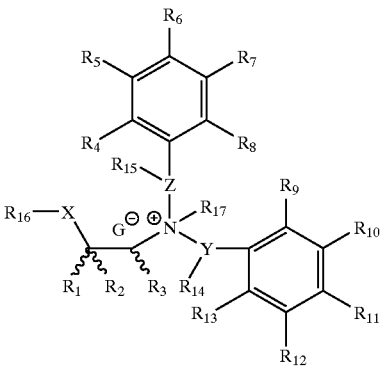

(VIIIAX)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, X, Y, and Z are as defined for the compounds of Formula VIIAX;

wherein $R_{17}$ and G as defined for the compounds of Formula VIAX;

or a pharmaceutically-acceptable salt thereof.

In yet another emodiment of the present invention, the novel compounds are selected from the compounds set forth in Tables 4, 5, 7, 8, 9, 12, 14, 15, 16, 17, and 18.

The use of generic terms in the description of the compounds are herein defined for clarity. Where the term "alkyl" is used, either alone or within other terms such as "haloalkyl" and "alkylthio", it embraces linear or branched radicals having one to about 10 carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, and the like. The term "alkenyl" denotes linear or branched radicals having from 1 to about 10 carbon atoms and having one or more double bonds. Examples of such radicals include ethenyl, pentenyl, butenyl, butadienyl, and decenyl. The term "alkynyl" denotes linear or branched radicals having from 1 to about 10 carbon atoms having one or more triple bonds. Examples of such radicals include propynyl, hexynyl, heptynyl, octynyl, and decynyl. The term "hydrido" denotes a single hydrogen atom (H). This hydrido radical may be attached, for example, to an oxygen atom to form a "hydroxyl" radical, one hydrido radical may be attached to a carbon atom to form a "methine" radical

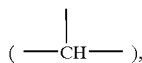

or two hydrido radicals may be attached to a carbon atom to form a "methylene" (—CH$_2$—) radical. The term "carbon" radical denotes a carbon atom without any covalent bonds and capable of forming four covalent bonds. The term "cyano" radical denotes a carbon radical having three of four covalent bonds shared by a nitrogen atom. The term "hydroxyalkyl" embraces radicals wherein any one or more of the alkyl carbon atoms is substituted with a hydroxyl as defined above. Specifically embraced are monohydroxyalkyl, dihydroxyalkyl and polyhydroxyalkyl radicals. The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl. The term "alkylene" radical denotes linear or branched radicals having from 1 to about 10 carbon atoms and having attachment points for two or more covalent bonds. Examples of such radicals are methylene, ethylene, methylethylene, and isopropylidene. The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "lower haloalkyl" radicals having one to about six carbon atoms. Examples of such haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyhaloalkyl" embraces radicals wherein any one or more of the haloalkyl carbon atoms is substituted with hydroxy as defined above. The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred haloalkylene radicals are "lower haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene. The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals. The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "lower alkoxy" radicals having one to six carbon atoms. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy. The term "haloalkoxyalkyl" also embraces alkyl radicals having one or more haloalkoxy radicals attached to the alkyl radical, that is, to form monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals. The term "alkylenedioxy" radicals denotes alkylene radicals having at least two oxygens bonded to a single alkylene group. Examples of "alkylenedioxy" radicals include methylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoroethylenedioxy, tetrachloroethylenedioxy, alkylsubstituted monofluoromethylenedioxy, and arylsubstituted monofluoromethylenedioxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Said "aryl" group may have 1 to 3 substituents such as heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamnino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydroxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "perhaloaryl" embraces aromatic radicals such as phenyl, naphthyl, tetrahydronaphthyl, indane and biphenyl wherein the aryl radical is substituted with 3 or more halo radicals as defined above. The term "heterocyclyl" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6 membered heteromonocyclic group containing 1 to 2 sulfur atoms and 1 to 3 nitrogen atoms [e.g., thiazolidinyl, etc.]. Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4- thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents such as heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, aridosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. Preferred heterocyclic radicals include five to ten membered fused or unfused radicals. More preferred examples of heteroaryl radicals include pyridyl, thienyl, thiazolyl, oxazolyl, furyl, and pyrazinyl. The term "sulfonyl", whether used alone or linked to other terms such as alkylsulfonyl, denotes respectively divalent radicals —$SO_2$—. "Alkylsulfonyl", embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals attached to a sulfonyl radical, where haloalkyl is defined as above. "Haloalkylsulfonylalkyl", embraces haloalkylsulfonyl radicals attached to an alkyl radical, where alkyl is defined as above. The term "sulfinyl", whether used alone or linked to other terms such as alkylsulfinyl, denotes respectively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfinylalkyl", embraces haloalkylsulfinyl radicals attached to an alkyl radical, where alkyl is defined as above. The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The aryl in said aralkyl may have additional substituents such as heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The terms benzyl and phenylmethyl are interchangeable. The term "heteroaralkyl" embraces heteroaryl-substituted alkyl radicals wherein the heteroaralkyl radical may be additionally substituted with three or more substituents as defined above for aralkyl radicals. The term "perhaloarakyl" embraces aryl-substituted alkyl radicals wherein the aralkyl radical is substituted with three or more halo radicals as defined above. The term "Aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above. The term "Aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above. The term "cycloalkyl" embraces radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Examples of such radicals include cyclohexylhexyl. The term "cycloalkenyl" embraces radicals having three to ten carbon atoms and one or more carbon-carbon double bonds. Preferred cycloalkenyl radicals are "lower cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. More preferred halocycloalkyl radicals are "lower halocycloalkyl" radicals having three to about eight carbon atoms. Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals. The term "halocycloalkoxy" also embraces cycloalkoxy radicals having one or more halo radicals attached to the cycloalkoxy radical, that is, to form monohalocycloalkoxy, dihalocycloalkoxy, and polycycloalkoxy radicals. The term "Cycloalkylsulfinyl", embraces cycloalkyl radicals attached to a sulfinyl radical, where cycloalkyl is defined as above. "Cycloalkylsulfinylalkyl", embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalkylsulfonyl radicals attached to an alkyl radical, where alkyl is defined as above. The term "alkylthio" embraces radicals containing a linear or branched alkyl radical, of one to ten carbon atoms, attached to a divalent sulfur atom. More preferred alkylthio radicals are "lower alkylthio" radicals having one to six carbon atoms. An example of "lower alkylthio" is methylthio ($CH_3$—S—). The term "alkylsulfinyl" embraces radicals containing a linear or branched alkyl radical, of one to ten carbon atoms, attached to a divalent —S(=O)— atom. The term "aminosulfonyl" denotes an amino radical attached to a sulfonyl radical. The terms alkylamino denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "Aralkylamino", embraces aralkyl radicals attached to an amino radical, where aralkyl is defined as above. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical. The term "arylsulfinyl" embraces radicals containing an aryl radical, as defined above, attached to a divalent —S(=O)— atom. The term "arylsulfinylalkyl" denotes arylsulfinyl radicals attached to a linear or branched alkyl radical, of one to ten carbon atoms. The term "Arylsulfonyl", embraces aryl radicals attached to a sulfonyl radical, where aryl is defined as above. "Arylsulfonylalkyl", embraces arylsulfonyl radicals attached to an alkyl radical, where alkyl is defined as above. The term "heleroarylsulfinyl" embraces radicals containing an heteroaryl radical, as defined above, attached to a divalent —S(=O)— atom. The term "heteroarylsulfinylalkyl" denotes heteroarylsulfinyl radicals attached to a linear or branched alkyl radical, of one to ten carbon atoms. The term "Heteroarylsulfonyl", embraces heteroaryl radicals attached to a sulfonyl radical, where heteroaryl is defined as above. "Heteroarylsulfonylalkyl", embraces heteroarylsulfonyl radicals attached to an alkyl radical, where alkyl is defined as above. The term "aryloxy" embraces aryl radicals, as defined above, attached to an oxygen atom. Examples of such radicals include phenoxy. The aryl in said aryloxy may be additionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "aroyl" embraces aryl radicals, as defined above, attached to an carbonyl radical as defined above. Examples of such radicals include benzoyl and toluoyl. The aroyl in said aroyl may be additionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "aralkanoyl" embraces aralkyl radicals, as defined herein, attached to an carbonyl radical as defined above. Examples of such radicals include, for example, phenylacetyl. The aryl in said aralalkanoyl may be additionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "aralkoxy" embraces oxy-containing aralkyl radicals attached through an oxygen atom to other radicals. More preferred aralkoxy radicals are "lower aralkoxy" radicals having phenyl radicals attached to lower alkoxy radical as described above. The aryl in said aralkoxy radicals may be additionally substituted with heteroarylarrino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The tern "aryloxyalkyl" embraces aryloxy radicals, as defined above, attached to an alkyl group. Examples of such radicals include phenoxymethyl. The aryl in said aryloxyalkyl may be additionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "haloaryloxyalkyl" embraces aryloxyalkyl radicals, as defined above, wherein one to five halo radicals are attached to an aryloxy group. The term "heteroaryloxy" embraces heteroaryl radicals, as defined above, attached to an oxygen atom. Examples of such radicals include pyridyloxy and furyloxy. The heteroaryl in said heteroaryloxy may be additionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "heteroaroyl" embraces heteroaryl radicals, as defined above, attached to an carbonyl radical as defined above. Examples of such radicals include furoyl and nicotinyl. The heteroaryl in said heteroaroyl may be additionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "heteroaralkanoyl" embraces heteroaralkyl radicals, as defined herein, attached to an carbonyl radical as defined above. Examples of such radicals include, for example, pyridylacetyl and furylbutyryl. The heteroaryl in said heteroaralalkanoyl may be additionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "heteroaralkoxy" embraces oxy-containing heteroaralkyl radicals attached through an oxygen atom to other radicals. More preferred heteroaralkoxy radicals are "lower heteroaralkoxy" radicals having heteroaryl radicals attached to lower alkoxy radical as described above. The heteroaryl in said heteroaralkoxy radicals may be additionally substituted with heteroarylamino. N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "heteroaryloxyalkyl" embraces heteroaryloxy radicals, as defined above, attached to an alkyl group. Examples of such radicals include pyridyloxymethyl. The heteroaryl in said heteroaryloxyalkyl may be additionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "haloheteroaryloxyalkyl" embraces heteroaryloxyalkyl radicals, as defined above, wherein one to four halo radicals are attached to an heteroaryloxy group. The term "arylthio" embraces aryl radicals, as defined above, attached to an sulfur atom. Examples of such radicals include phenylthio. The aryl in said arylthio may be additionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "arylthioalkyl" embraces arylthio radicals, as defined above, attached to an alkyl group. Examples of such radicals include phenylthiomethyl. The aryl in said arylthioalkyl may be additionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkyisulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloaltkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "alkylthioalkyl" embraces alkylthio radicals, as defined above, attached to an alkyl group. Examples of such radicals include methylthiomethyl. The term "alkoxyalkyl" embraces alkoxy radicals, as defined above, attached to an alkyl group. Examples of such radicals include methoxymethyl. The term "carbonyl" denotes a carbon radical having two of the four covalent bonds shared with an oxygen atom. The term "carboxy" embraces a hydroxyl radical, as defined above, attached to one of two unshared bonds in a carbonyl group. The term "carboxamide" embraces amino, monoalkylamino, and dialkylamino radicals, attached to one of two unshared bonds in a carbonyl group. The term "carboxamidoalkyl" embraces carboxamide radicals, as defined above, attached to an alkyl group. The term "carboxyalkyl" embraces a carboxy radical, as defined above, attached to an alkyl group. The term "carboalkoxy" embraces alkoxy radicals, as defined above, attached to one of two unshared bonds in a carbonyl group. The term "carboaralkoxy" embraces aralkoxy radicals, as defined above, attached to one of two unshared bonds in a carbonyl group. The term "monocarboalkoxyalkyl" embraces one carboalkoxy radical, as defined above, attached to an alkyl group. The term "dicarboalkoxyalkyl" embraces two carboalkoxy radicals, as defined above, attached to an alkylene group. The term "monocyanoalkyl" embraces one cyano radical, as defined above, attached to an alkyl group. The term "dicyanoalkylene" embraces two cyano radicals, as defined above, attached to an alkyl group. The term "carboalkoxycyanoalkyl" embraces one cyano radical, as defined above, attached to an alkylene group. The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like. The term "haloalkanoyl" embraces one or more halo radicals, as defined herein, attached to an alkanoyl radical as defined above. Examples of such radicals include, for example, chloroacetyl, trifluoroacetyl, bromopropanoyl, and heptafluorobutyryl. The alkanoyl in said haloalkanoyl may be additionally substituted with hydroxy, amino, thio, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy. The term "phosphono" embraces a pentavalent phosphorus attached with two covalent bonds to an oxygen radical. The term "dialkoxyphosphono" denotes two alkoxy radicals, as defined above, attached to a phosphono radical with two covalent bonds. The term "diaralkoxyphosphono" denotes two aralkoxy radicals, as defined above, attached to a phosphono radical with two covalent bonds. The term "dialkoxyphosphonoalkyl" denotes dialkoxyphosphono radicals, as defined above, attached to an alkyl radical. The term "diaralkoxyphosphonoalkyl" denotes diaralkoxyphosphono radicals, as defined above, attached to an alkyl radical.

The term "spacer" can include a covalent bond and a linear moiety having a backbone of 1 to 7 continous atoms. The spacer may have 1 to 7 atoms of a univalent or multi-valent chain. Univalent chains may be constituted by a radical selected from =C(H)—, =C($R_{17}$)—, —O—, —S—, —S(O)—, —S(O)$_2$—, —NH—, —N($R_{20}$)—, —N=, —CH(OH)—, =C(OH)—, —CH(O$R_{17}$)—, =C(O$R_{17}$)—, and —C(O)—. Multi-valent chains may consist of a straight chain of 1 or 2 or 3 or 4 or 5 or 6 or 7 atoms or a straight chain of 1 or 2 or 3 or 4 or 5 or 6 atoms with a side chain. The chain may be constituted of one or more radicals selected from: lower alkylene, lower alkenyl, —O—, —O—CH$_2$—, —S—CH$_2$—, —CH$_2$CH$_2$—, ethenyl, —CH=CH(OH)—, —OCH$_2$O—, —O(CH$_2$)$_2$O—, —NHCH$_2$—, —OCH($R_{17}$)O—, —O(CH$_2$CH$R_{17}$)O—, —O(CF$_2$O—, —O(CF$_2$)$_2$O—, —S—, —S(O)—, —S(O)$_2$—, —N(H)—, —N(H)O—, —N($R_{17}$)O—, —N($R_{17}$)—, —C(O)—, —C(O)NH—, —C(O)N$R_{17}$—, —N=, —OCH$_2$—, —SCH$_2$—, S(O)CH$_2$—, —CH2C(O)—, —CH(OH)—, =C(OH)—, —CH(O$R_{17}$)—, =C(O$R_{17}$)—, S(O)$_2$ CH$_2$—, and —N$R_{17}$CH$_2$— and many other radicals defined above or generally known or ascertained by one of skill-in-the art. Side chains may include substituents such as heteroarylamino, N-aryl-N-alkylamino. N-heteroarylamino-N-alkylamino, haloalkylthio, alkanoyloxy, alkoxy, heteroaralkoxy, cycloalkoxy, cycloalkenyloxy, hydroxy, amino, thio, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

The present invention comprises a pharmaceutical composition comprising a therapeutically-effective amount of a compound of Formulas I, II, III, IV, I-I, II-II, I-IA, II-IIA, III-III, IV-IV, III-IIIA, IV-IVA, V, VI, VA, VIA, V-H, VI-H, VX, VIX, V-HX, VI-HX, V-HA, VI-HA, V-HAX, VI-HAX, VAX, VIAX, VII, Cyclo-VII, VIIA, VIIAX, VIIX, VIII, VIIIA, VIIIX, and VIIIAX in association with at least one pharmaceutically-acceptable carrier, adjuvant or diluent.

The present invention also comprises a treatment and prophylaxis of coronary artery disease and other CETP-mediated disorders in a subject, comprising administering to the subject having such disorder a therapeutically-effective amount of a compound of Formula I:

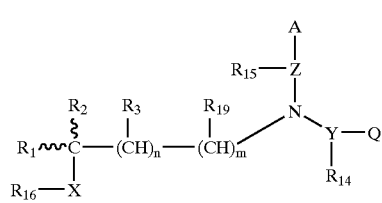

(I)

wherein $R_1$, $R_2$, $R_3$, $R_{14}$, $R_{15}$, $R_{16}$, $R_{19}$, A, Q, X, Y, and Z are as defined above for the compounds of Formula I;

or a pharmaceutically-acceptable salt thereof.

The present invention also comprises a treatment and prophylaxis of coronary artery disease and other CETP-mediated disorders in a subject, comprising administering to the subject having such disorder a therapeutically-effective amount of a compound of a quaternary ammonium salt of Formula II:

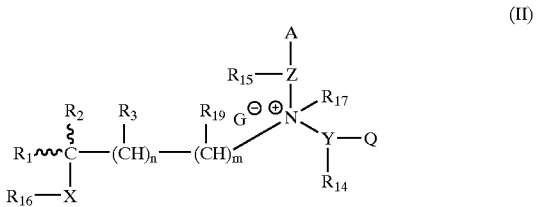

(II)

wherein $R_1$, $R_2$, $R_3$, $R_{14}$, $R_{15}$, $R_{16}$, $R_{19}$, A, Q, X, Y, and Z are as defined above for the compounds of Formula I;

wherein $R_{17}$ and G are as defined above for the compounds of Formula II;

or a pharmaceutically-acceptable salt thereof.

As a further embodiment, compounds of Formulas I, II, III, IV, I-I, II-II, I-IA, II-IIA, III-III, IV-IV, III-IIIA, IV-IVA, V, VI, VA, VIA, V-H, VI-H, VX, VIX, V-HX, VI-HX, V-HA, VI-HA, V-HAX, VI-HAX, VAX, VIAX, VII, Cyclo-VII, VIIA, VIIAX, VIIX, VIII, VIIIA, VIIIX, and VIIIAX of the present invention or a pharmaceutically-acceptable salt thereof as defined above comprise a treatment and prophylaxis of coronary artery disease and other CETP-mediated disorders in a subject, comprising administering to the subject having such disorder a therapeutically-effective amount of compounds I, II, III, IV, I-I, II-II, I-IA, II-IIA, III-III, IV-IV, III-IIIA, IV-IVA, V, VI, VA, VIA, V-H, VI-H, VX, VIX, V-HX, VI-HX, V-HA, VI-HA, V-HAX, VI-HAX, VAX, VIAX, VII, Cyclo-VII, VIIA, VIIAX, VIIX, VIII, VIIIA, VIIIX, and VIIIAX of the present invention or a pharmaceutically-acceptable salt thereof Compounds of Formulas I, II, III, IV, I-I, II-II, I-IA, II-IIA, III-III, IV-IV, III-III-A, IV-IVA, V, VI, VA, VIA, V-H, VI-H, VX, VIX, V-HX, VI-HX, V-HA, VI-HA, V-HAX, VI-HAX, VAX, VIAX, VII, Cyclo-VII, VIIA, VIIAX, VIIX, VIII, VIIIA, VIIIX, and VIIIAX are capable of inhibiting activity of cholesteryl ester transfer protein (CETP), and thus could be used in the manufacture of a medicament, a method for the prophylactic or therapeutic treatment of diseases mediated by CETP, such as peripheral vascular disease, hyperlipidaemia, hypercholesterolemia, and other diseases attributable to either high LDL and low HDL or a combination of both, or a procedure to study the mechanism of action of the cholesteryl ester transfer protein (CETP) to enable the design of better inhibitors. The compounds of Formula I and Formula II would be also useful in prevention of cerebral vascular accident (CVA) or stroke.

Also included in the family of compounds of Formula I, II, III, IV, I-I, II-II, I-IA, II-IIA, III-III, IV-IV, III-IIIA, IV-IVA, V, VI, VA, VIA, V-H, VI-H, VX, VIX, V-HX, VI-HX, V-HA, VI-HA, V-HAX, VI-HAX, VAX, VIAX, VII, Cyclo-VII, VIIA, VIIAX, VIIX, VIII, VIIIA, VIIIX, and VIIIAX are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula I and II may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula I and II include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula I and II by reacting, for example, the appropriate acid or base with the compound of Formula I and II.

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 15% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

All mentioned references are incorporated by reference as if here written.

Although this invention has been described with respect to specific embodiments, the details of these embodiments are not to be construed as limitations.

General Synthetic Procedures

The compounds of the present invention can be synthesized, for example, according to the following procedures of Schemes 1 to 18, wherein the substituents are as defined for Formulas I, II, III, IV, I-I, II-II, I-IA, II-IIA. III-III, IV-IV, III-IIIA, IV-IVA, V, VI, VA, VIA, V-H, VI-H, VX, VIX, V-HX, VI-HX, V-HA, VI-HA, V-HAX, VI-HAX, VAX, VIAX, VII, Cyclo-VII, VIIA, VIIAX, VIIX, VIII, VIIIA, VIIIAX, and VIIIX above except where further noted.

Synthetic Schemes 1 and 2 shows the preparation of compounds of formula XIII ("Generic Secondary Amines") which are intermediates in the preparation of the compounds of the present invention corresponding to Formula I ("Generic tertiary-OmegaHeteroalkylamine"), Formula I-I ("Generic Aromatic tertiary-OmegaHeteroalkylamine"), Formula III ("Generic tertiary-2-heteroalkylamine"), and Formula III-III and III-IIIA ("Generic Aromatictertiary-2-heteroalkylamines").

The "Generic Imine" corresponding to Formula XII can be prepared through reductive amination techniques generally known in the art and the preferred technique depending on the nature of "Generic Amine-1" of Formula X by reacting it with the "Generic Carbonyl Compound" of Formula XI. For example, when Z is a covalent bond, methylene, methine substituted with another subsitutent, or another substituent as defined in Formula I, the two reactants (X and XI) react by refluxing them in an aprotic solvent, such as hexane, toluene, cyclohexane, benzene, and the like, using a Dean-Stark type trap to remove water. After about 2–8 hours or until the removal of water is complete, the aprotic solvent is removed in vacuo to yield the "Generic Imine" of Formula XII. Alternately, when Z is an oxygen, the "Generic Imine" is an oxime derivative. Oxime type "Generic Imine" compounds are readily prepared from the corresponding O-substituted hydroxylamine and the appropriate aldehyde or ketone type "Generic Carbonyl Compound". Suitable procedures are described by Shriner, Fuson, and Curtin in The Systematic Indentification of Organic Compounds, 5th Edition, John Wiley & Sons and by Fieser and Fieser in Reagents for Organic Synthesis, Volume 1, John Wiley & Sons, which are incorporated herein by reference. Alternately, when Z is a nitrogen, the "Generic Imine" is a hydrazone derivative. Hydrazone type "Generic Imine" compounds are readily prepared from the corresponding hydrazine and the appropriate aldehyde or ketone type "Generic Carbonyl Compound". Suitable procedures for forming the hydrazone imines are also described by Shriner, Fuson, and Curtin in The Systematic Indentification of Organic Compounds, 5th Edition, John Wiley & Sons, and by Fieser and Fieser in Reagents for Organic Synthesis, Volume 1, John Wiley & Sons, which are incorporated herein by reference.

Scheme 1 shows the preparation of "Generic Imine" compounds in which the amine functionality is bonded to Z; Z is bonded to A; and Y is bonded to Q. One of skill in the art will recognize that A and Q as defined can be structurally interchanged to prepare "Generic Imine" compounds with similar, identical or different structures.

The "Generic Secondary Amines" of Formula XIII can be prepared from the corresponding "Generic Imine" of Formula XII in several ways.

For example, in one synthetic scheme (Reduction Method-1), which is preferred when Z is a nitrogen, the "Generic Imine" hydrazone of Formula XII is partially or completely dissolved in lower alkanols such as ethanol or like solvent containing sufficient organic acid such as acetic acid or mineral acid such as HCl or sulfuric acid to neutralize the hydrazone as described in WO Patent Application No. 9738973, Swiss Patent CH 441366 and U.S. Pat. Nos. 3,359,316 and 3,334,017, which are incorporated herein by reference. The resulting mixture is then hydrogenated at 0–100° C., more preferrably 20–50° C., and most preferrably between 20–30° C. and pressures of 10–200 psi hydrogen or more preferrably between 50–70 psi hydrogen in the presence of a noble metal catalyst such as $PtO_2$. The mixture is cooled, and a base such as sodium carbonate or sodium hydroxide added until the solution is neutral to just alkaline (pH 6–8).

Isolation of the desired product can be accomplished, for example, by removing the ethanol, adding water, and extracting the aqueous-organic mixture twice with a solvent, such as diethyl ether or methylene chloride, that is immiscible with water. The combined solvent extract is washed with saturated brine, dried with a drying agent such as anhydrous magnesium sulfate, and concentrated in vacuo to yield the "Generic Secondary Amines" hydrazine of Formula XIII. If needed the "Generic Secondary Amines" hydrazine can be further purified by crystallization, distillation at reduced pressure, or liquid chromatography.

In another synthetic scheme (Reduction Method-2), which is preferred when Z is a single bond or carbon based, the "Generic Imine" of Formula XII is slurried in a lower alcohol such as ethanol, methanol or like solvent at 0–10° C. and solid sodium borohydride is added in batches over 5–10 minutes at 0–10° C. with stirring. The reaction mixture is stirred below 10° C. for 30–90 minutes and then is warmed gradually to 15–30° C. After about 1–10 hours, the mixture is cooled and acid is added until the aqueous layer was just acidic (pH 5–7).

Isolation of the desired product can be accomplished, for example, by extracting the aqueous layer twice with a solvent, such as diethyl ether or methylene chloride, that is immiscible with water. The combined solvent extract is washed with saturated brine, dried with a drying agent such as anhydrous MgSO4, and concentrated in vacuo to yield the "Generic Secondary Amines" amine, aniline, or amine of Formula XIII. If needed the "Generic Secondary Amines" amine, aniline, or amine derivative can be further purified by crystallization, distillation at reduced pressure, or liquid chromatography.

In yet another synthetic scheme (Reduction Method-3), which is preferred when Z is an oxygen, the "Generic Imine" oxime of Formula XII is slurried in a lower alcohol solvent such methanol or like solvent at 0–10° C. and acidified to a pH less than 4. Solid sodium cyanoborohydride is added in batches over 30–90 minutes at 0–20° C. with stirring and addition of a suitable organic or mineral acid to keep the pH at or below 4. The reaction mixture is stirred and warmed gradually to about 20–25° C. After about 1–10 hours, the mixture is cooled and base added until the mixture was just slightly alkaline.

Isolation of the desired product can be accomplished, for example, by removing the methanol or other low boiling solvent in vacuo. The residue is slurried with water and aqueous-organic mixture is extracted twice with a solvent, such as diethyl ether or methylene chloride, that is immiscible with water. The combined solvent extract is washed with saturated brine, dried with a drying agent such as anhydrous MgSO4, and concentrated in vacuo to yield the "Generic Secondary Amines" hydoxylamine of Formula XIII. If needed the "Generic Secondary Amines" hydroxylamine can be further purified by crystallization, distillation at reduced pressure, or liquid chromatography.

The "Generic Secondary Amines" of Formula XIII can also be prepared, according to Scheme 1 by two alkylation procedures based on the nucleophilic substitution of bromides by amines. In one procedure, "Generic Amine-1" of Formula X is reacted with "Generic Bromide-1" of Formula XXI. In another alkylation procedure, "Generic Amine-2" of Formula XXII is reacted together with "Generic Bromide-2" of Formula XXIII.

In one synthetic alkylation scheme (Alkylation Method-1), a "Generic Amine-1" of Formula X is reacted with a "Generic Bromide-2" of Formula XXIII as described in Vogel's Textbook of Practical Organic Chemistry, Fifth Edition, 1989, pages 902 to 905 and references cited therein all of which are incorporated herein by reference. In this procedure, the "Generic Amine-1" is placed in a reaction vessel equipped with a reflux condenser with the capability to either cool or heat the vessel as dictated by the reaction. A suitable "Generic Amine-1" will be selected from primary amine and primary aromatic amine classes of compounds. Cooling may be needed and used should the reaction prove strongly exothermic. Heating may be needed and used to drive the reaction to completion. A suitable solvent may also be used to dissolve the "Generic Amine-1". Suitable solvents are hydrocarbons such as toluene, hexane, xylene, and cyclohexane, ethers, amides such as dimethylformamide, esters such as ethyl acetate, ketones such as acetone, and nitriles such as acetonitrile or mixtures of two or more of these solvents. A suitable base is also added to the reaction vessel. Suitable bases include cesium carbonate, calcium carbonate, sodium carbonate and sodium bicarbonate. The base will normally be added in at least a stoichmetric quantity compared to the "Generic Amine-1" so as to neutralize liberated acid as it forms.

The "Generic Bromide-1" of Formula XXIII is then added to the reaction vessel in portions so as to minimize the rate of heat evolution and minimize the concentration of the "Generic Bromide-1". The "Generic Bromide-1" will be selected from primary and secondary organic alkyl and substituted alkyl halide compounds. The halide will preferrably be a bromide although iodides and chlorides may also be generally used. One of skill in the art will also be able to readily select and utilize organic alkyl and substituted alkyl compounds containing readily displaceable primary and secondary groups such as tosylates, mesylates, triflates, and the like. Alternately, the halides can be generally prepared from the corresponding alcohols by reaction with, for example, concentrated hydrohalic acids such as HBr or by reaction with phosphorus trihalides such as $PBr_3$ as described in Fieser and Fieser in Reagents for Organic Synthesis, Volume 1, John Wiley & Sons, which are incorporated herein by reference. The appropriate alcohols can be converted to tosylates, mesylates, and triflates using procedures described below.

Addition of the "Generic Bromide-1" is carried out over a period of a few minutes to several hours at temperatures between 0 and 150° C. Preferrably, the addition will take 30–120 minutes at a temperature of 0 to 50° C. The reaction can be stirred until completion. Completion can be monitored, for example, spectroscopically using nuclear magnetic resonance or chromatographically using thin layer, liquid, or gas chromatographic procedures. If the reaction does not proceed to completion, the reactants may be heated until completion is obtained and verified.

Isolation of the desired product can be accomplished, for example, when a water immiscible solvent was used for the reaction, by adding water to the finished reaction. Additional base such as sodium carbonate can be added to ensure the reaction is basic (pH of 9 to 11). The organic layer containing the "Generic Secondary Amine" is washed with saturated brine, dried with a drying agent such as anhydrous MgSO4, and concentrated in vacuo to yield the "Generic Secondary Amine" amine, aniline, or amine of Formula XIII. If needed the "Generic Secondary Amine" amine, aniline, or amine derivative can be further purified by crystallization, distillation at reduced pressure, or liquid chromatography.

In a second synthetic alkylation scheme (Alkylation Method-2), a "Generic Amine-2" of Formula XXII is reacted with a "Generic Bromide-2" of Formula XXIII in a method employing pallladium catalyzed carbon-nitrogen bond formation. Suitable procedures for this conversion are described in Wagaw and Buchwald, J. Org. Chem. (1996), 61, 7240–7241, Wolfe, Wagaw and Buchwald, J. Am. Chem. Soc. (1996), 118, 7215–7216, and Wolfe and Buchwald, Tetrahedron Letters (1997), 38(36), 6359–6362 and references cited therein all of which are incorporated herein by reference. The preferred "Generic Bromide-2" of Formula XXIII are generally aryl bromides, aryl triflates, and heterocyclic bromides.

The "Generic Amine-1" and "Generic Amine-2" amines, hydroxylamines, and hydrazines, the "Generic Carbonyl Compound" aldehydes, ketones, hydrazones, and oximes, and "Generic Bromide-1" and "Generic Bromide-2" halides, tosylates, mesylates, triflates, and precursor alcohols required to prepare the "Generic Secondary Amine" compounds are available from commercial sources and/or can be prepared by one skilled in the art from published procedures. Commercial sources include but are not limited to Aldrich Chemical, TCI-America, Lancaster-Synthesis, Oakwood Products, Acros Organics, and Maybridge Chemical. Disclosed procedures for "Generic Amine" amines, hydroxylamines, and hydrazines include Sheradsky and Nov, J. Chem. Soc., Perkin Trans.1 (1980), (12), 2781–6; Marcoux, Doyc, and Buchwald, J. Am. Chem. Soc. (1997), 119, 1053–9; Stembach and Jamison, Tetrahedron Lett. (1981), 22(35), 3331–4; U.S. Pat. No. 5,306,718; EP No. 314435; WO No. 9001874; WO No. 9002113; JP No. 05320117; WO No. 9738973; Swiss Patent No. CH 441366; U.S. Pat. Nos. 3,359,316 and 3,334,017; and references cited therein which are incorporated herein by reference. Representative specific "Generic Secondary Amine" of Formula XIII compounds useful for the preparation of compounds of the present invention are listed in Tables 3, 6, 11 and 13.

Synthetic Scheme 2 shows the preparation of the class of compounds of the present invention corresponding to Formula I ("Generic tertiary-OmegaHeteroalkylamine"). Formula I-I ("Generic Aromatic tertiary-OmegaHeteroalkylamine"), Formula III ("Generic tertiary-2-heteroalkylamine"), and Formula III-III and III-IIIA ("Generic Aromatictertiary-2-heteroalkylamine").

Derivatives of "Generic tertiary-OmegaHeteroalkylamine" of Formula I and Formula I-I and I-IA ("Generic Aromatic tertiary-OmegaHeteroalkylamines") in which the hetero atom (—O—, —N═, or —S—) are attached to an alkyl group removed from the amine by two or more carbons are readily prepared by anion chemistry using Method B of Scheme 2. The anion of "Generic Secondary Amine" amines, hydroxylamines, and hydrazines of Formula XIII are readily formed by dissolving the specific amine, hydroxylamine, or hydrazine in an aprotic solvent, such as tetrahydrofuran, toluene, ether, dimethylformamide, and dimethylformamide, under anhydrous conditions. The solution is cooled to a temperature between −78 and 0° C., preferrably between −78 and −60° C. and the anion formed by the addition of at least one equivalent of a strong, aprotic, non-nucleophillic base such as NaH or n-butyllithium under an inert atmosphere for each acidic group present. Maintaining the temperature between −78 and 0° C., preferrably between −78 and −60° C., with suitable cooling, an appropriate alkyl halide, alkyl benzenesulfonate such as a alkyl tosylate, alkyl mesylate, alkyl triflate or similar alkylating reagent of the general structure,

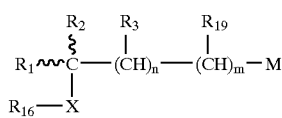

(XXX)

where M is a readily displaceable group such as chloride, bromide, iodide, tosylate, triflate, and mesylate. After allowing the reaction mixture to warm to room temperature, the reaction product is added to water, neutralized if necessary, and extracted with a water-immiscible solvent such as diethyl ether or methylene chloride. The combined aprotic solvent extract is washed with saturated brine, dried over drying agent such as anhydrous MgSO4 and concentrated in vacuo to yield crude Formula I ("Generic tertiary-OmegaHeteroalkylamine") and Formula I-I and I-IA ("Generic Aromatic tertiary-OmegaHeteroalkylamine"). This material is purified, for example, by eluting through silica gel with 5–40% of a medium polar solvent such as ethyl acetate in a non-polar solvent such as hexanes to yield Formula I ("Generic tertiary-OmegaHeteroalkylamine") and Formula I-I and I-IA ("Generic Aromatic tertiary-OmegaHeteroalkylamine"). Products are tested for purity by HPLC. If necessary, the Formula I ("Generic tertiary-OmegaHeteroalkylamine") and Formula I-I and I-IA ("Generic Aromatic tertiary-OmegaHeteroalkylamine") compounds are purified by additional chromatography or recrystallization. Products are structurally confirmed by low and high resolution mass spectrometry and NMR. Examples of specific Formula I ("Generic tertiary-OmegaHeteroalkylamine") and Formula I-I and I-IA ("Generic Aromatic tertiary-OmegaHeteroalkylamine"), compounds prepared are summarized in Tables 15 and 16.

Sources of specific, representative, non-limiting example alcohol-glycol derivatives of the general structure:

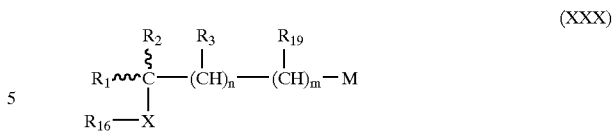

(XXX)

used to prepare the "Generic tertiary-omega-Heteroalkylamine" compounds of Tables 15 and 16 are given in Table 2. Reagents 2a and 3a in Table 2 are prepared from the corresponding alcohols available from the indicated sources. The tosylates are readily obtained by reacting the corresponding alcohol with tosyl chloride using procedures found in House's Modern Synthetic Reactions, Chapter 7, W. A. Benjamin. Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons, which are incorporated herein by reference.

A preferred procedure for Formula III ("Generic tertiary-2-heteroalkylamine"), and Formula III-III and III-IIIA ("Generic Aromatictertiary-2-heteroalkylamines") compounds is Method A of Scheme 2. Oxirane, thiiranes, and aziridine reagents useful in Method A are exemplified, but not limited to those in Table 1. Formula III ("Generic tertiary-2-heteroalkylamine"), and Formula III-III and III-IIA ("Generic Aromatictertiary-2-heteroalkylamines") compounds are prepared by using "Generic Secondary Amine" amines, hydroxylamines, and hydrazines of Formula XIII prepared above with oxiranes, thiiranes, or aziridines of the type listed in Table 1 and represented by the general structure:

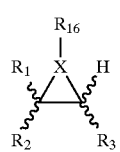

(XX)

In some cases as indicated by metachloroperbenzoic acid (MCPBA) in the source table, some of the oxiranes are prepared by reaction of epoxidation reagents such as MCPBA and similar type reagents readily selectable by a person of skill-in-the-art with alkenes. Fieser and Fieser in Reagents for Organic Synthesis, John Wiley & Sons provides, along with cited references, numerous suitable epoxidation reagents and reaction conditions, which are incorporated herein by reference. Oxiranes having a specific stereochemical arrangement of $R_1$, $R_2$ and $R_3$ can be prepared chiral using procedures such as those published in 1995 by Ramachandran, Gong, and Brown in the Journal of Organic Chemistry, Vol. 60, pages 41 to 46 along with cited references, which are incorporated herein by reference.

A mixture of a "Generic Secondary Amine" amine, hydroxylamine, or hydrazine of Formula XIII and an oxirane, thiirane, or aziridine of Formula XX are stirred and heated to 60–90° C. for 5 to 48 hours in a tightly capped or contained reaction vessel. A Lewis acid such as ytterbium triflate in tetrahydrofuran may be added to speed up reaction and improve yield. When a Lewis acid is used, the reaction should be carried out under inert, anhydrous conditions using a blanket of dry nitrogen or argon gas. After cooling to room temperature and testing the reaction mixture for complete reaction by thin layer chromatography or high pressure liquid chromatography (hplc), the reaction product is added to water and extracted with a solvent immisible such as diethyl ether or methylene chloride. (Note: If the above analysis indicates that reaction is incomplete, heating should be resumed until complete with the optional addition of more of the oxirane, thiirane, or aziridine.) The combined aprotic solvent extract is washed with saturated brine, dried over drying agent such as anhydrous MgSO4 and concentrated in vacuo to yield crude Formula III ("Generic tertiary-2-heteroalkylamine"), and Formula III-III and III-IIIA ("Generic Aromatic tertiary-2-heteroalkylamines") compounds. This material is purified by eluting through silica gel with 5–40% of a medium polar solvent such as ethyl acetate in a non-polar solvent such as hexanes to yield the Formula III ("Generic tertiary-2-heteroalkylamine"), and Formula III-III and III-IIIA ("Generic Aromatic tertiary-2-heteroalkylamines") Products are tested for purity by HPLC. If necessary, the Formula III ("Generic tertiary-2-heteroalkylamine"), and Formula III-III and III-IIIA ("Generic Aromatic tertiary-2-heteroalkylamines") compounds are purified by additional chromatography or recrystallization. Products are structurally confirmed by low and high resolution mass spectrometry and NMR. Examples of specific Formula III ("Generic tertiary-2-heteroalkylamine"), and Formula III-III and III-IIIA ("Generic Aromatic tertiary-2-heteroalkylamines") compounds prepared are summarized in Table 4, 5, 7, 8, 9, 12, and 14.

Synthetic Schemes 13, 14, 15, and 16 shows the preparation of a class of compounds of the present, invention corresponding to Formula I ("Generic tertiary-OmegaHeteroalkylamine"), Formula I-I ("Generic Aromatic tertiary-OmegaHeteroalkylamine"), Formula III ("Generic tertiary-2-heteroalkylamine"), Formula III-III and III-IIIA ("Generic Aromatic tertiary-2-heteroalkylamine"), Formula V-H, V-HA, V-HAX, and V-HX ("Generic Heteroaryl Tertiary Omegaheteroalkylamines), and Formula VII, VIIA, VIIAX, and VIIX ("Generic Phenyl Tertiary Omegaheteroalkylamines).

Derivatives of Formula I ("Generic tertiary-OmegaHeteroalkylamine"), Formula I-I ("Generic Aromatic tertiary-OmegaHeteroalkylamine"), Formula III ("Generic tertiary-2-heteroalkylamine"), Formula III-III and III-IIIA ("Generic Aromatic tertiary-2-heteroalkylamine"), Formula V-H, V-HA, V-HAX, and V-HX ("Generic Heteroaryl Tertiary Omegaheteroalkylamines), and Formula VII, VIIA, VIIAX, and VIIX ("Generic Phenyl Tertiary Omegaheteroalkylamines) in which a hydrogen or halogen such as fluoride has replaced the hetero atom (—O—, —N=, or —S—) in an alkyl group removed from the amine by two or more carbons are readily prepared by acylation chemistry using Schemes 13, 14, 15, and 16.

In the first step, the "Generic Secondary Amine" amines, hydroxylamines, and hydrazines of Formula XIII are first dissolved in an aprotic solvent, such as tetrahydrofuran, toluene, ether, dimethylformamide, and dimethylformamide, under anhydrous conditions in the present of at least one molecular equivalent of a tertiary amine such as triethylamine or tri-n-butylamine. The solution is cooled to a temperature between −78 and 50° C., preferably between −30 and 10° C., and at least one molar equivalent of an acylating agent added in portions so as to maintain the temperature between −78 and 50° C., preferably between −30 and 10° C., with suitable cooling. A suitable acylating agent, for example, will have the general structure,

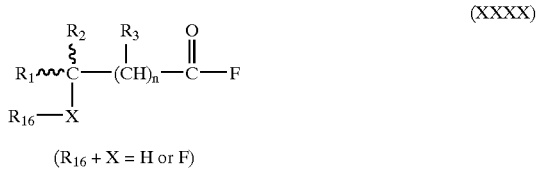

(XXXX)

($R_{16}$ + X = H or F)

where F is a readily displaceable group such as fluoride, chloride, or bromide, and $R_1$, $R_2$, $R_3$, and n are as defined previously herein. After allowing the reaction mixture to warm to room temperature, the reaction product is added to water, acidified if necessary, and extracted with a water-immiscible solvent such as diethyl ether or methylene chloride. The combined aprotic solvent extract is washed with saturated brine, dried over drying agent such as anhydrous MgSO4 and concentrated in vacuo to yield a crude acylated intermediate amide (XXXXI). This material can be used as is in the next step or, if judged to be impure, purified, for example, by eluting through silica gel, for example, with 5–90% of a medium polar solvent such as ethyl acetate in a non-polar solvent such as hexanes to yield materials of Formula (XXXXI).

In the second step, a resulting amide of Formula (XXXXI) can then be converted to a compound of Formula I ("Generic tertiary-OmegaHeteroalkylamine"), Formula I-I ("Generic Aromatic tertiary OmegaHeteroalkylamine"), Formula III ("Generic tertiary-2-heteroalkylamine"), Formula III-III and III-IIIA ("Generic Aromatic tertiary-2-heteroalkylamine"), Formula V-H, V-HA, V-HAX, and V-HX ("Generic Heteroaryl Tertiary Omegaheteroalkylamines), and Formula VII, VIIIA, VIIAX, and VIIX ("Generic Phenyl Tertiary Omegaheteroalkylamines) by reduction under anhydrous aprotic conditions with an inert atmosphere using borane-dimethylsulfide in a suitable solvent, such as tetrahydrofuran, toluene, or diethyl ether, or lithium aluminum hydride in a suitable solvent such as diethyl ether, tetrahydrofuran, glyme, or dioxane. The reaction is carried out at a temperature between −78 and 100° C., preferably between 25 and 100° C., most preferably at reflux of the solvent, with at least one molar equivalent of the reducing agent. When the reduction is completed in one to 24 hours, the reaction mixture is cooled and the excess reducing agent is destroyed by adding a minimal, sufficient amount of aqueous mineral acid. The resulting reaction mixture is added to water and then adjusted to pH 8 to 10 with an alkali metal hydroxide such as sodium hydroxide. The resulting mixture is then extracted multiple times with a water-immiscible solvent such as diethyl ether, toluene, or methylene chloride. The combined aprotic solvent extract is washed with saturated brine, dried over drying agent such as anhydrous $MgSO_4$ and concentrated in vacuo to yield crude Formula I ("Generic tertiary-OmegaHeteroalkylamine"), Formula I-I ("Generic Aromatic tertiary-OmegaHeteroalkylamine"), Formula III ("Generic tertiary-2-heteroalkylamine"), Formula III-III and III-IIIA ("Generic Aromatic tertiary-2-heteroalkylamine"), Formula V-H, V-HA, V-HAX, and V-HX ("Generic Heteroaryl Tertiary Omegaheteroalkylamines), and Formula VII, VIIA, VIIAX, and VIIX ("Generic Phenyl Tertiary Omegaheteroalkylamines) compounds. This material is purified by eluting through silica gel with 5–40% of a medium polar solvent such as ethyl acetate in a non-polar solvent such as hexanes to yield the desired compounds. Products are tested for purity by HPLC. If necessary, the compounds are purified by additional chromatography or recrystallization. Products are structurally confirmed by low and high resolution mass spectrometry and NMR.

Specific, representative, non-limiting example acylating derivatives of the general structure,

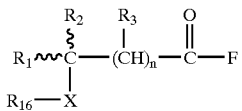

(XXXX)

($R_{16}$ + X = H or F)

wherein F is a readily displaceable group such as fluoride, chloride, or bromide, and $R_1$, $R_2$, $R_3$, and n are as previously defined, are readily available by reference to the scientific literature or commercial sources. Alternatively, the carboxylic acids corresponding to XXXX, wherein F equals OH, are readily available by reference to the scientific literature or commercial sources and can be readily converted with a suitable reagent to XXXX, wherein F equals fluoride, chloride, or bromide. Suitable reagents are well-known in the art and include thionyl chloride, phosphorus trichloride, 2,4,6-trifluorotriazene, and thionyl bromide.

Formula I ("Generic tertiary-OmegaHeteroalkylamine"), Formula I-I and I-IA ("Generic Aromatic tertiary-OmegaHeteroalkylamines"). Formula III ("Generic tertiary-2-heteroalkylamine"), and Formula III-III and III-IIIA ("Generic Aromatic tertiary-2-heteroalkylamines") compounds can be readily converted to a broad array and type of their corresponding quaternary ammonium salts II, II-II, II-IIA, IV, IV-IV, and IV-IVA, respectively. These quaternary ammonium salts are readily obtained using Schemes 3 and 4.

II, II-II, II-IIA, IV, IV-IV, and IV-IVA are readily obtained by reacting the compound $R_{17}$-G with the Formula I ("Generic tertiary-OmegaHeteroalkylamine"), Formula I-I and I-IA ("Generic Aromatic tertiary-OmegaHeteroalkylamines"), Formula III ("Generic tertiary-2-heteroalkylamine"), and Formula III-III and III-IIIA ("Generic Aromatictertiary-2-heteroalkylamines") compounds. $R_{17}$-G as defined above is typically a primary or secondary lower alkyl, higher alkyl, lower alkenyl, higher alkenyl, lower alkynyl, higher alkynyl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, and heteroarylalkenyl halide or sulfonate ester. A wide variety and types of $R_{17}$-G are commercially available or can be prepared from readily available precursor alcohols by well-established procedures known to those of skill-in-the-art. Suitable procedures for preparing II, II-II, II-IIA, IV, IV-IV, and IV-IVA can be found in in House's Modem Synthetic Reactions, Chapter 7, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons which are incorporated herein by reference.

Formula I ("Generic tertiary-OmegaHeteroalkylamine"), Formula I-I and I-IA ("Generic Aromatic tertiary-OmegaHeteroalkylamines"), Formula III ("Generic tertiary-2-heteroalkylamine"), and Formula III-III and III-IIIA ("Generic Aromatictertiary-2-heteroalkylamines") and other compounds of this invention can be converted to the corresponding acyl derivatives. The hydroxyl, thiol, and amino group X, wherein $R_{16}$ is a hydrogen or a hydrogen is present on the amino group, of compounds of Formulas I, II, III, IV, I-I, II-II, I-IA, II-IIA, III-III, IV-IV, III-IIIA, IV-IVA, V, VI, VA, VIA, V-H, VI-H, VX, VIX, V-HX, VI-HX, V-HA, VI-HA, V-HAX, VI-HAX, VAX, VIAX, VII, VIIA, VIIAX, VIIX, VIII, VIIIA, VIIIX, and VIIAX can be readily acylated to their corresponding esters, thioesters, and amides. Acylation is readily effected using a suitable acylating reagent such as an aliphatic or aromatic acid anhydride or acid chloride. Such reactions are generally carried out using an amine catalyst such as pyridine in an inert solvent.

Suitable procedures for preparing acylated derivatives can be found in House's Modem Synthetic Reactions, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons. Acylating agents of a wide variety that can be used are available from commerical sources or the references cited above, which are incorporated herein by reference.

Certain Formula I ("Generic tertiary-OmegaHeteroalkylamine"), Formula I-I and I-IA ("Generic Aromatic tertiary-OmegaHeteroalkylamines"), Formula III ("Generic tertiary-2-heteroalkylamine"), and Formula III-III and III-IIIA ("Generic Aromatictertiary-2-heteroalkylamines") and certain other compounds of this invention can be converted to the corresponding cyclic derivatives represented by the general designation "Tricyclic tertiary-heteroalkylamines" exemplified by Formula Cyclo-VII ("Substituted Tricyclic Phenyl tertiary-2-Heteroalkylamines"). The hydroxyl, thiol, or amino group X, wherein $R_{16}$ is a hydrogen or a hydrogen is present on the amino group, of compounds of Formulas I, II, III, IV, I-I, II-II, I-IA, II-IIA, III-III, IV-IV, III-IIIA, IV-IVA, V, VI, VA, VIA, V-H, VI-H, VX, VIX, V-HX, VI-HX, V-HA, VI-HA, V-HAX, VI-HAX, VAX, VIAX, VII, VIIA, VIIAX, VIIX, VIII, VIIIA, VIIIX, and VIIIAX can be cyclized to corresponding cyclic ethers, thioethers, and amines. Compounds suitable for cyclization will normally have at least one leaving group within 5 to 10 continuous atoms of the hydroxyl, thiol, and amino group X wherein $R_{16}$ is a hydrogen or a hydrogen is present on the amino group. Most preferrably the leaving group will be within 5 to 7 atoms of the hydroxyl, thiol, and amino group X so as to form a 5 to 7 membered ring heteroatom containing ring. When the leaving group is part of an aromatic ring system, the leaving group will be preferrably in an ortho position. Suitable leaving groups generally include halides, sulfates, sulfonates, trisubsituted amino, disubstituted sulfonium, diazonium, and like, and, in the case of aromatic systems, also includes nitro, alkoxy, aryloxy, heteroaryloxy, and alkylthio.

The cyclization reaction to form "Tricyclic tertiary-heteroalkylamines" can be accomplished by aromatic and aliphatic nucleophilic substitution reactions such as those disclosed in March's Advanced Organic Chemistry, 4th Edition, John Wiley & Sons, especially at pages 293–412 and 649–658 and the references cited therein, which are incorporated herein by reference. Hydroxyl, thiol, and amino containing suitably substituted compounds can be converted, according to Schemes 17 and 18, to a cyclic analog by heating a suitably substituted compound under anhydrous conditions in a suitable solvent, such as dimethylformamide (DMF), dimethylsulfoxide (DMSO), N-methylpyrrolidone, tetraglyme, or hexamethylphosphoramide (HMPA), in the presence of a suitable base such as potassium carbonate, cesium carbonate, sodium hydroxide, potassium tertiary-butoxide, or lithium diisopropylamide (LDA). Alternately, sodium amide in anhydrous ammonia solvent can be used. Temperatures in the range of –20° C. to 200° C. can be used for lime periods of 30 minutes to more than 24 hours. The preferred temperature can be selected by standard synthetic chemical technique balancing maximum yield, maximum purity, cost, ease of isolation and operation, and time required. Isolation of the "Tricyclic tertiary-heteroalkylamines" can be effected as described above for other tertiary-heteroalkylamines.

Schemes 5, 6, 7, 8, 9, 10, 11, 12, 13, 14, 15, 16, 17, and 18 given below provide synthetic routes for other embodiments of the compounds of the present invention. Schemes 5, 6, 7, 8, 9, 10, 11, 12, 13, 14, 15, 16, 17, and 18 can be readily used to prepare these compounds as well.

One skilled in the art may use these generic methods to prepare the following specific examples, which have been properly characterized by $^1$H NMR and mass spectrometry. These compounds also may be formed in vivo.

The following examples contain detailed descriptions of the methods of preparation of compound of Formula I. These detailed descriptions fall within the scope and are presented for illustrative purposes only and are not intended as a restriction on the scope of the invention. All parts are by weight and temperatures are Degrees centigrade unless otherwise indicated.

EXAMPLE 1

Preparation of Compound 1N

The 3-phenoxyaniline (2.78 g, 15 mmol) and 3-tetrafluoroethoxy-benzaldehyde 3.332 g, 15 mmol) were refluxed in cyclohexane (60 mL) using a Dean-Stark trap to remove water. After 4 hours, the cyclohexane was removed in vacuo to yield imine (5.63 g). The imine was slurried in methanol (60 mL) at 0° C. and solid NaBH$_4$ (1 g, 29 mmole) was added in batches over 5 minutes at 0° C. with stirring. The reaction mixture was stirred below 10° C. for 30 minutes and then warmed gradually to 20° C. After 4 hours, the mixture was cooled and 3% hydrochloric acid solution was added until the aqueous layer was just acidic. The aqueous solution was extracted twice with diethyl ether. The combined diethyl ether extract was washed with saturated brine (2 times) and water (1 time), dried over drying agent such as anhydrous MgSO$_4$ and concentrated in vacuo to yield the amine 1N (4.15 g, 70.1% yield overall). MS parent ion: 391. NMR (CDCl$_3$) ppm: 6.97–7.35 (10H, m), 6.37 (2H, m), 6.27 (1H, t, J=2.2 Hz), 5.90 (1H, tt, J=53.3, 2.9 Hz), 4.32 (2H bs).

Preparation of Amino Alcohol 1-1N

The amine 1N (3.13 g, 8 mmol) prepared above and 3,3,3-trifluoro-1,2-epoxypropane (1.26 g, 11.2 mmol) were stirred and heated to 90° C. for 24 hours in a tightly capped vessel. (A Lewis acid such as ytterbium triflate in tetrahydrofuran can be added to speed up reaction and improve yield provided that the reaction vessel in kept anhydrous by use of a blanket of dry nitrogen or argon gas.) Cool to room temperature, and test for product by TLC. The reaction product, was added to water and extracted with diethyl ether. The diethyl ether extract was washed with saturated brine (2 times) and water (1 time), dried over drying agent such as anhydrous MgSO$_4$ and concentrated in vacuo to yield crude amino alcohol 1-1N. This material was purified by eluting through silica gel with 5–6% ethyl acetate in hexanes to yield amino alcohol 1-1N (2.85 g, 70.8%). Product was one peak by HPLC, reverse phase. MS parent ion: 503. NMR (CDCl$_3$) ppm: 7.30 (3H, m), 7.06–7.20 (4H, m), 7.02 (1H, bs), 6.96 (2H, m), 6.48 (1H, dd, J=8.5, 2.0 Hz), 6.41 (1H, dd, J=7.92, 1.9 Hz), 6.37 (1H, m), 5.89 (1H, tt, J=53.4, 2.9 Hz), 4.64(2H ABq J=17.7, 2.8 Hz), 4.34 (1H, m), 3.87 (1H, dd, J=15.5, 2.9 Hz), 3.55 (1H, dd, J=15.5, 8,9 Hz), 2.41 (1H, bs).

Other substituted tertiary-2-heteroalkylamines including, substituted tertiary-2-hydroxyalkylamines, substituted tertiary-2-aminoalkylamines, and substituted tertiary-2-sulfhydrylalkylamines, can be prepared by one skilled in the art using similar methods. Examples of such compounds are summarized in Tables 4, 5, 7, 8, 9, 12, 14, and 17.

Other substituted tertiary-omega-heteroalkylamines can be prepared by one skilled in the art using similar methods. Examples of such compounds are summarized in Tables 15 and 16.

Other substituted tricyclictertiary-heteroalkylamines can be prepared by one skilled in the art using similar methods. Examples of such compounds are summarized in Table 18.

BIOLOGICAL EVALUATION

Whole Serum CETP Activity Assay (Tritiated Colesterol Eter)

Blood was obtained from healthy volunteers recruited from the personnel of Monsanto Company, Saint Louis, Mo. Blood was either collected in tubes containing EDTA (EDTA plasma pool) or without (spun to form the serum pool). The EDTA human plasma pool or human serum pool, previously stored at −20° C., was thawed at room temperature, and centrifuged for 5 minutes to remove any particulate matter. Tritiated HDL, radiolabeled in the cholesteryl ester moiety ([$^{13}$H]CE-HDL) as described by Morton and Zilversmit (J. Biol. Chem., 256, 11992–95 (1981)), was added to the plasma or serum to a final concentration of (25 µg/ml cholesterol). Inhibitor compounds were added to the plasma or serum as follows: Equal volumes of the plasma or serum containing the [$^3$H]CE-HDL (396 µl) were pipetted into micro tubes (Titertube®, Bio-Rad Laboratories,Hercules, Calif.). Compounds, usually dissolved as 20–50 mM stock solutions in DMSO, were serially diluted in DMSO (or an alternative solvent in some cases, such as dimethylformamide or ethanol). Four µl of each of the serial dilutions of inhibitor compounds or DMSO alone were then added to each of the plasma or serum tubes. The tubes were immediately mixed. Triplicate aliquots (110 µl) from each plasma or serum tube were then transferred to wells of 96-well round-bottomed polystyrene microtiter plates (Corning, Corning, N.Y.). Plates were sealed with plastic film and incubated at 37° C. for 4 hours. Test wells contained plasma or serum with dilutions of inhibitor compounds. Control wells contained plasma or serum with DMSO alone. Blank wells contained plasma or serum with DMSO alone that were left in the micro tubes at 4° C. for the 4 hour incubation and were added to the microtiter wells at the end of the incubation period. VLDL and LDL were precipitated by the addition of 10 µl of precipitating reagent (1% (w/v) Dextran Sulfate (Dextralip50) 0.5M magnesium chloride, pH 7.4) to all wells. The wells were mixed on a plate mixer and then incubated at ambient temperature for 10 min. The plates were then centrifuged at 1000×g for 30 mins at 10° C. The supernatants (50 µl) from each well were then transferred to Picoplate™ 96 plate wells (Packard, Meriden, Conn.) containing 250:1 Microscint™-40 (Packard, Meriden, Conn.). The plates were heat-sealed (TopSeal™-P, Packard, Meriden, Conn.) according to the manufacturers directions and mixed for 30 min. Radioactivity was measured on a microplate scintillation counter (TopCount, Packard, Meriden, Conn.). IC$_{50}$'s were determined as the concentration of inhibitor compound inhibiting transfer of [$^3$H]CE from the supernatant [$^3$H]CE-HDL to the precipitated VLDL and LDL by 50% compared to the transfer obtained in the control wells. The maximum percent transfer (in the control wells) was determined using the following equation:

$$\% \text{ Transfer} = \frac{[dpm_{blank} - dpm_{control}] \times 100}{dpm_{blank}}$$

The percent of control transfer determined in the wells containing inhibitor compounds was determined as follows:

$$\% \text{ Control} = \frac{[dpm_{blank} - dpm_{test}] \times 100}{dpm_{blank} - dpm_{control}}$$

IC$_{50}$ values were then calculated from plots of % control versus concentration of inhibitor compound. Examples of IC$_{50}$ values determined by this method are specified in Table 10

CETP Activity In Vitro

The ability of compounds to inhibit CETP were assessed using an in vitro assay that measured the rate of transfer of radiolabled cholesteryl ester ([3H]CE) from HDL donor particles to LDL acceptor particles. Details of the assay are provided by Glenn et al. ("Quantification of Cholesteryl Ester Transfer Protein (CETP): A) CETP Activity and B) Immunochemical Assay of CETP Protein," *Meth. Enzymol.*, Glenn and Melton (Meth. Enzymol., 263, 339–351 (1996)). CETP was obtained from the serum-free conditioned medium of CHO cells transfected with a cDNA for CETP (Wang, S, et al. *J. Biol Chem.* 267, 17487–17490 1992). To measure CETP activity, [$^3$H]CE-labeled HDL, LDL, CETP and assay buffer (50 mM tris(hydroxymethyl) aminomethane, pH 7.4; 150 mM sodium chloride; 2 mM ethylenediamine-tetraacetic acid; 1% bovine serum albumin) were incubated in a volume of 200μ, for 2 hours at 37° C. in 96 well plates. LDL was differentially precipitated by the addition of 50 μl of 1% (w/v) dextran sulfate/0.5 M magnesium chloride, mixed by vortex, and incubated at room temperature for 10 minutes. The solution (200 μl) was transferred to a filter plate (Millipore). After filtration, the radioactivity present in the precipitated LDL was measured by liquid scintillation counting. Correction for non-specific transfer or precipitation was made by including samples that did not contain CETP. The rate of [$^3$H]CE transfer using this assay was linear with respect to time and CETP concentration, up to 25–30% of [$^3$HCE transferred.

The potency of test compounds was determined by performing the above described assay in the presence of varying concentrations of the test compounds and determining the concentration required for 50% inhibition of transfer of [$^3$H]CE from HDL to LDL. This value was defined as the IC$_{50}$. Examples of IC$_{50}$ values determined by this method are specified in Table 10

Inhibition of CETP Activity In Vivo.

Inhibition of CETP by a test compound can be determined by administering the compound to an animal by intravenous injection, determining the rate of transfer of tritium-labeled cholesteryl ester ($^3$H]CE) from HDL to VLDL and LDL particles, and comparing the rate of transfer with the rate of transfer observed in control animals. Male golden Syrian hamsters were maintained on a diet of chow containing 0.24% cholesterol for at least two weeks prior to the study. Immediately before the experiment, animals were anesthetized with pentobarbital. Anesthesia was maintained throughout the experiment. In-dwelling catheters were inserted into the jugular vein and carotid artery. Test compound was dissolved as a 80 mM stock solution in vehicle (2% ethanol: 98% PEG 400, Sigma Chemical Company, St. Louis. Mo., USA). At the start of the experiment all animals received 0.2 ml of a solution containing [$^3$H]CE-HDL into the jugular vein. [$^3$H]CE-HDL is a preparation of human HDL containing tritium-labeled cholesteryl ester, and was prepared according to the method of Glenn et al. (Meth. Enzymol., 263, 339–351 (1996)). After 2 minutes, animals received 0.1 ml of the test solution injected into the jugular vein. Control animals received 0.1 ml of the vehicle solution without test compound. After 5 minutes, the first blood samples (0.5 ml) were taken from the carotid artery and collected in standard microtainer tubes containing ethylenediame tetraacetic acid. Saline (0.5 ml) was injected to flush the catheter and replace blood volume. Subsequent blood samples were taken at two hours and four hours by the same method. Blood samples were mixed well and kept on ice until the completion of the experiment. Plasma was obtained by centrifugation of the blood samples at 4° C. The plasma (50 μl) was treated with 5 μl of precipitating reagent (dextran sulfate, 10 g/l; 0.5 M magnesium chloride) to remove VLDL/LDL. After centrifugation, the resulting supernatant (25 μl) containing the HDL was analyzed for radioactivity using a liquid scintillation counter. The percentage [$^3$H]CE transferred from HDL to LDL and VLDL (% transfer) was calculated based on the total radioactivity in equivalent serum samples before precipitation. Typically, the amount of transfer from HDL to LDL and VLDL in control animals was 20 to 35% after 4 hours. The polyethylene glycol vehicle was determined to have no effect on CETP activity in this model.

Table 10 shows the results of experiments utilizing compounds of the present invention.

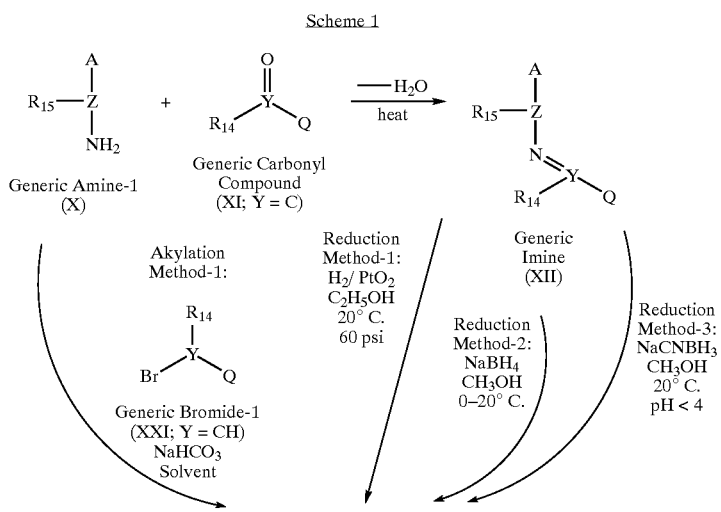

Scheme 1

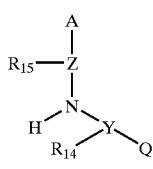
Generic
Secondary
Amine
(XIII)
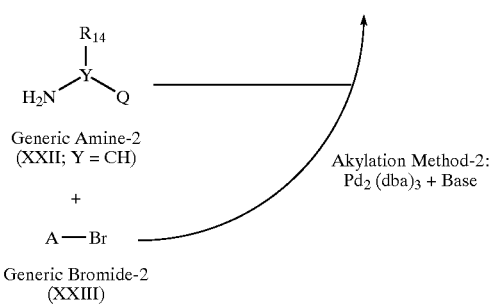
Akylation Method-2:
Pd$_2$(dba)$_3$ + Base
Generic Amine-2
(XXII; Y = CH)
+
A—Br
Generic Bromide-2
(XXIII)
Scheme 2
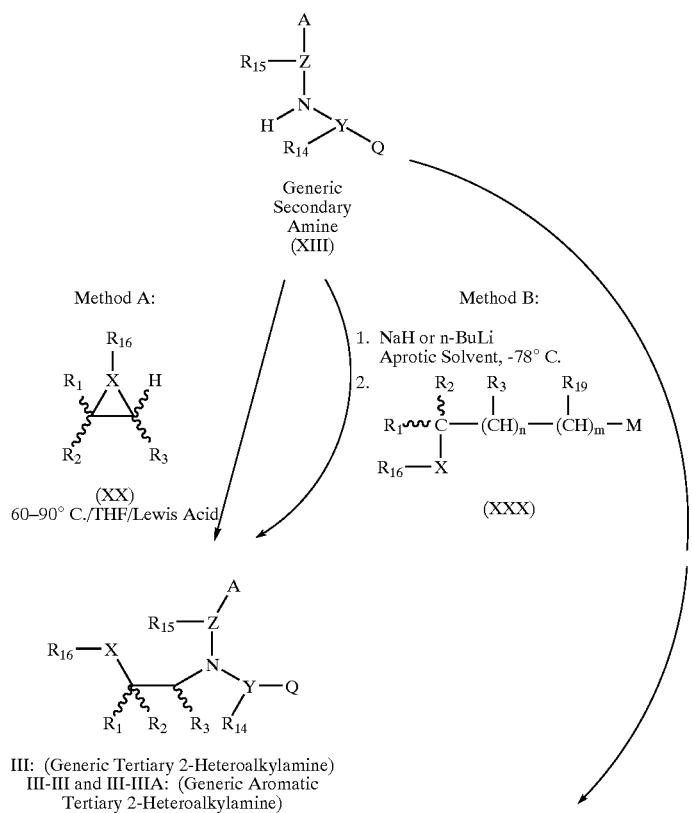
III: (Generic Tertiary 2-Heteroalkylamine)
III-III and III-IIIA: (Generic Aromatic
Tertiary 2-Heteroalkylamine)

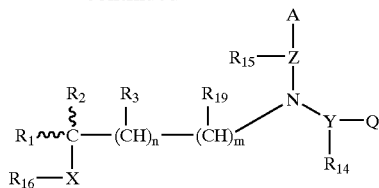

I: (Generic Tertiary OmegaHeteroalkylamine)
I-I and I-IA: (Generic AromaticTertiary OmegaHeteroalkylamine)

Scheme 3

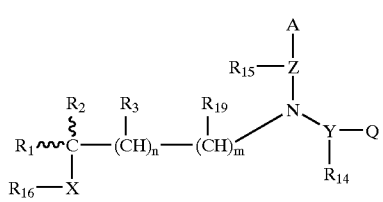

I: (Generic Tertiary Omega Heteroalkylamine)
I-I and I-IA: (Generic Aromatic Tertiary Omega Heteroalkylamine)

heat
$R_{17}$—G

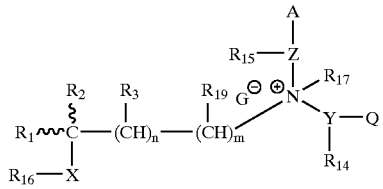

II: Generic Tertiary Omega Heteroalkyl amineammonium Salt
II-II and II-IIA: Generic Aromatic Tertiary OmegaHeteroalkylamineammonium Salt Scheme 4

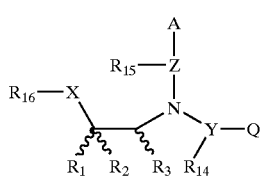

III: (Generic Tertiary 2-Heteroalkylamine)
III-III and III-IIIA: (Generic Aromatic Tertiary 2-Heteroalkylamine)

heat
$R_{17}$—G

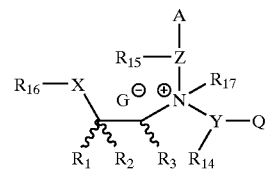

IV: Generic Tertiary 2-Heteroalkylammonium Salt
IV-IV and IV-IVA: Generic Aromatic Tertiary 2-Heteroalkylammonium Salt Scheme 5

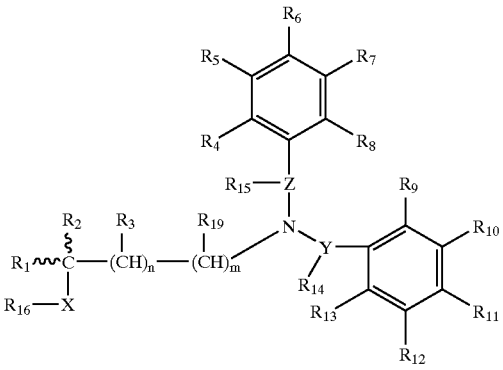

Generic PhenylTertiary OmegaHeteroalkylamines
(V, VA, VAX and VX)

Method B:

Step 1:
NaH or n-BuLi
Aprotic Solvent, -78° C.

Step 2:

(XXX)

Secondary Phenyl Amine
(XIIIA)

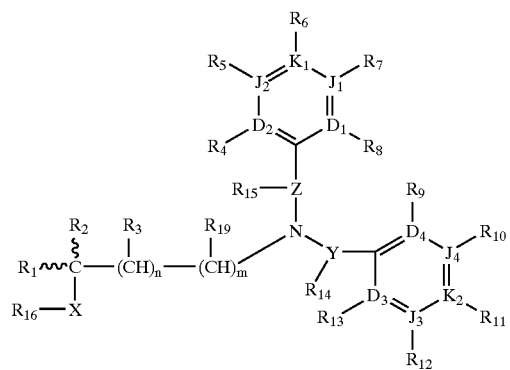

Generic Heteroaryl Tertiary
OmegaHeteroalkylamines
(V-H, V-HA, V-HAX and V-HX)

Scheme 7

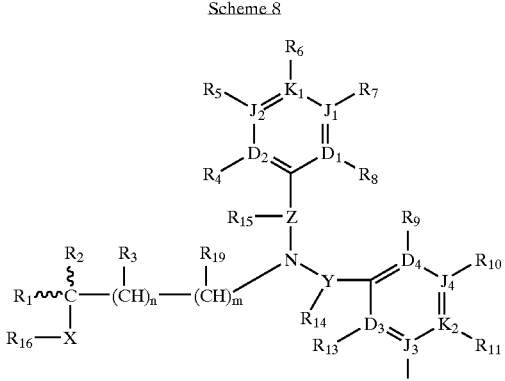

Generic Heteroaryl Tertiary
OmegaHeteroalkylamines
(V-H, V-HA, V-HAX and V-HX)

| heat
| $R_{17}$—G

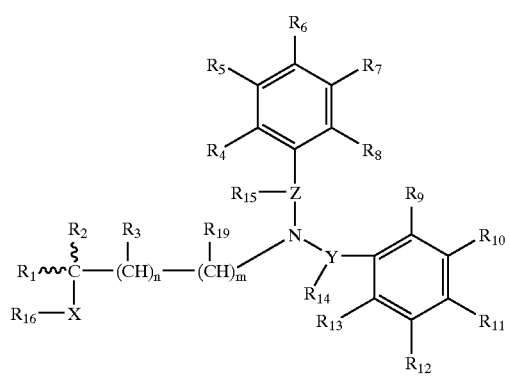

Generic PhenylTertiary
OmegaHeteroalkylamines
(V, VA, VAX and VX)

| heat
| $R_{17}$—G

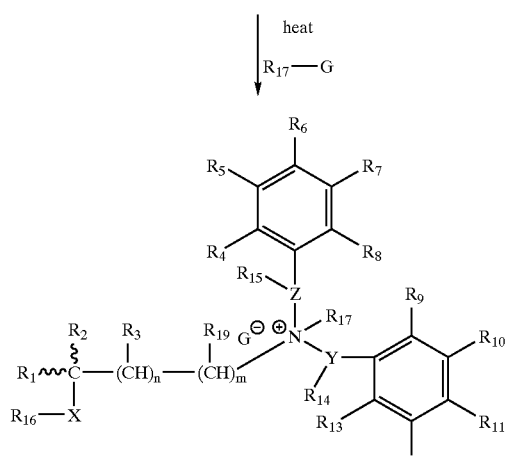

Generic PhenylTertiary
OmegaHeteroalkylammonium Salts
(VI, VIA, VIAX and VIX)

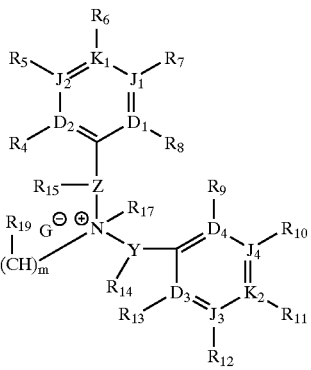

Generic Heteroaryl Tertiary
OmegaHeteroalkylammonium Salts
(VI-H, VI-HA, VI-HAX and VI-HX)

Scheme 8

Scheme 9
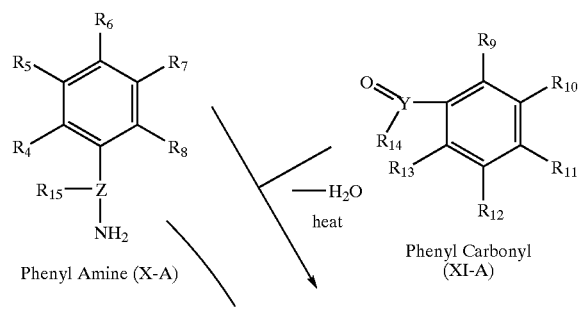
Phenyl Amine (X-A)
Phenyl Carbonyl (XI-A)
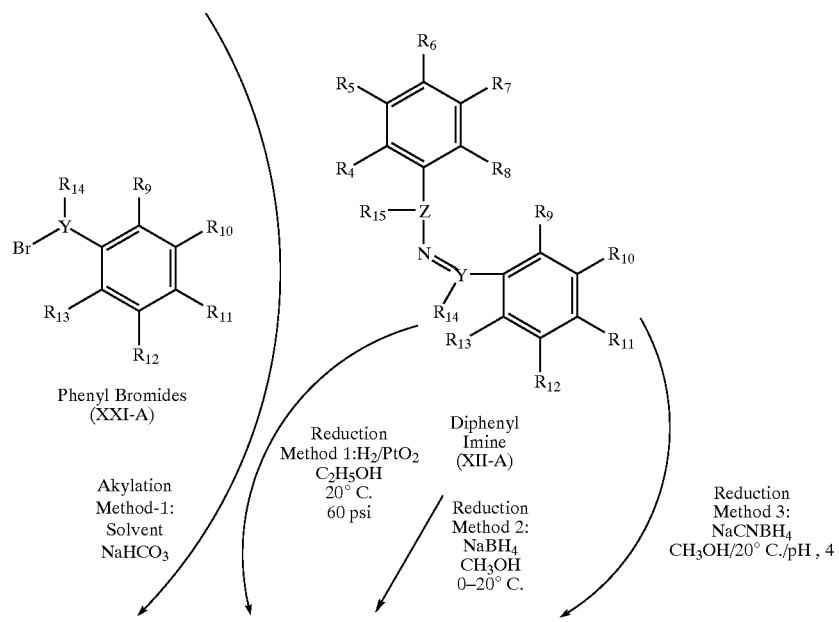
Phenyl Bromides (XXI-A)
Diphenyl Imine (XII-A)
Akylation Method-1: Solvent NaHCO$_3$
Reduction Method 1: H$_2$/PtO$_2$ C$_2$H$_5$OH 20° C. 60 psi
Reduction Method 2: NaBH$_4$ CH$_3$OH 0–20° C.
Reduction Method 3: NaCNBH$_4$ CH$_3$OH/20° C./pH , 4
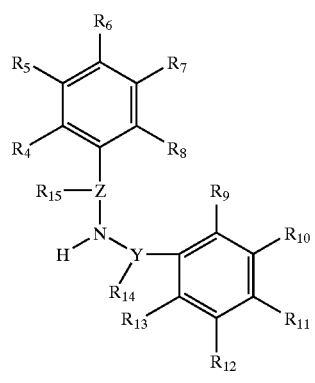
Secondary Phenyl Amine (XIII-A)

Scheme 10

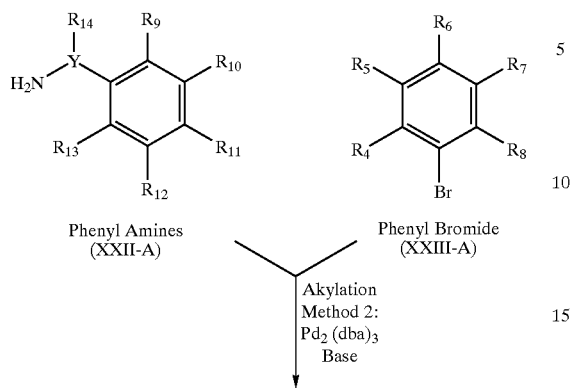

Phenyl Amines (XXII-A)     Phenyl Bromide (XXIII-A)

Akylation Method 2:
Pd₂(dba)₃
Base

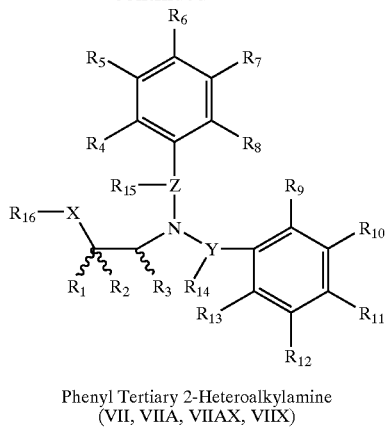

Secondary Phenyl Amine (XIII-A)

Scheme 11

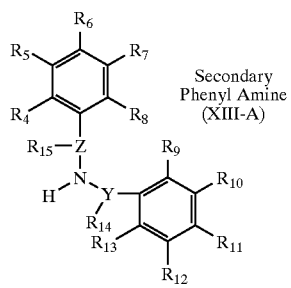

Secondary Phenyl Amine (XIII-A)

Method A:
R₁₆
R₁―X―H
R₂  R₃
(XX)
60–90° C.
THF
Lewis Acid

Method B:
1. NaH or n-BuLi
Aprotic Solvent
―78° C.
2. R₁₆
R₁―X―H
R₂  R₃
(XX)

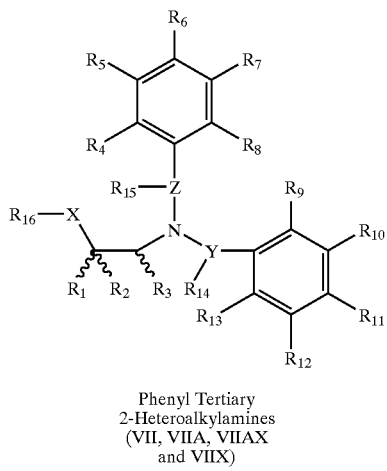

Phenyl Tertiary 2-Heteroalkylamine
(VII, VIIA, VIIAX, VIIX)

Scheme 12

Phenyl Tertiary
2-Heteroalkylamines
(VII, VIIA, VIIAX
and VIIX)

heat
R₁₇―G

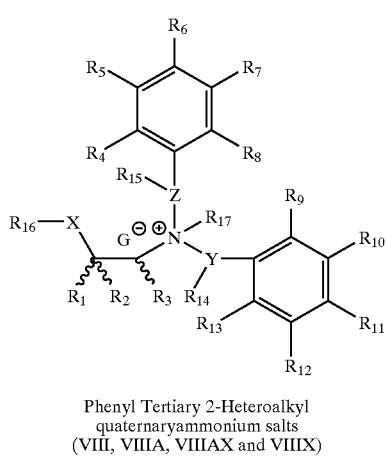

Phenyl Tertiary 2-Heteroalkyl
quaternaryammonium salts
(VIII, VIIIA, VIIIAX and VIIIX)

Scheme 13
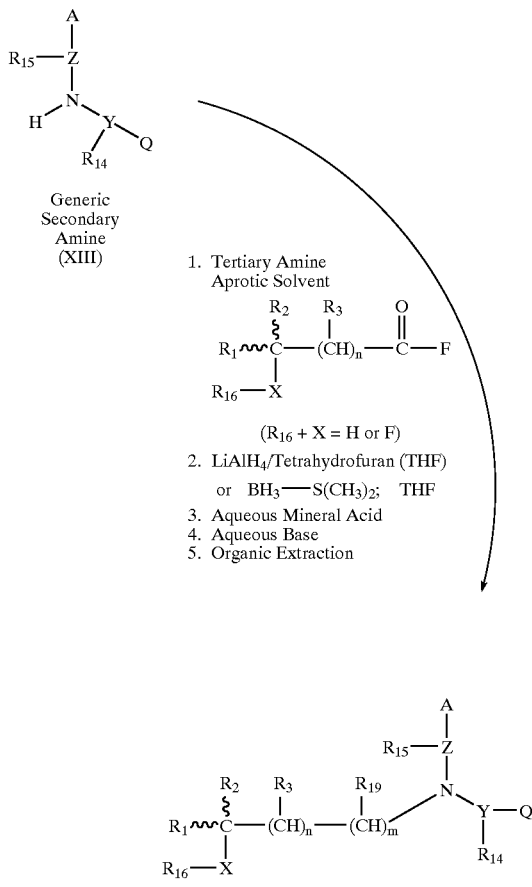
Scheme 14
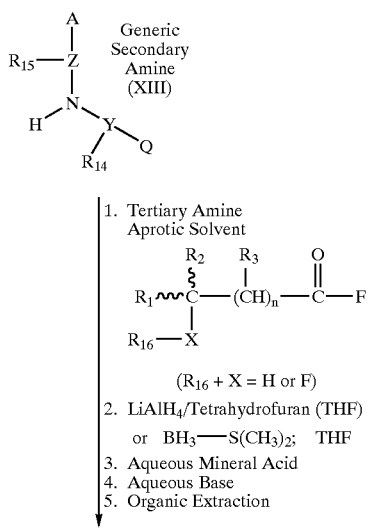
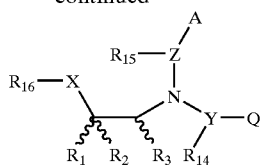
III: Generic Tertiary 2-Heteroalkylamine
($R_3$ = H; n = 0; $R_{16}$ + X = H or F)
III-III and III-IIIA:
Generic Aromatic Tertiary2-Heteroalkylamine
($R_3$ = H; n = 0; $R_{16}$ + X = H or F)
Scheme 15
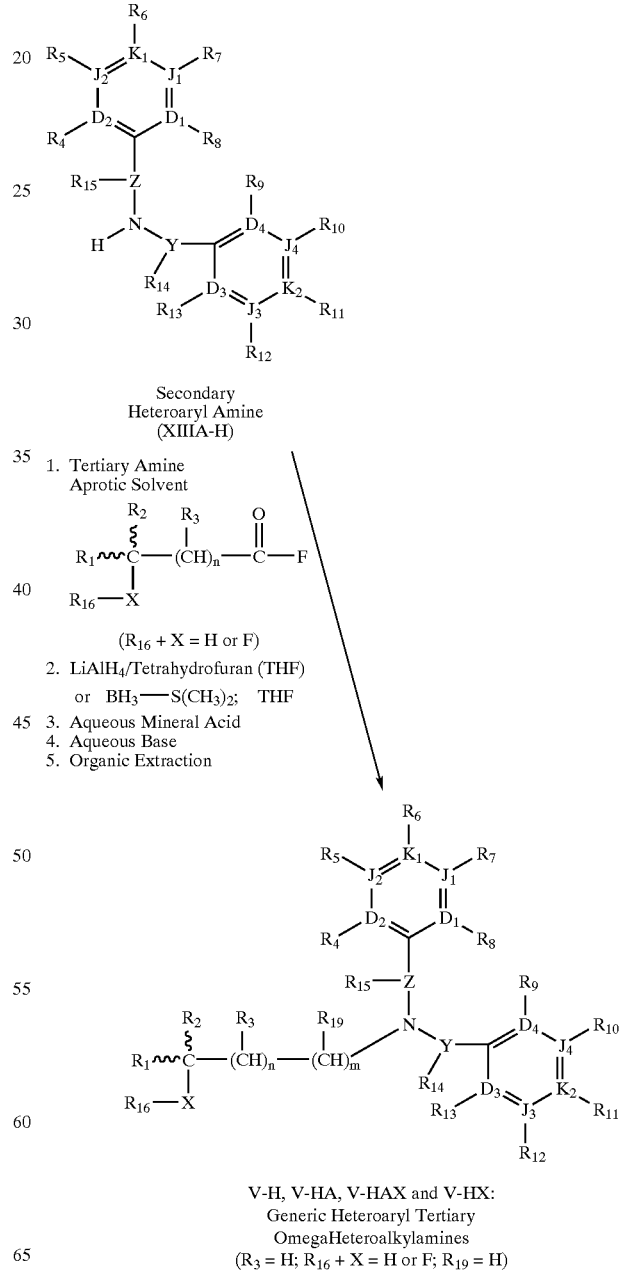

Scheme 16

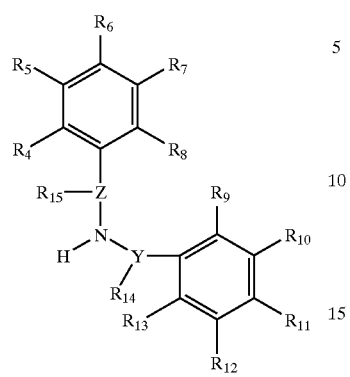

Secondary
Phenyl Amine
(XIII-A)

1. Tertiary Amine
   Aprotic Solvent

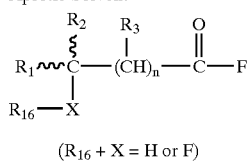

($R_{16}$ + X = H or F)
2. LiAlH$_4$/Tetrahydrofuran (THF)
   or BH$_3$—S(CH$_3$)$_2$; THF
3. Aqueous Mineral Acid
4. Aqueous Base
5. Organic Extraction

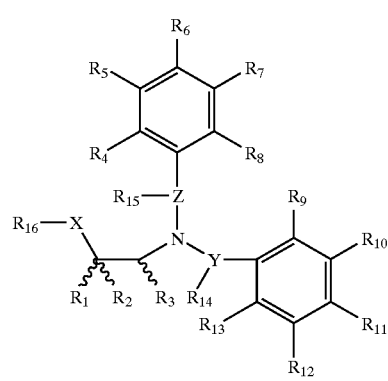

Phenyl Tertiary 2-Heteroalkylamine
(VII, VIIA, VIIAX and VIIX)
($R_3$ =H; $R_{16}$ + X = H or F; $R_{19}$ = H)

Scheme 17

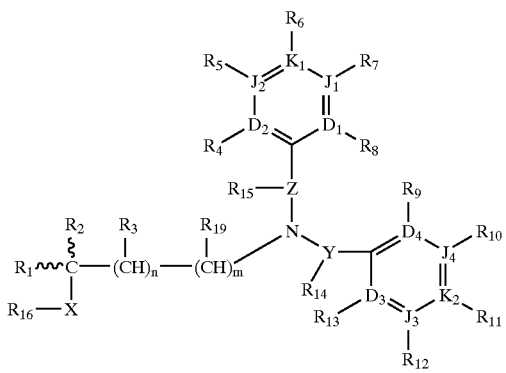

V-H, V-HA, V-HAX and V-HX:
Generic Heteroaryl Tertiary
OmegaHeteroalkylamines ($R_{16}$ = H)

LDA/DMF
or
NaNH$_2$/NH$_3$

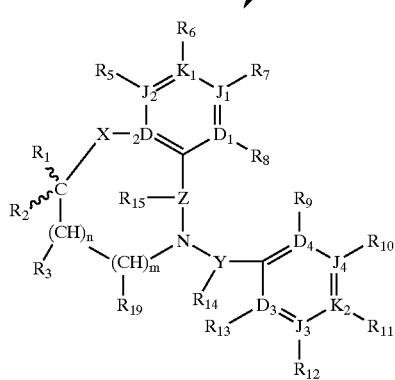

Heteroaryl Cyclo-VII: Substituted
Tricyclic Heteroaryl tertiary-2-Heteroalkylamines Scheme 18

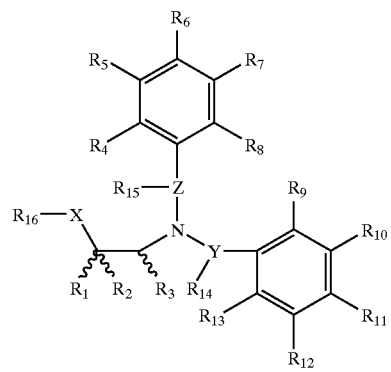

Phenyl Tertiary 2-Heteroalkylamine
(VII, VIIA, VIIAX and VIIX)
($R_{16}$ = H)

LDA/DMF
or
NaNH$_2$/NH$_3$

-continued

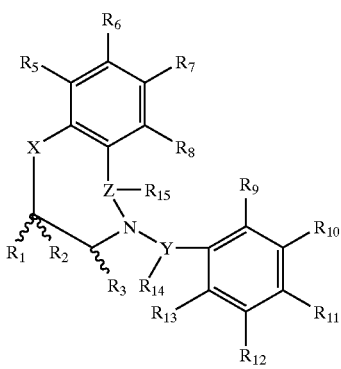

Phenyl Cyclo-VII: Substituted
Tricyclic Phenyl tertiary-2-Heteroalkylamines

TABLE 1

Structure and Source of Oxiranes, Thiaranes and Aziridine Reagents.

(XX)

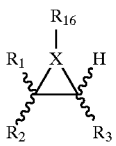

| Reagent Number | $R_1$ | $R_2$ | $R_3$ | $R_{16}$ | X | Source of Reagent |
|---|---|---|---|---|---|---|
| 1 | $CF_3$ | H | H | none | O | J. Org. Chem. (1995), 60(1), 41–46. |
| 2 | $CCl_3$ | H | H | none | O | Chem. --Eur. J. (1997), 3(4), 517–522. |
| 3 | $CF_3$ | $CH_3$ | H | none | O | Chem. Ber. (1986), 119(7), 2233–48. |
| 4 | $CF_3CF_2$ | H | H | none | O | Metalloorg. Khim. (1989), 2(4), 889–92. |
| 5 | $CF_3CF_2CF_2$ | H | H | none | O | Melalloorg. Khim. (1989), 2(4), 889–92. |
| 6 | $CF_3OCF_2CF_2$ | H | H | none | O | Metalloorg. Khim. (1989), 2(4), 889–92. |
| 7 | $CF_3CH_2$ | H | H | none | O | Metalloorg. Khim. (1989), 2(4), 889–92. |
| 8 | $CF_3$ | $CHF_2$ | H | none | O | Zh. Org. Khim. (1976), 12(7), 1377–9. |
| 9 | $CF_3$ | H | $CF_3$ | none | O | J. Flourine Chem. (1979), 14(1), 19–28. |
| 10 | $CF_3$ | $CF_3$ | H | none | O | Can. J. Chem. (1977), 55(13), 2465–72 and cited references. |
| 11 | $CF_3$ | $C_6H_5$ | H | none | O | Arch. Biochem. Biophys. (1980), 204(1), 255–63. |
| 12 | $CCl_3$ | $C_6H_5$ | H | none | O | SU 1212007 |
| 13 | $CCl_3$ | Cyclopropyl | H | none | O | SU 1212007 |
| 14 | $CCl_3$ | $CH_3$ | H | none | O | J. Chem. Res., Synop. (1994), (4), 150–1. |
| 15 | $CCl_3$ | $(CH_3)_2CH$ | H | none | O | J. Chem. Res., Synop. (1994), (4), 150–1. |
| 16 | $CHCl_2$ | H | H | none | O | US 3455996 and cited references. |
| 17 | $CHCl_2$ | Cl | H | none | O | Biochem. Pharmacol. (1981), 30(12), 1712–14 and cited references. |
| 18 | $CF_3$ | H | $CH_3$ | none | O | |
| 19 | $CF_3$ | $CF_3$ | H | H | N | Izv. Akad. Nauk SSSR, Ser. Khim. (1967), (3), 711 |
| 20 | $CF_3$ | H | H | H | N | JP 08092206 |
| 21 | $CF_3$ | H | H | Benzyl | N | JP 08092206 |
| 22 | $CF_3$ | H | H | $CH_3O$ | N | JP 08092206 |
| 23 | $CF_3$ | H | H | $CH_3$ | N | JP 08092206 |
| 24 | $CF_3$ | H | H | Benzyloxy | N | JP 08092206 |
| 25 | $CF_3$ | H | H | none | S | Izv. Akad. Nauk SSSR, Ser. Khim. (1989), (1), 116–22. |
| 26 | $CF_3CF_2$ | H | H | none | S | Izv. Akad. Nauk SSSR, Ser. Khim. (1989), (1), 116–22. |
| 27 | $CCl_3CH_2$ | H | H | none | O | Arch. Biochem. Biophys. (1980), 204(1), 255–63. |
| 28 | $CBr_3CH_2$ | H | H | none | O | US 3455996 and cited references. |
| 29 | $CHBr_2CH_2$ | H | H | none | O | US 3455996 and cited references. |
| 30 | $CBrCl_2$ | H | H | none | O | US 3455996 and cited references. |
| 31 | $CClF_2$ | H | H | none | O | US 3455996 and cited references. |
| 32 | $CCl_2F$ | H | H | none | O | US 3455996 and cited references. |
| 33 | $CCl_3CCl_2$ | H | H | none | O | US 3455996 and cited references. |
| 34 | $CH_3$ | H | H | none | O | Aldrich Chemical |
| 35 | $CH_3$ | $CH_3$ | H | none | O | Aldrich Chemical |
| 36 | $CH_3CH_2$ | H | H | none | O | Aldrich Chemical |
| 37 | $CH_2=CH$ | H | H | none | O | Aldrich Chemical |
| 38 | $CH_3CH_2CH_2$ | H | H | none | O | Aldrich Chemical |
| 39 | $CH_2=CHCH_2CH_2$ | H | H | none | O | Aldrich Chemical |

TABLE 1-continued

Structure and Source of Oxiranes, Thiaranes and Aziridine Reagents.

(XX)

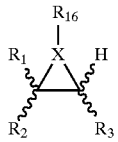

| Reagent Number | $R_1$ | $R_2$ | $R_3$ | $R_{16}$ | X | Source of Reagent |
|---|---|---|---|---|---|---|
| 40 | $CH_3(CH_2)_4CH_2$ | H | H | none | O | Aldrich Chemical |
| 41 | $CH_2=CH(CH_2)_3CH_2$ | H | H | none | O | Aldrich Chemical |
| 42 | $HOCH_2$ | H | H | none | O | Aldrich Chemical |
| 43 | $FCH_2$ | H | H | none | O | Aldrich Chemical |
| 44 | $(CH_3)_3COCH_2$ | H | H | none | O | Aldrich Chemical |
| 45 | $R_1 + R_2 = (CH_2)_5$ | | H | none | O | Heterocycles (1977), 8, 397–401. |
| 46 | $CF_3$ | $R_2 + R_3 = (CH_2)_3$ | | none | O | J. Flourine Chem. (1995), 70(2), 249–53 plus MCPBA |
| 47 | $CF_3$ | $R_2 + R_3 = (CH_2)_4$ | | none | O | Chem. Ber. (1985), 118(7), 3004–10 plus MCPBA |
| 48 | $CHF_2$ | $R_2 + R_3 = (CH_2)_4$ | | none | O | Chem. Ber. (1985), 118(7), 3004–10 plus MCPBA |
| 49 | H | $R_2 + R_3 = (CF_3)CH(CH_2)_3$ | | none | O | J. Org. Chem. (1996), 61(5), 1830–41. |
| 50 | H | $R_2 + R_3 = (CF_3)CH(CH_2)_2$ | | none | O | J. Flourine Chem. (1995), 70(2), 249–53 plus MCPBA |
| 51 | H | $R_2 + R_3 = CH_2(CF_3)CHCH_2$ | | none | O | J. Flourine Chem. (1995), 70(2), 249–53 plus MCPBA |
| 52 | $R_1 + R_2 = (CH_2)_6$ | | H | none | O | Heterocycles (1977), 8, 397–401. |
| 53 | $CH_3CH_2O_2C$ | H | H | none | O | Acros Organics |
| 54 | $CH_3CH_2CH_2$ | H | H | none | O | Aldrich Chemical |
| 55 | $CH_3OCH_2$ | H | H | none | O | TCI America |
| 56 | $CBrF_2CClFCH_2$ | H | H | none | O | Oakwood Products |
| 57 | $HCF_2CF_2OCH_2$ | H | H | none | O | Aldrich Chemical |
| 58 | $[(CH_3CH_2O)]_2POCH_2$ | H | H | none | O | Maybridge |
| 59 | H | $R_2 + R_3 = (CH_2)_2SO_2$ | | none | O | Aldrich Chemical |
| 60 | $Cl^{-(CH_3)_3}N^{\oplus CH_2}$ | H | H | none | O | Aldrich Chemical |
| 61 | N-piperidinyl-$CH_2$ | H | H | none | O | Oakwood Products |
| 62 | N-phthalimido-$CH_2$ | H | H | none | O | Aldrich Chemical |
| 63 | $C_6H_5$ | H | H | none | O | Aldrich Chemical |
| 64 | $C_6H_5$ | H | $CH_3$ | none | O | Aldrich Chemical |
| 65 | $C_6F_5$ | H | H | none | O | Arch. Biochem. Biophys. (1980), 204(1), 255–63. |
| 66 | $C_6F_5$ | $CH_3$ | H | none | O | Arch. Biochem. Biophys. (1980), 204(1), 255–63. |
| 67 | $C_6F_5$ | $CClH_2$ | H | none | O | Arch. Biochem. Biophys. (1980), 204(1), 255–63. |
| 68 | 2-$CH_3C_6H_4$ | H | H | none | O | EP 611826 and references cited therein. |
| 69 | 3-$CH_3C_6H_4$ | H | H | none | O | Tetrahedron Lett. (1995), 36(31), 5457–60. |
| 70 | 4-$CH_3C_6H_4$ | H | H | none | O | EP 611826 and references cited therein. |
| 71 | 2-$BrC_6H_4$ | H | H | none | O | Z. Chem. (1981), 21(11), 406–07. |
| 72 | 4-$BrC_6H_4$ | H | H | none | O | Z. Chem. (1981), 21(11), 406–07. |
| 73 | 2-$ClC_6H_4$ | H | H | none | O | EP 611826 and references cited therein. |
| 74 | 3-$ClC_6H_4$ | H | H | none | O | Z. Chem. (1981), 21(11), 406–07. |
| 75 | 4-$ClC_6H_4$ | H | H | none | O | Heterocycles (1977), 8, 397–401. |
| 76 | 2-$CH_3OC_6H_4$ | H | H | none | O | EP 611826 and references cited therein. |
| 77 | 3-$CH_3OC_6H_4$ | H | H | none | O | Z. Chem. (1981), 21(11), 406–07. |
| 78 | 4-$CH_3OC_6H_4$ | H | H | none | O | Heterocycles (1977), 8, 397–401. |
| 79 | 3-$CF_3C_6H_4$ | H | H | none | O | Tetrahedron Lett. (1995), 36(31), 5457–60. |
| 80 | $C_6H_5CH_2$ | H | H | none | O | Aldrich Chemical |
| 81 | 4F—$C_6H_4$ | H | H | none | O | Z. Chem. (1981), 21(11), 406–07. |
| 82 | 4F—$C_6H_4$ | H | 4F—$C_6H_4$ | none | O | Maybridge |
| 83 | 2-$CH_3O$-4-$CH_3OC_6H_3$ | H | H | none | O | Z. Chem. (1981), 21(11), 406–07. |
| 84 | 3,4-$OCH_2O$—$C_6H_3$ | H | H | none | O | Z. Chem. (1981), 21(11), 406–07. |
| 85 | 3-Cl-4-Cl—$C_6H_3$ | H | H | none | O | EP 611826 and references cited therein. |
| 86 | 3-Cl-5-Cl—$C_6H_3$ | H | H | none | O | EP 611826 and references cited therein. |
| 87 | $C_6H_5OCH_2$ | H | H | none | O | Aldrich Chemical |
| 88 | 4Cl—$C_6H_4OCH_2$ | H | H | none | O | Aldrich Chemical |
| 89 | $CH_3OC_6H_4OCH_2$ | H | H | none | O | Aldrich Chemical |
| 90 | $C_6H_5$ | H | $CO_2C_2H_5$ | none | O | Aldrich Chemical |
| 91 | 2-Pyridyl | H | H | none | O | EP 611826 and references cited therein. |

TABLE 2

Structure and Source of Alcohol and Glycol Reagents.

(XXX)

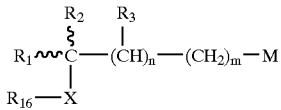

| Reagent Number | $R_1$ | n | M | m | $R_2$ | $R_3$ | $XR_{16}$ | Source of Reagent |
|---|---|---|---|---|---|---|---|---|
| 1A | $CF_3$ | 1 | Cl | 1 | H | H | $CH_2OH$ | Chem. Lett. (1987), (7), 1435–8. |
| 2A | $CF_3$ | 1 | OTs | 2 | H | H | OH | Tosylation of alcohol from Justus Liebigs Ann. Chem. (1969), 720, 81–97. |
| 3A | $CF_3CH_2CH_2$ | 1 | OTs | 1 | H | H | OH | Tosylation of alcohol from Z. Naturforsch., B: Chem. Sci. (1997), 52(3), 413–418 |
| 4A | $CF_3$ | 1 | Cl | 1 | H | H | OH | J. Fluorine Chem. (1982), 20(3), 301–6. |

TABLE 3

Structure of "Secondary Phenyl Amine" Reagents.

(XIIIA)

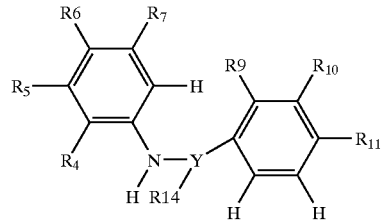

Secondary Phenyl Amine

| Reagent Number | $R_4$ | $R_5$ | $R_6$ | $R_7$ | $R_9$ | $R_{10}$ | $R_{11}$ | Y | $R_{14}$ |
|---|---|---|---|---|---|---|---|---|---|
| 1N | H | phenoxy | H | H | H | $OCF_2CF_2H$ | H | CH | H |
| 2N | H | $OCF_3$ | H | H | H | $OCF_2CF_2H$ | H | CH | H |
| 3N | F | H | H | F | H | $OCF_2CF_2H$ | H | CH | H |
| 4N | H | F | H | H | H | $OCF_2CF_2H$ | H | CH | H |
| 5N | H | phenoxy | H | H | H | $OCF_3$ | H | CH | H |
| 6N | H | $OCF_3$ | H | H | H | $OCF_3$ | H | CH | H |
| 7N | H | H | phenyl | H | H | $OCF_3$ | H | CH | H |
| 8N | H | phenyl | H | H | H | $OCF_3$ | H | CH | H |
| 9N | H | H | H | H | H | $OCF_3$ | H | CH | H |
| 10N | H | Br | H | H | H | $OCF_3$ | H | CH | H |
| 11N | H | $CF_3$ | F | H | H | $CF_3$ | H | CH | H |
| 12N | H | $CH_3$ | H | H | H | $CF_3$ | H | CH | H |
| 13N | H | $CF_3$ | H | H | H | $CF_3$ | H | CH | H |
| 14N | H | $CH_3$ | H | H | H | $OCF_3$ | H | CH | H |
| 15N | H | F | F | H | H | $OCF_3$ | H | CH | H |
| 16N | H | Br | H | H | H | $CF_3$ | H | CH | H |
| 17N | H | $CF_3$ | F | H | H | $OCF_3$ | H | CH | H |
| 18N | H | F | H | H | H | $OCF_3$ | H | CH | H |
| 19N | H | Cl | H | H | H | $OCF_3$ | H | CH | H |
| 20N | H | F | H | H | H | $CF_3$ | H | CH | H |
| 21N | H | F | F | H | H | $CF_3$ | H | CH | H |
| 22N | H | Cl | H | H | H | $CF_3$ | H | CH | H |
| 23N | H | F | H | H | H | phenoxy | H | CH | H |
| 24N | H | $CF_3$ | Cl | H | H | $CH_3$ | H | CH | H |
| 25N | H | $CF_3$ | F | H | H | $CH_3$ | H | CH | H |
| 26N | H | H | H | H | H | $CF_3$ | H | CH | H |
| 27N | F | F | H | H | H | $CF_3$ | H | CH | H |
| 28N | H | H | $OCH_3$ | H | H | $CF_3$ | H | CH | H |
| 29N | H | F | F | H | H | $CH_3$ | H | CH | H |
| 30N | H | $OCH_3$ | H | H | H | $CH_3$ | H | CH | H |
| 31N | H | H | $CH_3$ | H | H | H | H | CH | H |
| 32N | H | Cl | H | H | H | H | H | CH | H |
| 33N | H | F | H | H | H | F | H | CH | H |
| 34N | H | H | $OCH_3$ | H | H | $CH_3$ | H | CH | H |
| 35N | H | H | H | H | H | H | H | CH | H |
| 36N | H | H | $CH_3$ | H | H | $CH_3$ | H | CH | H |
| 37N | H | H | Cl | H | H | H | H | CH | H |

TABLE 3-continued

Structure of "Secondary Phenyl Amine" Reagents.

(XIIIA)

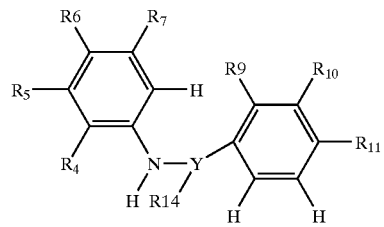

Secondary Phenyl Amine

| Reagent Number | $R_4$ | $R_5$ | $R_6$ | $R_7$ | $R_9$ | $R_{10}$ | $R_{11}$ | Y | $R_{14}$ |
|---|---|---|---|---|---|---|---|---|---|
| 38N | H | F | H | H | H | 3-$CF_3$-phenoxy | H | CH | H |
| 39N | H | F | H | H | H | 4-$CH_3$O-phenoxy | H | CH | H |
| 40N | H | F | H | H | H | 4-Cl-phenoxy | H | CH | H |
| 41N | H | F | H | H | H | H | H | CH | H |
| 42N | H | F | H | H | H | $CH_3$ | H | CH | H |
| 43N | H | F | H | F | H | $CH_3$ | H | CH | H |
| 44N | F | F | H | H | H | $CH_3$ | H | CH | H |
| 45N | H | Cl | H | H | H | $CH_3$ | H | CH | H |
| 46N | H | $CH_3$ | H | H | H | $CH_3$ | H | CH | H |
| 47N | $CH_3$ | H | H | H | H | H | H | CH | H |
| 48N | H | H | $CH_3$ | H | H | $CF_3$ | H | CH | H |
| 49N | $CH_3$ | H | H | H | H | $CF_3$ | H | CH | H |
| 50N | $CH_3$ | H | H | H | H | $CH_3$ | H | CH | H |
| 51N | H | H | $CH_3$ | H | H | F | H | CH | H |
| 52N | H | $CF_3$ | H | H | H | F | H | CH | H |
| 53N | H | $CF_3$ | H | H | H | $CH_3$ | H | CH | H |
| 54N | H | $OCH_3$ | H | H | H | $CF_3$ | H | CH | H |
| 55N | $OCH_3$ | H | H | H | H | $CH_3$ | H | CH | H |
| 56N | H | H | $CH_3$ | H | H | $CF_3$ | H | CH | H |
| 57N | H | phenoxy | H | H | H | H | $OCF_3$ | CH | H |
| 58N | H | H | H | H | H | H | $OCF_3$ | CH | H |
| 59N | H | $OCF_3$ | H | H | H | H | $OCF_3$ | CH | H |
| 60N | H | $CF_3$ | F | H | H | H | $CF_3$ | CH | H |
| 61N | H | H | $OCH_3$ | H | H | H | $CF_3$ | CH | H |
| 62N | H | $CH_3$ | H | H | H | H | $CF_3$ | CH | H |
| 63N | H | Cl | H | H | H | H | $CF_3$ | CH | H |
| 64N | H | $CF_3$ | H | H | H | H | $OCF_3$ | CH | H |
| 65N | H | F | H | H | H | H | $OCF_3$ | CH | H |
| 66N | H | F | H | F | H | H | $OCF_3$ | CH | H |
| 67N | H | Br | H | H | H | H | $OCF_3$ | CH | H |
| 68N | H | Cl | H | H | H | H | $OCF_3$ | CH | H |
| 69N | H | F | F | H | H | H | $OCF_3$ | CH | H |
| 70N | H | F | H | H | H | H | phenyl | CH | H |
| 71N | H | $CH_3$ | H | H | H | H | $OCF_3$ | CH | H |
| 72N | H | F | F | H | H | H | $CF_3$ | CH | H |
| 73N | H | Cl | H | H | H | H | $CH_3$ | CH | H |
| 74N | H | $OCH_3$ | H | H | H | H | $CH_3$ | CH | H |
| 75N | H | F | H | H | H | H | $CH_3$ | CH | H |
| 76N | F | F | H | H | H | H | $OCF_3$ | CH | H |
| 77N | $OCH_3$ | H | H | H | H | H | $CF_3$ | CH | H |
| 78N | H | H | $OCH_3$ | H | H | H | $CH_3$ | CH | H |
| 79N | H | H | $CH_3$ | H | H | H | $CH_3$ | CH | H |
| 80N | H | $CH_3$ | H | H | H | H | $CH_3$ | CH | H |
| 81N | $CH_3$ | H | H | H | H | H | $CH_3$ | CH | H |
| 82N | H | F | F | H | H | H | $CH_3$ | CH | H |
| 83N | H | F | H | F | H | H | $CH_3$ | CH | H |
| 84N | F | F | H | H | H | H | $CH_3$ | CH | H |
| 85N | F | $CF_3$ | H | H | H | H | $CH_3$ | CH | H |
| 86N | H | H | $CH_3$ | H | H | H | $CF_3$ | CH | H |
| 87N | $CH_3$ | H | H | H | H | H | $CF_3$ | CH | H |
| 88N | H | $CF_3$ | H | H | H | H | $CH_3$ | CH | H |
| 89N | $OCH_3$ | H | H | H | H | H | $CH_3$ | CH | H |
| 90N | H | H | $CF_3$ | H | H | H | $CH_3$ | CH | H |
| 91N | $CF_3$ | H | H | H | H | H | $CH_3$ | CH | H |
| 92N | H | $CF_3$ | F | H | H | H | $CH_3$ | CH | H |

TABLE 4

Structure of Substituted Phenyl tertiary-2-Heteroalkylamines (Z is covalent bond; Y is CH and $R_{14}$ is H).

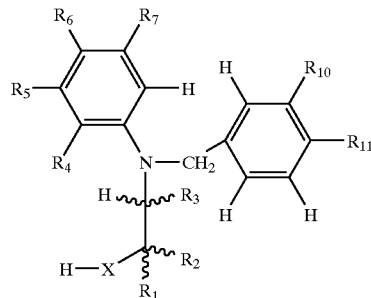

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 1 | 1N | $CF_3$ | H | H | O | H | $C_6H_5O$ | H | H | $OCF_2CF_2H$ | H |
| 1 | 2N | $CF_3$ | H | H | O | H | $OCF_3$ | H | H | $OCF_2CF_2H$ | H |
| 1 | 3N | $CF_3$ | H | H | O | F | H | H | F | $OCF_2CF_2H$ | H |
| 1 | 4N | $CF_3$ | H | H | O | H | F | H | H | $OCF_2CF_2H$ | H |
| 1 | 5N | $CF_3$ | H | H | O | H | $C_6H_5O$ | H | H | $OCF_3$ | H |
| 1 | 6N | $CF_3$ | H | H | O | H | $OCF_3$ | H | H | $OCF_3$ | H |
| 1 | 7N | $CF_3$ | H | H | O | H | H | phenyl | H | $OCF_3$ | H |
| 1 | 8N | $CF_3$ | H | H | O | H | phenyl | H | H | $OCF_3$ | H |
| 1 | 9N | $CF_3$ | H | H | O | H | H | H | H | $OCF_3$ | H |
| 1 | 10N | $CF_3$ | H | H | O | H | Br | H | H | $OCF_3$ | H |
| 1 | 11N | $CF_3$ | H | H | O | H | $CF_3$ | F | H | $CF_3$ | H |
| 1 | 12N | $CF_3$ | H | H | O | H | $CH_3$ | H | H | $CF_3$ | H |
| 1 | 13N | $CF_3$ | H | H | O | H | $CF_3$ | H | H | $CF_3$ | H |
| 1 | 14N | $CF_3$ | H | H | O | H | $CH_3$ | H | H | $OCF_3$ | H |
| 1 | 15N | $CF_3$ | H | H | O | H | F | F | H | $OCF_3$ | H |
| 1 | 16N | $CF_3$ | H | H | O | H | Br | H | H | $CF_3$ | H |
| 1 | 17N | $CF_3$ | H | H | O | H | $CF_3$ | F | H | $OCF_3$ | H |
| 1 | 18N | $CF_3$ | H | H | O | H | F | H | H | $OCF_3$ | H |
| 1 | 19N | $CF_3$ | H | H | O | H | Cl | H | H | $OCF_3$ | H |
| 1 | 20N | $CF_3$ | H | H | O | H | F | H | H | $CF_3$ | H |
| 1 | 21N | $CF_3$ | H | H | O | H | F | F | H | $CF_3$ | H |
| 1 | 22N | $CF_3$ | H | H | O | H | Cl | H | H | $CF_3$ | H |
| 1 | 23N | $CF_3$ | H | H | O | H | F | H | H | phenoxy | H |
| 1 | 24N | $CF_3$ | H | H | O | H | $CF_3$ | Cl | H | $CH_3$ | H |
| 1 | 25N | $CF_3$ | H | H | O | H | $CF_3$ | F | H | $CH_3$ | H |
| 1 | 26N | $CF_3$ | H | H | O | H | H | H | H | $CF_3$ | H |
| 1 | 27N | $CF_3$ | H | H | O | F | F | H | H | $CF_3$ | H |
| 1 | 28N | $CF_3$ | H | H | O | H | H | $OCH_3$ | H | $CF_3$ | H |
| 1 | 29N | $CF_3$ | H | H | O | H | F | F | H | $CH_3$ | H |
| 1 | 30N | $CF_3$ | H | H | O | H | $OCH_3$ | H | H | $CH_3$ | H |
| 1 | 31N | $CF_3$ | H | H | O | H | H | $CH_3$ | H | H | H |
| 1 | 32N | $CF_3$ | H | H | O | H | Cl | H | H | H | H |
| 1 | 33N | $CF_3$ | H | H | O | H | F | H | H | F | H |
| 1 | 34N | $CF_3$ | H | H | O | H | H | $OCH_3$ | H | $CH_3$ | H |
| 1 | 35N | $CF_3$ | H | H | O | H | H | H | H | H | H |
| 1 | 36N | $CF_3$ | H | H | O | H | H | $CH_3$ | H | $CH_3$ | H |
| 1 | 37N | $CF_3$ | H | H | O | H | H | Cl | H | H | H |
| 1 | 38N | $CF_3$ | H | H | O | H | F | H | H | 3-$CF_3$-phenoxy | H |
| 1 | 39N | $CF_3$ | H | H | O | H | F | H | H | 4-$CH_3$O-phenoxy | H |
| 1 | 40N | $CF_3$ | H | H | O | H | F | H | H | 4-Cl-phenoxy | H |
| 1 | 41N | $CF_3$ | H | H | O | H | F | H | H | H | H |
| 1 | 42N | $CF_3$ | H | H | O | H | F | H | H | $CH_3$ | H |
| 1 | 43N | $CF_3$ | H | H | O | H | F | H | F | $CH_3$ | H |
| 1 | 44N | $CF_3$ | H | H | O | F | F | H | H | $CH_3$ | H |
| 1 | 45N | $CF_3$ | H | H | O | H | Cl | H | H | $CH_3$ | H |
| 1 | 46N | $CF_3$ | H | H | O | H | $CH_3$ | H | H | $CH_3$ | H |
| 1 | 47N | $CF_3$ | H | H | O | $CH_3$ | H | H | H | H | H |
| 1 | 48N | $CF_3$ | H | H | O | H | H | $CH_3$ | H | $CF_3$ | H |
| 1 | 49N | $CF_3$ | H | H | O | $CH_3$ | H | H | H | $CF_3$ | H |
| 1 | 50N | $CF_3$ | H | H | O | $CH_3$ | H | H | H | $CH_3$ | H |
| 1 | 51N | $CF_3$ | H | H | O | H | H | $CH_3$ | H | F | H |
| 1 | 52N | $CF_3$ | H | H | O | H | $CF_3$ | H | H | F | H |
| 1 | 53N | $CF_3$ | H | H | O | H | $CF_3$ | H | H | $CH_3$ | H |
| 1 | 54N | $CF_3$ | H | H | O | H | $OCH_3$ | H | H | $CF_3$ | H |
| 1 | 55N | $CF_3$ | H | H | O | $OCH_3$ | H | H | H | $CH_3$ | H |
| 1 | 56N | $CF_3$ | H | H | O | H | H | $CH_3$ | H | $CF_3$ | H |

TABLE 4-continued

Structure of Substituted Phenyl tertiary-2-Heteroalkylamines (Z is covalent bond; Y is CH and $R_{14}$ is H).

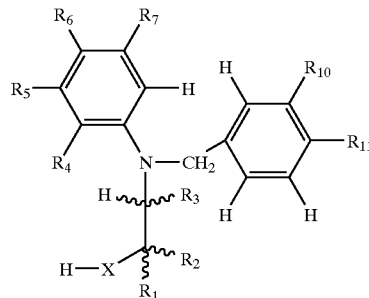

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 1 | 57N | $CF_3$ | H | H | O | H | $C_6H_5O$ | H | H | H | $OCF_3$ |
| 1 | 58N | $CF_3$ | H | H | O | H | H | H | H | H | $OCF_3$ |
| 1 | 59N | $CF_3$ | H | H | O | H | $OCF_3$ | H | H | H | $OCF_3$ |
| 1 | 60N | $CF_3$ | H | H | O | H | $CF_3$ | F | H | H | $CF_3$ |
| 1 | 61N | $CF_3$ | H | H | O | H | H | $OCH_3$ | H | H | $CF_3$ |
| 1 | 62N | $CF_3$ | H | H | O | H | $CH_3$ | H | H | H | $CF_3$ |
| 1 | 63N | $CF_3$ | H | H | O | H | Cl | H | H | H | $CF_3$ |
| 1 | 64N | $CF_3$ | H | H | O | H | $CF_3$ | H | H | H | $OCF_3$ |
| 1 | 65N | $CF_3$ | H | H | O | H | F | H | H | H | $OCF_3$ |
| 1 | 66N | $CF_3$ | H | H | O | H | F | H | F | H | $OCF_3$ |
| 1 | 67N | $CF_3$ | H | H | O | H | Br | H | H | H | $OCF_3$ |
| 1 | 68N | $CF_3$ | H | H | O | H | Cl | H | H | H | $OCF_3$ |
| 1 | 69N | $CF_3$ | H | H | O | H | F | F | H | H | $OCF_3$ |
| 1 | 70N | $CF_3$ | H | H | O | H | F | H | H | H | phenyl |
| 1 | 71N | $CF_3$ | H | H | O | H | $CH_3$ | H | H | H | $OCF_3$ |
| 1 | 72N | $CF_3$ | H | H | O | H | F | F | H | H | $CF_3$ |
| 1 | 73N | $CF_3$ | H | H | O | H | Cl | H | H | H | $CH_3$ |
| 1 | 74N | $CF_3$ | H | H | O | H | $OCH_3$ | H | H | H | $CH_3$ |
| 1 | 75N | $CF_3$ | H | H | O | H | F | H | H | H | $CH_3$ |
| 1 | 76N | $CF_3$ | H | H | O | F | F | H | H | H | $OCF_3$ |
| 1 | 77N | $CF_3$ | H | H | O | $OCH_3$ | H | H | H | H | $CF_3$ |
| 1 | 78N | $CF_3$ | H | H | O | H | H | $OCH_3$ | H | H | $CH_3$ |
| 1 | 79N | $CF_3$ | H | H | O | H | H | $CH_3$ | H | H | $CH_3$ |
| 1 | 80N | $CF_3$ | H | H | O | H | $CH_3$ | H | H | H | $CH_3$ |
| 1 | 81N | $CF_3$ | H | H | O | $CH_3$ | H | H | H | H | $CH_3$ |
| 1 | 82N | $CF_3$ | H | H | O | H | F | F | H | H | $CH_3$ |
| 1 | 83N | $CF_3$ | H | H | O | H | F | H | F | H | $CH_3$ |
| 1 | 84N | $CF_3$ | H | H | O | F | F | H | H | H | $CH_3$ |
| 1 | 85N | $CF_3$ | H | H | O | F | $CF_3$ | H | H | H | $CH_3$ |
| 1 | 86N | $CF_3$ | H | H | O | H | H | $CH_3$ | H | H | $CF_3$ |
| 1 | 87N | $CF_3$ | H | H | O | $CH_3$ | H | H | H | H | $CF_3$ |
| 1 | 88N | $CF_3$ | H | H | O | H | $CF_3$ | H | H | H | $CH_3$ |
| 1 | 89N | $CF_3$ | H | H | O | $OCH_3$ | H | H | H | H | $CH_3$ |
| 1 | 90N | $CF_3$ | H | H | O | H | H | $CF_3$ | H | H | $CH_3$ |
| 1 | 91N | $CF_3$ | H | H | O | $CF_3$ | H | H | H | H | $CH_3$ |
| 1 | 92N | $CF_3$ | H | H | O | H | $CF_3$ | F | H | H | $CH_3$ |
| 2 | 1N | $CCl_3$ | H | H | O | H | $C_6H_5O$ | H | H | $OCF_2CF_2H$ | H |
| 2 | 2N | $CCl_3$ | H | H | O | H | $OCF_3$ | H | H | $OCF_2CF_2H$ | H |
| 2 | 3N | $CCl_3$ | H | H | O | F | H | H | F | $OCF_2CF_2H$ | H |
| 2 | 4N | $CCl_3$ | H | H | O | H | F | H | H | $OCF_2CF_2H$ | H |
| 2 | 5N | $CCl_3$ | H | H | O | H | $C_6H_5O$ | H | H | $OCF_3$ | H |
| 2 | 6N | $CCl_3$ | H | H | O | H | $OCF_3$ | H | H | $OCF_3$ | H |
| 2 | 7N | $CCl_3$ | H | H | O | H | H | phenyl | H | $OCF_3$ | H |
| 2 | 8N | $CCl_3$ | H | H | O | H | phenyl | H | H | $OCF_3$ | H |
| 2 | 9N | $CCl_3$ | H | H | O | H | H | H | H | $OCF_3$ | H |
| 2 | 10N | $CCl_3$ | H | H | O | H | Br | H | H | $OCF_3$ | H |
| 2 | 11N | $CCl_3$ | H | H | O | H | $CF_3$ | F | H | $CF_3$ | H |
| 2 | 12N | $CCl_3$ | H | H | O | H | $CH_3$ | H | H | $CF_3$ | H |
| 2 | 13N | $CCl_3$ | H | H | O | H | $CF_3$ | H | H | $CF_3$ | H |
| 2 | 14N | $CCl_3$ | H | H | O | H | $CH_3$ | H | H | $OCF_3$ | H |
| 2 | 15N | $CCl_3$ | H | H | O | H | F | F | H | $OCF_3$ | H |
| 2 | 16N | $CCl_3$ | H | H | O | H | Br | H | H | $CF_3$ | H |
| 2 | 17N | $CCl_3$ | H | H | O | H | $CF_3$ | F | H | $OCF_3$ | H |
| 2 | 18N | $CCl_3$ | H | H | O | H | F | H | H | $OCF_3$ | H |
| 2 | 19N | $CCl_3$ | H | H | O | H | Cl | H | H | $OCF_3$ | H |
| 2 | 20N | $CCl_3$ | H | H | O | H | F | H | H | $CF_3$ | H |

TABLE 4-continued

Structure of Substituted Phenyl tertiary-2-Heteroalkylamines (Z is covalent bond; Y is CH and $R_{14}$ is H).

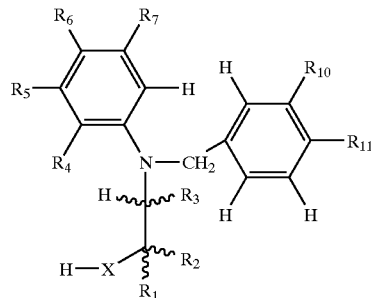

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 2 | 21N | $CCl_3$ | H | H | O | H | F | F | H | $CF_3$ | H |
| 2 | 22N | $CCl_3$ | H | H | O | H | Cl | H | H | $CF_3$ | H |
| 2 | 23N | $CCl_3$ | H | H | O | H | F | H | H | phenoxy | H |
| 2 | 24N | $CCl_3$ | H | H | O | H | $CF_3$ | Cl | H | $CH_3$ | H |
| 2 | 25N | $CCl_3$ | H | H | O | H | $CF_3$ | F | H | $CH_3$ | H |
| 2 | 26N | $CCl_3$ | H | H | O | H | H | H | H | $CF_3$ | H |
| 2 | 27N | $CCl_3$ | H | H | O | F | F | H | H | $CF_3$ | H |
| 2 | 28N | $CCl_3$ | H | H | O | H | H | $OCH_3$ | H | $CF_3$ | H |
| 2 | 29N | $CCl_3$ | H | H | O | H | F | F | H | $CH_3$ | H |
| 2 | 30N | $CCl_3$ | H | H | O | H | $OCH_3$ | H | H | $CH_3$ | H |
| 2 | 31N | $CCl_3$ | H | H | O | H | H | $CH_3$ | H | H | H |
| 2 | 32N | $CCl_3$ | H | H | O | H | Cl | H | H | H | H |
| 2 | 33N | $CCl_3$ | H | H | O | H | F | H | H | F | H |
| 2 | 34N | $CCl_3$ | H | H | O | H | H | $OCH_3$ | H | $CH_3$ | H |
| 2 | 35N | $CCl_3$ | H | H | O | H | H | H | H | H | H |
| 2 | 36N | $CCl_3$ | H | H | O | H | H | $CH_3$ | H | $CH_3$ | H |
| 2 | 37N | $CCl_3$ | H | H | O | H | H | Cl | H | H | H |
| 2 | 38N | $CCl_3$ | H | H | O | H | F | H | H | 3-$CF_3$-phenoxy | H |
| 2 | 39N | $CCl_3$ | H | H | O | H | F | H | H | 4-$CH_3O$-phenoxy | H |
| 2 | 40N | $CCl_3$ | H | H | O | H | F | H | H | 4-Cl-phenoxy | H |
| 2 | 41N | $CCl_3$ | H | H | O | H | F | H | H | H | H |
| 2 | 42N | $CCl_3$ | H | H | O | H | F | H | H | $CH_3$ | H |
| 2 | 43N | $CCl_3$ | H | H | O | H | F | H | F | $CH_3$ | H |
| 2 | 44N | $CCl_3$ | H | H | O | F | F | H | H | $CH_3$ | H |
| 2 | 45N | $CCl_3$ | H | H | O | H | Cl | H | H | $CH_3$ | H |
| 2 | 46N | $CCl_3$ | H | H | O | H | $CH_3$ | H | H | $CH_3$ | H |
| 2 | 47N | $CCl_3$ | H | H | O | $CH_3$ | H | H | H | H | H |
| 2 | 48N | $CCl_3$ | H | H | O | H | H | $CH_3$ | H | $CF_3$ | H |
| 2 | 49N | $CCl_3$ | H | H | O | $CH_3$ | H | H | H | $CF_3$ | H |
| 2 | 50N | $CCl_3$ | H | H | O | $CH_3$ | H | H | H | $CH_3$ | H |
| 2 | 51N | $CCl_3$ | H | H | O | H | H | $CH_3$ | H | F | H |
| 2 | 52N | $CCl_3$ | H | H | O | H | $CF_3$ | H | H | F | H |
| 2 | 53N | $CCl_3$ | H | H | O | H | $CF_3$ | H | H | $CH_3$ | H |
| 2 | 54N | $CCl_3$ | H | H | O | H | $OCH_3$ | H | H | $CF_3$ | H |
| 2 | 55N | $CCl_3$ | H | H | O | $OCH_3$ | H | H | H | $CH_3$ | H |
| 2 | 56N | $CCl_3$ | H | H | O | H | H | $CH_3$ | H | $CF_3$ | H |
| 2 | 57N | $CCl_3$ | H | H | O | H | $C_6H_5O$ | H | H | H | $OCF_3$ |
| 2 | 58N | $CCl_3$ | H | H | O | H | H | H | H | H | $OCF_3$ |
| 2 | 59N | $CCl_3$ | H | H | O | H | $OCF_3$ | H | H | H | $OCF_3$ |
| 2 | 60N | $CCl_3$ | H | H | O | H | $CF_3$ | F | H | H | $CF_3$ |
| 2 | 61N | $CCl_3$ | H | H | O | H | H | $OCH_3$ | H | H | $CF_3$ |
| 2 | 62N | $CCl_3$ | H | H | O | H | $CH_3$ | H | H | H | $CF_3$ |
| 2 | 63N | $CCl_3$ | H | H | O | H | Cl | H | H | H | $CF_3$ |
| 2 | 64N | $CCl_3$ | H | H | O | H | $CF_3$ | H | H | H | $OCF_3$ |
| 2 | 65N | $CCl_3$ | H | H | O | H | F | H | H | H | $OCF_3$ |
| 2 | 66N | $CCl_3$ | H | H | O | H | F | H | F | H | $OCF_3$ |
| 2 | 67N | $CCl_3$ | H | H | O | H | Br | H | H | H | $OCF_3$ |
| 2 | 68N | $CCl_3$ | H | H | O | H | Cl | H | H | H | $OCF_3$ |
| 2 | 69N | $CCl_3$ | H | H | O | H | F | F | H | H | $OCF_3$ |
| 2 | 70N | $CCl_3$ | H | H | O | H | F | H | H | H | phenyl |
| 2 | 71N | $CCl_3$ | H | H | O | H | $CH_3$ | H | H | H | $OCF_3$ |
| 2 | 72N | $CCl_3$ | H | H | O | H | F | F | H | H | $CF_3$ |
| 2 | 73N | $CCl_3$ | H | H | O | H | Cl | H | H | H | $CH_3$ |
| 2 | 74N | $CCl_3$ | H | H | O | H | $OCH_3$ | H | H | H | $CH_3$ |
| 2 | 75N | $CCl_3$ | H | H | O | H | F | H | H | H | $CH_3$ |
| 2 | 76N | $CCl_3$ | H | H | O | F | F | H | H | H | $OCF_3$ |

TABLE 4-continued

Structure of Substituted Phenyl tertiary-2-Heteroalkylamines (Z is covalent bond; Y is CH and $R_{14}$ is H).

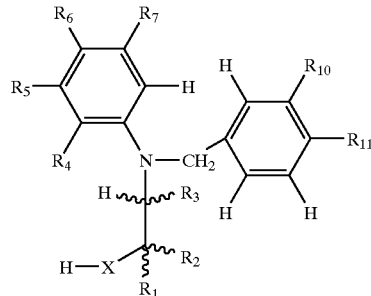

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 2 | 77N | $CCl_3$ | H | H | O | $OCH_3$ | H | H | H | H | $CF_3$ |
| 2 | 78N | $CCl_3$ | H | H | O | H | H | $OCH_3$ | H | H | $CH_3$ |
| 2 | 79N | $CCl_3$ | H | H | O | H | H | $CH_3$ | H | H | $CH_3$ |
| 2 | 80N | $CCl_3$ | H | H | O | H | $CH_3$ | H | H | H | $CH_3$ |
| 2 | 81N | $CCl_3$ | H | H | O | $CH_3$ | H | H | H | H | $CH_3$ |
| 2 | 82N | $CCl_3$ | H | H | O | H | F | F | H | H | $CH_3$ |
| 2 | 83N | $CCl_3$ | H | H | O | H | F | H | F | H | $CH_3$ |
| 2 | 84N | $CCl_3$ | H | H | O | F | F | H | H | H | $CH_3$ |
| 2 | 85N | $CCl_3$ | H | H | O | F | $CF_3$ | H | H | H | $CH_3$ |
| 2 | 86N | $CCl_3$ | H | H | O | H | H | $CH_3$ | H | H | $CF_3$ |
| 2 | 87N | $CCl_3$ | H | H | O | $CH_3$ | H | H | H | H | $CF_3$ |
| 2 | 88N | $CCl_3$ | H | H | O | H | $CF_3$ | H | H | H | $CH_3$ |
| 2 | 89N | $CCl_3$ | H | H | O | $OCH_3$ | H | H | H | H | $CH_3$ |
| 2 | 90N | $CCl_3$ | H | H | O | H | H | $CF_3$ | H | H | $CH_3$ |
| 2 | 91N | $CCl_3$ | H | H | O | $CF_3$ | H | H | H | H | $CH_3$ |
| 2 | 92N | $CCl_3$ | H | H | O | H | $CF_3$ | F | H | H | $CH_3$ |
| 3 | 1N | $CF_3$ | $CH_3$ | H | O | H | $C_6H_5O$ | H | H | $OCF_2CF_2H$ | H |
| 3 | 2N | $CF_3$ | $CH_3$ | H | O | H | $OCF_3$ | H | H | $OCF_2CF_2H$ | H |
| 3 | 3N | $CF_3$ | $CH_3$ | H | O | F | H | H | F | $OCF_2CF_2H$ | H |
| 3 | 4N | $CF_3$ | $CH_3$ | H | O | H | F | H | H | $OCF_2CF_2H$ | H |
| 3 | 5N | $CF_3$ | $CH_3$ | H | O | H | $C_6H_5O$ | H | H | $OCF_3$ | H |
| 3 | 6N | $CF_3$ | $CH_3$ | H | O | H | $OCF_3$ | H | H | $OCF_3$ | H |
| 3 | 7N | $CF_3$ | $CH_3$ | H | O | H | H | phenyl | H | $OCF_3$ | H |
| 3 | 8N | $CF_3$ | $CH_3$ | H | O | H | phenyl | H | H | $OCF_3$ | H |
| 3 | 9N | $CF_3$ | $CH_3$ | H | O | H | H | H | H | $OCF_3$ | H |
| 3 | 10N | $CF_3$ | $CH_3$ | H | O | H | Br | H | H | $OCF_3$ | H |
| 3 | 11N | $CF_3$ | $CH_3$ | H | O | H | $CF_3$ | F | H | $CF_3$ | H |
| 3 | 12N | $CF_3$ | $CH_3$ | H | O | H | $CH_3$ | H | H | $CF_3$ | H |
| 3 | 13N | $CF_3$ | $CH_3$ | H | O | H | $CF_3$ | H | H | $CF_3$ | H |
| 3 | 14N | $CF_3$ | $CH_3$ | H | O | H | $CH_3$ | H | H | $OCF_3$ | H |
| 3 | 15N | $CF_3$ | $CH_3$ | H | O | H | F | F | H | $OCF_3$ | H |
| 3 | 16N | $CF_3$ | $CH_3$ | H | O | H | Br | H | H | $CF_3$ | H |
| 3 | 17N | $CF_3$ | $CH_3$ | H | O | H | $CF_3$ | F | H | $OCF_3$ | H |
| 3 | 18N | $CF_3$ | $CH_3$ | H | O | H | F | H | H | $OCF_3$ | H |
| 3 | 19N | $CF_3$ | $CH_3$ | H | O | H | Cl | H | H | $OCF_3$ | H |
| 3 | 20N | $CF_3$ | $CH_3$ | H | O | H | F | H | H | $CF_3$ | H |
| 3 | 21N | $CF_3$ | $CH_3$ | H | O | H | F | F | H | $CF_3$ | H |
| 3 | 22N | $CF_3$ | $CH_3$ | H | O | H | Cl | H | H | $CF_3$ | H |
| 3 | 23N | $CF_3$ | $CH_3$ | H | O | H | F | H | H | phenoxy | H |
| 3 | 24N | $CF_3$ | $CH_3$ | H | O | H | $CF_3$ | Cl | H | $CH_3$ | H |
| 3 | 25N | $CF_3$ | $CH_3$ | H | O | H | $CF_3$ | F | H | $CH_3$ | H |
| 3 | 26N | $CF_3$ | $CH_3$ | H | O | H | H | H | H | $CF_3$ | H |
| 3 | 27N | $CF_3$ | $CH_3$ | H | O | F | F | H | H | $CF_3$ | H |
| 3 | 28N | $CF_3$ | $CH_3$ | H | O | H | H | $OCH_3$ | H | $CF_3$ | H |
| 3 | 29N | $CF_3$ | $CH_3$ | H | O | H | F | F | H | $CH_3$ | H |
| 3 | 30N | $CF_3$ | $CH_3$ | H | O | H | $OCH_3$ | H | H | $CH_3$ | H |
| 3 | 31N | $CF_3$ | $CH_3$ | H | O | H | H | $CH_3$ | H | H | H |
| 3 | 32N | $CF_3$ | $CH_3$ | H | O | H | Cl | H | H | H | H |
| 3 | 33N | $CF_3$ | $CH_3$ | H | O | H | F | H | H | F | H |
| 3 | 34N | $CF_3$ | $CH_3$ | H | O | H | H | $OCH_3$ | H | $CH_3$ | H |
| 3 | 35N | $CF_3$ | $CH_3$ | H | O | H | H | H | H | H | H |
| 3 | 36N | $CF_3$ | $CH_3$ | H | O | H | H | $CH_3$ | H | $CH_3$ | H |
| 3 | 37N | $CF_3$ | $CH_3$ | H | O | H | H | Cl | H | H | H |
| 3 | 38N | $CF_3$ | $CH_3$ | H | O | H | F | H | H | 3-$CF_3$-phenoxy | H |
| 3 | 39N | $CF_3$ | $CH_3$ | H | O | H | F | H | H | 4-$CH_3$O-phenoxy | H |
| 3 | 40N | $CF_3$ | $CH_3$ | H | O | H | F | H | H | 4-Cl-phenoxy | H |

TABLE 4-continued

Structure of Substituted Phenyl tertiary-2-Heteroalkylamines (Z is covalent bond; Y is CH and $R_{14}$ is H).

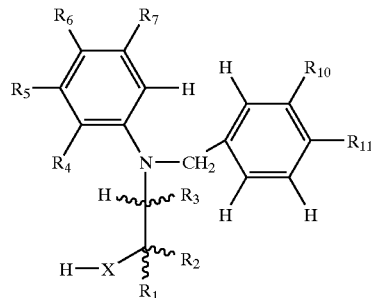

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 3 | 41N | $CF_3$ | $CH_3$ | H | O | H | F | H | H | H | H |
| 3 | 42N | $CF_3$ | $CH_3$ | H | O | H | F | H | H | $CH_3$ | H |
| 3 | 43N | $CF_3$ | $CH_3$ | H | O | H | F | H | F | $CH_3$ | H |
| 3 | 44N | $CF_3$ | $CH_3$ | H | O | F | F | H | H | $CH_3$ | H |
| 3 | 45N | $CF_3$ | $CH_3$ | H | O | H | Cl | H | H | $CH_3$ | H |
| 3 | 46N | $CF_3$ | $CH_3$ | H | O | H | $CH_3$ | H | H | $CH_3$ | H |
| 3 | 47N | $CF_3$ | $CH_3$ | H | O | $CH_3$ | H | H | H | H | H |
| 3 | 48N | $CF_3$ | $CH_3$ | H | O | H | H | $CH_3$ | H | $CF_3$ | H |
| 3 | 49N | $CF_3$ | $CH_3$ | H | O | $CH_3$ | H | H | H | $CF_3$ | H |
| 3 | 50N | $CF_3$ | $CH_3$ | H | O | $CH_3$ | H | H | H | $CH_3$ | H |
| 3 | 51N | $CF_3$ | $CH_3$ | H | O | H | H | $CH_3$ | H | F | H |
| 3 | 52N | $CF_3$ | $CH_3$ | H | O | H | $CF_3$ | H | H | F | H |
| 3 | 53N | $CF_3$ | $CH_3$ | H | O | H | $CF_3$ | H | H | $CH_3$ | H |
| 3 | 54N | $CF_3$ | $CH_3$ | H | O | H | $OCH_3$ | H | H | $CF_3$ | H |
| 3 | 55N | $CF_3$ | $CH_3$ | H | O | $OCH_3$ | H | H | H | $CH_3$ | H |
| 3 | 56N | $CF_3$ | $CH_3$ | H | O | H | H | $CH_3$ | H | $CF_3$ | H |
| 3 | 57N | $CF_3$ | $CH_3$ | H | O | H | $C_6H_5O$ | H | H | H | $OCF_3$ |
| 3 | 58N | $CF_3$ | $CH_3$ | H | O | H | H | H | H | H | $OCF_3$ |
| 3 | 59N | $CF_3$ | $CH_3$ | H | O | H | $OCF_3$ | H | H | H | $OCF_3$ |
| 3 | 60N | $CF_3$ | $CH_3$ | H | O | H | $CF_3$ | F | H | H | $CF_3$ |
| 3 | 61N | $CF_3$ | $CH_3$ | H | O | H | H | $OCH_3$ | H | H | $CF_3$ |
| 3 | 62N | $CF_3$ | $CH_3$ | H | O | H | $CH_3$ | H | H | H | $CF_3$ |
| 3 | 63N | $CF_3$ | $CH_3$ | H | O | H | Cl | H | H | H | $CF_3$ |
| 3 | 64N | $CF_3$ | $CH_3$ | H | O | H | $CF_3$ | H | H | H | $OCF_3$ |
| 3 | 65N | $CF_3$ | $CH_3$ | H | O | H | F | H | H | H | $OCF_3$ |
| 3 | 66N | $CF_3$ | $CH_3$ | H | O | H | F | H | F | H | $OCF_3$ |
| 3 | 67N | $CF_3$ | $CH_3$ | H | O | H | Br | H | H | H | $OCF_3$ |
| 3 | 68N | $CF_3$ | $CH_3$ | H | O | H | Cl | H | H | H | $OCF_3$ |
| 3 | 69N | $CF_3$ | $CH_3$ | H | O | H | F | F | H | H | $OCF_3$ |
| 3 | 70N | $CF_3$ | $CH_3$ | H | O | H | F | H | H | H | phenyl |
| 3 | 71N | $CF_3$ | $CH_3$ | H | O | H | $CH_3$ | H | H | H | $OCF_3$ |
| 3 | 72N | $CF_3$ | $CH_3$ | H | O | H | F | F | H | H | $CF_3$ |
| 3 | 73N | $CF_3$ | $CH_3$ | H | O | H | Cl | H | H | H | $CH_3$ |
| 3 | 74N | $CF_3$ | $CH_3$ | H | O | H | $OCH_3$ | H | H | H | $CH_3$ |
| 3 | 75N | $CF_3$ | $CH_3$ | H | O | H | F | H | H | H | $CH_3$ |
| 3 | 76N | $CF_3$ | $CH_3$ | H | O | F | F | H | H | H | $OCF_3$ |
| 3 | 77N | $CF_3$ | $CH_3$ | H | O | $OCH_3$ | H | H | H | H | $CF_3$ |
| 3 | 78N | $CF_3$ | $CH_3$ | H | O | H | H | $OCH_3$ | H | H | $CH_3$ |
| 3 | 79N | $CF_3$ | $CH_3$ | H | O | H | H | $CH_3$ | H | H | $CH_3$ |
| 3 | 80N | $CF_3$ | $CH_3$ | H | O | H | $CH_3$ | H | H | H | $CH_3$ |
| 3 | 81N | $CF_3$ | $CH_3$ | H | O | $CH_3$ | H | H | H | H | $CH_3$ |
| 3 | 82N | $CF_3$ | $CH_3$ | H | O | H | F | F | H | H | $CH_3$ |
| 3 | 83N | $CF_3$ | $CH_3$ | H | O | H | F | H | F | H | $CH_3$ |
| 3 | 84N | $CF_3$ | $CH_3$ | H | O | F | F | H | H | H | $CH_3$ |
| 3 | 85N | $CF_3$ | $CH_3$ | H | O | F | $CF_3$ | H | H | H | $CH_3$ |
| 3 | 86N | $CF_3$ | $CH_3$ | H | O | H | H | $CH_3$ | H | H | $CF_3$ |
| 3 | 87N | $CF_3$ | $CH_3$ | H | O | $CH_3$ | H | H | H | H | $CF_3$ |
| 3 | 88N | $CF_3$ | $CH_3$ | H | O | H | $CF_3$ | H | H | H | $CH_3$ |
| 3 | 89N | $CF_3$ | $CH_3$ | H | O | $OCH_3$ | H | H | H | H | $CH_3$ |
| 3 | 90N | $CF_3$ | $CH_3$ | H | O | H | H | $CF_3$ | H | H | $CH_3$ |
| 3 | 91N | $CF_3$ | $CH_3$ | H | O | $CF_3$ | H | H | H | H | $CH_3$ |
| 3 | 92N | $CF_3$ | $CH_3$ | H | O | H | $CF_3$ | F | H | H | $CH_3$ |
| 4 | 1N | $CF_3CF_2$ | H | H | O | H | $C_6H_5O$ | H | H | $OCF_2CF_2H$ | H |
| 4 | 2N | $CF_3CF_2$ | H | H | O | H | $OCF_3$ | H | H | $OCF_2CF_2H$ | H |
| 4 | 3N | $CF_3CF_2$ | H | H | O | F | H | H | F | $OCF_2CF_2H$ | H |
| 4 | 4N | $CF_3CF_2$ | H | H | O | H | F | H | H | $OCF_2CF_2H$ | H |

TABLE 4-continued

Structure of Substituted Phenyl tertiary-2-Heteroalkylamines (Z is covalent bond; Y is CH and $R_{14}$ is H).

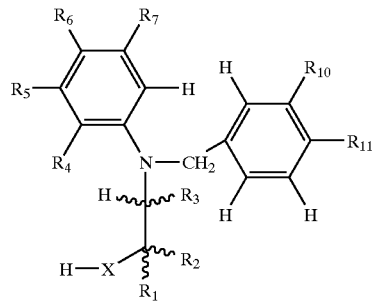

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 4 | 5N | $CF_3CF_2$ | H | H | O | H | $C_6H_5O$ | H | H | $OCF_3$ | H |
| 4 | 6N | $CF_3CF_2$ | H | H | O | H | $OCF_3$ | H | H | $OCF_3$ | H |
| 4 | 7N | $CF_3CF_2$ | H | H | O | H | H | phenyl | H | $OCF_3$ | H |
| 4 | 8N | $CF_3CF_2$ | H | H | O | H | phenyl | H | H | $OCF_3$ | H |
| 4 | 9N | $CF_3CF_2$ | H | H | O | H | H | H | H | $OCF_3$ | H |
| 4 | 10N | $CF_3CF_2$ | H | H | O | H | Br | H | H | $OCF_3$ | H |
| 4 | 11N | $CF_3CF_2$ | H | H | O | H | $CF_3$ | F | H | $CF_3$ | H |
| 4 | 12N | $CF_3CF_2$ | H | H | O | H | $CH_3$ | H | H | $CF_3$ | H |
| 4 | 13N | $CF_3CF_2$ | H | H | O | H | $CF_3$ | H | H | $CF_3$ | H |
| 4 | 14N | $CF_3CF_2$ | H | H | O | H | $CH_3$ | H | H | $OCF_3$ | H |
| 4 | 15N | $CF_3CF_2$ | H | H | O | H | F | F | H | $OCF_3$ | H |
| 4 | 16N | $CF_3CF_2$ | H | H | O | H | Br | H | H | $CF_3$ | H |
| 4 | 17N | $CF_3CF_2$ | H | H | O | H | $CF_3$ | F | H | $OCF_3$ | H |
| 4 | 18N | $CF_3CF_2$ | H | H | O | H | F | H | H | $OCF_3$ | H |
| 4 | 19N | $CF_3CF_2$ | H | H | O | H | Cl | H | H | $OCF_3$ | H |
| 4 | 20N | $CF_3CF_2$ | H | H | O | H | F | H | H | $CF_3$ | H |
| 4 | 21N | $CF_3CF_2$ | H | H | O | H | F | F | H | $CF_3$ | H |
| 4 | 22N | $CF_3CF_2$ | H | H | O | H | Cl | H | H | $CF_3$ | H |
| 4 | 23N | $CF_3CF_2$ | H | H | O | H | F | H | H | phenoxy | H |
| 4 | 24N | $CF_3CF_2$ | H | H | O | H | $CF_3$ | Cl | H | $CH_3$ | H |
| 4 | 25N | $CF_3CF_2$ | H | H | O | H | $CF_3$ | F | H | $CH_3$ | H |
| 4 | 26N | $CF_3CF_2$ | H | H | O | H | H | H | H | $CF_3$ | H |
| 4 | 27N | $CF_3CF_2$ | H | H | O | F | F | H | H | $CF_3$ | H |
| 4 | 28N | $CF_3CF_2$ | H | H | O | H | H | $OCH_3$ | H | $CF_3$ | H |
| 4 | 29N | $CF_3CF_2$ | H | H | O | H | F | F | H | $CH_3$ | H |
| 4 | 30N | $CF_3CF_2$ | H | H | O | H | $OCH_3$ | H | H | $CH_3$ | H |
| 4 | 31N | $CF_3CF_2$ | H | H | O | H | H | $CH_3$ | H | H | H |
| 4 | 32N | $CF_3CF_2$ | H | H | O | H | Cl | H | H | H | H |
| 4 | 33N | $CF_3CF_2$ | H | H | O | H | F | H | H | F | H |
| 4 | 34N | $CF_3CF_2$ | H | H | O | H | H | $OCH_3$ | H | $CH_3$ | H |
| 4 | 35N | $CF_3CF_2$ | H | H | O | H | H | H | H | H | H |
| 4 | 36N | $CF_3CF_2$ | H | H | O | H | H | $CH_3$ | H | $CH_3$ | H |
| 4 | 37N | $CF_3CF_2$ | H | H | O | H | H | Cl | H | H | H |
| 4 | 38N | $CF_3CF_2$ | H | H | O | H | F | H | H | 3-$CF_3$-phenoxy | H |
| 4 | 39N | $CF_3CF_2$ | H | H | O | H | F | H | H | 4-$CH_3O$-phenoxy | H |
| 4 | 40N | $CF_3CF_2$ | H | H | O | H | F | H | H | 4-Cl-phenoxy | H |
| 4 | 41N | $CF_3CF_2$ | H | H | O | H | F | H | H | H | H |
| 4 | 42N | $CF_3CF_2$ | H | H | O | H | F | H | H | $CH_3$ | H |
| 4 | 43N | $CF_3CF_2$ | H | H | O | H | F | H | F | $CH_3$ | H |
| 4 | 44N | $CF_3CF_2$ | H | H | O | F | F | H | H | $CH_3$ | H |
| 4 | 45N | $CF_3CF_2$ | H | H | O | H | Cl | H | H | $CH_3$ | H |
| 4 | 46N | $CF_3CF_2$ | H | H | O | H | $CH_3$ | H | H | $CH_3$ | H |
| 4 | 47N | $CF_3CF_2$ | H | H | O | $CH_3$ | H | H | H | H | H |
| 4 | 48N | $CF_3CF_2$ | H | H | O | H | H | $CH_3$ | H | $CF_3$ | H |
| 4 | 49N | $CF_3CF_2$ | H | H | O | $CH_3$ | H | H | H | $CF_3$ | H |
| 4 | 50N | $CF_3CF_2$ | H | H | O | $CH_3$ | H | H | H | $CH_3$ | H |
| 4 | 51N | $CF_3CF_2$ | H | H | O | H | H | $CH_3$ | H | F | H |
| 4 | 52N | $CF_3CF_2$ | H | H | O | H | $CF_3$ | H | H | F | H |
| 4 | 53N | $CF_3CF_2$ | H | H | O | H | $CF_3$ | H | H | $CH_3$ | H |
| 4 | 54N | $CF_3CF_2$ | H | H | O | H | $OCH_3$ | H | H | $CF_3$ | H |
| 4 | 55N | $CF_3CF_2$ | H | H | O | $OCH_3$ | H | H | H | $CH_3$ | H |
| 4 | 56N | $CF_3CF_2$ | H | H | O | H | H | $CH_3$ | H | $CF_3$ | H |
| 4 | 57N | $CF_3CF_2$ | H | H | O | H | $C_6H_5O$ | H | H | H | $OCF_3$ |
| 4 | 58N | $CF_3CF_2$ | H | H | O | H | H | H | H | H | $OCF_3$ |
| 4 | 59N | $CF_3CF_2$ | H | H | O | H | $OCF_3$ | H | H | H | $OCF_3$ |
| 4 | 60N | $CF_3CF_2$ | H | H | O | H | $CF_3$ | F | H | H | $CF_3$ |

TABLE 4-continued

Structure of Substituted Phenyl tertiary-2-Heteroalkylamines (Z is covalent bond; Y is CH and $R_{14}$ is H).

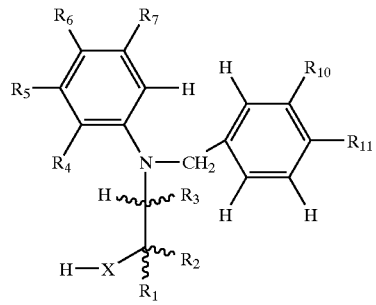

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 4 | 61N | $CF_3CF_2$ | H | H | O | H | H | $OCH_3$ | H | H | $CF_3$ |
| 4 | 62N | $CF_3CF_2$ | H | H | O | H | $CH_3$ | H | H | H | $CF_3$ |
| 4 | 63N | $CF_3CF_2$ | H | H | O | H | Cl | H | H | H | $CF_3$ |
| 4 | 64N | $CF_3CF_2$ | H | H | O | H | $CF_3$ | H | H | H | $OCF_3$ |
| 4 | 65N | $CF_3CF_2$ | H | H | O | H | F | H | H | H | $OCF_3$ |
| 4 | 66N | $CF_3CF_2$ | H | H | O | H | F | H | F | H | $OCF_3$ |
| 4 | 67N | $CF_3CF_2$ | H | H | O | H | Br | H | H | H | $OCF_3$ |
| 4 | 68N | $CF_3CF_2$ | H | H | O | H | Cl | H | H | H | $OCF_3$ |
| 4 | 69N | $CF_3CF_2$ | H | H | O | H | F | F | H | H | $OCF_3$ |
| 4 | 70N | $CF_3CF_2$ | H | H | O | H | F | H | H | H | phenyl |
| 4 | 71N | $CF_3CF_2$ | H | H | O | H | $CH_3$ | H | H | H | $OCF_3$ |
| 4 | 72N | $CF_3CF_2$ | H | H | O | H | F | F | H | H | $CF_3$ |
| 4 | 73N | $CF_3CF_2$ | H | H | O | H | Cl | H | H | H | $CH_3$ |
| 4 | 74N | $CF_3CF_2$ | H | H | O | H | $OCH_3$ | H | H | H | $CH_3$ |
| 4 | 75N | $CF_3CF_2$ | H | H | O | H | F | H | H | H | $CH_3$ |
| 4 | 76N | $CF_3CF_2$ | H | H | O | F | F | H | H | H | $OCF_3$ |
| 4 | 77N | $CF_3CF_2$ | H | H | O | $OCH_3$ | H | H | H | H | $CF_3$ |
| 4 | 78N | $CF_3CF_2$ | H | H | O | H | H | $OCH_3$ | H | H | $CH_3$ |
| 4 | 79N | $CF_3CF_2$ | H | H | O | H | H | $CH_3$ | H | H | $CH_3$ |
| 4 | 80N | $CF_3CF_2$ | H | H | O | H | $CH_3$ | H | H | H | $CH_3$ |
| 4 | 81N | $CF_3CF_2$ | H | H | O | $CH_3$ | H | H | H | H | $CH_3$ |
| 4 | 82N | $CF_3CF_2$ | H | H | O | H | F | F | H | H | $CH_3$ |
| 4 | 83N | $CF_3CF_2$ | H | H | O | H | F | H | F | H | $CH_3$ |
| 4 | 84N | $CF_3CF_2$ | H | H | O | F | F | H | H | H | $CH_3$ |
| 4 | 85N | $CF_3CF_2$ | H | H | O | F | $CF_3$ | H | H | H | $CH_3$ |
| 4 | 86N | $CF_3CF_2$ | H | H | O | H | H | $CH_3$ | H | H | $CF_3$ |
| 4 | 87N | $CF_3CF_2$ | H | H | O | $CH_3$ | H | H | H | H | $CF_3$ |
| 4 | 88N | $CF_3CF_2$ | H | H | O | H | $CF_3$ | H | H | H | $CH_3$ |
| 4 | 89N | $CF_3CF_2$ | H | H | O | $OCH_3$ | H | H | H | H | $CH_3$ |
| 4 | 90N | $CF_3CF_2$ | H | H | O | H | H | $CF_3$ | H | H | $CH_3$ |
| 4 | 91N | $CF_3CF_2$ | H | H | O | $CF_3$ | H | H | H | H | $CH_3$ |
| 4 | 92N | $CF_3CF_2$ | H | H | O | H | $CF_3$ | F | H | H | $CH_3$ |
| 5 | 1N | $CF_3CF_2CF_2$ | H | H | O | H | $C_6H_5O$ | H | H | $OCF_2CF_2H$ | H |
| 5 | 2N | $CF_3CF_2CF_2$ | H | H | O | H | $OCF_3$ | H | H | $OCF_2CF_2H$ | H |
| 5 | 3N | $CF_3CF_2CF_2$ | H | H | O | F | H | H | F | $OCF_2CF_2H$ | H |
| 5 | 4N | $CF_3CF_2CF_2$ | H | H | O | H | F | H | H | $OCF_2CF_2H$ | H |
| 5 | 5N | $CF_3CF_2CF_2$ | H | H | O | H | $C_6H_5O$ | H | H | $OCF_3$ | H |
| 5 | 6N | $CF_3CF_2CF_2$ | H | H | O | H | $OCF_3$ | H | H | $OCF_3$ | H |
| 5 | 7N | $CF_3CF_2CF_2$ | H | H | O | H | H | phenyl | H | $OCF_3$ | H |
| 5 | 8N | $CF_3CF_2CF_2$ | H | H | O | H | phenyl | H | H | $OCF_3$ | H |
| 5 | 9N | $CF_3CF_2CF_2$ | H | H | O | H | H | H | H | $OCF_3$ | H |
| 5 | 10N | $CF_3CF_2CF_2$ | H | H | O | H | Br | H | H | $OCF_3$ | H |
| 5 | 11N | $CF_3CF_2CF_2$ | H | H | O | H | $CF_3$ | F | H | $CF_3$ | H |
| 5 | 12N | $CF_3CF_2CF_2$ | H | H | O | H | $CH_3$ | H | H | $CF_3$ | H |
| 5 | 13N | $CF_3CF_2CF_2$ | H | H | O | H | $CF_3$ | H | H | $CF_3$ | H |
| 5 | 14N | $CF_3CF_2CF_2$ | H | H | O | H | $CH_3$ | H | H | $OCF_3$ | H |
| 5 | 15N | $CF_3CF_2CF_2$ | H | H | O | H | F | F | H | $OCF_3$ | H |
| 5 | 16N | $CF_3CF_2CF_2$ | H | H | O | H | Br | H | H | $CF_3$ | H |
| 5 | 17N | $CF_3CF_2CF_2$ | H | H | O | H | $CF_3$ | F | H | $OCF_3$ | H |
| 5 | 18N | $CF_3CF_2CF_2$ | H | H | O | H | F | H | H | $OCF_3$ | H |
| 5 | 19N | $CF_3CF_2CF_2$ | H | H | O | H | Cl | H | H | $OCF_3$ | H |
| 5 | 20N | $CF_3CF_2CF_2$ | H | H | O | H | F | H | H | $CF_3$ | H |
| 5 | 21N | $CF_3CF_2CF_2$ | H | H | O | H | F | F | H | $CF_3$ | H |
| 5 | 22N | $CF_3CF_2CF_2$ | H | H | O | H | Cl | H | H | $CF_3$ | H |
| 5 | 23N | $CF_3CF_2CF_2$ | H | H | O | H | F | H | H | phenoxy | H |
| 5 | 24N | $CF_3CF_2CF_2$ | H | H | O | H | $CF_3$ | Cl | H | $CH_3$ | H |

TABLE 4-continued

Structure of Substituted Phenyl tertiary-2-Heteroalkylamines (Z is covalent bond; Y is CH and $R_{14}$ is H).

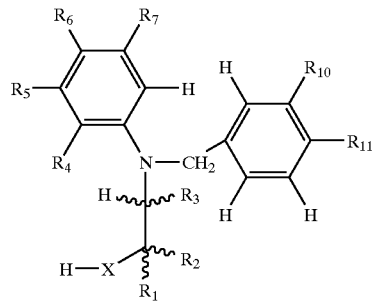

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 5 | 25N | $CF_3CF_2CF_2$ | H | H | O | H | $CF_3$ | F | H | $CH_3$ | H |
| 5 | 26N | $CF_3CF_2CF_2$ | H | H | O | H | H | H | H | $CF_3$ | H |
| 5 | 27N | $CF_3CF_2CF_2$ | H | H | O | F | F | H | H | $CF_3$ | H |
| 5 | 28N | $CF_3CF_2CF_2$ | H | H | O | H | H | $OCH_3$ | H | $CF_3$ | H |
| 5 | 29N | $CF_3CF_2CF_2$ | H | H | O | H | F | F | H | $CH_3$ | H |
| 5 | 30N | $CF_3CF_2CF_2$ | H | H | O | H | $OCH_3$ | H | H | $CH_3$ | H |
| 5 | 31N | $CF_3CF_2CF_2$ | H | H | O | H | H | $CH_3$ | H | H | H |
| 5 | 32N | $CF_3CF_2CF_2$ | H | H | O | H | Cl | H | H | H | H |
| 5 | 33N | $CF_3CF_2CF_2$ | H | H | O | H | F | H | H | F | H |
| 5 | 34N | $CF_3CF_2CF_2$ | H | H | O | H | H | $OCH_3$ | H | $CH_3$ | H |
| 5 | 35N | $CF_3CF_2CF_2$ | H | H | O | H | H | H | H | H | H |
| 5 | 36N | $CF_3CF_2CF_2$ | H | H | O | H | H | $CH_3$ | H | $CH_3$ | H |
| 5 | 37N | $CF_3CF_2CF_2$ | H | H | O | H | H | Cl | H | H | H |
| 5 | 38N | $CF_3CF_2CF_2$ | H | H | O | H | F | H | H | 3-$CF_3$-phenoxy | H |
| 5 | 39N | $CF_3CF_2CF_2$ | H | H | O | H | F | H | H | 4-$CH_3O$-phenoxy | H |
| 5 | 40N | $CF_3CF_2CF_2$ | H | H | O | H | F | H | H | 4-Cl-phenoxy | H |
| 5 | 41N | $CF_3CF_2CF_2$ | H | H | O | H | F | H | H | H | H |
| 5 | 42N | $CF_3CF_2CF_2$ | H | H | O | H | F | H | H | $CH_3$ | H |
| 5 | 43N | $CF_3CF_2CF_2$ | H | H | O | H | F | H | F | $CH_3$ | H |
| 5 | 44N | $CF_3CF_2CF_2$ | H | H | O | F | F | H | H | $CH_3$ | H |
| 5 | 45N | $CF_3CF_2CF_2$ | H | H | O | H | Cl | H | H | $CH_3$ | H |
| 5 | 46N | $CF_3CF_2CF_2$ | H | H | O | H | $CH_3$ | H | H | $CH_3$ | H |
| 5 | 47N | $CF_3CF_2CF_2$ | H | H | O | $CH_3$ | H | H | H | H | H |
| 5 | 48N | $CF_3CF_2CF_2$ | H | H | O | H | H | $CH_3$ | H | $CF_3$ | H |
| 5 | 49N | $CF_3CF_2CF_2$ | H | H | O | $CH_3$ | H | H | H | $CF_3$ | H |
| 5 | 50N | $CF_3CF_2CF_2$ | H | H | O | $CH_3$ | H | H | H | $CH_3$ | H |
| 5 | 51N | $CF_3CF_2CF_2$ | H | H | O | H | H | $CH_3$ | H | F | H |
| 5 | 52N | $CF_3CF_2CF_2$ | H | H | O | H | $CF_3$ | H | H | F | H |
| 5 | 53N | $CF_3CF_2CF_2$ | H | H | O | H | $CF_3$ | H | H | $CH_3$ | H |
| 5 | 54N | $CF_3CF_2CF_2$ | H | H | O | H | $OCH_3$ | H | H | $CF_3$ | H |
| 5 | 55N | $CF_3CF_2CF_2$ | H | H | O | $OCH_3$ | H | H | H | $CH_3$ | H |
| 5 | 56N | $CF_3CF_2CF_2$ | H | H | O | H | $CH_3$ | H | H | $CF_3$ | H |
| 5 | 57N | $CF_3CF_2CF_2$ | H | H | O | H | $C_6H_5O$ | H | H | H | $OCF_3$ |
| 5 | 58N | $CF_3CF_2CF_2$ | H | H | O | H | H | H | H | H | $OCF_3$ |
| 5 | 59N | $CF_3CF_2CF_2$ | H | H | O | H | $OCF_3$ | F | H | H | $OCF_3$ |
| 5 | 60N | $CF_3CF_2CF_2$ | H | H | O | H | $CF_3$ | F | H | H | $CF_3$ |
| 5 | 61N | $CF_3CF_2CF_2$ | H | H | O | H | H | $OCH_3$ | H | H | $CF_3$ |
| 5 | 62N | $CF_3CF_2CF_2$ | H | H | O | H | $CH_3$ | H | H | H | $CF_3$ |
| 5 | 63N | $CF_3CF_2CF_2$ | H | H | O | H | Cl | H | H | H | $CF_3$ |
| 5 | 64N | $CF_3CF_2CF_2$ | H | H | O | H | $CF_3$ | H | H | H | $OCF_3$ |
| 5 | 65N | $CF_3CF_2CF_2$ | H | H | O | H | F | H | H | H | $OCF_3$ |
| 5 | 66N | $CF_3CF_2CF_2$ | H | H | O | H | F | H | F | H | $OCF_3$ |
| 5 | 67N | $CF_3CF_2CF_2$ | H | H | O | H | Br | H | H | H | $OCF_3$ |
| 5 | 68N | $CF_3CF_2CF_2$ | H | H | O | H | Cl | H | H | H | $OCF_3$ |
| 5 | 69N | $CF_3CF_2CF_2$ | H | H | O | H | F | F | H | H | $OCF_3$ |
| 5 | 70N | $CF_3CF_2CF_2$ | H | H | O | H | F | H | H | H | phenyl |
| 5 | 71N | $CF_3CF_2CF_2$ | H | H | O | H | $CH_3$ | H | H | H | $OCF_3$ |
| 5 | 72N | $CF_3CF_2CF_2$ | H | H | O | H | F | F | H | H | $CF_3$ |
| 5 | 73N | $CF_3CF_2CF_2$ | H | H | O | H | Cl | H | H | H | $CH_3$ |
| 5 | 74N | $CF_3CF_2CF_2$ | H | H | O | H | $OCH_3$ | H | H | H | $CH_3$ |
| 5 | 75N | $CF_3CF_2CF_2$ | H | H | O | H | F | H | H | H | $CH_3$ |
| 5 | 76N | $CF_3CF_2CF_2$ | H | H | O | F | F | H | H | H | $OCF_3$ |
| 5 | 77N | $CF_3CF_2CF_2$ | H | H | O | $OCH_3$ | H | H | H | H | $CF_3$ |
| 5 | 78N | $CF_3CF_2CF_2$ | H | H | O | H | H | $OCH_3$ | H | H | $CH_3$ |
| 5 | 79N | $CF_3CF_2CF_2$ | H | H | O | H | H | $CH_3$ | H | H | $CH_3$ |
| 5 | 80N | $CF_3CF_2CF_2$ | H | H | O | H | $CH_3$ | H | H | H | $CH_3$ |

TABLE 4-continued

Structure of Substituted Phenyl tertiary-2-Heteroalkylamines (Z is covalent bond; Y is CH and $R_{14}$ is H).

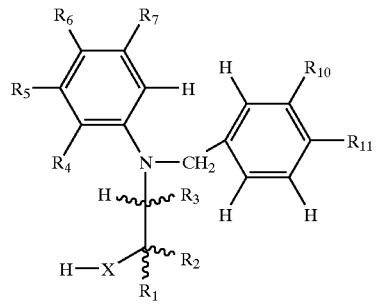

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 5 | 81N | $CF_3CF_2CF_2$ | H | H | O | $CH_3$ | H | H | H | H | $CH_3$ |
| 5 | 82N | $CF_3CF_2CF_2$ | H | H | O | H | F | F | H | H | $CH_3$ |
| 5 | 83N | $CF_3CF_2CF_2$ | H | H | O | H | F | H | F | H | $CH_3$ |
| 5 | 84N | $CF_3CF_2CF_2$ | H | H | O | F | F | H | H | H | $CH_3$ |
| 5 | 85N | $CF_3CF_2CF_2$ | H | H | O | F | $CF_3$ | H | H | H | $CH_3$ |
| 5 | 86N | $CF_3CF_2CF_2$ | H | H | O | H | H | $CH_3$ | H | H | $CF_3$ |
| 5 | 87N | $CF_3CF_2CF_2$ | H | H | O | $CH_3$ | H | H | H | H | $CF_3$ |
| 5 | 88N | $CF_3CF_2CF_2$ | H | H | O | H | $CF_3$ | H | H | H | $CH_3$ |
| 5 | 89N | $CF_3CF_2CF_2$ | H | H | O | $OCH_3$ | H | H | H | H | $CH_3$ |
| 5 | 90N | $CF_3CF_2CF_2$ | H | H | O | H | H | $CF_3$ | H | H | $CH_3$ |
| 5 | 91N | $CF_3CF_2CF_2$ | H | H | O | $CF_3$ | H | H | H | H | $CH_3$ |
| 5 | 92N | $CF_3CF_2CF_2$ | H | H | O | H | $CF_3$ | F | H | H | $CH_3$ |
| 6 | 1N | $CF_3OCF_2CF_2$ | H | H | O | H | $C_6H_5O$ | H | H | $OCF_2CF_2H$ | H |
| 6 | 2N | $CF_3OCF_2CF_2$ | H | H | O | H | $OCF_3$ | H | H | $OCF_2CF_2H$ | H |
| 6 | 3N | $CF_3OCF_2CF_2$ | H | H | O | F | H | H | F | $OCF_2CF_2H$ | H |
| 6 | 4N | $CF_3OCF_2CF_2$ | H | H | O | H | F | H | H | $OCF_2CF_2H$ | H |
| 6 | 5N | $CF_3OCF_2CF_2$ | H | H | O | H | $C_6H_5O$ | H | H | $OCF_3$ | H |
| 6 | 6N | $CF_3OCF_2CF_2$ | H | H | O | H | $OCF_3$ | H | H | $OCF_3$ | H |
| 6 | 7N | $CF_3OCF_2CF_2$ | H | H | O | H | H | phenyl | H | $OCF_3$ | H |
| 6 | 8N | $CF_3OCF_2CF_2$ | H | H | O | H | phenyl | H | H | $OCF_3$ | H |
| 6 | 9N | $CF_3OCF_2CF_2$ | H | H | O | H | H | H | H | $OCF_3$ | H |
| 6 | 10N | $CF_3OCF_2CF_2$ | H | H | O | H | Br | H | H | $OCF_3$ | H |
| 6 | 11N | $CF_3OCF_2CF_2$ | H | H | O | H | $CF_3$ | F | H | $CF_3$ | H |
| 6 | 12N | $CF_3OCF_2CF_2$ | H | H | O | H | $CH_3$ | H | H | $CF_3$ | H |
| 6 | 13N | $CF_3OCF_2CF_2$ | H | H | O | H | $CF_3$ | H | H | $CF_3$ | H |
| 6 | 14N | $CF_3OCF_2CF_2$ | H | H | O | H | $CH_3$ | H | H | $OCF_3$ | H |
| 6 | 15N | $CF_3OCF_2CF_2$ | H | H | O | H | F | F | H | $OCF_3$ | H |
| 6 | 16N | $CF_3OCF_2CF_2$ | H | H | O | H | Br | H | H | $CF_3$ | H |
| 6 | 17N | $CF_3OCF_2CF_2$ | H | H | O | H | $CF_3$ | F | H | $OCF_3$ | H |
| 6 | 18N | $CF_3OCF_2CF_2$ | H | H | O | H | F | H | H | $OCF_3$ | H |
| 6 | 19N | $CF_3OCF_2CF_2$ | H | H | O | H | Cl | H | H | $OCF_3$ | H |
| 6 | 20N | $CF_3OCF_2CF_2$ | H | H | O | H | F | H | H | $CF_3$ | H |
| 6 | 21N | $CF_3OCF_2CF_2$ | H | H | O | H | F | F | H | $CF_3$ | H |
| 6 | 22N | $CF_3OCF_2CF_2$ | H | H | O | H | Cl | H | H | $CF_3$ | H |
| 6 | 23N | $CF_3OCF_2CF_2$ | H | H | O | H | F | H | H | phenoxy | H |
| 6 | 24N | $CF_3OCF_2CF_2$ | H | H | O | H | $CF_3$ | Cl | H | $CH_3$ | H |
| 6 | 25N | $CF_3OCF_2CF_2$ | H | H | O | H | $CF_3$ | F | H | $CH_3$ | H |
| 6 | 26N | $CF_3OCF_2CF_2$ | H | H | O | H | H | H | H | $CF_3$ | H |
| 6 | 27N | $CF_3OCF_2CF_2$ | H | H | O | F | F | H | H | $CF_3$ | H |
| 6 | 28N | $CF_3OCF_2CF_2$ | H | H | O | H | H | $OCH_3$ | H | $CF_3$ | H |
| 6 | 29N | $CF_3OCF_2CF_2$ | H | H | O | H | F | F | H | $CH_3$ | H |
| 6 | 30N | $CF_3OCF_2CF_2$ | H | H | O | H | $OCH_3$ | H | H | $CH_3$ | H |
| 6 | 31N | $CF_3OCF_2CF_2$ | H | H | O | H | H | $CH_3$ | H | H | H |
| 6 | 32N | $CF_3OCF_2CF_2$ | H | H | O | H | Cl | H | H | H | H |
| 6 | 33N | $CF_3OCF_2CF_2$ | H | H | O | H | F | H | H | F | H |
| 6 | 34N | $CF_3OCF_2CF_2$ | H | H | O | H | H | $OCH_3$ | H | $CH_3$ | H |
| 6 | 35N | $CF_3OCF_2CF_2$ | H | H | O | H | H | H | H | H | H |
| 6 | 36N | $CF_3OCF_2CF_2$ | H | H | O | H | H | $CH_3$ | H | $CH_3$ | H |
| 6 | 37N | $CF_3OCF_2CF_2$ | H | H | O | H | H | Cl | H | H | H |
| 6 | 38N | $CF_3OCF_2CF_2$ | H | H | O | H | F | H | H | 3-$CF_3$-phenoxy | H |
| 6 | 39N | $CF_3OCF_2CF_2$ | H | H | O | H | F | H | H | 4-$CH_3$O-phenoxy | H |
| 6 | 40N | $CF_3OCF_2CF_2$ | H | H | O | H | F | H | H | 4-Cl-phenoxy | H |
| 6 | 41N | $CF_3OCF_2CF_2$ | H | H | O | H | F | H | H | H | H |
| 6 | 42N | $CF_3OCF_2CF_2$ | H | H | O | H | F | H | H | $CH_3$ | H |
| 6 | 43N | $CF_3OCF_2CF_2$ | H | H | O | H | F | H | F | $CH_3$ | H |
| 6 | 44N | $CF_3OCF_2CF_2$ | H | H | O | F | F | H | H | $CH_3$ | H |

TABLE 4-continued

Structure of Substituted Phenyl tertiary-2-Heteroalkylamines (Z is covalent bond; Y is CH and $R_{14}$ is H).

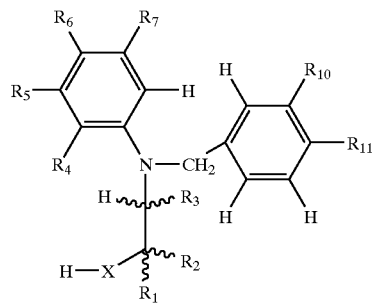

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 6 | 45N | $CF_3OCF_2CF_2$ | H | H | O | H | Cl | H | H | $CH_3$ | H |
| 6 | 46N | $CF_3OCF_2CF_2$ | H | H | O | H | $CH_3$ | H | H | $CH_3$ | H |
| 6 | 47N | $CF_3OCF_2CF_2$ | H | H | O | $CH_3$ | H | H | H | H | H |
| 6 | 48N | $CF_3OCF_2CF_2$ | H | H | O | H | H | $CH_3$ | H | $CF_3$ | H |
| 6 | 49N | $CF_3OCF_2CF_2$ | H | H | O | $CH_3$ | H | H | H | $CF_3$ | H |
| 6 | 50N | $CF_3OCF_2CF_2$ | H | H | O | $CH_3$ | H | H | H | $CH_3$ | H |
| 6 | 51N | $CF_3OCF_2CF_2$ | H | H | O | H | H | $CH_3$ | H | F | H |
| 6 | 52N | $CF_3OCF_2CF_2$ | H | H | O | H | $CF_3$ | H | H | F | H |
| 6 | 53N | $CF_3OCF_2CF_2$ | H | H | O | H | $CF_3$ | H | H | $CH_3$ | H |
| 6 | 54N | $CF_3OCF_2CF_2$ | H | H | O | H | $OCH_3$ | H | H | $CF_3$ | H |
| 6 | 55N | $CF_3OCF_2CF_2$ | H | H | O | $OCH_3$ | H | H | H | $CH_3$ | H |
| 6 | 56N | $CF_3OCF_2CF_2$ | H | H | O | H | H | $CH_3$ | H | $CF_3$ | H |
| 6 | 57N | $CF_3OCF_2CF_2$ | H | H | O | H | $C_6H_5O$ | H | H | H | $OCF_3$ |
| 6 | 58N | $CF_3OCF_2CF_2$ | H | H | O | H | H | H | H | H | $OCF_3$ |
| 6 | 59N | $CF_3OCF_2CF_2$ | H | H | O | H | $OCF_3$ | H | H | H | $OCF_3$ |
| 6 | 60N | $CF_3OCF_2CF_2$ | H | H | O | H | $CF_3$ | F | H | H | $CF_3$ |
| 6 | 61N | $CF_3OCF_2CF_2$ | H | H | O | H | H | $OCH_3$ | H | H | $CF_3$ |
| 6 | 62N | $CF_3OCF_2CF_2$ | H | H | O | H | $CH_3$ | H | H | H | $CF_3$ |
| 6 | 63N | $CF_3OCF_2CF_2$ | H | H | O | H | Cl | H | H | H | $CF_3$ |
| 6 | 64N | $CF_3OCF_2CF_2$ | H | H | O | H | $CF_3$ | H | H | H | $OCF_3$ |
| 6 | 65N | $CF_3OCF_2CF_2$ | H | H | O | H | F | H | H | H | $OCF_3$ |
| 6 | 66N | $CF_3OCF_2CF_2$ | H | H | O | H | F | H | F | H | $OCF_3$ |
| 6 | 67N | $CF_3OCF_2CF_2$ | H | H | O | H | Br | H | H | H | $OCF_3$ |
| 6 | 68N | $CF_3OCF_2CF_2$ | H | H | O | H | Cl | H | H | H | $OCF_3$ |
| 6 | 69N | $CF_3OCF_2CF_2$ | H | H | O | H | F | F | H | H | $OCF_3$ |
| 6 | 70N | $CF_3OCF_2CF_2$ | H | H | O | H | F | H | H | H | phenyl |
| 6 | 71N | $CF_3OCF_2CF_2$ | H | H | O | H | $CH_3$ | H | H | H | $OCF_3$ |
| 6 | 72N | $CF_3OCF_2CF_2$ | H | H | O | H | F | F | H | H | $CF_3$ |
| 6 | 73N | $CF_3OCF_2CF_2$ | H | H | O | H | Cl | H | H | H | $CH_3$ |
| 6 | 74N | $CF_3OCF_2CF_2$ | H | H | O | H | $OCH_3$ | H | H | H | $CH_3$ |
| 6 | 75N | $CF_3OCF_2CF_2$ | H | H | O | H | F | H | H | H | $CH_3$ |
| 6 | 76N | $CF_3OCF_2CF_2$ | H | H | O | F | F | H | H | H | $OCF_3$ |
| 6 | 77N | $CF_3OCF_2CF_2$ | H | H | O | $OCH_3$ | H | H | H | H | $CF_3$ |
| 6 | 78N | $CF_3OCF_2CF_2$ | H | H | O | H | H | $OCH_3$ | H | H | $CH_3$ |
| 6 | 79N | $CF_3OCF_2CF_2$ | H | H | O | H | H | $CH_3$ | H | H | $CH_3$ |
| 6 | 80N | $CF_3OCF_2CF_2$ | H | H | O | H | $CH_3$ | H | H | H | $CH_3$ |
| 6 | 81N | $CF_3OCF_2CF_2$ | H | H | O | $CH_3$ | H | H | H | H | $CH_3$ |
| 6 | 82N | $CF_3OCF_2CF_2$ | H | H | O | H | F | F | H | H | $CH_3$ |
| 6 | 83N | $CF_3OCF_2CF_2$ | H | H | O | H | F | H | F | H | $CH_3$ |
| 6 | 84N | $CF_3OCF_2CF_2$ | H | H | O | F | F | H | H | H | $CH_3$ |
| 6 | 85N | $CF_3OCF_2CF_2$ | H | H | O | F | $CF_3$ | H | H | H | $CH_3$ |
| 6 | 86N | $CF_3OCF_2CF_2$ | H | H | O | H | H | $CH_3$ | H | H | $CF_3$ |
| 6 | 87N | $CF_3OCF_2CF_2$ | H | H | O | $CH_3$ | H | H | H | H | $CF_3$ |
| 6 | 88N | $CF_3OCF_2CF_2$ | H | H | O | H | $CF_3$ | H | H | H | $CH_3$ |
| 6 | 89N | $CF_3OCF_2CF_2$ | H | H | O | $OCH_3$ | H | H | H | H | $CH_3$ |
| 6 | 90N | $CF_3OCF_2CF_2$ | H | H | O | H | H | $CF_3$ | H | H | $CH_3$ |
| 6 | 91N | $CF_3OCF_2CF_2$ | H | H | O | $CF_3$ | H | H | H | H | $CH_3$ |
| 6 | 92N | $CF_3OCF_2CF_2$ | H | H | O | H | $CF_3$ | F | H | H | $CH_3$ |
| 7 | 1N | $CF_3CH_2$ | H | H | O | H | $C_6H_5O$ | H | H | $OCF_2CF_2H$ | H |
| 7 | 2N | $CF_3CH_2$ | H | H | O | H | $OCF_3$ | H | H | $OCF_2CF_2H$ | H |
| 7 | 3N | $CF_3CH_2$ | H | H | O | F | H | H | F | $OCF_2CF_2H$ | H |
| 7 | 4N | $CF_3CH_2$ | H | H | O | H | F | H | H | $OCF_2CF_2H$ | H |
| 7 | 5N | $CF_3CH_2$ | H | H | O | H | $C_6H_5O$ | H | H | $OCF_3$ | H |
| 7 | 6N | $CF_3CH_2$ | H | H | O | H | $OCF_3$ | H | H | $OCF_3$ | H |
| 7 | 7N | $CF_3CH_2$ | H | H | O | H | H | phenyl | H | $OCF_3$ | H |
| 7 | 8N | $CF_3CH_2$ | H | H | O | H | phenyl | H | H | $OCF_3$ | H |

TABLE 4-continued

Structure of Substituted Phenyl tertiary-2-Heteroalkylamines (Z is covalent bond; Y is CH and $R_{14}$ is H).

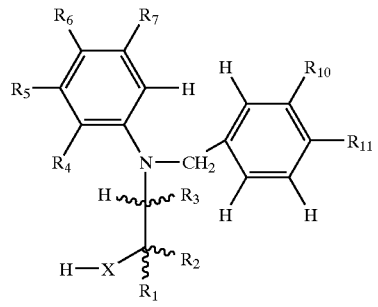

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 7 | 9N | $CF_3CH_2$ | H | H | O | H | H | H | H | $OCF_3$ | H |
| 7 | 10N | $CF_3CH_2$ | H | H | O | H | Br | H | H | $OCF_3$ | H |
| 7 | 11N | $CF_3CH_2$ | H | H | O | H | $CF_3$ | F | H | $CF_3$ | H |
| 7 | 12N | $CF_3CH_2$ | H | H | O | H | $CH_3$ | H | H | $CF_3$ | H |
| 7 | 13N | $CF_3CH_2$ | H | H | O | H | $CF_3$ | H | H | $CF_3$ | H |
| 7 | 14N | $CF_3CH_2$ | H | H | O | H | $CH_3$ | H | H | $OCF_3$ | H |
| 7 | 15N | $CF_3CH_2$ | H | H | O | H | F | F | H | $OCF_3$ | H |
| 7 | 16N | $CF_3CH_2$ | H | H | O | H | Br | H | H | $CF_3$ | H |
| 7 | 17N | $CF_3CH_2$ | H | H | O | H | $CF_3$ | F | H | $OCF_3$ | H |
| 7 | 18N | $CF_3CH_2$ | H | H | O | H | F | H | H | $OCF_3$ | H |
| 7 | 19N | $CF_3CH_2$ | H | H | O | H | Cl | H | H | $OCF_3$ | H |
| 7 | 20N | $CF_3CH_2$ | H | H | O | H | F | H | H | $CF_3$ | H |
| 7 | 21N | $CF_3CH_2$ | H | H | O | H | F | F | H | $CF_3$ | H |
| 7 | 22N | $CF_3CH_2$ | H | H | O | H | Cl | H | H | $CF_3$ | H |
| 7 | 23N | $CF_3CH_2$ | H | H | O | H | F | H | H | phenoxy | H |
| 7 | 24N | $CF_3CH_2$ | H | H | O | H | $CF_3$ | Cl | H | $CH_3$ | H |
| 7 | 25N | $CF_3CH_2$ | H | H | O | H | $CF_3$ | F | H | $CH_3$ | H |
| 7 | 26N | $CF_3CH_2$ | H | H | O | H | H | H | H | $CF_3$ | H |
| 7 | 27N | $CF_3CH_2$ | H | H | O | F | F | H | H | $CF_3$ | H |
| 7 | 28N | $CF_3CH_2$ | H | H | O | H | H | $OCH_3$ | H | $CF_3$ | H |
| 7 | 29N | $CF_3CH_2$ | H | H | O | H | F | F | H | $CH_3$ | H |
| 7 | 30N | $CF_3CH_2$ | H | H | O | H | $OCH_3$ | H | H | $CH_3$ | H |
| 7 | 31N | $CF_3CH_2$ | H | H | O | H | H | $CH_3$ | H | H | H |
| 7 | 32N | $CF_3CH_2$ | H | H | O | H | Cl | H | H | H | H |
| 7 | 33N | $CF_3CH_2$ | H | H | O | H | F | H | H | F | H |
| 7 | 34N | $CF_3CH_2$ | H | H | O | H | H | $OCH_3$ | H | $CH_3$ | H |
| 7 | 35N | $CF_3CH_2$ | H | H | O | H | H | H | H | H | H |
| 7 | 36N | $CF_3CH_2$ | H | H | O | H | H | $CH_3$ | H | $CH_3$ | H |
| 7 | 37N | $CF_3CH_2$ | H | H | O | H | H | Cl | H | H | H |
| 7 | 38N | $CF_3CH_2$ | H | H | O | H | F | H | H | 3-$CF_3$-phenoxy | H |
| 7 | 39N | $CF_3CH_2$ | H | H | O | H | F | H | H | 4-$CH_3O$-phenoxy | H |
| 7 | 40N | $CF_3CH_2$ | H | H | O | H | F | H | H | 4-Cl-phenoxy | H |
| 7 | 41N | $CF_3CH_2$ | H | H | O | H | F | H | H | H | H |
| 7 | 42N | $CF_3CH_2$ | H | H | O | H | F | H | H | $CH_3$ | H |
| 7 | 43N | $CF_3CH_2$ | H | H | O | H | F | H | F | $CH_3$ | H |
| 7 | 44N | $CF_3CH_2$ | H | H | O | F | F | H | H | $CH_3$ | H |
| 7 | 45N | $CF_3CH_2$ | H | H | O | H | Cl | H | H | $CH_3$ | H |
| 7 | 46N | $CF_3CH_2$ | H | H | O | H | $CH_3$ | H | H | $CH_3$ | H |
| 7 | 47N | $CF_3CH_2$ | H | H | O | $CH_3$ | H | H | H | H | H |
| 7 | 48N | $CF_3CH_2$ | H | H | O | H | H | $CH_3$ | H | $CF_3$ | H |
| 7 | 49N | $CF_3CH_2$ | H | H | O | $CH_3$ | H | H | H | $CF_3$ | H |
| 7 | 50N | $CF_3CH_2$ | H | H | O | $CH_3$ | H | H | H | $CH_3$ | H |
| 7 | 51N | $CF_3CH_2$ | H | H | O | H | H | $CH_3$ | H | F | H |
| 7 | 52N | $CF_3CH_2$ | H | H | O | H | $CF_3$ | H | H | F | H |
| 7 | 53N | $CF_3CH_2$ | H | H | O | H | $CF_3$ | H | H | $CH_3$ | H |
| 7 | 54N | $CF_3CH_2$ | H | H | O | H | $OCH_3$ | H | H | $CF_3$ | H |
| 7 | 55N | $CF_3CH_2$ | H | H | O | $OCH_3$ | H | H | H | $CH_3$ | H |
| 7 | 56N | $CF_3CH_2$ | H | H | O | H | H | $CH_3$ | H | $CF_3$ | H |
| 7 | 57N | $CF_3CH_2$ | H | H | O | H | $C_6H_5O$ | H | H | H | $OCF_3$ |
| 7 | 58N | $CF_3CH_2$ | H | H | O | H | H | H | H | H | $OCF_3$ |
| 7 | 59N | $CF_3CH_2$ | H | H | O | H | $OCF_3$ | H | H | H | $OCF_3$ |
| 7 | 60N | $CF_3CH_2$ | H | H | O | H | $CF_3$ | F | H | H | $CF_3$ |
| 7 | 61N | $CF_3CH_2$ | H | H | O | H | H | $OCH_3$ | H | H | $CF_3$ |
| 7 | 62N | $CF_3CH_2$ | H | H | O | H | $CH_3$ | H | H | H | $CF_3$ |
| 7 | 63N | $CF_3CH_2$ | H | H | O | H | Cl | H | H | H | $CF_3$ |
| 7 | 64N | $CF_3CH_2$ | H | H | O | H | $CF_3$ | H | H | H | $OCF_3$ |

TABLE 4-continued

Structure of Substituted Phenyl tertiary-2-Heteroalkylamines (Z is covalent bond; Y is CH and $R_{14}$ is H).

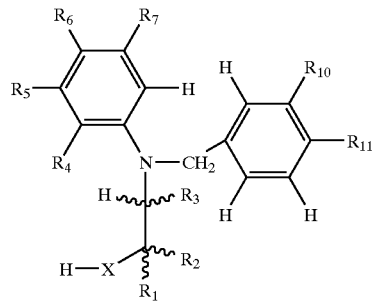

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 7 | 65N | $CF_3CH_2$ | H | H | O | H | F | H | H | H | $OCF_3$ |
| 7 | 66N | $CF_3CH_2$ | H | H | O | H | F | H | F | H | $OCF_3$ |
| 7 | 67N | $CF_3CH_2$ | H | H | O | H | Br | H | H | H | $OCF_3$ |
| 7 | 68N | $CF_3CH_2$ | H | H | O | H | Cl | H | H | H | $OCF_3$ |
| 7 | 69N | $CF_3CH_2$ | H | H | O | H | F | F | H | H | $OCF_3$ |
| 7 | 70N | $CF_3CH_2$ | H | H | O | H | F | H | H | H | phenyl |
| 7 | 71N | $CF_3CH_2$ | H | H | O | H | $CH_3$ | H | H | H | $OCF_3$ |
| 7 | 72N | $CF_3CH_2$ | H | H | O | H | F | F | H | H | $CF_3$ |
| 7 | 73N | $CF_3CH_2$ | H | H | O | H | Cl | H | H | H | $CH_3$ |
| 7 | 74N | $CF_3CH_2$ | H | H | O | H | $OCH_3$ | H | H | H | $CH_3$ |
| 7 | 75N | $CF_3CH_2$ | H | H | O | H | F | H | H | H | $CH_3$ |
| 7 | 76N | $CF_3CH_2$ | H | H | O | F | F | H | H | H | $OCF_3$ |
| 7 | 77N | $CF_3CH_2$ | H | H | O | $OCH_3$ | H | H | H | H | $CF_3$ |
| 7 | 78N | $CF_3CH_2$ | H | H | O | H | H | $OCH_3$ | H | H | $CH_3$ |
| 7 | 79N | $CF_3CH_2$ | H | H | O | H | H | $CH_3$ | H | H | $CH_3$ |
| 7 | 80N | $CF_3CH_2$ | H | H | O | H | $CH_3$ | H | H | H | $CH_3$ |
| 7 | 81N | $CF_3CH_2$ | H | H | O | $CH_3$ | H | H | H | H | $CH_3$ |
| 7 | 82N | $CF_3CH_2$ | H | H | O | H | F | F | H | H | $CH_3$ |
| 7 | 83N | $CF_3CH_2$ | H | H | O | H | F | H | F | H | $CH_3$ |
| 7 | 84N | $CF_3CH_2$ | H | H | O | F | F | H | H | H | $CH_3$ |
| 7 | 85N | $CF_3CH_2$ | H | H | O | F | $CF_3$ | H | H | H | $CH_3$ |
| 7 | 86N | $CF_3CH_2$ | H | H | O | H | H | $CH_3$ | H | H | $CF_3$ |
| 7 | 87N | $CF_3CH_2$ | H | H | O | $CH_3$ | H | H | H | H | $CF_3$ |
| 7 | 88N | $CF_3CH_2$ | H | H | O | H | $CF_3$ | H | H | H | $CH_3$ |
| 7 | 89N | $CF_3CH_2$ | H | H | O | $OCH_3$ | H | H | H | H | $CH_3$ |
| 7 | 90N | $CF_3CH_2$ | H | H | O | H | H | $CF_3$ | H | H | $CH_3$ |
| 7 | 91N | $CF_3CH_2$ | H | H | O | $CF_3$ | H | H | H | H | $CH_3$ |
| 7 | 92N | $CF_3CH_2$ | H | H | O | H | $CF_3$ | F | H | H | $CH_3$ |
| 8 | 1N | $CF_3$ | $CHF_2$ | H | O | H | $C_6H_5O$ | H | H | $OCF_2CF_2H$ | H |
| 8 | 2N | $CF_3$ | $CHF_2$ | H | O | H | $OCF_3$ | H | H | $OCF_2CF_2H$ | H |
| 8 | 3N | $CF_3$ | $CHF_2$ | H | O | F | H | H | F | $OCF_2CF_2H$ | H |
| 8 | 4N | $CF_3$ | $CHF_2$ | H | O | H | F | H | H | $OCF_2CF_2H$ | H |
| 8 | 5N | $CF_3$ | $CHF_2$ | H | O | H | $C_6H_5O$ | H | H | $OCF_3$ | H |
| 8 | 6N | $CF_3$ | $CHF_2$ | H | O | H | $OCF_3$ | H | H | $OCF_3$ | H |
| 8 | 7N | $CF_3$ | $CHF_2$ | H | O | H | H | phenyl | H | $OCF_3$ | H |
| 8 | 8N | $CF_3$ | $CHF_2$ | H | O | H | phenyl | H | H | $OCF_3$ | H |
| 8 | 9N | $CF_3$ | $CHF_2$ | H | O | H | H | H | H | $OCF_3$ | H |
| 8 | 10N | $CF_3$ | $CHF_2$ | H | O | H | Br | H | H | $OCF_3$ | H |
| 8 | 11N | $CF_3$ | $CHF_2$ | H | O | H | $CF_3$ | F | H | $CF_3$ | H |
| 8 | 12N | $CF_3$ | $CHF_2$ | H | O | H | $CH_3$ | H | H | $CF_3$ | H |
| 8 | 13N | $CF_3$ | $CHF_2$ | H | O | H | $CF_3$ | H | H | $CF_3$ | H |
| 8 | 14N | $CF_3$ | $CHF_2$ | H | O | H | $CH_3$ | H | H | $OCF_3$ | H |
| 8 | 15N | $CF_3$ | $CHF_2$ | H | O | H | F | F | H | $OCF_3$ | H |
| 8 | 16N | $CF_3$ | $CHF_2$ | H | O | H | Br | H | H | $C_F$ | H |
| 8 | 17N | $CF_3$ | $CHF_2$ | H | O | H | $CF_3$ | F | H | $OCF_3$ | H |
| 8 | 18N | $CF_3$ | $CHF_2$ | H | O | H | F | H | H | $OCF_3$ | H |
| 8 | 19N | $CF_3$ | $CHF_2$ | H | O | H | Cl | H | H | $OCF_3$ | H |
| 8 | 20N | $CF_3$ | $CHF_2$ | H | O | H | F | H | H | $CF_3$ | H |
| 8 | 21N | $CF_3$ | $CHF_2$ | H | O | H | F | F | H | $CF_3$ | H |
| 8 | 22N | $CF_3$ | $CHF_2$ | H | O | H | Cl | H | H | $CF_3$ | H |
| 8 | 23N | $CF_3$ | $CHF_2$ | H | O | H | F | H | H | phenoxy | H |
| 8 | 24N | $CF_3$ | $CHF_2$ | H | O | H | $CF_3$ | Cl | H | $CH_3$ | H |
| 8 | 25N | $CF_3$ | $CHF_2$ | H | O | H | $CF_3$ | F | H | $CH_3$ | H |
| 8 | 26N | $CF_3$ | $CHF_2$ | H | O | H | H | H | H | $CF_3$ | H |
| 8 | 27N | $CF_3$ | $CHF_2$ | H | O | F | F | H | H | $CF_3$ | H |
| 8 | 28N | $CF_3$ | $CHF_2$ | H | O | H | H | $OCH_3$ | H | $CF_3$ | H |

TABLE 4-continued

Structure of Substituted Phenyl tertiary-2-Heteroalkylamines (Z is covalent bond; Y is CH and $R_{14}$ is H).

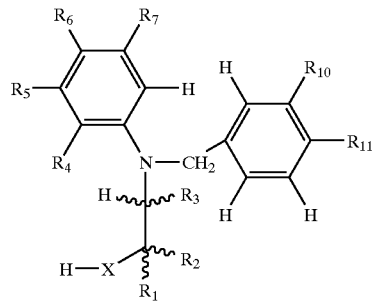

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 8 | 29N | $CF_3$ | $CHF_2$ | H | O | H | F | F | H | $CH_3$ | H |
| 8 | 30N | $CF_3$ | $CHF_2$ | H | O | H | $OCH_3$ | H | H | $CH_3$ | H |
| 8 | 31N | $CF_3$ | $CHF_2$ | H | O | H | H | $CH_3$ | H | H | H |
| 8 | 32N | $CF_3$ | $CHF_2$ | H | O | H | Cl | H | H | H | H |
| 8 | 33N | $CF_3$ | $CHF_2$ | H | O | H | F | H | H | F | H |
| 8 | 34N | $CF_3$ | $CHF_2$ | H | O | H | H | $OCH_3$ | H | $CH_3$ | H |
| 8 | 35N | $CF_3$ | $CHF_2$ | H | O | H | H | H | H | H | H |
| 8 | 36N | $CF_3$ | $CHF_2$ | H | O | H | H | $CH_3$ | H | $CH_3$ | H |
| 8 | 37N | $CF_3$ | $CHF_2$ | H | O | H | H | Cl | H | H | H |
| 8 | 38N | $CF_3$ | $CHF_2$ | H | O | H | F | H | H | 3-$CF_3$-phenoxy | H |
| 8 | 39N | $CF_3$ | $CHF_2$ | H | O | H | F | H | H | 4-$CH_3$O-phenoxy | H |
| 8 | 40N | $CF_3$ | $CHF_2$ | H | O | H | F | H | H | 4-Cl-phenoxy | H |
| 8 | 41N | $CF_3$ | $CHF_2$ | H | O | H | F | H | H | H | H |
| 8 | 42N | $CF_3$ | $CHF_2$ | H | O | H | F | H | H | $CH_3$ | H |
| 8 | 43N | $CF_3$ | $CHF_2$ | H | O | H | F | H | F | $CH_3$ | H |
| 8 | 44N | $CF_3$ | $CHF_2$ | H | O | F | F | H | H | $CH_3$ | H |
| 8 | 45N | $CF_3$ | $CHF_2$ | H | O | H | Cl | H | H | $CH_3$ | H |
| 8 | 46N | $CF_3$ | $CHF_2$ | H | O | H | $CH_3$ | H | H | $CH_3$ | H |
| 8 | 47N | $CF_3$ | $CHF_2$ | H | O | $CH_3$ | H | H | H | H | H |
| 8 | 48N | $CF_3$ | $CHF_2$ | H | O | H | H | $CH_3$ | H | $CF_3$ | H |
| 8 | 49N | $CF_3$ | $CHF_2$ | H | O | $CH_3$ | H | H | H | $CF_3$ | H |
| 8 | 50N | $CF_3$ | $CHF_2$ | H | O | $CH_3$ | H | H | H | $CH_3$ | H |
| 8 | 51N | $CF_3$ | $CHF_2$ | H | O | H | H | $CH_3$ | H | F | H |
| 8 | 52N | $CF_3$ | $CHF_2$ | H | O | H | $CF_3$ | H | H | F | H |
| 8 | 53N | $CF_3$ | $CHF_2$ | H | O | H | $CF_3$ | H | H | $CH_3$ | H |
| 8 | 54N | $CF_3$ | $CHF_2$ | H | O | H | $OCH_3$ | H | H | $CF_3$ | H |
| 8 | 55N | $CF_3$ | $CHF_2$ | H | O | $OCH_3$ | H | H | H | $CH_3$ | H |
| 8 | 56N | $CF_3$ | $CHF_2$ | H | O | H | H | $CH_3$ | H | $CF_3$ | H |
| 8 | 57N | $CF_3$ | $CHF_2$ | H | O | H | $C_6H_5O$ | H | H | H | $OCF_3$ |
| 8 | 58N | $CF_3$ | $CHF_2$ | H | O | H | H | H | H | H | $OCF_3$ |
| 8 | 59N | $CF_3$ | $CHF_2$ | H | O | H | $OCF_3$ | H | H | H | $OCF_3$ |
| 8 | 60N | $CF_3$ | $CHF_2$ | H | O | H | CF | F | H | H | $CF_3$ |
| 8 | 61N | $CF_3$ | $CHF_2$ | H | O | H | H | $OCH_3$ | H | H | $CF_3$ |
| 8 | 62N | $CF_3$ | $CHF_2$ | H | O | H | $CH_3$ | H | H | H | $CF_3$ |
| 8 | 63N | $CF_3$ | $CHF_2$ | H | O | H | Cl | H | H | H | $CF_3$ |
| 8 | 64N | $CF_3$ | $CHF_2$ | H | O | H | $CF_3$ | H | H | H | $OCF_3$ |
| 8 | 65N | $CF_3$ | $CHF_2$ | H | O | H | F | H | H | H | $OCF_3$ |
| 8 | 66N | $CF_3$ | $CHF_2$ | H | O | H | F | H | F | H | $OCF_3$ |
| 8 | 67N | $CF_3$ | $CHF_2$ | H | O | H | Br | H | H | H | $OCF_3$ |
| 8 | 68N | $CF_3$ | $CHF_2$ | H | O | H | Cl | H | H | H | $OCF_3$ |
| 8 | 69N | $CF_3$ | $CHF_2$ | H | O | H | F | F | H | H | $OCF_3$ |
| 8 | 70N | $CF_3$ | $CHF_2$ | H | O | H | F | H | H | H | phenyl |
| 8 | 71N | $CF_3$ | $CHF_2$ | H | O | H | $CH_3$ | H | H | H | $OCF_3$ |
| 8 | 72N | $CF_3$ | $CHF_2$ | H | O | H | F | F | H | H | $CF_3$ |
| 8 | 73N | $CF_3$ | $CHF_2$ | H | O | H | Cl | H | H | H | $CH_3$ |
| 8 | 74N | $CF_3$ | $CHF_2$ | H | O | H | $OCH_3$ | H | H | H | $CH_3$ |
| 8 | 75N | $CF_3$ | $CHF_2$ | H | O | H | F | H | H | H | $CH_3$ |
| 8 | 76N | $CF_3$ | $CHF_2$ | H | O | F | F | H | H | H | $OCF_3$ |
| 8 | 77N | $CF_3$ | $CHF_2$ | H | O | $OCH_3$ | H | H | H | H | $CF_3$ |
| 8 | 78N | $CF_3$ | $CHF_2$ | H | O | H | H | $OCH_3$ | H | H | $CH_3$ |
| 8 | 79N | $CF_3$ | $CHF_2$ | H | O | H | H | $CH_3$ | H | H | $CH_3$ |
| 8 | 80N | $CF_3$ | $CHF_2$ | H | O | H | $CH_3$ | H | H | H | $CH_3$ |
| 8 | 81N | $CF_3$ | $CHF_2$ | H | O | $CH_3$ | H | H | H | H | $CH_3$ |
| 8 | 82N | $CF_3$ | $CHF_2$ | H | O | H | F | F | H | H | $CH_3$ |
| 8 | 83N | $CF_3$ | $CHF_2$ | H | O | H | F | H | F | H | $CH_3$ |
| 8 | 84N | $CF_3$ | $CHF_2$ | H | O | F | F | H | H | H | $CH_3$ |

TABLE 4-continued

Structure of Substituted Phenyl tertiary-2-Heteroalkylamines (Z is covalent bond; Y is CH and $R_{14}$ is H).

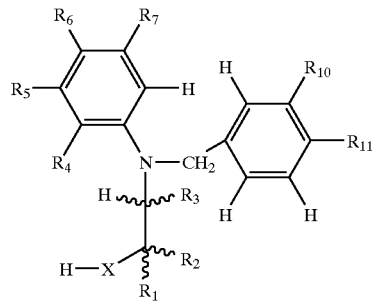

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 8 | 85N | $CF_3$ | $CHF_2$ | H | O | F | $CF_3$ | H | H | H | $CH_3$ |
| 8 | 86N | $CF_3$ | $CHF_2$ | H | O | H | H | $CH_3$ | H | H | $CF_3$ |
| 8 | 87N | $CF_3$ | $CHF_2$ | H | O | $CH_3$ | H | H | H | H | $CF_3$ |
| 8 | 88N | $CF_3$ | $CHF_2$ | H | O | H | $CF_3$ | H | H | H | $CH_3$ |
| 8 | 89N | $CF_3$ | $CHF_2$ | H | O | $OCH_3$ | H | H | H | H | $CH_3$ |
| 8 | 90N | $CF_3$ | $CHF_2$ | H | O | H | H | $CF_3$ | H | H | $CH_3$ |
| 8 | 91N | $CF_3$ | $CHF_2$ | H | O | $CF_3$ | H | H | H | H | $CH_3$ |
| 8 | 92N | $CF_3$ | $CHF_2$ | H | O | H | $CF_3$ | F | H | H | $CH_3$ |
| 9 | 1N | $CF_3$ | H | $CF_3$ | O | H | $C_6H_5O$ | H | H | $OCF_2CF_2H$ | H |
| 9 | 2N | $CF_3$ | H | $CF_3$ | O | H | $OCF_3$ | H | H | $OCF_2CF_2H$ | H |
| 9 | 3N | $CF_3$ | H | $CF_3$ | O | F | H | H | F | $OCF_2CF_2H$ | H |
| 9 | 4N | $CF_3$ | H | $CF_3$ | O | H | F | H | H | $OCF_2CF_2H$ | H |
| 9 | 5N | $CF_3$ | H | $CF_3$ | O | H | $C_6H_5O$ | H | H | $OCF_3$ | H |
| 9 | 6N | $CF_3$ | H | $CF_3$ | O | H | $OCF_3$ | H | H | $OCF_3$ | H |
| 9 | 7N | $CF_3$ | H | $CF_3$ | O | H | H | phenyl | H | $OCF_3$ | H |
| 9 | 8N | $CF_3$ | H | $CF_3$ | O | H | phenyl | H | H | $OCF_3$ | H |
| 9 | 9N | $CF_3$ | H | $CF_3$ | O | H | H | H | H | $OCF_3$ | H |
| 9 | 10N | $CF_3$ | H | $CF_3$ | O | H | Br | H | H | $OCF_3$ | H |
| 9 | 11N | $CF_3$ | H | $CF_3$ | O | H | $CF_3$ | F | H | $CF_3$ | H |
| 9 | 12N | $CF_3$ | H | $CF_3$ | O | H | $CH_3$ | H | H | $CF_3$ | H |
| 9 | 13N | $CF_3$ | H | $CF_3$ | O | H | $CF_3$ | H | H | $CF_3$ | H |
| 9 | 14N | $CF_3$ | H | $CF_3$ | O | H | $CH_3$ | H | H | $OCF_3$ | H |
| 9 | 15N | $CF_3$ | H | $CF_3$ | O | H | F | F | H | $OCF_3$ | H |
| 9 | 16N | $CF_3$ | H | $CF_3$ | O | H | Br | H | H | $CF_3$ | H |
| 9 | 17N | $CF_3$ | H | $CF_3$ | O | H | $CF_3$ | F | H | $OCF_3$ | H |
| 9 | 18N | $CF_3$ | H | $CF_3$ | O | H | F | H | H | $OCF_3$ | H |
| 9 | 19N | $CF_3$ | H | $CF_3$ | O | H | Cl | H | H | $OCF_3$ | H |
| 9 | 20N | $CF_3$ | H | $CF_3$ | O | H | F | H | H | $CF_3$ | H |
| 9 | 21N | $CF_3$ | H | $CF_3$ | O | H | F | F | H | $CF_3$ | H |
| 9 | 22N | $CF_3$ | H | $CF_3$ | O | H | Cl | H | H | $CF_3$ | H |
| 9 | 23N | $CF_3$ | H | $CF_3$ | O | H | F | H | H | phenoxy | H |
| 9 | 24N | $CF_3$ | H | $CF_3$ | O | H | $CF_3$ | Cl | H | $CH_3$ | H |
| 9 | 25N | $CF_3$ | H | $CF_3$ | O | H | $CF_3$ | F | H | $CH_3$ | H |
| 9 | 26N | $CF_3$ | H | $CF_3$ | O | H | H | H | H | $CF_3$ | H |
| 9 | 27N | $CF_3$ | H | $CF_3$ | O | F | F | H | H | $CF_3$ | H |
| 9 | 28N | $CF_3$ | H | $CF_3$ | O | H | H | $OCH_3$ | H | $CF_3$ | H |
| 9 | 29N | $CF_3$ | H | $CF_3$ | O | H | F | F | H | $CH_3$ | H |
| 9 | 30N | $CF_3$ | H | $CF_3$ | O | H | $OCH_3$ | H | H | $CH_3$ | H |
| 9 | 31N | $CF_3$ | H | $CF_3$ | O | H | H | $CH_3$ | H | H | H |
| 9 | 32N | $CF_3$ | H | $CF_3$ | O | H | Cl | H | H | H | H |
| 9 | 33N | $CF_3$ | H | $CF_3$ | O | H | F | H | H | F | H |
| 9 | 34N | $CF_3$ | H | $CF_3$ | O | H | H | $OCH_3$ | H | $CH_3$ | H |
| 9 | 35N | $CF_3$ | H | $CF_3$ | O | H | H | H | H | H | H |
| 9 | 36N | $CF_3$ | H | $CF_3$ | O | H | H | $CH_3$ | H | $CH_3$ | H |
| 9 | 37N | $CF_3$ | H | $CF_3$ | O | H | H | Cl | H | H | H |
| 9 | 38N | $CF_3$ | H | $CF_3$ | O | H | F | H | H | 3-$CF_3$-phenoxy | H |
| 9 | 39N | $CF_3$ | H | $CF_3$ | O | H | F | H | H | 4-$CH_3O$-phenoxy | H |
| 9 | 40N | $CF_3$ | H | $CF_3$ | O | H | F | H | H | 4-Cl-phenoxy | H |
| 9 | 41N | $CF_3$ | H | $CF_3$ | O | H | F | H | H | H | H |
| 9 | 42N | $CF_3$ | H | $CF_3$ | O | H | F | H | H | $CH_3$ | H |
| 9 | 43N | $CF_3$ | H | $CF_3$ | O | H | F | H | F | $CH_3$ | H |
| 9 | 44N | $CF_3$ | H | $CF_3$ | O | F | F | H | H | $CH_3$ | H |
| 9 | 45N | $CF_3$ | H | $CF_3$ | O | H | Cl | H | H | $CH_3$ | H |
| 9 | 46N | $CF_3$ | H | $CF_3$ | O | H | $CH_3$ | H | H | $CH_3$ | H |
| 9 | 47N | $CF_3$ | H | $CF_3$ | O | $CH_3$ | H | H | H | H | H |
| 9 | 48N | $CF_3$ | H | $CF_3$ | O | H | H | $CH_3$ | H | $CF_3$ | H |

TABLE 4-continued

Structure of Substituted Phenyl tertiary-2-Heteroalkylamines (Z is covalent bond; Y is CH and $R_{14}$ is H).

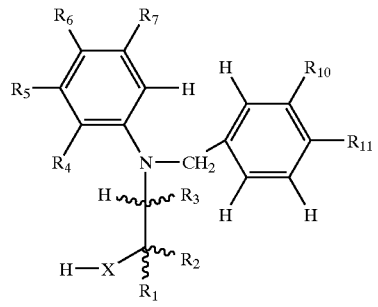

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 9 | 49N | $CF_3$ | H | $CF_3$ | O | $CH_3$ | H | H | H | $CF_3$ | H |
| 9 | 50N | $CF_3$ | H | $CF_3$ | O | $CH_3$ | H | H | H | $CH_3$ | H |
| 9 | 51N | $CF_3$ | H | $CF_3$ | O | H | H | $CH_3$ | H | F | H |
| 9 | 52N | $CF_3$ | H | $CF_3$ | O | H | $CF_3$ | H | H | F | H |
| 9 | 53N | $CF_3$ | H | $CF_3$ | O | H | $CF_3$ | H | H | $CH_3$ | H |
| 9 | 54N | $CF_3$ | H | $CF_3$ | O | H | $OCH_3$ | H | H | $CF_3$ | H |
| 9 | 55N | $CF_3$ | H | $CF_3$ | O | $OCH_3$ | H | H | H | $CH_3$ | H |
| 9 | 56N | $CF_3$ | H | $CF_3$ | O | H | H | $CH_3$ | H | $CF_3$ | H |
| 9 | 57N | $CF_3$ | H | $CF_3$ | O | H | $C_6H_5O$ | H | H | H | $OCF_3$ |
| 9 | 58N | $CF_3$ | H | $CF_3$ | O | H | H | H | H | H | $OCF_3$ |
| 9 | 59N | $CF_3$ | H | $CF_3$ | O | H | $OCF_3$ | H | H | H | $OCF_3$ |
| 9 | 60N | $CF_3$ | H | $CF_3$ | O | H | $CF_3$ | F | H | H | $CF_3$ |
| 9 | 61N | $CF_3$ | H | $CF_3$ | O | H | H | $OCH_3$ | H | H | $CF_3$ |
| 9 | 62N | $CF_3$ | H | $CF_3$ | O | H | $CH_3$ | H | H | H | $CF_3$ |
| 9 | 63N | $CF_3$ | H | $CF_3$ | O | H | Cl | H | H | H | $CF_3$ |
| 9 | 64N | $CF_3$ | H | $CF_3$ | O | H | $CF_3$ | H | H | H | $OCF_3$ |
| 9 | 65N | $CF_3$ | H | $CF_3$ | O | H | F | H | H | H | $OCF_3$ |
| 9 | 66N | $CF_3$ | H | $CF_3$ | O | H | F | H | F | H | $OCF_3$ |
| 9 | 67N | $CF_3$ | H | $CF_3$ | O | H | Br | H | H | H | $OCF_3$ |
| 9 | 68N | $CF_3$ | H | $CF_3$ | O | H | Cl | H | H | H | $OCF_3$ |
| 9 | 69N | $CF_3$ | H | $CF_3$ | O | H | F | F | H | H | $OCF_3$ |
| 9 | 70N | $CF_3$ | H | $CF_3$ | O | H | F | H | H | H | phenyl |
| 9 | 71N | $CF_3$ | H | $CF_3$ | O | H | $CH_3$ | H | H | H | $OCF_3$ |
| 9 | 72N | $CF_3$ | H | $CF_3$ | O | H | F | F | H | H | $CF_3$ |
| 9 | 73N | $CF_3$ | H | $CF_3$ | O | H | Cl | H | H | H | $CH_3$ |
| 9 | 74N | $CF_3$ | H | $CF_3$ | O | H | $OCH_3$ | H | H | H | $CH_3$ |
| 9 | 75N | $CF_3$ | H | $CF_3$ | O | H | F | H | H | H | $CH_3$ |
| 9 | 76N | $CF_3$ | H | $CF_3$ | O | F | F | H | H | H | $OCF_3$ |
| 9 | 77N | $CF_3$ | H | $CF_3$ | O | $OCH_3$ | H | H | H | H | $CF_3$ |
| 9 | 78N | $CF_3$ | H | $CF_3$ | O | H | H | $OCH_3$ | H | H | $CH_3$ |
| 9 | 79N | $CF_3$ | H | $CF_3$ | O | H | H | $CH_3$ | H | H | $CH_3$ |
| 9 | 80N | $CF_3$ | H | $CF_3$ | O | H | $CH_3$ | H | H | H | $CH_3$ |
| 9 | 81N | $CF_3$ | H | $CF_3$ | O | $CH_3$ | H | H | H | H | $CH_3$ |
| 9 | 82N | $CF_3$ | H | $CF_3$ | O | H | F | F | H | H | $CH_3$ |
| 9 | 83N | $CF_3$ | H | $CF_3$ | O | H | F | H | F | H | $CH_3$ |
| 9 | 84N | $CF_3$ | H | $CF_3$ | O | F | F | H | H | H | $CH_3$ |
| 9 | 85N | $CF_3$ | H | $CF_3$ | O | F | $CF_3$ | H | H | H | $CH_3$ |
| 9 | 86N | $CF_3$ | H | $CF_3$ | O | H | H | $CH_3$ | H | H | $CF_3$ |
| 9 | 87N | $CF_3$ | H | $CF_3$ | O | $CH_3$ | H | H | H | H | $CF_3$ |
| 9 | 88N | $CF_3$ | H | $CF_3$ | O | H | $CF_3$ | H | H | H | $CH_3$ |
| 9 | 89N | $CF_3$ | H | $CF_3$ | O | $OCH_3$ | H | H | H | H | $CH_3$ |
| 9 | 90N | $CF_3$ | H | $CF_3$ | O | H | H | $CF_3$ | H | H | $CH_3$ |
| 9 | 91N | $CF_3$ | H | $CF_3$ | O | $CF_3$ | H | H | H | H | $CH_3$ |
| 9 | 92N | $CF_3$ | H | $CF_3$ | O | H | $CF_3$ | F | H | H | $CH_3$ |
| 10 | 1N | $CF_3$ | $CF_3$ | H | O | H | $C_6H_5O$ | H | H | $OCF_2CF_2H$ | H |
| 10 | 2N | $CF_3$ | $CF_3$ | H | O | H | $OCF_3$ | H | H | $OCF_2CF_2H$ | H |
| 10 | 3N | $CF_3$ | $CF_3$ | H | O | F | H | H | F | $OCF_2CF_2H$ | H |
| 10 | 4N | $CF_3$ | $CF_3$ | H | O | H | F | H | H | $OCF_2CF_2H$ | H |
| 10 | 5N | $CF_3$ | $CF_3$ | H | O | H | $C_6H_5O$ | H | H | $OCF_3$ | H |
| 10 | 6N | $CF_3$ | $CF_3$ | H | O | H | $OCF_3$ | H | H | $OCF_3$ | H |
| 10 | 7N | $CF_3$ | $CF_3$ | H | O | H | H | phenyl | H | $OCF_3$ | H |
| 10 | 8N | $CF_3$ | $CF_3$ | H | O | H | phenyl | H | H | $OCF_3$ | H |
| 10 | 9N | $CF_3$ | $CF_3$ | H | O | H | H | H | H | $OCF_3$ | H |
| 10 | 10N | $CF_3$ | $CF_3$ | H | O | H | Br | H | H | $OCF_3$ | H |
| 10 | 11N | $CF_3$ | $CF_3$ | H | O | H | $CF_3$ | F | H | $CF_3$ | H |
| 10 | 12N | $CF_3$ | $CF_3$ | H | O | H | $CH_3$ | H | H | $CF_3$ | H |

TABLE 4-continued

Structure of Substituted Phenyl tertiary-2-Heteroalkylamines (Z is covalent bond; Y is CH and $R_{14}$ is H).

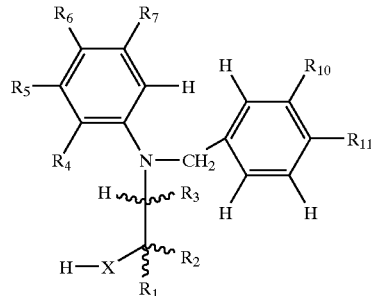

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 10 | 13N | $CF_3$ | $CF_3$ | H | O | H | $CF_3$ | H | H | $CF_3$ | H |
| 10 | 14N | $CF_3$ | $CF_3$ | H | O | H | $CH_3$ | H | H | $OCF_3$ | H |
| 10 | 15N | $CF_3$ | $CF_3$ | H | O | H | F | F | H | $OCF_3$ | H |
| 10 | 16N | $CF_3$ | $CF_3$ | H | O | H | Br | H | H | $CF_3$ | H |
| 10 | 17N | $CF_3$ | $CF_3$ | H | O | H | $CF_3$ | F | H | $OCF_3$ | H |
| 10 | 18N | $CF_3$ | $CF_3$ | H | O | H | F | H | H | $OCF_3$ | H |
| 10 | 19N | $CF_3$ | $CF_3$ | H | O | H | Cl | H | H | $OCF_3$ | H |
| 10 | 20N | $CF_3$ | $CF_3$ | H | O | H | F | H | H | $CF_3$ | H |
| 10 | 21N | $CF_3$ | $CF_3$ | H | O | H | F | F | H | $CF_3$ | H |
| 10 | 22N | $CF_3$ | $CF_3$ | H | O | H | Cl | H | H | $CF_3$ | H |
| 10 | 23N | $CF_3$ | $CF_3$ | H | O | H | F | H | H | phenoxy | H |
| 10 | 24N | $CF_3$ | $CF_3$ | H | O | H | $CF_3$ | Cl | H | $CH_3$ | H |
| 10 | 25N | $CF_3$ | $CF_3$ | H | O | H | $CF_3$ | F | H | $CH_3$ | H |
| 10 | 26N | $CF_3$ | $CF_3$ | H | O | H | H | H | H | $CF_3$ | H |
| 10 | 27N | $CF_3$ | $CF_3$ | H | O | F | F | H | H | $CF_3$ | H |
| 10 | 28N | $CF_3$ | $CF_3$ | H | O | H | H | $OCH_3$ | H | $CF_3$ | H |
| 10 | 29N | $CF_3$ | $CF_3$ | H | O | H | F | F | H | $CH_3$ | H |
| 10 | 30N | $CF_3$ | $CF_3$ | H | O | H | $OCH_3$ | H | H | $CH_3$ | H |
| 10 | 31N | $CF_3$ | $CF_3$ | H | O | H | H | $CH_3$ | H | H | H |
| 10 | 32N | $CF_3$ | $CF_3$ | H | O | H | Cl | H | H | H | H |
| 10 | 33N | $CF_3$ | $CF_3$ | H | O | H | F | H | H | F | H |
| 10 | 34N | $CF_3$ | $CF_3$ | H | O | H | H | $OCH_3$ | H | $CH_3$ | H |
| 10 | 35N | $CF_3$ | $CF_3$ | H | O | H | H | H | H | H | H |
| 10 | 36N | $CF_3$ | $CF_3$ | H | O | H | H | $CH_3$ | H | $CH_3$ | H |
| 10 | 37N | $CF_3$ | $CF_3$ | H | O | H | H | Cl | H | H | H |
| 10 | 38N | $CF_3$ | $CF_3$ | H | O | H | F | H | H | 3-$CF_3$-phenoxy | H |
| 10 | 39N | $CF_3$ | $CF_3$ | H | O | H | F | H | H | 4-$CH_3O$-phenoxy | H |
| 10 | 40N | $CF_3$ | $CF_3$ | H | O | H | F | H | H | 4-Cl-phenoxy | H |
| 10 | 41N | $CF_3$ | $CF_3$ | H | O | H | F | H | H | H | H |
| 10 | 42N | $CF_3$ | $CF_3$ | H | O | H | F | H | H | $CH_3$ | H |
| 10 | 43N | $CF_3$ | $CF_3$ | H | O | H | F | H | F | $CH_3$ | H |
| 10 | 44N | $CF_3$ | $CF_3$ | H | O | F | F | H | H | $CH_3$ | H |
| 10 | 45N | $CF_3$ | $CF_3$ | H | O | H | Cl | H | H | $CH_3$ | H |
| 10 | 46N | $CF_3$ | $CF_3$ | H | O | H | $CH_3$ | H | H | $CH_3$ | H |
| 10 | 47N | $CF_3$ | $CF_3$ | H | O | $CH_3$ | H | H | H | H | H |
| 10 | 48N | $CF_3$ | $CF_3$ | H | O | H | H | $CH_3$ | H | $CF_3$ | H |
| 10 | 49N | $CF_3$ | $CF_3$ | H | O | $CH_3$ | H | H | H | $CF_3$ | H |
| 10 | 50N | $CF_3$ | $CF_3$ | H | O | $CH_3$ | H | H | H | $CH_3$ | H |
| 10 | 51N | $CF_3$ | $CF_3$ | H | O | H | H | $CH_3$ | H | F | H |
| 10 | 52N | $CF_3$ | $CF_3$ | H | O | H | $CF_3$ | H | H | F | H |
| 10 | 53N | $CF_3$ | $CF_3$ | H | O | H | $CF_3$ | H | H | $CH_3$ | H |
| 10 | 54N | $CF_3$ | $CF_3$ | H | O | H | $OCH_3$ | H | H | $CF_3$ | H |
| 10 | 55N | $CF_3$ | $CF_3$ | H | O | $OCH_3$ | H | H | H | $CH_3$ | H |
| 10 | 56N | $CF_3$ | $CF_3$ | H | O | H | H | $CH_3$ | H | $CF_3$ | H |
| 10 | 57N | $CF_3$ | $CF_3$ | H | O | H | $C_6H_5O$ | H | H | H | $OCF_3$ |
| 10 | 58N | $CF_3$ | $CF_3$ | H | O | H | H | H | H | H | $OCF_3$ |
| 10 | 59N | $CF_3$ | $CF_3$ | H | O | H | $OCF_3$ | H | H | H | $OCF_3$ |
| 10 | 60N | $CF_3$ | $CF_3$ | H | O | H | $CF_3$ | F | H | H | $CF_3$ |
| 10 | 61N | $CF_3$ | $CF_3$ | H | O | H | H | $OCH_3$ | H | H | $CF_3$ |
| 10 | 62N | $CF_3$ | $CF_3$ | H | O | H | $CH_3$ | H | H | H | $CF_3$ |
| 10 | 63N | $CF_3$ | $CF_3$ | H | O | H | Cl | H | H | H | $CF_3$ |
| 10 | 64N | $CF_3$ | $CF_3$ | H | O | H | $CF_3$ | H | H | H | $OCF_3$ |
| 10 | 65N | $CF_3$ | $CF_3$ | H | O | H | F | H | H | H | $OCF_3$ |
| 10 | 66N | $CF_3$ | $CF_3$ | H | O | H | F | H | F | H | $OCF_3$ |
| 10 | 67N | $CF_3$ | $CF_3$ | H | O | H | Br | H | H | H | $OCF_3$ |
| 10 | 68N | $CF_3$ | $CF_3$ | H | O | H | Cl | H | H | H | $OCF_3$ |

TABLE 4-continued

Structure of Substituted Phenyl tertiary-2-Heteroalkylamines (Z is covalent bond; Y is CH and $R_{14}$ is H).

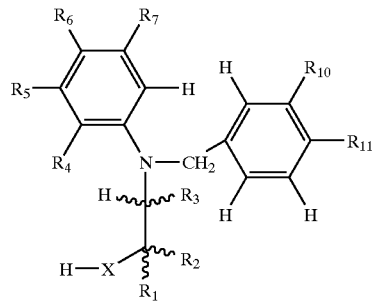

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 10 | 69N | $CF_3$ | $CF_3$ | H | O | H | F | F | H | H | $OCF_3$ |
| 10 | 70N | $CF_3$ | $CF_3$ | H | O | H | F | H | H | H | phenyl |
| 10 | 71N | $CF_3$ | $CF_3$ | H | O | H | $CH_3$ | H | H | H | $OCF_3$ |
| 10 | 72N | $CF_3$ | $CF_3$ | H | O | H | F | F | H | H | $CF_3$ |
| 10 | 73N | $CF_3$ | $CF_3$ | H | O | H | Cl | H | H | H | $CH_3$ |
| 10 | 74N | $CF_3$ | $CF_3$ | H | O | H | $OCH_3$ | H | H | H | $CH_3$ |
| 10 | 75N | $CF_3$ | $CF_3$ | H | O | H | F | H | H | H | $CH_3$ |
| 10 | 76N | $CF_3$ | $CF_3$ | H | O | F | F | H | H | H | $OCF_3$ |
| 10 | 77N | $CF_3$ | $CF_3$ | H | O | $OCH_3$ | H | H | H | H | $CF_3$ |
| 10 | 78N | $CF_3$ | $CF_3$ | H | O | H | H | $OCH_3$ | H | H | $CH_3$ |
| 10 | 79N | $CF_3$ | $CF_3$ | H | O | H | H | $CH_3$ | H | H | $CH_3$ |
| 10 | 80N | $CF_3$ | $CF_3$ | H | O | H | $CH_3$ | H | H | H | $CH_3$ |
| 10 | 81N | $CF_3$ | $CF_3$ | H | O | $CH_3$ | H | H | H | H | $CH_3$ |
| 10 | 82N | $CF_3$ | $CF_3$ | H | O | H | F | F | H | H | $CH_3$ |
| 10 | 83N | $CF_3$ | $CF_3$ | H | O | H | F | H | F | H | $CH_3$ |
| 10 | 84N | $CF_3$ | $CF_3$ | H | O | F | F | H | H | H | $CH_3$ |
| 10 | 85N | $CF_3$ | $CF_3$ | H | O | F | $CF_3$ | H | H | H | $CH_3$ |
| 10 | 86N | $CF_3$ | $CF_3$ | H | O | H | H | $CH_3$ | H | H | $CF_3$ |
| 10 | 87N | $CF_3$ | $CF_3$ | H | O | $CH_3$ | H | H | H | H | $CF_3$ |
| 10 | 88N | $CF_3$ | $CF_3$ | H | O | H | $CF_3$ | H | H | H | $CH_3$ |
| 10 | 89N | $CF_3$ | $CF_3$ | H | O | $OCH_3$ | H | H | H | H | $CH_3$ |
| 10 | 90N | $CF_3$ | $CF_3$ | H | O | H | H | $CF_3$ | H | H | $CH_3$ |
| 10 | 91N | $CF_3$ | $CF_3$ | H | O | $CF_3$ | H | H | H | H | $CH_3$ |
| 10 | 92N | $CF_3$ | $CF_3$ | H | O | H | $CF_3$ | F | H | H | $CH_3$ |
| 11 | 1N | $CF_3$ | $C_6H_5$ | H | O | H | $C_6H_5O$ | H | H | $OCF_2CF_2H$ | H |
| 11 | 2N | $CF_3$ | $C_6H_5$ | H | O | H | $OCF_3$ | H | H | $OCF_2CF_2H$ | H |
| 11 | 3N | $CF_3$ | $C_6H_5$ | H | O | F | H | H | F | $OCF_2CF_2H$ | H |
| 11 | 4N | $CF_3$ | $C_6H_5$ | H | O | H | F | H | H | $OCF_2CF_2H$ | H |
| 11 | 5N | $CF_3$ | $C_6H_5$ | H | O | H | $C_6H_5O$ | H | H | $OCF_3$ | H |
| 11 | 6N | $CF_3$ | $C_6H_5$ | H | O | H | $OCF_3$ | H | H | $OCF_3$ | H |
| 11 | 7N | $CF_3$ | $C_6H_5$ | H | O | H | H | phenyl | H | $OCF_3$ | H |
| 11 | 8N | $CF_3$ | $C_6H_5$ | H | O | H | phenyl | H | H | $OCF_3$ | H |
| 11 | 9N | $CF_3$ | $C_6H_5$ | H | O | H | H | H | H | $OCF_3$ | H |
| 11 | 10N | $CF_3$ | $C_6H_5$ | H | O | H | Br | H | H | $OCF_3$ | H |
| 11 | 11N | $CF_3$ | $C_6H_5$ | H | O | H | $CF_3$ | F | H | $CF_3$ | H |
| 11 | 12N | $CF_3$ | $C_6H_5$ | H | O | H | $CH_3$ | H | H | $CF_3$ | H |
| 11 | 13N | $CF_3$ | $C_6H_5$ | H | O | H | $CF_3$ | H | H | $CF_3$ | H |
| 11 | 14N | $CF_3$ | $C_6H_5$ | H | O | H | $CH_3$ | H | H | $OCF_3$ | H |
| 11 | 15N | $CF_3$ | $C_6H_5$ | H | O | H | F | F | H | $OCF_3$ | H |
| 11 | 16N | $CF_3$ | $C_6H_5$ | H | O | H | Br | H | H | $CF_3$ | H |
| 11 | 17N | $CF_3$ | $C_6H_5$ | H | O | H | $CF_3$ | F | H | $OCF_3$ | H |
| 11 | 18N | $CF_3$ | $C_6H_5$ | H | O | H | F | H | H | $OCF_3$ | H |
| 11 | 19N | $CF_3$ | $C_6H_5$ | H | O | H | Cl | H | H | $OCF_3$ | H |
| 11 | 20N | $CF_3$ | $C_6H_5$ | H | O | H | F | H | H | $CF_3$ | H |
| 11 | 21N | $CF_3$ | $C_6H_5$ | H | O | H | F | F | H | $CF_3$ | H |
| 11 | 22N | $CF_3$ | $C_6H_5$ | H | O | H | Cl | H | H | $CF_3$ | H |
| 11 | 23N | $CF_3$ | $C_6H_5$ | H | O | H | F | H | H | phenoxy | H |
| 11 | 24N | $CF_3$ | $C_6H_5$ | H | O | H | $CF_3$ | Cl | H | $CH_3$ | H |
| 11 | 25N | $CF_3$ | $C_6H_5$ | H | O | H | $CF_3$ | F | H | $CH_3$ | H |
| 11 | 26N | $CF_3$ | $C_6H_5$ | H | O | H | H | H | H | $CF_3$ | H |
| 11 | 27N | $CF_3$ | $C_6H_5$ | H | O | F | F | H | H | $CF_3$ | H |
| 11 | 28N | $CF_3$ | $C_6H_5$ | H | O | H | H | $OCH_3$ | H | $CF_3$ | H |
| 11 | 29N | $CF_3$ | $C_6H_5$ | H | O | H | F | F | H | $CH_3$ | H |
| 11 | 30N | $CF_3$ | $C_6H_5$ | H | O | H | $OCH_3$ | H | H | $CH_3$ | H |
| 11 | 31N | $CF_3$ | $C_6H_5$ | H | O | H | H | $CH_3$ | H | H | H |
| 11 | 32N | $CF_3$ | $C_6H_5$ | H | O | H | Cl | H | H | H | H |

TABLE 4-continued

Structure of Substituted Phenyl tertiary-2-Heteroalkylamines (Z is covalent bond; Y is CH and $R_{14}$ is H).

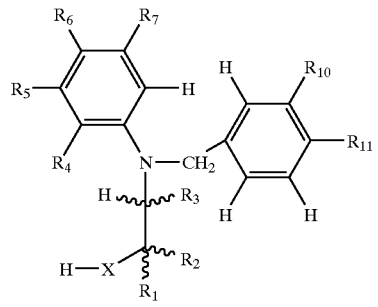

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 11 | 33N | $CF_3$ | $C_6H_5$ | H | O | H | F | H | H | F | H |
| 11 | 34N | $CF_3$ | $C_6H_5$ | H | O | H | H | $OCH_3$ | H | $CH_3$ | H |
| 11 | 35N | $CF_3$ | $C_6H_5$ | H | O | H | H | H | H | H | H |
| 11 | 36N | $CF_3$ | $C_6H_5$ | H | O | H | H | $CH_3$ | H | $CH_3$ | H |
| 11 | 37N | $CF_3$ | $C_6H_5$ | H | O | H | H | Cl | H | H | H |
| 11 | 38N | $CF_3$ | $C_6H_5$ | H | O | H | F | H | H | 3-$CF_3$-phenoxy | H |
| 11 | 39N | $CF_3$ | $C_6H_5$ | H | O | H | F | H | H | 4-$CH_3O$-phenoxy | H |
| 11 | 40N | $CF_3$ | $C_6H_5$ | H | O | H | F | H | H | 4-Cl-phenoxy | H |
| 11 | 41N | $CF_3$ | $C_6H_5$ | H | O | H | F | H | H | H | H |
| 11 | 42N | $CF_3$ | $C_6H_5$ | H | O | H | F | H | H | $CH_3$ | H |
| 11 | 43N | $CF_3$ | $C_6H_5$ | H | O | H | F | H | F | $CH_3$ | H |
| 11 | 44N | $CF_3$ | $C_6H_5$ | H | O | F | F | H | H | $CH_3$ | H |
| 11 | 45N | $CF_3$ | $C_6H_5$ | H | O | H | Cl | H | H | $CH_3$ | H |
| 11 | 46N | $CF_3$ | $C_6H_5$ | H | O | H | $CH_3$ | H | H | $CH_3$ | H |
| 11 | 47N | $CF_3$ | $C_6H_5$ | H | O | $CH_3$ | H | H | H | H | H |
| 11 | 48N | $CF_3$ | $C_6H_5$ | H | O | H | H | $CH_3$ | H | $CF_3$ | H |
| 11 | 49N | $CF_3$ | $C_6H_5$ | H | O | $CH_3$ | H | H | H | $CF_3$ | H |
| 11 | 50N | $CF_3$ | $C_6H_5$ | H | O | $CH_3$ | H | H | H | $CH_3$ | H |
| 11 | 51N | $CF_3$ | $C_6H_5$ | H | O | H | H | $CH_3$ | H | F | H |
| 11 | 52N | $CF_3$ | $C_6H_5$ | H | O | H | $CF_3$ | H | H | F | H |
| 11 | 53N | $CF_3$ | $C_6H_5$ | H | O | H | $CF_3$ | H | H | $CH_3$ | H |
| 11 | 54N | $CF_3$ | $C_6H_5$ | H | O | H | $OCH_3$ | H | H | $CF_3$ | H |
| 11 | 55N | $CF_3$ | $C_6H_5$ | H | O | $OCH_3$ | H | H | H | $CH_3$ | H |
| 11 | 56N | $CF_3$ | $C_6H_5$ | H | O | H | H | $CH_3$ | H | $CF_3$ | H |
| 11 | 57N | $CF_3$ | $C_6H_5$ | H | O | H | $C_6H_5O$ | H | H | H | $OCF_3$ |
| 11 | 58N | $CF_3$ | $C_6H_5$ | H | O | H | H | H | H | H | $OCF_3$ |
| 11 | 59N | $CF_3$ | $C_6H_5$ | H | O | H | $OCF_3$ | H | H | H | $OCF_3$ |
| 11 | 60N | $CF_3$ | $C_6H_5$ | H | O | H | $CF_3$ | F | H | H | $CF_3$ |
| 11 | 61N | $CF_3$ | $C_6H_5$ | H | O | H | H | $OCH_3$ | H | H | $CF_3$ |
| 11 | 62N | $CF_3$ | $C_6H_5$ | H | O | H | $CH_3$ | H | H | H | $CF_3$ |
| 11 | 63N | $CF_3$ | $C_6H_5$ | H | O | H | Cl | H | H | H | $CF_3$ |
| 11 | 64N | $CF_3$ | $C_6H_5$ | H | O | H | $CF_3$ | H | H | H | $OCF_3$ |
| 11 | 65N | $CF_3$ | $C_6H_5$ | H | O | H | F | H | H | H | $OCF_3$ |
| 11 | 66N | $CF_3$ | $C_6H_5$ | H | O | H | F | H | F | H | $OCF_3$ |
| 11 | 67N | $CF_3$ | $C_6H_5$ | H | O | H | Br | H | H | H | $OCF_3$ |
| 11 | 68N | $CF_3$ | $C_6H_5$ | H | O | H | Cl | H | H | H | $OCF_3$ |
| 11 | 69N | $CF_3$ | $C_6H_5$ | H | O | H | F | F | H | H | $OCF_3$ |
| 11 | 70N | $CF_3$ | $C_6H_5$ | H | O | H | F | H | H | H | phenyl |
| 11 | 71N | $CF_3$ | $C_6H_5$ | H | O | H | $CH_3$ | H | H | H | $OCF_3$ |
| 11 | 72N | $CF_3$ | $C_6H_5$ | H | O | H | F | F | H | H | $CF_3$ |
| 11 | 73N | $CF_3$ | $C_6H_5$ | H | O | H | Cl | H | H | H | $CH_3$ |
| 11 | 74N | $CF_3$ | $C_6H_5$ | H | O | H | $OCH_3$ | H | H | H | $CH_3$ |
| 11 | 75N | $CF_3$ | $C_6H_5$ | H | O | H | F | H | H | H | $CH_3$ |
| 11 | 76N | $CF_3$ | $C_6H_5$ | H | O | F | F | H | H | H | $OCF_3$ |
| 11 | 77N | $CF_3$ | $C_6H_5$ | H | O | $OCH_3$ | H | H | H | H | $CF_3$ |
| 11 | 78N | $CF_3$ | $C_6H_5$ | H | O | H | H | $OCH_3$ | H | H | $CH_3$ |
| 11 | 79N | $CF_3$ | $C_6H_5$ | H | O | H | H | $CH_3$ | H | H | $CH_3$ |
| 11 | 80N | $CF_3$ | $C_6H_5$ | H | O | H | $CH_3$ | H | H | H | $CH_3$ |
| 11 | 81N | $CF_3$ | $C_6H_5$ | H | O | $CH_3$ | H | H | H | H | $CH_3$ |
| 11 | 82N | $CF_3$ | $C_6H_5$ | H | O | H | F | F | H | H | $CH_3$ |
| 11 | 83N | $CF_3$ | $C_6H_5$ | H | O | H | F | H | F | H | $CH_3$ |
| 11 | 84N | $CF_3$ | $C_6H_5$ | H | O | F | F | H | H | H | $CH_3$ |
| 11 | 85N | $CF_3$ | $C_6H_5$ | H | O | F | $CF_3$ | H | H | H | $CH_3$ |
| 11 | 86N | $CF_3$ | $C_6H_5$ | H | O | H | H | $CH_3$ | H | H | $CF_3$ |
| 11 | 87N | $CF_3$ | $C_6H_5$ | H | O | $CH_3$ | H | H | H | H | $CF_3$ |
| 11 | 88N | $CF_3$ | $C_6H_5$ | H | O | H | $CF_3$ | H | H | H | $CH_3$ |

TABLE 4-continued

Structure of Substituted Phenyl tertiary-2-Heteroalkylamines (Z is covalent bond; Y is CH and $R_{14}$ is H).

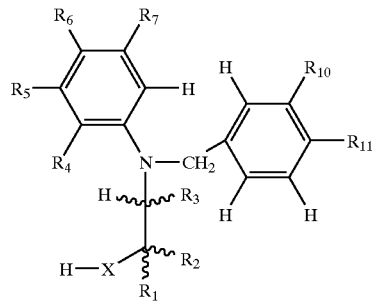

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 11 | 89N | $CF_3$ | $C_6H_5$ | H | O | $OCH_3$ | H | H | H | H | $CH_3$ |
| 11 | 90N | $CF_3$ | $C_6H_5$ | H | O | H | H | $CF_3$ | H | H | $CH_3$ |
| 11 | 91N | $CF_3$ | $C_6H_5$ | H | O | $CF_3$ | H | H | H | H | $CH_3$ |
| 11 | 92N | $CF_3$ | $C_6H_5$ | H | O | H | $CF_3$ | F | H | H | $CH_3$ |
| 12 | 1N | $CCl_3$ | $C_6H_5$ | H | O | H | $C_6H_5O$ | H | H | $OCF_2CF_2H$ | H |
| 12 | 2N | $CCl_3$ | $C_6H_5$ | H | O | H | $OCF_3$ | H | H | $OCF_2CF_2H$ | H |
| 12 | 3N | $CCl_3$ | $C_6H_5$ | H | O | F | H | H | F | $OCF_2CF_2H$ | H |
| 12 | 4N | $CCl_3$ | $C_6H_5$ | H | O | H | F | H | H | $OCF_2CF_2H$ | H |
| 12 | 5N | $CCl_3$ | $C_6H_5$ | H | O | H | $C_6H_5O$ | H | H | $OCF_3$ | H |
| 12 | 6N | $CCl_3$ | $C_6H_5$ | H | O | H | $OCF_3$ | H | H | $OCF_3$ | H |
| 12 | 7N | $CCl_3$ | $C_6H_5$ | H | O | H | H | phenyl | H | $OCF_3$ | H |
| 12 | 8N | $CCl_3$ | $C_6H_5$ | H | O | H | phenyl | H | H | $OCF_3$ | H |
| 12 | 9N | $CCl_3$ | $C_6H_5$ | H | O | H | H | H | H | $OCF_3$ | H |
| 12 | 10N | $CCl_3$ | $C_6H_5$ | H | O | H | Br | H | H | $OCF_3$ | H |
| 12 | 11N | $CCl_3$ | $C_6H_5$ | H | O | H | $CF_3$ | F | H | $CF_3$ | H |
| 12 | 12N | $CCl_3$ | $C_6H_5$ | H | O | H | $CH_3$ | H | H | $CF_3$ | H |
| 12 | 13N | $CCl_3$ | $C_6H_5$ | H | O | H | $CF_3$ | H | H | $CF_3$ | H |
| 12 | 14N | $CCl_3$ | $C_6H_5$ | H | O | H | $CH_3$ | H | H | $OCF_3$ | H |
| 12 | 15N | $CCl_3$ | $C_6H_5$ | H | O | H | F | F | H | $OCF_3$ | H |
| 12 | 16N | $CCl_3$ | $C_6H_5$ | H | O | H | Br | H | H | $CF_3$ | H |
| 12 | 17N | $CCl_3$ | $C_6H_5$ | H | O | H | $CF_3$ | F | H | $OCF_3$ | H |
| 12 | 18N | $CCl_3$ | $C_6H_5$ | H | O | H | F | H | H | $OCF_3$ | H |
| 12 | 19N | $CCl_3$ | $C_6H_5$ | H | O | H | Cl | H | H | $OCF_3$ | H |
| 12 | 20N | $CCl_3$ | $C_6H_5$ | H | O | H | F | H | H | $CF_3$ | H |
| 12 | 21N | $CCl_3$ | $C_6H_5$ | H | O | H | F | F | H | $CF_3$ | H |
| 12 | 22N | $CCl_3$ | $C_6H_5$ | H | O | H | Cl | H | H | $CF_3$ | H |
| 12 | 23N | $CCl_3$ | $C_6H_5$ | H | O | H | F | H | H | phenoxy | H |
| 12 | 24N | $CCl_3$ | $C_6H_5$ | H | O | H | $CF_3$ | Cl | H | $CH_3$ | H |
| 12 | 25N | $CCl_3$ | $C_6H_5$ | H | O | H | $CF_3$ | F | H | $CH_3$ | H |
| 12 | 26N | $CCl_3$ | $C_6H_5$ | H | O | H | H | H | H | $CF_3$ | H |
| 12 | 27N | $CCl_3$ | $C_6H_5$ | H | O | F | F | H | H | $CF_3$ | H |
| 12 | 28N | $CCl_3$ | $C_6H_5$ | H | O | H | H | $OCH_3$ | H | $CF_3$ | H |
| 12 | 29N | $CCl_3$ | $C_6H_5$ | H | O | H | F | F | H | $CH_3$ | H |
| 12 | 30N | $CCl_3$ | $C_6H_5$ | H | O | H | $OCH_3$ | H | H | $CH_3$ | H |
| 12 | 31N | $CCl_3$ | $C_6H_5$ | H | O | H | H | $CH_3$ | H | H | H |
| 12 | 32N | $CCl_3$ | $C_6H_5$ | H | O | H | Cl | H | H | H | H |
| 12 | 33N | $CCl_3$ | $C_6H_5$ | H | O | H | F | H | H | F | H |
| 12 | 34N | $CCl_3$ | $C_6H_5$ | H | O | H | H | $OCH_3$ | H | $CH_3$ | H |
| 12 | 35N | $CCl_3$ | $C_6H_5$ | H | O | H | H | H | H | H | H |
| 12 | 36N | $CCl_3$ | $C_6H_5$ | H | O | H | H | $CH_3$ | H | $CH_3$ | H |
| 12 | 37N | $CCl_3$ | $C_6H_5$ | H | O | H | H | Cl | H | H | H |
| 12 | 38N | $CCl_3$ | $C_6H_5$ | H | O | H | F | H | H | 3-$CF_3$-phenoxy | H |
| 12 | 39N | $CCl_3$ | $C_6H_5$ | H | O | H | F | H | H | 4-$CH_3O$-phenoxy | H |
| 12 | 40N | $CCl_3$ | $C_6H_5$ | H | O | H | F | H | H | 4-Cl-phenoxy | H |
| 12 | 41N | $CCl_3$ | $C_6H_5$ | H | O | H | F | H | H | H | H |
| 12 | 42N | $CCl_3$ | $C_6H_5$ | H | O | H | F | H | H | $CH_3$ | H |
| 12 | 43N | $CCl_3$ | $C_6H_5$ | H | O | H | F | H | F | $CH_3$ | H |
| 12 | 44N | $CCl_3$ | $C_6H_5$ | H | O | F | F | H | H | $CH_3$ | H |
| 12 | 45N | $CCl_3$ | $C_6H_5$ | H | O | H | Cl | H | H | $CH_3$ | H |
| 12 | 46N | $CCl_3$ | $C_6H_5$ | H | O | H | $CH_3$ | H | H | $CH_3$ | H |
| 12 | 47N | $CCl_3$ | $C_6H_5$ | H | O | $CH_3$ | H | H | H | H | H |
| 12 | 48N | $CCl_3$ | $C_6H_5$ | H | O | H | H | $CH_3$ | H | $CF_3$ | H |
| 12 | 49N | $CCl_3$ | $C_6H_5$ | H | O | $CH_3$ | H | H | H | $CF_3$ | H |
| 12 | 50N | $CCl_3$ | $C_6H_5$ | H | O | $CH_3$ | H | H | H | $CH_3$ | H |
| 12 | 51N | $CCl_3$ | $C_6H_5$ | H | O | H | H | $CH_3$ | H | F | H |
| 12 | 52N | $CCl_3$ | $C_6H_5$ | H | O | H | $CF_3$ | H | H | F | H |

TABLE 4-continued

Structure of Substituted Phenyl tertiary-2-Heteroalkylamines (Z is covalent bond; Y is CH and $R_{14}$ is H).

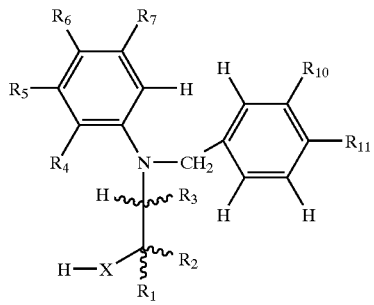

Inhibitor Number
Column 1 + Column 2

| Reagent | Reagent | $R_1$ | $R_2$ | $R_3$ | X | $R_4$ | $R_5$ | $R_6$ | $R_7$ | $R_{10}$ | $R_{11}$ |
|---|---|---|---|---|---|---|---|---|---|---|---|
| 12 | 53N | $CCl_3$ | $C_6H_5$ | H | O | H | $CF_3$ | H | H | $CH_3$ | H |
| 12 | 54N | $CCl_3$ | $C_6H_5$ | H | O | H | $OCH_3$ | H | H | $CF_3$ | H |
| 12 | 55N | $CCl_3$ | $C_6H_5$ | H | O | $OCH_3$ | H | H | H | $CH_3$ | H |
| 12 | 56N | $CCl_3$ | $C_6H_5$ | H | O | H | H | $CH_3$ | H | $CF_3$ | H |
| 12 | 57N | $CCl_3$ | $C_6H_5$ | H | O | H | $C_6H_5O$ | H | H | H | $OCF_3$ |
| 12 | 58N | $CCl_3$ | $C_6H_5$ | H | O | H | H | H | H | H | $OCF_3$ |
| 12 | 59N | $CCl_3$ | $C_6H_5$ | H | O | H | $OCF_3$ | H | H | H | $OCF_3$ |
| 12 | 60N | $CCl_3$ | $C_6H_5$ | H | O | H | $CF_3$ | F | H | H | $CF_3$ |
| 12 | 61N | $CCl_3$ | $C_6H_5$ | H | O | H | H | $OCH_3$ | H | H | $CF_3$ |
| 12 | 62N | $CCl_3$ | $C_6H_5$ | H | O | H | $CH_3$ | H | H | H | $CF_3$ |
| 12 | 63N | $CCl_3$ | $C_6H_5$ | H | O | H | Cl | H | H | H | $CF_3$ |
| 12 | 64N | $CCl_3$ | $C_6H_5$ | H | O | H | $CF_3$ | H | H | H | $OCF_3$ |
| 12 | 65N | $CCl_3$ | $C_6H_5$ | H | O | H | F | H | H | H | $OCF_3$ |
| 12 | 66N | $CCl_3$ | $C_6H_5$ | H | O | H | F | H | F | H | $OCF_3$ |
| 12 | 67N | $CCl_3$ | $C_6H_5$ | H | O | H | Br | H | H | H | $OCF_3$ |
| 12 | 68N | $CCl_3$ | $C_6H_5$ | H | O | H | Cl | H | H | H | $OCF_3$ |
| 12 | 69N | $CCl_3$ | $C_6H_5$ | H | O | H | F | F | H | H | $OCF_3$ |
| 12 | 70N | $CCl_3$ | $C_6H_5$ | H | O | H | F | H | H | H | phenyl |
| 12 | 71N | $CCl_3$ | $C_6H_5$ | H | O | H | $CH_3$ | H | H | H | $OCF_3$ |
| 12 | 72N | $CCl_3$ | $C_6H_5$ | H | O | H | F | F | H | H | $CF_3$ |
| 12 | 73N | $CCl_3$ | $C_6H_5$ | H | O | H | Cl | H | H | H | $CH_3$ |
| 12 | 74N | $CCl_3$ | $C_6H_5$ | H | O | H | $OCH_3$ | H | H | H | $CH_3$ |
| 12 | 75N | $CCl_3$ | $C_6H_5$ | H | O | H | F | H | H | H | $CH_3$ |
| 12 | 76N | $CCl_3$ | $C_6H_5$ | H | O | F | F | H | H | H | $OCF_3$ |
| 12 | 77N | $CCl_3$ | $C_6H_5$ | H | O | $OCH_3$ | H | H | H | H | $CF_3$ |
| 12 | 78N | $CCl_3$ | $C_6H_5$ | H | O | H | H | $OCH_3$ | H | H | $CH_3$ |
| 12 | 79N | $CCl_3$ | $C_6H_5$ | H | O | H | H | $CH_3$ | H | H | $CH_3$ |
| 12 | 80N | $CCl_3$ | $C_6H_5$ | H | O | H | $CH_3$ | H | H | H | $CH_3$ |
| 12 | 81N | $CCl_3$ | $C_6H_5$ | H | O | $CH_3$ | H | H | H | H | $CH_3$ |
| 12 | 82N | $CCl_3$ | $C_6H_5$ | H | O | H | F | F | H | H | $CH_3$ |
| 12 | 83N | $CCl_3$ | $C_6H_5$ | H | O | H | F | H | F | H | $CH_3$ |
| 12 | 84N | $CCl_3$ | $C_6H_5$ | H | O | F | F | H | H | H | $CH_3$ |
| 12 | 85N | $CCl_3$ | $C_6H_5$ | H | O | F | $CF_3$ | H | H | H | $CH_3$ |
| 12 | 86N | $CCl_3$ | $C_6H_5$ | H | O | H | H | $CH_3$ | H | H | $CF_3$ |
| 12 | 87N | $CCl_3$ | $C_6H_5$ | H | O | $CH_3$ | H | H | H | H | $CF_3$ |
| 12 | 88N | $CCl_3$ | $C_6H_5$ | H | O | H | $CF_3$ | H | H | H | $CH_3$ |
| 12 | 89N | $CCl_3$ | $C_6H_5$ | H | O | $OCH_3$ | H | H | H | H | $CH_3$ |
| 12 | 90N | $CCl_3$ | $C_6H_5$ | H | O | H | H | $CF_3$ | H | H | $CH_3$ |
| 12 | 91N | $CCl_3$ | $C_6H_5$ | H | O | $CF_3$ | H | H | H | H | $CH_3$ |
| 12 | 92N | $CCl_3$ | $C_6H_5$ | H | O | H | $CF_3$ | F | H | H | $CH_3$ |

TABLE 5

Structure of Substituted Phenyl tertiary-2-Heteroalkylamines (Z is covalent bond; Y is CH and $R_{14}$ is H).

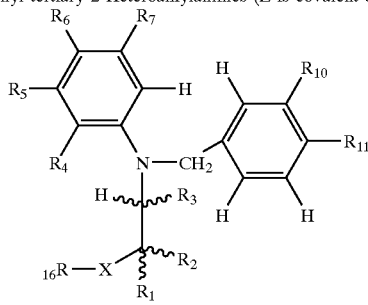

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 13 | 1N | $CCl_3$ | cyclo-propyl | H | H | O | H | $C_6H_5O$ | H | H | $OCF_2CF_2H$ | H |
| 13 | 2N | $CCl_3$ | cyclo-propyl | H | H | O | H | $OCF_3$ | H | H | $OCF_2CF_2H$ | H |
| 13 | 3N | $CCl_3$ | cyclo-propyl | H | H | O | F | H | H | F | $OCF_2CF_2H$ | H |
| 13 | 4N | $CCl_3$ | cyclo-propyl | H | H | O | H | F | H | H | $OCF_2CF_2H$ | H |
| 13 | 5N | $CCl_3$ | cyclo-propyl | H | H | O | H | $C_6H_5O$ | H | H | $OCF_3$ | H |
| 13 | 6N | $CCl_3$ | cyclo-propyl | H | H | O | H | $OCF_3$ | H | H | $OCF_3$ | H |
| 13 | 7N | $CCl_3$ | cyclo-propyl | H | H | O | H | H | $C_6H_5$ | H | $OCF_3$ | H |
| 13 | 8N | $CCl_3$ | cyclo-propyl | H | H | O | H | $C_6H_5$ | H | H | $OCF_3$ | H |
| 13 | 9N | $CCl_3$ | cyclo-propyl | H | H | O | H | H | H | H | $OCF_3$ | H |
| 13 | 10N | $CCl_3$ | cyclo-propyl | H | H | O | H | Br | H | H | $OCF_3$ | H |
| 13 | 11N | $CCl_3$ | cyclo-propyl | H | H | O | H | $CF_3$ | F | H | $CF_3$ | H |
| 13 | 12N | $CCl_3$ | cyclo-propyl | H | H | O | H | $CH_3$ | H | H | $CF_3$ | H |
| 13 | 13N | $CCl_3$ | cyclo-propyl | H | H | O | H | $CF_3$ | H | H | $CF_3$ | H |
| 13 | 14N | $CCl_3$ | cyclo-propyl | H | H | O | H | $CH_3$ | H | H | $OCF_3$ | H |
| 13 | 15N | $CCl_3$ | cyclo-propyl | H | H | O | H | F | F | H | $OCF_3$ | H |
| 13 | 16N | $CCl_3$ | cyclo-propyl | H | H | O | H | Br | H | H | $CF_3$ | H |
| 13 | 17N | $CCl_3$ | cyclo-propyl | H | H | O | H | $CF_3$ | F | H | $OCF_3$ | H |
| 13 | 18N | $CCl_3$ | cyclo-propyl | H | H | O | H | F | H | H | $OCF_3$ | H |
| 13 | 19N | $CCl_3$ | cyclo-propyl | H | H | O | H | Cl | H | H | $OCF_3$ | H |
| 13 | 20N | $CCl_3$ | cyclo-propyl | H | H | O | H | F | H | H | $CF_3$ | H |
| 13 | 21N | $CCl_3$ | cyclo-propyl | H | H | O | H | F | F | H | $CF_3$ | H |
| 13 | 22N | $CCl_3$ | cyclo-propyl | H | H | O | H | Cl | H | H | $CF_3$ | H |
| 13 | 23N | $CCl_3$ | cyclo-propyl | H | H | O | H | F | H | H | phenoxy | H |
| 13 | 24N | $CCl_3$ | cyclo-propyl | H | H | O | H | $CF_3$ | Cl | H | $CH_3$ | H |
| 13 | 25N | $CCl_3$ | cyclo-propyl | H | H | O | H | $CF_3$ | F | H | $CH_3$ | H |
| 13 | 26N | $CCl_3$ | cyclo-propyl | H | H | O | H | H | H | H | $CF_3$ | H |
| 13 | 27N | $CCl_3$ | cyclo-propyl | H | H | O | F | F | H | H | $CF_3$ | H |
| 13 | 28N | $CCl_3$ | cyclo-propyl | H | H | O | H | H | $OCH_3$ | H | $CF_3$ | H |
| 13 | 29N | $CCl_3$ | cyclo-propyl | H | H | O | H | F | F | H | $CH_3$ | H |
| 13 | 30N | $CCl_3$ | cyclo-propyl | H | H | O | H | $OCH_3$ | H | H | $CH_3$ | H |
| 13 | 31N | $CCl_3$ | cyclo-propyl | H | H | O | H | H | $CH_3$ | H | H | H |
| 13 | 32N | $CCl_3$ | cyclo-propyl | H | H | O | H | Cl | H | H | H | H |
| 13 | 33N | $CCl_3$ | cyclo-propyl | H | H | O | H | F | H | H | F | H |
| 13 | 34N | $CCl_3$ | cyclo-propyl | H | H | O | H | H | $OCH_3$ | H | $CH_3$ | H |
| 13 | 35N | $CCl_3$ | cyclo-propyl | H | H | O | H | H | H | H | H | H |
| 13 | 36N | $CCl_3$ | cyclo-propyl | H | H | O | H | H | $CH_3$ | H | $CH_3$ | H |
| 13 | 37N | $CCl_3$ | cyclo-propyl | H | H | O | H | H | Cl | H | H | H |
| 13 | 38N | $CCl_3$ | cyclo-propyl | H | H | O | H | F | H | H | 3-$CF_3$-phenoxy | H |
| 13 | 39N | $CCl_3$ | cyclo-propyl | H | H | O | H | F | H | H | 4-$CH_3O$-phenoxy | H |
| 13 | 40N | $CCl_3$ | cyclo-propyl | H | H | O | H | F | H | H | 4-Cl-phenoxy | H |
| 13 | 41N | $CCl_3$ | cyclo-propyl | H | H | O | H | F | H | H | H | H |
| 13 | 42N | $CCl_3$ | cyclo-propyl | H | H | O | H | F | H | H | $CH_3$ | H |
| 13 | 43N | $CCl_3$ | cyclo-propyl | H | H | O | H | F | H | F | $CH_3$ | H |
| 13 | 44N | $CCl_3$ | cyclo-propyl | H | H | O | F | F | H | H | $CH_3$ | H |
| 13 | 45N | $CCl_3$ | cyclo-propyl | H | H | O | H | Cl | H | H | $CH_3$ | H |
| 13 | 46N | $CCl_3$ | cyclo-propyl | H | H | O | H | $CH_3$ | H | H | $CH_3$ | H |
| 13 | 47N | $CCl_3$ | cyclo-propyl | H | H | O | $CH_3$ | H | H | H | H | H |
| 13 | 48N | $CCl_3$ | cyclo-propyl | H | H | O | H | H | $CH_3$ | H | $CF_3$ | H |
| 13 | 49N | $CCl_3$ | cyclo-propyl | H | H | O | $CH_3$ | H | H | H | $CF_3$ | H |
| 13 | 50N | $CCl_3$ | cyclo-propyl | H | H | O | $CH_3$ | H | H | H | $CH_3$ | H |
| 13 | 51N | $CCl_3$ | cyclo-propyl | H | H | O | H | H | $CH_3$ | H | F | H |
| 13 | 52N | $CCl_3$ | cyclo-propyl | H | H | O | H | $CF_3$ | H | H | F | H |
| 13 | 53N | $CCl_3$ | cyclo-propyl | H | H | O | H | $CF_3$ | H | H | $CH_3$ | H |
| 13 | 54N | $CCl_3$ | cyclo-propyl | H | H | O | H | $OCH_3$ | H | H | $CF_3$ | H |
| 13 | 55N | $CCl_3$ | cyclo-propyl | H | H | O | $OCH_3$ | H | H | H | $CH_3$ | H |
| 13 | 56N | $CCl_3$ | cyclo-propyl | H | H | O | H | H | $CH_3$ | H | $CF_3$ | H |
| 13 | 57N | $CCl_3$ | cyclo-propyl | H | H | O | H | $C_6H_5O$ | H | H | H | $OCF_3$ |

TABLE 5-continued

Structure of Substituted Phenyl tertiary-2-Heteroalkylamines (Z is covalent bond; Y is CH and $R_{14}$ is H).

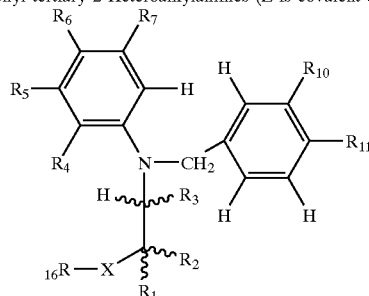

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 13 | 58N | $CCl_3$ | cyclo-propyl | H | H | O | H | H | H | H | H | $OCF_3$ |
| 13 | 59N | $CCl_3$ | cyclo-propyl | H | H | O | H | $OCF_3$ | H | H | H | $OCF_3$ |
| 13 | 60N | $CCl_3$ | cyclo-propyl | H | H | O | H | $CF_3$ | F | H | H | $CF_3$ |
| 13 | 61N | $CCl_3$ | cyclo-propyl | H | H | O | H | H | $OCH_3$ | H | H | $CF_3$ |
| 13 | 62N | $CCl_3$ | cyclo-propyl | H | H | O | H | $CH_3$ | H | H | H | $CF_3$ |
| 13 | 63N | $CCl_3$ | cyclo-propyl | H | H | O | H | Cl | H | H | H | $CF_3$ |
| 13 | 64N | $CCl_3$ | cyclo-propyl | H | H | O | H | $CF_3$ | H | H | H | $OCF_3$ |
| 13 | 65N | $CCl_3$ | cyclo-propyl | H | H | O | H | F | H | H | H | $OCF_3$ |
| 13 | 66N | $CCl_3$ | cyclo-propyl | H | H | O | H | F | H | F | H | $OCF_3$ |
| 13 | 67N | $CCl_3$ | cyclo-propyl | H | H | O | H | Br | H | H | H | $OCF_3$ |
| 13 | 68N | $CCl_3$ | cyclo-propyl | H | H | O | H | Cl | H | H | H | $OCF_3$ |
| 13 | 69N | $CCl_3$ | cyclo-propyl | H | H | O | H | F | F | H | H | $OCF_3$ |
| 13 | 70N | $CCl_3$ | cyclo-propyl | H | H | O | H | F | H | H | H | $C_6H_5$ |
| 13 | 71N | $CCl_3$ | cyclo-propyl | H | H | O | H | $CH_3$ | H | H | H | $OCF_3$ |
| 13 | 72N | $CCl_3$ | cyclo-propyl | H | H | O | H | F | F | H | H | $CF_3$ |
| 13 | 73N | $CCl_3$ | cyclo-propyl | H | H | O | H | Cl | H | H | H | $CH_3$ |
| 13 | 74N | $CCl_3$ | cyclo-propyl | H | H | O | H | $OCH_3$ | H | H | H | $CH_3$ |
| 13 | 75N | $CCl_3$ | cyclo-propyl | H | H | O | H | F | H | H | H | $CH_3$ |
| 13 | 76N | $CCl_3$ | cyclo-propyl | H | H | O | F | F | H | H | H | $OCF_3$ |
| 13 | 77N | $CCl_3$ | cyclo-propyl | H | H | O | $OCH_3$ | H | H | H | H | $CF_3$ |
| 13 | 78N | $CCl_3$ | cyclo-propyl | H | H | O | H | H | $OCH_3$ | H | H | $CH_3$ |
| 13 | 79N | $CCl_3$ | cyclo-propyl | H | H | O | H | H | $CH_3$ | H | H | $CH_3$ |
| 13 | 80N | $CCl_3$ | cyclo-propyl | H | H | O | H | $CH_3$ | H | H | H | $CH_3$ |
| 13 | 81N | $CCl_3$ | cyclo-propyl | H | H | O | $CH_3$ | H | H | H | H | $CH_3$ |
| 13 | 82N | $CCl_3$ | cyclo-propyl | H | H | O | H | F | F | H | H | $CH_3$ |
| 13 | 83N | $CCl_3$ | cyclo-propyl | H | H | O | H | F | H | F | H | $CH_3$ |
| 13 | 84N | $CCl_3$ | cyclo-propyl | H | H | O | F | F | H | H | H | $CH_3$ |
| 13 | 85N | $CCl_3$ | cyclo-propyl | H | H | O | F | $CF_3$ | H | H | H | $CH_3$ |
| 13 | 86N | $CCl_3$ | cyclo-propyl | H | H | O | H | H | $CH_3$ | H | H | $CF_3$ |
| 13 | 87N | $CCl_3$ | cyclo-propyl | H | H | O | $CH_3$ | H | H | H | H | $CF_3$ |
| 13 | 88N | $CCl_3$ | cyclo-propyl | H | H | O | H | $CF_3$ | H | H | H | $CH_3$ |
| 13 | 89N | $CCl_3$ | cyclo-propyl | H | H | O | $OCH_3$ | H | H | H | H | $CH_3$ |
| 13 | 90N | $CCl_3$ | cyclo-propyl | H | H | O | H | H | $CF_3$ | H | H | $CH_3$ |
| 13 | 91N | $CCl_3$ | cyclo-propyl | H | H | O | $CF_3$ | H | H | H | H | $CH_3$ |
| 13 | 92N | $CCl_3$ | cyclo-propyl | H | H | O | H | $CF_3$ | F | H | H | $CH_3$ |
| 14 | 1N | $CCl_3$ | $CH_3$ | H | H | O | H | $C_6H_5O$ | H | H | $OCF_2CF_2H$ | H |
| 14 | 2N | $CCl_3$ | $CH_3$ | H | H | O | H | $OCF_3$ | H | H | $OCF_2CF_2H$ | H |
| 14 | 3N | $CCl_3$ | $CH_3$ | H | H | O | F | H | H | F | $OCF_2CF_2H$ | H |
| 14 | 4N | $CCl_3$ | $CH_3$ | H | H | O | H | F | H | H | $OCF_2CF_2H$ | H |
| 14 | 5N | $CCl_3$ | $CH_3$ | H | H | O | H | $C_6H_5O$ | H | H | $OCF_3$ | H |
| 14 | 6N | $CCl_3$ | $CH_3$ | H | H | O | H | $OCF_3$ | H | H | $OCF_3$ | H |
| 14 | 7N | $CCl_3$ | $CH_3$ | H | H | O | H | H | phenyl | H | $OCF_3$ | H |
| 14 | 8N | $CCl_3$ | $CH_3$ | H | H | O | H | phenyl | H | H | $OCF_3$ | H |
| 14 | 9N | $CCl_3$ | $CH_3$ | H | H | O | H | H | H | H | $OCF_3$ | H |
| 14 | 10N | $CCl_3$ | $CH_3$ | H | H | O | H | Br | H | H | $OCF_3$ | H |
| 14 | 11N | $CCl_3$ | $CH_3$ | H | H | O | H | $CF_3$ | F | H | $CF_3$ | H |
| 14 | 12N | $CCl_3$ | $CH_3$ | H | H | O | H | $CH_3$ | H | H | $CF_3$ | H |
| 14 | 13N | $CCl_3$ | $CH_3$ | H | H | O | H | $CF_3$ | H | H | $CF_3$ | H |
| 14 | 14N | $CCl_3$ | $CH_3$ | H | H | O | H | $CH_3$ | H | H | $OCF_3$ | H |
| 14 | 15N | $CCl_3$ | $CH_3$ | H | H | O | H | F | F | H | $OCF_3$ | H |
| 14 | 16N | $CCl_3$ | $CH_3$ | H | H | O | H | Br | H | H | $CF_3$ | H |
| 14 | 17N | $CCl_3$ | $CH_3$ | H | H | O | H | $CF_3$ | F | H | $OCF_3$ | H |
| 14 | 18N | $CCl_3$ | $CH_3$ | H | H | O | H | F | H | H | $OCF_3$ | H |
| 14 | 19N | $CCl_3$ | $CH_3$ | H | H | O | H | Cl | H | H | $OCF_3$ | H |
| 14 | 20N | $CCl_3$ | $CH_3$ | H | H | O | H | F | H | H | $CF_3$ | H |
| 14 | 21N | $CCl_3$ | $CH_3$ | H | H | O | H | F | F | H | $CF_3$ | H |
| 14 | 22N | $CCl_3$ | $CH_3$ | H | H | O | H | Cl | H | H | $CF_3$ | H |

TABLE 5-continued

Structure of Substituted Phenyl tertiary-2-Heteroalkylamines (Z is covalent bond; Y is CH and $R_{14}$ is H).

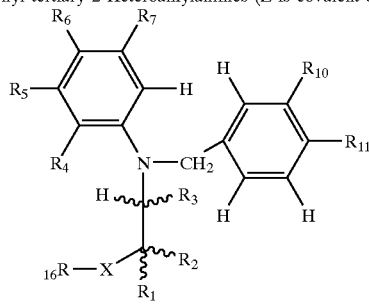

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 14 | 23N | $CCl_3$ | $CH_3$ | H | H | O | H | F | H | H | phenoxy | H |
| 14 | 24N | $CCl_3$ | $CH_3$ | H | H | O | H | $CF_3$ | Cl | H | $CH_3$ | H |
| 14 | 25N | $CCl_3$ | $CH_3$ | H | H | O | H | $CF_3$ | F | H | $CH_3$ | H |
| 14 | 26N | $CCl_3$ | $CH_3$ | H | H | O | H | H | H | H | $CF_3$ | H |
| 14 | 27N | $CCl_3$ | $CH_3$ | H | H | O | F | F | H | H | $CF_3$ | H |
| 14 | 28N | $CCl_3$ | $CH_3$ | H | H | O | H | H | $OCH_3$ | H | $CF_3$ | H |
| 14 | 29N | $CCl_3$ | $CH_3$ | H | H | O | H | F | F | H | $CH_3$ | H |
| 14 | 30N | $CCl_3$ | $CH_3$ | H | H | O | H | $OCH_3$ | H | H | $CH_3$ | H |
| 14 | 31N | $CCl_3$ | $CH_3$ | H | H | O | H | H | $CH_3$ | H | H | H |
| 14 | 32N | $CCl_3$ | $CH_3$ | H | H | O | H | Cl | H | H | H | H |
| 14 | 33N | $CCl_3$ | $CH_3$ | H | H | O | H | F | H | H | F | H |
| 14 | 34N | $CCl_3$ | $CH_3$ | H | H | O | H | H | $OCH_3$ | H | $CH_3$ | H |
| 14 | 35N | $CCl_3$ | $CH_3$ | H | H | O | H | H | H | H | H | H |
| 14 | 36N | $CCl_3$ | $CH_3$ | H | H | O | H | H | $CH_3$ | H | $CH_3$ | H |
| 14 | 37N | $CCl_3$ | $CH_3$ | H | H | O | H | H | Cl | H | H | H |
| 14 | 38N | $CCl_3$ | $CH_3$ | H | H | O | H | F | H | H | 3-$CF_3$-phenoxy | H |
| 14 | 39N | $CCl_3$ | $CH_3$ | H | H | O | H | F | H | H | 4-$CH_3$O-phenoxy | H |
| 14 | 40N | $CCl_3$ | $CH_3$ | H | H | O | H | F | H | H | 4-Cl-phenoxy | H |
| 14 | 41N | $CCl_3$ | $CH_3$ | H | H | O | H | F | H | H | H | H |
| 14 | 42N | $CCl_3$ | $CH_3$ | H | H | O | H | F | H | H | $CH_3$ | H |
| 14 | 43N | $CCl_3$ | $CH_3$ | H | H | O | H | F | H | F | $CH_3$ | H |
| 14 | 44N | $CCl_3$ | $CH_3$ | H | H | O | F | F | H | H | $CH_3$ | H |
| 14 | 45N | $CCl_3$ | $CH_3$ | H | H | O | H | Cl | H | H | $CH_3$ | H |
| 14 | 46N | $CCl_3$ | $CH_3$ | H | H | O | H | $CH_3$ | H | H | $CH_3$ | H |
| 14 | 47N | $CCl_3$ | $CH_3$ | H | H | O | $CH_3$ | H | H | H | H | H |
| 14 | 48N | $CCl_3$ | $CH_3$ | H | H | O | H | H | $CH_3$ | H | $CF_3$ | H |
| 14 | 49N | $CCl_3$ | $CH_3$ | H | H | O | $CH_3$ | H | H | H | $CF_3$ | H |
| 14 | 50N | $CCl_3$ | $CH_3$ | H | H | O | $CH_3$ | H | H | H | $CH_3$ | H |
| 14 | 51N | $CCl_3$ | $CH_3$ | H | H | O | H | H | $CH_3$ | H | F | H |
| 14 | 52N | $CCl_3$ | $CH_3$ | H | H | O | H | $CF_3$ | H | H | F | H |
| 14 | 53N | $CCl_3$ | $CH_3$ | H | H | O | H | $CF_3$ | H | H | $CH_3$ | H |
| 14 | 54N | $CCl_3$ | $CH_3$ | H | H | O | H | $OCH_3$ | H | H | $CF_3$ | H |
| 14 | 55N | $CCl_3$ | $CH_3$ | H | H | O | $OCH_3$ | H | H | H | $CH_3$ | H |
| 14 | 56N | $CCl_3$ | $CH_3$ | H | H | O | H | H | $CH_3$ | H | $CF_3$ | H |
| 14 | 57N | $CCl_3$ | $CH_3$ | H | H | O | H | $C_6H_5O$ | H | H | H | $OCF_3$ |
| 14 | 58N | $CCl_3$ | $CH_3$ | H | H | O | H | H | H | H | H | $OCF_3$ |
| 14 | 59N | $CCl_3$ | $CH_3$ | H | H | O | H | $OCF_3$ | H | H | H | $OCF_3$ |
| 14 | 60N | $CCl_3$ | $CH_3$ | H | H | O | H | $CF_3$ | F | H | H | $CF_3$ |
| 14 | 61N | $CCl_3$ | $CH_3$ | H | H | O | H | H | $OCH_3$ | H | H | $CF_3$ |
| 14 | 62N | $CCl_3$ | $CH_3$ | H | H | O | H | $CH_3$ | H | H | H | $CF_3$ |
| 14 | 63N | $CCl_3$ | $CH_3$ | H | H | O | H | Cl | H | H | H | $CF_3$ |
| 14 | 64N | $CCl_3$ | $CH_3$ | H | H | O | H | $CF_3$ | H | H | H | $OCF_3$ |
| 14 | 65N | $CCl_3$ | $CH_3$ | H | H | O | H | F | H | H | H | $OCF_3$ |
| 14 | 66N | $CCl_3$ | $CH_3$ | H | H | O | H | F | H | F | H | $OCF_3$ |
| 14 | 67N | $CCl_3$ | $CH_3$ | H | H | O | H | Br | H | H | H | $OCF_3$ |
| 14 | 68N | $CCl_3$ | $CH_3$ | H | H | O | H | Cl | H | H | H | $OCF_3$ |
| 14 | 69N | $CCl_3$ | $CH_3$ | H | H | O | H | F | F | H | H | $OCF_3$ |
| 14 | 70N | $CCl_3$ | $CH_3$ | H | H | O | H | F | H | H | H | $C_6H_5$ |
| 14 | 71N | $CCl_3$ | $CH_3$ | H | H | O | H | $CH_3$ | H | H | H | $OCF_3$ |
| 14 | 72N | $CCl_3$ | $CH_3$ | H | H | O | H | F | F | H | H | $CF_3$ |
| 14 | 73N | $CCl_3$ | $CH_3$ | H | H | O | H | Cl | H | H | H | $CH_3$ |
| 14 | 74N | $CCl_3$ | $CH_3$ | H | H | O | H | $OCH_3$ | H | H | H | $CH_3$ |
| 14 | 75N | $CCl_3$ | $CH_3$ | H | H | O | H | F | H | H | H | $CH_3$ |
| 14 | 76N | $CCl_3$ | $CH_3$ | H | H | O | F | F | H | H | H | $OCF_3$ |
| 14 | 77N | $CCl_3$ | $CH_3$ | H | H | O | $OCH_3$ | H | H | H | H | $CF_3$ |
| 14 | 78N | $CCl_3$ | $CH_3$ | H | H | O | H | H | $OCH_3$ | H | H | $CH_3$ |
| 14 | 79N | $CCl_3$ | $CH_3$ | H | H | O | H | H | $CH_3$ | H | H | $CH_3$ |

TABLE 5-continued

Structure of Substituted Phenyl tertiary-2-Heteroalkylamines (Z is covalent bond; Y is CH and $R_{14}$ is H).

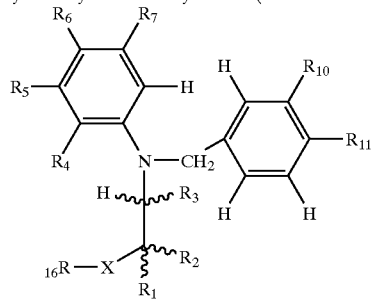

| Inhibitor Number Column 1 + Column 2 | | | | | | | | | | | | |
|---|---|---|---|---|---|---|---|---|---|---|---|---|
| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
| 14 | 80N | $CCl_3$ | $CH_3$ | H | H | O | H | $CH_3$ | H | H | H | $CH_3$ |
| 14 | 81N | $CCl_3$ | $CH_3$ | H | H | O | $CH_3$ | H | H | H | H | $CH_3$ |
| 14 | 82N | $CCl_3$ | $CH_3$ | H | H | O | H | F | F | H | H | $CH_3$ |
| 14 | 83N | $CCl_3$ | $CH_3$ | H | H | O | H | F | H | F | H | $CH_3$ |
| 14 | 84N | $CCl_3$ | $CH_3$ | H | H | O | F | F | H | H | H | $CH_3$ |
| 14 | 85N | $CCl_3$ | $CH_3$ | H | H | O | F | $CF_3$ | H | H | H | $CH_3$ |
| 14 | 86N | $CCl_3$ | $CH_3$ | H | H | O | H | H | $CH_3$ | H | H | $CF_3$ |
| 14 | 87N | $CCl_3$ | $CH_3$ | H | H | O | $CH_3$ | H | H | H | H | $CF_3$ |
| 14 | 88N | $CCl_3$ | $CH_3$ | H | H | O | H | $CF_3$ | H | H | H | $CH_3$ |
| 14 | 89N | $CCl_3$ | $CH_3$ | H | H | O | $OCH_3$ | H | H | H | H | $CH_3$ |
| 14 | 90N | $CCl_3$ | $CH_3$ | H | H | O | H | H | $CF_3$ | H | H | $CH_3$ |
| 14 | 91N | $CCl_3$ | $CH_3$ | H | H | O | $CF_3$ | H | H | H | H | $CH_3$ |
| 14 | 92N | $CCl_3$ | $CH_3$ | H | H | O | H | $CF_3$ | F | H | H | $CH_3$ |
| 15 | 1N | $CCl_3$ | $(CH_3)_2CH$ | H | H | O | H | $C_6H_5O$ | H | H | $OCF_2CF_2H$ | H |
| 15 | 2N | $CCl_3$ | $(CH_3)_2CH$ | H | H | O | H | $OCF_3$ | H | H | $OCF_2CF_2H$ | H |
| 15 | 3N | $CCl_3$ | $(CH_3)_2CH$ | H | H | O | F | H | H | F | $OCF_2CF_2H$ | H |
| 15 | 4N | $CCl_3$ | $(CH_3)_2CH$ | H | H | O | H | F | H | H | $OCF_2CF_2H$ | H |
| 15 | 5N | $CCl_3$ | $(CH_3)_2CH$ | H | H | O | H | $C_6H_5O$ | H | H | $OCF_3$ | H |
| 15 | 6N | $CCl_3$ | $(CH_3)_2CH$ | H | H | O | H | $OCF_3$ | H | H | $OCF_3$ | H |
| 15 | 7N | $CCl_3$ | $(CH_3)_2CH$ | H | H | O | H | H | phenyl | H | $OCF_3$ | H |
| 15 | 8N | $CCl_3$ | $(CH_3)_2CH$ | H | H | O | H | phenyl | H | H | $OCF_3$ | H |
| 15 | 9N | $CCl_3$ | $(CH_3)_2CH$ | H | H | O | H | H | H | H | $OCF_3$ | H |
| 15 | 10N | $CCl_3$ | $(CH_3)_2CH$ | H | H | O | H | Br | H | H | $OCF_3$ | H |
| 15 | 11N | $CCl_3$ | $(CH_3)_2CH$ | H | H | O | H | $CF_3$ | F | H | $CF_3$ | H |
| 15 | 12N | $CCl_3$ | $(CH_3)_2CH$ | H | H | O | H | $CH_3$ | H | H | $CF_3$ | H |
| 15 | 13N | $CCl_3$ | $(CH_3)_2CH$ | H | H | O | H | $CF_3$ | H | H | $CF_3$ | H |
| 15 | 14N | $CCl_3$ | $(CH_3)_2CH$ | H | H | O | H | $CH_3$ | H | H | $OCF_3$ | H |
| 15 | 15N | $CCl_3$ | $(CH_3)_2CH$ | H | H | O | H | F | F | H | $OCF_3$ | H |
| 15 | 16N | $CCl_3$ | $(CH_3)_2CH$ | H | H | O | H | Br | H | H | $CF_3$ | H |
| 15 | 17N | $CCl_3$ | $(CH_3)_2CH$ | H | H | O | H | $CF_3$ | F | H | $OCF_3$ | H |
| 15 | 18N | $CCl_3$ | $(CH_3)_2CH$ | H | H | O | H | F | H | H | $OCF_3$ | H |
| 15 | 19N | $CCl_3$ | $(CH_3)_2CH$ | H | H | O | H | Cl | H | H | $OCF_3$ | H |
| 15 | 20N | $CCl_3$ | $(CH_3)_2CH$ | H | H | O | H | F | H | H | $CF_3$ | H |
| 15 | 21N | $CCl_3$ | $(CH_3)_2CH$ | H | H | O | H | F | F | H | $CF_3$ | H |
| 15 | 22N | $CCl_3$ | $(CH_3)_2CH$ | H | H | O | H | Cl | H | H | $CF_3$ | H |
| 15 | 23N | $CCl_3$ | $(CH_3)_2CH$ | H | H | O | H | F | H | H | phenoxy | H |
| 15 | 24N | $CCl_3$ | $(CH_3)_2CH$ | H | H | O | H | $CF_3$ | Cl | H | $CH_3$ | H |
| 15 | 25N | $CCl_3$ | $(CH_3)_2CH$ | H | H | O | H | $CF_3$ | F | H | $CH_3$ | H |
| 15 | 26N | $CCl_3$ | $(CH_3)_2CH$ | H | H | O | H | H | H | H | $CF_3$ | H |
| 15 | 27N | $CCl_3$ | $(CH_3)_2CH$ | H | H | O | F | F | H | H | $CF_3$ | H |
| 15 | 28N | $CCl_3$ | $(CH_3)_2CH$ | H | H | O | H | H | $OCH_3$ | H | $CF_3$ | H |
| 15 | 29N | $CCl_3$ | $(CH_3)_2CH$ | H | H | O | H | H | F | F | $CH_3$ | H |
| 15 | 30N | $CCl_3$ | $(CH_3)_2CH$ | H | H | O | H | $OCH_3$ | H | H | $CH_3$ | H |
| 15 | 31N | $CCl_3$ | $(CH_3)_2CH$ | H | H | O | H | H | $CH_3$ | H | H | H |
| 15 | 32N | $CCl_3$ | $(CH_3)_2CH$ | H | H | O | H | Cl | H | H | H | H |
| 15 | 33N | $CCl_3$ | $(CH_3)_2CH$ | H | H | O | H | F | H | H | F | H |
| 15 | 34N | $CCl_3$ | $(CH_3)_2CH$ | H | H | O | H | H | $OCH_3$ | H | $CH_3$ | H |
| 15 | 35N | $CCl_3$ | $(CH_3)_2CH$ | H | H | O | H | H | H | H | H | H |
| 15 | 36N | $CCl_3$ | $(CH_3)_2CH$ | H | H | O | H | H | $CH_3$ | H | $CH_3$ | H |
| 15 | 37N | $CCl_3$ | $(CH_3)_2CH$ | H | H | O | H | H | Cl | H | H | H |
| 15 | 38N | $CCl_3$ | $(CH_3)_2CH$ | H | H | O | H | F | H | H | 3-$CF_3$-phenoxy | H |
| 15 | 39N | $CCl_3$ | $(CH_3)_2CH$ | H | H | O | H | F | H | H | 4-$CH_3O$-phenoxy | H |
| 15 | 40N | $CCl_3$ | $(CH_3)_2CH$ | H | H | O | H | F | H | H | 4-Cl-phenoxy | H |
| 15 | 41N | $CCl_3$ | $(CH_3)_2CH$ | H | H | O | H | F | H | H | H | H |
| 15 | 42N | $CCl_3$ | $(CH_3)_2CH$ | H | H | O | H | F | H | H | $CH_3$ | H |
| 15 | 43N | $CCl_3$ | $(CH_3)_2CH$ | H | H | O | H | F | H | F | $CH_3$ | H |
| 15 | 44N | $CCl_3$ | $(CH_3)_2CH$ | H | H | O | F | F | H | H | $CH_3$ | H |

TABLE 5-continued

Structure of Substituted Phenyl tertiary-2-Heteroalkylamines (Z is covalent bond; Y is CH and $R_{14}$ is H).

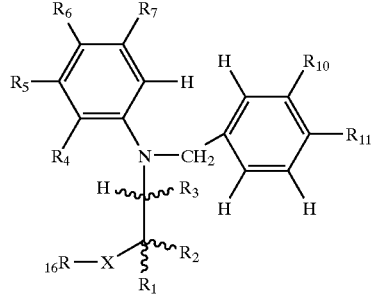

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 15 | 45N | $CCl_3$ | $(CH_3)_2CH$ | H | H | O | H | Cl | H | H | $CH_3$ | H |
| 15 | 46N | $CCl_3$ | $(CH_3)_2CH$ | H | H | O | H | $CH_3$ | H | H | $CH_3$ | H |
| 15 | 47N | $CCl_3$ | $(CH_3)_2CH$ | H | H | O | $CH_3$ | H | H | H | H | H |
| 15 | 48N | $CCl_3$ | $(CH_3)_2CH$ | H | H | O | H | H | $CH_3$ | H | $CF_3$ | H |
| 15 | 49N | $CCl_3$ | $(CH_3)_2CH$ | H | H | O | $CH_3$ | H | H | H | $CF_3$ | H |
| 15 | 50N | $CCl_3$ | $(CH_3)_2CH$ | H | H | O | $CH_3$ | H | H | H | $CH_3$ | H |
| 15 | 51N | $CCl_3$ | $(CH_3)_2CH$ | H | H | O | H | H | $CH_3$ | H | F | H |
| 15 | 52N | $CCl_3$ | $(CH_3)_2CH$ | H | H | O | H | $CF_3$ | H | H | F | H |
| 15 | 53N | $CCl_3$ | $(CH_3)_2CH$ | H | H | O | H | $CF_3$ | H | H | $CH_3$ | H |
| 15 | 54N | $CCl_3$ | $(CH_3)_2CH$ | H | H | O | H | $OCH_3$ | H | H | $CF_3$ | H |
| 15 | 55N | $CCl_3$ | $(CH_3)_2CH$ | H | H | O | $OCH_3$ | H | H | H | $CH_3$ | H |
| 15 | 56N | $CCl_3$ | $(CH_3)_2CH$ | H | H | O | H | H | $CH_3$ | H | $CF_3$ | H |
| 15 | 57N | $CCl_3$ | $(CH_3)_2CH$ | H | H | O | H | $C_6H_5O$ | H | H | H | $OCF_3$ |
| 15 | 58N | $CCl_3$ | $(CH_3)_2CH$ | H | H | O | H | H | H | H | H | $OCF_3$ |
| 15 | 59N | $CCl_3$ | $(CH_3)_2CH$ | H | H | O | H | $OCF_3$ | H | H | H | $OCF_3$ |
| 15 | 60N | $CCl_3$ | $(CH_3)_2CH$ | H | H | O | H | $CF_3$ | F | H | H | $CF_3$ |
| 15 | 61N | $CCl_3$ | $(CH_3)_2CH$ | H | H | O | H | H | $OCH_3$ | H | H | $CF_3$ |
| 15 | 62N | $CCl_3$ | $(CH_3)_2CH$ | H | H | O | H | $CH_3$ | H | H | H | $CF_3$ |
| 15 | 63N | $CCl_3$ | $(CH_3)_2CH$ | H | H | O | H | Cl | H | H | H | $CF_3$ |
| 15 | 64N | $CCl_3$ | $(CH_3)_2CH$ | H | H | O | H | $CF_3$ | H | H | H | $OCF_3$ |
| 15 | 65N | $CCl_3$ | $(CH_3)_2CH$ | H | H | O | H | F | H | H | H | $OCF_3$ |
| 15 | 66N | $CCl_3$ | $(CH_3)_2CH$ | H | H | O | H | F | H | F | H | $OCF_3$ |
| 15 | 67N | $CCl_3$ | $(CH_3)_2CH$ | H | H | O | H | Br | H | H | H | $OCF_3$ |
| 15 | 68N | $CCl_3$ | $(CH_3)_2CH$ | H | H | O | H | Cl | H | H | H | $OCF_3$ |
| 15 | 69N | $CCl_3$ | $(CH_3)_2CH$ | H | H | O | H | F | F | H | H | $OCF_3$ |
| 15 | 70N | $CCl_3$ | $(CH_3)_2CH$ | H | H | O | H | F | H | H | H | $C_6H_5$ |
| 15 | 71N | $CCl_3$ | $(CH_3)_2CH$ | H | H | O | H | $CH_3$ | H | H | H | $OCF_3$ |
| 15 | 72N | $CCl_3$ | $(CH_3)_2CH$ | H | H | O | H | F | F | H | H | $CF_3$ |
| 15 | 73N | $CCl_3$ | $(CH_3)_2CH$ | H | H | O | H | Cl | H | H | H | $CH_3$ |
| 15 | 74N | $CCl_3$ | $(CH_3)_2CH$ | H | H | O | H | $OCH_3$ | H | H | H | $CH_3$ |
| 15 | 75N | $CCl_3$ | $(CH_3)_2CH$ | H | H | O | H | F | H | H | H | $CH_3$ |
| 15 | 76N | $CCl_3$ | $(CH_3)_2CH$ | H | H | O | F | F | H | H | H | $OCF_3$ |
| 15 | 77N | $CCl_3$ | $(CH_3)_2CH$ | H | H | O | $OCH_3$ | H | H | H | H | $CF_3$ |
| 15 | 78N | $CCl_3$ | $(CH_3)_2CH$ | H | H | O | H | H | $OCH_3$ | H | H | $CH_3$ |
| 15 | 79N | $CCl_3$ | $(CH_3)_2CH$ | H | H | O | H | H | $CH_3$ | H | H | $CH_3$ |
| 15 | 80N | $CCl_3$ | $(CH_3)_2CH$ | H | H | O | H | $CH_3$ | H | H | H | $CH_3$ |
| 15 | 81N | $CCl_3$ | $(CH_3)_2CH$ | H | H | O | $CH_3$ | H | H | H | H | $CH_3$ |
| 15 | 82N | $CCl_3$ | $(CH_3)_2CH$ | H | H | O | H | F | F | H | H | $CH_3$ |
| 15 | 83N | $CCl_3$ | $(CH_3)_2CH$ | H | H | O | H | F | H | F | H | $CH_3$ |
| 15 | 84N | $CCl_3$ | $(CH_3)_2CH$ | H | H | O | F | F | H | H | H | $CH_3$ |
| 15 | 85N | $CCl_3$ | $(CH_3)_2CH$ | H | H | O | F | $CF_3$ | H | H | H | $CH_3$ |
| 15 | 86N | $CCl_3$ | $(CH_3)_2CH$ | H | H | O | H | H | $CH_3$ | H | H | $CF_3$ |
| 15 | 87N | $CCl_3$ | $(CH_3)_2CH$ | H | H | O | $CH_3$ | H | H | H | H | $CF_3$ |
| 15 | 88N | $CCl_3$ | $(CH_3)_2CH$ | H | H | O | H | $CF_3$ | H | H | H | $CH_3$ |
| 15 | 89N | $CCl_3$ | $(CH_3)_2CH$ | H | H | O | $OCH_3$ | H | H | H | H | $CH_3$ |
| 15 | 90N | $CCl_3$ | $(CH_3)_2CH$ | H | H | O | H | H | $CF_3$ | H | H | $CH_3$ |
| 15 | 91N | $CCl_3$ | $(CH_3)_2CH$ | H | H | O | $CF_3$ | H | H | H | H | $CH_3$ |
| 15 | 92N | $CCl_3$ | $(CH_3)_2CH$ | H | H | O | H | $CF_3$ | F | H | H | $CH_3$ |
| 16 | 1N | $CHCl_2$ | H | H | H | O | H | $C_6H_5O$ | H | H | $OCF_2CF_2H$ | H |
| 16 | 2N | $CHCl_2$ | H | H | H | O | H | $OCF_3$ | H | H | $OCF_2CF_2H$ | H |
| 16 | 3N | $CHCl_2$ | H | H | H | O | F | H | H | F | $OCF_2CF_2H$ | H |
| 16 | 4N | $CHCl_2$ | H | H | H | O | F | H | H | H | $OCF_2CF_2H$ | H |
| 16 | 5N | $CHCl_2$ | H | H | H | O | H | $C_6H_5O$ | H | H | $OCF_3$ | H |
| 16 | 6N | $CHCl_2$ | H | H | H | O | H | $OCF_3$ | H | H | $OCF_3$ | H |
| 16 | 7N | $CHCl_2$ | H | H | H | O | H | H | phenyl | H | $OCF_3$ | H |
| 16 | 8N | $CHCl_2$ | H | H | H | O | H | phenyl | H | H | $OCF_3$ | H |
| 16 | 9N | $CHCl_2$ | H | H | H | O | H | H | H | H | $OCF_3$ | H |

TABLE 5-continued

Structure of Substituted Phenyl tertiary-2-Heteroalkylamines (Z is covalent bond; Y is CH and $R_{14}$ is H).

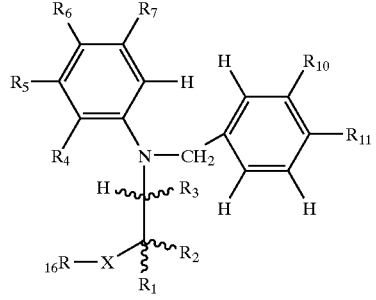

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 16 | 10N | $CHCl_2$ | H | H | H | O | H | Br | H | H | $OCF_3$ | H |
| 16 | 11N | $CHCl_2$ | H | H | H | O | H | $CF_3$ | F | H | $CF_3$ | H |
| 16 | 12N | $CHCl_2$ | H | H | H | O | H | $CH_3$ | H | H | $CF_3$ | H |
| 16 | 13N | $CHCl_2$ | H | H | H | O | H | $CF_3$ | H | H | $CF_3$ | H |
| 16 | 14N | $CHCl_2$ | H | H | H | O | H | $CH_3$ | H | H | $OCF_3$ | H |
| 16 | 15N | $CHCl_2$ | H | H | H | O | H | F | F | H | $OCF_3$ | H |
| 16 | 16N | $CHCl_2$ | H | H | H | O | H | Br | H | H | $CF_3$ | H |
| 16 | 17N | $CHCl_2$ | H | H | H | O | H | $CF_3$ | F | H | $OCF_3$ | H |
| 16 | 18N | $CHCl_2$ | H | H | H | O | H | F | H | H | $OCF_3$ | H |
| 16 | 19N | $CHCl_2$ | H | H | H | O | H | Cl | H | H | $OCF_3$ | H |
| 16 | 20N | $CHCl_2$ | H | H | H | O | H | F | H | H | $CF_3$ | H |
| 16 | 21N | $CHCl_2$ | H | H | H | O | H | F | F | H | $CF_3$ | H |
| 16 | 22N | $CHCl_2$ | H | H | H | O | H | Cl | H | H | $CF_3$ | H |
| 16 | 23N | $CHCl_2$ | H | H | H | O | H | F | H | H | phenoxy | H |
| 16 | 24N | $CHCl_2$ | H | H | H | O | H | $CF_3$ | Cl | H | $CH_3$ | H |
| 16 | 25N | $CHCl_2$ | H | H | H | O | H | $CF_3$ | F | H | $CH_3$ | H |
| 16 | 26N | $CHCl_2$ | H | H | H | O | H | H | H | H | $CF_3$ | H |
| 16 | 27N | $CHCl_2$ | H | H | H | O | F | F | H | H | $CF_3$ | H |
| 16 | 28N | $CHCl_2$ | H | H | H | O | H | H | $OCH_3$ | H | $CF_3$ | H |
| 16 | 29N | $CHCl_2$ | H | H | H | O | H | F | F | H | $CH_3$ | H |
| 16 | 30N | $CHCl_2$ | H | H | H | O | H | $OCH_3$ | H | H | $CH_3$ | H |
| 16 | 31N | $CHCl_2$ | H | H | H | O | H | H | $CH_3$ | H | H | H |
| 16 | 32N | $CHCl_2$ | H | H | H | O | H | Cl | H | H | H | H |
| 16 | 33N | $CHCl_2$ | H | H | H | O | H | F | H | H | F | H |
| 16 | 34N | $CHCl_2$ | H | H | H | O | H | H | $OCH_3$ | H | $CH_3$ | H |
| 16 | 35N | $CHCl_2$ | H | H | H | O | H | H | H | H | H | H |
| 16 | 36N | $CHCl_2$ | H | H | H | O | H | H | $CH_3$ | H | $CH_3$ | H |
| 16 | 37N | $CHCl_2$ | H | H | H | O | H | H | Cl | H | H | H |
| 16 | 38N | $CHCl_2$ | H | H | H | O | H | F | H | H | 3-$CF_3$-phenoxy | H |
| 16 | 39N | $CHCl_2$ | H | H | H | O | H | F | H | H | 4-$CH_3O$-phenoxy | H |
| 16 | 40N | $CHCl_2$ | H | H | H | O | H | F | H | H | 4-Cl-phenoxy | H |
| 16 | 41N | $CHCl_2$ | H | H | H | O | H | F | H | H | H | H |
| 16 | 42N | $CHCl_2$ | H | H | H | O | H | F | H | H | $CH_3$ | H |
| 16 | 43N | $CHCl_2$ | H | H | H | O | H | F | H | F | $CH_3$ | H |
| 16 | 44N | $CHCl_2$ | H | H | H | O | F | F | H | H | $CH_3$ | H |
| 16 | 45N | $CHCl_2$ | H | H | H | O | H | Cl | H | H | $CH_3$ | H |
| 16 | 46N | $CHCl_2$ | H | H | H | O | H | $CH_3$ | H | H | $CH_3$ | H |
| 16 | 47N | $CHCl_2$ | H | H | H | O | $CH_3$ | H | H | H | H | H |
| 16 | 48N | $CHCl_2$ | H | H | H | O | H | H | $CH_3$ | H | $CF_3$ | H |
| 16 | 49N | $CHCl_2$ | H | H | H | O | $CH_3$ | H | H | H | $CF_3$ | H |
| 16 | 50N | $CHCl_2$ | H | H | H | O | $CH_3$ | H | H | H | $CH_3$ | H |
| 16 | 51N | $CHCl_2$ | H | H | H | O | H | H | $CH_3$ | H | F | H |
| 16 | 52N | $CHCl_2$ | H | H | H | O | H | $CF_3$ | H | H | F | H |
| 16 | 53N | $CHCl_2$ | H | H | H | O | H | $CF_3$ | H | H | $CH_3$ | H |
| 16 | 54N | $CHCl_2$ | H | H | H | O | H | $OCH_3$ | H | H | $CF_3$ | H |
| 16 | 55N | $CHCl_2$ | H | H | H | O | $OCH_3$ | H | H | H | $CH_3$ | H |
| 16 | 56N | $CHCl_2$ | H | H | H | O | H | H | $CH_3$ | H | $CF_3$ | H |
| 16 | 57N | $CHCl_2$ | H | H | H | O | H | $C_6H_5O$ | H | H | H | $OCF_3$ |
| 16 | 58N | $CHCl_2$ | H | H | H | O | H | H | H | H | H | $OCF_3$ |
| 16 | 59N | $CHCl_2$ | H | H | H | O | H | $OCF_3$ | H | H | H | $OCF_3$ |
| 16 | 60N | $CHCl_2$ | H | H | H | O | H | $CF_3$ | F | H | H | $CF_3$ |
| 16 | 61N | $CHCl_2$ | H | H | H | O | H | H | $OCH_3$ | H | H | $CF_3$ |
| 16 | 62N | $CHCl_2$ | H | H | H | O | H | $CH_3$ | H | H | H | $CF_3$ |
| 16 | 63N | $CHCl_2$ | H | H | H | O | H | Cl | H | H | H | $CF_3$ |
| 16 | 64N | $CHCl_2$ | H | H | H | O | H | $CF_3$ | H | H | H | $OCF_3$ |
| 16 | 65N | $CHCl_2$ | H | H | H | O | H | F | H | H | H | $OCF_3$ |
| 16 | 66N | $CHCl_2$ | H | H | H | O | H | F | H | F | H | $OCF_3$ |

TABLE 5-continued

Structure of Substituted Phenyl tertiary-2-Heteroalkylamines (Z is covalent bond; Y is CH and $R_{14}$ is H).

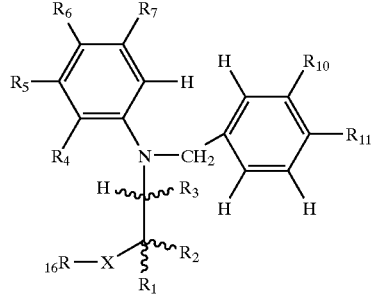

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 16 | 67N | $CHCl_2$ | H | H | H | O | H | Br | H | H | H | $OCF_3$ |
| 16 | 68N | $CHCl_2$ | H | H | H | O | H | Cl | H | H | H | $OCF_3$ |
| 16 | 69N | $CHCl_2$ | H | H | H | O | H | F | F | H | H | $OCF_3$ |
| 16 | 70N | $CHCl_2$ | H | H | H | O | H | F | H | H | H | $C_6H_5$ |
| 16 | 71N | $CHCl_2$ | H | H | H | O | H | $CH_3$ | H | H | H | $OCF_3$ |
| 16 | 72N | $CHCl_2$ | H | H | H | O | H | F | F | H | H | $CF_3$ |
| 16 | 73N | $CHCl_2$ | H | H | H | O | H | Cl | H | H | H | $CH_3$ |
| 16 | 74N | $CHCl_2$ | H | H | H | O | H | $OCH_3$ | H | H | H | $CH_3$ |
| 16 | 75N | $CHCl_2$ | H | H | H | O | H | F | H | H | H | $CH_3$ |
| 16 | 76N | $CHCl_2$ | H | H | H | O | F | F | H | H | H | $OCF_3$ |
| 16 | 77N | $CHCl_2$ | H | H | H | O | $OCH_3$ | H | H | H | H | $CF_3$ |
| 16 | 78N | $CHCl_2$ | H | H | H | O | H | H | $OCH_3$ | H | H | $CH_3$ |
| 16 | 79N | $CHCl_2$ | H | H | H | O | H | H | $CH_3$ | H | H | $CH_3$ |
| 16 | 80N | $CHCl_2$ | H | H | H | O | H | $CH_3$ | H | H | H | $CH_3$ |
| 16 | 81N | $CHCl_2$ | H | H | H | O | $CH_3$ | H | H | H | H | $CH_3$ |
| 16 | 82N | $CHCl_2$ | H | H | H | O | H | F | F | H | H | $CH_3$ |
| 16 | 83N | $CHCl_2$ | H | H | H | O | H | F | H | F | H | $CH_3$ |
| 16 | 84N | $CHCl_2$ | H | H | H | O | F | F | H | H | H | $CH_3$ |
| 16 | 85N | $CHCl_2$ | H | H | H | O | F | $CF_3$ | H | H | H | $CH_3$ |
| 16 | 86N | $CHCl_2$ | H | H | H | O | H | H | $CH_3$ | H | H | $CF_3$ |
| 16 | 87N | $CHCl_2$ | H | H | H | O | $CH_3$ | H | H | H | H | $CF_3$ |
| 16 | 88N | $CHCl_2$ | H | H | H | O | H | $CF_3$ | H | H | H | $CH_3$ |
| 16 | 89N | $CHCl_2$ | H | H | H | O | $OCH_3$ | H | H | H | H | $CH_3$ |
| 16 | 90N | $CHCl_2$ | H | H | H | O | H | H | $CF_3$ | H | H | $CH_3$ |
| 16 | 91N | $CHCl_2$ | H | H | H | O | $CF_3$ | H | H | H | H | $CH_3$ |
| 16 | 92N | $CHCl_2$ | H | H | H | O | H | $CF_3$ | F | H | H | $CH_3$ |
| 18 | 1N | $CF_3$ | H | $CH_3$ | H | O | H | $C_6H_5O$ | H | H | $OCF_2CF_2H$ | H |
| 18 | 2N | $CF_3$ | H | $CH_3$ | H | O | H | $OCF_3$ | H | H | $OCF_2CF_2H$ | H |
| 18 | 3N | $CF_3$ | H | $CH_3$ | H | O | F | H | H | F | $OCF_2CF_2H$ | H |
| 18 | 4N | $CF_3$ | H | $CH_3$ | H | O | H | F | H | H | $OCF_2CF_2H$ | H |
| 18 | 5N | $CF_3$ | H | $CH_3$ | H | O | H | $C_6H_5O$ | H | H | $OCF_3$ | H |
| 18 | 6N | $CF_3$ | H | $CH_3$ | H | O | H | $OCF_3$ | H | H | $OCF_3$ | H |
| 18 | 7N | $CF_3$ | H | $CH_3$ | H | O | H | H | phenyl | H | $OCF_3$ | H |
| 18 | 8N | $CF_3$ | H | $CH_3$ | H | O | H | phenyl | H | H | $OCF_3$ | H |
| 18 | 9N | $CF_3$ | H | $CH_3$ | H | O | H | H | H | H | $OCF_3$ | H |
| 18 | 10N | $CF_3$ | H | $CH_3$ | H | O | H | Br | H | H | $OCF_3$ | H |
| 18 | 11N | $CF_3$ | H | $CH_3$ | H | O | H | $CF_3$ | F | H | $CF_3$ | H |
| 18 | 12N | $CF_3$ | H | $CH_3$ | H | O | H | $CH_3$ | H | H | $CF_3$ | H |
| 18 | 13N | $CF_3$ | H | $CH_3$ | H | O | H | $CF_3$ | H | H | $CF_3$ | H |
| 18 | 14N | $CF_3$ | H | $CH_3$ | H | O | H | $CH_3$ | H | H | $OCF_3$ | H |
| 18 | 15N | $CF_3$ | H | $CH_3$ | H | O | H | F | F | H | $OCF_3$ | H |
| 18 | 16N | $CF_3$ | H | $CH_3$ | H | O | H | Br | H | H | $CF_3$ | H |
| 18 | 17N | $CF_3$ | H | $CH_3$ | H | O | H | $CF_3$ | F | H | $OCF_3$ | H |
| 18 | 18N | $CF_3$ | H | $CH_3$ | H | O | H | F | H | H | $OCF_3$ | H |
| 18 | 19N | $CF_3$ | H | $CH_3$ | H | O | H | Cl | H | H | $OCF_3$ | H |
| 18 | 20N | $CF_3$ | H | $CH_3$ | H | O | H | F | H | H | $CF_3$ | H |
| 18 | 21N | $CF_3$ | H | $CH_3$ | H | O | H | F | F | H | $CF_3$ | H |
| 18 | 22N | $CF_3$ | H | $CH_3$ | H | O | H | Cl | H | H | $CF_3$ | H |
| 18 | 23N | $CF_3$ | H | $CH_3$ | H | O | H | F | H | H | phenoxy | H |
| 18 | 24N | $CF_3$ | H | $CH_3$ | H | O | H | $CF_3$ | Cl | H | $CH_3$ | H |
| 18 | 25N | $CF_3$ | H | $CH_3$ | H | O | H | $CF_3$ | F | H | $CH_3$ | H |
| 18 | 26N | $CF_3$ | H | $CH_3$ | H | O | H | H | H | H | $CF_3$ | H |
| 18 | 27N | $CF_3$ | H | $CH_3$ | H | O | F | F | H | H | $CF_3$ | H |
| 18 | 28N | $CF_3$ | H | $CH_3$ | H | O | H | H | $OCH_3$ | H | $CF_3$ | H |
| 18 | 29N | $CF_3$ | H | $CH_3$ | H | O | H | F | F | H | $CH_3$ | H |
| 18 | 30N | $CF_3$ | H | $CH_3$ | H | O | H | $OCH_3$ | H | H | $CH_3$ | H |
| 18 | 31N | $CF_3$ | H | $CH_3$ | H | O | H | H | $CH_3$ | H | H | H |

TABLE 5-continued

Structure of Substituted Phenyl tertiary-2-Heteroalkylamines (Z is covalent bond; Y is CH and $R_{14}$ is H).

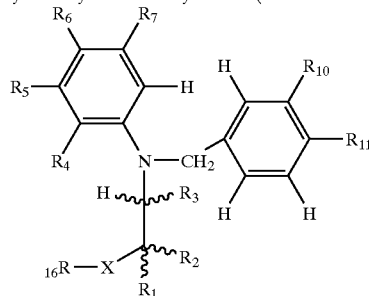

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 18 | 32N | $CF_3$ | H | $CH_3$ | H | O | H | Cl | H | H | H | H |
| 18 | 33N | $CF_3$ | H | $CH_3$ | H | O | H | F | H | H | F | H |
| 18 | 34N | $CF_3$ | H | $CH_3$ | H | O | H | H | $OCH_3$ | H | $CH_3$ | H |
| 18 | 35N | $CF_3$ | H | $CH_3$ | H | O | H | H | H | H | H | H |
| 18 | 36N | $CF_3$ | H | $CH_3$ | H | O | H | H | $CH_3$ | H | $CH_3$ | H |
| 18 | 37N | $CF_3$ | H | $CH_3$ | H | O | H | H | Cl | H | H | H |
| 18 | 38N | $CF_3$ | H | $CH_3$ | H | O | H | F | H | H | 3-$CF_3$-phenoxy | H |
| 18 | 39N | $CF_3$ | H | $CH_3$ | H | O | H | F | H | H | 4-$CH_3O$-phenoxy | H |
| 18 | 40N | $CF_3$ | H | $CH_3$ | H | O | H | F | H | H | 4-Cl-phenoxy | H |
| 18 | 41N | $CF_3$ | H | $CH_3$ | H | O | H | F | H | H | H | H |
| 18 | 42N | $CF_3$ | H | $CH_3$ | H | O | H | F | H | H | $CH_3$ | H |
| 18 | 43N | $CF_3$ | H | $CH_3$ | H | O | H | F | H | F | $CH_3$ | H |
| 18 | 44N | $CF_3$ | H | $CH_3$ | H | O | F | F | H | H | $CH_3$ | H |
| 18 | 45N | $CF_3$ | H | $CH_3$ | H | O | H | Cl | H | H | $CH_3$ | H |
| 18 | 46N | $CF_3$ | H | $CH_3$ | H | O | H | $CH_3$ | H | H | $CH_3$ | H |
| 18 | 47N | $CF_3$ | H | $CH_3$ | H | O | $CH_3$ | H | H | H | H | H |
| 18 | 48N | $CF_3$ | H | $CH_3$ | H | O | H | H | $CH_3$ | H | $CF_3$ | H |
| 18 | 49N | $CF_3$ | H | $CH_3$ | H | O | $CH_3$ | H | H | H | $CF_3$ | H |
| 18 | 50N | $CF_3$ | H | $CH_3$ | H | O | $CH_3$ | H | H | H | $CH_3$ | H |
| 18 | 51N | $CF_3$ | H | $CH_3$ | H | O | H | H | $CH_3$ | H | F | H |
| 18 | 52N | $CF_3$ | H | $CH_3$ | H | O | H | $CF_3$ | H | H | F | H |
| 18 | 53N | $CF_3$ | H | $CH_3$ | H | O | H | $CF_3$ | H | H | $CH_3$ | H |
| 18 | 54N | $CF_3$ | H | $CH_3$ | H | O | H | $OCH_3$ | H | H | $CF_3$ | H |
| 18 | 55N | $CF_3$ | H | $CH_3$ | H | O | $OCH_3$ | H | H | H | $CH_3$ | H |
| 18 | 56N | $CF_3$ | H | $CH_3$ | H | O | H | H | $CH_3$ | H | $CF_3$ | H |
| 18 | 57N | $CF_3$ | H | $CH_3$ | H | O | H | $C_6H_5O$ | H | H | H | $OCF_3$ |
| 18 | 58N | $CF_3$ | H | $CH_3$ | H | O | H | H | H | H | H | $OCF_3$ |
| 18 | 59N | $CF_3$ | H | $CH_3$ | H | O | H | $OCF_3$ | H | H | H | $OCF_3$ |
| 18 | 60N | $CF_3$ | H | $CH_3$ | H | O | H | $CF_3$ | F | H | H | $CF_3$ |
| 18 | 61N | $CF_3$ | H | $CH_3$ | H | O | H | H | $OCH_3$ | H | H | $CF_3$ |
| 18 | 62N | $CF_3$ | H | $CH_3$ | H | O | H | $CH_3$ | H | H | H | $CF_3$ |
| 18 | 63N | $CF_3$ | H | $CH_3$ | H | O | H | Cl | H | H | H | $CF_3$ |
| 18 | 64N | $CF_3$ | H | $CH_3$ | H | O | H | $CF_3$ | H | H | H | $OCF_3$ |
| 18 | 65N | $CF_3$ | H | $CH_3$ | H | O | H | F | H | H | H | $OCF_3$ |
| 18 | 66N | $CF_3$ | H | $CH_3$ | H | O | H | F | H | F | H | $OCF_3$ |
| 18 | 67N | $CF_3$ | H | $CH_3$ | H | O | H | Br | H | H | H | $OCF_3$ |
| 18 | 68N | $CF_3$ | H | $CH_3$ | H | O | H | Cl | H | H | H | $OCF_3$ |
| 18 | 69N | $CF_3$ | H | $CH_3$ | H | O | H | F | F | H | H | $OCF_3$ |
| 18 | 70N | $CF_3$ | H | $CH_3$ | H | O | H | F | H | H | H | $C_6H_5$ |
| 18 | 71N | $CF_3$ | H | $CH_3$ | H | O | H | $CH_3$ | H | H | H | $OCF_3$ |
| 18 | 72N | $CF_3$ | H | $CH_3$ | H | O | H | F | F | H | H | $CF_3$ |
| 18 | 73N | $CF_3$ | H | $CH_3$ | H | O | H | Cl | H | H | H | $CH_3$ |
| 18 | 74N | $CF_3$ | H | $CH_3$ | H | O | H | $OCH_3$ | H | H | H | $CH_3$ |
| 18 | 75N | $CF_3$ | H | $CH_3$ | H | O | H | F | H | H | H | $CH_3$ |
| 18 | 76N | $CF_3$ | H | $CH_3$ | H | O | F | F | H | H | H | $OCF_3$ |
| 18 | 77N | $CF_3$ | H | $CH_3$ | H | O | $OCH_3$ | H | H | H | H | $CF_3$ |
| 18 | 78N | $CF_3$ | H | $CH_3$ | H | O | H | H | $OCH_3$ | H | H | $CH_3$ |
| 18 | 79N | $CF_3$ | H | $CH_3$ | H | O | H | H | $CH_3$ | H | H | $CH_3$ |
| 18 | 80N | $CF_3$ | H | $CH_3$ | H | O | H | $CH_3$ | H | H | H | $CH_3$ |
| 18 | 81N | $CF_3$ | H | $CH_3$ | H | O | $CH_3$ | H | H | H | H | $CH_3$ |
| 18 | 82N | $CF_3$ | H | $CH_3$ | H | O | H | F | F | H | H | $CH_3$ |
| 18 | 83N | $CF_3$ | H | $CH_3$ | H | O | H | F | H | F | H | $CH_3$ |
| 18 | 84N | $CF_3$ | H | $CH_3$ | H | O | F | F | H | H | H | $CH_3$ |
| 18 | 85N | $CF_3$ | H | $CH_3$ | H | O | F | $CF_3$ | H | H | H | $CH_3$ |
| 18 | 86N | $CF_3$ | H | $CH_3$ | H | O | H | H | $CH_3$ | H | H | $CF_3$ |
| 18 | 87N | $CF_3$ | H | $CH_3$ | H | O | $CH_3$ | H | H | H | H | $CF_3$ |
| 18 | 88N | $CF_3$ | H | $CH_3$ | H | O | H | $CF_3$ | H | H | H | $CH_3$ |

TABLE 5-continued

Structure of Substituted Phenyl tertiary-2-Heteroalkylamines (Z is covalent bond; Y is CH and $R_{14}$ is H).

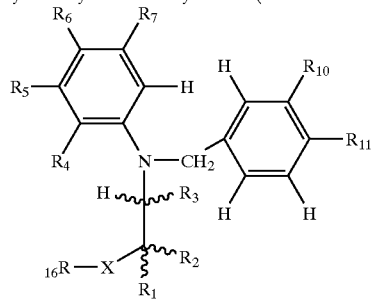

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 18 | 89N | $CF_3$ | H | $CH_3$ | H | O | $OCH_3$ | H | H | H | H | $CH_3$ |
| 18 | 90N | $CF_3$ | H | $CH_3$ | H | O | H | H | $CF_3$ | H | H | $CH_3$ |
| 18 | 91N | $CF_3$ | H | $CH_3$ | H | O | $CF_3$ | H | H | H | H | $CH_3$ |
| 18 | 92N | $CF_3$ | H | $CH_3$ | H | O | H | $CF_3$ | H | H | H | $CH_3$ |
| 19 | 1N | $CF_3$ | $CF_3$ | H | H | N | H | $C_6H_5O$ | H | H | $OCF_2CF_2H$ | H |
| 19 | 2N | $CF_3$ | $CF_3$ | H | H | N | H | $OCF_3$ | H | H | $OCF_2CF_2H$ | H |
| 19 | 3N | $CF_3$ | $CF_3$ | H | H | N | F | H | H | F | $OCF_2CF_2H$ | H |
| 19 | 4N | $CF_3$ | $CF_3$ | H | H | N | H | F | H | H | $OCF_2CF_2H$ | H |
| 19 | 5N | $CF_3$ | $CF_3$ | H | H | N | H | $C_6H_5O$ | H | H | $OCF_3$ | H |
| 19 | 6N | $CF_3$ | $CF_3$ | H | H | N | H | $OCF_3$ | H | H | $OCF_3$ | H |
| 19 | 7N | $CF_3$ | $CF_3$ | H | H | N | H | H | phenyl | H | $OCF_3$ | H |
| 19 | 8N | $CF_3$ | $CF_3$ | H | H | N | H | phenyl | H | H | $OCF_3$ | H |
| 19 | 9N | $CF_3$ | $CF_3$ | H | H | N | H | H | H | H | $OCF_3$ | H |
| 19 | 10N | $CF_3$ | $CF_3$ | H | H | N | H | Br | H | H | $OCF_3$ | H |
| 19 | 11N | $CF_3$ | $CF_3$ | H | H | N | H | $CF_3$ | F | H | $CF_3$ | H |
| 19 | 12N | $CF_3$ | $CF_3$ | H | H | N | H | $CH_3$ | H | H | $CF_3$ | H |
| 19 | 13N | $CF_3$ | $CF_3$ | H | H | N | H | $CF_3$ | H | H | $CF_3$ | H |
| 19 | 14N | $CF_3$ | $CF_3$ | H | H | N | H | $CH_3$ | H | H | $OCF_3$ | H |
| 19 | 15N | $CF_3$ | $CF_3$ | H | H | N | H | F | F | H | $OCF_3$ | H |
| 19 | 16N | $CF_3$ | $CF_3$ | H | H | N | H | Br | H | H | $CF_3$ | H |
| 19 | 17N | $CF_3$ | $CF_3$ | H | H | N | H | $CF_3$ | F | H | $OCF_3$ | H |
| 19 | 18N | $CF_3$ | $CF_3$ | H | H | N | H | F | H | H | $OCF_3$ | H |
| 19 | 19N | $CF_3$ | $CF_3$ | H | H | N | H | Cl | H | H | $OCF_3$ | H |
| 19 | 20N | $CF_3$ | $CF_3$ | H | H | N | H | F | H | H | $CF_3$ | H |
| 19 | 21N | $CF_3$ | $CF_3$ | H | H | N | H | F | F | H | $CF_3$ | H |
| 19 | 22N | $CF_3$ | $CF_3$ | H | H | N | H | Cl | H | H | $CF_3$ | H |
| 19 | 23N | $CF_3$ | $CF_3$ | H | H | N | H | F | H | H | phenoxy | H |
| 19 | 24N | $CF_3$ | $CF_3$ | H | H | N | H | $CF_3$ | Cl | H | $CH_3$ | H |
| 19 | 25N | $CF_3$ | $CF_3$ | H | H | N | H | $CF_3$ | F | H | $CH_3$ | H |
| 19 | 26N | $CF_3$ | $CF_3$ | H | H | N | H | H | H | H | $CF_3$ | H |
| 19 | 27N | $CF_3$ | $CF_3$ | H | H | N | F | F | H | H | $CF_3$ | H |
| 19 | 28N | $CF_3$ | $CF_3$ | H | H | N | H | H | $OCH_3$ | H | $CF_3$ | H |
| 19 | 29N | $CF_3$ | $CF_3$ | H | H | N | H | F | F | H | $CH_3$ | H |
| 19 | 30N | $CF_3$ | $CF_3$ | H | H | N | H | $OCH_3$ | H | H | $CH_3$ | H |
| 19 | 31N | $CF_3$ | $CF_3$ | H | H | N | H | H | $CH_3$ | H | H | H |
| 19 | 32N | $CF_3$ | $CF_3$ | H | H | N | H | Cl | H | H | H | H |
| 19 | 33N | $CF_3$ | $CF_3$ | H | H | N | H | F | H | H | F | H |
| 19 | 34N | $CF_3$ | $CF_3$ | H | H | N | H | H | $OCH_3$ | H | $CH_3$ | H |
| 19 | 35N | $CF_3$ | $CF_3$ | H | H | N | H | H | H | H | H | H |
| 19 | 36N | $CF_3$ | $CF_3$ | H | H | N | H | H | $CH_3$ | H | $CH_3$ | H |
| 19 | 37N | $CF_3$ | $CF_3$ | H | H | N | H | H | Cl | H | H | H |
| 19 | 38N | $CF_3$ | $CF_3$ | H | H | N | H | F | H | H | 3-$CF_3$-phenoxy | H |
| 19 | 39N | $CF_3$ | $CF_3$ | H | H | N | H | F | H | H | 4-$CH_3$O-phenoxy | H |
| 19 | 40N | $CF_3$ | $CF_3$ | H | H | N | H | F | H | H | 4-Cl-phenoxy | H |
| 19 | 41N | $CF_3$ | $CF_3$ | H | H | N | H | F | H | H | H | H |
| 19 | 42N | $CF_3$ | $CF_3$ | H | H | N | H | F | H | H | $CH_3$ | H |
| 19 | 43N | $CF_3$ | $CF_3$ | H | H | N | H | F | H | F | $CH_3$ | H |
| 19 | 44N | $CF_3$ | $CF_3$ | H | H | N | F | F | H | H | $CH_3$ | H |
| 19 | 45N | $CF_3$ | $CF_3$ | H | H | N | H | Cl | H | H | $CH_3$ | H |
| 19 | 46N | $CF_3$ | $CF_3$ | H | H | N | H | $CH_3$ | H | H | $CH_3$ | H |
| 19 | 47N | $CF_3$ | $CF_3$ | H | H | N | $CH_3$ | H | H | H | H | H |
| 19 | 48N | $CF_3$ | $CF_3$ | H | H | N | H | H | $CH_3$ | H | $CF_3$ | H |
| 19 | 49N | $CF_3$ | $CF_3$ | H | H | N | $CH_3$ | H | H | H | $CF_3$ | H |
| 19 | 50N | $CF_3$ | $CF_3$ | H | H | N | $CH_3$ | H | H | H | $CH_3$ | H |
| 19 | 51N | $CF_3$ | $CF_3$ | H | H | N | H | H | $CH_3$ | H | F | H |
| 19 | 52N | $CF_3$ | $CF_3$ | H | H | N | H | $CF_3$ | H | H | F | H |
| 19 | 53N | $CF_3$ | $CF_3$ | H | H | N | H | $CF_3$ | H | H | $CH_3$ | H |

TABLE 5-continued

Structure of Substituted Phenyl tertiary-2-Heteroalkylamines (Z is covalent bond; Y is CH and $R_{14}$ is H).

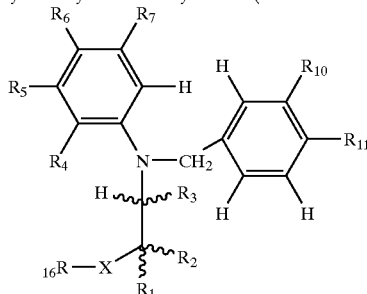

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 19 | 54N | $CF_3$ | $CF_3$ | H | H | N | H | $OCH_3$ | H | H | $CF_3$ | H |
| 19 | 55N | $CF_3$ | $CF_3$ | H | H | N | $OCH_3$ | H | H | H | $CH_3$ | H |
| 19 | 56N | $CF_3$ | $CF_3$ | H | H | N | H | H | $CH_3$ | H | $CF_3$ | H |
| 19 | 57N | $CF_3$ | $CF_3$ | H | H | N | H | $C_6H_5O$ | H | H | H | $OCF_3$ |
| 19 | 58N | $CF_3$ | $CF_3$ | H | H | N | H | H | H | H | H | $OCF_3$ |
| 19 | 59N | $CF_3$ | $CF_3$ | H | H | N | H | $OCF_3$ | H | H | H | $OCF_3$ |
| 19 | 60N | $CF_3$ | $CF_3$ | H | H | N | H | $CF_3$ | F | H | H | $CF_3$ |
| 19 | 61N | $CF_3$ | $CF_3$ | H | H | N | H | H | $OCH_3$ | H | H | $CF_3$ |
| 19 | 62N | $CF_3$ | $CF_3$ | H | H | N | H | $CH_3$ | H | H | H | $CF_3$ |
| 19 | 63N | $CF_3$ | $CF_3$ | H | H | N | H | Cl | H | H | H | $CF_3$ |
| 19 | 64N | $CF_3$ | $CF_3$ | H | H | N | H | $CF_3$ | H | H | H | $OCF_3$ |
| 19 | 65N | $CF_3$ | $CF_3$ | H | H | N | H | F | H | H | H | $OCF_3$ |
| 19 | 66N | $CF_3$ | $CF_3$ | H | H | N | H | F | H | F | H | $OCF_3$ |
| 19 | 67N | $CF_3$ | $CF_3$ | H | H | N | H | Br | H | H | H | $OCF_3$ |
| 19 | 68N | $CF_3$ | $CF_3$ | H | H | N | H | Cl | H | H | H | $OCF_3$ |
| 19 | 69N | $CF_3$ | $CF_3$ | H | H | N | H | F | F | H | H | $OCF_3$ |
| 19 | 70N | $CF_3$ | $CF_3$ | H | H | N | H | F | H | H | H | $C_6H_5$ |
| 19 | 71N | $CF_3$ | $CF_3$ | H | H | N | H | $CH_3$ | H | H | H | $OCF_3$ |
| 19 | 72N | $CF_3$ | $CF_3$ | H | H | N | H | F | F | H | H | $CF_3$ |
| 19 | 73N | $CF_3$ | $CF_3$ | H | H | N | H | Cl | H | H | H | $CH_3$ |
| 19 | 74N | $CF_3$ | $CF_3$ | H | H | N | H | $OCH_3$ | H | H | H | $CH_3$ |
| 19 | 75N | $CF_3$ | $CF_3$ | H | H | N | H | F | H | H | H | $CH_3$ |
| 19 | 76N | $CF_3$ | $CF_3$ | H | H | N | F | F | H | H | H | $OCF_3$ |
| 19 | 77N | $CF_3$ | $CF_3$ | H | H | N | $OCH_3$ | H | H | H | H | $CF_3$ |
| 19 | 78N | $CF_3$ | $CF_3$ | H | H | N | H | H | $OCH_3$ | H | H | $CH_3$ |
| 19 | 79N | $CF_3$ | $CF_3$ | H | H | N | H | H | $CH_3$ | H | H | $CH_3$ |
| 19 | 80N | $CF_3$ | $CF_3$ | H | H | N | H | $CH_3$ | H | H | H | $CH_3$ |
| 19 | 81N | $CF_3$ | $CF_3$ | H | H | N | $CH_3$ | H | H | H | H | $CH_3$ |
| 19 | 82N | $CF_3$ | $CF_3$ | H | H | N | H | F | F | H | H | $CH_3$ |
| 19 | 83N | $CF_3$ | $CF_3$ | H | H | N | H | F | H | F | H | $CH_3$ |
| 19 | 84N | $CF_3$ | $CF_3$ | H | H | N | F | F | H | H | H | $CH_3$ |
| 19 | 85N | $CF_3$ | $CF_3$ | H | H | N | F | $CF_3$ | H | H | H | $CH_3$ |
| 19 | 86N | $CF_3$ | $CF_3$ | H | H | N | H | H | $CH_3$ | H | H | $CF_3$ |
| 19 | 87N | $CF_3$ | $CF_3$ | H | H | N | $CH_3$ | H | H | H | H | $CF_3$ |
| 19 | 88N | $CF_3$ | $CF_3$ | H | H | N | H | $CF_3$ | H | H | H | $CH_3$ |
| 19 | 89N | $CF_3$ | $CF_3$ | H | H | N | $OCH_3$ | H | H | H | H | $CH_3$ |
| 19 | 90N | $CF_3$ | $CF_3$ | H | H | N | H | H | $CF_3$ | H | H | $CH_3$ |
| 19 | 91N | $CF_3$ | $CF_3$ | H | H | N | $CF_3$ | H | H | H | H | $CH_3$ |
| 19 | 92N | $CF_3$ | $CF_3$ | H | H | N | H | $CF_3$ | F | H | H | $CH_3$ |
| 20 | 1N | $CF_3$ | H | H | H | N | H | $C_6H_5O$ | H | H | $OCF_2CF_2H$ | H |
| 20 | 2N | $CF_3$ | H | H | H | N | H | $OCF_3$ | H | H | $OCF_2CF_2H$ | H |
| 20 | 3N | $CF_3$ | H | H | H | N | F | H | H | F | $OCF_2CF_2H$ | H |
| 20 | 4N | $CF_3$ | H | H | H | N | H | F | H | H | $OCF_2CF_2H$ | H |
| 20 | 5N | $CF_3$ | H | H | H | N | H | $C_6H_5O$ | H | H | $OCF_3$ | H |
| 20 | 6N | $CF_3$ | H | H | H | N | H | $OCF_3$ | H | H | $OCF_3$ | H |
| 20 | 7N | $CF_3$ | H | H | H | N | H | H | phenyl | H | $OCF_3$ | H |
| 20 | 8N | $CF_3$ | H | H | H | N | H | phenyl | H | H | $OCF_3$ | H |
| 20 | 9N | $CF_3$ | H | H | H | N | H | H | H | H | $OCF_3$ | H |
| 20 | 10N | $CF_3$ | H | H | H | N | H | Br | H | H | $OCF_3$ | H |
| 20 | 11N | $CF_3$ | H | H | H | N | H | $CF_3$ | F | H | $CF_3$ | H |
| 20 | 12N | $CF_3$ | H | H | H | N | H | $CH_3$ | H | H | $CF_3$ | H |
| 20 | 13N | $CF_3$ | H | H | H | N | H | $CF_3$ | H | H | $CF_3$ | H |
| 20 | 14N | $CF_3$ | H | H | H | N | H | $CH_3$ | H | H | $OCF_3$ | H |
| 20 | 15N | $CF_3$ | H | H | H | N | H | F | F | H | $OCF_3$ | H |
| 20 | 16N | $CF_3$ | H | H | H | N | H | Br | H | H | $CF_3$ | H |
| 20 | 17N | $CF_3$ | H | H | H | N | H | $CF_3$ | F | H | $OCF_3$ | H |
| 20 | 18N | $CF_3$ | H | H | H | N | H | F | H | H | $OCF_3$ | H |

TABLE 5-continued

Structure of Substituted Phenyl tertiary-2-Heteroalkylamines (Z is covalent bond; Y is CH and $R_{14}$ is H).

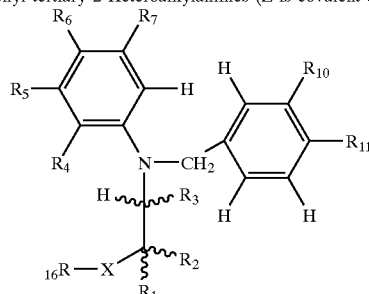

| Inhibitor Number Column 1 + Column 2 | | | | | | | | | | | | |
|---|---|---|---|---|---|---|---|---|---|---|---|---|
| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
| 20 | 19N | $CF_3$ | H | H | H | N | H | Cl | H | H | $OCF_3$ | H |
| 20 | 20N | $CF_3$ | H | H | H | N | H | F | H | H | $CF_3$ | H |
| 20 | 21N | $CF_3$ | H | H | H | N | H | F | F | H | $CF_3$ | H |
| 20 | 22N | $CF_3$ | H | H | H | N | H | Cl | H | H | $CF_3$ | H |
| 20 | 23N | $CF_3$ | H | H | H | N | H | F | H | H | phenoxy | H |
| 20 | 24N | $CF_3$ | H | H | H | N | H | $CF_3$ | Cl | H | $CH_3$ | H |
| 20 | 25N | $CF_3$ | H | H | H | N | H | $CF_3$ | F | H | $CH_3$ | H |
| 20 | 26N | $CF_3$ | H | H | H | N | H | H | H | H | $CF_3$ | H |
| 20 | 27N | $CF_3$ | H | H | H | N | F | F | H | H | $CF_3$ | H |
| 20 | 28N | $CF_3$ | H | H | H | N | H | H | $OCH_3$ | H | $CF_3$ | H |
| 20 | 29N | $CF_3$ | H | H | H | N | H | F | F | H | $CH_3$ | H |
| 20 | 30N | $CF_3$ | H | H | H | N | H | $OCH_3$ | H | H | $CH_3$ | H |
| 20 | 31N | $CF_3$ | H | H | H | N | H | H | $CH_3$ | H | H | H |
| 20 | 32N | $CF_3$ | H | H | H | N | H | Cl | H | H | H | H |
| 20 | 33N | $CF_3$ | H | H | H | N | H | F | H | H | F | H |
| 20 | 34N | $CF_3$ | H | H | H | N | H | H | $OCH_3$ | H | $CH_3$ | H |
| 20 | 35N | $CF_3$ | H | H | H | N | H | H | H | H | H | H |
| 20 | 36N | $CF_3$ | H | H | H | N | H | H | $CH_3$ | H | $CH_3$ | H |
| 20 | 37N | $CF_3$ | H | H | H | N | H | H | Cl | H | H | H |
| 20 | 38N | $CF_3$ | H | H | H | N | H | F | H | H | 3-$CF_3$-phenoxy | H |
| 20 | 39N | $CF_3$ | H | H | H | N | H | F | H | H | 4-$CH_3O$-phenoxy | H |
| 20 | 40N | $CF_3$ | H | H | H | N | H | F | H | H | 4-Cl-phenoxy | H |
| 20 | 41N | $CF_3$ | H | H | H | N | H | F | H | H | H | H |
| 20 | 42N | $CF_3$ | H | H | H | N | H | F | H | H | $CH_3$ | H |
| 20 | 43N | $CF_3$ | H | H | H | N | H | F | H | F | $CH_3$ | H |
| 20 | 44N | $CF_3$ | H | H | H | N | F | F | H | H | $CH_3$ | H |
| 20 | 45N | $CF_3$ | H | H | H | N | H | Cl | H | H | $CH_3$ | H |
| 20 | 46N | $CF_3$ | H | H | H | N | H | $CH_3$ | H | H | $CH_3$ | H |
| 20 | 47N | $CF_3$ | H | H | H | N | $CH_3$ | H | H | H | H | H |
| 20 | 48N | $CF_3$ | H | H | H | N | H | H | $CH_3$ | H | $CF_3$ | H |
| 20 | 49N | $CF_3$ | H | H | H | N | $CH_3$ | H | H | H | $CF_3$ | H |
| 20 | 50N | $CF_3$ | H | H | H | N | $CH_3$ | H | H | H | $CH_3$ | H |
| 20 | 51N | $CF_3$ | H | H | H | N | H | H | $CH_3$ | H | F | H |
| 20 | 52N | $CF_3$ | H | H | H | N | H | $CF_3$ | H | H | F | H |
| 20 | 53N | $CF_3$ | H | H | H | N | H | $CF_3$ | H | H | $CH_3$ | H |
| 20 | 54N | $CF_3$ | H | H | H | N | H | $OCH_3$ | H | H | $CF_3$ | H |
| 20 | 55N | $CF_3$ | H | H | H | N | $OCH_3$ | H | H | H | $CH_3$ | H |
| 20 | 56N | $CF_3$ | H | H | H | N | H | H | $CH_3$ | H | $CF_3$ | H |
| 20 | 57N | $CF_3$ | H | H | H | N | H | $C_6H_5O$ | H | H | H | $OCF_3$ |
| 20 | 58N | $CF_3$ | H | H | H | N | H | H | H | H | H | $OCF_3$ |
| 20 | 59N | $CF_3$ | H | H | H | N | H | $OCF_3$ | H | H | H | $OCF_3$ |
| 20 | 60N | $CF_3$ | H | H | H | N | H | $CF_3$ | F | H | H | $CF_3$ |
| 20 | 61N | $CF_3$ | H | H | H | N | H | H | $OCH_3$ | H | H | $CF_3$ |
| 20 | 62N | $CF_3$ | H | H | H | N | H | $CH_3$ | H | H | H | $CF_3$ |
| 20 | 63N | $CF_3$ | H | H | H | N | H | Cl | H | H | H | $CF_3$ |
| 20 | 64N | $CF_3$ | H | H | H | N | H | $CF_3$ | H | H | H | $OCF_3$ |
| 20 | 65N | $CF_3$ | H | H | H | N | H | F | H | H | H | $OCF_3$ |
| 20 | 66N | $CF_3$ | H | H | H | N | H | F | H | F | H | $OCF_3$ |
| 20 | 67N | $CF_3$ | H | H | H | N | H | Br | H | H | H | $OCF_3$ |
| 20 | 68N | $CF_3$ | H | H | H | N | H | Cl | H | H | H | $OCF_3$ |
| 20 | 69N | $CF_3$ | H | H | H | N | H | F | F | H | H | $OCF_3$ |
| 20 | 70N | $CF_3$ | H | H | H | N | H | F | H | H | H | $C_6H_5$ |
| 20 | 71N | $CF_3$ | H | H | H | N | H | $CH_3$ | H | H | H | $OCF_3$ |
| 20 | 72N | $CF_3$ | H | H | H | N | H | F | F | H | H | $CF_3$ |
| 20 | 73N | $CF_3$ | H | H | H | N | H | Cl | H | H | H | $CH_3$ |
| 20 | 74N | $CF_3$ | H | H | H | N | H | $OCH_3$ | H | H | H | $CH_3$ |
| 20 | 75N | $CF_3$ | H | H | H | N | H | F | H | H | H | $CH_3$ |

TABLE 5-continued

Structure of Substituted Phenyl tertiary-2-Heteroalkylamines (Z is covalent bond; Y is CH and $R_{14}$ is H).

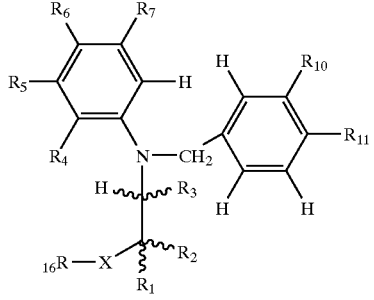

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 20 | 76N | $CF_3$ | H | H | H | N | F | F | H | H | H | $OCF_3$ |
| 20 | 77N | $CF_3$ | H | H | H | N | $OCH_3$ | H | H | H | H | $CF_3$ |
| 20 | 78N | $CF_3$ | H | H | H | N | H | H | $OCH_3$ | H | H | $CH_3$ |
| 20 | 79N | $CF_3$ | H | H | H | N | H | H | $CH_3$ | H | H | $CH_3$ |
| 20 | 80N | $CF_3$ | H | H | H | N | H | $CH_3$ | H | H | H | $CH_3$ |
| 20 | 81N | $CF_3$ | H | H | H | N | $CH_3$ | H | H | H | H | $CH_3$ |
| 20 | 82N | $CF_3$ | H | H | H | N | H | F | F | H | H | $CH_3$ |
| 20 | 83N | $CF_3$ | H | H | H | N | H | F | H | F | H | $CH_3$ |
| 20 | 84N | $CF_3$ | H | H | H | N | F | F | H | H | H | $CH_3$ |
| 20 | 85N | $CF_3$ | H | H | H | N | F | $CF_3$ | H | H | H | $CH_3$ |
| 20 | 86N | $CF_3$ | H | H | H | N | H | H | $CH_3$ | H | H | $CF_3$ |
| 20 | 87N | $CF_3$ | H | H | H | N | $CH_3$ | H | H | H | H | $CF_3$ |
| 20 | 88N | $CF_3$ | H | H | H | N | H | $CF_3$ | H | H | H | $CH_3$ |
| 20 | 89N | $CF_3$ | H | H | H | N | $OCH_3$ | H | H | H | H | $CH_3$ |
| 20 | 90N | $CF_3$ | H | H | H | N | H | H | $CF_3$ | H | H | $CH_3$ |
| 20 | 91N | $CF_3$ | H | H | H | N | $CF_3$ | H | H | H | H | $CH_3$ |
| 20 | 92N | $CF_3$ | H | H | H | N | H | $CF_3$ | F | H | H | $CH_3$ |
| 23 | 1N | $CF_3$ | H | H | $CH_3$ | N | H | $C_6H_5O$ | H | H | $OCF_2CF_2H$ | H |
| 23 | 2N | $CF_3$ | H | H | $CH_3$ | N | H | $OCF_3$ | H | H | $OCF_2CF_2H$ | H |
| 23 | 3N | $CF_3$ | H | H | $CH_3$ | N | F | H | H | F | $OCF_2CF_2H$ | H |
| 23 | 4N | $CF_3$ | H | H | $CH_3$ | N | H | F | H | H | $OCF_2CF_2H$ | H |
| 23 | 5N | $CF_3$ | H | H | $CH_3$ | N | H | $C_6H_5O$ | H | H | $OCF_3$ | H |
| 23 | 6N | $CF_3$ | H | H | $CH_3$ | N | H | $OCF_3$ | H | H | $OCF_3$ | H |
| 23 | 7N | $CF_3$ | H | H | $CH_3$ | N | H | H | phenyl | H | $OCF_3$ | H |
| 23 | 8N | $CF_3$ | H | H | $CH_3$ | N | H | phenyl | H | H | $OCF_3$ | H |
| 23 | 9N | $CF_3$ | H | H | $CH_3$ | N | H | H | H | H | $OCF_3$ | H |
| 23 | 10N | $CF_3$ | H | H | $CH_3$ | N | H | Br | H | H | $OCF_3$ | H |
| 23 | 11N | $CF_3$ | H | H | $CH_3$ | N | H | $CF_3$ | F | H | $CF_3$ | H |
| 23 | 12N | $CF_3$ | H | H | $CH_3$ | N | H | $CH_3$ | H | H | $CF_3$ | H |
| 23 | 13N | $CF_3$ | H | H | $CH_3$ | N | H | $CF_3$ | H | H | $CF_3$ | H |
| 23 | 14N | $CF_3$ | H | H | $CH_3$ | N | H | $CH_3$ | H | H | $OCF_3$ | H |
| 23 | 15N | $CF_3$ | H | H | $CH_3$ | N | H | F | F | H | $OCF_3$ | H |
| 23 | 16N | $CF_3$ | H | H | $CH_3$ | N | H | Br | H | H | $CF_3$ | H |
| 23 | 17N | $CF_3$ | H | H | $CH_3$ | N | H | $CF_3$ | F | H | $OCF_3$ | H |
| 23 | 18N | $CF_3$ | H | H | $CH_3$ | N | H | F | H | H | $OCF_3$ | H |
| 23 | 19N | $CF_3$ | H | H | $CH_3$ | N | H | Cl | H | H | $OCF_3$ | H |
| 23 | 20N | $CF_3$ | H | H | $CH_3$ | N | H | F | H | H | $CF_3$ | H |
| 23 | 21N | $CF_3$ | H | H | $CH_3$ | N | H | F | F | H | $CF_3$ | H |
| 23 | 22N | $CF_3$ | H | H | $CH_3$ | N | H | Cl | H | H | $CF_3$ | H |
| 23 | 23N | $CF_3$ | H | H | $CH_3$ | N | H | F | H | H | phenoxy | H |
| 23 | 24N | $CF_3$ | H | H | $CH_3$ | N | H | $CF_3$ | Cl | H | $CH_3$ | H |
| 23 | 25N | $CF_3$ | H | H | $CH_3$ | N | H | $CF_3$ | F | H | $CH_3$ | H |
| 23 | 26N | $CF_3$ | H | H | $CH_3$ | N | H | H | H | H | $CF_3$ | H |
| 23 | 27N | $CF_3$ | H | H | $CH_3$ | N | F | F | H | H | $CF_3$ | H |
| 23 | 28N | $CF_3$ | H | H | $CH_3$ | N | H | H | $OCH_3$ | H | $CF_3$ | H |
| 23 | 29N | $CF_3$ | H | H | $CH_3$ | N | H | F | F | H | $CH_3$ | H |
| 23 | 30N | $CF_3$ | H | H | $CH_3$ | N | H | $OCH_3$ | H | H | $CH_3$ | H |
| 23 | 31N | $CF_3$ | H | H | $CH_3$ | N | H | H | $CH_3$ | H | H | H |
| 23 | 32N | $CF_3$ | H | H | $CH_3$ | N | H | Cl | H | H | H | H |
| 23 | 33N | $CF_3$ | H | H | $CH_3$ | N | H | F | H | H | F | H |
| 23 | 34N | $CF_3$ | H | H | $CH_3$ | N | H | H | $OCH_3$ | H | $CH_3$ | H |
| 23 | 35N | $CF_3$ | H | H | $CH_3$ | N | H | H | H | H | H | H |
| 23 | 36N | $CF_3$ | H | H | $CH_3$ | N | H | H | $CH_3$ | H | $CH_3$ | H |
| 23 | 37N | $CF_3$ | H | H | $CH_3$ | N | H | H | Cl | H | H | H |
| 23 | 38N | $CF_3$ | H | H | $CH_3$ | N | H | F | H | H | 3-$CF_3$-phenoxy | H |
| 23 | 39N | $CF_3$ | H | H | $CH_3$ | N | H | F | H | H | 4-$CH_3O$-phenoxy | H |
| 23 | 40N | $CF_3$ | H | H | $CH_3$ | N | H | F | H | H | 4-Cl-phenoxy | H |

TABLE 5-continued

Structure of Substituted Phenyl tertiary-2-Heteroalkylamines (Z is covalent bond; Y is CH and $R_{14}$ is H).

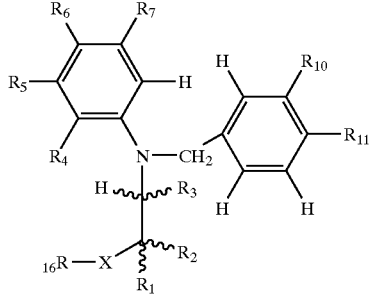

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 23 | 41N | $CF_3$ | H | H | $CH_3$ | N | H | F | H | H | H | H |
| 23 | 42N | $CF_3$ | H | H | $CH_3$ | N | H | F | H | H | $CH_3$ | H |
| 23 | 43N | $CF_3$ | H | H | $CH_3$ | N | H | F | H | F | $CH_3$ | H |
| 23 | 44N | $CF_3$ | H | H | $CH_3$ | N | F | F | H | H | $CH_3$ | H |
| 23 | 45N | $CF_3$ | H | H | $CH_3$ | N | H | Cl | H | H | $CH_3$ | H |
| 23 | 46N | $CF_3$ | H | H | $CH_3$ | N | H | $CH_3$ | H | H | $CH_3$ | H |
| 23 | 47N | $CF_3$ | H | H | $CH_3$ | N | $CH_3$ | H | H | H | H | H |
| 23 | 48N | $CF_3$ | H | H | $CH_3$ | N | H | H | $CH_3$ | H | $CF_3$ | H |
| 23 | 49N | $CF_3$ | H | H | $CH_3$ | N | $CH_3$ | H | H | H | $CF_3$ | H |
| 23 | 50N | $CF_3$ | H | H | $CH_3$ | N | $CH_3$ | H | H | H | $CH_3$ | H |
| 23 | 51N | $CF_3$ | H | H | $CH_3$ | N | H | H | $CH_3$ | H | F | H |
| 23 | 52N | $CF_3$ | H | H | $CH_3$ | N | H | $CF_3$ | H | H | F | H |
| 23 | 53N | $CF_3$ | H | H | $CH_3$ | N | H | $CF_3$ | H | H | $CH_3$ | H |
| 23 | 54N | $CF_3$ | H | H | $CH_3$ | N | H | $OCH_3$ | H | H | $CF_3$ | H |
| 23 | 55N | $CF_3$ | H | H | $CH_3$ | N | $OCH_3$ | H | H | H | $CH_3$ | H |
| 23 | 56N | $CF_3$ | H | H | $CH_3$ | N | H | H | $CH_3$ | H | $CF_3$ | H |
| 23 | 57N | $CF_3$ | H | H | $CH_3$ | N | H | $C_6H_5O$ | H | H | H | $OCF_3$ |
| 23 | 58N | $CF_3$ | H | H | $CH_3$ | N | H | H | H | H | H | $OCF_3$ |
| 23 | 59N | $CF_3$ | H | H | $CH_3$ | N | H | $OCF_3$ | H | H | H | $OCF_3$ |
| 23 | 60N | $CF_3$ | H | H | $CH_3$ | N | H | $CF_3$ | F | H | H | $CF_3$ |
| 23 | 61N | $CF_3$ | H | H | $CH_3$ | N | H | H | $OCH_3$ | H | H | $CF_3$ |
| 23 | 62N | $CF_3$ | H | H | $CH_3$ | N | H | $CH_3$ | H | H | H | $CF_3$ |
| 23 | 63N | $CF_3$ | H | H | $CH_3$ | N | H | Cl | H | H | H | $CF_3$ |
| 23 | 64N | $CF_3$ | H | H | $CH_3$ | N | H | $CF_3$ | H | H | H | $OCF_3$ |
| 23 | 65N | $CF_3$ | H | H | $CH_3$ | N | H | F | H | H | H | $OCF_3$ |
| 23 | 66N | $CF_3$ | H | H | $CH_3$ | N | H | F | H | F | H | $OCF_3$ |
| 23 | 67N | $CF_3$ | H | H | $CH_3$ | N | H | Br | H | H | H | $OCF_3$ |
| 23 | 68N | $CF_3$ | H | H | $CH_3$ | N | H | Cl | H | H | H | $OCF_3$ |
| 23 | 69N | $CF_3$ | H | H | $CH_3$ | N | H | F | F | H | H | $OCF_3$ |
| 23 | 70N | $CF_3$ | H | H | $CH_3$ | N | H | F | H | H | H | $C_6H_5$ |
| 23 | 71N | $CF_3$ | H | H | $CH_3$ | N | H | $CH_3$ | H | H | H | $OCF_3$ |
| 23 | 72N | $CF_3$ | H | H | $CH_3$ | N | H | F | F | H | H | $CF_3$ |
| 23 | 73N | $CF_3$ | H | H | $CH_3$ | N | H | Cl | H | H | H | $CH_3$ |
| 23 | 74N | $CF_3$ | H | H | $CH_3$ | N | H | $OCH_3$ | H | H | H | $CH_3$ |
| 23 | 75N | $CF_3$ | H | H | $CH_3$ | N | H | F | H | H | H | $CH_3$ |
| 23 | 76N | $CF_3$ | H | H | $CH_3$ | N | F | F | H | H | H | $OCF_3$ |
| 23 | 77N | $CF_3$ | H | H | $CH_3$ | N | $OCH_3$ | H | H | H | H | $CF_3$ |
| 23 | 78N | $CF_3$ | H | H | $CH_3$ | N | H | H | $OCH_3$ | H | H | $CH_3$ |
| 23 | 79N | $CF_3$ | H | H | $CH_3$ | N | H | H | $CH_3$ | H | H | $CH_3$ |
| 23 | 80N | $CF_3$ | H | H | $CH_3$ | N | H | $CH_3$ | H | H | H | $CH_3$ |
| 23 | 81N | $CF_3$ | H | H | $CH_3$ | N | $CH_3$ | H | H | H | H | $CH_3$ |
| 23 | 82N | $CF_3$ | H | H | $CH_3$ | N | H | F | H | H | H | $CH_3$ |
| 23 | 83N | $CF_3$ | H | H | $CH_3$ | N | H | F | H | F | H | $CH_3$ |
| 23 | 84N | $CF_3$ | H | H | $CH_3$ | N | F | F | H | H | H | $CH_3$ |
| 23 | 85N | $CF_3$ | H | H | $CH_3$ | N | F | $CF_3$ | H | H | H | $CH_3$ |
| 23 | 86N | $CF_3$ | H | H | $CH_3$ | N | H | H | $CH_3$ | H | H | $CF_3$ |
| 23 | 87N | $CF_3$ | H | H | $CH_3$ | N | $CH_3$ | H | H | H | H | $CF_3$ |
| 23 | 88N | $CF_3$ | H | H | $CH_3$ | N | H | $CF_3$ | H | H | H | $CH_3$ |
| 23 | 89N | $CF_3$ | H | H | $CH_3$ | N | $OCH_3$ | H | H | H | H | $CH_3$ |
| 23 | 90N | $CF_3$ | H | H | $CH_3$ | N | H | H | H | $CF_3$ | H | $CH_3$ |
| 23 | 91N | $CF_3$ | H | H | $CH_3$ | N | $CF_3$ | H | H | H | H | $CH_3$ |
| 23 | 92N | $CF_3$ | H | H | $CH_3$ | N | H | $CF_3$ | F | H | H | $CH_3$ |
| 25 | 1N | $CF_3$ | H | H | H | S | H | $C_6H_5O$ | H | H | $OCF_2CF_2H$ | H |
| 25 | 2N | $CF_3$ | H | H | H | S | H | $OCF_3$ | H | H | $OCF_2CF_2H$ | H |
| 25 | 3N | $CF_3$ | H | H | H | S | F | H | H | F | $OCF_2CF_2H$ | H |
| 25 | 4N | $CF_3$ | H | H | H | S | H | F | H | H | $OCF_2CF_2H$ | H |
| 25 | 5N | $CF_3$ | H | H | H | S | H | $C_6H_5O$ | H | H | $OCF_3$ | H |

TABLE 5-continued

Structure of Substituted Phenyl tertiary-2-Heteroalkylamines (Z is covalent bond; Y is CH and $R_{14}$ is H).

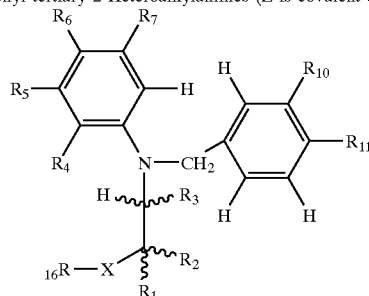

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 25 | 6N | $CF_3$ | H | H | H | S | H | $OCF_3$ | H | H | $OCF_3$ | H |
| 25 | 7N | $CF_3$ | H | H | H | S | H | H | phenyl | H | $OCF_3$ | H |
| 25 | 8N | $CF_3$ | H | H | H | S | H | phenyl | H | H | $OCF_3$ | H |
| 25 | 9N | $CF_3$ | H | H | H | S | H | H | H | H | $OCF_3$ | H |
| 25 | 10N | $CF_3$ | H | H | H | S | H | Br | H | H | $OCF_3$ | H |
| 25 | 11N | $CF_3$ | H | H | H | S | H | $CF_3$ | F | H | $CF_3$ | H |
| 25 | 12N | $CF_3$ | H | H | H | S | H | $CH_3$ | H | H | $CF_3$ | H |
| 25 | 13N | $CF_3$ | H | H | H | S | H | $CF_3$ | H | H | $CF_3$ | H |
| 25 | 14N | $CF_3$ | H | H | H | S | H | $CH_3$ | H | H | $OCF_3$ | H |
| 25 | 15N | $CF_3$ | H | H | H | S | H | F | F | H | $OCF_3$ | H |
| 25 | 16N | $CF_3$ | H | H | H | S | H | Br | H | H | $CF_3$ | H |
| 25 | 17N | $CF_3$ | H | H | H | S | H | $CF_3$ | F | H | $OCF_3$ | H |
| 25 | 18N | $CF_3$ | H | H | H | S | H | F | H | H | $OCF_3$ | H |
| 25 | 19N | $CF_3$ | H | H | H | S | H | Cl | H | H | $OCF_3$ | H |
| 25 | 20N | $CF_3$ | H | H | H | S | H | F | H | H | $CF_3$ | H |
| 25 | 21N | $CF_3$ | H | H | H | S | H | F | F | H | $CF_3$ | H |
| 25 | 22N | $CF_3$ | H | H | H | S | H | Cl | H | H | $CF_3$ | H |
| 25 | 23N | $CF_3$ | H | H | H | S | H | F | H | H | phenoxy | H |
| 25 | 24N | $CF_3$ | H | H | H | S | H | $CF_3$ | Cl | H | $CH_3$ | H |
| 25 | 25N | $CF_3$ | H | H | H | S | H | $CF_3$ | F | H | $CH_3$ | H |
| 25 | 26N | $CF_3$ | H | H | H | S | H | H | H | H | $CF_3$ | H |
| 25 | 27N | $CF_3$ | H | H | H | S | F | F | H | H | $CF_3$ | H |
| 25 | 28N | $CF_3$ | H | H | H | S | H | H | $OCH_3$ | H | $CF_3$ | H |
| 25 | 29N | $CF_3$ | H | H | H | S | H | F | F | H | $CH_3$ | H |
| 25 | 30N | $CF_3$ | H | H | H | S | H | $OCH_3$ | H | H | $CH_3$ | H |
| 25 | 31N | $CF_3$ | H | H | H | S | H | H | $CH_3$ | H | H | H |
| 25 | 32N | $CF_3$ | H | H | H | S | H | Cl | H | H | H | H |
| 25 | 33N | $CF_3$ | H | H | H | S | H | F | H | H | F | H |
| 25 | 34N | $CF_3$ | H | H | H | S | H | H | $OCH_3$ | H | $CH_3$ | H |
| 25 | 35N | $CF_3$ | H | H | H | S | H | H | H | H | H | H |
| 25 | 36N | $CF_3$ | H | H | H | S | H | H | $CH_3$ | H | $CH_3$ | H |
| 25 | 37N | $CF_3$ | H | H | H | S | H | H | Cl | H | H | H |
| 25 | 38N | $CF_3$ | H | H | H | S | H | F | H | H | 3-$CF_3$-phenoxy | H |
| 25 | 39N | $CF_3$ | H | H | H | S | H | F | H | H | 4-$CH_3O$-phenoxy | H |
| 25 | 40N | $CF_3$ | H | H | H | S | H | F | H | H | 4-Cl-phenoxy | H |
| 25 | 41N | $CF_3$ | H | H | H | S | H | F | H | H | H | H |
| 25 | 42N | $CF_3$ | H | H | H | S | H | F | H | H | $CH_3$ | H |
| 25 | 43N | $CF_3$ | H | H | H | S | H | F | H | F | $CH_3$ | H |
| 25 | 44N | $CF_3$ | H | H | H | S | F | F | H | H | $CH_3$ | H |
| 25 | 45N | $CF_3$ | H | H | H | S | H | Cl | H | H | $CH_3$ | H |
| 25 | 46N | $CF_3$ | H | H | H | S | H | H | $CH_3$ | H | $CH_3$ | H |
| 25 | 47N | $CF_3$ | H | H | H | S | $CH_3$ | H | H | H | H | H |
| 25 | 48N | $CF_3$ | H | H | H | S | H | H | $CH_3$ | H | $CF_3$ | H |
| 25 | 49N | $CF_3$ | H | H | H | S | $CH_3$ | H | H | H | $CF_3$ | H |
| 25 | 50N | $CF_3$ | H | H | H | S | $CH_3$ | H | H | H | $CH_3$ | H |
| 25 | 51N | $CF_3$ | H | H | H | S | H | H | $CH_3$ | H | F | H |
| 25 | 52N | $CF_3$ | H | H | H | S | H | $CF_3$ | H | H | F | H |
| 25 | 53N | $CF_3$ | H | H | H | S | H | $CF_3$ | H | H | $CH_3$ | H |
| 25 | 54N | $CF_3$ | H | H | H | S | H | $OCH_3$ | H | H | $CF_3$ | H |
| 25 | 55N | $CF_3$ | H | H | H | S | $OCH_3$ | H | H | H | $CH_3$ | H |
| 25 | 56N | $CF_3$ | H | H | H | S | H | H | $CH_3$ | H | $CF_3$ | H |
| 25 | 57N | $CF_3$ | H | H | H | S | H | $C_6H_5O$ | H | H | H | $OCF_3$ |
| 25 | 58N | $CF_3$ | H | H | H | S | H | H | H | H | H | $OCF_3$ |
| 25 | 59N | $CF_3$ | H | H | H | S | H | $OCF_3$ | H | H | H | $OCF_3$ |
| 25 | 60N | $CF_3$ | H | H | H | S | H | $CF_3$ | F | H | H | $CF_3$ |
| 25 | 61N | $CF_3$ | H | H | H | S | H | H | $OCH_3$ | H | H | $CF_3$ |
| 25 | 62N | $CF_3$ | H | H | H | S | H | $CH_3$ | H | H | H | $CF_3$ |

TABLE 5-continued

Structure of Substituted Phenyl tertiary-2-Heteroalkylamines (Z is covalent bond; Y is CH and $R_{14}$ is H).

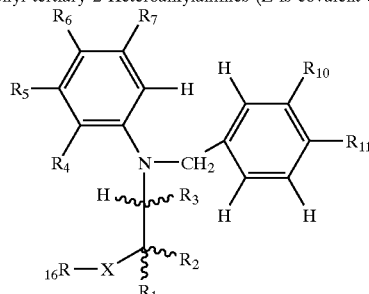

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 25 | 63N | $CF_3$ | H | H | H | S | H | Cl | H | H | H | $CF_3$ |
| 25 | 64N | $CF_3$ | H | H | H | S | H | $CF_3$ | H | H | H | $OCF_3$ |
| 25 | 65N | $CF_3$ | H | H | H | S | H | F | H | H | H | $OCF_3$ |
| 25 | 66N | $CF_3$ | H | H | H | S | H | F | H | F | H | $OCF_3$ |
| 25 | 67N | $CF_3$ | H | H | H | S | H | Br | H | H | H | $OCF_3$ |
| 25 | 68N | $CF_3$ | H | H | H | S | H | Cl | H | H | H | $OCF_3$ |
| 25 | 69N | $CF_3$ | H | H | H | S | H | F | F | H | H | $OCF_3$ |
| 25 | 70N | $CF_3$ | H | H | H | S | H | F | H | H | H | $C_6H_5$ |
| 25 | 71N | $CF_3$ | H | H | H | S | H | $CH_3$ | H | H | H | $OCF_3$ |
| 25 | 72N | $CF_3$ | H | H | H | S | H | F | F | H | H | $CF_3$ |
| 25 | 73N | $CF_3$ | H | H | H | S | H | Cl | H | H | H | $CH_3$ |
| 25 | 74N | $CF_3$ | H | H | H | S | H | $OCH_3$ | H | H | H | $CH_3$ |
| 25 | 75N | $CF_3$ | H | H | H | S | H | F | H | H | H | $CH_3$ |
| 25 | 76N | $CF_3$ | H | H | H | S | F | F | H | H | H | $OCF_3$ |
| 25 | 77N | $CF_3$ | H | H | H | S | $OCH_3$ | H | H | H | H | $CF_3$ |
| 25 | 78N | $CF_3$ | H | H | H | S | H | H | $OCH_3$ | H | H | $CH_3$ |
| 25 | 79N | $CF_3$ | H | H | H | S | H | H | $CH_3$ | H | H | $CH_3$ |
| 25 | 80N | $CF_3$ | H | H | H | S | H | $CH_3$ | H | H | H | $CH_3$ |
| 25 | 81N | $CF_3$ | H | H | H | S | $CH_3$ | H | H | H | H | $CH_3$ |
| 25 | 82N | $CF_3$ | H | H | H | S | H | F | F | H | H | $CH_3$ |
| 25 | 83N | $CF_3$ | H | H | H | S | H | F | H | F | H | $CH_3$ |
| 25 | 84N | $CF_3$ | H | H | H | S | F | F | H | H | H | $CH_3$ |
| 25 | 85N | $CF_3$ | H | H | H | S | F | $CF_3$ | H | H | H | $CH_3$ |
| 25 | 86N | $CF_3$ | H | H | H | S | H | H | $CH_3$ | H | H | $CF_3$ |
| 25 | 87N | $CF_3$ | H | H | H | S | $CH_3$ | H | H | H | H | $CF_3$ |
| 25 | 88N | $CF_3$ | H | H | H | S | H | $CF_3$ | H | H | H | $CH_3$ |
| 25 | 89N | $CF_3$ | H | H | H | S | $OCH_3$ | H | H | H | H | $CH_3$ |
| 25 | 90N | $CF_3$ | H | H | H | S | H | H | $CF_3$ | H | H | $CH_3$ |
| 25 | 91N | $CF_3$ | H | H | H | S | $CF_3$ | H | H | H | H | $CH_3$ |
| 25 | 92N | $CF_3$ | H | H | H | S | H | $CF_3$ | F | H | H | $CH_3$ |
| 26 | 1N | $CF_3CF_2$ | H | H | H | S | H | $C_6H_5O$ | H | H | $OCF_2CF_2H$ | H |
| 26 | 2N | $CF_3CF_2$ | H | H | H | S | H | $OCF_3$ | H | H | $OCF_2CF_2H$ | H |
| 26 | 3N | $CF_3CF_2$ | H | H | H | S | F | H | H | F | $OCF_2CF_2H$ | H |
| 26 | 4N | $CF_3CF_2$ | H | H | H | S | H | F | H | H | $OCF_2CF_2H$ | H |
| 26 | 5N | $CF_3CF_2$ | H | H | H | S | H | $C_6H_5O$ | H | H | $OCF_3$ | H |
| 26 | 6N | $CF_3CF_2$ | H | H | H | S | H | $OCF_3$ | H | H | $OCF_3$ | H |
| 26 | 7N | $CF_3CF_2$ | H | H | H | S | H | H | phenyl | H | $OCF_3$ | H |
| 26 | 8N | $CF_3CF_2$ | H | H | H | S | H | phenyl | H | H | $OCF_3$ | H |
| 26 | 9N | $CF_3CF_2$ | H | H | H | S | H | H | H | H | $OCF_3$ | H |
| 26 | 10N | $CF_3CF_2$ | H | H | H | S | H | Br | H | H | $OCF_3$ | H |
| 26 | 11N | $CF_3CF_2$ | H | H | H | S | H | $CF_3$ | F | H | $CF_3$ | H |
| 26 | 12N | $CF_3CF_2$ | H | H | H | S | H | $CH_3$ | H | H | $CF_3$ | H |
| 26 | 13N | $CF_3CF_2$ | H | H | H | S | H | $CF_3$ | H | H | $CF_3$ | H |
| 26 | 14N | $CF_3CF_2$ | H | H | H | S | H | $CH_3$ | H | H | $OCF_3$ | H |
| 26 | 15N | $CF_3CF_2$ | H | H | H | S | H | F | F | H | $OCF_3$ | H |
| 26 | 16N | $CF_3CF_2$ | H | H | H | S | H | Br | H | H | $CF_3$ | H |
| 26 | 17N | $CF_3CF_2$ | H | H | H | S | H | $CF_3$ | F | H | $OCF_3$ | H |
| 26 | 18N | $CF_3CF_2$ | H | H | H | S | H | F | H | H | $OCF_3$ | H |
| 26 | 19N | $CF_3CF_2$ | H | H | H | S | H | Cl | H | H | $OCF_3$ | H |
| 26 | 20N | $CF_3CF_2$ | H | H | H | S | H | F | H | H | $CF_3$ | H |
| 26 | 21N | $CF_3CF_2$ | H | H | H | S | H | F | F | H | $CF_3$ | H |
| 26 | 22N | $CF_3CF_2$ | H | H | H | S | H | Cl | H | H | $CF_3$ | H |
| 26 | 23N | $CF_3CF_2$ | H | H | H | S | H | F | H | H | phenoxy | H |
| 26 | 24N | $CF_3CF_2$ | H | H | H | S | H | $CF_3$ | Cl | H | $CH_3$ | H |
| 26 | 25N | $CF_3CF_2$ | H | H | H | S | H | $CF_3$ | F | H | $CH_3$ | H |
| 26 | 26N | $CF_3CF_2$ | H | H | H | S | H | H | H | H | $CF_3$ | H |
| 26 | 27N | $CF_3CF_2$ | H | H | H | S | F | F | H | H | $CF_3$ | H |

TABLE 5-continued

Structure of Substituted Phenyl tertiary-2-Heteroalkylamines (Z is covalent bond; Y is CH and $R_{14}$ is H).

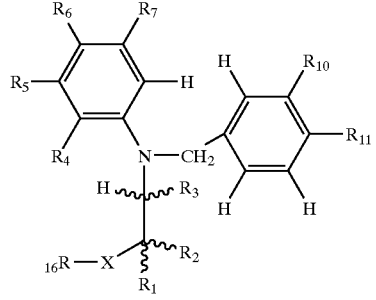

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 26 | 28N | $CF_3CF_2$ | H | H | H | S | H | H | $OCH_3$ | H | $CF_3$ | H |
| 26 | 29N | $CF_3CF_2$ | H | H | H | S | H | F | F | H | $CH_3$ | H |
| 26 | 30N | $CF_3CF_2$ | H | H | H | S | H | $OCH_3$ | H | H | $CH_3$ | H |
| 26 | 31N | $CF_3CF_2$ | H | H | H | S | H | H | $CH_3$ | H | H | H |
| 26 | 32N | $CF_3CF_2$ | H | H | H | S | H | Cl | H | H | H | H |
| 26 | 33N | $CF_3CF_2$ | H | H | H | S | H | F | H | H | F | H |
| 26 | 34N | $CF_3CF_2$ | H | H | H | S | H | H | $OCH_3$ | H | $CH_3$ | H |
| 26 | 35N | $CF_3CF_2$ | H | H | H | S | H | H | H | H | H | H |
| 26 | 36N | $CF_3CF_2$ | H | H | H | S | H | H | $CH_3$ | H | $CH_3$ | H |
| 26 | 37N | $CF_3CF_2$ | H | H | H | S | H | H | Cl | H | H | H |
| 26 | 38N | $CF_3CF_2$ | H | H | H | S | H | F | H | H | 3-$CF_3$-phenoxy | H |
| 26 | 39N | $CF_3CF_2$ | H | H | H | S | H | F | H | H | 4-$CH_3O$-phenoxy | H |
| 26 | 40N | $CF_3CF_2$ | H | H | H | S | H | F | H | H | 4-Cl-phenoxy | H |
| 26 | 41N | $CF_3CF_2$ | H | H | H | S | H | F | H | H | H | H |
| 26 | 42N | $CF_3CF_2$ | H | H | H | S | H | F | H | H | $CH_3$ | H |
| 26 | 43N | $CF_3CF_2$ | H | H | H | S | H | F | H | F | $CH_3$ | H |
| 26 | 44N | $CF_3CF_2$ | H | H | H | S | F | F | H | H | $CH_3$ | H |
| 26 | 45N | $CF_3CF_2$ | H | H | H | S | H | Cl | H | H | $CH_3$ | H |
| 26 | 46N | $CF_3CF_2$ | H | H | H | S | H | $CH_3$ | H | H | $CH_3$ | H |
| 26 | 47N | $CF_3CF_2$ | H | H | H | S | $CH_3$ | H | H | H | H | H |
| 26 | 48N | $CF_3CF_2$ | H | H | H | S | H | H | $CH_3$ | H | $CF_3$ | H |
| 26 | 49N | $CF_3CF_2$ | H | H | H | S | $CH_3$ | H | H | H | $CF_3$ | H |
| 26 | 50N | $CF_3CF_2$ | H | H | H | S | $CH_3$ | H | H | H | $CH_3$ | H |
| 26 | 51N | $CF_3CF_2$ | H | H | H | S | H | H | $CH_3$ | H | F | H |
| 26 | 52N | $CF_3CF_2$ | H | H | H | S | H | $CF_3$ | H | H | F | H |
| 26 | 53N | $CF_3CF_2$ | H | H | H | S | H | $CF_3$ | H | H | $CH_3$ | H |
| 26 | 54N | $CF_3CF_2$ | H | H | H | S | H | $OCH_3$ | H | H | $CF_3$ | H |
| 26 | 55N | $CF_3CF_2$ | H | H | H | S | $OCH_3$ | H | H | H | $CH_3$ | H |
| 26 | 56N | $CF_3CF_2$ | H | H | H | S | H | H | $CH_3$ | H | $CF_3$ | H |
| 26 | 57N | $CF_3CF_2$ | H | H | H | S | H | $C_6H_5O$ | H | H | H | $OCF_3$ |
| 26 | 58N | $CF_3CF_2$ | H | H | H | S | H | H | H | H | H | $OCF_3$ |
| 26 | 59N | $CF_3CF_2$ | H | H | H | S | H | $OCF_3$ | H | H | H | $OCF_3$ |
| 26 | 60N | $CF_3CF_2$ | H | H | H | S | H | $CF_3$ | F | H | H | $CF_3$ |
| 26 | 61N | $CF_3CF_2$ | H | H | H | S | H | H | $OCH_3$ | H | H | $CF_3$ |
| 26 | 62N | $CF_3CF_2$ | H | H | H | S | H | $CH_3$ | H | H | H | $CF_3$ |
| 26 | 63N | $CF_3CF_2$ | H | H | H | S | H | Cl | H | H | H | $CF_3$ |
| 26 | 64N | $CF_3CF_2$ | H | H | H | S | H | $CF_3$ | H | H | H | $OCF_3$ |
| 26 | 65N | $CF_3CF_2$ | H | H | H | S | H | F | H | H | H | $OCF_3$ |
| 26 | 66N | $CF_3CF_2$ | H | H | H | S | H | F | H | F | H | $OCF_3$ |
| 26 | 67N | $CF_3CF_2$ | H | H | H | S | H | Br | H | H | H | $OCF_3$ |
| 26 | 68N | $CF_3CF_2$ | H | H | H | S | H | Cl | H | H | H | $OCF_3$ |
| 26 | 69N | $CF_3CF_2$ | H | H | H | S | H | F | F | H | H | $OCF_3$ |
| 26 | 70N | $CF_3CF_2$ | H | H | H | S | H | F | H | H | H | $C_6H_5$ |
| 26 | 71N | $CF_3CF_2$ | H | H | H | S | H | $CH_3$ | H | H | H | $OCF_3$ |
| 26 | 72N | $CF_3CF_2$ | H | H | H | S | H | F | F | H | H | $CF_3$ |
| 26 | 73N | $CF_3CF_2$ | H | H | H | S | H | Cl | H | H | H | $CH_3$ |
| 26 | 74N | $CF_3CF_2$ | H | H | H | S | H | $OCH_3$ | H | H | H | $CH_3$ |
| 26 | 75N | $CF_3CF_2$ | H | H | H | S | H | F | H | H | H | $CH_3$ |
| 26 | 76N | $CF_3CF_2$ | H | H | H | S | F | F | H | H | H | $OCF_3$ |
| 26 | 77N | $CF_3CF_2$ | H | H | H | S | $OCH_3$ | H | H | H | H | $CF_3$ |
| 26 | 78N | $CF_3CF_2$ | H | H | H | S | H | H | $OCH_3$ | H | H | $CH_3$ |
| 26 | 79N | $CF_3CF_2$ | H | H | H | S | H | H | $CH_3$ | H | H | $CH_3$ |
| 26 | 80N | $CF_3CF_2$ | H | H | H | S | H | $CH_3$ | H | H | H | $CH_3$ |
| 26 | 81N | $CF_3CF_2$ | H | H | H | S | $CH_3$ | H | H | H | H | $CH_3$ |
| 26 | 82N | $CF_3CF_2$ | H | H | H | S | H | F | F | H | H | $CH_3$ |
| 26 | 83N | $CF_3CF_2$ | H | H | H | S | H | F | H | F | H | $CH_3$ |
| 26 | 84N | $CF_3CF_2$ | H | H | H | S | F | F | H | H | H | $CH_3$ |

TABLE 5-continued

Structure of Substituted Phenyl tertiary-2-Heteroalkylamines (Z is covalent bond; Y is CH and $R_{14}$ is H).

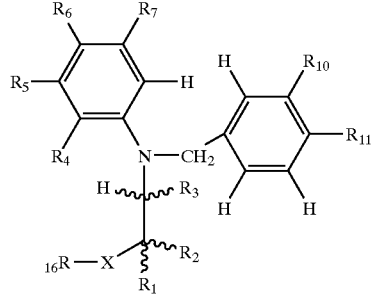

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 26 | 85N | $CF_3CF_2$ | H | H | H | S | F | $CF_3$ | H | H | H | $CH_3$ |
| 26 | 86N | $CF_3CF_2$ | H | H | H | S | H | H | $CH_3$ | H | H | $CF_3$ |
| 26 | 87N | $CF_3CF_2$ | H | H | H | S | $CH_3$ | H | H | H | H | $CF_3$ |
| 26 | 88N | $CF_3CF_2$ | H | H | H | S | H | $CF_3$ | H | H | H | $CH_3$ |
| 26 | 89N | $CF_3CF_2$ | H | H | H | S | $OCH_3$ | H | H | H | H | $CH_3$ |
| 26 | 90N | $CF_3CF_2$ | H | H | H | S | H | H | $CF_3$ | H | H | $CH_3$ |
| 26 | 91N | $CF_3CF_2$ | H | H | H | S | $CF_3$ | H | H | H | H | $CH_3$ |
| 26 | 92N | $CF_3CF_2$ | H | H | H | S | H | $CF_3$ | H | H | H | $CH_3$ |
| 27 | 1N | $CCl_3CH_2$ | H | H | H | O | H | $C_6H_5O$ | H | H | $OCF_2CF_2H$ | H |
| 27 | 2N | $CCl_3CH_2$ | H | H | H | O | H | $OCF_3$ | H | H | $OCF_2CF_2H$ | H |
| 27 | 3N | $CCl_3CH_2$ | H | H | H | O | F | H | H | F | $OCF_2CF_2H$ | H |
| 27 | 4N | $CCl_3CH_2$ | H | H | H | O | H | F | H | H | $OCF_2CF_2H$ | H |
| 27 | 5N | $CCl_3CH_2$ | H | H | H | O | H | $C_6H_5O$ | H | H | $OCF_3$ | H |
| 27 | 6N | $CCl_3CH_2$ | H | H | H | O | H | $OCF_3$ | H | H | $OCF_3$ | H |
| 27 | 7N | $CCl_3CH_2$ | H | H | H | O | H | H | phenyl | H | $OCF_3$ | H |
| 27 | 8N | $CCl_3CH_2$ | H | H | H | O | H | phenyl | H | H | $OCF_3$ | H |
| 27 | 9N | $CCl_3CH_2$ | H | H | H | O | H | H | H | H | $OCF_3$ | H |
| 27 | 10N | $CCl_3CH_2$ | H | H | H | O | H | Br | H | H | $OCF_3$ | H |
| 27 | 11N | $CCl_3CH_2$ | H | H | H | O | H | $CF_3$ | F | H | $CF_3$ | H |
| 27 | 12N | $CCl_3CH_2$ | H | H | H | O | H | $CH_3$ | H | H | $CF_3$ | H |
| 27 | 13N | $CCl_3CH_2$ | H | H | H | O | H | $CF_3$ | H | H | $CF_3$ | H |
| 27 | 14N | $CCl_3CH_2$ | H | H | H | O | H | $CH_3$ | H | H | $OCF_3$ | H |
| 27 | 15N | $CCl_3CH_2$ | H | H | H | O | H | F | F | H | $OCF_3$ | H |
| 27 | 16N | $CCl_3CH_2$ | H | H | H | O | H | Br | H | H | $CF_3$ | H |
| 27 | 17N | $CCl_3CH_2$ | H | H | H | O | H | $CF_3$ | F | H | $OCF_3$ | H |
| 27 | 18N | $CCl_3CH_2$ | H | H | H | O | H | F | H | H | $OCF_3$ | H |
| 27 | 19N | $CCl_3CH_2$ | H | H | H | O | H | Cl | H | H | $OCF_3$ | H |
| 27 | 20N | $CCl_3CH_2$ | H | H | H | O | H | F | H | H | $CF_3$ | H |
| 27 | 21N | $CCl_3CH_2$ | H | H | H | O | H | F | F | H | $CF_3$ | H |
| 27 | 22N | $CCl_3CH_2$ | H | H | H | O | H | Cl | H | H | $CF_3$ | H |
| 27 | 23N | $CCl_3CH_2$ | H | H | H | O | H | F | H | H | phenoxy | H |
| 27 | 24N | $CCl_3CH_2$ | H | H | H | O | H | $CF_3$ | Cl | H | $CH_3$ | H |
| 27 | 25N | $CCl_3CH_2$ | H | H | H | O | H | $CF_3$ | F | H | $CH_3$ | H |
| 27 | 26N | $CCl_3CH_2$ | H | H | H | O | H | H | H | H | $CF_3$ | H |
| 27 | 27N | $CCl_3CH_2$ | H | H | H | O | F | F | H | H | $CF_3$ | H |
| 27 | 28N | $CCl_3CH_2$ | H | H | H | O | H | H | $OCH_3$ | H | $CF_3$ | H |
| 27 | 29N | $CCl_3CH_2$ | H | H | H | O | H | F | F | H | $CH_3$ | H |
| 27 | 30N | $CCl_3CH_2$ | H | H | H | O | H | $OCH_3$ | H | H | $CH_3$ | H |
| 27 | 31N | $CCl_3CH_2$ | H | H | H | O | H | H | $CH_3$ | H | H | H |
| 27 | 32N | $CCl_3CH_2$ | H | H | H | O | H | Cl | H | H | H | H |
| 27 | 33N | $CCl_3CH_2$ | H | H | H | O | H | F | H | H | F | H |
| 27 | 34N | $CCl_3CH_2$ | H | H | H | O | H | H | $OCH_3$ | H | $CH_3$ | H |
| 27 | 35N | $CCl_3CH_2$ | H | H | H | O | H | H | H | H | H | H |
| 27 | 36N | $CCl_3CH_2$ | H | H | H | O | H | H | $CH_3$ | H | $CH_3$ | H |
| 27 | 37N | $CCl_3CH_2$ | H | H | H | O | H | H | Cl | H | H | H |
| 27 | 38N | $CCl_3CH_2$ | H | H | H | O | H | F | H | H | 3-$CF_3$-phenoxy | H |
| 27 | 39N | $CCl_3CH_2$ | H | H | H | O | H | F | H | H | 4-$CH_3O$-phenoxy | H |
| 27 | 40N | $CCl_3CH_2$ | H | H | H | O | H | F | H | H | 4-Cl-phenoxy | H |
| 27 | 41N | $CCl_3CH_2$ | H | H | H | O | H | F | H | H | H | H |
| 27 | 42N | $CCl_3CH_2$ | H | H | H | O | H | F | H | H | $CH_3$ | H |
| 27 | 43N | $CCl_3CH_2$ | H | H | H | O | H | F | H | F | $CH_3$ | H |
| 27 | 44N | $CCl_3CH_2$ | H | H | H | O | F | F | H | H | $CH_3$ | H |
| 27 | 45N | $CCl_3CH_2$ | H | H | H | O | H | Cl | H | H | $CH_3$ | H |
| 27 | 46N | $CCl_3CH_2$ | H | H | H | O | H | $CH_3$ | H | H | $CH_3$ | H |
| 27 | 47N | $CCl_3CH_2$ | H | H | H | O | $CH_3$ | H | H | H | H | H |
| 27 | 48N | $CCl_3CH_2$ | H | H | H | O | H | H | $CH_3$ | H | $CF_3$ | H |
| 27 | 49N | $CCl_3CH_2$ | H | H | H | O | $CH_3$ | H | H | H | $CF_3$ | H |

TABLE 5-continued

Structure of Substituted Phenyl tertiary-2-Heteroalkylamines (Z is covalent bond; Y is CH and $R_{14}$ is H).

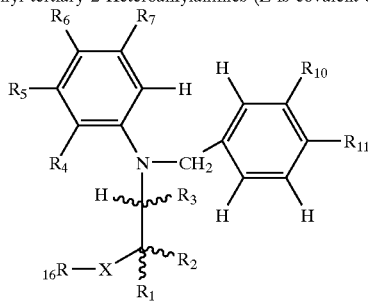

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 27 | 50N | $CCl_3CH_2$ | H | H | H | O | $CH_3$ | H | H | H | $CH_3$ | H |
| 27 | 51N | $CCl_3CH_2$ | H | H | H | O | H | H | $CH_3$ | H | F | H |
| 27 | 52N | $CCl_3CH_2$ | H | H | H | O | H | $CF_3$ | H | H | F | H |
| 27 | 53N | $CCl_3CH_2$ | H | H | H | O | H | $CF_3$ | H | H | $CH_3$ | H |
| 27 | 54N | $CCl_3CH_2$ | H | H | H | O | H | $OCH_3$ | H | H | $CF_3$ | H |
| 27 | 55N | $CCl_3CH_2$ | H | H | H | O | $OCH_3$ | H | H | H | $CH_3$ | H |
| 27 | 56N | $CCl_3CH_2$ | H | H | H | O | H | H | $CH_3$ | H | $CF_3$ | H |
| 27 | 57N | $CCl_3CH_2$ | H | H | H | O | H | $C_6H_5O$ | H | H | H | $OCF_3$ |
| 27 | 58N | $CCl_3CH_2$ | H | H | H | O | H | H | H | H | H | $OCF_3$ |
| 27 | 59N | $CCl_3CH_2$ | H | H | H | O | H | $OCF_3$ | H | H | H | $OCF_3$ |
| 27 | 60N | $CCl_3CH_2$ | H | H | H | O | H | $CF_3$ | F | H | H | $CF_3$ |
| 27 | 61N | $CCl_3CH_2$ | H | H | H | O | H | H | $OCH_3$ | H | H | $CF_3$ |
| 27 | 62N | $CCl_3CH_2$ | H | H | H | O | H | $CH_3$ | H | H | H | $CF_3$ |
| 27 | 63N | $CCl_3CH_2$ | H | H | H | O | H | Cl | H | H | H | $CF_3$ |
| 27 | 64N | $CCl_3CH_2$ | H | H | H | O | H | $CF_3$ | H | H | H | $OCF_3$ |
| 27 | 65N | $CCl_3CH_2$ | H | H | H | O | H | F | H | H | H | $OCF_3$ |
| 27 | 66N | $CCl_3CH_2$ | H | H | H | O | H | F | H | F | H | $OCF_3$ |
| 27 | 67N | $CCl_3CH_2$ | H | H | H | O | H | Br | H | H | H | $OCF_3$ |
| 27 | 68N | $CCl_3CH_2$ | H | H | H | O | H | Cl | H | H | H | $OCF_3$ |
| 27 | 69N | $CCl_3CH_2$ | H | H | H | O | H | F | F | H | H | $OCF_3$ |
| 27 | 70N | $CCl_3CH_2$ | H | H | H | O | H | F | H | H | H | $C_6H_5$ |
| 27 | 71N | $CCl_3CH_2$ | H | H | H | O | H | $CH_3$ | H | H | H | $OCF_3$ |
| 27 | 72N | $CCl_3CH_2$ | H | H | H | O | H | F | F | H | H | $CF_3$ |
| 27 | 73N | $CCl_3CH_2$ | H | H | H | O | H | Cl | H | H | H | $CH_3$ |
| 27 | 74N | $CCl_3CH_2$ | H | H | H | O | H | $OCH_3$ | H | H | H | $CH_3$ |
| 27 | 75N | $CCl_3CH_2$ | H | H | H | O | H | F | H | H | H | $CH_3$ |
| 27 | 76N | $CCl_3CH_2$ | H | H | H | O | F | F | H | H | H | $OCF_3$ |
| 27 | 77N | $CCl_3CH_2$ | H | H | H | O | $OCH_3$ | H | H | H | H | $CF_3$ |
| 27 | 78N | $CCl_3CH_2$ | H | H | H | O | H | H | $OCH_3$ | H | H | $CH_3$ |
| 27 | 79N | $CCl_3CH_2$ | H | H | H | O | H | H | $CH_3$ | H | H | $CH_3$ |
| 27 | 80N | $CCl_3CH_2$ | H | H | H | O | H | $CH_3$ | H | H | H | $CH_3$ |
| 27 | 81N | $CCl_3CH_2$ | H | H | H | O | $CH_3$ | H | H | H | H | $CH_3$ |
| 27 | 82N | $CCl_3CH_2$ | H | H | H | O | H | F | F | H | H | $CH_3$ |
| 27 | 83N | $CCl_3CH_2$ | H | H | H | O | H | F | H | F | H | $CH_3$ |
| 27 | 84N | $CCl_3CH_2$ | H | H | H | O | F | F | H | H | H | $CH_3$ |
| 27 | 85N | $CCl_3CH_2$ | H | H | H | O | F | $CF_3$ | H | H | H | $CH_3$ |
| 27 | 86N | $CCl_3CH_2$ | H | H | H | O | H | H | $CH_3$ | H | H | $CF_3$ |
| 27 | 87N | $CCl_3CH_2$ | H | H | H | O | $CH_3$ | H | H | H | H | $CF_3$ |
| 27 | 88N | $CCl_3CH_2$ | H | H | H | O | H | $CF_3$ | H | H | H | $CH_3$ |
| 27 | 89N | $CCl_3CH_2$ | H | H | H | O | $OCH_3$ | H | H | H | H | $CH_3$ |
| 27 | 90N | $CCl_3CH_2$ | H | H | H | O | H | H | $CF_3$ | H | H | $CH_3$ |
| 27 | 91N | $CCl_3CH_2$ | H | H | H | O | $CF_3$ | H | H | H | H | $CH_3$ |
| 27 | 92N | $CCl_3CH_2$ | H | H | H | O | H | $CF_3$ | F | H | H | $CH_3$ |
| 28 | 1N | $CBr_3CH_2$ | H | H | H | O | H | $C_6H_5O$ | H | H | $OCF_2CF_2H$ | H |
| 28 | 2N | $CBr_3CH_2$ | H | H | H | O | H | $OCF_3$ | H | H | $OCF_2CF_2H$ | H |
| 28 | 3N | $CBr_3CH_2$ | H | H | H | O | F | H | H | F | $OCF_2CF_2H$ | H |
| 28 | 4N | $CBr_3CH_2$ | H | H | H | O | H | F | H | H | $OCF_2CF_2H$ | H |
| 28 | 5N | $CBr_3CH_2$ | H | H | H | O | H | $C_6H_5O$ | H | H | $OCF_3$ | H |
| 28 | 6N | $CBr_3CH_2$ | H | H | H | O | H | $OCF_3$ | H | H | $OCF_3$ | H |
| 28 | 7N | $CBr_3CH_2$ | H | H | H | O | H | H | phenyl | H | $OCF_3$ | H |
| 28 | 8N | $CBr_3CH_2$ | H | H | H | O | H | phenyl | H | H | $OCF_3$ | H |
| 28 | 9N | $CBr_3CH_2$ | H | H | H | O | H | H | H | H | $OCF_3$ | H |
| 28 | 10N | $CBr_3CH_2$ | H | H | H | O | H | Br | H | H | $OCF_3$ | H |
| 28 | 11N | $CBr_3CH_2$ | H | H | H | O | H | $CF_3$ | F | H | $CF_3$ | H |
| 28 | 12N | $CBr_3CH_2$ | H | H | H | O | H | $CH_3$ | H | H | $CF_3$ | H |
| 28 | 13N | $CBr_3CH_2$ | H | H | H | O | H | $CF_3$ | H | H | $CF_3$ | H |
| 28 | 14N | $CBr_3CH_2$ | H | H | H | O | H | $CH_3$ | H | H | $OCF_3$ | H |

TABLE 5-continued

Structure of Substituted Phenyl tertiary-2-Heteroalkylamines (Z is covalent bond; Y is CH and $R_{14}$ is H).

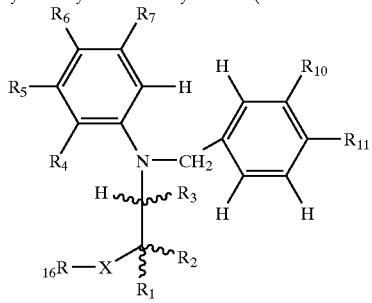

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 28 | 15N | $CBr_3CH_2$ | H | H | H | O | H | F | F | H | $OCF_3$ | H |
| 28 | 16N | $CBr_3CH_2$ | H | H | H | O | H | Br | H | H | $CF_3$ | H |
| 28 | 17N | $CBr_3CH_2$ | H | H | H | O | H | $CF_3$ | F | H | $OCF_3$ | H |
| 28 | 18N | $CBr_3CH_2$ | H | H | H | O | H | F | H | H | $OCF_3$ | H |
| 28 | 19N | $CBr_3CH_2$ | H | H | H | O | H | Cl | H | H | $OCF_3$ | H |
| 28 | 20N | $CBr_3CH_2$ | H | H | H | O | H | F | H | H | $CF_3$ | H |
| 28 | 21N | $CBr_3CH_2$ | H | H | H | O | H | F | F | H | $CF_3$ | H |
| 28 | 22N | $CBr_3CH_2$ | H | H | H | O | H | Cl | H | H | $CF_3$ | H |
| 28 | 23N | $CBr_3CH_2$ | H | H | H | O | H | F | H | H | phenoxy | H |
| 28 | 24N | $CBr_3CH_2$ | H | H | H | O | H | $CF_3$ | Cl | H | $CH_3$ | H |
| 28 | 25N | $CBr_3CH_2$ | H | H | H | O | H | $CF_3$ | F | H | $CH_3$ | H |
| 28 | 26N | $CBr_3CH_2$ | H | H | H | O | H | H | H | H | $CF_3$ | H |
| 28 | 27N | $CBr_3CH_2$ | H | H | H | O | F | F | H | H | $CF_3$ | H |
| 28 | 28N | $CBr_3CH_2$ | H | H | H | O | H | H | $OCH_3$ | H | $CF_3$ | H |
| 28 | 29N | $CBr_3CH_2$ | H | H | H | O | H | F | F | H | $CH_3$ | H |
| 28 | 30N | $CBr_3CH_2$ | H | H | H | O | H | $OCH_3$ | H | H | $CH_3$ | H |
| 28 | 31N | $CBr_3CH_2$ | H | H | H | O | H | H | $CH_3$ | H | H | H |
| 28 | 32N | $CBr_3CH_2$ | H | H | H | O | H | Cl | H | H | H | H |
| 28 | 33N | $CBr_3CH_2$ | H | H | H | O | H | F | H | H | F | H |
| 28 | 34N | $CBr_3CH_2$ | H | H | H | O | H | H | $OCH_3$ | H | $CH_3$ | H |
| 28 | 35N | $CBr_3CH_2$ | H | H | H | O | H | H | H | H | H | H |
| 28 | 36N | $CBr_3CH_2$ | H | H | H | O | H | H | $CH_3$ | H | $CH_3$ | H |
| 28 | 37N | $CBr_3CH_2$ | H | H | H | O | H | H | Cl | H | H | H |
| 28 | 38N | $CBr_3CH_2$ | H | H | H | O | H | F | H | H | 3-$CF_3$-phenoxy | H |
| 28 | 39N | $CBr_3CH_2$ | H | H | H | O | H | F | H | H | 4-$CH_3O$-phenoxy | H |
| 28 | 40N | $CBr_3CH_2$ | H | H | H | O | H | F | H | H | 4-Cl-phenoxy | H |
| 28 | 41N | $CBr_3CH_2$ | H | H | H | O | H | F | H | H | H | H |
| 28 | 42N | $CBr_3CH_2$ | H | H | H | O | H | F | H | H | $CH_3$ | H |
| 28 | 43N | $CBr_3CH_2$ | H | H | H | O | H | F | H | F | $CH_3$ | H |
| 28 | 44N | $CBr_3CH_2$ | H | H | H | O | F | F | H | H | $CH_3$ | H |
| 28 | 45N | $CBr_3CH_2$ | H | H | H | O | H | Cl | H | H | $CH_3$ | H |
| 28 | 46N | $CBr_3CH_2$ | H | H | H | O | H | $CH_3$ | H | H | $CH_3$ | H |
| 28 | 47N | $CBr_3CH_2$ | H | H | H | O | $CH_3$ | H | H | H | H | H |
| 28 | 48N | $CBr_3CH_2$ | H | H | H | O | H | H | $CH_3$ | H | $CF_3$ | H |
| 28 | 49N | $CBr_3CH_2$ | H | H | H | O | $CH_3$ | H | H | H | $CF_3$ | H |
| 28 | 50N | $CBr_3CH_2$ | H | H | H | O | $CH_3$ | H | H | H | $CH_3$ | H |
| 28 | 51N | $CBr_3CH_2$ | H | H | H | O | H | H | $CH_3$ | H | F | H |
| 28 | 52N | $CBr_3CH_2$ | H | H | H | O | H | $CF_3$ | H | H | F | H |
| 28 | 53N | $CBr_3CH_2$ | H | H | H | O | H | $CF_3$ | H | H | $CH_3$ | H |
| 28 | 54N | $CBr_3CH_2$ | H | H | H | O | H | $OCH_3$ | H | H | $CF_3$ | H |
| 28 | 55N | $CBr_3CH_2$ | H | H | H | O | $OCH_3$ | H | H | H | $CH_3$ | H |
| 28 | 56N | $CBr_3CH_2$ | H | H | H | O | H | H | $CH_3$ | H | $CF_3$ | H |
| 28 | 57N | $CBr_3CH_2$ | H | H | H | O | H | $C_6H_5O$ | H | H | H | $OCF_3$ |
| 28 | 58N | $CBr_3CH_2$ | H | H | H | O | H | H | H | H | H | $OCF_3$ |
| 28 | 59N | $CBr_3CH_2$ | H | H | H | O | H | $OCF_3$ | H | H | H | $OCF_3$ |
| 28 | 60N | $CBr_3CH_2$ | H | H | H | O | H | $CF_3$ | F | H | H | $CF_3$ |
| 28 | 61N | $CBr_3CH_2$ | H | H | H | O | H | H | $OCH_3$ | H | H | $CF_3$ |
| 28 | 62N | $CBr_3CH_2$ | H | H | H | O | H | $CH_3$ | H | H | H | $CF_3$ |
| 28 | 63N | $CBr_3CH_2$ | H | H | H | O | H | Cl | H | H | H | $CF_3$ |
| 28 | 64N | $CBr_3CH_2$ | H | H | H | O | H | $CF_3$ | H | H | H | $OCF_3$ |
| 28 | 65N | $CBr_3CH_2$ | H | H | H | O | H | F | H | H | H | $OCF_3$ |
| 28 | 66N | $CBr_3CH_2$ | H | H | H | O | H | F | H | F | H | $OCF_3$ |
| 28 | 67N | $CBr_3CH_2$ | H | H | H | O | H | Br | H | H | H | $OCF_3$ |
| 28 | 68N | $CBr_3CH_2$ | H | H | H | O | H | Cl | H | H | H | $OCF_3$ |
| 28 | 69N | $CBr_3CH_2$ | H | H | H | O | H | F | F | H | H | $OCF_3$ |
| 28 | 70N | $CBr_3CH_2$ | H | H | H | O | H | F | H | H | H | $C_6H_5$ |
| 28 | 71N | $CBr_3CH_2$ | H | H | H | O | H | $CH_3$ | H | H | H | $OCF_3$ |

TABLE 5-continued

Structure of Substituted Phenyl tertiary-2-Heteroalkylamines (Z is covalent bond; Y is CH and $R_{14}$ is H).

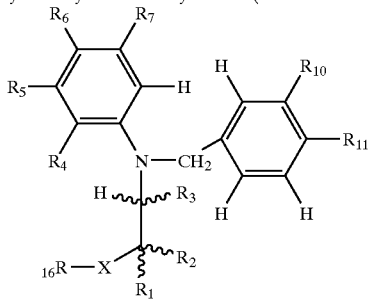

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 28 | 72N | $CBr_3CH_2$ | H | H | H | O | H | F | F | H | H | $CF_3$ |
| 28 | 73N | $CBr_3CH_2$ | H | H | H | O | H | Cl | H | H | H | $CH_3$ |
| 28 | 74N | $CBr_3CH_2$ | H | H | H | O | H | $OCH_3$ | H | H | H | $CH_3$ |
| 28 | 75N | $CBr_3CH_2$ | H | H | H | O | H | F | H | H | H | $CH_3$ |
| 28 | 76N | $CBr_3CH_2$ | H | H | H | O | F | F | H | H | H | $OCF_3$ |
| 28 | 77N | $CBr_3CH_2$ | H | H | H | O | $OCH_3$ | H | H | H | H | $CF_3$ |
| 28 | 78N | $CBr_3CH_2$ | H | H | H | O | H | H | $OCH_3$ | H | H | $CH_3$ |
| 28 | 79N | $CBr_3CH_2$ | H | H | H | O | H | H | $CH_3$ | H | H | $CH_3$ |
| 28 | 80N | $CBr_3CH_2$ | H | H | H | O | H | $CH_3$ | H | H | H | $CH_3$ |
| 28 | 81N | $CBr_3CH_2$ | H | H | H | O | $CH_3$ | H | H | H | H | $CH_3$ |
| 28 | 82N | $CBr_3CH_2$ | H | H | H | O | H | F | F | H | H | $CH_3$ |
| 28 | 83N | $CBr_3CH_2$ | H | H | H | O | H | F | H | F | H | $CH_3$ |
| 28 | 84N | $CBr_3CH_2$ | H | H | H | O | F | F | H | H | H | $CH_3$ |
| 28 | 85N | $CBr_3CH_2$ | H | H | H | O | F | $CF_3$ | H | H | H | $CH_3$ |
| 28 | 86N | $CBr_3CH_2$ | H | H | H | O | H | H | $CH_3$ | H | H | $CF_3$ |
| 28 | 87N | $CBr_3CH_2$ | H | H | H | O | $CH_3$ | H | H | H | H | $CF_3$ |
| 28 | 88N | $CBr_3CH_2$ | H | H | H | O | H | $CF_3$ | H | H | H | $CH_3$ |
| 28 | 89N | $CBr_3CH_2$ | H | H | H | O | $OCH_3$ | H | H | H | H | $CH_3$ |
| 28 | 90N | $CBr_3CH_2$ | H | H | H | O | H | H | $CF_3$ | H | H | $CH_3$ |
| 28 | 91N | $CBr_3CH_2$ | H | H | H | O | $CF_3$ | H | H | H | H | $CH_3$ |
| 28 | 92N | $CBr_3CH_2$ | H | H | H | O | H | $CF_3$ | F | H | H | $CH_3$ |
| 41 | 1N | $CH_3(CH_2)_4CH_2$ | H | H | H | O | H | $C_6H_5O$ | H | H | $OCF_2CF_2H$ | H |
| 41 | 2N | $CH_3(CH_2)_4CH_2$ | H | H | H | O | H | $OCF_3$ | H | H | $OCF_2CF_2H$ | H |
| 41 | 3N | $CH_3(CH_2)_4CH_2$ | H | H | H | O | F | H | H | F | $OCF_2CF_2H$ | H |
| 41 | 4N | $CH_3(CH_2)_4CH_2$ | H | H | H | O | H | F | H | H | $OCF_2CF_2H$ | H |
| 41 | 5N | $CH_3(CH_2)_4CH_2$ | H | H | H | O | H | $C_6H_5O$ | H | H | $OCF_3$ | H |
| 41 | 6N | $CH_3(CH_2)_4CH_2$ | H | H | H | O | H | $OCF_3$ | H | H | $OCF_3$ | H |
| 41 | 7N | $CH_3(CH_2)_4CH_2$ | H | H | H | O | H | H | phenyl | H | $OCF_3$ | H |
| 41 | 8N | $CH_3(CH_2)_4CH_2$ | H | H | H | O | H | phenyl | H | H | $OCF_3$ | H |
| 41 | 9N | $CH_3(CH_2)_4CH_2$ | H | H | H | O | H | H | H | H | $OCF_3$ | H |
| 41 | 10N | $CH_3(CH_2)_4CH_2$ | H | H | H | O | H | Br | H | H | $OCF_3$ | H |
| 41 | 11N | $CH_3(CH_2)_4CH_2$ | H | H | H | O | H | $CF_3$ | F | H | $CF_3$ | H |
| 41 | 12N | $CH_3(CH_2)_4CH_2$ | H | H | H | O | H | $CH_3$ | H | H | $CF_3$ | H |
| 41 | 13N | $CH_3(CH_2)_4CH_2$ | H | H | H | O | H | $CF_3$ | H | H | $CF_3$ | H |
| 41 | 14N | $CH_3(CH_2)_4CH_2$ | H | H | H | O | H | $CH_3$ | H | H | $OCF_3$ | H |
| 41 | 15N | $CH_3(CH_2)_4CH_2$ | H | H | H | O | H | F | F | H | $OCF_3$ | H |
| 41 | 16N | $CH_3(CH_2)_4CH_2$ | H | H | H | O | H | Br | H | H | $CF_3$ | H |
| 41 | 17N | $CH_3(CH_2)_4CH_2$ | H | H | H | O | H | $CF_3$ | F | H | $OCF_3$ | H |
| 41 | 18N | $CH_3(CH_2)_4CH_2$ | H | H | H | O | H | F | H | H | $OCF_3$ | H |
| 41 | 19N | $CH_3(CH_2)_4CH_2$ | H | H | H | O | H | Cl | H | H | $OCF_3$ | H |
| 41 | 20N | $CH_3(CH_2)_4CH_2$ | H | H | H | O | H | F | H | H | $CF_3$ | H |
| 41 | 21N | $CH_3(CH_2)_4CH_2$ | H | H | H | O | H | F | F | H | $CF_3$ | H |
| 41 | 22N | $CH_3(CH_2)_4CH_2$ | H | H | H | O | H | Cl | H | H | $CF_3$ | H |
| 41 | 23N | $CH_3(CH_2)_4CH_2$ | H | H | H | O | H | F | H | H | phenoxy | H |
| 41 | 24N | $CH_3(CH_2)_4CH_2$ | H | H | H | O | H | $CF_3$ | Cl | H | $CH_3$ | H |
| 41 | 25N | $CH_3(CH_2)_4CH_2$ | H | H | H | O | H | $CF_3$ | F | H | $CH_3$ | H |
| 41 | 26N | $CH_3(CH_2)_4CH_2$ | H | H | H | O | H | H | H | H | $CF_3$ | H |
| 41 | 27N | $CH_3(CH_2)_4CH_2$ | H | H | H | O | F | F | H | H | $CF_3$ | H |
| 41 | 28N | $CH_3(CH_2)_4CH_2$ | H | H | H | O | H | H | $OCH_3$ | H | $CF_3$ | H |
| 41 | 29N | $CH_3(CH_2)_4CH_2$ | H | H | H | O | H | F | F | H | $CH_3$ | H |
| 41 | 30N | $CH_3(CH_2)_4CH_2$ | H | H | H | O | H | $OCH_3$ | H | H | $CH_3$ | H |
| 41 | 31N | $CH_3(CH_2)_4CH_2$ | H | H | H | O | H | H | $CH_3$ | H | H | H |
| 41 | 32N | $CH_3(CH_2)_4CH_2$ | H | H | H | O | H | Cl | H | H | H | H |
| 41 | 33N | $CH_3(CH_2)_4CH_2$ | H | H | H | O | H | F | H | H | F | H |
| 41 | 34N | $CH_3(CH_2)_4CH_2$ | H | H | H | O | H | H | $OCH_3$ | H | $CH_3$ | H |
| 41 | 35N | $CH_3(CH_2)_4CH_2$ | H | H | H | O | H | H | H | H | H | H |
| 41 | 36N | $CH_3(CH_2)_4CH_2$ | H | H | H | O | H | H | $CH_3$ | H | $CH_3$ | H |

TABLE 5-continued

Structure of Substituted Phenyl tertiary-2-Heteroalkylamines (Z is covalent bond; Y is CH and $R_{14}$ is H).

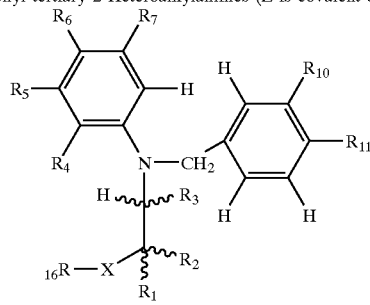

Inhibitor Number
Column 1 + Column 2

| Reagent | Reagent | $R_1$ | $R_2$ | $R_3$ | $R_{16}$ | X | $R_4$ | $R_5$ | $R_6$ | $R_7$ | $R_{10}$ | $R_{11}$ |
|---|---|---|---|---|---|---|---|---|---|---|---|---|
| 41 | 37N | $CH_3(CH_2)_4CH_2$ | H | H | H | O | H | H | Cl | H | H | H |
| 41 | 38N | $CH_3(CH_2)_4CH_2$ | H | H | H | O | H | F | H | H | 3-$CF_3$-phenoxy | H |
| 41 | 39N | $CH_3(CH_2)_4CH_2$ | H | H | H | O | H | F | H | H | 4-$CH_3O$-phenoxy | H |
| 41 | 40N | $CH_3(CH_2)_4CH_2$ | H | H | H | O | H | F | H | H | 4-Cl-phenoxy | H |
| 41 | 41N | $CH_3(CH_2)_4CH_2$ | H | H | H | O | H | F | H | H | H | H |
| 41 | 42N | $CH_3(CH_2)_4CH_2$ | H | H | H | O | H | F | H | H | $CH_3$ | H |
| 41 | 43N | $CH_3(CH_2)_4CH_2$ | H | H | H | O | H | F | H | F | $CH_3$ | H |
| 41 | 44N | $CH_3(CH_2)_4CH_2$ | H | H | H | O | F | F | H | H | $CH_3$ | H |
| 41 | 45N | $CH_3(CH_2)_4CH_2$ | H | H | H | O | H | Cl | H | H | $CH_3$ | H |
| 41 | 46N | $CH_3(CH_2)_4CH_2$ | H | H | H | O | H | $CH_3$ | H | H | $CH_3$ | H |
| 41 | 47N | $CH_3(CH_2)_4CH_2$ | H | H | H | O | $CH_3$ | H | H | H | H | H |
| 41 | 48N | $CH_3(CH_2)_4CH_2$ | H | H | H | O | H | H | $CH_3$ | H | $CF_3$ | H |
| 41 | 49N | $CH_3(CH_2)_4CH_2$ | H | H | H | O | $CH_3$ | H | H | H | $CF_3$ | H |
| 41 | 50N | $CH_3(CH_2)_4CH_2$ | H | H | H | O | $CH_3$ | H | H | H | $CH_3$ | H |
| 41 | 51N | $CH_3(CH_2)_4CH_2$ | H | H | H | O | H | H | $CH_3$ | H | F | H |
| 41 | 52N | $CH_3(CH_2)_4CH_2$ | H | H | H | O | H | $CF_3$ | H | H | F | H |
| 41 | 53N | $CH_3(CH_2)_4CH_2$ | H | H | H | O | H | $CF_3$ | H | H | $CH_3$ | H |
| 41 | 54N | $CH_3(CH_2)_4CH_2$ | H | H | H | O | H | $OCH_3$ | H | H | $CF_3$ | H |
| 41 | 55N | $CH_3(CH_2)_4CH_2$ | H | H | H | O | $OCH_3$ | H | H | H | $CH_3$ | H |
| 41 | 56N | $CH_3(CH_2)_4CH_2$ | H | H | H | O | H | H | $CH_3$ | H | $CF_3$ | H |
| 41 | 57N | $CH_3(CH_2)_4CH_2$ | H | H | H | O | H | $C_6H_5O$ | H | H | H | $OCF_3$ |
| 41 | 58N | $CH_3(CH_2)_4CH_2$ | H | H | H | O | H | H | H | H | H | $OCF_3$ |
| 41 | 59N | $CH_3(CH_2)_4CH_2$ | H | H | H | O | H | $OCF_3$ | H | H | H | $OCF_3$ |
| 41 | 60N | $CH_3(CH_2)_4CH_2$ | H | H | H | O | H | $CF_3$ | F | H | H | $CF_3$ |
| 41 | 61N | $CH_3(CH_2)_4CH_2$ | H | H | H | O | H | H | $OCH_3$ | H | H | $CF_3$ |
| 41 | 62N | $CH_3(CH_2)_4CH_2$ | H | H | H | O | H | $CH_3$ | H | H | H | $CF_3$ |
| 41 | 63N | $CH_3(CH_2)_4CH_2$ | H | H | H | O | H | Cl | H | H | H | $CF_3$ |
| 41 | 64N | $CH_3(CH_2)_4CH_2$ | H | H | H | O | H | $CF_3$ | H | H | H | $OCF_3$ |
| 41 | 65N | $CH_3(CH_2)_4CH_2$ | H | H | H | O | H | F | H | H | H | $OCF_3$ |
| 41 | 66N | $CH_3(CH_2)_4CH_2$ | H | H | H | O | H | F | H | F | H | $OCF_3$ |
| 41 | 67N | $CH_3(CH_2)_4CH_2$ | H | H | H | O | H | Br | H | H | H | $OCF_3$ |
| 41 | 68N | $CH_3(CH_2)_4CH_2$ | H | H | H | O | H | Cl | H | H | H | $OCF_3$ |
| 41 | 69N | $CH_3(CH_2)_4CH_2$ | H | H | H | O | H | F | F | H | H | $OCF_3$ |
| 41 | 70N | $CH_3(CH_2)_4CH_2$ | H | H | H | O | H | F | H | H | H | $C_6H_5$ |
| 41 | 71N | $CH_3(CH_2)_4CH_2$ | H | H | H | O | H | $CH_3$ | H | H | H | $OCF_3$ |
| 41 | 72N | $CH_3(CH_2)_4CH_2$ | H | H | H | O | H | F | F | H | H | $CF_3$ |
| 41 | 73N | $CH_3(CH_2)_4CH_2$ | H | H | H | O | H | Cl | H | H | H | $CH_3$ |
| 41 | 74N | $CH_3(CH_2)_4CH_2$ | H | H | H | O | H | $OCH_3$ | H | H | H | $CH_3$ |
| 41 | 75N | $CH_3(CH_2)_4CH_2$ | H | H | H | O | H | F | H | H | H | $CH_3$ |
| 41 | 76N | $CH_3(CH_2)_4CH_2$ | H | H | H | O | F | F | H | H | H | $OCF_3$ |
| 41 | 77N | $CH_3(CH_2)_4CH_2$ | H | H | H | O | $OCH_3$ | H | H | H | H | $CF_3$ |
| 41 | 78N | $CH_3(CH_2)_4CH_2$ | H | H | H | O | H | H | $OCH_3$ | H | H | $CH_3$ |
| 41 | 79N | $CH_3(CH_2)_4CH_2$ | H | H | H | O | H | H | $CH_3$ | H | H | $CH_3$ |
| 41 | 80N | $CH_3(CH_2)_4CH_2$ | H | H | H | O | H | $CH_3$ | H | H | H | $CH_3$ |
| 41 | 81N | $CH_3(CH_2)_4CH_2$ | H | H | H | O | $CH_3$ | H | H | H | H | $CH_3$ |
| 41 | 82N | $CH_3(CH_2)_4CH_2$ | H | H | H | O | H | F | F | H | H | $CH_3$ |
| 41 | 83N | $CH_3(CH_2)_4CH_2$ | H | H | H | O | H | F | H | F | H | $CH_3$ |
| 41 | 84N | $CH_3(CH_2)_4CH_2$ | H | H | H | O | F | F | H | H | H | $CH_3$ |
| 41 | 85N | $CH_3(CH_2)_4CH_2$ | H | H | H | O | F | $CF_3$ | H | H | H | $CH_3$ |
| 41 | 86N | $CH_3(CH_2)_4CH_2$ | H | H | H | O | H | H | $CH_3$ | H | H | $CF_3$ |
| 41 | 87N | $CH_3(CH_2)_4CH_2$ | H | H | H | O | $CH_3$ | H | H | H | H | $CF_3$ |
| 41 | 88N | $CH_3(CH_2)_4CH_2$ | H | H | H | O | H | $CF_3$ | H | H | H | $CH_3$ |
| 41 | 89N | $CH_3(CH_2)_4CH_2$ | H | H | H | O | $OCH_3$ | H | H | H | H | $CH_3$ |
| 41 | 90N | $CH_3(CH_2)_4CH_2$ | H | H | H | O | H | H | $CF_3$ | H | H | $CH_3$ |
| 41 | 91N | $CH_3(CH_2)_4CH_2$ | H | H | H | O | $CF_3$ | H | H | H | H | $CH_3$ |
| 41 | 92N | $CH_3(CH_2)_4CH_2$ | H | H | H | O | H | $CF_3$ | F | H | H | $CH_3$ |

TABLE 6

Structure of "Secondary Phenyl Amine" Reagents (Z is covalent bond; there is no $R_{15}$ substituent, $R_4$ and $R_{13}$ equal H).

(XIII-A)

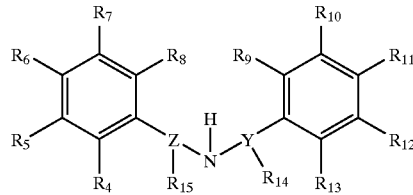

Secondary Phenyl Amine

| Reagent Number | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 93N | Br | H | H | | CH | H | | H | H | $OCF_3$ | —O— | $R_8 + R_9$ |
| 94N | $OCF_3$ | H | H | | CH | H | | H | H | $OCF_3$ | — | $R_8 + R_9$ |
| 95N | Br | H | H | | C | | H | $OCF_3$ | H | H | =CH— | $R_8 + R_{14}$ |
| 96N | OH | OH | H | H | CH | H | H | $C_6H_5O$ | H | H | none | none |
| 97N | $C_6H_5O$ | H | H | H | CH | H | H | OH | OH | H | none | none |
| 98N | 3-pyridyl | H | H | H | CH | H | H | $CF_3$ | H | H | none | none |
| 99N | $SO_2N(CH_3)_2$ | H | H | H | CH | H | H | $OCF_3$ | H | H | none | none |
| 100N | $SO_2CH_3$ | H | H | H | CH | H | H | $OCF_3$ | H | H | none | none |
| 101N | $C_6H_5O$ | H | H | H | CH | H | H | $C_6H_5O$ | H | H | none | none |
| 102N | $CF_3O$ | H | H | H | CH | H | H | $C_6H_5O$ | H | H | none | none |
| 103N | $C_6H_5$ | H | H | H | CH | H | H | $C_6H_5O$ | H | H | none | none |
| 104N | H | $C_6H_5$ | H | H | CH | H | H | $C_6H_5O$ | H | H | none | none |
| 105N | $C_6H_5O$ | H | H | H | CH | H | H | 4-Cl—$C_6H_4O$ | H | H | none | none |
| 106N | $CF_3O$ | H | H | H | CH | H | H | 4-Cl—$C_6H_4O$ | H | H | none | none |
| 107N | $C_6H_5O$ | H | H | H | CH | H | H | 3,4-$Cl_2$—$C_6H_3O$ | H | H | none | none |
| 108N | $CF_3O$ | H | H | H | CH | H | H | 3,4-$Cl_2$—$C_6H_3O$ | H | H | none | none |
| 109N | $CF_3O$ | H | H | H | CH | H | H | 3,5-$Cl_2$—$C_6H_3O$ | H | H | none | none |
| 110N | $CF_3O$ | H | H | H | CH | H | H | 3-$CH_3O$—$C_6H_4O$ | H | H | none | none |
| 111N | $CF_3O$ | H | H | H | CH | H | H | H | 3-$CH_3O$—$C_6H_4O$ | H | none | none |
| 112N | $CF_3O$ | H | H | H | CH | H | H | 3-$CF_3$—$C_6H_4O$ | H | H | none | none |
| 113N | $CF_3O$ | H | H | H | CH | H | H | $C_6H_5$—$CH_2O$ | H | H | none | none |
| 114N | $CF_3O$ | H | H | H | CH | H | H | $C_6H_5$—$CH_2O$ | $CH_3O$ | H | none | none |
| 115N | $CF_3O$ | H | H | H | CH | H | H | $C_6H_5$—$CH_2O$ | $C_6H_5$—$CH_2O$ | H | none | none |
| 116N | $CF_3O$ | H | H | H | CH | H | H | ethoxy | H | H | none | none |
| 117N | $CF_3O$ | H | H | H | CH | H | H | $CH_3CO_2$ | H | H | none | none |
| 118N | $CF_3O$ | H | H | H | CH | H | H | $HOCH_2$—$CH_2O$ | H | H | none | none |
| 119N | $CF_3O$ | H | H | H | CH | H | H | (glycidyloxy) | H | H | none | none |
| 120N | $CF_3O$ | H | H | H | CH | H | H | $R_{10} + R_{11} = OCH_2O$ | | H | none | none |
| 121N | $CF_3O$ | H | H | H | CH | H | H | $R_{10} + R_{11} = OCH_2CH_2O$ | | H | none | none |
| 122N | $CF_3O$ | H | H | H | CH | H | H | $CH_3O$ | $CH_3O$ | H | none | none |
| 123N | $CF_3O$ | H | H | H | CH | H | H | ethoxy | $CH_3O$ | H | none | none |
| 124N | $CF_3O$ | H | H | H | CH | H | H | ethoxy | ethoxy | H | none | none |
| 125N | $CF_3O$ | H | H | H | CH | H | H | $CH_3CO_2$ | $CH_3CO_2$ | H | none | none |
| 126N | $CF_3O$ | H | H | H | CH | H | H | $CH_3O$ | $CH_3CO_2$ | H | none | none |
| 127N | $CF_3O$ | H | H | H | CH | H | H | n-butoxy | H | H | none | none |
| 128N | $CF_3O$ | H | H | H | CH | H | H | $CH_3O$ | H | H | none | none |
| 129N | $CF_3O$ | H | H | H | CH | H | H | H | $CH_3O$ | H | none | none |
| 130N | $CH_3O$ | H | H | H | CH | H | H | $CH_3O$ | H | H | none | none |
| 131N | $CH_3O$ | H | H | H | CH | H | H | H | $CF_3O$ | H | none | none |
| 132N | $CF_3O$ | H | H | H | CH | H | H | H | ethoxy | H | none | none |
| 133N | $CF_3O$ | H | H | H | CH | H | H | H | n-propoxy | H | none | none |
| 134N | $C_6H_5$—$CH_2O$ | H | H | H | CH | H | H | $CF_3O$ | H | H | none | none |
| 135N | $C_6H_5$—$CH_2O$ | H | H | H | CH | H | H | $C_6H_5O$ | H | H | none | none |
| 136N | ethoxy | H | H | H | CH | H | H | $CF_3O$ | H | H | none | none |
| 137N | $R_5 + R_6 = OCH_2O$ | | H | H | CH | H | H | $CF_3O$ | H | H | none | none |
| 138N | $R_5 + R_6 = OCH_2O$ | | H | H | CH | H | H | $C_6H_5O$ | H | H | none | none |
| 139N | $R_5 + R_6 = OCH_2CH_2O$ | | H | H | CH | H | H | $CF_3O$ | H | H | none | none |
| 140N | $CH_3O$ | $CH_3O$ | H | H | CH | H | H | $CF_3O$ | H | H | none | none |
| 141N | $R_5 + R_6 = OCH_2CH_2CH_2O$ | | H | H | CH | H | H | $CF_3O$ | H | H | none | none |
| 142N | cyclopentoxy | $CH_3O$ | H | H | CH | H | H | $CF_3O$ | H | H | none | none |
| 143N | H | $C_6H_5O$ | H | H | CH | H | H | $CF_3O$ | H | H | none | none |
| 144N | $CH_3O$ | $CH_3O$ | $CH_3O$ | H | CH | H | H | $CF_3O$ | H | H | none | none |
| 145N | H | $CF_3O$ | H | H | CH | H | H | $CF_3O$ | H | H | none | none |
| 146N | H | $C_6H_5$—$CH_2$ | H | H | CH | H | H | $CF_3O$ | H | H | none | none |
| 147N | $C_6H_5O$ | H | H | H | CH | H | H | $R_{10} + R_{11} = OCH_2CH_2O$ | | H | none | none |

TABLE 6-continued

Structure of "Secondary Phenyl Amine" Reagents (Z is covalent bond; there is no $R_{15}$ substituent, $R_4$ and $R_{13}$ equal H).

(XIII-A)

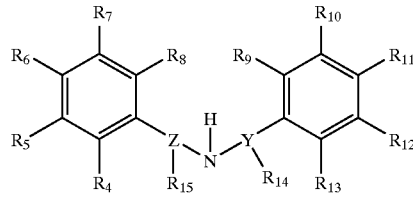

Secondary
Phenyl Amine

| Reagent Number | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 148N | H | $CF_3O$ | H | H | CH | H | H | $CF_3$ | H | H | none | none |
| 149N | $C_6H_5O$ | H | H | H | CH | H | H | $CF_3$ | H | H | none | none |
| 150N | $C_6H_5$ | H | H | H | CH | H | H | $CF_3$ | H | H | none | none |
| 151N | H | $C_6H_5$ | H | H | CH | H | H | $CF_3$ | H | H | none | none |
| 152N | CN | H | H | H | CH | H | H | $CF_3$ | H | H | none | none |
| 153N | H | $OCF_3$ | H | H | CH | H | H | $CF_3$ | H | H | none | none |
| 154N | $OCF_3$ | H | H | H | CH | H | H | H | $CF_3$ | H | none | none |
| 155N | $C_6H_5O$ | H | H | H | CH | H | H | H | $CF_3$ | H | none | none |
| 156N | $C_6H_5$ | H | H | H | CH | H | H | H | $CF_3$ | H | none | none |
| 157N | H | $C_6H_5$ | H | H | CH | H | H | H | $CF_3$ | H | none | none |
| 158N | CN | H | H | H | CH | H | H | H | $CF_3$ | H | none | none |
| 159N | $OCF_3$ | H | H | H | CH | H | H | H | $CF_3$ | H | none | none |
| 160N | $CF_3$ | H | H | H | CH | H | H | H | $C_6H_5$ | H | none | none |
| 161N | $CF_3$ | H | H | H | CH | H | H | 3-$CF_3$—$C_6H_5O$ | H | H | none | none |
| 162N | $CF_3$ | H | H | H | CH | H | H | $C_6H_5O$ | H | H | none | none |
| 163N | $CF_3$ | H | H | H | CH | H | H | $CF_3O$ | H | H | none | none |
| 164N | H | $CF_3$ | H | H | CH | H | H | H | $C_6H_5$ | H | none | none |
| 165N | H | $CF_3$ | H | H | CH | H | H | 3-$CF_3$-$C_6H_5O$ | H | H | none | none |
| 166N | H | $CF_3$ | H | H | CH | H | H | $CF_3O$ | H | H | none | none |
| 167N | H | $CF_3$ | H | H | CH | H | H | $C_6H_5O$ | H | H | none | none |
| 168N | $CF_3$ | H | $CF_3$ | H | CH | H | H | $CF_3O$ | H | H | none | none |
| 169N | $CF_3$ | H | $CF_3$ | H | CH | H | H | $C_6H_5O$ | H | H | none | none |
| 170N | $CF_3O$ | H | H | H | CH | H | H | $CF_3$ | H | $CF_3$ | none | none |
| 171N | $C_6H_5O$ | H | H | H | CH | H | H | $CF_3$ | H | $CF_3$ | none | none |
| 172N | H | $C_6H_5O$ | H | H | CH | H | H | $C_6H_5O$ | H | H | none | none |
| 173N | H | $CF_3O$ | H | H | CH | H | H | $CF_3O$ | H | H | none | none |
| 174N | H | $CF_3O$ | H | H | CH | H | H | H | $C_6H_5O$ | H | none | none |
| 175N | $C_6H_5O$ | H | H | H | CH | H | H | H | $C_6H_5O$ | H | none | none |
| 176N | H | $C_6H_5O$ | H | H | CH | H | H | H | $OCF_3$ | H | none | none |
| 177N | H | $C_6H_5O$ | H | H | CH | H | H | H | $C_6H_5O$ | H | none | none |
| 178N | $C_6H_5O$ | H | H | H | CH | H | H | H | CN | H | none | none |
| 179N | $C_6H_5O$ | H | H | H | CH | H | H | CN | H | H | none | none |
| 180N | $C_6H_5O$ | H | H | H | CH | H | H | $NO_2$ | H | H | none | none |
| 181N | $C_6H_5O$ | H | H | H | CH | H | H | H | $NO_2$ | H | none | none |
| 182N | $C_6H_5O$ | H | H | H | CH | H | H | H | $SO_2CH_3$ | H | none | none |
| 183N | $C_6H_5O$ | H | H | H | CH | H | H | H | 2-$NO_2$4-Cl—$C_6H_3O$ | H | none | none |
| 184N | $C_6H_5O$ | H | H | H | CH | H | H | 4-Cl—$C_6H_4O$ | H | H | none | none |
| 185N | $C_6H_5O$ | H | H | H | CH | H | H | 3,4-Cl—$C_6H_3O$ | H | H | none | none |
| 186N | $C_6H_5O$ | H | H | H | CH | H | H | 3-$CF_3$–$C_6H_3O$ | H | H | none | none |
| 187N | $C_6H_5O$ | H | H | H | CH | H | H | 3,5-Cl—$C_6H_3O$ | H | H | none | none |
| 188N | $C_6H_5O$ | H | H | H | CH | H | H | H | $CH_3O$ | H | none | none |
| 189N | $C_6H_5O$ | H | H | H | CH | H | H | H | $CO_2CH_3$ | H | none | none |
| 190N | $C_6H_5O$ | H | H | H | CH | H | H | 3-$CH_3OC_6H_5O$ | H | H | none | none |
| 191N | $C_6H_5O$ | H | H | H | CH | H | H | 4-$CH_3OC_6H_5O$ | H | H | none | none |
| 193N | $C_6H_5O$ | H | H | H | CH | H | H | $CO_2CH_3$ | H | H | none | none |
| 194N | CN | H | H | H | CH | H | H | $OCF_3$ | H | H | none | none |
| 195N | $NO_2$ | H | H | H | CH | H | H | $OCF_3$ | H | H | none | none |
| 196N | H | CN | H | H | CH | H | H | $OCF_3$ | H | H | none | none |
| 197N | H | $NO_2$ | H | H | CH | H | H | $OCF_3$ | H | H | none | none |
| 198N | $SO_2CH_3$ | H | H | H | CH | H | H | $OCF_3$ | H | H | none | none |
| 199N | H | $SO_2CH_3$ | H | H | CH | H | H | $OCF_3$ | H | H | none | none |
| 200N | H | 4-F—$C_6H_5SO_2$ | H | H | CH | H | H | $OCF_3$ | H | H | none | none |
| 201N | $SO_2N(CH_3)_2$ | H | H | H | CH | H | H | $OCF_3$ | H | H | none | none |
| 202N | H | $SO_2N(CH_3)_2$ | H | H | CH | H | H | $OCF_3$ | H | H | none | none |
| 203N | H | $CONH_2$ | H | H | CH | H | H | $OCF_3$ | H | H | none | none |
| 204N | H | CONH—$C_6H_5$ | H | H | CH | H | H | $OCF_3$ | H | H | none | none |

TABLE 6-continued

Structure of "Secondary Phenyl Amine" Reagents (Z is covalent bond; there is no $R_{15}$ substituent, $R_4$ and $R_{13}$ equal H).

(XIII-A)

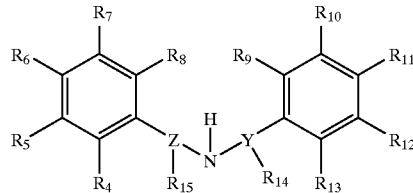

Secondary
Phenyl Amine

| Reagent Number | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 205N | H | $CO_2CH_3$ | H | H | CH | H | H | $OCF_3$ | H | H | none | none |
| 206N | H | $CO_2C_4H_9$ | H | H | CH | H | H | $OCF_3$ | H | H | none | none |
| 207N | H | 4-Cl—$C_6H_5$ | H | H | CH | H | H | $C_6H_5O$ | H | H | none | none |
| 208N | H | 4-$CF_3$O—$C_6H_5$ | H | H | CH | H | H | $CF_3O$ | H | H | none | none |
| 209N | 4-F—$C_6H_4O$ | H | H | H | CH | H | H | $CF_3O$ | H | H | none | none |
| 210N | $C_6F_5O$ | H | H | H | CH | H | H | $CF_3O$ | H | H | none | none |
| 211N | H | 4-F—$C_6H_5$ | H | H | CH | H | H | $CF_3O$ | H | H | none | none |
| 212N | H | 4-CN—$C_6H_5$ | H | H | CH | H | H | $CF_3O$ | H | H | none | none |
| 213N | H | 4-$C_6H_5$—$C_6H_5$ | H | H | CH | H | H | $CF_3O$ | H | H | none | none |
| 214N | $C_6H_5O$ | H | H | H | CH | $CH_3$ | H | $CF_3O$ | H | H | none | none |
| 215N | $C_6H_5O$ | H | H | H | CH | $CH_3$ | H | $NO_2$ | H | H | none | none |
| 216N | $C_6H_5O$ | H | H | H | CH | $CH_3$ | H | H | CN | H | none | none |
| 217N | $C_6H_5O$ | H | H | H | CH | 3-$CF_3C_6H_5$ | H | $CF_3$ | H | H | none | none |
| 218N | $C_6H_5O$ | H | H | H | CH | $C_6H_5$ | H | H | $C_6H_5$ | H | none | none |
| 219N | $C_6H_5O$ | H | H | H | CH | $C_6H_5$ | H | $CF_3$ | H | H | none | none |
| 220N | $C_6H_5O$ | H | H | H | CH | $CH_3$ | H | F | H | H | none | none |
| 221N | $C_6H_5O$ | H | H | H | CH | $CF_3$ | H | H | H | H | none | none |
| 222N | bond to —O— of $R_6$ aryl group | (2-methylphenoxy structure) | H | H | CH | H | H | $CF_3O$ | H | H | none | none |
| 223N | to $CH_2$ of $R_6$ aryl group | (Br-substituted structure) | H | H | CH | H | H | $CF_3O$ | H | H | none | none |
| 224N | $C_6H_5O$ | H | H | H | CH | H | H | $OCF_2CF_2H$ | H | H | none | none |
| 225N | 4-Cl—$C_6H_5O$ | H | H | H | CH | H | H | $OCF_2CF_2H$ | H | H | none | none |
| 226N | 4-F—$C_6H_5O$ | H | H | H | CH | H | H | $OCF_2CF_2H$ | H | H | none | none |
| 227N | 3,4-Cl—$C_6H_5O$ | H | H | H | CH | H | H | $OCF_2CF_2H$ | H | H | none | none |
| 228N | H | $C_6H_5$ | H | H | CH | H | H | $OCF_2CF_2H$ | H | H | none | none |
| 229N | H | 4-Cl—$C_6H_5$ | H | H | CH | H | H | $OCF_2CF_2H$ | H | H | none | none |
| 230N | H | 4-F—$C_6H_5$ | H | H | CH | H | H | $OCF_2CF_2H$ | H | H | none | none |
| 231N | H | 4-Br—$C_6H_5$ | H | H | CH | H | H | $OCF_2CF_2H$ | H | H | none | none |
| 232N | 4-Br—$C_6H_5O$ | H | H | H | CH | H | H | $OCF_2CF_2H$ | H | H | none | none |
| 233N | $C_6H_5O$ | H | H | H | CH | H | H | $OCF_2CF_3$ | H | H | none | none |
| 234N | 4-Cl—$C_6H_5O$ | H | H | H | CH | H | H | $OCF_2CF_3$ | H | H | none | none |
| 235N | 4-F—$C_6H_5O$ | H | H | H | CH | H | H | $OCF_2CF_3$ | H | H | none | none |
| 236N | 3,4-Cl—$C_6H_5O$ | H | H | H | CH | H | H | $OCF_2CF_3$ | H | H | none | none |
| 237N | H | $C_6H_5$ | H | H | CH | H | H | $OCF_2CF_3$ | H | H | none | none |
| 238N | H | 4-Cl—$C_6H_5$ | H | H | CH | H | H | $OCF_2CF_3$ | H | H | none | none |
| 239N | H | 4-F-$C_6H_5$ | H | H | CH | H | H | $OCF_2CF_3$ | H | H | none | none |
| 240N | H | 4-Br—$C_6H_5$ | H | H | CH | H | H | $OCF_2CF_3$ | H | H | none | none |
| 241N | 4-Br—$C_6H_5O$ | H | H | H | CH | H | H | $OCF_2CF_3$ | H | H | none | none |

TABLE 6-continued

Structure of "Secondary Phenyl Amine" Reagents (Z is covalent bond; there is no $R_{15}$ substituent, $R_4$ and $R_{13}$ equal H).

(XIII-A)

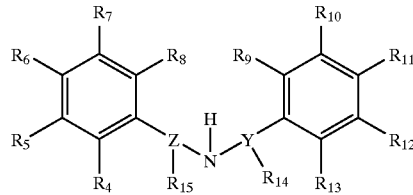

Secondary
Phenyl Amine

| Reagent Number | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 242N | $C_6H_5O$ | H | H | H | CH | H | H | $OCCl_2CCl_2H$ | H | H | none | none |
| 243N | 4-Cl—$C_6H_5O$ | H | H | H | CH | H | H | $OCCl_2CCl_2H$ | H | H | none | none |
| 244N | 4-F-$C_6H_5O$ | H | H | H | CH | H | H | $OCCl_2CCl_2H$ | H | H | none | none |
| 245N | 3,4-Cl—$C_6H_5O$ | H | H | H | CH | H | H | $OCCl_2CCl_2H$ | H | H | none | none |
| 246N | H | $C_6H_5$ | H | H | CH | H | H | $OCCl_2CCl_2H$ | H | H | none | none |
| 247N | H | 4-Cl—$C_6H_5$ | H | H | CH | H | H | $OCCl_2CCl_2H$ | H | H | none | none |
| 248N | H | 4-F—$C_6H_5$ | H | H | CH | H | H | $OCCl_2CCl_2H$ | H | H | none | none |
| 249N | H | 4-Br—$C_6H_5$ | H | H | CH | H | H | $OCCl_2CCl_2H$ | H | H | none | none |
| 250N | 4-Br—$C_6H_5O$ | H | H | H | CH | H | H | $OCCl_2CCl_2H$ | H | H | none | none |
| 251N | $C_6H_5O$ | H | H | H | CH | H | H | $OCCl_2CCl_3$ | H | H | none | none |
| 252N | 4-Cl—$C_6H_5O$ | H | H | H | CH | H | H | $OCCl_2CCl_3$ | H | H | none | none |
| 253N | 4-F—$C_6H_5O$ | H | H | H | CH | H | H | $OCCl_2CCl_3$ | H | H | none | none |
| 254N | 3,4-Cl—$C_6H_5O$ | H | H | H | CH | H | H | $OCCl_2CCl_3$ | H | H | none | none |
| 255N | H | $C_6H_5$ | H | H | CH | H | H | $OCCl_2CCl_3$ | H | H | none | none |
| 256N | H | 4-Cl—$C_6H_5$ | H | H | CH | H | H | $OCCl_2CCl_3$ | H | H | none | none |
| 257N | H | 4-F—$C_6H_5$ | H | H | CH | H | H | $OCCl_2CCl_3$ | H | H | none | none |
| 258N | H | 4-Br—$C_6H_5$ | H | H | CH | H | H | $OCCl_2CCl_3$ | H | H | none | none |
| 259N | 4-Br—$C_6H_5O$ | H | H | H | CH | H | H | $OCCl_2CCl_3$ | H | H | none | none |
| 260N | $C_6H_5O$ | H | H | H | CH | H | H | $OCCl_2CF_3$ | H | H | none | none |
| 261N | 4-Cl—$C_6H_5O$ | H | H | H | CH | H | H | $OCCl_2CF_3$ | H | H | none | none |
| 262N | 4-F—$C_6H_5O$ | H | H | H | CH | H | H | $OCCl_2CF_3$ | H | H | none | none |
| 263N | 3,4-Cl—$C_6H_5O$ | H | H | H | CH | H | H | $OCCl_2CF_3$ | H | H | none | none |
| 264N | H | $C_6H_5$ | H | H | CH | H | H | $OCCl_2CF_3$ | H | H | none | none |
| 265N | H | 4-Cl—$C_6H_5$ | H | H | CH | H | H | $OCCl_2CF_3$ | H | H | none | none |
| 266N | H | 4-F—$C_6H_5$ | H | H | CH | H | H | $OCCl_2CF_3$ | H | H | none | none |
| 267N | H | 4-Br—$C_6H_5$ | H | H | CH | H | H | $OCCl_2CF_3$ | H | H | none | none |
| 268N | 4-Br—$C_6H_5O$ | H | H | H | CH | H | H | $OCCl_2CF_3$ | H | H | none | none |
| 269N | $C_6H_5O$ | H | H | H | CH | H | H | $OCF_2CCl_3$ | H | H | none | none |
| 270N | 4-Cl—$C_6H_5O$ | H | H | H | CH | H | H | $OCF_2CCl_3$ | H | H | none | none |
| 271N | 4-F—$C_6H_5O$ | H | H | H | CH | H | H | $OCF_2CCl_3$ | H | H | none | none |
| 272N | 3,4-Cl—$C_6H_5O$ | H | H | H | CH | H | H | $OCF_2CCl_3$ | H | H | none | none |
| 273N | H | $C_6H_5$ | H | H | CH | H | H | $OCF_2CCl_3$ | H | H | none | none |
| 274N | H | 4-Cl—$C_6H_5$ | H | H | CH | H | H | $OCF_2CCl_3$ | H | H | none | none |
| 275N | H | 4-F—$C_6H_5$ | H | H | CH | H | H | $OCF_2CCl_3$ | H | H | none | none |
| 276N | H | 4-Br—$C_6H_5$ | H | H | CH | H | H | $OCF_2CCl_3$ | H | H | none | none |
| 277N | 4-Br—$C_6H_5O$ | H | H | H | CH | H | H | $OCF_2CCl_3$ | H | H | none | none |
| 278N | $C_6H_5O$ | H | H | H | CH | H | H | $OCF_2CF_2H$ | $OCF_2CF_2H$ | H | none | none |
| 279N | 4-Cl—$C_6H_5O$ | H | H | H | CH | H | H | $OCF_2CF_2H$ | $OCF_2CF_2H$ | H | none | none |
| 280N | 4-F—$C_6H_5O$ | H | H | H | CH | H | H | $OCF_2CF_2H$ | $OCF_2CF_2H$ | H | none | none |
| 281N | 3,4-Cl—$C_6H_5O$ | H | H | H | CH | H | H | $OCF_2CF_2H$ | $OCF_2CF_2H$ | H | none | none |
| 282N | H | $C_6H_5$ | H | H | CH | H | H | $OcF_2CF_2H$ | $OCF_2CF_2H$ | H | none | none |
| 283N | H | 4-Cl—$C_6H_5$ | H | H | CH | H | H | $OCF_2CF_2H$ | $OCF_2CF_2H$ | H | none | none |
| 284N | H | 4-F—$C_6H_5$ | H | H | CH | H | H | $OCF_2CF_2H$ | $OCF_2CF_2H$ | H | none | none |
| 285N | H | 4-Br—$C_6H_5$ | H | H | CH | H | H | $OCF_2CF_2H$ | $OCF_2CF_2H$ | H | none | none |
| 286N | 4-Br—$C_6H_5O$ | H | H | H | CH | H | H | $OCF_2CF_2H$ | $OCF_2CF_2H$ | H | none | none |
| 287N | $C_6H_5O$ | H | H | H | CH | H | H | $OCF_3$ | $OCF_3$ | H | none | none |
| 288N | 4-Cl—$C_6H_5O$ | H | H | H | CH | H | H | $OCF_3$ | $OCF_3$ | H | none | none |
| 289N | 4-F—$C_6H_5O$ | H | H | H | CH | H | H | $OCF_3$ | $OCF_3$ | H | none | none |
| 290N | 3,4-Cl—$C_6H_5O$ | H | H | H | CH | H | H | $OCF_3$ | $OCF_3$ | H | none | none |
| 291N | H | $C_6H_5$ | H | H | CH | H | H | $OCF_3$ | $OCF_3$ | H | none | none |
| 292N | H | 4-Cl—$C_6H_5$ | H | H | CH | H | H | $OCF_3$ | $OCF_3$ | H | none | none |
| 293N | H | 4-F—$C_6H_5$ | H | H | CH | H | H | $OCF_3$ | $OCF_3$ | H | none | none |
| 294N | H | 4-Br—$C_6H_5$ | H | H | CH | H | H | $OCF_3$ | $OCF_3$ | H | none | none |

TABLE 6-continued

Structure of "Secondary Phenyl Amine" Reagents (Z is covalent bond; there is no $R_{15}$ substituent, $R_4$ and $R_{13}$ equal H).

(XIII-A)

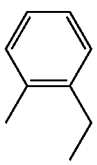

Secondary Phenyl Amine

| Reagent Number | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 295N | 4-Br—$C_6H_5$O | H | H | H | CH | H | H | $OCF_3$ | $OCF_3$ | H | none | none |
| 296N | $C_6H_5$O | H | H | H | CH | H | H | $OCF_2$H | $OCF_2$H | H | none | none |
| 297N | 4-Cl—$C_6H_5$O | H | H | H | CH | H | H | $OCF_2$H | $OCF_2$H | H | none | none |
| 298N | 4-F—$C_6H_5$O | H | H | H | CH | H | H | $OCF_2$H | $OCF_2$H | H | none | none |
| 299N | 3,4-Cl—$C_6H_5$O | H | H | H | CH | H | H | $OCF_2$H | $OCF_2$H | H | none | none |
| 300N | H | $C_6H_5$ | H | H | CH | H | H | $OCF_2$H | $OCF_2$H | H | none | none |
| 301N | H | 4-Cl—$C_6H_5$ | H | H | CH | H | H | $OCF_2$H | $OCF_2$H | H | none | none |
| 302N | H | 4-F—$C_6H_5$ | H | H | CH | H | H | $OCF_2$H | $OCF_2$H | H | none | none |
| 303N | H | 4-Br—$C_6H_5$ | H | H | CH | H | H | $OCF_2$H | $OCF_2$H | H | none | none |
| 304N | 4-Br—$C_6H_5$O | H | H | H | CH | H | H | $OCF_2$H | $OCF_2$H | H | none | none |
| 305N | $C_6H_5$O | H | H | H | CH | H | H | $R_{10} + R_{11} = OCF_2CF_2O$ | | H | none | none |
| 306N | 4-Cl—$C_6H_5$O | H | H | H | CH | H | H | $R_{10} + R_{11} = OCF_2CF_2O$ | | H | none | none |
| 307N | 4-F—$C_6H_5$O | H | H | H | CH | H | H | $R_{10} + R_{11} = OCF_2CF_2O$ | | H | none | none |
| 308N | 3,4-Cl—$C_6H_5$O | H | H | H | CH | H | H | $R_{10} + R_{11} = OCF_2CF_2O$ | | H | none | none |
| 309N | H | $C_6H_5$ | H | H | CH | H | H | $R_{10} + R_{11} = OCF_2CF_2O$ | | H | none | none |
| 310N | H | 4-Cl—$C_6H_5$ | H | H | CH | H | H | $R_{10} + R_{11} = OCF_2CF_2O$ | | H | none | none |
| 311N | H | 4-F—$C_6H_5$ | H | H | CH | H | H | $R_{10} + R_{11} = OCF_2CF_2O$ | | H | none | none |
| 312N | H | 4-Br—$C_6H_5$ | H | H | CH | H | H | $R_{10} + R_{11} = OCF_2CF_2O$ | | H | none | none |
| 313N | 4-Br—$C_6H_5$O | H | H | H | CH | H | H | $R_{10} + R_{11} = OCF_2CF_2O$ | | H | none | none |
| 314N | $C_6H_5$O | H | H | H | CH | H | H | $R_{10} + R_{11} = OCCl_2CCl_2O$ | | H | none | none |
| 315N | 4-Cl—$C_6H_5$O | H | H | H | CH | H | H | $R_{10} + R_{11} = OCCl_2CCl_2O$ | | H | none | none |
| 316N | 4-F—$C_6H_5$O | H | H | H | CH | H | H | $R_{10} + R_{11} = OCCl_2CCl_2O$ | | H | none | none |
| 317N | 3-4-Cl—$C_6H_5$O | H | H | H | CH | H | H | $R_{10} + R_{11} = OCCl_2CCl_2O$ | | H | none | none |
| 318N | H | $C_6H_5$ | H | H | CH | H | H | $R_{10} + R_{11} = OCCl_2CCl_2O$ | | H | none | none |
| 319N | H | 4-Cl—$C_6H_5$ | H | H | CH | H | H | $R_{10} + R_{11} = OCCl_2CCl_2O$ | | H | none | none |
| 320N | H | 4-F—$C_6H_5$ | H | H | CH | H | H | $R_{10} + R_{11} = OCCl_2CCl_2O$ | | H | none | none |
| 321N | H | 4-Br—$C_6H_5$ | H | H | CH | H | H | $R_{10} + R_{11} = OCCl_2CCl_2O$ | | H | none | none |
| 322N | 4-Br—$C_6H_5$O | H | H | H | CH | H | H | $R_{10} + R_{11} = OCCl_2CCl_2O$ | | H | none | none |
| 323N | H | H | H | H | CH | H | H | OH | H | H | none | none |
| 324N | H | H | H | H | CH | H | H | OH | OH | H | none | none |
| 325N | H | H | H | H | CH | H | H | H | OH | H | none | none |
| 326N | H | H | H | H | CH | H | H | $OCH_2CF_3$ | H | H | none | none |
| 327N | H | H | H | H | CH | H | H | H | $OCH_2CF_3$ | H | none | none |
| 328N | H | H | H | H | CH | H | H | $OCH_2CF_2CF_3$ | H | H | none | none |
| 329N | H | H | H | H | CH | H | H | $OCH_2CH_2CF_3$ | H | H | none | none |
| 330N | H | H | H | H | CH | H | H | $OCH(CF_3)_3$ | H | H | none | none |
| 331N | H | 4-F—$C_6H_5$O | H | H | CH | H | H | H | H | H | none | none |
| 332N | 4-F—$C_6H_5$O | H | H | H | CH | H | H | H | H | H | none | none |
| 333N | H | cyclohexoxy | H | H | CH | H | H | H | H | H | none | none |
| 334N | cyclohexoxy | H | H | H | CH | H | H | H | H | H | none | none |
| 335N | H | $CH(CH_3)_3$ | H | H | CH | H | H | H | H | H | none | none |
| 336N | F | H | H | H | CH | H | H | 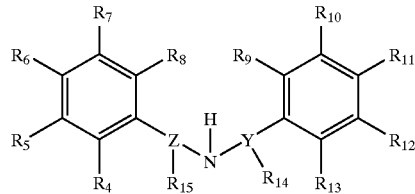 | bond to indicated phenyl carbon of $R_{10}$ substituent | H | none | none |

TABLE 7

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

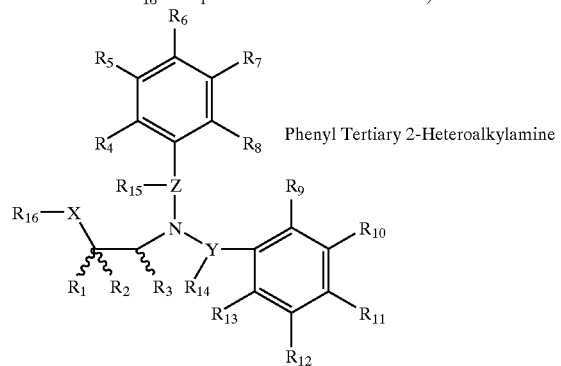

Phenyl Tertiary 2-Heteroalkylamine

Inhibitor Number Column 1 + Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 1 | 96N | $CF_3$ | H | O | OH | OH | H | H | $C_6H_5O$ | H | H |
| 1 | 97N | $CF_3$ | H | O | $C_6H_5O$ | H | H | H | OH | OH | H |
| 1 | 98N | $CF_3$ | H | O | 3-pyridyl | H | H | H | $CF_3$ | H | H |
| 1 | 99N | $CF_3$ | H | O | $SO_2N(CH_3)_2$ | H | H | H | $OCF_3$ | H | H |
| 1 | 100N | $CF_3$ | H | O | $SO_2CH_3$ | H | H | H | $OCF_3$ | H | H |
| 1 | 101N | $CF_3$ | H | O | $C_6H_5O$ | H | H | H | $C_6H_5O$ | H | H |
| 1 | 102N | $CF_3$ | H | O | $CF_3O$ | H | H | H | $C_6H_5O$ | H | H |
| 1 | 103N | $CF_3$ | H | O | $C_6H_5$ | H | H | H | $C_6H_5O$ | H | H |
| 1 | 104N | $CF_3$ | H | O | H | $C_6H_5$ | H | H | $C_6H_5O$ | H | H |
| 1 | 105N | $CF_3$ | H | O | $C_6H_5O$ | H | H | H | 4-Cl—$C_6H_4O$ | H | H |
| 1 | 106N | $CF_3$ | H | O | $CF_3O$ | H | H | H | 4-Cl—$C_6H_4O$ | H | H |
| 1 | 107N | $CF_3$ | H | O | $C_6H_5O$ | H | H | H | 3,4-Cl—$C_6H_3O$ | H | H |
| 1 | 108N | $CF_3$ | H | O | $CF_3O$ | H | H | H | 3,4-Cl—$C_6H_3O$ | H | H |
| 1 | 109N | $CF_3$ | H | O | $CF_3O$ | H | H | H | 3,5-Cl—$C_6H_3O$ | H | H |
| 1 | 110N | $CF_3$ | H | O | $CF_3O$ | H | H | H | 3-$CH_3O$—$C_6H_4O$ | H | H |
| 1 | 111N | $CF_3$ | H | O | $CF_3O$ | H | H | H | H | 3-$CH_3O$—$C_6H_4O$ | H |
| 1 | 112N | $CF_3$ | H | O | $CF_3O$ | H | H | H | 3-$CF_3$—$C_6H_4O$ | H | H |
| 1 | 113N | $CF_3$ | H | O | $CF_3O$ | H | H | H | $C_6H_5$—$CH_2O$ | H | H |
| 1 | 114N | $CF_3$ | H | O | $CF_3O$ | H | H | H | $C_6H_5$—$CH_2O$ | $CH_3O$ | H |
| 1 | 115N | $CF_3$ | H | O | $CF_3O$ | H | H | H | $C_6H_5$—$CH_2O$ | $C_6H_5$—$CH_2O$ | H |
| 1 | 116N | $CF_3$ | H | O | $CF_3O$ | H | H | H | ethoxy | H | H |
| 1 | 117N | $CF_3$ | H | O | $CF_3O$ | H | H | H | $CH_3CO_2$ | H | H |
| 1 | 118N | $CF_3$ | H | O | $CF_3O$ | H | H | H | $HOCH_2$—$CH_2O$ | H | H |
| 1 | 119N | $CF_3$ | H | O | $CF_3O$ | H | H | H | (epoxide group) | H | H |
| 1 | 120N | $CF_3$ | H | O | $CF_3O$ | H | H | H | $R_{10} + R_{11}$ = $OCH_2O$ | | H |
| 1 | 121N | $CF_3$ | H | O | $CF_3O$ | H | H | H | $R_{10} + R_{11}$ = $OCH_2CH_2O$ | | H |
| 1 | 122N | $CF_3$ | H | O | $CF_3O$ | H | H | H | $CH_3O$ | $CH_3O$ | H |
| 1 | 123N | $CF_3$ | H | O | $CF_3O$ | H | H | H | ethoxy | $CH_3O$ | H |
| 1 | 124N | $CF_3$ | H | O | $CF_3O$ | H | H | H | ethoxy | ethoxy | H |
| 1 | 125N | $CF_3$ | H | O | $CF_3O$ | H | H | H | $CH_3CO_2$ | $CH_3CO_2$ | H |
| 1 | 126N | $CF_3$ | H | O | $CF_3O$ | H | H | H | $CH_3O$ | $CH_3CO_2$ | H |
| 1 | 127N | $CF_3$ | H | O | $CF_3O$ | H | H | H | n-butoxy | H | H |
| 1 | 128N | $CF_3$ | H | O | $CF_3O$ | H | H | H | $CH_3O$ | H | H |
| 1 | 129N | $CF_3$ | H | O | $CF_3O$ | H | H | H | H | $CH_3O$ | H |
| 1 | 130N | $CF_3$ | H | O | $CH_3O$ | H | H | H | $CH_3O$ | H | H |
| 1 | 131N | $CF_3$ | H | O | $CH_3O$ | H | H | H | H | $CF_3O$ | H |
| 1 | 132N | $CF_3$ | H | O | $CF_3O$ | H | H | H | H | ethoxy | H |
| 1 | 133N | $CF_3$ | H | O | $CF_3O$ | H | H | H | H | n-propoxy | H |
| 1 | 134N | $CF_3$ | H | O | $C_6H_5$—$CH_2O$ | H | H | H | $CF_3O$ | H | H |
| 1 | 135N | $CF_3$ | H | O | $C_6H_5$—$CH_2O$ | H | H | H | $C_6H_5O$ | H | H |
| 1 | 136N | $CF_3$ | H | O | ethoxy | H | H | H | $CF_3O$ | H | H |
| 1 | 137N | $CF_3$ | H | O | $R_5 + R_6$ = $OCH_2O$ | | H | H | $CF_3O$ | H | H |
| 1 | 138N | $CF_3$ | H | O | $R_5 + R_6$ = $OCH_2O$ | | H | H | $C_6H_5O$ | H | H |
| 1 | 139N | $CF_3$ | H | O | $R_5 + R_6$ = $OCH_2CH_2O$ | | H | H | $CF_3O$ | H | H |
| 1 | 140N | $CF_3$ | H | O | $CH_3O$ | $CH_3O$ | H | H | $CF_3O$ | H | H |
| 1 | 141N | $CF_3$ | H | O | $R_5 + R_6$ = $OCH_2CH_2CH_2O$ | | H | H | $CF_3O$ | H | H |
| 1 | 142N | $CF_3$ | H | O | cyclo | $CH_3O$ | H | H | $CF_3O$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

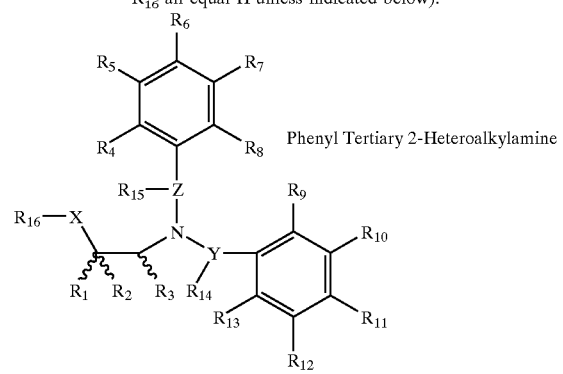

Phenyl Tertiary 2-Heteroalkylamine

Inhibitor Number
Column 1 + Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| | | | | | pentoxy | | | | | | |
| 1 | 143N | $CF_3$ | H | O | H | $C_6H_5O$ | H | H | $CF_3O$ | H | H |
| 1 | 144N | $CF_3$ | H | O | $CH_3O$ | $CH_3O$ | $CH_3O$ | H | $CF_3O$ | H | H |
| 1 | 145N | $CF_3$ | H | O | H | $CF_3O$ | H | H | $CF_3O$ | H | H |
| 1 | 146N | $CF_3$ | H | O | H | $C_6H_5$—$CH_2$ | H | H | $CF_3O$ | H | H |
| 1 | 147N | $CF_3$ | H | O | $C_6H_5O$ | H | H | H | $R_{10} + R_{11} = OCH_2CH_2O$ | | H |
| 1 | 148N | $CF_3$ | H | O | H | $CF_3O$ | H | H | $CF_3$ | H | H |
| 1 | 149N | $CF_3$ | H | O | $C_6H_5O$ | H | H | H | $CF_3$ | H | H |
| 1 | 150N | $CF_3$ | H | O | $C_6H_5$ | H | H | H | $CF_3$ | H | H |
| 1 | 151N | $CF_3$ | H | O | H | $C_6H_5$ | H | H | $CF_3$ | H | H |
| 1 | 152N | $CF_3$ | H | O | CN | H | H | H | $CF_3$ | H | H |
| 1 | 153N | $CF_3$ | H | O | H | $OCF_3$ | H | H | $CF_3$ | H | H |
| 1 | 154N | $CF_3$ | H | O | $OCF_3$ | H | H | H | H | $CF_3$ | H |
| 1 | 155N | $CF_3$ | H | O | $C_6H_5O$ | H | H | H | H | $CF_3$ | H |
| 1 | 156N | $CF_3$ | H | O | $C_6H_5$ | H | H | H | H | $CF_3$ | H |
| 1 | 157N | $CF_3$ | H | O | H | $C_6H_5$ | H | H | H | $CF_3$ | H |
| 1 | 158N | $CF_3$ | H | O | CN | H | H | H | H | $CF_3$ | H |
| 1 | 159N | $CF_3$ | H | O | $OCF_3$ | H | H | H | H | $CF_3$ | H |
| 1 | 160N | $CF_3$ | H | O | $CF_3$ | H | H | H | H | $C_6H_5$ | H |
| 1 | 161N | $CF_3$ | H | O | $CF_3$ | H | H | H | 3-$CF_3$—$C_6H_5O$ | H | H |
| 1 | 162N | $CF_3$ | H | O | $CF_3$ | H | H | H | $C_6H_5O$ | H | H |
| 1 | 163N | $CF_3$ | H | O | $CF_3$ | H | H | H | $CF_3O$ | H | H |
| 1 | 164N | $CF_3$ | H | O | H | $CF_3$ | H | H | H | $C_6H_5$ | H |
| 1 | 165N | $CF_3$ | H | O | H | $CF_3$ | H | H | 3-$CF_3$—$C_6H_5O$ | H | H |
| 1 | 166N | $CF_3$ | H | O | H | $CF_3$ | H | H | $CF_3O$ | H | H |
| 1 | 167N | $CF_3$ | H | O | H | $CF_3$ | H | H | $C_6H_5O$ | H | H |
| 1 | 168N | $CF_3$ | H | O | $CF_3$ | H | $CF_3$ | H | $CF_3O$ | H | H |
| 1 | 169N | $CF_3$ | H | O | $CF_3$ | H | $CF_3$ | H | $C_6H_5O$ | H | H |
| 1 | 170N | $CF_3$ | H | O | $CF_3O$ | H | H | H | $CF_3$ | H | $CF_3$ |
| 1 | 171N | $CF_3$ | H | O | $C_6H_5O$ | H | H | H | $CF_3$ | H | $CF_3$ |
| 1 | 172N | $CF_3$ | H | O | H | $C_6H_5O$ | H | H | $C_6H_5O$ | H | H |
| 1 | 173N | $CF_3$ | H | O | H | $CF_3O$ | H | H | $CF_3O$ | H | H |
| 1 | 174N | $CF_3$ | H | O | H | $CF_3O$ | H | H | H | $C_6H_5O$ | H |
| 1 | 175N | $CF_3$ | H | O | $C_6H_5O$ | H | H | H | H | $C_6H_5O$ | H |
| 1 | 176N | $CF_3$ | H | O | H | $C_6H_5O$ | H | H | H | $OCF_3$ | H |
| 1 | 177N | $CF_3$ | H | O | H | $C_6H_5O$ | H | H | H | $C_6H_5O$ | H |
| 1 | 178N | $CF_3$ | H | O | $C_6H_5O$ | H | H | H | H | CN | H |
| 1 | 179N | $CF_3$ | H | O | $C_6H_5O$ | H | H | H | CN | H | H |
| 1 | 180N | $CF_3$ | H | O | $C_6H_5O$ | H | H | H | $NO_2$ | H | H |
| 1 | 181N | $CF_3$ | H | O | $C_6H_5O$ | H | H | H | H | $NO_2$ | H |
| 1 | 182N | $CF_3$ | H | O | $C_6H_5O$ | H | H | H | H | $SO_2CH_3$ | H |
| 1 | 183N | $CF_3$ | H | O | $C_6H_5O$ | H | H | H | H | 2-$NO_2$-4-Cl—$C_6H_3O$ | H |
| 1 | 184N | $CF_3$ | H | O | $C_6H_5O$ | H | H | H | 4-Cl—$C_6H_4O$ | H | H |
| 1 | 185N | $CF_3$ | H | O | $C_6H_5O$ | H | H | H | 3,4-Cl—$C_6H_3O$ | H | H |
| 1 | 186N | $CF_3$ | H | O | $C_6H_5O$ | H | H | H | 3-$CF_3$—$C_6H_3O$ | H | H |
| 1 | 187N | $CF_3$ | H | O | $C_6H_5O$ | H | H | H | 3,5-Cl—$C_6H_3O$ | H | H |
| 1 | 188N | $CF_3$ | H | O | $C_6H_5O$ | H | H | H | H | $CH_3O$ | H |
| 1 | 189N | $CF_3$ | H | O | $C_6H_5O$ | H | H | H | H | $CO_2CH_3$ | H |
| 1 | 190N | $CF_3$ | H | O | $C_6H_5O$ | H | H | H | 3-$CH_3O$ $C_6H_5O$ | H | H |
| 1 | 191N | $CF_3$ | H | O | $C_6H_5O$ | H | H | H | 4-$CH_3O$ $C_6H_5O$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

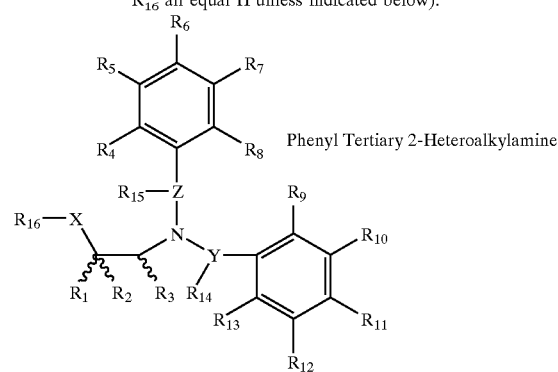

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 1 | 193N | $CF_3$ | H | O | $C_6H_5O$ | H | H | H | $CO_2CH_3$ | H | H |
| 1 | 194N | $CF_3$ | H | O | CN | H | H | H | $OCF_3$ | H | H |
| 1 | 195N | $CF_3$ | H | O | $NO_2$ | H | H | H | $OCF_3$ | H | H |
| 1 | 196N | $CF_3$ | H | O | H | CN | H | H | $OCF_3$ | H | H |
| 1 | 197N | $CF_3$ | H | O | H | $NO_2$ | H | H | $OCF_3$ | H | H |
| 1 | 198N | $CF_3$ | H | O | $SO_2CH_3$ | H | H | H | $OCF_3$ | H | H |
| 1 | 199N | $CF_3$ | H | O | H | $SO_2CH_3$ | H | H | $OCF_3$ | H | H |
| 1 | 200N | $CF_3$ | H | O | H | 4-F—$C_6H_5SO_2$ | H | H | $OCF_3$ | H | H |
| 1 | 201N | $CF_3$ | H | O | $SO_2N(CH_3)_2$ | H | H | H | $OCF_3$ | H | H |
| 1 | 202N | $CF_3$ | H | O | H | $SO_2N(CH_3)_2$ | H | H | $OCF_3$ | H | H |
| 1 | 203N | $CF_3$ | H | O | H | $CONH_2$ | H | H | $OCF_3$ | H | H |
| 1 | 204N | $CF_3$ | H | O | H | CONH—$C_6H_5$ | H | H | $OCF_3$ | H | H |
| 1 | 205N | $CF_3$ | H | O | H | $CO_2CH_3$ | H | H | $OCF_3$ | H | H |
| 1 | 206N | $CF_3$ | H | O | H | $CO_2C_4H_9$ | H | H | $OCF_3$ | H | H |
| 1 | 207N | $CF_3$ | H | O | H | 4-Cl—$C_6H_5$ | H | H | $C_6H_5O$ | H | H |
| 1 | 208N | $CF_3$ | H | O | H | 4-$CF_3O$—$C_6H_5$ | H | H | $CF_3O$ | H | H |
| 1 | 209N | $CF_3$ | H | O | 4-F—$C_6H_4O$ | H | H | H | $CF_3O$ | H | H |
| 1 | 210N | $CF_3$ | H | O | $C_6F_5O$ | H | H | H | $CF_3O$ | H | H |
| 1 | 211N | $CF_3$ | H | O | H | 4-F—$C_6H_5$ | H | H | $CF_3O$ | H | H |
| 1 | 212N | $CF_3$ | H | O | H | 4-CN—$C_6H_5$ | H | H | $CF_3O$ | H | H |
| 1 | 213N | $CF_3$ | H | O | H | 4-$C_6H_5$—$C_6H_5$ | H | H | $CF_3O$ | H | H |
| 1 | 214N | $CF_3$ | H | O | $C_6H_5O$ | H | H | $CH_3$ | $CF_3O$ | H | H |
| 1 | 215N | $CF_3$ | H | O | $C_6H_5O$ | H | H | $CH_3$ | $NO_2$ | H | H |
| 1 | 216N | $CF_3$ | H | O | $C_6H_5O$ | H | H | $CH_3$ | H | CN | H |
| 1 | 217N | $CF_3$ | H | O | $C_6H_5O$ | H | H | 3-$CF_3$ $C_6H_5$ | $CF_3$ | H | H |
| 1 | 218N | $CF_3$ | H | O | $C_6H_5O$ | H | H | $C_6H_5$ | H | $C_6H_5$ | H |
| 1 | 219N | $CF_3$ | H | O | $C_6H_5O$ | H | H | $C_6H_5$ | $CF_3$ | H | H |
| 1 | 220N | $CF_3$ | H | O | $C_6H_5O$ | H | H | $CH_3$ | F | H | H |
| 1 | 221N | $CF_3$ | H | O | $C_6H_5O$ | H | H | $CF_3$ | H | H | H |
| 1 | 222N | $CF_3$ | H | O | bond to —O— of $R_6$ aryl group | (structure) | H | H | $CF_3O$ | H | H |
| 1 | 223N | $CF_3$ | H | O | to $CH_2$ of $R_6$ aryl group | (structure) | H | H | $CF_3O$ | H | H |
| 2 | 96N | $CCl_3$ | H | O | OH | OH | H | H | $C_6H_5O$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 2 | 97N | CCl$_3$ | H | O | C$_6$H$_5$O | H | H | H | OH | OH | H |
| 2 | 98N | CCl$_3$ | H | O | 3-pyridyl | H | H | H | CF$_3$ | H | H |
| 2 | 99N | CCl$_3$ | H | O | SO$_2$N(CH$_3$)$_2$ | H | H | H | OCF$_3$ | H | H |
| 2 | 100N | CCl$_3$ | H | O | SO$_2$CH$_3$ | H | H | H | OCF$_3$ | H | H |
| 2 | 101N | CCl$_3$ | H | O | C$_6$H$_5$O | H | H | H | C$_6$H$_5$O | H | H |
| 2 | 102N | CCl$_3$ | H | O | CF$_3$O | H | H | H | C$_6$H$_5$O | H | H |
| 2 | 103N | CCl$_3$ | H | O | C$_6$H$_5$ | H | H | H | C$_6$H$_5$O | H | H |
| 2 | 104N | CCl$_3$ | H | O | H | C$_6$H$_5$ | H | H | C$_6$H$_5$O | H | H |
| 2 | 105N | CCl$_3$ | H | O | C$_6$H$_5$O | H | H | H | 4-Cl—C$_6$H$_4$O | H | H |
| 2 | 106N | CCl$_3$ | H | O | CF$_3$O | H | H | H | 4-Cl—C$_6$H$_4$O | H | H |
| 2 | 107N | CCl$_3$ | H | O | C$_6$H$_5$O | H | H | H | 3,4-Cl—C$_6$H$_3$O | H | H |
| 2 | 108N | CCl$_3$ | H | O | CF$_3$O | H | H | H | 3,4-Cl—C$_6$H$_3$O | H | H |
| 2 | 109N | CCl$_3$ | H | O | CF$_3$O | H | H | H | 3,5-Cl—C$_6$H$_3$O | H | H |
| 2 | 110N | CCl$_3$ | H | O | CF$_3$O | H | H | H | 3-CH$_3$O—C$_6$H$_4$O | H | H |
| 2 | 111N | CCl$_3$ | H | O | CF$_3$O | H | H | H | H | 3-CH$_3$O—C$_6$H$_4$O | H |
| 2 | 112N | CCl$_3$ | H | O | CF$_3$O | H | H | H | 3-CF$_3$—C$_6$H$_4$O | H | H |
| 2 | 113N | CCl$_3$ | H | O | CF$_3$O | H | H | H | C$_6$H$_5$—CH$_2$O | H | H |
| 2 | 114N | CCl$_3$ | H | O | CF$_3$O | H | H | H | C$_6$H$_5$—CH$_2$O | CH$_3$O | H |
| 2 | 115N | CCl$_3$ | H | O | CF$_3$O | H | H | H | C$_6$H$_5$—CH$_2$O | C$_6$H$_5$—CH$_2$O | H |
| 2 | 116N | CCl$_3$ | H | O | CF$_3$O | H | H | H | ethoxy | H | H |
| 2 | 117N | CCl$_3$ | H | O | CF$_3$O | H | H | H | CH$_3$CO$_2$ | H | H |
| 2 | 118N | CCl$_3$ | H | O | CF$_3$O | H | H | H | HOCH$_2$—CH$_2$O | H | H |
| 2 | 119N | CCl$_3$ | H | O | CF$_3$O | H | H | H | 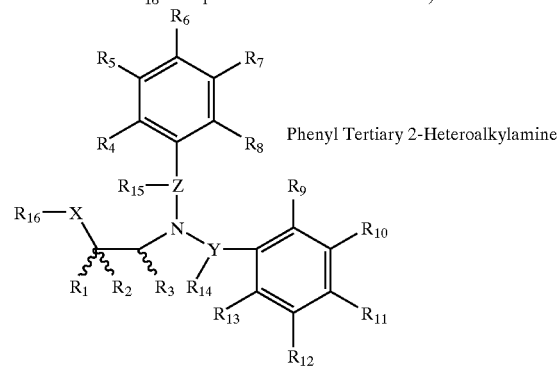 | H | H |
| 2 | 120N | CCl$_3$ | H | O | CF$_3$O | H | H | H | $R_{10}$ + $R_{11}$ = OCH$_2$O | | H |
| 2 | 121N | CCl$_3$ | H | O | CF$_3$O | H | H | H | $R_{10}$ + $R_{11}$ = OCH$_2$CH$_2$O | | H |
| 2 | 122N | CCl$_3$ | H | O | CF$_3$O | H | H | H | CH$_3$O | CH$_3$O | H |
| 2 | 123N | CCl$_3$ | H | O | CF$_3$O | H | H | H | ethoxy | CH$_3$O | H |
| 2 | 124N | CCl$_3$ | H | O | CF$_3$O | H | H | H | ethoxy | ethoxy | H |
| 2 | 125N | CCl$_3$ | H | O | CF$_3$O | H | H | H | CH$_3$CO$_2$ | CH$_3$CO$_2$ | H |
| 2 | 126N | CCl$_3$ | H | O | CF$_3$O | H | H | H | CH$_3$O | CH$_3$CO$_2$ | H |
| 2 | 127N | CCl$_3$ | H | O | CF$_3$O | H | H | H | n-butoxy | H | H |
| 2 | 128N | CCl$_3$ | H | O | CF$_3$O | H | H | H | CH$_3$O | H | H |
| 2 | 129N | CCl$_3$ | H | O | CF$_3$O | H | H | H | H | CH$_3$O | H |
| 2 | 130N | CCl$_3$ | H | O | CH$_3$O | H | H | H | CH$_3$O | H | H |
| 2 | 131N | CCl$_3$ | H | O | CH$_3$O | H | H | H | H | CF$_3$O | H |
| 2 | 132N | CCl$_3$ | H | O | CF$_3$O | H | H | H | H | ethoxy | H |
| 2 | 133N | CCl$_3$ | H | O | CF$_3$O | H | H | H | H | n-propoxy | H |
| 2 | 134N | CCl$_3$ | H | O | C$_6$H$_5$—CH$_2$O | H | H | H | CF$_3$O | H | H |
| 2 | 135N | CCl$_3$ | H | O | C$_6$H$_5$—CH$_2$O | H | H | H | C$_6$H$_5$O | H | H |
| 2 | 136N | CCl$_3$ | H | O | ethoxy | H | H | H | CF$_3$O | H | H |
| 2 | 137N | CCl$_3$ | H | O | $R_5$ + $R_6$ = OCH$_2$O | | H | H | CF$_3$O | H | H |
| 2 | 138N | CCl$_3$ | H | O | $R_5$ + $R_6$ = OCH$_2$O | | H | H | C$_6$H$_5$O | H | H |
| 2 | 139N | CCl$_3$ | H | O | $R_5$ + $R_6$ = OCH$_2$CH$_2$O | | H | H | CF$_3$O | H | H |
| 2 | 140N | CCl$_3$ | H | O | CH$_3$O | CH$_3$O | H | H | CF$_3$O | H | H |
| 2 | 141N | CCl$_3$ | H | O | $R_5$ + $R_6$ = OCH$_2$CH$_2$CH$_2$O | | H | H | CF$_3$O | H | H |
| 2 | 142N | CCl$_3$ | H | O | cyclo pentoxy | CH$_3$O | H | H | CF$_3$O | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

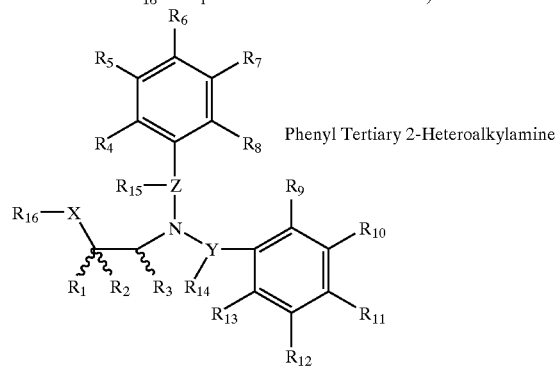

Phenyl Tertiary 2-Heteroalkylamine

| Inhibitor Number Column 1 + Column 2 | | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| Reagent | Reagent | | | | | | | | | | |
| 2 | 143N | $CCl_3$ | H | O | H | $C_6H_5O$ | H | H | $CF_3O$ | H | H |
| 2 | 144N | $CCl_3$ | H | O | $CH_3O$ | $CH_3O$ | $CH_3O$ | H | $CF_3O$ | H | H |
| 2 | 145N | $CCl_3$ | H | O | H | $CF_3O$ | H | H | $CF_3O$ | H | H |
| 2 | 146N | $CCl_3$ | H | O | H | $C_6H_5—CH_2$ | H | H | $CF_3O$ | H | H |
| 2 | 147N | $CCl_3$ | H | O | $C_6H_5O$ | H | H | H | $R_{10} + R_{11} = OCH_2CH_2O$ | | H |
| 2 | 148N | $CCl_3$ | H | O | H | $CF_3O$ | H | H | $CF_3$ | H | H |
| 2 | 149N | $CCl_3$ | H | O | $C_6H_5O$ | H | H | H | $CF_3$ | H | H |
| 2 | 150N | $CCl_3$ | H | O | $C_6H_5$ | H | H | H | $CF_3$ | H | H |
| 2 | 151N | $CCl_3$ | H | O | H | $C_6H_5$ | H | H | $CF_3$ | H | H |
| 2 | 152N | $CCl_3$ | H | O | CN | H | H | H | $CF_3$ | H | H |
| 2 | 153N | $CCl_3$ | H | O | H | $OCF_3$ | H | H | $CF_3$ | H | H |
| 2 | 154N | $CCl_3$ | H | O | $OCF_3$ | H | H | H | H | $CF_3$ | H |
| 2 | 155N | $CCl_3$ | H | O | $C_6H_5O$ | H | H | H | H | $CF_3$ | H |
| 2 | 156N | $CCl_3$ | H | O | $C_6H_5$ | H | H | H | H | $CF_3$ | H |
| 2 | 157N | $CCl_3$ | H | O | H | $C_6H_5$ | H | H | H | $CF_3$ | H |
| 2 | 158N | $CCl_3$ | H | O | CN | H | H | H | H | $CF_3$ | H |
| 2 | 159N | $CCl_3$ | H | O | $OCF_3$ | H | H | H | H | $CF_3$ | H |
| 2 | 160N | $CCl_3$ | H | O | $CF_3$ | H | H | H | H | $C_6H_5$ | H |
| 2 | 161N | $CCl_3$ | H | O | $CF_3$ | H | H | H | 3-$CF_3$—$C_6H_5O$ | H | H |
| 2 | 162N | $CCl_3$ | H | O | $CF_3$ | H | H | H | $C_6H_5O$ | H | H |
| 2 | 163N | $CCl_3$ | H | O | $CF_3$ | H | H | H | $CF_3O$ | H | H |
| 2 | 164N | $CCl_3$ | H | O | H | $CF_3$ | H | H | H | $C_6H_5$ | H |
| 2 | 165N | $CCl_3$ | H | O | H | $CF_3$ | H | H | 3-$CF_3$—$C_6H_5O$ | H | H |
| 2 | 166N | $CCl_3$ | H | O | H | $CF_3$ | H | H | $CF_3O$ | H | H |
| 2 | 167N | $CCl_3$ | H | O | H | $CF_3$ | H | H | $C_6H_5O$ | H | H |
| 2 | 168N | $CCl_3$ | H | O | $CF_3$ | H | $CF_3$ | H | $CF_3O$ | H | H |
| 2 | 169N | $CCl_3$ | H | O | $CF_3$ | H | $CF_3$ | H | $C_6H_5O$ | H | H |
| 2 | 170N | $CCl_3$ | H | O | $CF_3O$ | H | H | H | $CF_3$ | H | $CF_3$ |
| 2 | 171N | $CCl_3$ | H | O | $C_6H_5O$ | H | H | H | $CF_3$ | H | $CF_3$ |
| 2 | 172N | $CCl_3$ | H | O | H | $C_6H_5O$ | H | H | $C_6H_5O$ | H | H |
| 2 | 173N | $CCl_3$ | H | O | H | $CF_3O$ | H | H | $CF_3O$ | H | H |
| 2 | 174N | $CCl_3$ | H | O | H | $CF_3O$ | H | H | H | $C_6H_5O$ | H |
| 2 | 175N | $CCl_3$ | H | O | $C_6H_5O$ | H | H | H | H | $C_6H_5O$ | H |
| 2 | 176N | $CCl_3$ | H | O | H | $C_6H_5O$ | H | H | H | $OCF_3$ | H |
| 2 | 177N | $CCl_3$ | H | O | H | $C_6H_5O$ | H | H | H | $C_6H_5O$ | H |
| 2 | 178N | $CCl_3$ | H | O | $C_6H_5O$ | H | H | H | H | CN | H |
| 2 | 179N | $CCl_3$ | H | O | $C_6H_5O$ | H | H | H | CN | H | H |
| 2 | 180N | $CCl_3$ | H | O | $C_6H_5O$ | H | H | H | $NO_2$ | H | H |
| 2 | 181N | $CCl_3$ | H | O | $C_6H_5O$ | H | H | H | H | $NO_2$ | H |
| 2 | 182N | $CCl_3$ | H | O | $C_6H_5O$ | H | H | H | H | $SO_2CH_3$ | H |
| 2 | 183N | $CCl_3$ | H | O | $C_6H_5O$ | H | H | H | H | 2-$NO_2$-4-Cl—$C_6H_3O$ | H |
| 2 | 184N | $CCl_3$ | H | O | $C_6H_5O$ | H | H | H | 4-Cl—$C_6H_4O$ | H | H |
| 2 | 185N | $CCl_3$ | H | O | $C_6H_5O$ | H | H | H | 3,4-Cl—$C_6H_3O$ | H | H |
| 2 | 186N | $CCl_3$ | H | O | $C_6H_5O$ | H | H | H | 3-$CF_3$—$C_6H_3O$ | H | H |
| 2 | 187N | $CCl_3$ | H | O | $C_6H_5O$ | H | H | H | 3,5-Cl—$C_6H_3O$ | H | H |
| 2 | 188N | $CCl_3$ | H | O | $C_6H_5O$ | H | H | H | H | $CH_3O$ | H |
| 2 | 189N | $CCl_3$ | H | O | $C_6H_5O$ | H | H | H | H | $CO_2CH_3$ | H |
| 2 | 190N | $CCl_3$ | H | O | $C_6H_5O$ | H | H | H | 3-$CH_3O$ $C_6H_5O$ | H | H |
| 2 | 191N | $CCl_3$ | H | O | $C_6H_5O$ | H | H | H | 4-$CH_3O$ $C_6H_5O$ | H | H |
| 2 | 193N | $CCl_3$ | H | O | $C_6H_5O$ | H | H | H | $CO_2CH_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

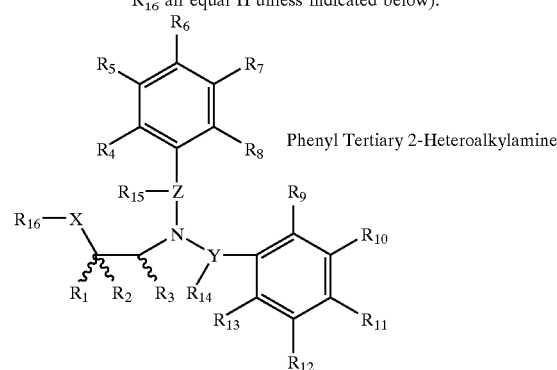

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 2 | 194N | CCl₃ | H | O | CN | H | H | H | OCF₃ | H | H |
| 2 | 195N | CCl₃ | H | O | NO₂ | H | H | H | OCF₃ | H | H |
| 2 | 196N | CCl₃ | H | O | H | CN | H | H | OCF₃ | H | H |
| 2 | 197N | CCl₃ | H | O | H | NO₂ | H | H | OCF₃ | H | H |
| 2 | 198N | CCl₃ | H | O | SO₂CH₃ | H | H | H | OCF₃ | H | H |
| 2 | 199N | CCl₃ | H | O | H | SO₂CH₃ | H | H | OCF₃ | H | H |
| 2 | 200N | CCl₃ | H | O | H | 4-F—C₆H₅SO₂ | H | H | OCF₃ | H | H |
| 2 | 201N | CCl₃ | H | O | SO₂N(CH₃)₂ | H | H | H | OCF₃ | H | H |
| 2 | 202N | CCl₃ | H | O | H | SO₂N(CH₃)₂ | H | H | OCF₃ | H | H |
| 2 | 203N | CCl₃ | H | O | H | CONH₂ | H | H | OCF₃ | H | H |
| 2 | 204N | CCl₃ | H | O | H | CONH—C₆H₅ | H | H | OCF₃ | H | H |
| 2 | 205N | CCl₃ | H | O | H | CO₂CH₃ | H | H | OCF₃ | H | H |
| 2 | 206N | CCl₃ | H | O | H | CO₂C₄H₉ | H | H | OCF₃ | H | H |
| 2 | 207N | CCl₃ | H | O | H | 4-Cl—C₆H₅ | H | H | C₆H₅O | H | H |
| 2 | 208N | CCl₃ | H | O | H | 4-CF₃O—C₆H₅ | H | H | CF₃O | H | H |
| 2 | 209N | CCl₃ | H | O | 4-F—C₆H₄O | H | H | H | CF₃O | H | H |
| 2 | 210N | CCl₃ | H | O | C₆F₅O | H | H | H | CF₃O | H | H |
| 2 | 211N | CCl₃ | H | O | H | 4-F—C₆H₅ | H | H | CF₃O | H | H |
| 2 | 212N | CCl₃ | H | O | H | 4-CN—C₆H₅ | H | H | CF₃O | H | H |
| 2 | 213N | CCl₃ | H | O | H | 4-C₆H₅—C₆H₅ | H | H | CF₃O | H | H |
| 2 | 214N | CCl₃ | H | O | C₆H₅O | H | H | CH₃ | CF₃O | H | H |
| 2 | 215N | CCl₃ | H | O | C₆H₅O | H | H | CH₃ | NO₂ | H | H |
| 2 | 216N | CCl₃ | H | O | C₆H₅O | H | H | CH₃ | H | CN | H |
| 2 | 217N | CCl₃ | H | O | C₆H₅O | H | H | 3-CF₃ C₆H₅ | CF₃ | H | H |
| 2 | 218N | CCl₃ | H | O | C₆H₅O | H | H | C₆H₅ | H | C₆H₅ | H |
| 2 | 219N | CCl₃ | H | O | C₆H₅O | H | H | C₆H₅ | CF₃ | H | H |
| 2 | 220N | CCl₃ | H | O | C₆H₅O | H | H | CH₃ | F | H | H |
| 2 | 221N | CCl₃ | H | O | C₆H₅O | H | H | CF₃ | H | H | H |
| 2 | 222N | CCl₃ | H | O | bond to —O— of R₆ aryl group | | H | H | CF₃O | H | H |
| 2 | 223N | CCl₃ | H | O | to CH₂ of R₆ aryl group | | H | H | CF₃O | H | H |
| 3 | 96N | CF₃ | CH₃ | O | OH | OH | H | H | C₆H₅O | H | H |
| 3 | 97N | CF₃ | CH₃ | O | C₆H₅O | H | H | H | OH | OH | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

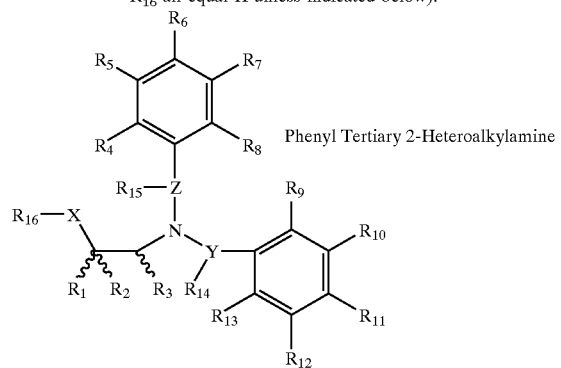

Phenyl Tertiary 2-Heteroalkylamine

Inhibitor Number
Column 1 + Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 3 | 98N | $CF_3$ | $CH_3$ | O | 3-pyridyl | H | H | H | $CF_3$ | H | H |
| 3 | 99N | $CF_3$ | $CH_3$ | O | $SO_2N(CH_3)_2$ | H | H | H | $OCF_3$ | H | H |
| 3 | 100N | $CF_3$ | $CH_3$ | O | $SO_2CH_3$ | H | H | H | $OCF_3$ | H | H |
| 3 | 101N | $CF_3$ | $CH_3$ | O | $C_6H_5O$ | H | H | H | $C_6H_5O$ | H | H |
| 3 | 102N | $CF_3$ | $CH_3$ | O | $CF_3O$ | H | H | H | $C_6H_5O$ | H | H |
| 3 | 103N | $CF_3$ | $CH_3$ | O | $C_6H_5$ | H | H | H | $C_6H_5O$ | H | H |
| 3 | 104N | $CF_3$ | $CH_3$ | O | H | $C_6H_5$ | H | H | $C_6H_5O$ | H | H |
| 3 | 105N | $CF_3$ | $CH_3$ | O | $C_6H_5O$ | H | H | H | 4-Cl—$C_6H_4O$ | H | H |
| 3 | 106N | $CF_3$ | $CH_3$ | O | $CF_3O$ | H | H | H | 4-Cl—$C_6H_4O$ | H | H |
| 3 | 107N | $CF_3$ | $CH_3$ | O | $C_6H_5O$ | H | H | H | 3,4-Cl—$C_6H_3O$ | H | H |
| 3 | 108N | $CF_3$ | $CH_3$ | O | $CF_3O$ | H | H | H | 3,4-Cl—$C_6H_3O$ | H | H |
| 3 | 109N | $CF_3$ | $CH_3$ | O | $CF_3O$ | H | H | H | 3,5-Cl—$C_6H_3O$ | H | H |
| 3 | 110N | $CF_3$ | $CH_3$ | O | $CF_3O$ | H | H | H | 3-$CH_3O$—$C_6H_4O$ | H | H |
| 3 | 111N | $CF_3$ | $CH_3$ | O | $CF_3O$ | H | H | H | H | 3-$CH_3O$—$C_6H_4O$ | H |
| 3 | 112N | $CF_3$ | $CH_3$ | O | $CF_3O$ | H | H | H | 3-$CF_3$—$C_6H_4O$ | H | H |
| 3 | 113N | $CF_3$ | $CH_3$ | O | $CF_3O$ | H | H | H | $C_6H_5$—$CH_2O$ | H | H |
| 3 | 114N | $CF_3$ | $CH_3$ | O | $CF_3O$ | H | H | H | $C_6H_5$—$CH_2O$ | $CH_3O$ | H |
| 3 | 115N | $CF_3$ | $CH_3$ | O | $CF_3O$ | H | H | H | $C_6H_5$—$CH_2O$ | $C_6H_5$—$CH_2O$ | H |
| 3 | 116N | $CF_3$ | $CH_3$ | O | $CF_3O$ | H | H | H | ethoxy | H | H |
| 3 | 117N | $CF_3$ | $CH_3$ | O | $CF_3O$ | H | H | H | $CH_3CO_2$ | H | H |
| 3 | 118N | $CF_3$ | $CH_3$ | O | $CF_3O$ | H | H | H | $HOCH_2$—$CH_2O$ | H | H |
| 3 | 119N | $CF_3$ | $CH_3$ | O | $CF_3O$ | H | H | H |  | H | H |
| 3 | 120N | $CF_3$ | $CH_3$ | O | $CF_3O$ | H | H | H | $R_{10} + R_{11} = OCH_2O$ | | H |
| 3 | 121N | $CF_3$ | $CH_3$ | O | $CF_3O$ | H | H | H | $R_{10} + R_{11} = OCH_2CH_2O$ | | H |
| 3 | 122N | $CF_3$ | $CH_3$ | O | $CF_3O$ | H | H | H | $CH_3O$ | $CH_3O$ | H |
| 3 | 123N | $CF_3$ | $CH_3$ | O | $CF_3O$ | H | H | H | ethoxy | $CH_3O$ | H |
| 3 | 124N | $CF_3$ | $CH_3$ | O | $CF_3O$ | H | H | H | ethoxy | ethoxy | H |
| 3 | 125N | $CF_3$ | $CH_3$ | O | $CF_3O$ | H | H | H | $CH_3CO_2$ | $CH_3CO_2$ | H |
| 3 | 126N | $CF_3$ | $CH_3$ | O | $CF_3O$ | H | H | H | $CH_3O$ | $CH_3CO_2$ | H |
| 3 | 127N | $CF_3$ | $CH_3$ | O | $CF_3O$ | H | H | H | n-butoxy | H | H |
| 3 | 128N | $CF_3$ | $CH_3$ | O | $CF_3O$ | H | H | H | $CH_3O$ | H | H |
| 3 | 129N | $CF_3$ | $CH_3$ | O | $CF_3O$ | H | H | H | H | $CH_3O$ | H |
| 3 | 130N | $CF_3$ | $CH_3$ | O | $CH_3O$ | H | H | H | $CH_3O$ | H | H |
| 3 | 131N | $CF_3$ | $CH_3$ | O | $CH_3O$ | H | H | H | H | $CF_3O$ | H |
| 3 | 132N | $CF_3$ | $CH_3$ | O | $CF_3O$ | H | H | H | H | ethoxy | H |
| 3 | 133N | $CF_3$ | $CH_3$ | O | $CF_3O$ | H | H | H | H | n-propoxy | H |
| 3 | 134N | $CF_3$ | $CH_3$ | O | $C_6H_5$—$CH_2O$ | H | H | H | $CF_3O$ | H | H |
| 3 | 135N | $CF_3$ | $CH_3$ | O | $C_6H_5$—$CH_2O$ | H | H | H | $C_6H_5O$ | H | H |
| 3 | 136N | $CF_3$ | $CH_3$ | O | ethoxy | H | H | H | $CF_3O$ | H | H |
| 3 | 137N | $CF_3$ | $CH_3$ | O | $R_5 + R_6 = OCH_2O$ | | H | H | $CF_3O$ | H | H |
| 3 | 138N | $CF_3$ | $CH_3$ | O | $R_5 + R_6 = OCH_2O$ | | H | H | $C_6H_5O$ | H | H |
| 3 | 139N | $CF_3$ | $CH_3$ | O | $R_5 + R_6 = OCH_2CH_2O$ | | H | H | $CF_3O$ | H | H |
| 3 | 140N | $CF_3$ | $CH_3$ | O | $CH_3O$ | $CH_3O$ | H | H | $CF_3O$ | H | H |
| 3 | 141N | $CF_3$ | $CH_3$ | O | $R_5 + R_6 = OCH_2CH_2CH_2O$ | | H | H | $CF_3O$ | H | H |
| 3 | 142N | $CF_3$ | $CH_3$ | O | cyclo pentoxy | $CH_3O$ | H | H | $CF_3O$ | H | H |
| 3 | 143N | $CF_3$ | $CH_3$ | O | H | $C_6H_5O$ | H | H | $CF_3O$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

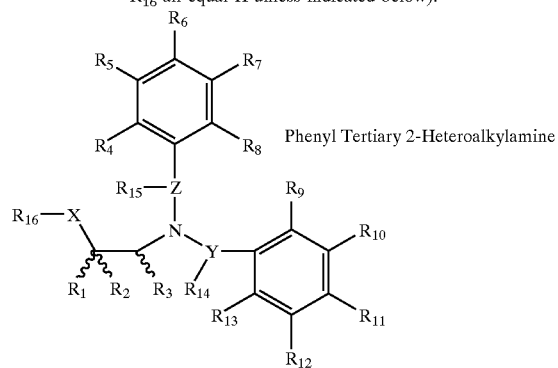

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 3 | 144N | $CF_3$ | $CH_3$ | O | $CH_3O$ | $CH_3O$ | $CH_3O$ | H | $CF_3O$ | H | H |
| 3 | 145N | $CF_3$ | $CH_3$ | O | H | $CF_3O$ | H | H | $CF_3O$ | H | H |
| 3 | 146N | $CF_3$ | $CH_3$ | O | H | $C_6H_5-CH_2$ | H | H | $CF_3O$ | H | H |
| 3 | 147N | $CF_3$ | $CH_3$ | O | $C_6H_5O$ | H | H | H | $R_{10} + R_{11} = OCH_2CH_2O$ | | H |
| 3 | 148N | $CF_3$ | $CH_3$ | O | H | $CF_3O$ | H | H | $CF_3$ | H | H |
| 3 | 149N | $CF_3$ | $CH_3$ | O | $C_6H_5O$ | H | H | H | $CF_3$ | H | H |
| 3 | 150N | $CF_3$ | $CH_3$ | O | $C_6H_5$ | H | H | H | $CF_3$ | H | H |
| 3 | 151N | $CF_3$ | $CH_3$ | O | H | $C_6H_5$ | H | H | $CF_3$ | H | H |
| 3 | 152N | $CF_3$ | $CH_3$ | O | CN | H | H | H | $CF_3$ | H | H |
| 3 | 153N | $CF_3$ | $CH_3$ | O | H | $OCF_3$ | H | H | $CF_3$ | H | H |
| 3 | 154N | $CF_3$ | $CH_3$ | O | $OCF_3$ | H | H | H | H | $CF_3$ | H |
| 3 | 155N | $CF_3$ | $CH_3$ | O | $C_6H_5O$ | H | H | H | H | $CF_3$ | H |
| 3 | 156N | $CF_3$ | $CH_3$ | O | $C_6H_5$ | H | H | H | H | $CF_3$ | H |
| 3 | 157N | $CF_3$ | $CH_3$ | O | H | $C_6H_5$ | H | H | H | $CF_3$ | H |
| 3 | 158N | $CF_3$ | $CH_3$ | O | CN | H | H | H | H | $CF_3$ | H |
| 3 | 159N | $CF_3$ | $CH_3$ | O | $OCF_3$ | H | H | H | H | $CF_3$ | H |
| 3 | 160N | $CF_3$ | $CH_3$ | O | $CF_3$ | H | H | H | H | $C_6H_5$ | H |
| 3 | 161N | $CF_3$ | $CH_3$ | O | $CF_3$ | H | H | H | 3-$CF_3$—$C_6H_5O$ | H | H |
| 3 | 162N | $CF_3$ | $CH_3$ | O | $CF_3$ | H | H | H | $C_6H_5O$ | H | H |
| 3 | 163N | $CF_3$ | $CH_3$ | O | $CF_3$ | H | H | H | $CF_3O$ | H | H |
| 3 | 164N | $CF_3$ | $CH_3$ | O | H | $CF_3$ | H | H | H | $C_6H_5$ | H |
| 3 | 165N | $CF_3$ | $CH_3$ | O | H | $CF_3$ | H | H | 3-$CF_3$—$C_6H_5O$ | H | H |
| 3 | 166N | $CF_3$ | $CH_3$ | O | H | $CF_3$ | H | H | $CF_3O$ | H | H |
| 3 | 167N | $CF_3$ | $CH_3$ | O | H | $CF_3$ | H | H | $C_6H_5O$ | H | H |
| 3 | 168N | $CF_3$ | $CH_3$ | O | $CF_3$ | H | $CF_3$ | H | $CF_3O$ | H | H |
| 3 | 169N | $CF_3$ | $CH_3$ | O | $CF_3$ | H | $CF_3$ | H | $C_6H_5O$ | H | H |
| 3 | 170N | $CF_3$ | $CH_3$ | O | $CF_3O$ | H | H | H | $CF_3$ | H | $CF_3$ |
| 3 | 171N | $CF_3$ | $CH_3$ | O | $C_6H_5O$ | H | H | H | $CF_3$ | H | $CF_3$ |
| 3 | 172N | $CF_3$ | $CH_3$ | O | H | $C_6H_5O$ | H | H | $C_6H_5O$ | H | H |
| 3 | 173N | $CF_3$ | $CH_3$ | O | H | $CF_3O$ | H | H | $CF_3O$ | H | H |
| 3 | 174N | $CF_3$ | $CH_3$ | O | H | $CF_3O$ | H | H | H | $C_6H_5O$ | H |
| 3 | 175N | $CF_3$ | $CH_3$ | O | $C_6H_5O$ | H | H | H | H | $C_6H_5O$ | H |
| 3 | 176N | $CF_3$ | $CH_3$ | O | H | $C_6H_5O$ | H | H | H | $OCF_3$ | H |
| 3 | 177N | $CF_3$ | $CH_3$ | O | H | $C_6H_5O$ | H | H | H | $C_6H_5O$ | H |
| 3 | 178N | $CF_3$ | $CH_3$ | O | $C_6H_5O$ | H | H | H | H | CN | H |
| 3 | 179N | $CF_3$ | $CH_3$ | O | $C_6H_5O$ | H | H | H | CN | H | H |
| 3 | 180N | $CF_3$ | $CH_3$ | O | $C_6H_5O$ | H | H | H | $NO_2$ | H | H |
| 3 | 181N | $CF_3$ | $CH_3$ | O | $C_6H_5O$ | H | H | H | H | $NO_2$ | H |
| 3 | 182N | $CF_3$ | $CH_3$ | O | $C_6H_5O$ | H | H | H | H | $SO_2CH_3$ | H |
| 3 | 183N | $CF_3$ | $CH_3$ | O | $C_6H_5O$ | H | H | H | H | 2-$NO_2$-4-Cl—$C_6H_3O$ | H |
| 3 | 184N | $CF_3$ | $CH_3$ | O | $C_6H_5O$ | H | H | H | 4-Cl—$C_6H_4O$ | H | H |
| 3 | 185N | $CF_3$ | $CH_3$ | O | $C_6H_5O$ | H | H | H | 3,4-Cl—$C_6H_3O$ | H | H |
| 3 | 186N | $CF_3$ | $CH_3$ | O | $C_6H_5O$ | H | H | H | 3-$CF_3$—$C_6H_3O$ | H | H |
| 3 | 187N | $CF_3$ | $CH_3$ | O | $C_6H_5O$ | H | H | H | 3,5-Cl—$C_6H_3O$ | H | H |
| 3 | 188N | $CF_3$ | $CH_3$ | O | $C_6H_5O$ | H | H | H | H | $CH_3O$ | H |
| 3 | 189N | $CF_3$ | $CH_3$ | O | $C_6H_5O$ | H | H | H | H | $CO_2CH_3$ | H |
| 3 | 190N | $CF_3$ | $CH_3$ | O | $C_6H_5O$ | H | H | H | 3-$CH_3O$ $C_6H_5O$ | H | H |
| 3 | 191N | $CF_3$ | $CH_3$ | O | $C_6H_5O$ | H | H | H | 4-$CH_3O$ $C_6H_5O$ | H | H |
| 3 | 193N | $CF_3$ | $CH_3$ | O | $C_6H_5O$ | H | H | H | $CO_2CH_3$ | H | H |
| 3 | 194N | $CF_3$ | $CH_3$ | O | CN | H | H | H | $OCF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

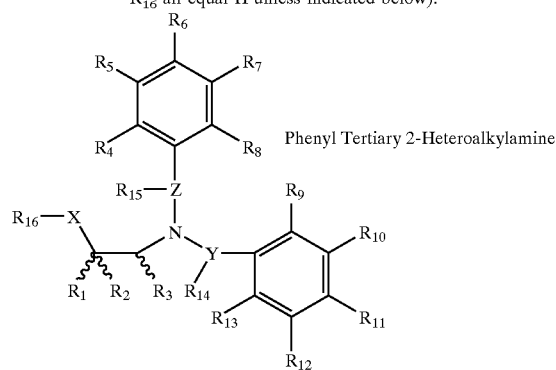

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 3 | 195N | $CF_3$ | $CH_3$ | O | $NO_2$ | H | H | H | $OCF_3$ | H | H |
| 3 | 196N | $CF_3$ | $CH_3$ | O | H | CN | H | H | $OCF_3$ | H | H |
| 3 | 197N | $CF_3$ | $CH_3$ | O | H | $NO_2$ | H | H | $OCF_3$ | H | H |
| 3 | 198N | $CF_3$ | $CH_3$ | O | $SO_2CH_3$ | H | H | H | $OCF_3$ | H | H |
| 3 | 199N | $CF_3$ | $CH_3$ | O | H | $SO_2CH_3$ | H | H | $OCF_3$ | H | H |
| 3 | 200N | $CF_3$ | $CH_3$ | O | H | 4-F—$C_6H_5SO_2$ | H | H | $OCF_3$ | H | H |
| 3 | 201N | $CF_3$ | $CH_3$ | O | $SO_2N(CH_3)_2$ | H | H | H | $OCF_3$ | H | H |
| 3 | 202N | $CF_3$ | $CH_3$ | O | H | $SO_2N(CH_3)_2$ | H | H | $OCF_3$ | H | H |
| 3 | 203N | $CF_3$ | $CH_3$ | O | H | $CONH_2$ | H | H | $OCF_3$ | H | H |
| 3 | 204N | $CF_3$ | $CH_3$ | O | H | CONH—$C_6H_5$ | H | H | $OCF_3$ | H | H |
| 3 | 205N | $CF_3$ | $CH_3$ | O | H | $CO_2CH_3$ | H | H | $OCF_3$ | H | H |
| 3 | 206N | $CF_3$ | $CH_3$ | O | H | $CO_2C_4H_9$ | H | H | $OCF_3$ | H | H |
| 3 | 207N | $CF_3$ | $CH_3$ | O | H | 4-Cl—$C_6H_5$ | H | H | $C_6H_5O$ | H | H |
| 3 | 208N | $CF_3$ | $CH_3$ | O | H | 4-$CF_3O$—$C_6H_5$ | H | H | $CF_3O$ | H | H |
| 3 | 209N | $CF_3$ | $CH_3$ | O | 4-F—$C_6H_4O$ | H | H | H | $CF_3O$ | H | H |
| 3 | 210N | $CF_3$ | $CH_3$ | O | $C_6F_5O$ | H | H | H | $CF_3O$ | H | H |
| 3 | 211N | $CF_3$ | $CH_3$ | O | H | 4-F—$C_6H_5$ | H | H | $CF_3O$ | H | H |
| 3 | 212N | $CF_3$ | $CH_3$ | O | H | 4-CN—$C_6H_5$ | H | H | $CF_3O$ | H | H |
| 3 | 213N | $CF_3$ | $CH_3$ | O | H | 4-$C_6H_5$—$C_6H_5$ | H | H | $CF_3O$ | H | H |
| 3 | 214N | $CF_3$ | $CH_3$ | O | $C_6H_5O$ | H | H | $CH_3$ | $CF_3O$ | H | H |
| 3 | 215N | $CF_3$ | $CH_3$ | O | $C_6H_5O$ | H | H | $CH_3$ | $NO_2$ | H | H |
| 3 | 216N | $CF_3$ | $CH_3$ | O | $C_6H_5O$ | H | H | $CH_3$ | H | CN | H |
| 3 | 217N | $CF_3$ | $CH_3$ | O | $C_6H_5O$ | H | H | 3-$CF_3$ $C_6H_5$ | $CF_3$ | H | H |
| 3 | 218N | $CF_3$ | $CH_3$ | O | $C_6H_5O$ | H | H | $C_6H_5$ | H | $C_6H_5$ | H |
| 3 | 219N | $CF_3$ | $CH_3$ | O | $C_6H_5O$ | H | H | $C_6H_5$ | $CF_3$ | H | H |
| 3 | 220N | $CF_3$ | $CH_3$ | O | $C_6H_5O$ | H | H | $CH_3$ | F | H | H |
| 3 | 221N | $CF_3$ | $CH_3$ | O | $C_6H_5O$ | H | H | $CF_3$ | H | H | H |
| 3 | 222N | $CF_3$ | $CH_3$ | O | bond to —O— of $R_6$ aryl group | (2-methylphenyl-O-) | H | H | $CF_3O$ | H | H |
| 3 | 223N | $CF_3$ | $CH_3$ | O | to $CH_2$ of $R_6$ aryl group | (Br, methyl substituted phenyl) | H | H | $CF_3O$ | H | H |
| 4 | 96N | $CF_3CF_2$ | H | O | OH | OH | H | H | $C_6H_5O$ | H | H |
| 4 | 97N | $CF_3CF_2$ | H | O | $C_6H_5O$ | H | H | H | OH | OH | H |
| 4 | 98N | $CF_3CF_2$ | H | O | 3-pyridyl | H | H | H | $CF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

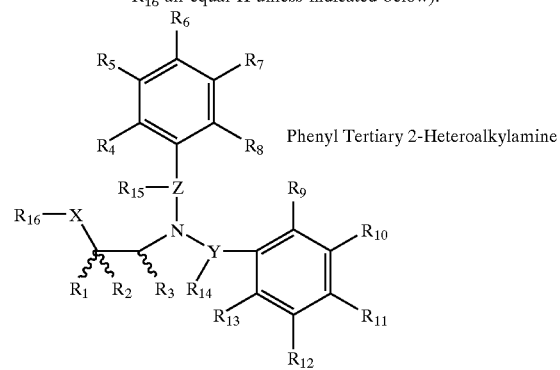

Phenyl Tertiary 2-Heteroalkylamine

Inhibitor Number Column 1 + Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 4 | 99N | $CF_3CF_2$ | H | O | $SO_2N(CH_3)_2$ | H | H | H | $OCF_3$ | H | H |
| 4 | 100N | $CF_3CF_2$ | H | O | $SO_2CH_3$ | H | H | H | $OCF_3$ | H | H |
| 4 | 101N | $CF_3CF_2$ | H | O | $C_6H_5O$ | H | H | H | $C_6H_5O$ | H | H |
| 4 | 102N | $CF_3CF_2$ | H | O | $CF_3O$ | H | H | H | $C_6H_5O$ | H | H |
| 4 | 103N | $CF_3CF_2$ | H | O | $C_6H_5$ | H | H | H | $C_6H_5O$ | H | H |
| 4 | 104N | $CF_3CF_2$ | H | O | H | $C_6H_5$ | H | H | $C_6H_5O$ | H | H |
| 4 | 105N | $CF_3CF_2$ | H | O | $C_6H_5O$ | H | H | H | 4-Cl—$C_6H_4O$ | H | H |
| 4 | 106N | $CF_3CF_2$ | H | O | $CF_3O$ | H | H | H | 4-Cl—$C_6H_4O$ | H | H |
| 4 | 107N | $CF_3CF_2$ | H | O | $C_6H_5O$ | H | H | H | 3,4-Cl—$C_6H_3O$ | H | H |
| 4 | 108N | $CF_3CF_2$ | H | O | $CF_3O$ | H | H | H | 3,4-Cl—$C_6H_3O$ | H | H |
| 4 | 109N | $CF_3CF_2$ | H | O | $CF_3O$ | H | H | H | 3,5-Cl—$C_6H_3O$ | H | H |
| 4 | 110N | $CF_3CF_2$ | H | O | $CF_3O$ | H | H | H | 3-$CH_3O$—$C_6H_4O$ | H | H |
| 4 | 111N | $CF_3CF_2$ | H | O | $CF_3O$ | H | H | H | H | 3-$CH_3O$—$C_6H_4O$ | H |
| 4 | 112N | $CF_3CF_2$ | H | O | $CF_3O$ | H | H | H | 3-$CF_3$—$C_6H_4O$ | H | H |
| 4 | 113N | $CF_3CF_2$ | H | O | $CF_3O$ | H | H | H | $C_6H_5$—$CH_2O$ | H | H |
| 4 | 114N | $CF_3CF_2$ | H | O | $CF_3O$ | H | H | H | $C_6H_5$—$CH_2O$ | $CH_3O$ | H |
| 4 | 115N | $CF_3CF_2$ | H | O | $CF_3O$ | H | H | H | $C_6H_5$—$CH_2O$ | $C_6H_5$—$CH_2O$ | H |
| 4 | 116N | $CF_3CF_2$ | H | O | $CF_3O$ | H | H | H | ethoxy | H | H |
| 4 | 117N | $CF_3CF_2$ | H | O | $CF_3O$ | H | H | H | $CH_3CO_2$ | H | H |
| 4 | 118N | $CF_3CF_2$ | H | O | $CF_3O$ | H | H | H | $HOCH_2$—$CH_2O$ | H | H |
| 4 | 119N | $CF_3CF_2$ | H | O | $CF_3O$ | H | H | H | (glycidyloxy) | H | H |
| 4 | 120N | $CF_3CF_2$ | H | O | $CF_3O$ | H | H | H | $R_{10} + R_{11} = OCH_2O$ | | H |
| 4 | 121N | $CF_3CF_2$ | H | O | $CF_3O$ | H | H | H | $R_{10} + R_{11} = OCH_2CH_2O$ | | H |
| 4 | 122N | $CF_3CF_2$ | H | O | $CF_3O$ | H | H | H | $CH_3O$ | $CH_3O$ | H |
| 4 | 123N | $CF_3CF_2$ | H | O | $CF_3O$ | H | H | H | ethoxy | $CH_3O$ | H |
| 4 | 124N | $CF_3CF_2$ | H | O | $CF_3O$ | H | H | H | ethoxy | ethoxy | H |
| 4 | 125N | $CF_3CF_2$ | H | O | $CF_3O$ | H | H | H | $CH_3CO_2$ | $CH_3CO_2$ | H |
| 4 | 126N | $CF_3CF_2$ | H | O | $CF_3O$ | H | H | H | $CH_3O$ | $CH_3CO_2$ | H |
| 4 | 127N | $CF_3CF_2$ | H | O | $CF_3O$ | H | H | H | n-butoxy | H | H |
| 4 | 128N | $CF_3CF_2$ | H | O | $CF_3O$ | H | H | H | $CH_3O$ | H | H |
| 4 | 129N | $CF_3CF_2$ | H | O | $CF_3O$ | H | H | H | H | $CH_3O$ | H |
| 4 | 130N | $CF_3CF_2$ | H | O | $CH_3O$ | H | H | H | $CH_3O$ | H | H |
| 4 | 131N | $CF_3CF_2$ | H | O | $CH_3O$ | H | H | H | H | $CF_3O$ | H |
| 4 | 132N | $CF_3CF_2$ | H | O | $CF_3O$ | H | H | H | H | ethoxy | H |
| 4 | 133N | $CF_3CF_2$ | H | O | $CF_3O$ | H | H | H | H | n-propoxy | H |
| 4 | 134N | $CF_3CF_2$ | H | O | $C_6H_5$—$CH_2O$ | H | H | H | $CF_3O$ | H | H |
| 4 | 135N | $CF_3CF_2$ | H | O | $C_6H_5$—$CH_2O$ | H | H | H | $C_6H_5O$ | H | H |
| 4 | 136N | $CF_3CF_2$ | H | O | ethoxy | H | H | H | $CF_3O$ | H | H |
| 4 | 137N | $CF_3CF_2$ | H | O | $R_5 + R_6 = OCH_2O$ | | H | H | $CF_3O$ | H | H |
| 4 | 138N | $CF_3CF_2$ | H | O | $R_5 + R_6 = OCH_2O$ | | H | H | $C_6H_5O$ | H | H |
| 4 | 139N | $CF_3CF_2$ | H | O | $R_5 + R_6 = OCH_2CH_2O$ | | H | H | $CF_3O$ | H | H |
| 4 | 140N | $CF_3CF_2$ | H | O | $CH_3O$ | $CH_3O$ | H | H | $CF_3O$ | H | H |
| 4 | 141N | $CF_3CF_2$ | H | O | $R_5 + R_6 = OCH_2CH_2CH_2O$ | | H | H | $CF_3O$ | H | H |
| 4 | 142N | $CF_3CF_2$ | H | O | cyclo pentoxy | $CH_3O$ | H | H | $CF_3O$ | H | H |
| 4 | 143N | $CF_3CF_2$ | H | O | H | $C_6H_5$ | H | H | $CF_3O$ | H | H |
| 4 | 144N | $CF_3CF_2$ | H | O | $CH_3O$ | $CH_3O$ | $CH_3O$ | H | $CF_3O$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

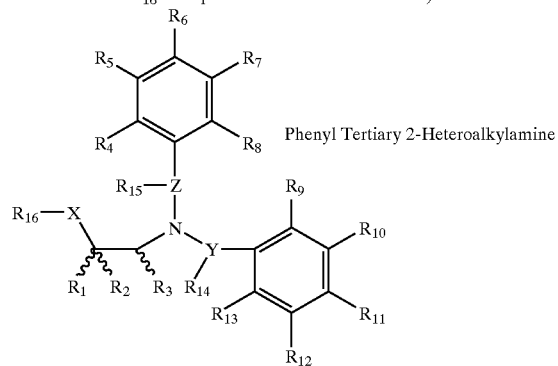

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 4 | 145N | $CF_3CF_2$ | H | O | H | $CF_3O$ | H | H | $CF_3O$ | H | H |
| 4 | 146N | $CF_3CF_2$ | H | O | H | $C_6H_5$—$CH_2$ | H | H | $CF_3O$ | H | H |
| 4 | 147N | $CF_3CF_2$ | H | O | $C_6H_5O$ | H | H | H | $R_{10} + R_{11} = OCH_2CH_2O$ | | H |
| 4 | 148N | $CF_3CF_2$ | H | O | H | $CF_3O$ | H | H | $CF_3$ | H | H |
| 4 | 149N | $CF_3CF_2$ | H | O | $C_6H_5O$ | H | H | H | $CF_3$ | H | H |
| 4 | 150N | $CF_3CF_2$ | H | O | $C_6H_5$ | H | H | H | $CF_3$ | H | H |
| 4 | 151N | $CF_3CF_2$ | H | O | H | $C_6H_5$ | H | H | $CF_3$ | H | H |
| 4 | 152N | $CF_3CF_2$ | H | O | CN | H | H | H | $CF_3$ | H | H |
| 4 | 153N | $CF_3CF_2$ | H | O | H | $OCF_3$ | H | H | $CF_3$ | H | H |
| 4 | 154N | $CF_3CF_2$ | H | O | $OCF_3$ | H | H | H | H | $CF_3$ | H |
| 4 | 155N | $CF_3CF_2$ | H | O | $C_6H_5O$ | H | H | H | H | $CF_3$ | H |
| 4 | 156N | $CF_3CF_2$ | H | O | $C_6H_5$ | H | H | H | H | $CF_3$ | H |
| 4 | 157N | $CF_3CF_2$ | H | O | H | $C_6H_5$ | H | H | H | $CF_3$ | H |
| 4 | 158N | $CF_3CF_2$ | H | O | CN | H | H | H | H | $CF_3$ | H |
| 4 | 159N | $CF_3CF_2$ | H | O | $OCF_3$ | H | H | H | H | $CF_3$ | H |
| 4 | 160N | $CF_3CF_2$ | H | O | $CF_3$ | H | H | H | H | $C_6H_5$ | H |
| 4 | 161N | $CF_3CF_2$ | H | O | $CF_3$ | H | H | H | 3-$CF_3$—$C_6H_5O$ | H | H |
| 4 | 162N | $CF_3CF_2$ | H | O | $CF_3$ | H | H | H | $C_6H_5O$ | H | H |
| 4 | 163N | $CF_3CF_2$ | H | O | $CF_3$ | H | H | H | $CF_3O$ | H | H |
| 4 | 164N | $CF_3CF_2$ | H | O | H | $CF_3$ | H | H | H | $C_6H_5$ | H |
| 4 | 165N | $CF_3CF_2$ | H | O | H | $CF_3$ | H | H | 3-$CF_3$—$C_6H_5O$ | H | H |
| 4 | 166N | $CF_3CF_2$ | H | O | H | $CF_3$ | H | H | $CF_3O$ | H | H |
| 4 | 167N | $CF_3CF_2$ | H | O | H | $CF_3$ | H | H | $C_6H_5O$ | H | H |
| 4 | 168N | $CF_3CF_2$ | H | O | $CF_3$ | H | $CF_3$ | H | $CF_3O$ | H | H |
| 4 | 169N | $CF_3CF_2$ | H | O | $CF_3$ | H | $CF_3$ | H | $C_6H_5O$ | H | H |
| 4 | 170N | $CF_3CF_2$ | H | O | $CF_3O$ | H | H | H | $CF_3$ | H | $CF_3$ |
| 4 | 171N | $CF_3CF_2$ | H | O | $C_6H_5O$ | H | H | H | $CF_3$ | H | $CF_3$ |
| 4 | 172N | $CF_3CF_2$ | H | O | H | $C_6H_5O$ | H | H | $C_6H_5O$ | H | H |
| 4 | 173N | $CF_3CF_2$ | H | O | H | $CF_3O$ | H | H | $CF_3O$ | H | H |
| 4 | 174N | $CF_3CF_2$ | H | O | H | $CF_3O$ | H | H | H | $C_6H_5O$ | H |
| 4 | 175N | $CF_3CF_2$ | H | O | $C_6H_5O$ | H | H | H | H | $C_6H_5O$ | H |
| 4 | 176N | $CF_3CF_2$ | H | O | H | $C_6H_5O$ | H | H | H | $OCF_3$ | H |
| 4 | 177N | $CF_3CF_2$ | H | O | H | $C_6H_5O$ | H | H | H | $C_6H_5O$ | H |
| 4 | 178N | $CF_3CF_2$ | H | O | $C_6H_5O$ | H | H | H | H | CN | H |
| 4 | 179N | $CF_3CF_2$ | H | O | $C_6H_5O$ | H | H | H | CN | H | H |
| 4 | 180N | $CF_3CF_2$ | H | O | $C_6H_5O$ | H | H | H | $NO_2$ | H | H |
| 4 | 181N | $CF_3CF_2$ | H | O | $C_6H_5O$ | H | H | H | H | $NO_2$ | H |
| 4 | 182N | $CF_3CF_2$ | H | O | $C_6H_5O$ | H | H | H | H | $SO_2CH_3$ | H |
| 4 | 183N | $CF_3CF_2$ | H | O | $C_6H_5O$ | H | H | H | H | 2-$NO_2$-4-Cl—$C_6H_3O$ | H |
| 4 | 184N | $CF_3CF_2$ | H | O | $C_6H_5O$ | H | H | H | 4-Cl—$C_6H_4O$ | H | H |
| 4 | 185N | $CF_3CF_2$ | H | O | $C_6H_5O$ | H | H | H | 3,4-Cl—$C_6H_3O$ | H | H |
| 4 | 186N | $CF_3CF_2$ | H | O | $C_6H_5O$ | H | H | H | 3-$CF_3$—$C_6H_3O$ | H | H |
| 4 | 187N | $CF_3CF_2$ | H | O | $C_6H_5O$ | H | H | H | 3,5-Cl—$C_6H_3O$ | H | H |
| 4 | 188N | $CF_3CF_2$ | H | O | $C_6H_5O$ | H | H | H | H | $CH_3O$ | H |
| 4 | 189N | $CF_3CF_2$ | H | O | $C_6H_5O$ | H | H | H | H | $CO_2CH_3$ | H |
| 4 | 190N | $CF_3CF_2$ | H | O | $C_6H_5O$ | H | H | H | 3-$CH_3O$ $C_6H_5O$ | H | H |
| 4 | 191N | $CF_3CF_2$ | H | O | $C_6H_5O$ | H | H | H | 4-$CH_3O$ $C_6H_5O$ | H | H |
| 4 | 193N | $CF_3CF_2$ | H | O | $C_6H_5O$ | H | H | H | $CO_2CH_3$ | H | H |
| 4 | 194N | $CF_3CF_2$ | H | O | CN | H | H | H | $OCF_3$ | H | H |
| 4 | 195N | $CF_3CF_2$ | H | O | $NO_2$ | H | H | H | $OCF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

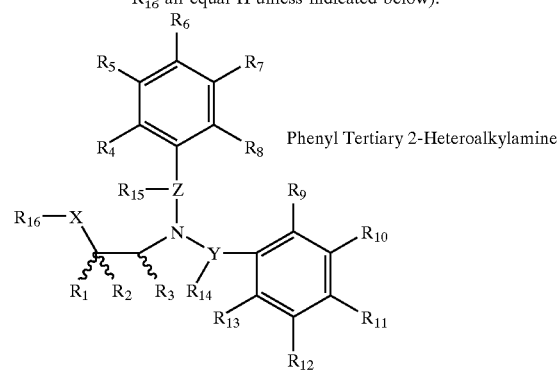

Phenyl Tertiary 2-Heteroalkylamine

Inhibitor Number
Column 1 + Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 4 | 196N | $CF_3CF_2$ | H | O | H | CN | H | H | $OCF_3$ | H | H |
| 4 | 197N | $CF_3CF_2$ | H | O | H | $NO_2$ | H | H | $OCF_3$ | H | H |
| 4 | 198N | $CF_3CF_2$ | H | O | $SO_2CH_3$ | H | H | H | $OCF_3$ | H | H |
| 4 | 199N | $CF_3CF_2$ | H | O | H | $SO_2CH_3$ | H | H | $OCF_3$ | H | H |
| 4 | 200N | $CF_3CF_2$ | H | O | H | 4-F—$C_6H_5SO_2$ | H | H | $OCF_3$ | H | H |
| 4 | 201N | $CF_3CF_2$ | H | O | $SO_2N(CH_3)_2$ | H | H | H | $OCF_3$ | H | H |
| 4 | 202N | $CF_3CF_2$ | H | O | H | $SO_2N(CH_3)_2$ | H | H | $OCF_3$ | H | H |
| 4 | 203N | $CF_3CF_2$ | H | O | H | $CONH_2$ | H | H | $OCF_3$ | H | H |
| 4 | 204N | $CF_3CF_2$ | H | O | H | CONH—$C_6H_5$ | H | H | $OCF_3$ | H | H |
| 4 | 205N | $CF_3CF_2$ | H | O | H | $CO_2CH_3$ | H | H | $OCF_3$ | H | H |
| 4 | 206N | $CF_3CF_2$ | H | O | H | $CO_2C_4H_9$ | H | H | $OCF_3$ | H | H |
| 4 | 207N | $CF_3CF_2$ | H | O | H | 4-Cl—$C_6H_5$ | H | H | $C_6H_5O$ | H | H |
| 4 | 208N | $CF_3CF_2$ | H | O | H | 4-$CF_3$O—$C_6H_5$ | H | H | $CF_3O$ | H | H |
| 4 | 209N | $CF_3CF_2$ | H | O | 4-F—$C_6H_4O$ | H | H | H | $CF_3O$ | H | H |
| 4 | 210N | $CF_3CF_2$ | H | O | $C_6F_5O$ | H | H | H | $CF_3O$ | H | H |
| 4 | 211N | $CF_3CF_2$ | H | O | H | 4-F—$C_6H_5$ | H | H | $CF_3O$ | H | H |
| 4 | 212N | $CF_3CF_2$ | H | O | H | 4-CN—$C_6H_5$ | H | H | $CF_3O$ | H | H |
| 4 | 213N | $CF_3CF_2$ | H | O | H | 4-$C_6H_5$—$C_6H_5$ | H | H | $CF_3O$ | H | H |
| 4 | 214N | $CF_3CF_2$ | H | O | $C_6H_5O$ | H | H | $CH_3$ | $CF_3O$ | H | H |
| 4 | 215N | $CF_3CF_2$ | H | O | $C_6H_5O$ | H | H | $CH_3$ | $NO_2$ | H | H |
| 4 | 216N | $CF_3CF_2$ | H | O | $C_6H_5O$ | H | H | $CH_3$ | H | CN | H |
| 4 | 217N | $CF_3CF_2$ | H | O | $C_6H_5O$ | H | H | 3-$CF_3$ $C_6H_5$ | $CF_3$ | H | H |
| 4 | 218N | $CF_3CF_2$ | H | O | $C_6H_5O$ | H | H | $C_6H_5$ | H | $C_6H_5$ | H |
| 4 | 219N | $CF_3CF_2$ | H | O | $C_6H_5O$ | H | H | $C_6H_5$ | $CF_3$ | H | H |
| 4 | 220N | $CF_3CF_2$ | H | O | $C_6H_5O$ | H | H | $CH_3$ | F | H | H |
| 4 | 221N | $CF_3CF_2$ | H | O | $C_6H_5O$ | H | H | $CF_3$ | H | H | H |
| 4 | 222N | $CF_3CF_2$ | H | O | bond to —O— of $R_6$ aryl group | ![structure] | H | H | $CF_3O$ | H | H |
| 4 | 223N | $CF_3CF_2$ | H | O | to $CH_2$ of $R_6$ aryl group | ![structure with Br] | H | H | $CF_3O$ | H | H |
| 5 | 96N | $CF_3CF_2CF_2$ | H | O | OH | OH | H | H | $C_6H_5O$ | H | H |
| 5 | 97N | $CF_3CF_2CF_2$ | H | O | $C_6H_5O$ | H | H | H | OH | OH | H |
| 5 | 98N | $CF_3CF_2CF_2$ | H | O | 3-pyridyl | H | H | H | $CF_3$ | H | H |
| 5 | 99N | $CF_3CF_2CF_2$ | H | O | $SO_2N$ | H | H | H | $OCF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

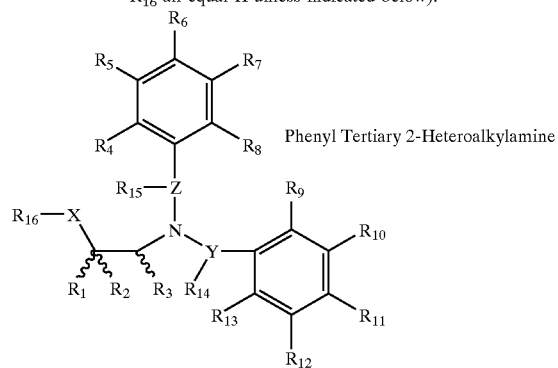

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 5 | 100N | $CF_3CF_2CF_2$ | H | O | $(CH_3)_2$ $SO_2CH_3$ | H | H | H | $OCF_3$ | H | H |
| 5 | 101N | $CF_3CF_2CF_2$ | H | O | $C_6H_5O$ | H | H | H | $C_6H_5O$ | H | H |
| 5 | 102N | $CF_3CF_2CF_2$ | H | O | $CF_3O$ | H | H | H | $C_6H_5O$ | H | H |
| 5 | 103N | $CF_3CF_2CF_2$ | H | O | $C_6H_5$ | H | H | H | $C_6H_5O$ | H | H |
| 5 | 104N | $CF_3CF_2CF_2$ | H | O | H | $C_6H_5$ | H | H | $C_6H_5O$ | H | H |
| 5 | 105N | $CF_3CF_2CF_2$ | H | O | $C_6H_5O$ | H | H | H | 4-Cl—$C_6H_4O$ | H | H |
| 5 | 106N | $CF_3CF_2CF_2$ | H | O | $CF_3O$ | H | H | H | 4-Cl—$C_6H_4O$ | H | H |
| 5 | 107N | $CF_3CF_2CF_2$ | H | O | $C_6H_5O$ | H | H | H | 3,4-Cl—$C_6H_3O$ | H | H |
| 5 | 108N | $CF_3CF_2CF_2$ | H | O | $CF_3O$ | H | H | H | 3,4-Cl—$C_6H_3O$ | H | H |
| 5 | 109N | $CF_3CF_2CF_2$ | H | O | $CF_3O$ | H | H | H | 3,5-Cl—$C_6H_3O$ | H | H |
| 5 | 110N | $CF_3CF_2CF_2$ | H | O | $CF_3O$ | H | H | H | 3-$CH_3O$—$C_6H_4O$ | H | H |
| 5 | 111N | $CF_3CF_2CF_2$ | H | O | $CF_3O$ | H | H | H | H | 3-$CH_3O$—$C_6H_4O$ | H |
| 5 | 112N | $CF_3CF_2CF_2$ | H | O | $CF_3O$ | H | H | H | 3-$CF_3$—$C_6H_4O$ | H | H |
| 5 | 113N | $CF_3CF_2CF_2$ | H | O | $CF_3O$ | H | H | H | $C_6H_5$—$CH_2O$ | H | H |
| 5 | 114N | $CF_3CF_2CF_2$ | H | O | $CF_3O$ | H | H | H | $C_6H_5$—$CH_2O$ | $CH_3O$ | H |
| 5 | 115N | $CF_3CF_2CF_2$ | H | O | $CF_3O$ | H | H | H | $C_6H_5$—$CH_2O$ | $C_6H_5$—$CH_2O$ | H |
| 5 | 116N | $CF_3CF_2CF_2$ | H | O | $CF_3O$ | H | H | H | ethoxy | H | H |
| 5 | 117N | $CF_3CF_2CF_2$ | H | O | $CF_3O$ | H | H | H | $CH_3CO_2$ | H | H |
| 5 | 118N | $CF_3CF_2CF_2$ | H | O | $CF_3O$ | H | H | H | $HOCH_2$—$CH_2O$ | H | H |
| 5 | 119N | $CF_3CF_2CF_2$ | H | O | $CF_3O$ | H | H | H | (oxiranylmethoxy) | H | H |
| 5 | 120N | $CF_3CF_2CF_2$ | H | O | $CF_3O$ | H | H | H | $R_{10}$ + $R_{11}$ = $OCH_2O$ | | H |
| 5 | 121N | $CF_3CF_2CF_2$ | H | O | $CF_3O$ | H | H | H | $R_{10}$ + $R_{11}$ = $OCH_2CH_2O$ | | H |
| 5 | 122N | $CF_3CF_2CF_2$ | H | O | $CF_3O$ | H | H | H | $CH_3O$ | $CH_3O$ | H |
| 5 | 123N | $CF_3CF_2CF_2$ | H | O | $CF_3O$ | H | H | H | ethoxy | $CH_3O$ | H |
| 5 | 124N | $CF_3CF_2CF_2$ | H | O | $CF_3O$ | H | H | H | ethoxy | ethoxy | H |
| 5 | 125N | $CF_3CF_2CF_2$ | H | O | $CF_3O$ | H | H | H | $CH_3CO_2$ | $CH_3CO_2$ | H |
| 5 | 126N | $CF_3CF_2CF_2$ | H | O | $CF_3O$ | H | H | H | $CH_3O$ | $CH_3CO_2$ | H |
| 5 | 127N | $CF_3CF_2CF_2$ | H | O | $CF_3O$ | H | H | H | n-butoxy | H | H |
| 5 | 128N | $CF_3CF_2CF_2$ | H | O | $CF_3O$ | H | H | H | $CH_3O$ | H | H |
| 5 | 129N | $CF_3CF_2CF_2$ | H | O | $CF_3O$ | H | H | H | H | $CH_3O$ | H |
| 5 | 130N | $CF_3CF_2CF_2$ | H | O | $CH_3O$ | H | H | H | $CH_3O$ | H | H |
| 5 | 131N | $CF_3CF_2CF_2$ | H | O | $CH_3O$ | H | H | H | H | $CF_3O$ | H |
| 5 | 132N | $CF_3CF_2CF_2$ | H | O | $CF_3O$ | H | H | H | H | ethoxy | H |
| 5 | 133N | $CF_3CF_2CF_2$ | H | O | $CF_3O$ | H | H | H | H | n-propoxy | H |
| 5 | 134N | $CF_3CF_2CF_2$ | H | O | $C_6H_5$—$CH_2O$ | H | H | H | $CF_3O$ | H | H |
| 5 | 135N | $CF_3CF_2CF_2$ | H | O | $C_6H_5$—$CH_2O$ | H | H | H | $C_6H_5O$ | H | H |
| 5 | 136N | $CF_3CF_2CF_2$ | H | O | ethoxy | H | H | H | $CF_3O$ | H | H |
| 5 | 137N | $CF_3CF_2CF_2$ | H | O | $R_5$ + $R_6$ = $OCH_2O$ | | H | H | $CF_3O$ | H | H |
| 5 | 138N | $CF_3CF_2CF_2$ | H | O | $R_5$ + $R_6$ = $OCH_2O$ | | H | H | $C_6H_5O$ | H | H |
| 5 | 139N | $CF_3CF_2CF_2$ | H | O | $R_5$ + $R_6$ = $OCH_2CH_2O$ | | H | H | $CF_3O$ | H | H |
| 5 | 140N | $CF_3CF_2CF_2$ | H | O | $CH_3O$ | $CH_3O$ | H | H | $CF_3O$ | H | H |
| 5 | 141N | $CF_3CF_2CF_2$ | H | O | $R_5$ + $R_6$ = $OCH_2CH_2CH_2O$ | | H | H | $CF_3O$ | H | H |
| 5 | 142N | $CF_3CF_2CF_2$ | H | O | cyclo pentoxy | $CH_3O$ | H | H | $CF_3O$ | H | H |
| 5 | 143N | $CF_3CF_2CF_2$ | H | O | H | $C_6H_5O$ | H | H | $CF_3O$ | H | H |
| 5 | 144N | $CF_3CF_2CF_2$ | H | O | $CH_3O$ | $CH_3O$ | $CH_3O$ | H | $CF_3O$ | H | H |
| 5 | 145N | $CF_3CF_2CF_2$ | H | O | H | $CF_3O$ | H | H | $CF_3O$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

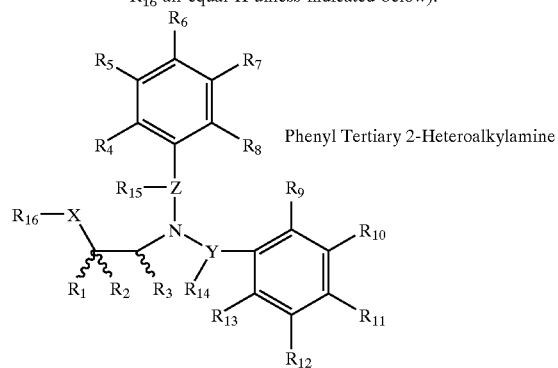

Phenyl Tertiary 2-Heteroalkylamine

Inhibitor Number
Column 1 +
Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 5 | 146N | $CF_3CF_2CF_2$ | H | O | H | $C_6H_5$—$CH_2$ | H | H | $CF_3O$ | H | H |
| 5 | 147N | $CF_3CF_2CF_2$ | H | O | $C_6H_5O$ | H | H | H | $R_{10} + R_{11} = OCH_2CH_2O$ | | H |
| 5 | 148N | $CF_3CF_2CF_2$ | H | O | H | $CF_3O$ | H | H | $CF_3$ | H | H |
| 5 | 149N | $CF_3CF_2CF_2$ | H | O | $C_6H_5O$ | H | H | H | $CF_3$ | H | H |
| 5 | 150N | $CF_3CF_2CF_2$ | H | O | $C_6H_5$ | H | H | H | $CF_3$ | H | H |
| 5 | 151N | $CF_3CF_2CF_2$ | H | O | H | $C_6H_5$ | H | H | $CF_3$ | H | H |
| 5 | 152N | $CF_3CF_2CF_2$ | H | O | CN | H | H | H | $CF_3$ | H | H |
| 5 | 153N | $CF_3CF_2CF_2$ | H | O | H | $OCF_3$ | H | H | $CF_3$ | H | H |
| 5 | 154N | $CF_3CF_2CF_2$ | H | O | $OCF_3$ | H | H | H | H | $CF_3$ | H |
| 5 | 155N | $CF_3CF_2CF_2$ | H | O | $C_6H_5O$ | H | H | H | H | $CF_3$ | H |
| 5 | 156N | $CF_3CF_2CF_2$ | H | O | $C_6H_5$ | H | H | H | H | $CF_3$ | H |
| 5 | 157N | $CF_3CF_2CF_2$ | H | O | H | $C_6H_5$ | H | H | H | $CF_3$ | H |
| 5 | 158N | $CF_3CF_2CF_2$ | H | O | CN | H | H | H | H | $CF_3$ | H |
| 5 | 159N | $CF_3CF_2CF_2$ | H | O | $OCF_3$ | H | H | H | H | $CF_3$ | H |
| 5 | 160N | $CF_3CF_2CF_2$ | H | O | $CF_3$ | H | H | H | H | $C_6H_5$ | H |
| 5 | 161N | $CF_3CF_2CF_2$ | H | O | $CF_3$ | H | H | H | 3-$CF_3$—$C_6H_5O$ | H | H |
| 5 | 162N | $CF_3CF_2CF_2$ | H | O | $CF_3$ | H | H | H | $C_6H_5O$ | H | H |
| 5 | 163N | $CF_3CF_2CF_2$ | H | O | $CF_3$ | H | H | H | $CF_3O$ | H | H |
| 5 | 164N | $CF_3CF_2CF_2$ | H | O | H | $CF_3$ | H | H | H | $C_6H_5$ | H |
| 5 | 165N | $CF_3CF_2CF_2$ | H | O | H | $CF_3$ | H | H | 3-$CF_3$—$C_6H_5O$ | H | H |
| 5 | 166N | $CF_3CF_2CF_2$ | H | O | H | $CF_3$ | H | H | $CF_3O$ | H | H |
| 5 | 167N | $CF_3CF_2CF_2$ | H | O | H | $CF_3$ | H | H | $C_6H_5O$ | H | H |
| 5 | 168N | $CF_3CF_2CF_2$ | H | O | $CF_3$ | H | $CF_3$ | H | $CF_3O$ | H | H |
| 5 | 169N | $CF_3CF_2CF_2$ | H | O | $CF_3$ | H | $CF_3$ | H | $C_6H_5O$ | H | H |
| 5 | 170N | $CF_3CF_2CF_2$ | H | O | $CF_3O$ | H | H | H | $CF_3$ | H | $CF_3$ |
| 5 | 171N | $CF_3CF_2CF_2$ | H | O | $C_6H_5O$ | H | H | H | $CF_3$ | H | $CF_3$ |
| 5 | 172N | $CF_3CF_2CF_2$ | H | O | H | $C_6H_5O$ | H | H | $C_6H_5O$ | H | H |
| 5 | 173N | $CF_3CF_2CF_2$ | H | O | H | $CF_3O$ | H | H | $CF_3O$ | H | H |
| 5 | 174N | $CF_3CF_2CF_2$ | H | O | H | $CF_3O$ | H | H | H | $C_6H_5O$ | H |
| 5 | 175N | $CF_3CF_2CF_2$ | H | O | $C_6H_5O$ | H | H | H | H | $C_6H_5O$ | H |
| 5 | 176N | $CF_3CF_2CF_2$ | H | O | H | $C_6H_5O$ | H | H | H | $OCF_3$ | H |
| 5 | 177N | $CF_3CF_2CF_2$ | H | O | H | $C_6H_5O$ | H | H | H | $C_6H_5O$ | H |
| 5 | 178N | $CF_3CF_2CF_2$ | H | O | $C_6H_5O$ | H | H | H | H | CN | H |
| 5 | 179N | $CF_3CF_2CF_2$ | H | O | $C_6H_5O$ | H | H | H | CN | H | H |
| 5 | 180N | $CF_3CF_2CF_2$ | H | O | $C_6H_5O$ | H | H | H | $NO_2$ | H | H |
| 5 | 181N | $CF_3CF_2CF_2$ | H | O | $C_6H_5O$ | H | H | H | H | $NO_2$ | H |
| 5 | 182N | $CF_3CF_2CF_2$ | H | O | $C_6H_5O$ | H | H | H | H | $SO_2CH_3$ | H |
| 5 | 183N | $CF_3CF_2CF_2$ | H | O | $C_6H_5O$ | H | H | H | H | 2-$NO_2$-4-Cl—$C_6H_3O$ | H |
| 5 | 184N | $CF_3CF_2CF_2$ | H | O | $C_6H_5O$ | H | H | H | 4-Cl—$C_6H_4O$ | H | H |
| 5 | 185N | $CF_3CF_2CF_2$ | H | O | $C_6H_5O$ | H | H | H | 3,4-Cl—$C_6H_3O$ | H | H |
| 5 | 186N | $CF_3CF_2CF_2$ | H | O | $C_6H_5O$ | H | H | H | 3-$CF_3$—$C_6H_5O$ | H | H |
| 5 | 187N | $CF_3CF_2CF_2$ | H | O | $C_6H_5O$ | H | H | H | 3,5-Cl—$C_6H_3O$ | H | H |
| 5 | 188N | $CF_3CF_2CF_2$ | H | O | $C_6H_5O$ | H | H | H | H | $CH_3O$ | H |
| 5 | 189N | $CF_3CF_2CF_2$ | H | O | $C_6H_5O$ | H | H | H | H | $CO_2CH_3$ | H |
| 5 | 190N | $CF_3CF_2CF_2$ | H | O | $C_6H_5O$ | H | H | H | 3-$CH_3O$ $C_6H_5O$ | H | H |
| 5 | 191N | $CF_3CF_2CF_2$ | H | O | $C_6H_5O$ | H | H | H | 4-$CH_3O$ $C_6H_5O$ | H | H |
| 5 | 193N | $CF_3CF_2CF_2$ | H | O | $C_6H_5O$ | H | H | H | $CO_2CH_3$ | H | H |
| 5 | 194N | $CF_3CF_2CF_2$ | H | O | CN | H | H | H | $OCF_3$ | H | H |
| 5 | 195N | $CF_3CF_2CF_2$ | H | O | $NO_2$ | H | H | H | $OCF_3$ | H | H |
| 5 | 196N | $CF_3CF_2CF_2$ | H | O | H | CN | H | H | $OCF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

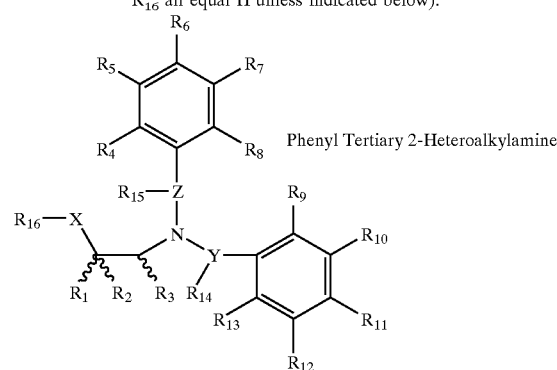

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 5 | 197N | $CF_3CF_2CF_2$ | H | O | H | $NO_2$ | H | H | $OCF_3$ | H | H |
| 5 | 198N | $CF_3CF_2CF_2$ | H | O | $SO_2CH_3$ | H | H | H | $OCF_3$ | H | H |
| 5 | 199N | $CF_3CF_2CF_2$ | H | O | H | $SO_2CH_3$ | H | H | $OCF_3$ | H | H |
| 5 | 200N | $CF_3CF_2CF_2$ | H | O | H | 4-F—$C_6H_5SO_2$ | H | H | $OCF_3$ | H | H |
| 5 | 201N | $CF_3CF_2CF_2$ | H | O | $SO_2N(CH_3)_2$ | H | H | H | $OCF_3$ | H | H |
| 5 | 202N | $CF_3CF_2CF_2$ | H | O | H | $SO_2N(CH_3)_2$ | H | H | $OCF_3$ | H | H |
| 5 | 203N | $CF_3CF_2CF_2$ | H | O | H | $CONH_2$ | H | H | $OCF_3$ | H | H |
| 5 | 204N | $CF_3CF_2CF_2$ | H | O | H | CONH—$C_6H_5$ | H | H | $OCF_3$ | H | H |
| 5 | 205N | $CF_3CF_2CF_2$ | H | O | H | $CO_2CH_3$ | H | H | $OCF_3$ | H | H |
| 5 | 206N | $CF_3CF_2CF_2$ | H | O | H | $CO_2C_4H_9$ | H | H | $OCF_3$ | H | H |
| 5 | 207N | $CF_3CF_2CF_2$ | H | O | H | 4-Cl—$C_6H_5$ | H | H | $C_6H_5O$ | H | H |
| 5 | 208N | $CF_3CF_2CF_2$ | H | O | H | 4-$CF_3O$—$C_6H_5$ | H | H | $CF_3O$ | H | H |
| 5 | 209N | $CF_3CF_2CF_2$ | H | O | 4-F—$C_6H_4O$ | H | H | H | $CF_3O$ | H | H |
| 5 | 210N | $CF_3CF_2CF_2$ | H | O | $C_6F_5O$ | H | H | H | $CF_3O$ | H | H |
| 5 | 211N | $CF_3CF_2CF_2$ | H | O | H | 4-F—$C_6H_5$ | H | H | $CF_3O$ | H | H |
| 5 | 212N | $CF_3CF_2CF_2$ | H | O | H | 4-CN—$C_6H_5$ | H | H | $CF_3O$ | H | H |
| 5 | 213N | $CF_3CF_2CF_2$ | H | O | H | 4-$C_6H_5$—$C_6H_5$ | H | H | $CF_3O$ | H | H |
| 5 | 214N | $CF_3CF_2CF_2$ | H | O | $C_6H_5O$ | H | H | $CH_3$ | $CF_3O$ | H | H |
| 5 | 215N | $CF_3CF_2CF_2$ | H | O | $C_6H_5O$ | H | H | $CH_3$ | $NO_2$ | H | H |
| 5 | 216N | $CF_3CF_2CF_2$ | H | O | $C_6H_5O$ | H | H | $CH_3$ | H | CN | H |
| 5 | 217N | $CF_3CF_2CF_2$ | H | O | $C_6H_5O$ | H | H | 3-$CF_3$ $C_6H_5$ | $CF_3$ | H | H |
| 5 | 218N | $CF_3CF_2CF_2$ | H | O | $C_6H_5O$ | H | H | $C_6H_5$ | H | $C_6H_5$ | H |
| 5 | 219N | $CF_3CF_2CF_2$ | H | O | $C_6H_5O$ | H | H | $C_6H_5$ | $CF_3$ | H | H |
| 5 | 220N | $CF_3CF_2CF_2$ | H | O | $C_6H_5O$ | H | H | $CH_3$ | F | H | H |
| 5 | 221N | $CF_3CF_2CF_2$ | H | O | $C_6H_5O$ | H | H | $CF_3$ | H | H | H |
| 5 | 222N | $CF_3CF_2CF_2$ | H | O | bond to —O— of $R_6$ aryl group | (2-methylphenoxy) | H | H | $CF_3O$ | H | H |
| 5 | 223N | $CF_3CF_2CF_2$ | H | O | to $CH_2$ of $R_6$ aryl group | (4-bromo-2-ethyl-phenyl) | H | H | $CF_3O$ | H | H |
| 6 | 96N | $CF_3OCF_2CF_2$ | H | O | OH | OH | H | H | $C_6H_5O$ | H | H |
| 6 | 97N | $CF_3OCF_2CF_2$ | H | O | $C_6H_5O$ | H | H | H | OH | OH | H |
| 6 | 98N | $CF_3OCF_2CF_2$ | H | O | 3-pyridyl | H | H | H | $CF_3$ | H | H |
| 6 | 99N | $CF_3OCF_2CF_2$ | H | O | $SO_2N(CH_3)_2$ | H | H | H | $OCF_3$ | H | H |
| 6 | 100N | $CF_3OCF_2CF_2$ | H | O | $SO_2CH_3$ | H | H | H | $OCF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

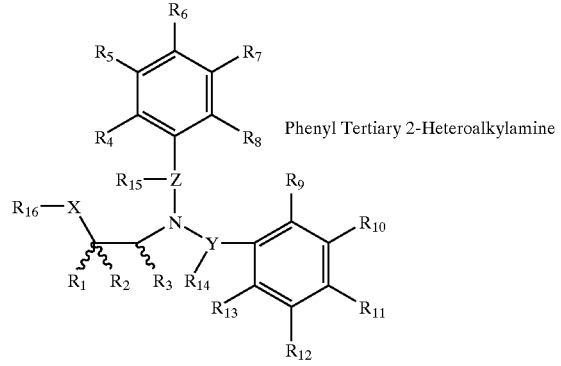

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 6 | 101N | $CF_3OCF_2CF_2$ | H | O | $C_6H_5O$ | H | H | H | $C_6H_5O$ | H | H |
| 6 | 102N | $CF_3OCF_2CF_2$ | H | O | $CF_3O$ | H | H | H | $C_6H_5O$ | H | H |
| 6 | 103N | $CF_3OCF_2CF_2$ | H | O | $C_6H_5$ | H | H | H | $C_6H_5O$ | H | H |
| 6 | 104N | $CF_3OCF_2CF_2$ | H | O | H | $C_6H_5$ | H | H | $C_6H_5O$ | H | H |
| 6 | 105N | $CF_3OCF_2CF_2$ | H | O | $C_6H_5O$ | H | H | H | 4-Cl—$C_6H_4O$ | H | H |
| 6 | 106N | $CF_3OCF_2CF_2$ | H | O | $CF_3O$ | H | H | H | 4-Cl—$C_6H_4O$ | H | H |
| 6 | 107N | $CF_3OCF_2CF_2$ | H | O | $C_6H_5O$ | H | H | H | 3,4-Cl—$C_6H_3O$ | H | H |
| 6 | 108N | $CF_3OCF_2CF_2$ | H | O | $CF_3O$ | H | H | H | 3,4-Cl—$C_6H_3O$ | H | H |
| 6 | 109N | $CF_3OCF_2CF_2$ | H | O | $CF_3O$ | H | H | H | 3,5-Cl—$C_6H_3O$ | H | H |
| 6 | 110N | $CF_3OCF_2CF_2$ | H | O | $CF_3O$ | H | H | H | 3-$CH_3O$—$C_6H_4O$ | H | H |
| 6 | 111N | $CF_3OCF_2CF_2$ | H | O | $CF_3O$ | H | H | H | H | 3-$CH_3O$—$C_6H_4O$ | H |
| 6 | 112N | $CF_3OCF_2CF_2$ | H | O | $CF_3O$ | H | H | H | 3-$CF_3$—$C_6H_4O$ | H | H |
| 6 | 113N | $CF_3OCF_2CF_2$ | H | O | $CF_3O$ | H | H | H | $C_6H_5$—$CH_2O$ | H | H |
| 6 | 114N | $CF_3OCF_2CF_2$ | H | O | $CF_3O$ | H | H | H | $C_6H_5$—$CH_2O$ | $CH_3O$ | H |
| 6 | 115N | $CF_3OCF_2CF_2$ | H | O | $CF_3O$ | H | H | H | $C_6H_5$—$CH_2O$ | $C_6H_5$—$CH_2O$ | H |
| 6 | 116N | $CF_3OCF_2CF_2$ | H | O | $CF_3O$ | H | H | H | ethoxy | H | H |
| 6 | 117N | $CF_3OCF_2CF_2$ | H | O | $CF_3O$ | H | H | H | $CH_3CO_2$ | H | H |
| 6 | 118N | $CF_3OCF_2CF_2$ | H | O | $CF_3O$ | H | H | H | $HOCH_2$—$CH_2O$ | H | H |
| 6 | 119N | $CF_3OCF_2CF_2$ | H | O | $CF_3O$ | H | H | H | ![epoxide] | H | H |
| 6 | 120N | $CF_3OCF_2CF_2$ | H | O | $CF_3O$ | H | H | H | $R_{10}$ + $R_{11}$ = $OCH_2O$ | | H |
| 6 | 121N | $CF_3OCF_2CF_2$ | H | O | $CF_3O$ | H | H | H | $R_{10}$ + $R_{11}$ = $OCH_2CH_2O$ | | H |
| 6 | 122N | $CF_3OCF_2CF_2$ | H | O | $CF_3O$ | H | H | H | $CH_3O$ | $CH_3O$ | H |
| 6 | 123N | $CF_3OCF_2CF_2$ | H | O | $CF_3O$ | H | H | H | ethoxy | $CH_3O$ | H |
| 6 | 124N | $CF_3OCF_2CF_2$ | H | O | $CF_3O$ | H | H | H | ethoxy | ethoxy | H |
| 6 | 125N | $CF_3OCF_2CF_2$ | H | O | $CF_3O$ | H | H | H | $CH_3CO_2$ | $CH_3CO_2$ | H |
| 6 | 126N | $CF_3OCF_2CF_2$ | H | O | $CF_3O$ | H | H | H | $CH_3O$ | $CH_3CO_2$ | H |
| 6 | 127N | $CF_3OCF_2CF_2$ | H | O | $CF_3O$ | H | H | H | n-butoxy | H | H |
| 6 | 128N | $CF_3OCF_2CF_2$ | H | O | $CF_3O$ | H | H | H | $CH_3O$ | H | H |
| 6 | 129N | $CF_3OCF_2CF_2$ | H | O | $CF_3O$ | H | H | H | H | $CH_3O$ | H |
| 6 | 130N | $CF_3OCF_2CF_2$ | H | O | $CH_3O$ | H | H | H | $CH_3O$ | H | H |
| 6 | 131N | $CF_3OCF_2CF_2$ | H | O | $CH_3O$ | H | H | H | H | $CF_3O$ | H |
| 6 | 132N | $CF_3OCF_2CF_2$ | H | O | $CF_3O$ | H | H | H | H | ethoxy | H |
| 6 | 133N | $CF_3OCF_2CF_2$ | H | O | $CF_3O$ | H | H | H | H | n-propoxy | H |
| 6 | 134N | $CF_3OCF_2CF_2$ | H | O | $C_6H_5$—$CH_2O$ | H | H | H | $CF_3O$ | H | H |
| 6 | 135N | $CF_3OCF_2CF_2$ | H | O | $C_6H_5$—$CH_2O$ | H | H | H | $C_6H_5O$ | H | H |
| 6 | 136N | $CF_3OCF_2CF_2$ | H | O | ethoxy | H | H | H | $CF_3O$ | H | H |
| 6 | 137N | $CF_3OCF_2CF_2$ | H | O | $R_5$ + $R_6$ = $OCH_2O$ | | H | H | $CF_3O$ | H | H |
| 6 | 138N | $CF_3OCF_2CF_2$ | H | O | $R_5$ + $R_6$ = $OCH_2O$ | | H | H | $C_6H_5O$ | H | H |
| 6 | 139N | $CF_3OCF_2CF_2$ | H | O | $R_5$ + $R_6$ = $OCH_2CH_2O$ | | H | H | $CF_3O$ | H | H |
| 6 | 140N | $CF_3OCF_2CF_2$ | H | O | $CH_3O$ | $CH_3O$ | H | H | $CF_3O$ | H | H |
| 6 | 141N | $CF_3OCF_2CF_2$ | H | O | $R_5$ + $R_6$ = $OCH_2CH_2CH_2O$ | | H | H | $CF_3O$ | H | H |
| 6 | 142N | $CF_3OCF_2CF_2$ | H | O | cyclo pentoxy | $CH_3O$ | H | H | $CF_3O$ | H | H |
| 6 | 143N | $CF_3OCF_2CF_2$ | H | O | H | $C_6H_5O$ | H | H | $CF_3O$ | H | H |
| 6 | 144N | $CF_3OCF_2CF_2$ | H | O | $CH_3O$ | $CH_3O$ | $CH_3O$ | H | $CF_3O$ | H | H |
| 6 | 145N | $CF_3OCF_2CF_2$ | H | O | H | $CF_3O$ | H | H | $CF_3O$ | H | H |
| 6 | 146N | $CF_3OCF_2CF_2$ | H | O | H | $C_6H_5$—$CH_2$ | H | H | $CF_3O$ | H | H |
| 6 | 147N | $CF_3OCF_2CF_2$ | H | O | $C_6H_5O$ | H | H | H | $R_{10}$ + $R_{11}$ = $OCH_2CH_2O$ | | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

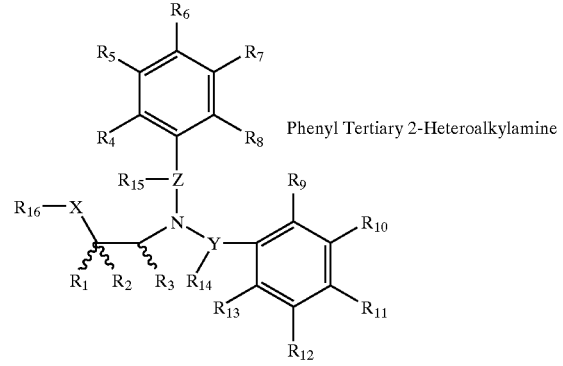

Phenyl Tertiary 2-Heteroalkylamine

Inhibitor Number
Column 1 +
Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 6 | 148N | $CF_3OCF_2CF_2$ | H | O | H | $CF_3O$ | H | H | $CF_3$ | H | H |
| 6 | 149N | $CF_3OCF_2CF_2$ | H | O | $C_6H_5O$ | H | H | H | $CF_3$ | H | H |
| 6 | 150N | $CF_3OCF_2CF_2$ | H | O | $C_6H_5$ | H | H | H | $CF_3$ | H | H |
| 6 | 151N | $CF_3OCF_2CF_2$ | H | O | H | $C_6H_5$ | H | H | $CF_3$ | H | H |
| 6 | 152N | $CF_3OCF_2CF_2$ | H | O | CN | H | H | H | $CF_3$ | H | H |
| 6 | 153N | $CF_3OCF_2CF_2$ | H | O | H | $OCF_3$ | H | H | $CF_3$ | H | H |
| 6 | 154N | $CF_3OCF_2CF_2$ | H | O | $OCF_3$ | H | H | H | H | $CF_3$ | H |
| 6 | 155N | $CF_3OCF_2CF_2$ | H | O | $C_6H_5O$ | H | H | H | H | $CF_3$ | H |
| 6 | 156N | $CF_3OCF_2CF_2$ | H | O | $C_6H_5$ | H | H | H | H | $CF_3$ | H |
| 6 | 157N | $CF_3OCF_2CF_2$ | H | O | H | $C_6H_5$ | H | H | H | $CF_3$ | H |
| 6 | 158N | $CF_3OCF_2CF_2$ | H | O | CN | H | H | H | H | $CF_3$ | H |
| 6 | 159N | $CF_3OCF_2CF_2$ | H | O | $OCF_3$ | H | H | H | H | $CF_3$ | H |
| 6 | 160N | $CF_3OCF_2CF_2$ | H | O | $CF_3$ | H | H | H | H | $C_6H_5$ | H |
| 6 | 161N | $CF_3OCF_2CF_2$ | H | O | $CF_3$ | H | H | H | 3-$CF_3$—$C_6H_5O$ | H | H |
| 6 | 162N | $CF_3OCF_2CF_2$ | H | O | $CF_3$ | H | H | H | $C_6H_5O$ | H | H |
| 6 | 163N | $CF_3OCF_2CF_2$ | H | O | $CF_3$ | H | H | H | $CF_3O$ | H | H |
| 6 | 164N | $CF_3OCF_2CF_2$ | H | O | H | $CF_3$ | H | H | H | $C_6H_5$ | H |
| 6 | 165N | $CF_3OCF_2CF_2$ | H | O | H | $CF_3$ | H | H | 3-$CF_3$—$C_6H_5O$ | H | H |
| 6 | 166N | $CF_3OCF_2CF_2$ | H | O | H | $CF_3$ | H | H | $CF_3O$ | H | H |
| 6 | 167N | $CF_3OCF_2CF_2$ | H | O | H | $CF_3$ | H | H | $C_6H_5O$ | H | H |
| 6 | 168N | $CF_3OCF_2CF_2$ | H | O | $CF_3$ | H | $CF_3$ | H | $CF_3O$ | H | H |
| 6 | 169N | $CF_3OCF_2CF_2$ | H | O | $CF_3$ | H | $CF_3$ | H | $C_6H_5O$ | H | H |
| 6 | 170N | $CF_3OCF_2CF_2$ | H | O | $CF_3O$ | H | H | H | $CF_3$ | H | $CF_3$ |
| 6 | 171N | $CF_3OCF_2CF_2$ | H | O | $C_6H_5O$ | H | H | H | $CF_3$ | H | $CF_3$ |
| 6 | 172N | $CF_3OCF_2CF_2$ | H | O | H | $C_6H_5O$ | H | H | $C_6H_5O$ | H | H |
| 6 | 173N | $CF_3OCF_2CF_2$ | H | O | H | $CF_3O$ | H | H | $CF_3O$ | H | H |
| 6 | 174N | $CF_3OCF_2CF_2$ | H | O | H | $CF_3O$ | H | H | H | $C_6H_5O$ | H |
| 6 | 175N | $CF_3OCF_2CF_2$ | H | O | $C_6H_5O$ | H | H | H | H | $C_6H_5O$ | H |
| 6 | 176N | $CF_3OCF_2CF_2$ | H | O | H | $C_6H_5O$ | H | H | H | $OCF_3$ | H |
| 6 | 177N | $CF_3OCF_2CF_2$ | H | O | H | $C_6H_5O$ | H | H | H | $C_6H_5O$ | H |
| 6 | 178N | $CF_3OCF_2CF_2$ | H | O | $C_6H_5O$ | H | H | H | H | CN | H |
| 6 | 179N | $CF_3OCF_2CF_2$ | H | O | $C_6H_5O$ | H | H | H | CN | H | H |
| 6 | 180N | $CF_3OCF_2CF_2$ | H | O | $C_6H_5O$ | H | H | H | $NO_2$ | H | H |
| 6 | 181N | $CF_3OCF_2CF_2$ | H | O | $C_6H_5O$ | H | H | H | H | $NO_2$ | H |
| 6 | 182N | $CF_3OCF_2CF_2$ | H | O | $C_6H_5O$ | H | H | H | H | $SO_2CH_3$ | H |
| 6 | 183N | $CF_3OCF_2CF_2$ | H | O | $C_6H_5O$ | H | H | H | H | 2-$NO_2$-4-Cl—$C_6H_3O$ | H |
| 6 | 184N | $CF_3OCF_2CF_2$ | H | O | $C_6H_5O$ | H | H | H | 4-Cl—$C_6H_4O$ | H | H |
| 6 | 185N | $CF_3OCF_2CF_2$ | H | O | $C_6H_5O$ | H | H | H | 3,4-Cl—$C_6H_3O$ | H | H |
| 6 | 186N | $CF_3OCF_2CF_2$ | H | O | $C_6H_5O$ | H | H | H | 3-$CF_3$—$C_6H_3O$ | H | H |
| 6 | 187N | $CF_3OCF_2CF_2$ | H | O | $C_6H_5O$ | H | H | H | 3,5-Cl—$C_6H_3O$ | H | H |
| 6 | 188N | $CF_3OCF_2CF_2$ | H | O | $C_6H_5O$ | H | H | H | H | $CH_3O$ | H |
| 6 | 189N | $CF_3OCF_2CF_2$ | H | O | $C_6H_5O$ | H | H | H | H | $CO_2CH_3$ | H |
| 6 | 190N | $CF_3OCF_2CF_2$ | H | O | $C_6H_5O$ | H | H | H | 3-$CH_3O$ $C_6H_5O$ | H | H |
| 6 | 191N | $CF_3OCF_2CF_2$ | H | O | $C_6H_5O$ | H | H | H | 4-$CH_3O$ $C_6H_5O$ | H | H |
| 6 | 193N | $CF_3OCF_2CF_2$ | H | O | $C_6H_5O$ | H | H | H | $CO_2CH_3$ | H | H |
| 6 | 194N | $CF_3OCF_2CF_2$ | H | O | CN | H | H | H | $OCF_3$ | H | H |
| 6 | 195N | $CF_3OCF_2CF_2$ | H | O | $NO_2$ | H | H | H | $OCF_3$ | H | H |
| 6 | 196N | $CF_3OCF_2CF_2$ | H | O | H | CN | H | H | $OCF_3$ | H | H |
| 6 | 197N | $CF_3OCF_2CF_2$ | H | O | H | $NO_2$ | H | H | $OCF_3$ | H | H |
| 6 | 198N | $CF_3OCF_2CF_2$ | H | O | $SO_2CH_3$ | H | H | H | $OCF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

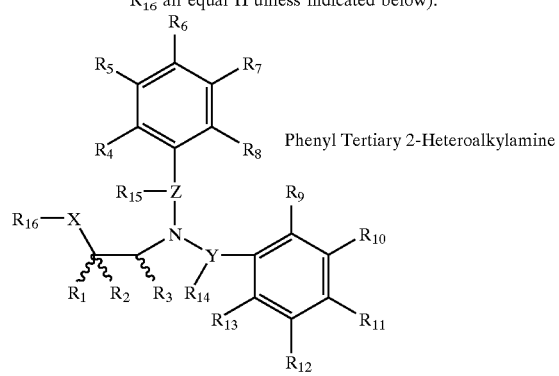

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 6 | 199N | $CF_3OCF_2CF_2$ | H | O | H | $SO_2CH_3$ | H | H | $OCF_3$ | H | H |
| 6 | 200N | $CF_3OCF_2CF_2$ | H | O | H | 4-F—$C_6H_5SO_2$ | H | H | $OCF_3$ | H | H |
| 6 | 201N | $CF_3OCF_2CF_2$ | H | O | $SO_2N(CH_3)_2$ | H | H | H | $OCF_3$ | H | H |
| 6 | 202N | $CF_3OCF_2CF_2$ | H | O | H | $SO_2N(CH_3)_2$ | H | H | $OCF_3$ | H | H |
| 6 | 203N | $CF_3OCF_2CF_2$ | H | O | H | $CONH_2$ | H | H | $OCF_3$ | H | H |
| 6 | 204N | $CF_3OCF_2CF_2$ | H | O | H | CONH—$C_6H_5$ | H | H | $OCF_3$ | H | H |
| 6 | 205N | $CF_3OCF_2CF_2$ | H | O | H | $CO_2CH_3$ | H | H | $OCF_3$ | H | H |
| 6 | 206N | $CF_3OCF_2CF_2$ | H | O | H | $CO_2C_4H_9$ | H | H | $OCF_3$ | H | H |
| 6 | 207N | $CF_3OCF_2CF_2$ | H | O | H | 4-Cl—$C_6H_5$ | H | H | $C_6H_5O$ | H | H |
| 6 | 208N | $CF_3OCF_2CF_2$ | H | O | H | 4-$CF_3O$—$C_6H_5$ | H | H | $CF_3O$ | H | H |
| 6 | 209N | $CF_3OCF_2CF_2$ | H | O | 4-F—$C_6H_4O$ | H | H | H | $CF_3O$ | H | H |
| 6 | 210N | $CF_3OCF_2CF_2$ | H | O | $C_6F_5O$ | H | H | H | $CF_3O$ | H | H |
| 6 | 211N | $CF_3OCF_2CF_2$ | H | O | H | 4-F—$C_6H_5$ | H | H | $CF_3O$ | H | H |
| 6 | 212N | $CF_3OCF_2CF_2$ | H | O | H | 4-CN—$C_6H_5$ | H | H | $CF_3O$ | H | H |
| 6 | 213N | $CF_3OCF_2CF_2$ | H | O | H | 4-$C_6H_5$—$C_6H_5$ | H | H | $CF_3O$ | H | H |
| 6 | 214N | $CF_3OCF_2CF_2$ | H | O | $C_6H_5O$ | H | H | $CH_3$ | $CF_3O$ | H | H |
| 6 | 215N | $CF_3OCF_2CF_2$ | H | O | $C_6H_5O$ | H | H | $CH_3$ | $NO_2$ | H | H |
| 6 | 216N | $CF_3OCF_2CF_2$ | H | O | $C_6H_5O$ | H | H | $CH_3$ | H | CN | H |
| 6 | 217N | $CF_3OCF_2CF_2$ | H | O | $C_6H_5O$ | H | H | 3-$CF_3$ $C_6H_5$ | $CF_3$ | H | H |
| 6 | 218N | $CF_3OCF_2CF_2$ | H | O | $C_6H_5O$ | H | H | $C_6H_5$ | H | $C_6H_5$ | H |
| 6 | 219N | $CF_3OCF_2CF_2$ | H | O | $C_6H_5O$ | H | H | $C_6H_5$ | $CF_3$ | H | H |
| 6 | 220N | $CF_3OCF_2CF_2$ | H | O | $C_6H_5O$ | H | H | $CH_3$ | F | H | H |
| 6 | 221N | $CF_3OCF_2CF_2$ | H | O | $C_6H_5O$ | H | H | $CF_3$ | H | H | H |
| 6 | 222N | $CF_3OCF_2CF_2$ | H | O | bond to —O— of $R_6$ aryl group | ![structure] | H | H | $CF_3O$ | H | H |
| 6 | 223N | $CF_3OCF_2CF_2$ | H | O | to $CH_2$ of $R_6$ aryl group | ![structure] Br | H | H | $CF_3O$ | H | H |
| 7 | 96N | $CF_3CH_2$ | $CH_3$ | O | OH | OH | H | H | $C_6H_5O$ | H | H |
| 7 | 97N | $CF_3CH_2$ | $CH_3$ | O | $C_6H_5O$ | H | H | H | OH | OH | H |
| 7 | 98N | $CF_3CH_2$ | $CH_3$ | O | 3-pyridyl | H | H | H | $CF_3$ | H | H |
| 7 | 99N | $CF_3CH_2$ | $CH_3$ | O | $SO_2N(CH_3)_2$ | H | H | H | $OCF_3$ | H | H |
| 7 | 100N | $CF_3CH_2$ | $CH_3$ | O | $SO_2CH_3$ | H | H | H | $OCF_3$ | H | H |
| 7 | 101N | $CF_3CH_2$ | $CH_3$ | O | $C_6H_5O$ | H | H | H | $C_6H_5O$ | H | H |
| 7 | 102N | $CF_3CH_2$ | $CH_3$ | O | $CF_3O$ | H | H | H | $C_6H_5O$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

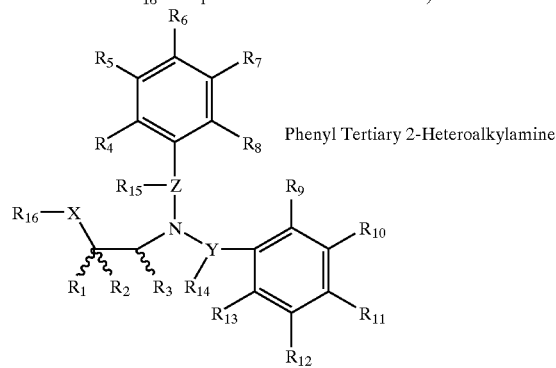

Phenyl Tertiary 2-Heteroalkylamine

Inhibitor Number
Column 1 +
Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 7 | 103N | $CF_3CH_2$ | $CH_3$ | O | $C_6H_5$ | H | H | H | $C_6H_5O$ | H | H |
| 7 | 104N | $CF_3CH_2$ | $CH_3$ | O | H | $C_6H_5$ | H | H | $C_6H_5O$ | H | H |
| 7 | 105N | $CF_3CH_2$ | $CH_3$ | O | $C_6H_5O$ | H | H | H | 4-Cl—$C_6H_4O$ | H | H |
| 7 | 106N | $CF_3CH_2$ | $CH_3$ | O | $CF_3O$ | H | H | H | 4-Cl—$C_6H_4O$ | H | H |
| 7 | 107N | $CF_3CH_2$ | $CH_3$ | O | $C_6H_5O$ | H | H | H | 3,4-Cl—$C_6H_3O$ | H | H |
| 7 | 108N | $CF_3CH_2$ | $CH_3$ | O | $CF_3O$ | H | H | H | 3,4-Cl—$C_6H_3O$ | H | H |
| 7 | 109N | $CF_3CH_2$ | $CH_3$ | O | $CF_3O$ | H | H | H | 3,5-Cl—$C_6H_3O$ | H | H |
| 7 | 110N | $CF_3CH_2$ | $CH_3$ | O | $CF_3O$ | H | H | H | 3-$CH_3O$—$C_6H_4O$ | H | H |
| 7 | 111N | $CF_3CH_2$ | $CH_3$ | O | $CF_3O$ | H | H | H | H | 3-$CH_3O$—$C_6H_4O$ | H |
| 7 | 112N | $CF_3CH_2$ | $CH_3$ | O | $CF_3O$ | H | H | H | 3-$CF_3$—$C_6H_4O$ | H | H |
| 7 | 113N | $CF_3CH_2$ | $CH_3$ | O | $CF_3O$ | H | H | H | $C_6H_5$—$CH_2O$ | H | H |
| 7 | 114N | $CF_3CH_2$ | $CH_3$ | O | $CF_3O$ | H | H | H | $C_6H_5$—$CH_2O$ | $CH_3O$ | H |
| 7 | 115N | $CF_3CH_2$ | $CH_3$ | O | $CF_3O$ | H | H | H | $C_6H_5$—$CH_2O$ | $C_6H_5$—$CH_2O$ | H |
| 7 | 116N | $CF_3CH_2$ | $CH_3$ | O | $CF_3O$ | H | H | H | ethoxy | H | H |
| 7 | 117N | $CF_3CH_2$ | $CH_3$ | O | $CF_3O$ | H | H | H | $CH_3CO_2$ | H | H |
| 7 | 118N | $CF_3CH_2$ | $CH_3$ | O | $CF_3O$ | H | H | H | $HOCH_2$—$CH_2O$ | H | H |
| 7 | 119N | $CF_3CH_2$ | $CH_3$ | O | $CF_3O$ | H | H | H | epoxide group | H | H |
| 7 | 120N | $CF_3CH_2$ | $CH_3$ | O | $CF_3O$ | H | H | H | $R_{10} + R_{11} = OCH_2O$ | | H |
| 7 | 121N | $CF_3CH_2$ | $CH_3$ | O | $CF_3O$ | H | H | H | $R_{10} + R_{11} = OCH_2CH_2O$ | | H |
| 7 | 122N | $CF_3CH_2$ | $CH_3$ | O | $CF_3O$ | H | H | H | $CH_3O$ | $CH_3O$ | H |
| 7 | 123N | $CF_3CH_2$ | $CH_3$ | O | $CF_3O$ | H | H | H | ethoxy | $CH_3O$ | H |
| 7 | 124N | $CF_3CH_2$ | $CH_3$ | O | $CF_3O$ | H | H | H | ethoxy | ethoxy | H |
| 7 | 125N | $CF_3CH_2$ | $CH_3$ | O | $CF_3O$ | H | H | H | $CH_3CO_2$ | $CH_3CO_2$ | H |
| 7 | 126N | $CF_3CH_2$ | $CH_3$ | O | $CF_3O$ | H | H | H | $CH_3O$ | $CH_3CO_2$ | H |
| 7 | 127N | $CF_3CH_2$ | $CH_3$ | O | $CF_3O$ | H | H | H | n-butoxy | H | H |
| 7 | 128N | $CF_3CH_2$ | $CH_3$ | O | $CF_3O$ | H | H | H | $CH_3O$ | H | H |
| 7 | 129N | $CF_3CH_2$ | $CH_3$ | O | $CF_3O$ | H | H | H | H | $CH_3O$ | H |
| 7 | 130N | $CF_3CH_2$ | $CH_3$ | O | $CH_3O$ | H | H | H | $CH_3O$ | H | H |
| 7 | 131N | $CF_3CH_2$ | $CH_3$ | O | $CH_3O$ | H | H | H | H | $CF_3O$ | H |
| 7 | 132N | $CF_3CH_2$ | $CH_3$ | O | $CF_3O$ | H | H | H | H | ethoxy | H |
| 7 | 133N | $CF_3CH_2$ | $CH_3$ | O | $CF_3O$ | H | H | H | H | n-propoxy | H |
| 7 | 134N | $CF_3CH_2$ | $CH_3$ | O | $C_6H_5$—$CH_2O$ | H | H | H | $CF_3O$ | H | H |
| 7 | 135N | $CF_3CH_2$ | $CH_3$ | O | $C_6H_5$—$CH_2O$ | H | H | H | $C_6H_5O$ | H | H |
| 7 | 136N | $CF_3CH_2$ | $CH_3$ | O | ethoxy | H | H | H | $CF_3O$ | H | H |
| 7 | 137N | $CF_3CH_2$ | $CH_3$ | O | $R_5 + R_6 = OCH_2O$ | | H | H | $CF_3O$ | H | H |
| 7 | 138N | $CF_3CH_2$ | $CH_3$ | O | $R_5 + R_6 = OCH_2O$ | | H | H | $C_6H_5O$ | H | H |
| 7 | 139N | $CF_3CH_2$ | $CH_3$ | O | $R_5 + R_6 = OCH_2CH_2O$ | | H | H | $CF_3O$ | H | H |
| 7 | 140N | $CF_3CH_2$ | $CH_3$ | O | $CH_3O$ | $CH_3O$ | H | H | $CF_3O$ | H | H |
| 7 | 141N | $CF_3CH_2$ | $CH_3$ | O | $R_5 + R_6 = OCH_2CH_2CH_2O$ | | H | H | $CF_3O$ | H | H |
| 7 | 142N | $CF_3CH_2$ | $CH_3$ | O | cyclo pentoxy | $CH_3O$ | H | H | $CF_3O$ | H | H |
| 7 | 143N | $CF_3CH_2$ | $CH_3$ | O | H | $C_6H_5O$ | H | H | $CF_3O$ | H | H |
| 7 | 144N | $CF_3CH_2$ | $CH_3$ | O | $CH_3O$ | $CH_3O$ | $CH_3O$ | H | $CF_3O$ | H | H |
| 7 | 145N | $CF_3CH_2$ | $CH_3$ | O | H | $CF_3O$ | H | H | $CF_3O$ | H | H |
| 7 | 146N | $CF_3CH_2$ | $CH_3$ | O | H | $C_6H_5$—$CH_2$ | H | H | $CF_3O$ | H | H |
| 7 | 147N | $CF_3CH_2$ | $CH_3$ | O | $C_6H_5O$ | H | H | H | $R_{10} + R_{11} = OCH_2CH_2O$ | | H |
| 7 | 148N | $CF_3CH_2$ | $CH_3$ | O | H | $CF_3O$ | H | H | $CF_3$ | H | H |
| 7 | 149N | $CF_3CH_2$ | $CH_3$ | O | $C_6H_5O$ | H | H | H | $CF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

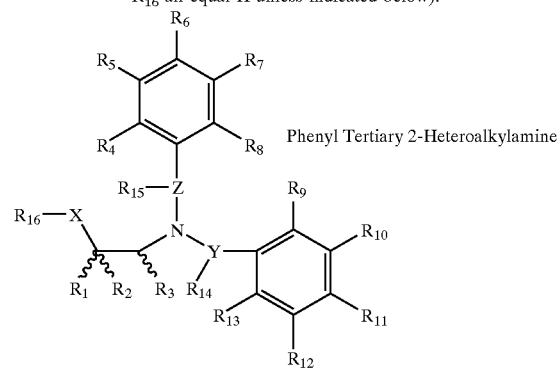

Phenyl Tertiary 2-Heteroalkylamine

Inhibitor Number
Column 1 +
Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 7 | 150N | $CF_3CH_2$ | $CH_3$ | O | $C_6H_5$ | H | H | H | $CF_3$ | H | H |
| 7 | 151N | $CF_3CH_2$ | $CH_3$ | O | H | $C_6H_5$ | H | H | $CF_3$ | H | H |
| 7 | 152N | $CF_3CH_2$ | $CH_3$ | O | CN | H | H | H | $CF_3$ | H | H |
| 7 | 153N | $CF_3CH_2$ | $CH_3$ | O | H | $OCF_3$ | H | H | $CF_3$ | H | H |
| 7 | 154N | $CF_3CH_2$ | $CH_3$ | O | $OCF_3$ | H | H | H | H | $CF_3$ | H |
| 7 | 155N | $CF_3CH_2$ | $CH_3$ | O | $C_6H_5O$ | H | H | H | H | $CF_3$ | H |
| 7 | 156N | $CF_3CH_2$ | $CH_3$ | O | $C_6H_5$ | H | H | H | H | $CF_3$ | H |
| 7 | 157N | $CF_3CH_2$ | $CH_3$ | O | H | $C_6H_5$ | H | H | H | $CF_3$ | H |
| 7 | 158N | $CF_3CH_2$ | $CH_3$ | O | CN | H | H | H | H | $CF_3$ | H |
| 7 | 159N | $CF_3CH_2$ | $CH_3$ | O | $OCF_3$ | H | H | H | H | $CF_3$ | H |
| 7 | 160N | $CF_3CH_2$ | $CH_3$ | O | $CF_3$ | H | H | H | H | $C_6H_5$ | H |
| 7 | 161N | $CF_3CH_2$ | $CH_3$ | O | $CF_3$ | H | H | H | 3-$CF_3$—$C_6H_5O$ | H | H |
| 7 | 162N | $CF_3CH_2$ | $CH_3$ | O | $CF_3$ | H | H | H | $C_6H_5O$ | H | H |
| 7 | 163N | $CF_3CH_2$ | $CH_3$ | O | $CF_3$ | H | H | H | $CF_3O$ | H | H |
| 7 | 164N | $CF_3CH_2$ | $CH_3$ | O | H | $CF_3$ | H | H | H | $C_6H_5$ | H |
| 7 | 165N | $CF_3CH_2$ | $CH_3$ | O | H | $CF_3$ | H | H | 3-$CF_3$—$C_6H_5O$ | H | H |
| 7 | 166N | $CF_3CH_2$ | $CH_3$ | O | H | $CF_3$ | H | H | $CF_3O$ | H | H |
| 7 | 167N | $CF_3CH_2$ | $CH_3$ | O | H | $CF_3$ | H | H | $C_6H_5O$ | H | H |
| 7 | 168N | $CF_3CH_2$ | $CH_3$ | O | $CF_3$ | H | $CF_3$ | H | $CF_3O$ | H | H |
| 7 | 169N | $CF_3CH_2$ | $CH_3$ | O | $CF_3$ | H | $CF_3$ | H | $C_6H_5O$ | H | H |
| 7 | 170N | $CF_3CH_2$ | $CH_3$ | O | $CF_3O$ | H | H | H | $CF_3$ | H | $CF_3$ |
| 7 | 171N | $CF_3CH_2$ | $CH_3$ | O | $C_6H_5O$ | H | H | H | $CF_3$ | H | $CF_3$ |
| 7 | 172N | $CF_3CH_2$ | $CH_3$ | O | H | $C_6H_5O$ | H | H | $C_6H_5O$ | H | H |
| 7 | 173N | $CF_3CH_2$ | $CH_3$ | O | H | $CF_3O$ | H | H | $CF_3O$ | H | H |
| 7 | 174N | $CF_3CH_2$ | $CH_3$ | O | H | $CF_3O$ | H | H | H | $C_6H_5O$ | H |
| 7 | 175N | $CF_3CH_2$ | $CH_3$ | O | $C_6H_5O$ | H | H | H | H | $C_6H_5O$ | H |
| 7 | 176N | $CF_3CH_2$ | $CH_3$ | O | H | $C_6H_5O$ | H | H | H | $OCF_3$ | H |
| 7 | 177N | $CF_3CH_2$ | $CH_3$ | O | H | $C_6H_5O$ | H | H | H | $C_6H_5O$ | H |
| 7 | 178N | $CF_3CH_2$ | $CH_3$ | O | $C_6H_5O$ | H | H | H | H | CN | H |
| 7 | 179N | $CF_3CH_2$ | $CH_3$ | O | $C_6H_5O$ | H | H | H | CN | H | H |
| 7 | 180N | $CF_3CH_2$ | $CH_3$ | O | $C_6H_5O$ | H | H | H | $NO_2$ | H | H |
| 7 | 181N | $CF_3CH_2$ | $CH_3$ | O | $C_6H_5O$ | H | H | H | H | $NO_2$ | H |
| 7 | 182N | $CF_3CH_2$ | $CH_3$ | O | $C_6H_5O$ | H | H | H | H | $SO_2CH_3$ | H |
| 7 | 183N | $CF_3CH_2$ | $CH_3$ | O | $C_6H_5O$ | H | H | H | H | 2-$NO_2$-4-Cl—$C_6H_3O$ | H |
| 7 | 184N | $CF_3CH_2$ | $CH_3$ | O | $C_6H_5O$ | H | H | H | 4-Cl—$C_6H_4O$ | H | H |
| 7 | 185N | $CF_3CH_2$ | $CH_3$ | O | $C_6H_5O$ | H | H | H | 3,4-Cl—$C_6H_3O$ | H | H |
| 7 | 186N | $CF_3CH_2$ | $CH_3$ | O | $C_6H_5O$ | H | H | H | 3-$CF_3$—$C_6H_3O$ | H | H |
| 7 | 187N | $CF_3CH_2$ | $CH_3$ | O | $C_6H_5O$ | H | H | H | 3,5-Cl—$C_6H_3O$ | H | H |
| 7 | 188N | $CF_3CH_2$ | $CH_3$ | O | $C_6H_5O$ | H | H | H | H | $CH_3O$ | H |
| 7 | 189N | $CF_3CH_2$ | $CH_3$ | O | $C_6H_5O$ | H | H | H | H | $CO_2CH_3$ | H |
| 7 | 190N | $CF_3CH_2$ | $CH_3$ | O | $C_6H_5O$ | H | H | H | 3-$CH_3O$ $C_6H_5O$ | H | H |
| 7 | 191N | $CF_3CH_2$ | $CH_3$ | O | $C_6H_5O$ | H | H | H | 4-$CH_3O$ $C_6H_5O$ | H | H |
| 7 | 193N | $CF_3CH_2$ | $CH_3$ | O | $C_6H_5O$ | H | H | H | $CO_2CH_3$ | H | H |
| 7 | 194N | $CF_3CH_2$ | $CH_3$ | O | CN | H | H | H | $OCF_3$ | H | H |
| 7 | 195N | $CF_3CH_2$ | $CH_3$ | O | $NO_2$ | H | H | H | $OCF_3$ | H | H |
| 7 | 196N | $CF_3CH_2$ | $CH_3$ | O | H | CN | H | H | $OCF_3$ | H | H |
| 7 | 197N | $CF_3CH_2$ | $CH_3$ | O | H | $NO_2$ | H | H | $OCF_3$ | H | H |
| 7 | 198N | $CF_3CH_2$ | $CH_3$ | O | $SO_2CH_3$ | H | H | H | $OCF_3$ | H | H |
| 7 | 199N | $CF_3CH_2$ | $CH_3$ | O | H | $SO_2CH_3$ | H | H | $OCF_3$ | H | H |
| 7 | 200N | $CF_3CH_2$ | $CH_3$ | O | H | 4-F—$C_6H_5SO_2$ | H | H | $OCF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).


Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 7 | 201N | $CF_3CH_2$ | $CH_3$ | O | $SO_2N(CH_3)_2$ | H | H | H | $OCF_3$ | H | H |
| 7 | 202N | $CF_3CH_2$ | $CH_3$ | O | H | $SO_2N(CH_3)_2$ | H | H | $OCF_3$ | H | H |
| 7 | 203N | $CF_3CH_2$ | $CH_3$ | O | H | $CONH_2$ | H | H | $OCF_3$ | H | H |
| 7 | 204N | $CF_3CH_2$ | $CH_3$ | O | H | $CONH-C_6H_5$ | H | H | $OCF_3$ | H | H |
| 7 | 205N | $CF_3CH_2$ | $CH_3$ | O | H | $CO_2CH_3$ | H | H | $OCF_3$ | H | H |
| 7 | 206N | $CF_3CH_2$ | $CH_3$ | O | H | $CO_2C_4H_9$ | H | H | $OCF_3$ | H | H |
| 7 | 207N | $CF_3CH_2$ | $CH_3$ | O | H | $4\text{-Cl}-C_6H_5$ | H | H | $C_6H_5O$ | H | H |
| 7 | 208N | $CF_3CH_2$ | $CH_3$ | O | H | $4\text{-CF}_3O-C_6H_5$ | H | H | $CF_3O$ | H | H |
| 7 | 209N | $CF_3CH_2$ | $CH_3$ | O | $4\text{-F}-C_6H_4O$ | H | H | H | $CF_3O$ | H | H |
| 7 | 210N | $CF_3CH_2$ | $CH_3$ | O | $C_6F_5O$ | H | H | H | $CF_3O$ | H | H |
| 7 | 211N | $CF_3CH_2$ | $CH_3$ | O | H | $4\text{-F}-C_6H_5$ | H | H | $CF_3O$ | H | H |
| 7 | 212N | $CF_3CH_2$ | $CH_3$ | O | H | $4\text{-CN}-C_6H_5$ | H | H | $CF_3O$ | H | H |
| 7 | 213N | $CF_3CH_2$ | $CH_3$ | O | H | $4\text{-}C_6H_5-C_6H_5$ | H | H | $CF_3O$ | H | H |
| 7 | 214N | $CF_3CH_2$ | $CH_3$ | O | $C_6H_5O$ | H | H | $CH_3$ | $CF_3O$ | H | H |
| 7 | 215N | $CF_3CH_2$ | $CH_3$ | O | $C_6H_5O$ | H | H | $CH_3$ | $NO_2$ | H | H |
| 7 | 216N | $CF_3CH_2$ | $CH_3$ | O | $C_6H_5O$ | H | H | $CH_3$ | H | CN | H |
| 7 | 217N | $CF_3CH_2$ | $CH_3$ | O | $C_6H_5O$ | H | H | $3\text{-CF}_3\ C_6H_5$ | $CF_3$ | H | H |
| 7 | 218N | $CF_3CH_2$ | $CH_3$ | O | $C_6H_5O$ | H | H | $C_6H_5$ | H | $C_6H_5$ | H |
| 7 | 219N | $CF_3CH_2$ | $CH_3$ | O | $C_6H_5O$ | H | H | $C_6H_5$ | $CF_3$ | H | H |
| 7 | 220N | $CF_3CH_2$ | $CH_3$ | O | $C_6H_5O$ | H | H | $CH_3$ | F | H | H |
| 7 | 221N | $CF_3CH_2$ | $CH_3$ | O | $C_6H_5O$ | H | H | $CF_3$ | H | H | H |
| 7 | 222N | $CF_3CH_2$ | $CH_3$ | O | bond to —O— of $R_6$ aryl group | (2-methylphenoxy) | H | H | $CF_3O$ | H | H |
| 7 | 223N | $CF_3CH_2$ | $CH_3$ | O | to $CH_2$ of $R_6$ aryl group | (4-bromo-2-methylbenzyl) | H | H | $CF_3O$ | H | H |
| 10 | 96N | $CF_3$ | $CF_3$ | O | OH | OH | H | H | $C_6H_5O$ | H | H |
| 10 | 97N | $CF_3$ | $CF_3$ | O | $C_6H_5O$ | H | H | H | OH | OH | H |
| 10 | 98N | $CF_3$ | $CF_3$ | O | 3-pyridyl | H | H | H | $CF_3$ | H | H |
| 10 | 99N | $CF_3$ | $CF_3$ | O | $SO_2N(CH_3)_2$ | H | H | H | $OCF_3$ | H | H |
| 10 | 100N | $CF_3$ | $CF_3$ | O | $SO_2CH_3$ | H | H | H | $OCF_3$ | H | H |
| 10 | 101N | $CF_3$ | $CF_3$ | O | $C_6H_5O$ | H | H | H | $C_6H_5O$ | H | H |
| 10 | 102N | $CF_3$ | $CF_3$ | O | $CF_3O$ | H | H | H | $C_6H_5O$ | H | H |
| 10 | 103N | $CF_3$ | $CF_3$ | O | $C_6H_5$ | H | H | H | $C_6H_5O$ | H | H |
| 10 | 104N | $CF_3$ | $CF_3$ | O | H | $C_6H_5$ | H | H | $C_6H_5O$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

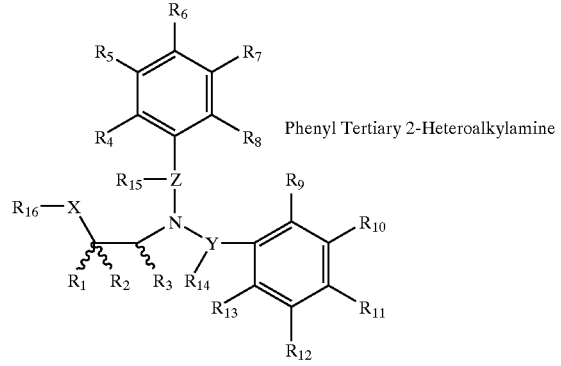

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 10 | 105N | $CF_3$ | $CF_3$ | O | $C_6H_5O$ | H | H | H | 4-Cl—$C_6H_4O$ | H | H |
| 10 | 106N | $CF_3$ | $CF_3$ | O | $CF_3O$ | H | H | H | 4-Cl—$C_6H_4O$ | H | H |
| 10 | 107N | $CF_3$ | $CF_3$ | O | $C_6H_5O$ | H | H | H | 3,4-Cl—$C_6H_3O$ | H | H |
| 10 | 108N | $CF_3$ | $CF_3$ | O | $CF_3O$ | H | H | H | 3,4-Cl—$C_6H_3O$ | H | H |
| 10 | 109N | $CF_3$ | $CF_3$ | O | $CF_3O$ | H | H | H | 3,5-Cl—$C_6H_3O$ | H | H |
| 10 | 110N | $CF_3$ | $CF_3$ | O | $CF_3O$ | H | H | H | 3-$CH_3O$—$C_6H_4O$ | H | H |
| 10 | 111N | $CF_3$ | $CF_3$ | O | $CF_3O$ | H | H | H | H | 3-$CH_3O$—$C_6H_4O$ | H |
| 10 | 112N | $CF_3$ | $CF_3$ | O | $CF_3O$ | H | H | H | 3-$CF_3$—$C_6H_4O$ | H | H |
| 10 | 113N | $CF_3$ | $CF_3$ | O | $CF_3O$ | H | H | H | $C_6H_5$—$CH_2O$ | H | H |
| 10 | 114N | $CF_3$ | $CF_3$ | O | $CF_3O$ | H | H | H | $C_6H_5$—$CH_2O$ | $CH_3O$ | H |
| 10 | 115N | $CF_3$ | $CF_3$ | O | $CF_3O$ | H | H | H | $C_6H_5$—$CH_2O$ | $C_6H_5$—$CH_2O$ | H |
| 10 | 116N | $CF_3$ | $CF_3$ | O | $CF_3O$ | H | H | H | ethoxy | H | H |
| 10 | 117N | $CF_3$ | $CF_3$ | O | $CF_3O$ | H | H | H | $CH_3CO_2$ | H | H |
| 10 | 118N | $CF_3$ | $CF_3$ | O | $CF_3O$ | H | H | H | $HOCH_2$—$CH_2O$ | H | H |
| 10 | 119N | $CF_3$ | $CF_3$ | O | $CF_3O$ | H | H | H | ![epoxide] | H | H |
| 10 | 120N | $CF_3$ | $CF_3$ | O | $CF_3O$ | H | H | H | $R_{10} + R_{11} = OCH_2O$ | | H |
| 10 | 121N | $CF_3$ | $CF_3$ | O | $CF_3O$ | H | H | H | $R_{10} + R_{11} = OCH_2CH_2O$ | | H |
| 10 | 122N | $CF_3$ | $CF_3$ | O | $CF_3O$ | H | H | H | $CH_3O$ | $CH_3O$ | H |
| 10 | 123N | $CF_3$ | $CF_3$ | O | $CF_3O$ | H | H | H | ethoxy | $CH_3O$ | H |
| 10 | 124N | $CF_3$ | $CF_3$ | O | $CF_3O$ | H | H | H | ethoxy | ethoxy | H |
| 10 | 125N | $CF_3$ | $CF_3$ | O | $CF_3O$ | H | H | H | $CH_3CO_2$ | $CH_3CO_2$ | H |
| 10 | 126N | $CF_3$ | $CF_3$ | O | $CF_3O$ | H | H | H | $CH_3O$ | $CH_3CO_2$ | H |
| 10 | 127N | $CF_3$ | $CF_3$ | O | $CF_3O$ | H | H | H | n-butoxy | H | H |
| 10 | 128N | $CF_3$ | $CF_3$ | O | $CF_3O$ | H | H | H | $CH_3O$ | H | H |
| 10 | 129N | $CF_3$ | $CF_3$ | O | $CF_3O$ | H | H | H | H | $CH_3O$ | H |
| 10 | 130N | $CF_3$ | $CF_3$ | O | $CH_3O$ | H | H | H | $CH_3O$ | H | H |
| 10 | 131N | $CF_3$ | $CF_3$ | O | $CH_3O$ | H | H | H | H | $CF_3O$ | H |
| 10 | 132N | $CF_3$ | $CF_3$ | O | $CF_3O$ | H | H | H | H | ethoxy | H |
| 10 | 133N | $CF_3$ | $CF_3$ | O | $CF_3O$ | H | H | H | H | n-propoxy | H |
| 10 | 134N | $CF_3$ | $CF_3$ | O | $C_6H_5$—$CH_2O$ | H | H | H | $CF_3O$ | H | H |
| 10 | 135N | $CF_3$ | $CF_3$ | O | $C_6H_5$—$CH_2O$ | H | H | H | $C_6H_5O$ | H | H |
| 10 | 136N | $CF_3$ | $CF_3$ | O | ethoxy | H | H | H | $CF_3O$ | H | H |
| 10 | 137N | $CF_3$ | $CF_3$ | O | $R_5 + R_6 = OCH_2O$ | | H | H | $CF_3O$ | H | H |
| 10 | 138N | $CF_3$ | $CF_3$ | O | $R_5 + R_6 = OCH_2O$ | | H | H | $C_6H_5O$ | H | H |
| 10 | 139N | $CF_3$ | $CF_3$ | O | $R_5 + R_6 = OCH_2CH_2O$ | | H | H | $CF_3O$ | H | H |
| 10 | 140N | $CF_3$ | $CF_3$ | O | $CH_3O$ | $CH_3O$ | H | H | $CF_3O$ | H | H |
| 10 | 141N | $CF_3$ | $CF_3$ | O | $R_5 + R_6 = OCH_2CH_2CH_2O$ | | H | H | $CF_3O$ | H | H |
| 10 | 142N | $CF_3$ | $CF_3$ | O | cyclo pentoxy | $CH_3O$ | H | H | $CF_3O$ | H | H |
| 10 | 143N | $CF_3$ | $CF_3$ | O | H | $C_6H_5O$ | H | H | $CF_3O$ | H | H |
| 10 | 144N | $CF_3$ | $CF_3$ | O | $CH_3O$ | $CH_3O$ | $CH_3O$ | H | $CF_3O$ | H | H |
| 10 | 145N | $CF_3$ | $CF_3$ | O | H | $CF_3O$ | H | H | $CF_3O$ | H | H |
| 10 | 146N | $CF_3$ | $CF_3$ | O | H | $C_6H_5$—$CH_2$ | H | H | $CF_3O$ | H | H |
| 10 | 147N | $CF_3$ | $CF_3$ | O | $C_6H_5O$ | H | H | H | $R_{10} + R_{11} = OCH_2CH_2O$ | | H |
| 10 | 148N | $CF_3$ | $CF_3$ | O | H | $CF_3O$ | H | H | $CF_3$ | H | H |
| 10 | 149N | $CF_3$ | $CF_3$ | O | $C_6H_5O$ | H | H | H | $CF_3$ | H | H |
| 10 | 150N | $CF_3$ | $CF_3$ | O | $C_6H_5$ | H | H | H | $CF_3$ | H | H |
| 10 | 151N | $CF_3$ | $CF_3$ | O | H | $C_6H_5$ | H | H | $CF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

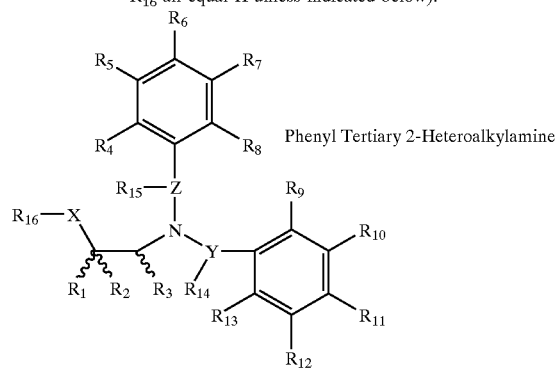

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 10 | 152N | $CF_3$ | $CF_3$ | O | CN | H | H | H | $CF_3$ | H | H |
| 10 | 153N | $CF_3$ | $CF_3$ | O | H | $OCF_3$ | H | H | $CF_3$ | H | H |
| 10 | 154N | $CF_3$ | $CF_3$ | O | $OCF_3$ | H | H | H | H | $CF_3$ | H |
| 10 | 155N | $CF_3$ | $CF_3$ | O | $C_6H_5O$ | H | H | H | H | $CF_3$ | H |
| 10 | 156N | $CF_3$ | $CF_3$ | O | $C_6H_5$ | H | H | H | H | $CF_3$ | H |
| 10 | 157N | $CF_3$ | $CF_3$ | O | H | $C_6H_5$ | H | H | H | $CF_3$ | H |
| 10 | 158N | $CF_3$ | $CF_3$ | O | CN | H | H | H | H | $CF_3$ | H |
| 10 | 159N | $CF_3$ | $CF_3$ | O | $OCF_3$ | H | H | H | H | $CF_3$ | H |
| 10 | 160N | $CF_3$ | $CF_3$ | O | $CF_3$ | H | H | H | H | $C_6H_5$ | H |
| 10 | 161N | $CF_3$ | $CF_3$ | O | $CF_3$ | H | H | H | 3-$CF_3$—$C_6H_5O$ | H | H |
| 10 | 162N | $CF_3$ | $CF_3$ | O | $CF_3$ | H | H | H | $C_6H_5O$ | H | H |
| 10 | 163N | $CF_3$ | $CF_3$ | O | $CF_3$ | H | H | H | $CF_3O$ | H | H |
| 10 | 164N | $CF_3$ | $CF_3$ | O | H | $CF_3$ | H | H | H | $C_6H_5$ | H |
| 10 | 165N | $CF_3$ | $CF_3$ | O | H | $CF_3$ | H | H | 3-$CF_3$—$C_6H_5O$ | H | H |
| 10 | 166N | $CF_3$ | $CF_3$ | O | H | $CF_3$ | H | H | $CF_3O$ | H | H |
| 10 | 167N | $CF_3$ | $CF_3$ | O | H | $CF_3$ | H | H | $C_6H_5O$ | H | H |
| 10 | 168N | $CF_3$ | $CF_3$ | O | $CF_3$ | H | $CF_3$ | H | $CF_3O$ | H | H |
| 10 | 169N | $CF_3$ | $CF_3$ | O | $CF_3$ | H | $CF_3$ | H | $C_6H_5O$ | H | H |
| 10 | 170N | $CF_3$ | $CF_3$ | O | $CF_3O$ | H | H | H | $CF_3$ | H | $CF_3$ |
| 10 | 171N | $CF_3$ | $CF_3$ | O | $C_6H_5O$ | H | H | H | $CF_3$ | H | $CF_3$ |
| 10 | 172N | $CF_3$ | $CF_3$ | O | H | $C_6H_5O$ | H | H | $C_6H_5O$ | H | H |
| 10 | 173N | $CF_3$ | $CF_3$ | O | H | $CF_3O$ | H | H | $CF_3O$ | H | H |
| 10 | 174N | $CF_3$ | $CF_3$ | O | H | $CF_3O$ | H | H | H | $C_6H_5O$ | H |
| 10 | 175N | $CF_3$ | $CF_3$ | O | $C_6H_5O$ | H | H | H | H | $C_6H_5O$ | H |
| 10 | 176N | $CF_3$ | $CF_3$ | O | H | $C_6H_5O$ | H | H | H | $OCF_3$ | H |
| 10 | 177N | $CF_3$ | $CF_3$ | O | H | $C_6H_5O$ | H | H | H | $C_6H_5O$ | H |
| 10 | 178N | $CF_3$ | $CF_3$ | O | $C_6H_5O$ | H | H | H | H | CN | H |
| 10 | 179N | $CF_3$ | $CF_3$ | O | $C_6H_5O$ | H | H | H | CN | H | H |
| 10 | 180N | $CF_3$ | $CF_3$ | O | $C_6H_5O$ | H | H | H | $NO_2$ | H | H |
| 10 | 181N | $CF_3$ | $CF_3$ | O | $C_6H_5O$ | H | H | H | H | $NO_2$ | H |
| 10 | 182N | $CF_3$ | $CF_3$ | O | $C_6H_5O$ | H | H | H | H | $SO_2CH_3$ | H |
| 10 | 183N | $CF_3$ | $CF_3$ | O | $C_6H_5O$ | H | H | H | H | 2-$NO_2$-4-Cl—$C_6H_3O$ | H |
| 10 | 184N | $CF_3$ | $CF_3$ | O | $C_6H_5O$ | H | H | H | 4-Cl—$C_6H_4O$ | H | H |
| 10 | 185N | $CF_3$ | $CF_3$ | O | $C_6H_5O$ | H | H | H | 3,4-Cl—$C_6H_3O$ | H | H |
| 10 | 186N | $CF_3$ | $CF_3$ | O | $C_6H_5O$ | H | H | H | 3-$CF_3$—$C_6H_3O$ | H | H |
| 10 | 187N | $CF_3$ | $CF_3$ | O | $C_6H_5O$ | H | H | H | 3,5-Cl—$C_6H_3O$ | H | H |
| 10 | 188N | $CF_3$ | $CF_3$ | O | $C_6H_5O$ | H | H | H | H | $CH_3O$ | H |
| 10 | 189N | $CF_3$ | $CF_3$ | O | $C_6H_5O$ | H | H | H | H | $CO_2CH_3$ | H |
| 10 | 190N | $CF_3$ | $CF_3$ | O | $C_6H_5O$ | H | H | H | 3-$CH_3O$ $C_6H_5O$ | H | H |
| 10 | 191N | $CF_3$ | $CF_3$ | O | $C_6H_5O$ | H | H | H | 4-$CH_3O$ $C_6H_5O$ | H | H |
| 10 | 193N | $CF_3$ | $CF_3$ | O | $C_6H_5O$ | H | H | H | $CO_2CH_3$ | H | H |
| 10 | 194N | $CF_3$ | $CF_3$ | O | CN | H | H | H | $OCF_3$ | H | H |
| 10 | 195N | $CF_3$ | $CF_3$ | O | $NO_2$ | H | H | H | $OCF_3$ | H | H |
| 10 | 196N | $CF_3$ | $CF_3$ | O | H | CN | H | H | $OCF_3$ | H | H |
| 10 | 197N | $CF_3$ | $CF_3$ | O | H | $NO_2$ | H | H | $OCF_3$ | H | H |
| 10 | 198N | $CF_3$ | $CF_3$ | O | $SO_2CH_3$ | H | H | H | $OCF_3$ | H | H |
| 10 | 199N | $CF_3$ | $CF_3$ | O | H | $SO_2CH_3$ | H | H | $OCF_3$ | H | H |
| 10 | 200N | $CF_3$ | $CF_3$ | O | H | 4-F—$C_6H_5SO_2$ | H | H | $OCF_3$ | H | H |
| 10 | 201N | $CF_3$ | $CF_3$ | O | $SO_2N(CH_3)_2$ | H | H | H | $OCF_3$ | H | H |

TABLE 7-continued

Structure of Substituted Phenyltertiary-2-Heteroalkylamines (Y = CH; Z is covalent bond; $R_{15}$ absent; $R_3$, $R_4$, $R_8$, $R_9$, $R_{13}$, $R_{14}$, and $R_{16}$ all equal H unless indicated below).

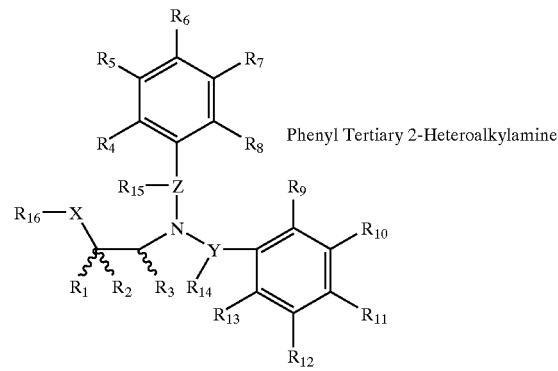

Phenyl Tertiary 2-Heteroalkylamine

| Inhibitor Number Column 1 + Column 2 Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 10 | 202N | $CF_3$ | $CF_3$ | O | H | $SO_2N(CH_3)_2$ | H | H | $OCF_3$ | H | H |
| 10 | 203N | $CF_3$ | $CF_3$ | O | H | $CONH_2$ | H | H | $OCF_3$ | H | H |
| 10 | 204N | $CF_3$ | $CF_3$ | O | H | $CONH\text{—}C_6H_5$ | H | H | $OCF_3$ | H | H |
| 10 | 205N | $CF_3$ | $CF_3$ | O | H | $CO_2CH_3$ | H | H | $OCF_3$ | H | H |
| 10 | 206N | $CF_3$ | $CF_3$ | O | H | $CO_2C_4H_9$ | H | H | $OCF_3$ | H | H |
| 10 | 207N | $CF_3$ | $CF_3$ | O | H | $4\text{-Cl}\text{—}C_6H_5$ | H | H | $C_6H_5O$ | H | H |
| 10 | 208N | $CF_3$ | $CF_3$ | O | H | $4\text{-}CF_3O\text{—}C_6H_5$ | H | H | $CF_3O$ | H | H |
| 10 | 209N | $CF_3$ | $CF_3$ | O | $4\text{-F}\text{—}C_6H_4O$ | H | H | H | $CF_3O$ | H | H |
| 10 | 210N | $CF_3$ | $CF_3$ | O | $C_6F_5O$ | H | H | H | $CF_3O$ | H | H |
| 10 | 211N | $CF_3$ | $CF_3$ | O | H | $4\text{-F}\text{—}C_6H_5$ | H | H | $CF_3O$ | H | H |
| 10 | 212N | $CF_3$ | $CF_3$ | O | H | $4\text{-CN}\text{—}C_6H_5$ | H | H | $CF_3O$ | H | H |
| 10 | 213N | $CF_3$ | $CF_3$ | O | H | $4\text{-}C_6H_5\text{—}C_6H_5$ | H | H | $CF_3O$ | H | H |
| 10 | 214N | $CF_3$ | $CF_3$ | O | $C_6H_5O$ | H | H | $CH_3$ | $CF_3O$ | H | H |
| 10 | 215N | $CF_3$ | $CF_3$ | O | $C_6H_5O$ | H | H | $CH_3$ | $NO_2$ | H | H |
| 10 | 216N | $CF_3$ | $CF_3$ | O | $C_6H_5O$ | H | H | $CH_3$ | H | CN | H |
| 10 | 217N | $CF_3$ | $CF_3$ | O | $C_6H_5O$ | H | H | $3\text{-}CF_3\, C_6H_5$ | $CF_3$ | H | H |
| 10 | 218N | $CF_3$ | $CF_3$ | O | $C_6H_5O$ | H | H | $C_6H_5$ | H | $C_6H_5$ | H |
| 10 | 219N | $CF_3$ | $CF_3$ | O | $C_6H_5O$ | H | H | $C_6H_5$ | $CF_3$ | H | H |
| 10 | 220N | $CF_3$ | $CF_3$ | O | $C_6H_5O$ | H | H | $CH_3$ | F | H | H |
| 10 | 221N | $CF_3$ | $CF_3$ | O | $C_6H_5O$ | H | H | $CF_3$ | H | H | H |
| 10 | 222N | $CF_3$ | $CF_3$ | O | bond to —O— of $R_6$ aryl group | (2-methylphenoxy) | H | H | $CF_3O$ | H | H |
| 10 | 223N | $CF_3$ | $CF_3$ | O | to $CH_2$ of $R_6$ aryl group | (2-bromo-4-ethylphenyl) | H | H | $CF_3O$ | H | H |

TABLE 8

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

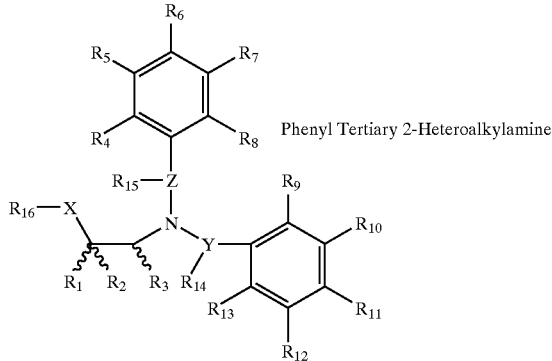

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 19 | 96N | $CF_3$ | $CF_3$ | NH | OH | OH | H | H | $C_6H_5O$ | H | H |
| 19 | 97N | $CF_3$ | $CF_3$ | NH | $C_6H_5O$ | H | H | H | OH | OH | H |
| 19 | 98N | $CF_3$ | $CF_3$ | NH | 3-pyridyl | H | H | H | $CF_3$ | H | H |
| 19 | 99N | $CF_3$ | $CF_3$ | NH | $SO_2N(CH_3)_2$ | H | H | H | $OCF_3$ | H | H |
| 19 | 100N | $CF_3$ | $CF_3$ | NH | $SO_2CH_3$ | H | H | H | $OCF_3$ | H | H |
| 19 | 101N | $CF_3$ | $CF_3$ | NH | $C_6H_5O$ | H | H | H | $C_6H_5O$ | H | H |
| 19 | 102N | $CF_3$ | $CF_3$ | NH | $CF_3O$ | H | H | H | $C_6H_5O$ | H | H |
| 19 | 103N | $CF_3$ | $CF_3$ | NH | $C_6H_5$ | H | H | H | $C_6H_5O$ | H | H |
| 19 | 104N | $CF_3$ | $CF_3$ | NH | H | $C_6H_5$ | H | H | $C_6H_5O$ | H | H |
| 19 | 105N | $CF_3$ | $CF_3$ | NH | $C_6H_5O$ | H | H | H | 4-Cl—$C_6H_4O$ | H | H |
| 19 | 106N | $CF_3$ | $CF_3$ | NH | $CF_3O$ | H | H | H | 4-Cl—$C_6H_4O$ | H | H |
| 19 | 107N | $CF_3$ | $CF_3$ | NH | $C_6H_5O$ | H | H | H | 3,4-Cl—$C_6H_3O$ | H | H |
| 19 | 108N | $CF_3$ | $CF_3$ | NH | $CF_3O$ | H | H | H | 3,4-Cl—$C_6H_3O$ | H | H |
| 19 | 109N | $CF_3$ | $CF_3$ | NH | $CF_3O$ | H | H | H | 3,5-Cl—$C_6H_3O$ | H | H |
| 19 | 110N | $CF_3$ | $CF_3$ | NH | $CF_3O$ | H | H | H | 3-$CH_3O$—$C_6H_4O$ | H | H |
| 19 | 111N | $CF_3$ | $CF_3$ | NH | $CF_3O$ | H | H | H | H | 3-$CH_3O$—$C_6H_4O$ | H |
| 19 | 112N | $CF_3$ | $CF_3$ | NH | $CF_3O$ | H | H | H | 3-$CF_3$—$C_6H_4O$ | H | H |
| 19 | 113N | $CF_3$ | $CF_3$ | NH | $CF_3O$ | H | H | H | $C_6H_5$—$CH_2O$ | H | H |
| 19 | 114N | $CF_3$ | $CF_3$ | NH | $CF_3O$ | H | H | H | $C_6H_5$—$CH_2O$ | $CH_3O$ | H |
| 19 | 115N | $CF_3$ | $CF_3$ | NH | $CF_3O$ | H | H | H | $C_6H_5$—$CH_2O$ | $C_6H_5$—$CH_2O$ | H |
| 19 | 116N | $CF_3$ | $CF_3$ | NH | $CF_3O$ | H | H | H | ethoxy | H | H |
| 19 | 117N | $CF_3$ | $CF_3$ | NH | $CF_3O$ | H | H | H | $CH_3CO_2$ | H | H |
| 19 | 118N | $CF_3$ | $CF_3$ | NH | $CF_3O$ | H | H | H | $HOCH_2$—$CH_2O$ | H | H |
| 19 | 119N | $CF_3$ | $CF_3$ | NH | $CF_3O$ | H | H | H | (glycidyloxy) | H | H |
| 19 | 120N | $CF_3$ | $CF_3$ | NH | $CF_3O$ | H | H | H | $R_{10} + R_{11}$ = $OCH_2O$ | | H |
| 19 | 121N | $CF_3$ | $CF_3$ | NH | $CF_3O$ | H | H | H | $R_{10} + R_{11}$ = $OCH_2CH_2O$ | | H |
| 19 | 122N | $CF_3$ | $CF_3$ | NH | $CF_3O$ | H | H | H | $CH_3O$ | $CH_3O$ | H |
| 19 | 123N | $CF_3$ | $CF_3$ | NH | $CF_3O$ | H | H | H | ethoxy | $CH_3O$ | H |
| 19 | 124N | $CF_3$ | $CF_3$ | NH | $CF_3O$ | H | H | H | ethoxy | ethoxy | H |
| 19 | 125N | $CF_3$ | $CF_3$ | NH | $CF_3O$ | H | H | H | $CH_3CO_2$ | $CH_3CO_2$ | H |
| 19 | 126N | $CF_3$ | $CF_3$ | NH | $CF_3O$ | H | H | H | $CH_3O$ | $CH_3CO_2$ | H |
| 19 | 127N | $CF_3$ | $CF_3$ | NH | $CF_3O$ | H | H | H | n-butoxy | H | H |
| 19 | 128N | $CF_3$ | $CF_3$ | NH | $CF_3O$ | H | H | H | $CH_3O$ | H | H |
| 19 | 129N | $CF_3$ | $CF_3$ | NH | $CF_3O$ | H | H | H | H | $CH_3O$ | H |
| 19 | 130N | $CF_3$ | $CF_3$ | NH | $CH_3O$ | H | H | H | $CH_3O$ | H | H |
| 19 | 131N | $CF_3$ | $CF_3$ | NH | $CH_3O$ | H | H | H | H | $CF_3O$ | H |
| 19 | 132N | $CF_3$ | $CF_3$ | NH | $CF_3O$ | H | H | H | H | ethoxy | H |
| 19 | 133N | $CF_3$ | $CF_3$ | NH | $CF_3O$ | H | H | H | H | n-propoxy | H |
| 19 | 134N | $CF_3$ | $CF_3$ | NH | $C_6H_5$—$CH_2O$ | H | H | H | $CF_3O$ | H | H |
| 19 | 135N | $CF_3$ | $CF_3$ | NH | $C_6H_5$—$CH_2O$ | H | H | H | $C_6H_5O$ | H | H |
| 19 | 136N | $CF_3$ | $CF_3$ | NH | ethoxy | H | H | H | $CF_3O$ | H | H |
| 19 | 137N | $CF_3$ | $CF_3$ | NH | $R_5 + R_6$ = $OCH_2O$ | | H | H | $CF_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

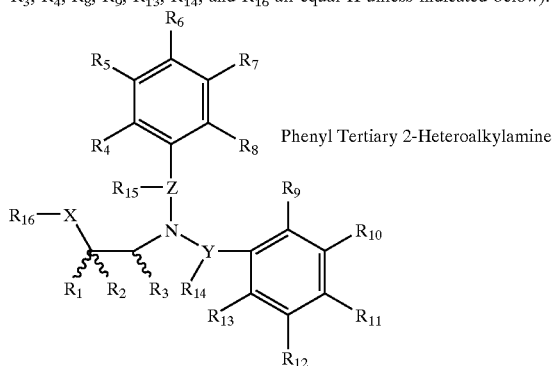

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 19 | 138N | $CF_3$ | $CF_3$ | NH | $R_5 + R_6 = OCH_2O$ | | H | H | $C_6H_5O$ | H | H |
| 19 | 139N | $CF_3$ | $CF_3$ | NH | $R_5 + R_6 = OCH_2CH_2O$ | | H | H | $CF_3O$ | H | H |
| 19 | 140N | $CF_3$ | $CF_3$ | NH | $CH_3O$ | $CH_3O$ | H | H | $CF_3O$ | H | H |
| 19 | 141N | $CF_3$ | $CF_3$ | NH | $R_5 + R_6 = OCH_2CH_2CH_2O$ | | H | H | $CF_3O$ | H | H |
| 19 | 142N | $CF_3$ | $CF_3$ | NH | cyclo pentoxy | $CH_3O$ | H | H | $CF_3O$ | H | H |
| 19 | 143N | $CF_3$ | $CF_3$ | NH | H | $C_6H_5O$ | H | H | $CF_3O$ | H | H |
| 19 | 144N | $CF_3$ | $CF_3$ | NH | $CH_3O$ | $CH_3O$ | $CH_3O$ | H | $CF_3O$ | H | H |
| 19 | 145N | $CF_3$ | $CF_3$ | NH | H | $CF_3O$ | H | H | $CF_3O$ | H | H |
| 19 | 146N | $CF_3$ | $CF_3$ | NH | H | $C_6H_5$—$CH_2$ | H | H | $CF_3O$ | H | H |
| 19 | 147N | $CF_3$ | $CF_3$ | NH | $C_6H_5O$ | H | H | H | $R_{10} + R_{11} = OCH_2CH_2O$ | | H |
| 19 | 148N | $CF_3$ | $CF_3$ | NH | H | $CF_3O$ | H | H | $CF_3$ | H | H |
| 19 | 149N | $CF_3$ | $CF_3$ | NH | $C_6H_5O$ | H | H | H | $CF_3$ | H | H |
| 19 | 150N | $CF_3$ | $CF_3$ | NH | $C_6H_5$ | H | H | H | $CF_3$ | H | H |
| 19 | 151N | $CF_3$ | $CF_3$ | NH | H | $C_6H_5$ | H | H | $CF_3$ | H | H |
| 19 | 152N | $CF_3$ | $CF_3$ | NH | CN | H | H | H | $CF_3$ | H | H |
| 19 | 153N | $CF_3$ | $CF_3$ | NH | H | $OCF_3$ | H | H | $CF_3$ | H | H |
| 19 | 154N | $CF_3$ | $CF_3$ | NH | $OCF_3$ | H | H | H | H | $CF_3$ | H |
| 19 | 155N | $CF_3$ | $CF_3$ | NH | $C_6H_5O$ | H | H | H | H | $CF_3$ | H |
| 19 | 156N | $CF_3$ | $CF_3$ | NH | $C_6H_5$ | H | H | H | H | $CF_3$ | H |
| 19 | 157N | $CF_3$ | $CF_3$ | NH | H | $C_6H_5$ | H | H | H | $CF_3$ | H |
| 19 | 158N | $CF_3$ | $CF_3$ | NH | CN | H | H | H | H | $CF_3$ | H |
| 19 | 159N | $CF_3$ | $CF_3$ | NH | $OCF_3$ | H | H | H | H | $CF_3$ | H |
| 19 | 160N | $CF_3$ | $CF_3$ | NH | $CF_3$ | H | H | H | H | $C_6H_5$ | H |
| 19 | 161N | $CF_3$ | $CF_3$ | NH | $CF_3$ | H | H | H | 3-$CF_3$—$C_6H_5O$ | H | H |
| 19 | 162N | $CF_3$ | $CF_3$ | NH | $CF_3$ | H | H | H | $C_6H_5O$ | H | H |
| 19 | 163N | $CF_3$ | $CF_3$ | NH | $CF_3$ | H | H | H | $CF_3O$ | H | H |
| 19 | 164N | $CF_3$ | $CF_3$ | NH | H | $CF_3$ | H | H | H | $C_6H_5$ | H |
| 19 | 165N | $CF_3$ | $CF_3$ | NH | H | $CF_3$ | H | H | 3-$CF_3$—$C_6H_5O$ | H | H |
| 19 | 166N | $CF_3$ | $CF_3$ | NH | H | $CF_3$ | H | H | $CF_3O$ | H | H |
| 19 | 167N | $CF_3$ | $CF_3$ | NH | H | $CF_3$ | H | H | $C_6H_5O$ | H | H |
| 19 | 168N | $CF_3$ | $CF_3$ | NH | $CF_3$ | H | $CF_3$ | H | $CF_3O$ | H | H |
| 19 | 169N | $CF_3$ | $CF_3$ | NH | $CF_3$ | H | $CF_3$ | H | $C_6H_5O$ | H | H |
| 19 | 170N | $CF_3$ | $CF_3$ | NH | $CF_3O$ | H | H | H | $CF_3$ | H | $CF_3$ |
| 19 | 171N | $CF_3$ | $CF_3$ | NH | $C_6H_5O$ | H | H | H | $CF_3$ | H | $CF_3$ |
| 19 | 172N | $CF_3$ | $CF_3$ | NH | H | $C_6H_5O$ | H | H | $C_6H_5O$ | H | H |
| 19 | 173N | $CF_3$ | $CF_3$ | NH | H | $CF_3O$ | H | H | $CF_3O$ | H | H |
| 19 | 174N | $CF_3$ | $CF_3$ | NH | H | $CF_3O$ | H | H | H | $C_6H_5O$ | H |
| 19 | 175N | $CF_3$ | $CF_3$ | NH | $C_6H_5O$ | H | H | H | H | $C_6H_5O$ | H |
| 19 | 176N | $CF_3$ | $CF_3$ | NH | H | $C_6H_5O$ | H | H | H | $OCF_3$ | H |
| 19 | 177N | $CF_3$ | $CF_3$ | NH | H | $C_6H_5O$ | H | H | H | $C_6H_5O$ | H |
| 19 | 178N | $CF_3$ | $CF_3$ | NH | $C_6H_5O$ | H | H | H | H | CN | H |
| 19 | 179N | $CF_3$ | $CF_3$ | NH | $C_6H_5O$ | H | H | H | CN | H | H |
| 19 | 180N | $CF_3$ | $CF_3$ | NH | $C_6H_5O$ | H | H | H | $NO_2$ | H | H |
| 19 | 181N | $CF_3$ | $CF_3$ | NH | $C_6H_5O$ | H | H | H | H | $NO_2$ | H |
| 19 | 182N | $CF_3$ | $CF_3$ | NH | $C_6H_5O$ | H | H | H | H | $SO_2CH_3$ | H |
| 19 | 183N | $CF_3$ | $CF_3$ | NH | $C_6H_5O$ | H | H | H | H | 2-$NO_2$-4-Cl—$C_6H_3O$ | H |
| 19 | 184N | $CF_3$ | $CF_3$ | NH | $C_6H_5O$ | H | H | H | 4-Cl—$C_6H_4O$ | H | H |
| 19 | 185N | $CF_3$ | $CF_3$ | NH | $C_6H_5O$ | H | H | H | 3,4-Cl—$C_6H_3O$ | H | H |
| 19 | 186N | $CF_3$ | $CF_3$ | NH | $C_6H_5O$ | H | H | H | 3-$CF_3$—$C_6H_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

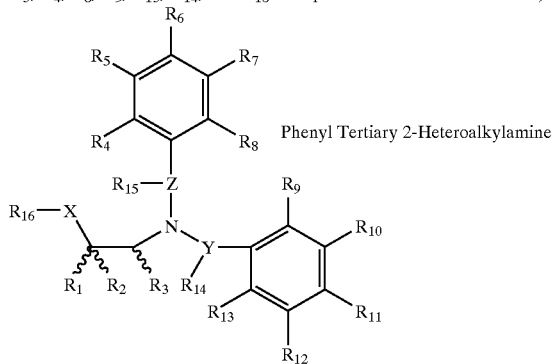

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 19 | 187N | $CF_3$ | $CF_3$ | NH | $C_6H_5O$ | H | H | H | 3,5-Cl—$C_6H_3O$ | H | H |
| 19 | 188N | $CF_3$ | $CF_3$ | NH | $C_6H_5O$ | H | H | H | H | $CH_3O$ | H |
| 19 | 189N | $CF_3$ | $CF_3$ | NH | $C_6H_5O$ | H | H | H | H | $CO_2CH_3$ | H |
| 19 | 190N | $CF_3$ | $CF_3$ | NH | $C_6H_5O$ | H | H | H | 3-$CH_3O$ $C_6H_5O$ | H | H |
| 19 | 191N | $CF_3$ | $CF_3$ | NH | $C_6H_5O$ | H | H | H | 4-$CH_3O$ $C_6H_5O$ | H | H |
| 19 | 193N | $CF_3$ | $CF_3$ | NH | $C_6H_5O$ | H | H | H | $CO_2CH_3$ | H | H |
| 19 | 194N | $CF_3$ | $CF_3$ | NH | CN | H | H | H | $OCF_3$ | H | H |
| 19 | 195N | $CF_3$ | $CF_3$ | NH | $NO_2$ | H | H | H | $OCF_3$ | H | H |
| 19 | 196N | $CF_3$ | $CF_3$ | NH | H | CN | H | H | $OCF_3$ | H | H |
| 19 | 197N | $CF_3$ | $CF_3$ | NH | H | $NO_2$ | H | H | $OCF_3$ | H | H |
| 19 | 198N | $CF_3$ | $CF_3$ | NH | $SO_2CH_3$ | H | H | H | $OCF_3$ | H | H |
| 19 | 199N | $CF_3$ | $CF_3$ | NH | H | $SO_2CH_3$ | H | H | $OCF_3$ | H | H |
| 19 | 200N | $CF_3$ | $CF_3$ | NH | H | 4-F—$C_6H_5$ $SO_2$ | H | H | $OCF_3$ | H | H |
| 19 | 201N | $CF_3$ | $CF_3$ | NH | $SO_2N(CH_3)_2$ | H | H | H | $OCF_3$ | H | H |
| 19 | 202N | $CF_3$ | $CF_3$ | NH | H | $SO_2N(CH_3)_2$ | H | H | $OCF_3$ | H | H |
| 19 | 203N | $CF_3$ | $CF_3$ | NH | H | $CONH_2$ | H | H | $OCF_3$ | H | H |
| 19 | 204N | $CF_3$ | $CF_3$ | NH | H | CONH—$C_6H_5$ | H | H | $OCF_3$ | H | H |
| 19 | 205N | $CF_3$ | $CF_3$ | NH | H | $CO_2CH_3$ | H | H | $OCF_3$ | H | H |
| 19 | 206N | $CF_3$ | $CF_3$ | NH | H | $CO_2C_4H_9$ | H | H | $OCF_3$ | H | H |
| 19 | 207N | $CF_3$ | $CF_3$ | NH | H | 4-Cl—$C_6H_5$ | H | H | $C_6H_5O$ | H | H |
| 19 | 208N | $CF_3$ | $CF_3$ | NH | H | 4-$CF_3O$—$C_6H_5$ | H | H | $CF_3O$ | H | H |
| 19 | 209N | $CF_3$ | $CF_3$ | NH | 4-F—$C_6H_4O$ | H | H | H | $CF_3O$ | H | H |
| 19 | 210N | $CF_3$ | $CF_3$ | NH | $C_6F_5O$ | H | H | H | $CF_3O$ | H | H |
| 19 | 211N | $CF_3$ | $CF_3$ | NH | H | 4-F—$C_6H_5$ | H | H | $CF_3O$ | H | H |
| 19 | 212N | $CF_3$ | $CF_3$ | NH | H | 4-CN—$C_6H_5$ | H | H | $CF_3O$ | H | H |
| 19 | 213N | $CF_3$ | $CF_3$ | NH | H | 4-$C_6H_5$—$C_6H_5$ | H | H | $CF_3O$ | H | H |
| 19 | 214N | $CF_3$ | $CF_3$ | NH | $C_6H_5O$ | H | H | $CH_3$ | $CF_3O$ | H | H |
| 19 | 215N | $CF_3$ | $CF_3$ | NH | $C_6H_5O$ | H | H | $CH_3$ | $NO_2$ | H | H |
| 19 | 216N | $CF_3$ | $CF_3$ | NH | $C_6H_5O$ | H | H | $CH_3$ | H | CN | H |
| 19 | 217N | $CF_3$ | $CF_3$ | NH | $C_6H_5O$ | H | H | 3-$CF_3$ $C_6H_5$ | $CF_3$ | H | H |
| 19 | 218N | $CF_3$ | $CF_3$ | NH | $C_6H_5O$ | H | H | $C_6H_5$ | H | $C_6H_5$ | H |
| 19 | 219N | $CF_3$ | $CF_3$ | NH | $C_6H_5O$ | H | H | $C_6H_5$ | $CF_3$ | H | H |
| 19 | 220N | $CF_3$ | $CF_3$ | NH | $C_6H_5O$ | H | H | $CH_3$ | F | H | H |
| 19 | 221N | $CF_3$ | $CF_3$ | NH | $C_6H_5O$ | H | H | $CF_3$ | H | H | H |
| 19 | 222N | $CF_3$ | $CF_3$ | NH | bond to —O— of $R_6$ aryl group | | H | H | $CF_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

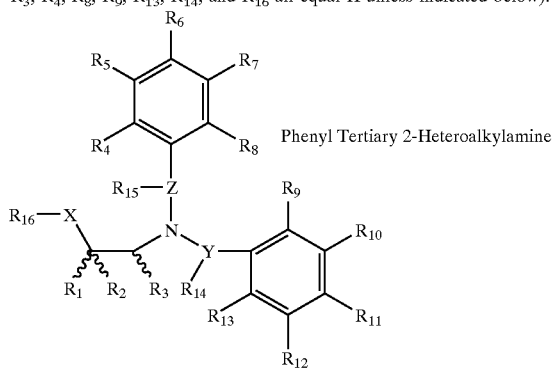

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 19 | 223N | $CF_3$ | $CF_3$ | NH | to $CH_2$ of $R_6$ aryl group | (2-bromo-4-ethyl-5-methylphenyl) | H | H | $CF_3O$ | H | H |
| 20 | 96N | $CF_3$ | H | NH | OH | OH | H | H | $C_6H_5O$ | H | H |
| 20 | 97N | $CF_3$ | H | NH | $C_6H_5O$ | H | H | H | OH | OH | H |
| 20 | 98N | $CF_3$ | H | NH | 3-pyridyl | H | H | H | $CF_3$ | H | H |
| 20 | 99N | $CF_3$ | H | NH | $SO_2N(CH_3)_2$ | H | H | H | $OCF_3$ | H | H |
| 20 | 100N | $CF_3$ | H | NH | $SO_2CH_3$ | H | H | H | $OCF_3$ | H | H |
| 20 | 101N | $CF_3$ | H | NH | $C_6H_5O$ | H | H | H | $C_6H_5O$ | H | H |
| 20 | 102N | $CF_3$ | H | NH | $CF_3O$ | H | H | H | $C_6H_5O$ | H | H |
| 20 | 103N | $CF_3$ | H | NH | $C_6H_5$ | H | H | H | $C_6H_5O$ | H | H |
| 20 | 104N | $CF_3$ | H | NH | H | $C_6H_5$ | H | H | $C_6H_5O$ | H | H |
| 20 | 105N | $CF_3$ | H | NH | $C_6H_5O$ | H | H | H | 4-Cl—$C_6H_4O$ | H | H |
| 20 | 106N | $CF_3$ | H | NH | $CF_3O$ | H | H | H | 4-Cl—$C_6H_4O$ | H | H |
| 20 | 107N | $CF_3$ | H | NH | $C_6H_5O$ | H | H | H | 3,4-Cl—$C_6H_3O$ | H | H |
| 20 | 108N | $CF_3$ | H | NH | $CF_3O$ | H | H | H | 3,4-Cl—$C_6H_3O$ | H | H |
| 20 | 109N | $CF_3$ | H | NH | $CF_3O$ | H | H | H | 3,5-Cl—$C_6H_3O$ | H | H |
| 20 | 110N | $CF_3$ | H | NH | $CF_3O$ | H | H | H | 3-$CH_3$O—$C_6H_4O$ | H | H |
| 20 | 111N | $CF_3$ | H | NH | $CF_3O$ | H | H | H | H | 3-$CH_3$O—$C_6H_4O$ | H |
| 20 | 112N | $CF_3$ | H | NH | $CF_3O$ | H | H | H | 3-$CF_3$—$C_6H_4O$ | H | H |
| 20 | 113N | $CF_3$ | H | NH | $CF_3O$ | H | H | H | $C_6H_5$—$CH_2O$ | H | H |
| 20 | 114N | $CF_3$ | H | NH | $CF_3O$ | H | H | H | $C_6H_5$—$CH_2O$ | $CH_3O$ | H |
| 20 | 115N | $CF_3$ | H | NH | $CF_3O$ | H | H | H | $C_6H_5$—$CH_2O$ | $C_6H_5$—$CH_2O$ | H |
| 20 | 116N | $CF_3$ | H | NH | $CF_3O$ | H | H | H | ethoxy | H | H |
| 20 | 117N | $CF_3$ | H | NH | $CF_3O$ | H | H | H | $CH_3CO_2$ | H | H |
| 20 | 118N | $CF_3$ | H | NH | $CF_3O$ | H | H | H | $HOCH_2$—$CH_2O$ | H | H |
| 20 | 119N | $CF_3$ | H | NH | $CF_3O$ | H | H | H | (glycidyloxy) | H | H |
| 20 | 120N | $CF_3$ | H | NH | $CF_3O$ | H | H | H | $R_{10}$ + $R_{11}$ = $OCH_2O$ | | H |
| 20 | 121N | $CF_3$ | H | NH | $CF_3O$ | H | H | H | $R_{10}$ + $R_{11}$ = $OCH_2CH_2O$ | | H |
| 20 | 122N | $CF_3$ | H | NH | $CF_3O$ | H | H | H | $CH_3O$ | $CH_3O$ | H |
| 20 | 123N | $CF_3$ | H | NH | $CF_3O$ | H | H | H | ethoxy | $CH_3O$ | H |
| 20 | 124N | $CF_3$ | H | NH | $CF_3O$ | H | H | H | ethoxy | ethoxy | H |
| 20 | 125N | $CF_3$ | H | NH | $CF_3O$ | H | H | H | $CH_3CO_2$ | $CH_3CO_2$ | H |
| 20 | 126N | $CF_3$ | H | NH | $CF_3O$ | H | H | H | $CH_3O$ | $CH_3CO_2$ | H |
| 20 | 127N | $CF_3$ | H | NH | $CF_3O$ | H | H | H | n-butoxy | H | H |
| 20 | 128N | $CF_3$ | H | NH | $CF_3O$ | H | H | H | $CH_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

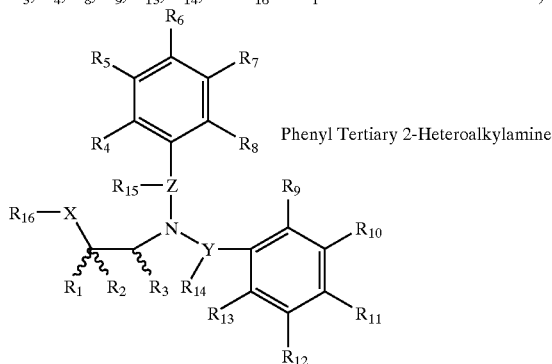

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 20 | 129N | $CF_3$ | H | NH | $CF_3O$ | H | H | H | H | $CH_3O$ | H |
| 20 | 130N | $CF_3$ | H | NH | $CH_3O$ | H | H | H | $CH_3O$ | H | H |
| 20 | 131N | $CF_3$ | H | NH | $CH_3O$ | H | H | H | H | $CF_3O$ | H |
| 20 | 132N | $CF_3$ | H | NH | $CF_3O$ | H | H | H | H | ethoxy | H |
| 20 | 133N | $CF_3$ | H | NH | $CF_3O$ | H | H | H | H | n-propoxy | H |
| 20 | 134N | $CF_3$ | H | NH | $C_6H_5$—$CH_2O$ | H | H | H | $CF_3O$ | H | H |
| 20 | 135N | $CF_3$ | H | NH | $C_6H_5$—$CH_2O$ | H | H | H | $C_6H_5O$ | H | H |
| 20 | 136N | $CF_3$ | H | NH | ethoxy | H | H | H | $CF_3O$ | H | H |
| 20 | 137N | $CF_3$ | H | NH | $R_5 + R_6 = OCH_2O$ | | H | H | $CF_3O$ | H | H |
| 20 | 138N | $CF_3$ | H | NH | $R_5 + R_6 = OCH_2O$ | | H | H | $C_6H_5O$ | H | H |
| 20 | 139N | $CF_3$ | H | NH | $R_5 + R_6 = OCH_2CH_2O$ | | H | H | $CF_3O$ | H | H |
| 20 | 140N | $CF_3$ | H | NH | $CH_3O$ | $CH_3O$ | H | H | $CF_3O$ | H | H |
| 20 | 141N | $CF_3$ | H | NH | $R_5 + R_6 = OCH_2CH_2CH_2O$ | | H | H | $CF_3O$ | H | H |
| 20 | 142N | $CF_3$ | H | NH | cyclo pentoxy | $CH_3O$ | H | H | $CF_3O$ | H | H |
| 20 | 143N | $CF_3$ | H | NH | H | $C_6H_5O$ | H | H | $CF_3O$ | H | H |
| 20 | 144N | $CF_3$ | H | NH | $CH_3O$ | $CH_3O$ | $CH_3O$ | H | $CF_3O$ | H | H |
| 20 | 145N | $CF_3$ | H | NH | H | $CF_3O$ | H | H | $CF_3O$ | H | H |
| 20 | 146N | $CF_3$ | H | NH | H | $C_6H_5$—$CH_2$ | H | H | $CF_3O$ | H | H |
| 20 | 147N | $CF_3$ | H | NH | $C_6H_5O$ | H | H | H | $R_{10} + R_{11} = OCH_2CH_2O$ | | H |
| 20 | 148N | $CF_3$ | H | NH | H | $CF_3O$ | H | H | $CF_3$ | H | H |
| 20 | 149N | $CF_3$ | H | NH | $C_6H_5O$ | H | H | H | $CF_3$ | H | H |
| 20 | 150N | $CF_3$ | H | NH | $C_6H_5$ | H | H | H | $CF_3$ | H | H |
| 20 | 151N | $CF_3$ | H | NH | H | $C_6H_5$ | H | H | $CF_3$ | H | H |
| 20 | 152N | $CF_3$ | H | NH | CN | H | H | H | $CF_3$ | H | H |
| 20 | 153N | $CF_3$ | H | NH | H | $OCF_3$ | H | H | $CF_3$ | H | H |
| 20 | 154N | $CF_3$ | H | NH | $OCF_3$ | H | H | H | H | $CF_3$ | H |
| 20 | 155N | $CF_3$ | H | NH | $C_6H_5O$ | H | H | H | H | $CF_3$ | H |
| 20 | 156N | $CF_3$ | H | NH | $C_6H_5$ | H | H | H | H | $CF_3$ | H |
| 20 | 157N | $CF_3$ | H | NH | H | $C_6H_5$ | H | H | H | $CF_3$ | H |
| 20 | 158N | $CF_3$ | H | NH | CN | H | H | H | H | $CF_3$ | H |
| 20 | 159N | $CF_3$ | H | NH | $OCF_3$ | H | H | H | H | $CF_3$ | H |
| 20 | 160N | $CF_3$ | H | NH | $CF_3$ | H | H | H | H | $C_6H_5$ | H |
| 20 | 161N | $CF_3$ | H | NH | $CF_3$ | H | H | H | 3-$CF_3$—$C_6H_5O$ | H | H |
| 20 | 162N | $CF_3$ | H | NH | $CF_3$ | H | H | H | $C_6H_5O$ | H | H |
| 20 | 163N | $CF_3$ | H | NH | $CF_3$ | H | H | H | $CF_3O$ | H | H |
| 20 | 164N | $CF_3$ | H | NH | H | $CF_3$ | H | H | H | $C_6H_5$ | H |
| 20 | 165N | $CF_3$ | H | NH | H | $CF_3$ | H | H | 3-$CF_3$—$C_6H_5O$ | H | H |
| 20 | 166N | $CF_3$ | H | NH | H | $CF_3$ | H | H | $CF_3O$ | H | H |
| 20 | 167N | $CF_3$ | H | NH | H | $CF_3$ | H | H | $C_6H_5O$ | H | H |
| 20 | 168N | $CF_3$ | H | NH | $CF_3$ | H | $CF_3$ | H | $CF_3O$ | H | H |
| 20 | 169N | $CF_3$ | H | NH | $CF_3$ | H | $CF_3$ | H | $C_6H_5O$ | H | H |
| 20 | 170N | $CF_3$ | H | NH | $CF_3O$ | H | H | H | $CF_3$ | H | $CF_3$ |
| 20 | 171N | $CF_3$ | H | NH | $C_6H_5O$ | H | H | H | $CF_3$ | H | $CF_3$ |
| 20 | 172N | $CF_3$ | H | NH | H | $C_6H_5O$ | H | H | $C_6H_5O$ | H | H |
| 20 | 173N | $CF_3$ | H | NH | H | $CF_3O$ | H | H | $CF_3O$ | H | H |
| 20 | 174N | $CF_3$ | H | NH | H | $CF_3O$ | H | H | H | $C_6H_5O$ | H |
| 20 | 175N | $CF_3$ | H | NH | $C_6H_5O$ | H | H | H | H | $C_6H_5O$ | H |
| 20 | 176N | $CF_3$ | H | NH | H | $C_6H_5O$ | H | H | H | $OCF_3$ | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

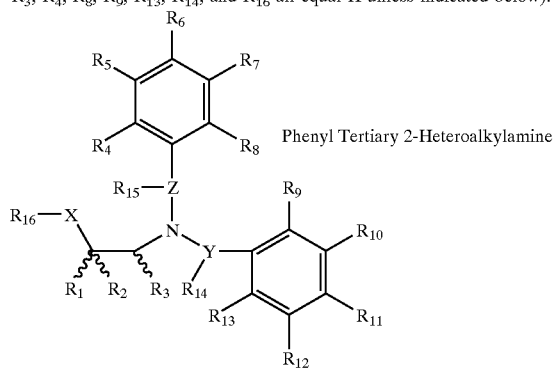

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 20 | 177N | $CF_3$ | H | NH | H | $C_6H_5O$ | H | H | H | $C_6H_5O$ | H |
| 20 | 178N | $CF_3$ | H | NH | $C_6H_5O$ | H | H | H | H | CN | H |
| 20 | 179N | $CF_3$ | H | NH | $C_6H_5O$ | H | H | H | CN | H | H |
| 20 | 180N | $CF_3$ | H | NH | $C_6H_5O$ | H | H | H | $NO_2$ | H | H |
| 20 | 181N | $CF_3$ | H | NH | $C_6H_5O$ | H | H | H | H | $NO_2$ | H |
| 20 | 182N | $CF_3$ | H | NH | $C_6H_5O$ | H | H | H | H | $SO_2CH_3$ | H |
| 20 | 183N | $CF_3$ | H | NH | $C_6H_5O$ | H | H | H | H | 2-$NO_2$-4-Cl—$C_6H_3O$ | H |
| 20 | 184N | $CF_3$ | H | NH | $C_6H_5O$ | H | H | H | 4-Cl—$C_6H_4O$ | H | H |
| 20 | 185N | $CF_3$ | H | NH | $C_6H_5O$ | H | H | H | 3,4-Cl—$C_6H_3O$ | H | H |
| 20 | 186N | $CF_3$ | H | NH | $C_6H_5O$ | H | H | H | 3-$CF_3$—$C_6H_3O$ | H | H |
| 20 | 187N | $CF_3$ | H | NH | $C_6H_5O$ | H | H | H | 3,5-Cl—$C_6H_3O$ | H | H |
| 20 | 188N | $CF_3$ | H | NH | $C_6H_5O$ | H | H | H | H | $CH_3O$ | H |
| 20 | 189N | $CF_3$ | H | NH | $C_6H_5O$ | H | H | H | H | $CO_2CH_3$ | H |
| 20 | 190N | $CF_3$ | H | NH | $C_6H_5O$ | H | H | H | 3-$CH_3O$ $C_6H_5O$ | H | H |
| 20 | 191N | $CF_3$ | H | NH | $C_6H_5O$ | H | H | H | 4-$CH_3O$ $C_6H_5O$ | H | H |
| 20 | 193N | $CF_3$ | H | NH | $C_6H_5O$ | H | H | H | $CO_2CH_3$ | H | H |
| 20 | 194N | $CF_3$ | H | NH | CN | H | H | H | $OCF_3$ | H | H |
| 20 | 195N | $CF_3$ | H | NH | $NO_2$ | H | H | H | $OCF_3$ | H | H |
| 20 | 196N | $CF_3$ | H | NH | H | CN | H | H | $OCF_3$ | H | H |
| 20 | 197N | $CF_3$ | H | NH | H | $NO_2$ | H | H | $OCF_3$ | H | H |
| 20 | 198N | $CF_3$ | H | NH | $SO_2CH_3$ | H | H | H | $OCF_3$ | H | H |
| 20 | 199N | $CF_3$ | H | NH | H | $SO_2CH_3$ | H | H | $OCF_3$ | H | H |
| 20 | 200N | $CF_3$ | H | NH | H | 4-F—$C_6H_5$ $SO_2$ | H | H | $OCF_3$ | H | H |
| 20 | 201N | $CF_3$ | H | NH | $SO_2N(CH_3)_2$ | H | H | H | $OCF_3$ | H | H |
| 20 | 202N | $CF_3$ | H | NH | H | $SO_2N(CH_3)_2$ | H | H | $OCF_3$ | H | H |
| 20 | 203N | $CF_3$ | H | NH | H | $CONH_2$ | H | H | $OCF_3$ | H | H |
| 20 | 204N | $CF_3$ | H | NH | H | CONH—$C_6H_5$ | H | H | $OCF_3$ | H | H |
| 20 | 205N | $CF_3$ | H | NH | H | $CO_2CH_3$ | H | H | $OCF_3$ | H | H |
| 20 | 206N | $CF_3$ | H | NH | H | $CO_2C_4H_9$ | H | H | $OCF_3$ | H | H |
| 20 | 207N | $CF_3$ | H | NH | H | 4-Cl—$C_6H_5$ | H | H | $C_6H_5O$ | H | H |
| 20 | 208N | $CF_3$ | H | NH | H | 4-$CF_3O$—$C_6H_5$ | H | H | $CF_3O$ | H | H |
| 20 | 209N | $CF_3$ | H | NH | 4-F—$C_6H_4O$ | H | H | H | $CF_3O$ | H | H |
| 20 | 210N | $CF_3$ | H | NH | $C_6F_5O$ | H | H | H | $CF_3O$ | H | H |
| 20 | 211N | $CF_3$ | H | NH | H | 4-F—$C_6H_5$ | H | H | $CF_3O$ | H | H |
| 20 | 212N | $CF_3$ | H | NH | H | 4-CN—$C_6H_5$ | H | H | $CF_3O$ | H | H |
| 20 | 213N | $CF_3$ | H | NH | H | 4-$C_6H_5$—$C_6H_5$ | H | H | $CF_3O$ | H | H |
| 20 | 214N | $CF_3$ | H | NH | $C_6H_5O$ | H | H | $CH_3$ | $CF_3O$ | H | H |
| 20 | 215N | $CF_3$ | H | NH | $C_6H_5O$ | H | H | $CH_3$ | $NO_2$ | H | H |
| 20 | 216N | $CF_3$ | H | NH | $C_6H_5O$ | H | H | $CH_3$ | H | CN | H |
| 20 | 217N | $CF_3$ | H | NH | $C_6H_5O$ | H | H | 3-$CF_3$ $C_6H_5$ | $CF_3$ | H | H |
| 20 | 218N | $CF_3$ | H | NH | $C_6H_5O$ | H | H | $C_6H_5$ | H | $C_6H_5$ | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

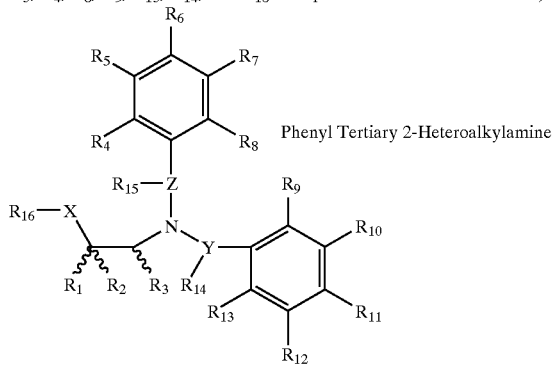

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 20 | 219N | $CF_3$ | H | NH | $C_6H_5O$ | H | H | $C_6H_5$ | $CF_3$ | H | H |
| 20 | 220N | $CF_3$ | H | NH | $C_6H_5O$ | H | H | $CH_3$ | F | H | H |
| 20 | 221N | $CF_3$ | H | NH | $C_6H_5O$ | H | H | $CF_3$ | H | H | H |
| 20 | 222N | $CF_3$ | H | NH | bond to —O— of $R_6$ aryl group | | H | H | $CF_3O$ | H | H |
| 20 | 223N | $CF_3$ | H | NH | to $CH_2$ of $R_6$ aryl group | | H | H | $CF_3O$ | H | H |
| 25 | 96N | $CF_3$ | H | S | OH | OH | H | H | $C_6H_5O$ | H | H |
| 25 | 97N | $CF_3$ | H | S | $C_6H_5O$ | H | H | H | OH | OH | H |
| 25 | 98N | $CF_3$ | H | S | 3-pyridyl | H | H | H | $CF_3$ | H | H |
| 25 | 99N | $CF_3$ | H | S | $SO_2N(CH_3)_2$ | H | H | H | $OCF_3$ | H | H |
| 25 | 100N | $CF_3$ | H | S | $SO_2CH_3$ | H | H | H | $OCF_3$ | H | H |
| 25 | 101N | $CF_3$ | H | S | $C_6H_5O$ | H | H | H | $C_6H_5O$ | H | H |
| 25 | 102N | $CF_3$ | H | S | $CF_3O$ | H | H | H | $C_6H_5O$ | H | H |
| 25 | 103N | $CF_3$ | H | S | $C_6H_5$ | H | H | H | $C_6H_5O$ | H | H |
| 25 | 104N | $CF_3$ | H | S | H | $C_6H_5$ | H | H | $C_6H_5O$ | H | H |
| 25 | 105N | $CF_3$ | H | S | $C_6H_5O$ | H | H | H | 4-Cl—$C_6H_4O$ | H | H |
| 25 | 106N | $CF_3$ | H | S | $CF_3O$ | H | H | H | 4-Cl—$C_6H_4O$ | H | H |
| 25 | 107N | $CF_3$ | H | S | $C_6H_5O$ | H | H | H | 3,4-Cl—$C_6H_3O$ | H | H |
| 25 | 108N | $CF_3$ | H | S | $CF_3O$ | H | H | H | 3,4-Cl—$C_6H_3O$ | H | H |
| 25 | 109N | $CF_3$ | H | S | $CF_3O$ | H | H | H | 3,5-Cl—$C_6H_3O$ | H | H |
| 25 | 110N | $CF_3$ | H | S | $CF_3O$ | H | H | H | 3-$CH_3O$—$C_6H_4O$ | H | H |
| 25 | 111N | $CF_3$ | H | S | $CF_3O$ | H | H | H | H | 3-$CH_3O$—$C_6H_4O$ | H |
| 25 | 112N | $CF_3$ | H | S | $CF_3O$ | H | H | H | 3-$CF_3$—$C_6H_4O$ | H | H |
| 25 | 113N | $CF_3$ | H | S | $CF_3O$ | H | H | H | $C_6H_5$—$CH_2O$ | H | H |
| 25 | 114N | $CF_3$ | H | S | $CF_3O$ | H | H | H | $C_6H_5$—$CH_2O$ | $CH_3O$ | H |
| 25 | 115N | $CF_3$ | H | S | $CF_3O$ | H | H | H | $C_6H_5$—$CH_2O$ | $C_6H_5$—$CH_2O$ | H |
| 25 | 116N | $CF_3$ | H | S | $CF_3O$ | H | H | H | ethoxy | H | H |
| 25 | 117N | $CF_3$ | H | S | $CF_3O$ | H | H | H | $CH_3CO_2$ | H | H |
| 25 | 118N | $CF_3$ | H | S | $CF_3O$ | H | H | H | $HOCH_2$—$CH_2O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

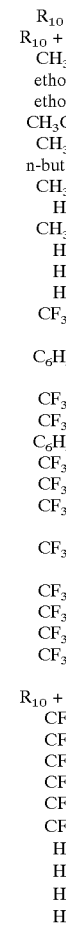

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 25 | 119N | $CF_3$ | H | S | $CF_3O$ | H | H | H | 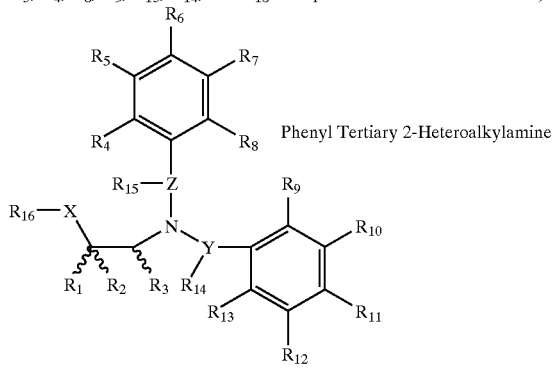 | H | H |
| 25 | 120N | $CF_3$ | H | S | $CF_3O$ | H | H | H | $R_{10} + R_{11} = OCH_2O$ | | H |
| 25 | 121N | $CF_3$ | H | S | $CF_3O$ | H | H | H | $R_{10} + R_{11} = OCH_2CH_2O$ | | H |
| 25 | 122N | $CF_3$ | H | S | $CF_3O$ | H | H | H | $CH_3O$ | $CH_3O$ | H |
| 25 | 123N | $CF_3$ | H | S | $CF_3O$ | H | H | H | ethoxy | $CH_3O$ | H |
| 25 | 124N | $CF_3$ | H | S | $CF_3O$ | H | H | H | ethoxy | ethoxy | H |
| 25 | 125N | $CF_3$ | H | S | $CF_3O$ | H | H | H | $CH_3CO_2$ | $CH_3CO_2$ | H |
| 25 | 126N | $CF_3$ | H | S | $CF_3O$ | H | H | H | $CH_3O$ | $CH_3CO_2$ | H |
| 25 | 127N | $CF_3$ | H | S | $CF_3O$ | H | H | H | n-butoxy | H | H |
| 25 | 128N | $CF_3$ | H | S | $CF_3O$ | H | H | H | $CH_3O$ | H | H |
| 25 | 129N | $CF_3$ | H | S | $CF_3O$ | H | H | H | H | $CH_3O$ | H |
| 25 | 130N | $CF_3$ | H | S | $CH_3O$ | H | H | H | $CH_3O$ | H | H |
| 25 | 131N | $CF_3$ | H | S | $CH_3O$ | H | H | H | H | $CF_3O$ | H |
| 25 | 132N | $CF_3$ | H | S | $CF_3O$ | H | H | H | H | ethoxy | H |
| 25 | 133N | $CF_3$ | H | S | $CF_3O$ | H | H | H | H | n-propoxy | H |
| 25 | 134N | $CF_3$ | H | S | $C_6H_5$—$CH_2O$ | H | H | H | $CF_3O$ | H | H |
| 25 | 135N | $CF_3$ | H | S | $C_6H_5$—$CH_2O$ | H | H | H | $C_6H_5O$ | H | H |
| 25 | 136N | $CF_3$ | H | S | ethoxy | H | H | H | $CF_3O$ | H | H |
| 25 | 137N | $CF_3$ | H | S | $R_5 + R_6 = OCH_2O$ | | H | H | $CF_3O$ | H | H |
| 25 | 138N | $CF_3$ | H | S | $R_5 + R_6 = OCH_2O$ | | H | H | $C_6H_5O$ | H | H |
| 25 | 139N | $CF_3$ | H | S | $R_5 + R_6 = OCH_2CH_2O$ | | H | H | $CF_3O$ | H | H |
| 25 | 140N | $CF_3$ | H | S | $CH_3O$ | $CH_3O$ | H | H | $CF_3O$ | H | H |
| 25 | 141N | $CF_3$ | H | S | $R_5 + R_6 = OCH_2CH_2CH_2O$ | | H | H | $CF_3O$ | H | H |
| 25 | 142N | $CF_3$ | H | S | cyclopentoxy | $CH_3O$ | H | H | $CF_3O$ | H | H |
| 25 | 143N | $CF_3$ | H | S | H | $C_6H_5O$ | H | H | $CF_3O$ | H | H |
| 25 | 144N | $CF_3$ | H | S | $CH_3O$ | $CH_3O$ | $CH_3O$ | H | $CF_3O$ | H | H |
| 25 | 145N | $CF_3$ | H | S | H | $CF_3O$ | H | H | $CF_3O$ | H | H |
| 25 | 146N | $CF_3$ | H | S | H | $C_6H_5$—$CH_2$ | H | H | $CF_3O$ | H | H |
| 25 | 147N | $CF_3$ | H | S | $C_6H_5O$ | H | H | H | $R_{10} + R_{11} = OCH_2CH_2O$ | | H |
| 25 | 148N | $CF_3$ | H | S | H | $CF_3O$ | H | H | $CF_3$ | H | H |
| 25 | 149N | $CF_3$ | H | S | $C_6H_5O$ | H | H | H | $CF_3$ | H | H |
| 25 | 150N | $CF_3$ | H | S | $C_6H_5$ | H | H | H | $CF_3$ | H | H |
| 25 | 151N | $CF_3$ | H | S | H | $C_6H_5$ | H | H | $CF_3$ | H | H |
| 25 | 152N | $CF_3$ | H | S | CN | H | H | H | $CF_3$ | H | H |
| 25 | 153N | $CF_3$ | H | S | H | $OCF_3$ | H | H | $CF_3$ | H | H |
| 25 | 154N | $CF_3$ | H | S | $OCF_3$ | H | H | H | H | $CF_3$ | H |
| 25 | 155N | $CF_3$ | H | S | $C_6H_5O$ | H | H | H | H | $CF_3$ | H |
| 25 | 156N | $CF_3$ | H | S | $C_6H_5$ | H | H | H | H | $CF_3$ | H |
| 25 | 157N | $CF_3$ | H | S | H | $C_6H_5$ | H | H | H | $CF_3$ | H |
| 25 | 158N | $CF_3$ | H | S | CN | H | H | H | H | $CF_3$ | H |
| 25 | 159N | $CF_3$ | H | S | $OCF_3$ | H | H | H | H | $CF_3$ | H |
| 25 | 160N | $CF_3$ | H | S | $CF_3$ | H | H | H | H | $C_6H_5$ | H |
| 25 | 161N | $CF_3$ | H | S | $CF_3$ | H | H | H | 3-$CF_3$—$C_6H_5O$ | H | H |
| 25 | 162N | $CF_3$ | H | S | $CF_3$ | H | H | H | $C_6H_5O$ | H | H |
| 25 | 163N | $CF_3$ | H | S | $CF_3$ | H | H | H | $CF_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

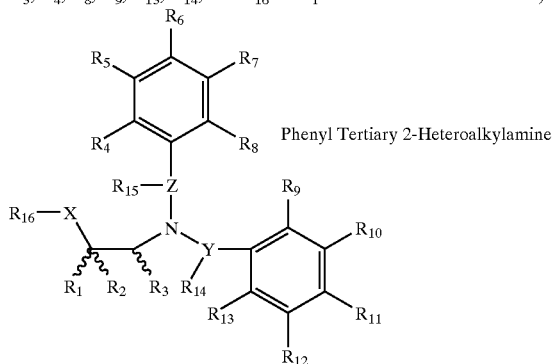

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 25 | 164N | $CF_3$ | H | S | H | $CF_3$ | H | H | H | $C_6H_5$ | H |
| 25 | 165N | $CF_3$ | H | S | H | $CF_3$ | H | H | 3-$CF_3$—$C_6H_5O$ | H | H |
| 25 | 166N | $CF_3$ | H | S | H | $CF_3$ | H | H | $CF_3O$ | H | H |
| 25 | 167N | $CF_3$ | H | S | H | $CF_3$ | H | H | $C_6H_5O$ | H | H |
| 25 | 168N | $CF_3$ | H | S | $CF_3$ | H | $CF_3$ | H | $CF_3O$ | H | H |
| 25 | 169N | $CF_3$ | H | S | $CF_3$ | H | $CF_3$ | H | $C_6H_5O$ | H | H |
| 25 | 170N | $CF_3$ | H | S | $CF_3O$ | H | H | H | $CF_3$ | H | $CF_3$ |
| 25 | 171N | $CF_3$ | H | S | $C_6H_5O$ | H | H | H | $CF_3$ | H | $CF_3$ |
| 25 | 172N | $CF_3$ | H | S | H | $C_6H_5O$ | H | H | $C_6H_5O$ | H | H |
| 25 | 173N | $CF_3$ | H | S | H | $CF_3O$ | H | H | $CF_3O$ | H | H |
| 25 | 174N | $CF_3$ | H | S | H | $CF_3O$ | H | H | H | $C_6H_5O$ | H |
| 25 | 175N | $CF_3$ | H | S | $C_6H_5O$ | H | H | H | H | $C_6H_5O$ | H |
| 25 | 176N | $CF_3$ | H | S | H | $C_6H_5O$ | H | H | H | $OCF_3$ | H |
| 25 | 177N | $CF_3$ | H | S | H | $C_6H_5O$ | H | H | H | $C_6H_5O$ | H |
| 25 | 178N | $CF_3$ | H | S | $C_6H_5O$ | H | H | H | H | CN | H |
| 25 | 179N | $CF_3$ | H | S | $C_6H_5O$ | H | H | H | CN | H | H |
| 25 | 180N | $CF_3$ | H | S | $C_6H_5O$ | H | H | H | $NO_2$ | H | H |
| 25 | 181N | $CF_3$ | H | S | $C_6H_5O$ | H | H | H | H | $NO_2$ | H |
| 25 | 182N | $CF_3$ | H | S | $C_6H_5O$ | H | H | H | H | $SO_2CH_3$ | H |
| 25 | 183N | $CF_3$ | H | S | $C_6H_5O$ | H | H | H | H | 2-$NO_2$-4-Cl—$C_6H_3O$ | H |
| 25 | 184N | $CF_3$ | H | S | $C_6H_5O$ | H | H | H | 4-Cl—$C_6H_4O$ | H | H |
| 25 | 185N | $CF_3$ | H | S | $C_6H_5O$ | H | H | H | 3,4-$Cl_2$—$C_6H_3O$ | H | H |
| 25 | 186N | $CF_3$ | H | S | $C_6H_5O$ | H | H | H | 3-$CF_3$—$C_6H_3O$ | H | H |
| 25 | 187N | $CF_3$ | H | S | $C_6H_5O$ | H | H | H | 3,5-$Cl_2$—$C_6H_3O$ | H | H |
| 25 | 188N | $CF_3$ | H | S | $C_6H_5O$ | H | H | H | H | $CH_3O$ | H |
| 25 | 189N | $CF_3$ | H | S | $C_6H_5O$ | H | H | H | H | $CO_2CH_3$ | H |
| 25 | 190N | $CF_3$ | H | S | $C_6H_5O$ | H | H | H | 3-$CH_3O$ $C_6H_5O$ | H | H |
| 25 | 191N | $CF_3$ | H | S | $C_6H_5O$ | H | H | H | 4-$CH_3O$ $C_6H_5O$ | H | H |
| 25 | 193N | $CF_3$ | H | S | $C_6H_5O$ | H | H | H | $CO_2CH_3$ | H | H |
| 25 | 194N | $CF_3$ | H | S | CN | H | H | H | $OCF_3$ | H | H |
| 25 | 195N | $CF_3$ | H | S | $NO_2$ | H | H | H | $OCF_3$ | H | H |
| 25 | 196N | $CF_3$ | H | S | H | CN | H | H | $OCF_3$ | H | H |
| 25 | 197N | $CF_3$ | H | S | H | $NO_2$ | H | H | $OCF_3$ | H | H |
| 25 | 198N | $CF_3$ | H | S | $SO_2CH_3$ | H | H | H | $OCF_3$ | H | H |
| 25 | 199N | $CF_3$ | H | S | H | $SO_2CH_3$ | H | H | $OCF_3$ | H | H |
| 25 | 200N | $CF_3$ | H | S | H | 4-F—$C_6H_5$ $SO_2$ | H | H | $OCF_3$ | H | H |
| 25 | 201N | $CF_3$ | H | S | $SO_2N(CH_3)_2$ | H | H | H | $OCF_3$ | H | H |
| 25 | 202N | $CF_3$ | H | S | H | $SO_2N(CH_3)_2$ | H | H | $OCF_3$ | H | H |
| 25 | 203N | $CF_3$ | H | S | H | $CONH_2$ | H | H | $OCF_3$ | H | H |
| 25 | 204N | $CF_3$ | H | S | H | CONH—$C_6H_5$ | H | H | $OCF_3$ | H | H |
| 25 | 205N | $CF_3$ | H | S | H | $CO_2CH_3$ | H | H | $OCF_3$ | H | H |
| 25 | 206N | $CF_3$ | H | S | H | $CO_2C_4H_9$ | H | H | $OCF_3$ | H | H |
| 25 | 207N | $CF_3$ | H | S | H | 4-Cl—$C_6H_5$ | H | H | $C_6H_5O$ | H | H |
| 25 | 208N | $CF_3$ | H | S | H | 4-$CF_3O$—$C_6H_5$ | H | H | $CF_3O$ | H | H |
| 25 | 209N | $CF_3$ | H | S | 4-F— | H | H | H | $CF_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

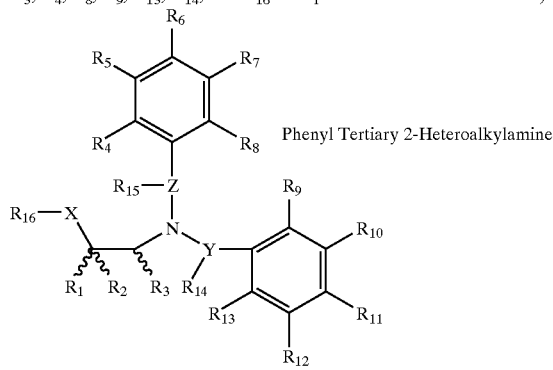

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 25 | 210N | $CF_3$ | H | S | $C_6H_4O$ $C_6F_5O$ | H | H | H | $CF_3O$ | H | H |
| 25 | 211N | $CF_3$ | H | S | H | 4-F—$C_6H_5$ | H | H | $CF_3O$ | H | H |
| 25 | 212N | $CF_3$ | H | S | H | 4-CN—$C_6H_5$ | H | H | $CF_3O$ | H | H |
| 25 | 213N | $CF_3$ | H | S | H | 4-$C_6H_5$—$C_6H_5$ | H | H | $CF_3O$ | H | H |
| 25 | 214N | $CF_3$ | H | S | $C_6H_5O$ | H | H | $CH_3$ | $CF_3O$ | H | H |
| 25 | 215N | $CF_3$ | H | S | $C_6H_5O$ | H | H | $CH_3$ | $NO_2$ | H | H |
| 25 | 216N | $CF_3$ | H | S | $C_6H_5O$ | H | H | $CH_3$ | H | CN | H |
| 25 | 217N | $CF_3$ | H | S | $C_6H_5O$ | H | H | 3-$CF_3$ $C_6H_5$ | $CF_3$ | H | H |
| 25 | 218N | $CF_3$ | H | S | $C_6H_5O$ | H | H | $C_6H_5$ | H | $C_6H_5$ | H |
| 25 | 219N | $CF_3$ | H | S | $C_6H_5O$ | H | H | $C_6H_5$ | $CF_3$ | H | H |
| 25 | 220N | $CF_3$ | H | S | $C_6H_5O$ | H | H | $CH_3$ | F | H | H |
| 25 | 221N | $CF_3$ | H | S | $C_6H_5O$ | H | H | $CF_3$ | H | H | H |
| 25 | 222N | $CF_3$ | H | S | bond to —O— of $R_6$ aryl group | | H | H | $CF_3O$ | H | H |
| 25 | 223N | $CF_3$ | H | S | to $CH_2$ of $R_6$ aryl group | | H | H | $CF_3O$ | H | H |
| 26 | 96N | $CF_3CF_2$ | H | S | OH | OH | H | H | $C_6H_5O$ | H | H |
| 26 | 97N | $CF_3CF_2$ | H | S | $C_6H_5O$ | H | H | H | OH | OH | H |
| 26 | 98N | $CF_3CF_2$ | H | S | 3-pyridyl | H | H | H | $CF_3$ | H | H |
| 26 | 99N | $CF_3CF_2$ | H | S | $SO_2N(CH_3)_2$ | H | H | H | $OCF_3$ | H | H |
| 26 | 100N | $CF_3CF_2$ | H | S | $SO_2CH_3$ | H | H | H | $OCF_3$ | H | H |
| 26 | 101N | $CF_3CF_2$ | H | S | $C_6H_5O$ | H | H | H | $C_6H_5O$ | H | H |
| 26 | 102N | $CF_3CF_2$ | H | S | $CF_3O$ | H | H | H | $C_6H_5O$ | H | H |
| 26 | 103N | $CF_3CF_2$ | H | S | $C_6H_5$ | H | H | H | $C_6H_5O$ | H | H |
| 26 | 104N | $CF_3CF_2$ | H | S | H | $C_6H_5$ | H | H | $C_6H_5O$ | H | H |
| 26 | 105N | $CF_3CF_2$ | H | S | $C_6H_5O$ | H | H | H | 4-Cl—$C_6H_4O$ | H | H |
| 26 | 106N | $CF_3CF_2$ | H | S | $CF_3O$ | H | H | H | 4-Cl—$C_6H_4O$ | H | H |
| 26 | 107N | $CF_3CF_2$ | H | S | $C_6H_5O$ | H | H | H | 3,4-Cl—$C_6H_3O$ | H | H |
| 26 | 108N | $CF_3CF_2$ | H | S | $CF_3O$ | H | H | H | 3,4-Cl—$C_6H_3O$ | H | H |
| 26 | 109N | $CF_3CF_2$ | H | S | $CF_3O$ | H | H | H | 3,5-Cl—$C_6H_3O$ | H | H |
| 26 | 110N | $CF_3CF_2$ | H | S | $CF_3O$ | H | H | H | 3-$CH_3O$—$C_6H_4O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

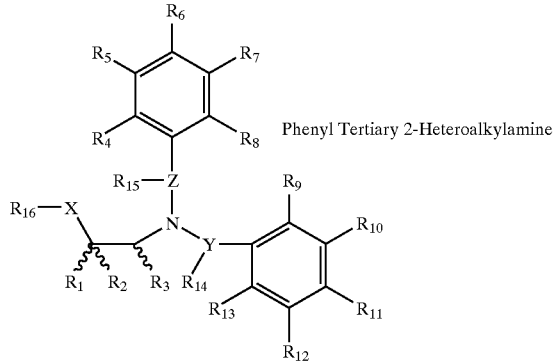

Phenyl Tertiary 2-Heteroalkylamine

Inhibitor Number
Column 1 + Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 26 | 111N | $CF_3CF_2$ | H | S | $CF_3O$ | H | H | H | H | 3-$CH_3O$—$C_6H_4O$ | H |
| 26 | 112N | $CF_3CF_2$ | H | S | $CF_3O$ | H | H | H | 3-$CF_3$—$C_6H_4O$ | H | H |
| 26 | 113N | $CF_3CF_2$ | H | S | $CF_3O$ | H | H | H | $C_6H_5$—$CH_2O$ | H | H |
| 26 | 114N | $CF_3CF_2$ | H | S | $CF_3O$ | H | H | H | $C_6H_5$—$CH_2O$ | $CH_3O$ | H |
| 26 | 115N | $CF_3CF_2$ | H | S | $CF_3O$ | H | H | H | $C_6H_5$—$CH_2O$ | $C_6H_5$—$CH_2O$ | H |
| 26 | 116N | $CF_3CF_2$ | H | S | $CF_3O$ | H | H | H | ethoxy | H | H |
| 26 | 117N | $CF_3CF_2$ | H | S | $CF_3O$ | H | H | H | $CH_3CO_2$ | H | H |
| 26 | 118N | $CF_3CF_2$ | H | S | $CF_3O$ | H | H | H | $HOCH_2$—$CH_2O$ | H | H |
| 26 | 119N | $CF_3CF_2$ | H | S | $CF_3O$ | H | H | H | (epoxide) | H | H |
| 26 | 120N | $CF_3CF_2$ | H | S | $CF_3O$ | H | H | H | $R_{10} + R_{11} = OCH_2O$ | | H |
| 26 | 121N | $CF_3CF_2$ | H | S | $CF_3O$ | H | H | H | $R_{10} + R_{11} = OCH_2CH_2O$ | | H |
| 26 | 122N | $CF_3CF_2$ | H | S | $CF_3O$ | H | H | H | $CH_3O$ | $CH_3O$ | H |
| 26 | 123N | $CF_3CF_2$ | H | S | $CF_3O$ | H | H | H | ethoxy | $CH_3O$ | H |
| 26 | 124N | $CF_3CF_2$ | H | S | $CF_3O$ | H | H | H | ethoxy | ethoxy | H |
| 26 | 125N | $CF_3CF_2$ | H | S | $CF_3O$ | H | H | H | $CH_3CO_2$ | $CH_3CO_2$ | H |
| 26 | 126N | $CF_3CF_2$ | H | S | $CF_3O$ | H | H | H | $CH_3O$ | $CH_3CO_2$ | H |
| 26 | 127N | $CF_3CF_2$ | H | S | $CF_3O$ | H | H | H | n-butoxy | H | H |
| 26 | 128N | $CF_3CF_2$ | H | S | $CF_3O$ | H | H | H | $CH_3O$ | H | H |
| 26 | 129N | $CF_3CF_2$ | H | S | $CF_3O$ | H | H | H | H | $CH_3O$ | H |
| 26 | 130N | $CF_3CF_2$ | H | S | $CH_3O$ | H | H | H | $CH_3O$ | H | H |
| 26 | 131N | $CF_3CF_2$ | H | S | $CH_3O$ | H | H | H | H | $CF_3O$ | H |
| 26 | 132N | $CF_3CF_2$ | H | S | $CF_3O$ | H | H | H | H | ethoxy | H |
| 26 | 133N | $CF_3CF_2$ | H | S | $CF_3O$ | H | H | H | H | n-propoxy | H |
| 26 | 134N | $CF_3CF_2$ | H | S | $C_6H_5$—$CH_2O$ | H | H | H | $CF_3O$ | H | H |
| 26 | 135N | $CF_3CF_2$ | H | S | $C_6H_5$—$CH_2O$ | H | H | H | $C_6H_5O$ | H | H |
| 26 | 136N | $CF_3CF_2$ | H | S | ethoxy | H | H | H | $CF_3O$ | H | H |
| 26 | 137N | $CF_3CF_2$ | H | S | $R_5 + R_6 = OCH_2O$ | | H | H | $CF_3O$ | H | H |
| 26 | 138N | $CF_3CF_2$ | H | S | $R_5 + R_6 = OCH_2O$ | | H | H | $C_6H_5O$ | H | H |
| 26 | 139N | $CF_3CF_2$ | H | S | $R_5 + R_6 = OCH_2CH_2O$ | | H | H | $CF_3O$ | H | H |
| 26 | 140N | $CF_3CF_2$ | H | S | $CH_3O$ | $CH_3O$ | H | H | $CF_3O$ | H | H |
| 26 | 141N | $CF_3CF_2$ | H | S | $R_5 + R_6 = OCH_2CH_2CH_2O$ | | H | H | $CF_3O$ | H | H |
| 26 | 142N | $CF_3CF_2$ | H | S | cyclopentoxy | $CH_3O$ | H | H | $CF_3O$ | H | H |
| 26 | 143N | $CF_3CF_2$ | H | S | H | $C_6H_5O$ | H | H | $CF_3O$ | H | H |
| 26 | 144N | $CF_3CF_2$ | H | S | $CH_3O$ | $CH_3O$ | $CH_3O$ | H | $CF_3O$ | H | H |
| 26 | 145N | $CF_3CF_2$ | H | S | H | $CF_3O$ | H | H | $CF_3O$ | H | H |
| 26 | 146N | $CF_3CF_2$ | H | S | H | $C_6H_5$—$CH_2$ | H | H | $CF_3O$ | H | H |
| 26 | 147N | $CF_3CF_2$ | H | S | $C_6H_5O$ | H | H | H | $R_{10} + R_{11} = OCH_2CH_2O$ | | H |
| 26 | 148N | $CF_3CF_2$ | H | S | H | $CF_3O$ | H | H | $CF_3$ | H | H |
| 26 | 149N | $CF_3CF_2$ | H | S | $C_6H_5O$ | H | H | H | $CF_3$ | H | H |
| 26 | 150N | $CF_3CF_2$ | H | S | $C_6H_5$ | H | H | H | $CF_3$ | H | H |
| 26 | 151N | $CF_3CF_2$ | H | S | H | $C_6H_5$ | H | H | $CF_3$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

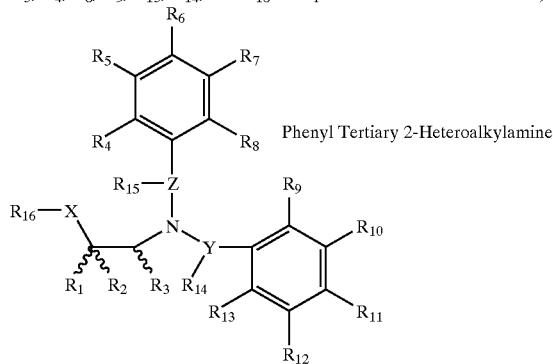

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 26 | 152N | $CF_3CF_2$ | H | S | CN | H | H | H | $CF_3$ | H | H |
| 26 | 153N | $CF_3CF_2$ | H | S | H | $OCF_3$ | H | H | $CF_3$ | H | H |
| 26 | 154N | $CF_3CF_2$ | H | S | $OCF_3$ | H | H | H | H | $CF_3$ | H |
| 26 | 155N | $CF_3CF_2$ | H | S | $C_6H_5O$ | H | H | H | H | $CF_3$ | H |
| 26 | 156N | $CF_3CF_2$ | H | S | $C_6H_5$ | H | H | H | H | $CF_3$ | H |
| 26 | 157N | $CF_3CF_2$ | H | S | H | $C_6H_5$ | H | H | H | $CF_3$ | H |
| 26 | 158N | $CF_3CF_2$ | H | S | CN | H | H | H | H | $CF_3$ | H |
| 26 | 159N | $CF_3CF_2$ | H | S | $OCF_3$ | H | H | H | H | $CF_3$ | H |
| 26 | 160N | $CF_3CF_2$ | H | S | $CF_3$ | H | H | H | H | $C_6H_5$ | H |
| 26 | 161N | $CF_3CF_2$ | H | S | $CF_3$ | H | H | H | 3-$CF_3$—$C_6H_5O$ | H | H |
| 26 | 162N | $CF_3CF_2$ | H | S | $CF_3$ | H | H | H | $C_6H_5O$ | H | H |
| 26 | 163N | $CF_3CF_2$ | H | S | $CF_3$ | H | H | H | $CF_3O$ | H | H |
| 26 | 164N | $CF_3CF_2$ | H | S | H | $CF_3$ | H | H | H | $C_6H_5$ | H |
| 26 | 165N | $CF_3CF_2$ | H | S | H | $CF_3$ | H | H | 3-$CF_3$—$C_6H_5O$ | H | H |
| 26 | 166N | $CF_3CF_2$ | H | S | H | $CF_3$ | H | H | $CF_3O$ | H | H |
| 26 | 167N | $CF_3CF_2$ | H | S | H | $CF_3$ | H | H | $C_6H_5O$ | H | H |
| 26 | 168N | $CF_3CF_2$ | H | S | $CF_3$ | H | $CF_3$ | H | $CF_3O$ | H | H |
| 26 | 169N | $CF_3CF_2$ | H | S | $CF_3$ | H | $CF_3$ | H | $C_6H_5O$ | H | H |
| 26 | 170N | $CF_3CF_2$ | H | S | $CF_3O$ | H | H | H | $CF_3$ | H | $CF_3$ |
| 26 | 171N | $CF_3CF_2$ | H | S | $C_6H_5O$ | H | H | H | $CF_3$ | H | $CF_3$ |
| 26 | 172N | $CF_3CF_2$ | H | S | H | $C_6H_5O$ | H | H | $C_6H_5O$ | H | H |
| 26 | 173N | $CF_3CF_2$ | H | S | H | $CF_3O$ | H | H | $CF_3O$ | H | H |
| 26 | 174N | $CF_3CF_2$ | H | S | H | $CF_3O$ | H | H | H | $C_6H_5O$ | H |
| 26 | 175N | $CF_3CF_2$ | H | S | $C_6H_5O$ | H | H | H | H | $C_6H_5O$ | H |
| 26 | 176N | $CF_3CF_2$ | H | S | H | $C_6H_5O$ | H | H | H | $OCF_3$ | H |
| 26 | 177N | $CF_3CF_2$ | H | S | H | $C_6H_5O$ | H | H | H | $C_6H_5O$ | H |
| 26 | 178N | $CF_3CF_2$ | H | S | $C_6H_5O$ | H | H | H | H | CN | H |
| 26 | 179N | $CF_3CF_2$ | H | S | $C_6H_5O$ | H | H | H | CN | H | H |
| 26 | 180N | $CF_3CF_2$ | H | S | $C_6H_5O$ | H | H | H | $NO_2$ | H | H |
| 26 | 181N | $CF_3CF_2$ | H | S | $C_6H_5O$ | H | H | H | H | $NO_2$ | H |
| 26 | 182N | $CF_3CF_2$ | H | S | $C_6H_5O$ | H | H | H | H | $SO_2CH_3$ | H |
| 26 | 183N | $CF_3CF_2$ | H | S | $C_6H_5O$ | H | H | H | H | 2-$NO_2$-4-Cl—$C_6H_3O$ | H |
| 26 | 184N | $CF_3CF_2$ | H | S | $C_6H_5O$ | H | H | H | 4-Cl—$C_6H_4O$ | H | H |
| 26 | 185N | $CF_3CF_2$ | H | S | $C_6H_5O$ | H | H | H | 3,4-Cl—$C_6H_3O$ | H | H |
| 26 | 186N | $CF_3CF_2$ | H | S | $C_6H_5O$ | H | H | H | 3-$CF_3$—$C_6H_3O$ | H | H |
| 26 | 187N | $CF_3CF_2$ | H | S | $C_6H_5O$ | H | H | H | 3,5-Cl—$C_6H_3O$ | H | H |
| 26 | 188N | $CF_3CF_2$ | H | S | $C_6H_5O$ | H | H | H | H | $CH_3O$ | H |
| 26 | 189N | $CF_3CF_2$ | H | S | $C_6H_5O$ | H | H | H | H | $CO_2CH_3$ | H |
| 26 | 190N | $CF_3CF_2$ | H | S | $C_6H_5O$ | H | H | H | 3-$CH_3O$ $C_6H_5O$ | H | H |
| 26 | 191N | $CF_3CF_2$ | H | S | $C_6H_5O$ | H | H | H | 4-$CH_3O$ $C_6H_5O$ | H | H |
| 26 | 193N | $CF_3CF_2$ | H | S | $C_6H_5O$ | H | H | H | $CO_2CH_3$ | H | H |
| 26 | 194N | $CF_3CF_2$ | H | S | CN | H | H | H | $OCF_3$ | H | H |
| 26 | 195N | $CF_3CF_2$ | H | S | $NO_2$ | H | H | H | $OCF_3$ | H | H |
| 26 | 196N | $CF_3CF_2$ | H | S | H | CN | H | H | $OCF_3$ | H | H |
| 26 | 197N | $CF_3CF_2$ | H | S | H | $NO_2$ | H | H | $OCF_3$ | H | H |
| 26 | 198N | $CF_3CF_2$ | H | S | $SO_2CH_3$ | H | H | H | $OCF_3$ | H | H |
| 26 | 199N | $CF_3CF_2$ | H | S | H | $SO_2CH_3$ | H | H | $OCF_3$ | H | H |
| 26 | 200N | $CF_3CF_2$ | H | S | H | 4-F—$C_6H_5$ $SO_2$ | H | H | $OCF_3$ | H | H |
| 26 | 201N | $CF_3CF_2$ | H | S | $SO_2N$ | H | H | H | $OCF_3$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

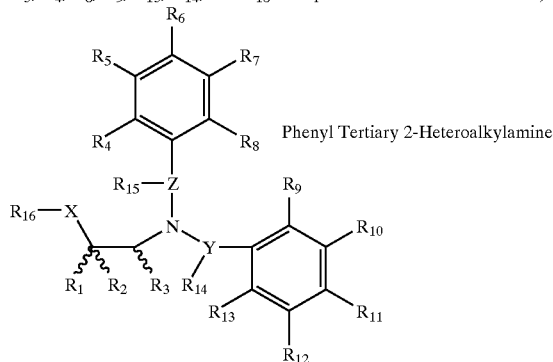

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 26 | 202N | $CF_3CF_2$ | H | S | H | $SO_2N(CH_3)_2$ | H | H | $OCF_3$ | H | H |
| 26 | 203N | $CF_3CF_2$ | H | S | H | $CONH_2$ | H | H | $OCF_3$ | H | H |
| 26 | 204N | $CF_3CF_2$ | H | S | H | CONH—$C_6H_5$ | H | H | $OCF_3$ | H | H |
| 26 | 205N | $CF_3CF_2$ | H | S | H | $CO_2CH_3$ | H | H | $OCF_3$ | H | H |
| 26 | 206N | $CF_3CF_2$ | H | S | H | $CO_2C_4H_9$ | H | H | $OCF_3$ | H | H |
| 26 | 207N | $CF_3CF_2$ | H | S | H | 4-Cl—$C_6H_5$ | H | H | $C_6H_5O$ | H | H |
| 26 | 208N | $CF_3CF_2$ | H | S | H | 4-$CF_3O$—$C_6H_5$ | H | H | $CF_3O$ | H | H |
| 26 | 209N | $CF_3CF_2$ | H | S | 4-F—$C_6H_4O$ | H | H | H | $CF_3O$ | H | H |
| 26 | 210N | $CF_3CF_2$ | H | S | $C_6F_5O$ | H | H | H | $CF_3O$ | H | H |
| 26 | 211N | $CF_3CF_2$ | H | S | H | 4-F—$C_6H_5$ | H | H | $CF_3O$ | H | H |
| 26 | 212N | $CF_3CF_2$ | H | S | H | 4-CN—$C_6H_5$ | H | H | $CF_3O$ | H | H |
| 26 | 213N | $CF_3CF_2$ | H | S | H | 4-$C_6H_5$—$C_6H_5$ | H | H | $CF_3O$ | H | H |
| 26 | 214N | $CF_3CF_2$ | H | S | $C_6H_5O$ | H | H | $CH_3$ | $CF_3O$ | H | H |
| 26 | 215N | $CF_3CF_2$ | H | S | $C_6H_5O$ | H | H | $CH_3$ | $NO_2$ | H | H |
| 26 | 216N | $CF_3CF_2$ | H | S | $C_6H_5O$ | H | H | $CH_3$ | H | CN | H |
| 26 | 217N | $CF_3CF_2$ | H | S | $C_6H_5O$ | H | H | 3-$CF_3$ $C_6H_5$ | $CF_3$ | H | H |
| 26 | 218N | $CF_3CF_2$ | H | S | $C_6H_5O$ | H | H | $C_6H_5$ | H | $C_6H_5$ | H |
| 26 | 219N | $CF_3CF_2$ | H | S | $C_6H_5O$ | H | H | $C_6H_5$ | $CF_3$ | H | H |
| 26 | 220N | $CF_3CF_2$ | H | S | $C_6H_5O$ | H | H | $CH_3$ | F | H | H |
| 26 | 221N | $CF_3CF_2$ | H | S | $C_6H_5O$ | H | H | $CF_3$ | H | H | H |
| 26 | 222N | $CF_3CF_2$ | H | S | bond to —O— of $R_6$ aryl group | (2-methylphenoxy) | H | H | $CF_3O$ | H | H |
| 26 | 223N | $CF_3CF_2$ | H | S | to $CH_2$ of $R_6$ aryl group | (bromo-methyl-ethylphenyl) | H | H | $CF_3O$ | H | H |
| 63 | 96N | $C_6H_5$ | H | O | OH | OH | H | H | $C_6H_5O$ | H | H |
| 63 | 97N | $C_6H_5$ | H | O | $C_6H_5O$ | H | H | H | OH | OH | H |
| 63 | 98N | $C_6H_5$ | H | O | 3-pyridyl | H | H | H | $CF_3$ | H | H |
| 63 | 99N | $C_6H_5$ | H | O | $SO_2N(CH_3)_2$ | H | H | H | $OCF_3$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

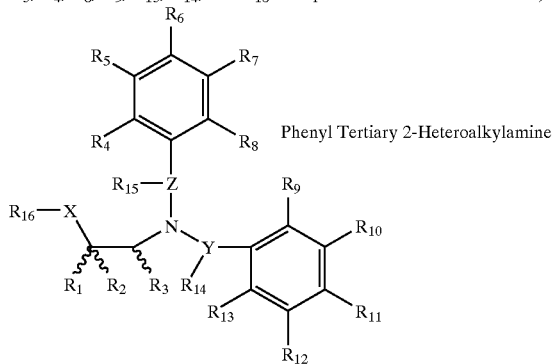

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 63 | 100N | $C_6H_5$ | H | O | $SO_2CH_3$ | H | H | H | $OCF_3$ | H | H |
| 63 | 101N | $C_6H_5$ | H | O | $C_6H_5O$ | H | H | H | $C_6H_5O$ | H | H |
| 63 | 102N | $C_6H_5$ | H | O | $CF_3O$ | H | H | H | $C_6H_5O$ | H | H |
| 63 | 103N | $C_6H_5$ | H | O | $C_6H_5$ | H | H | H | $C_6H_5O$ | H | H |
| 63 | 104N | $C_6H_5$ | H | O | H | $C_6H_5$ | H | H | $C_6H_5O$ | H | H |
| 63 | 105N | $C_6H_5$ | H | O | $C_6H_5O$ | H | H | H | 4-Cl—$C_6H_4O$ | H | H |
| 63 | 106N | $C_6H_5$ | H | O | $CF_3O$ | H | H | H | 4-Cl—$C_6H_4O$ | H | H |
| 63 | 107N | $C_6H_5$ | H | O | $C_6H_5O$ | H | H | H | 3,4-Cl—$C_6H_3O$ | H | H |
| 63 | 108N | $C_6H_5$ | H | O | $CF_3O$ | H | H | H | 3,4-Cl—$C_6H_3O$ | H | H |
| 63 | 109N | $C_6H_5$ | H | O | $CF_3O$ | H | H | H | 3,5-Cl—$C_6H_3O$ | H | H |
| 63 | 110N | $C_6H_5$ | H | O | $CF_3O$ | H | H | H | 3-$CH_3O$—$C_6H_4O$ | H | H |
| 63 | 111N | $C_6H_5$ | H | O | $CF_3O$ | H | H | H | H | 3-$CH_3O$—$C_6H_4O$ | H |
| 63 | 112N | $C_6H_5$ | H | O | $CF_3O$ | H | H | H | 3-$CF_3$—$C_6H_4O$ | H | H |
| 63 | 113N | $C_6H_5$ | H | O | $CF_3O$ | H | H | H | $C_6H_5$—$CH_2O$ | H | H |
| 63 | 114N | $C_6H_5$ | H | O | $CF_3O$ | H | H | H | $C_6H_5$—$CH_2O$ | $CH_3O$ | H |
| 63 | 115N | $C_6H_5$ | H | O | $CF_3O$ | H | H | H | $C_6H_5$—$CH_2O$ | $C_6H_5$—$CH_2O$ | H |
| 63 | 116N | $C_6H_5$ | H | O | $CF_3O$ | H | H | H | ethoxy | H | H |
| 63 | 117N | $C_6H_5$ | H | O | $CF_3O$ | H | H | H | $CH_3CO_2$ | H | H |
| 63 | 118N | $C_6H_5$ | H | O | $CF_3O$ | H | H | H | $HOCH_2$—$CH_2O$ | H | H |
| 63 | 119N | $C_6H_5$ | H | O | $CF_3O$ | H | H | H | (epoxide) | H | H |
| 63 | 120N | $C_6H_5$ | H | O | $CF_3O$ | H | H | H | $R_{10} + R_{11} = OCH_2O$ | | H |
| 63 | 121N | $C_6H_5$ | H | O | $CF_3O$ | H | H | H | $R_{10} + R_{11} = OCH_2CH_2O$ | | H |
| 63 | 122N | $C_6H_5$ | H | O | $CF_3O$ | H | H | H | $CH_3O$ | $CH_3O$ | H |
| 63 | 123N | $C_6H_5$ | H | O | $CF_3O$ | H | H | H | ethoxy | $CH_3O$ | H |
| 63 | 124N | $C_6H_5$ | H | O | $CF_3O$ | H | H | H | ethoxy | ethoxy | H |
| 63 | 125N | $C_6H_5$ | H | O | $CF_3O$ | H | H | H | $CH_3CO_2$ | $CH_3CO_2$ | H |
| 63 | 126N | $C_6H_5$ | H | O | $CF_3O$ | H | H | H | $CH_3O$ | $CH_3CO_2$ | H |
| 63 | 127N | $C_6H_5$ | H | O | $CF_3O$ | H | H | H | n-butoxy | H | H |
| 63 | 128N | $C_6H_5$ | H | O | $CF_3O$ | H | H | H | $CH_3O$ | H | H |
| 63 | 129N | $C_6H_5$ | H | O | $CF_3O$ | H | H | H | H | $CH_3O$ | H |
| 63 | 130N | $C_6H_5$ | H | O | $CH_3O$ | H | H | H | $CH_3O$ | H | H |
| 63 | 131N | $C_6H_5$ | H | O | $CH_3O$ | H | H | H | H | $CF_3O$ | H |
| 63 | 132N | $C_6H_5$ | H | O | $CF_3O$ | H | H | H | H | ethoxy | H |
| 63 | 133N | $C_6H_5$ | H | O | $CF_3O$ | H | H | H | H | n-propoxy | H |
| 63 | 134N | $C_6H_5$ | H | O | $C_6H_5$—$CH_2O$ | H | H | H | $CF_3O$ | H | H |
| 63 | 135N | $C_6H_5$ | H | O | $C_6H_5$—$CH_2O$ | H | H | H | $C_6H_5O$ | H | H |
| 63 | 136N | $C_6H_5$ | H | O | ethoxy | H | H | H | $CF_3O$ | H | H |
| 63 | 137N | $C_6H_5$ | H | O | $R_5 + R_6 = OCH_2O$ | | H | H | $CF_3O$ | H | H |
| 63 | 138N | $C_6H_5$ | H | O | $R_5 + R_6 = OCH_2O$ | | H | H | $C_6H_5O$ | H | H |
| 63 | 139N | $C_6H_5$ | H | O | $R_5 + R_6 = OCH_2CH_2O$ | | H | H | $CF_3O$ | H | H |
| 63 | 140N | $C_6H_5$ | H | O | $CH_3O$ | $CH_3O$ | H | H | $CF_3O$ | H | H |
| 63 | 141N | $C_6H_5$ | H | O | $R_5 + R_6 =$ | | H | H | $CF_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

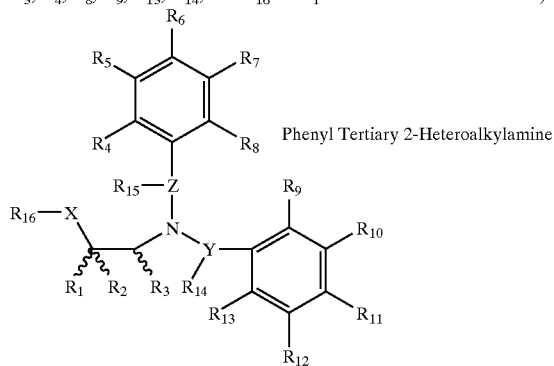

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 63 | 142N | $C_6H_5$ | H | O | $OCH_2CH_2CH_2O$ cyclo pentoxy | $CH_3O$ | H | H | $CF_3O$ | H | H |
| 63 | 143N | $C_6H_5$ | H | O | H | $C_6H_5O$ | H | H | $CF_3O$ | H | H |
| 63 | 144N | $C_6H_5$ | H | O | $CH_3O$ | $CH_3O$ | $CH_3O$ | H | $CF_3O$ | H | H |
| 63 | 145N | $C_6H_5$ | H | O | H | $CF_3O$ | H | H | $CF_3O$ | H | H |
| 63 | 146N | $C_6H_5$ | H | O | H | $C_6H_5$—$CH_2$ | H | H | $CF_3O$ | H | H |
| 63 | 147N | $C_6H_5$ | H | O | $C_6H_5O$ | H | H | H | $R_{10} + R_{11} = OCH_2CH_2O$ | | H |
| 63 | 148N | $C_6H_5$ | H | O | H | $CF_3O$ | H | H | $CF_3$ | H | H |
| 63 | 149N | $C_6H_5$ | H | O | $C_6H_5O$ | H | H | H | $CF_3$ | H | H |
| 63 | 150N | $C_6H_5$ | H | O | $C_6H_5$ | H | H | H | $CF_3$ | H | H |
| 63 | 151N | $C_6H_5$ | H | O | H | $C_6H_5$ | H | H | $CF_3$ | H | H |
| 63 | 152N | $C_6H_5$ | H | O | CN | H | H | H | $CF_3$ | H | H |
| 63 | 153N | $C_6H_5$ | H | O | H | $OCF_3$ | H | H | $CF_3$ | H | H |
| 63 | 154N | $C_6H_5$ | H | O | $OCF_3$ | H | H | H | H | $CF_3$ | H |
| 63 | 155N | $C_6H_5$ | H | O | $C_6H_5O$ | H | H | H | H | $CF_3$ | H |
| 63 | 156N | $C_6H_5$ | H | O | $C_6H_5$ | H | H | H | H | $CF_3$ | H |
| 63 | 157N | $C_6H_5$ | H | O | H | $C_6H_5$ | H | H | H | $CF_3$ | H |
| 63 | 158N | $C_6H_5$ | H | O | CN | H | H | H | H | $CF_3$ | H |
| 63 | 159N | $C_6H_5$ | H | O | $OCF_3$ | H | H | H | H | $CF_3$ | H |
| 63 | 160N | $C_6H_5$ | H | O | $CF_3$ | H | H | H | H | $C_6H_5$ | H |
| 63 | 161N | $C_6H_5$ | H | O | $CF_3$ | H | H | H | 3-$CF_3$—$C_6H_5O$ | H | H |
| 63 | 162N | $C_6H_5$ | H | O | $CF_3$ | H | H | H | $C_6H_5O$ | H | H |
| 63 | 163N | $C_6H_5$ | H | O | $CF_3$ | H | H | H | $CF_3O$ | H | H |
| 63 | 164N | $C_6H_5$ | H | O | H | $CF_3$ | H | H | H | $C_6H_5$ | H |
| 63 | 165N | $C_6H_5$ | H | O | H | $CF_3$ | H | H | 3-$CF_3$—$C_6H_5O$ | H | H |
| 63 | 166N | $C_6H_5$ | H | O | H | $CF_3$ | H | H | $CF_3O$ | H | H |
| 63 | 167N | $C_6H_5$ | H | O | H | $CF_3$ | H | H | $C_6H_5O$ | H | H |
| 63 | 168N | $C_6H_5$ | H | O | $CF_3$ | H | $CF_3$ | H | $CF_3O$ | H | H |
| 63 | 169N | $C_6H_5$ | H | O | $CF_3$ | H | $CF_3$ | H | $C_6H_5O$ | H | H |
| 63 | 170N | $C_6H_5$ | H | O | $CF_3O$ | H | H | H | $CF_3$ | H | $CF_3$ |
| 63 | 171N | $C_6H_5$ | H | O | $C_6H_5O$ | H | H | H | $CF_3$ | H | $CF_3$ |
| 63 | 172N | $C_6H_5$ | H | O | H | $C_6H_5O$ | H | H | $C_6H_5O$ | H | H |
| 63 | 173N | $C_6H_5$ | H | O | H | $CF_3O$ | H | H | $CF_3O$ | H | H |
| 63 | 174N | $C_6H_5$ | H | O | H | $CF_3O$ | H | H | H | $C_6H_5O$ | H |
| 63 | 175N | $C_6H_5$ | H | O | $C_6H_5O$ | H | H | H | H | $C_6H_5O$ | H |
| 63 | 176N | $C_6H_5$ | H | O | H | $C_6H_5O$ | H | H | H | $OCF_3$ | H |
| 63 | 177N | $C_6H_5$ | H | O | H | $C_6H_5O$ | H | H | H | $C_6H_5O$ | H |
| 63 | 178N | $C_6H_5$ | H | O | $C_6H_5O$ | H | H | H | H | CN | H |
| 63 | 179N | $C_6H_5$ | H | O | $C_6H_5O$ | H | H | H | CN | H | H |
| 63 | 180N | $C_6H_5$ | H | O | $C_6H_5O$ | H | H | H | $NO_2$ | H | H |
| 63 | 181N | $C_6H_5$ | H | O | $C_6H_5O$ | H | H | H | H | $NO_2$ | H |
| 63 | 182N | $C_6H_5$ | H | O | $C_6H_5O$ | H | H | H | H | $SO_2CH_3$ | H |
| 63 | 183N | $C_6H_5$ | H | O | $C_6H_5O$ | H | H | H | H | 2-$NO_2$-4-Cl—$C_6H_3O$ | H |
| 63 | 184N | $C_6H_5$ | H | O | $C_6H_5O$ | H | H | H | 4-Cl—$C_6H_4O$ | H | H |
| 63 | 185N | $C_6H_5$ | H | O | $C_6H_5O$ | H | H | H | 3,4-Cl—$C_6H_3O$ | H | H |
| 63 | 186N | $C_6H_5$ | H | O | $C_6H_5O$ | H | H | H | 3-$CF_3$—$C_6H_3O$ | H | H |
| 63 | 187N | $C_6H_5$ | H | O | $C_6H_5O$ | H | H | H | 3,5-Cl—$C_6H_3O$ | H | H |
| 63 | 188N | $C_6H_5$ | H | O | $C_6H_5O$ | H | H | H | H | $CH_3O$ | H |
| 63 | 189N | $C_6H_5$ | H | O | $C_6H_5O$ | H | H | H | H | $CO_2CH_3$ | H |
| 63 | 190N | $C_6H_5$ | H | O | $C_6H_5O$ | H | H | H | 3-$CH_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

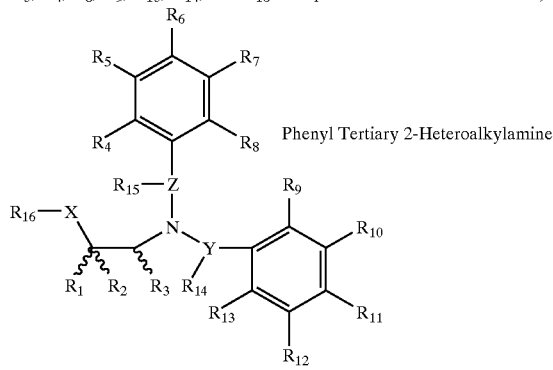

Phenyl Tertiary 2-Heteroalkylamine

Inhibitor Number
Column 1 + Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 63 | 191N | $C_6H_5$ | H | O | $C_6H_5O$ | H | H | H | $C_6H_5O$ 4-$CH_3O$ | H | H |
| 63 | 193N | $C_6H_5$ | H | O | $C_6H_5O$ | H | H | H | $C_6H_5O$ $CO_2CH_3$ | H | H |
| 63 | 194N | $C_6H_5$ | H | O | CN | H | H | H | $OCF_3$ | H | H |
| 63 | 195N | $C_6H_5$ | H | O | $NO_2$ | H | H | H | $OCF_3$ | H | H |
| 63 | 196N | $C_6H_5$ | H | O | H | CN | H | H | $OCF_3$ | H |   |
| 63 | 197N | $C_6H_5$ | H | O | H | $NO_2$ | H | H | $OCF_3$ | H | H |
| 63 | 198N | $C_6H_5$ | H | O | $SO_2CH_3$ | H | H | H | $OCF_3$ | H | H |
| 63 | 199N | $C_6H_5$ | H | O | H | $SO_2CH_3$ | H | H | $OCF_3$ | H | H |
| 63 | 200N | $C_6H_5$ | H | O | H | 4-F—$C_6H_5$—$SO_2$ | H | H | $OCF_3$ | H | H |
| 63 | 201N | $C_6H_5$ | H | O | $SO_2N(CH_3)_2$ | H | H | H | $OCF_3$ | H | H |
| 63 | 202N | $C_6H_5$ | H | O | H | $SO_2N(CH_3)_2$ | H | H | $OCF_3$ | H | H |
| 63 | 203N | $C_6H_5$ | H | O | H | $CONH_2$ | H | H | $OCF_3$ | H | H |
| 63 | 204N | $C_6H_5$ | H | O | H | CONH—$C_6H_5$ | H | H | $OCF_3$ | H | H |
| 63 | 205N | $C_6H_5$ | H | O | H | $CO_2CH_3$ | H | H | $OCF_3$ | H | H |
| 63 | 206N | $C_6H_5$ | H | O | H | $CO_2C_4H_9$ | H | H | $OCF_3$ | H | H |
| 63 | 207N | $C_6H_5$ | H | O | H | 4-Cl—$C_6H_5$ | H | H | $C_6H_5O$ | H | H |
| 63 | 208N | $C_6H_5$ | H | O | H | 4-$CF_3O$—$C_6H_5$ | H | H | $CF_3O$ | H | H |
| 63 | 209N | $C_6H_5$ | H | O | 4-F—$C_6H_4O$ | H | H | H | $CF_3O$ | H | H |
| 63 | 210N | $C_6H_5$ | H | O | $C_6F_5O$ | H | H | H | $CF_3O$ | H | H |
| 63 | 211N | $C_6H_5$ | H | O | H | 4-F—$C_6H_5$ | H | H | $CF_3O$ | H | H |
| 63 | 212N | $C_6H_5$ | H | O | H | 4-CN—$C_6H_5$ | H | H | $CF_3O$ | H | H |
| 63 | 213N | $C_6H_5$ | H | O | H | 4-$C_6H_5$—$C_6H_5$ | H | H | $CF_3O$ | H | H |
| 63 | 214N | $C_6H_5$ | H | O | $C_6H_5O$ | H | H | $CH_3$ | $CF_3O$ | H | H |
| 63 | 215N | $C_6H_5$ | H | O | $C_6H_5O$ | H | H | $CH_3$ | $NO_2$ | H | H |
| 63 | 216N | $C_6H_5$ | H | O | $C_6H_5O$ | H | H | $CH_3$ | H | CN | H |
| 63 | 217N | $C_6H_5$ | H | O | $C_6H_5O$ | H | H | 3-$CF_3$ $C_6H_5$ | $CF_3$ | H | H |
| 63 | 218N | $C_6H_5$ | H | O | $C_6H_5O$ | H | H | $C_6H_5$ | H | $C_6H_5$ | H |
| 63 | 219N | $C_6H_5$ | H | O | $C_6H_5O$ | H | H | $C_6H_5$ | $CF_3$ | H | H |
| 63 | 220N | $C_6H_5$ | H | O | $C_6H_5O$ | H | H | $CH_3$ | F | H | H |
| 63 | 221N | $C_6H_5$ | H | O | $C_6H_5O$ | H | H | $CF_3$ | H | H | H |
| 63 | 222N | $C_6H_5$ | H | O | bond to —O— of $R_6$ aryl group | | H | H | $CF_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

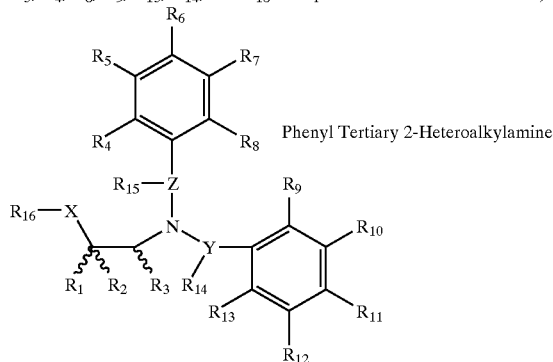

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 63 | 223N | $C_6H_5$ | H | O | to $CH_2$ of $R_6$ aryl group | Br (2-Br-4-ethyl-phenyl-like) | H | H | $CF_3O$ | H | H |
| 65 | 96N | $C_6F_5$ | H | O | OH | OH | H | H | $C_6H_5O$ | H | H |
| 65 | 97N | $C_6F_5$ | H | O | $C_6H_5O$ | H | H | H | OH | OH | H |
| 65 | 98N | $C_6F_5$ | H | O | 3-pyridyl | H | H | H | $CF_3$ | H | H |
| 65 | 99N | $C_6F_5$ | H | O | $SO_2N(CH_3)_2$ | H | H | H | $OCF_3$ | H | H |
| 65 | 100N | $C_6F_5$ | H | O | $SO_2CH_3$ | H | H | H | $OCF_3$ | H | H |
| 65 | 101N | $C_6F_5$ | H | O | $C_6H_5O$ | H | H | H | $C_6H_5O$ | H | H |
| 65 | 102N | $C_6F_5$ | H | O | $CF_3O$ | H | H | H | $C_6H_5O$ | H | H |
| 65 | 103N | $C_6F_5$ | H | O | $C_6H_5$ | H | H | H | $C_6H_5O$ | H | H |
| 65 | 104N | $C_6F_5$ | H | O | H | $C_6H_5$ | H | H | $C_6H_5O$ | H | H |
| 65 | 105N | $C_6F_5$ | H | O | $C_6H_5O$ | H | H | H | 4-Cl—$C_6H_4O$ | H | H |
| 65 | 106N | $C_6F_5$ | H | O | $CF_3O$ | H | H | H | 4-Cl—$C_6H_4O$ | H | H |
| 65 | 107N | $C_6F_5$ | H | O | $C_6H_5O$ | H | H | H | 3,4-Cl—$C_6H_3O$ | H | H |
| 65 | 108N | $C_6F_5$ | H | O | $CF_3O$ | H | H | H | 3,4-Cl—$C_6H_3O$ | H | H |
| 65 | 109N | $C_6F_5$ | H | O | $CF_3O$ | H | H | H | 3,5-Cl—$C_6H_3O$ | H | H |
| 65 | 110N | $C_6F_5$ | H | O | $CF_3O$ | H | H | H | 3-$CH_3O$—$C_6H_4O$ | H | H |
| 65 | 111N | $C_6F_5$ | H | O | $CF_3O$ | H | H | H | H | 3-$CH_3O$—$C_6H_4O$ | H |
| 65 | 112N | $C_6F_5$ | H | O | $CF_3O$ | H | H | H | 3-$CF_3$—$C_6H_4O$ | H | H |
| 65 | 113N | $C_6F_5$ | H | O | $CF_3O$ | H | H | H | $C_6H_5$—$CH_2O$ | H | H |
| 65 | 114N | $C_6F_5$ | H | O | $CF_3O$ | H | H | H | $C_6H_5$—$CH_2O$ | $CH_3O$ | H |
| 65 | 115N | $C_6F_5$ | H | O | $CF_3O$ | H | H | H | $C_6H_5$—$CH_2O$ | $C_6H_5$—$CH_2O$ | H |
| 65 | 116N | $C_6F_5$ | H | O | $CF_3O$ | H | H | H | ethoxy | H | H |
| 65 | 117N | $C_6F_5$ | H | O | $CF_3O$ | H | H | H | $CH_3CO_2$ | H | H |
| 65 | 118N | $C_6F_5$ | H | O | $CF_3O$ | H | H | H | $HOCH_2$—$CH_2O$ | H | H |
| 65 | 119N | $C_6F_5$ | H | O | $CF_3O$ | H | H | H | epoxide | H | H |
| 65 | 120N | $C_6F_5$ | H | O | $CF_3O$ | H | H | H | $R_{10} + R_{11} = OCH_2O$ | | H |
| 65 | 121N | $C_6F_5$ | H | O | $CF_3O$ | H | H | H | $R_{10} + R_{11} = OCH_2CH_2O$ | | H |
| 65 | 122N | $C_6F_5$ | H | O | $CF_3O$ | H | H | H | $CH_3O$ | $CH_3O$ | H |
| 65 | 123N | $C_6F_5$ | H | O | $CF_3O$ | H | H | H | ethoxy | $CH_3O$ | H |
| 65 | 124N | $C_6F_5$ | H | O | $CF_3O$ | H | H | H | ethoxy | ethoxy | H |
| 65 | 125N | $C_6F_5$ | H | O | $CF_3O$ | H | H | H | $CH_3CO_2$ | $CH_3CO_2$ | H |
| 65 | 126N | $C_6F_5$ | H | O | $CF_3O$ | H | H | H | $CH_3O$ | $CH_3CO_2$ | H |
| 65 | 127N | $C_6F_5$ | H | O | $CF_3O$ | H | H | H | n-butoxy | H | H |
| 65 | 128N | $C_6F_5$ | H | O | $CF_3O$ | H | H | H | $CH_3O$ | H | H |
| 65 | 129N | $C_6F_5$ | H | O | $CF_3O$ | H | H | H | H | $CH_3O$ | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

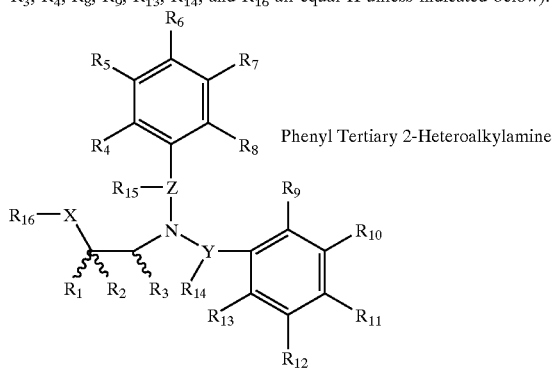

Phenyl Tertiary 2-Heteroalkylamine

Inhibitor Number Column 1 + Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 65 | 130N | $C_6F_5$ | H | O | $CH_3O$ | H | H | H | $CH_3O$ | H | H |
| 65 | 131N | $C_6F_5$ | H | O | $CH_3O$ | H | H | H | H | $CF_3O$ | H |
| 65 | 132N | $C_6F_5$ | H | O | $CF_3O$ | H | H | H | H | ethoxy | H |
| 65 | 133N | $C_6F_5$ | H | O | $CF_3O$ | H | H | H | H | n-propoxy | H |
| 65 | 134N | $C_6F_5$ | H | O | $C_6H_5$—$CH_2O$ | H | H | H | $CF_3O$ | H | H |
| 65 | 135N | $C_6F_5$ | H | O | $C_6H_5$—$CH_2O$ | H | H | H | $C_6H_5O$ | H | H |
| 65 | 136N | $C_6F_5$ | H | O | ethoxy | H | H | H | $CF_3O$ | H | H |
| 65 | 137N | $C_6F_5$ | H | O | $R_5 + R_6 = OCH_2O$ | | H | H | $CF_3O$ | H | H |
| 65 | 138N | $C_6F_5$ | H | O | $R_5 + R_6 = OCH_2O$ | | H | H | $C_6H_5O$ | H | H |
| 65 | 139N | $C_6F_5$ | H | O | $R_5 + R_6 = OCH_2CH_2O$ | | H | H | $CF_3O$ | H | H |
| 65 | 140N | $C_6F_5$ | H | O | $CH_3O$ | $CH_3O$ | H | H | $CF_3O$ | H | H |
| 65 | 141N | $C_6F_5$ | H | O | $R_5 + R_6 = OCH_2CH_2CH_2O$ | | H | H | $CF_3O$ | H | H |
| 65 | 142N | $C_6F_5$ | H | O | cyclo pentoxy | $CH_3O$ | H | H | $CF_3O$ | H | H |
| 65 | 143N | $C_6F_5$ | H | O | H | $C_6H_5O$ | H | H | $CF_3O$ | H | H |
| 65 | 144N | $C_6F_5$ | H | O | $CH_3O$ | $CH_3O$ | $CH_3O$ | H | $CF_3O$ | H | H |
| 65 | 145N | $C_6F_5$ | H | O | H | $CF_3O$ | H | H | $CF_3O$ | H | H |
| 65 | 146N | $C_6F_5$ | H | O | H | $C_6H_5$—$CH_2$ | H | H | $CF_3O$ | H | H |
| 65 | 147N | $C_6F_5$ | H | O | $C_6H_5O$ | H | H | H | $R_{10} = R_{11} = OCH_2CH_2O$ | | H |
| 65 | 148N | $C_6F_5$ | H | O | H | $CF_3O$ | H | H | $CF_3$ | H | H |
| 65 | 149N | $C_6F_5$ | H | O | $C_6H_5O$ | H | H | H | $CF_3$ | H | H |
| 65 | 150N | $C_6F_5$ | H | O | $C_6H_5$ | H | H | H | $CF_3$ | H | H |
| 65 | 151N | $C_6F_5$ | H | O | H | $C_6H_5$ | H | H | $CF_3$ | H | H |
| 65 | 152N | $C_6F_5$ | H | O | CN | H | H | H | $CF_3$ | H | H |
| 65 | 153N | $C_6F_5$ | H | O | H | $OCF_3$ | H | H | $CF_3$ | H | H |
| 65 | 154N | $C_6F_5$ | H | O | $OCF_3$ | H | H | H | H | $CF_3$ | H |
| 65 | 155N | $C_6F_5$ | H | O | $C_6H_5O$ | H | H | H | H | $CF_3$ | H |
| 65 | 156N | $C_6F_5$ | H | O | $C_6H_5$ | H | H | H | H | $CF_3$ | H |
| 65 | 157N | $C_6F_5$ | H | O | H | $C_6H_5$ | H | H | H | $CF_3$ | H |
| 65 | 158N | $C_6F_5$ | H | O | CN | H | H | H | H | $CF_3$ | H |
| 65 | 159N | $C_6F_5$ | H | O | $OCF_3$ | H | H | H | H | $CF_3$ | H |
| 65 | 160N | $C_6F_5$ | H | O | $CF_3$ | H | H | H | H | $C_6H_5$ | H |
| 65 | 161N | $C_6F_5$ | H | O | $CF_3$ | H | H | H | 3-$CF_3$—$C_6H_5O$ | H | H |
| 65 | 162N | $C_6F_5$ | H | O | $CF_3$ | H | H | H | $C_6H_5O$ | H | H |
| 65 | 163N | $C_6F_5$ | H | O | $CF_3$ | H | H | H | $CF_3O$ | H | H |
| 65 | 164N | $C_6F_5$ | H | O | H | $CF_3$ | H | H | H | $C_6H_5$ | H |
| 65 | 165N | $C_6F_5$ | H | O | H | $CF_3$ | H | H | 3-$CF_3$—$C_6H_5O$ | H | H |
| 65 | 166N | $C_6F_5$ | H | O | H | $CF_3$ | H | H | $CF_3O$ | H | H |
| 65 | 167N | $C_6F_5$ | H | O | H | $CF_3$ | H | H | $C_6H_5O$ | H | H |
| 65 | 168N | $C_6F_5$ | H | O | $CF_3$ | H | $CF_3$ | H | $CF_3O$ | H | H |
| 65 | 169N | $C_6F_5$ | H | O | $CF_3$ | H | $CF_3$ | H | $C_6H_5O$ | H | H |
| 65 | 170N | $C_6F_5$ | H | O | $CF_3O$ | H | H | H | $CF_3$ | H | $CF_3$ |
| 65 | 171N | $C_6F_5$ | H | O | $C_6H_5O$ | H | H | H | $CF_3$ | H | $CF_3$ |
| 65 | 172N | $C_6F_5$ | H | O | H | $C_6H_5O$ | H | H | $C_6H_5O$ | H | H |
| 65 | 173N | $C_6F_5$ | H | O | H | $CF_3O$ | H | H | $CF_3O$ | H | H |
| 65 | 174N | $C_6F_5$ | H | O | H | $CF_3O$ | H | H | H | $C_6H_5O$ | H |
| 65 | 175N | $C_6F_5$ | H | O | $C_6H_5O$ | H | H | H | H | $C_6H_5O$ | H |
| 65 | 176N | $C_6F_5$ | H | O | H | $C_6H_5O$ | H | H | H | $OCF_3$ | H |
| 65 | 177N | $C_6F_5$ | H | O | H | $C_6H_5O$ | H | H | H | $C_6H_5O$ | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

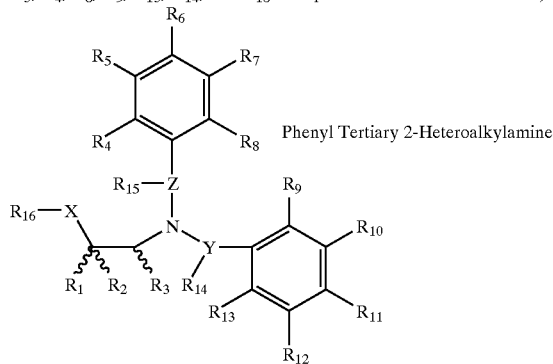

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 65 | 178N | $C_6F_5$ | H | O | $C_6H_5O$ | H | H | H | H | CN | H |
| 65 | 179N | $C_6F_5$ | H | O | $C_6H_5O$ | H | H | H | CN | H | H |
| 65 | 180N | $C_6F_5$ | H | O | $C_6H_5O$ | H | H | H | $NO_2$ | H | H |
| 65 | 181N | $C_6F_5$ | H | O | $C_6H_5O$ | H | H | H | H | $NO_2$ | H |
| 65 | 182N | $C_6F_5$ | H | O | $C_6H_5O$ | H | H | H | H | $SO_2CH_3$ | H |
| 65 | 183N | $C_6F_5$ | H | O | $C_6H_5O$ | H | H | H | H | 2-$NO_2$-4-Cl—$C_6H_3O$ | H |
| 65 | 184N | $C_6F_5$ | H | O | $C_6H_5O$ | H | H | H | 4-Cl—$C_6H_4O$ | H | H |
| 65 | 185N | $C_6F_5$ | H | O | $C_6H_5O$ | H | H | H | 3,4-Cl—$C_6H_3O$ | H | H |
| 65 | 186N | $C_6F_5$ | H | O | $C_6H_5O$ | H | H | H | 3-$CF_3$—$C_6H_3O$ | H | H |
| 65 | 187N | $C_6F_5$ | H | O | $C_6H_5O$ | H | H | H | 3,5-Cl—$C_6H_3O$ | H | H |
| 65 | 188N | $C_6F_5$ | H | O | $C_6H_5O$ | H | H | H | H | $CH_3O$ | H |
| 65 | 189N | $C_6F_5$ | H | O | $C_6H_5O$ | H | H | H | H | $CO_2CH_3$ | H |
| 65 | 190N | $C_6F_5$ | H | O | $C_6H_5O$ | H | H | H | 3-$CH_3O$ $C_6H_5O$ | H | H |
| 65 | 191N | $C_6F_5$ | H | O | $C_6H_5O$ | H | H | H | 4-$CH_3O$ $C_6H_5O$ | H | H |
| 65 | 193N | $C_6F_5$ | H | O | $C_6H_5O$ | H | H | H | $CO_2CH_3$ | H | H |
| 65 | 194N | $C_6F_5$ | H | O | CN | H | H | H | $OCF_3$ | H | H |
| 65 | 195N | $C_6F_5$ | H | O | $NO_2$ | H | H | H | $OCF_3$ | H | H |
| 65 | 196N | $C_6F_5$ | H | O | H | CN | H | H | $OCF_3$ | H | H |
| 65 | 197N | $C_6F_5$ | H | O | H | $NO_2$ | H | H | $OCF_3$ | H | H |
| 65 | 198N | $C_6F_5$ | H | O | $SO_2CH_3$ | H | H | H | $OCF_3$ | H | H |
| 65 | 199N | $C_6F_5$ | H | O | H | $SO_2CH_3$ | H | H | $OCF_3$ | H | H |
| 65 | 200N | $C_6F_5$ | H | O | H | 4-F—$C_6H_5$ $SO_2$ | H | H | $OCF_3$ | H | H |
| 65 | 201N | $C_6F_5$ | H | O | $SO_2N(CH_3)_2$ | H | H | H | $OCF_3$ | H | H |
| 65 | 202N | $C_6F_5$ | H | O | H | $SO_2N(CH_3)_2$ | H | H | $OCF_3$ | H | H |
| 65 | 203N | $C_6F_5$ | H | O | H | $CONH_2$ | H | H | $OCF_3$ | H | H |
| 65 | 204N | $C_6F_5$ | H | O | H | CONH—$C_6H_5$ | H | H | $OCF_3$ | H | H |
| 65 | 205N | $C_6F_5$ | H | O | H | $CO_2CH_3$ | H | H | $OCF_3$ | H | H |
| 65 | 206N | $C_6F_5$ | H | O | H | $CO_2C_4H_9$ | H | H | $OCF_3$ | H | H |
| 65 | 207N | $C_6F_5$ | H | O | H | 4-Cl—$C_6H_5$ | H | H | $C_6H_5O$ | H | H |
| 65 | 208N | $C_6F_5$ | H | O | H | 4-$CF_3O$—$C_6H_5$ | H | H | $CF_3O$ | H | H |
| 65 | 209N | $C_6F_5$ | H | O | 4-F—$C_6H_4O$ | H | H | H | $CF_3O$ | H | H |
| 65 | 210N | $C_6F_5$ | H | O | $C_6F_5O$ | H | H | H | $CF_3O$ | H | H |
| 65 | 211N | $C_6F_5$ | H | O | H | 4-F—$C_6H_5$ | H | H | $CF_3O$ | H | H |
| 65 | 212N | $C_6F_5$ | H | O | H | 4-CN—$C_6H_5$ | H | H | $CF_3O$ | H | H |
| 65 | 213N | $C_6F_5$ | H | O | H | 4-$C_6H_5$—$C_6H_5$ | H | H | $CF_3O$ | H | H |
| 65 | 214N | $C_6F_5$ | H | O | $C_6H_5O$ | H | H | $CH_3$ | $CF_3O$ | H | H |
| 65 | 215N | $C_6F_5$ | H | O | $C_6H_5O$ | H | H | $CH_3$ | $NO_2$ | H | H |
| 65 | 216N | $C_6F_5$ | H | O | $C_6H_5O$ | H | H | $CH_3$ | H | CN | H |
| 65 | 217N | $C_6F_5$ | H | O | $C_6H_5O$ | H | H | 3-$CF_3$ $C_6H_5$ | $CF_3$ | H | H |
| 65 | 218N | $C_6F_5$ | H | O | $C_6H_5O$ | H | H | $C_6H_5$ | H | $C_6H_5$ | H |
| 65 | 219N | $C_6F_5$ | H | O | $C_6H_5O$ | H | H | $C_6H_5$ | $CF_3$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

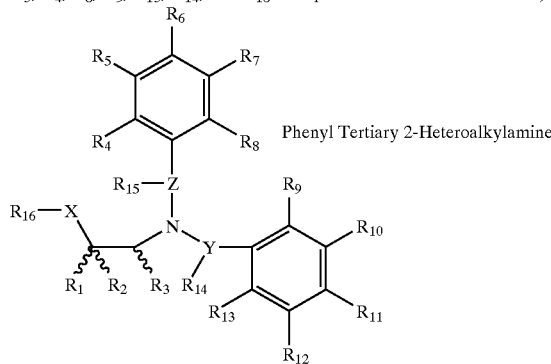

Phenyl Tertiary 2-Heteroalkylamine

| Inhibitor Number Column 1 | Column 2 | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 65 | 220N | $C_6F_5$ | H | O | $C_6H_5O$ | H | H | $CH_3$ | F | H | H |
| 65 | 221N | $C_6F_5$ | H | O | $C_6H_5O$ | H | H | $CF_3$ | H | H | H |
| 46 | 101N | $CF_3$ | $R_2 + R_3 = (CH_2)_3$ | O | $C_6H_5O$ | H | H | H | $C_6H_5O$ | H | H |
| 46 | 102N | $CF_3$ | $R_2 + R_3 = (CH_2)_3$ | O | $CF_3O$ | H | H | H | $C_6H_5O$ | H | H |
| 46 | 103N | $CF_3$ | $R_2 + R_3 = (CH_2)_3$ | O | $C_6H_5$ | H | H | H | $C_6H_5O$ | H | H |
| 46 | 104N | $CF_3$ | $R_2 + R_3 = (CH_2)_3$ | O | H | $C_6H_5$ | H | H | $C_6H_5O$ | H | H |
| 46 | 105N | $CF_3$ | $R_2 + R_3 = (CH_2)_3$ | O | $C_6H_5O$ | H | H | H | 4-Cl—$C_6H_4O$ | H | H |
| 46 | 106N | $CF_3$ | $R_2 + R_3 = (CH_2)_3$ | O | $CF_3O$ | H | H | H | 4-Cl—$C_6H_4O$ | H | H |
| 46 | 99N | $CF_3$ | $R_2 + R_3 = (CH_2)_3$ | O | $SO_2N(CH_3)_2$ | H | H | H | $OCF_3$ | H | H |
| 46 | 100N | $CF_3$ | $R_2 + R_3 = (CH_2)_3$ | O | $SO_2CH_3$ | H | H | H | $OCF_3$ | H | H |
| 46 | 101N | $CF_3$ | $R_2 + R_3 = (CH_2)_3$ | O | $C_6H_5O$ | H | H | H | $C_6H_5O$ | H | H |
| 46 | 102N | $CF_3$ | $R_2 + R_3 = (CH_2)_3$ | O | $CF_3O$ | H | H | H | $C_6H_5O$ | H | H |
| 46 | 103N | $CF_3$ | $R_2 + R_3 = (CH_2)_3$ | O | $C_6H_5$ | H | H | H | $C_6H_5O$ | H | H |
| 46 | 104N | $CF_3$ | $R_2 + R_3 = (CH_2)_3$ | O | H | $C_6H_5$ | H | H | $C_6H_5O$ | H | H |
| 46 | 105N | $CF_3$ | $R_2 + R_3 = (CH_2)_3$ | O | $C_6H_5O$ | H | H | H | 4-Cl—$C_6H_4O$ | H | H |
| 46 | 106N | $CF_3$ | $R_2 + R_3 = (CH_2)_3$ | O | $CF_3O$ | H | H | H | 4-Cl—$C_6H_4O$ | H | H |
| 46 | 107N | $CF_3$ | $R_2 + R_3 = (CH_2)_3$ | O | $C_6H_5O$ | H | H | H | 3,4-Cl—$C_6H_3O$ | H | H |
| 46 | 108N | $CF_3$ | $R_2 + R_3 = (CH_2)_3$ | O | $CF_3O$ | H | H | H | 3,4-Cl—$C_6H_3O$ | H | H |
| 46 | 109N | $CF_3$ | $R_2 + R_3 = (CH_2)_3$ | O | $CF_3O$ | H | H | H | 3,5-Cl—$C_6H_3O$ | H | H |
| 46 | 110N | $CF_3$ | $R_2 + R_3 = (CH_2)_3$ | O | $CF_3O$ | H | H | H | 3-$CH_3O$—$C_6H_4O$ | H | H |
| 46 | 111N | $CF_3$ | $R_2 + R_3 = (CH_2)_3$ | O | $CF_3O$ | H | H | H | H | 3-$CH_3O$—$C_6H_4O$ | H |
| 46 | 112N | $CF_3$ | $R_2 + R_3 = (CH_2)_3$ | O | $CF_3O$ | H | H | H | 3-$CF_3$—$C_6H_4O$ | H | H |
| 46 | 113N | $CF_3$ | $R_2 + R_3 = (CH_2)_3$ | O | $CF_3O$ | H | H | H | $C_6H_5$—$CH_2O$ | H | H |
| 46 | 114N | $CF_3$ | $R_2 + R_3 = (CH_2)_3$ | O | $CF_3O$ | H | H | H | $C_6H_5$—$CH_2O$ | $CH_3O$ | H |
| 46 | 115N | $CF_3$ | $R_2 + R_3 = (CH_2)_3$ | O | $CF_3O$ | H | H | H | $C_6H_5$—$CH_2O$ | $C_6H_5$—$CH_2O$ | H |
| 46 | 116N | $CF_3$ | $R_2 + R_3 = (CH_2)_3$ | O | $CF_3O$ | H | H | H | ethoxy | H | H |
| 46 | 117N | $CF_3$ | $R_2 + R_3 = (CH_2)_3$ | O | $CF_3O$ | H | H | H | $CH_3CO_2$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

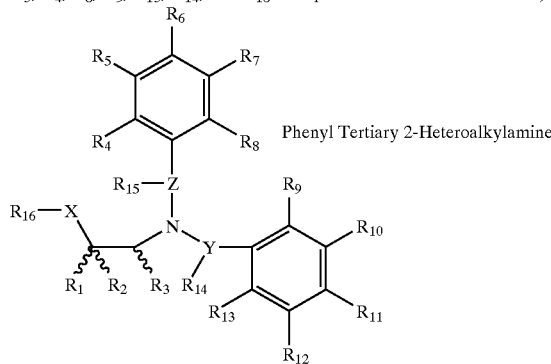

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 46 | 118N | $CF_3$ | $R_2 + R_3 =$ $(CH_2)_3$ | O | $CF_3O$ | H | H | H | $HOCH_2$— $CH_2O$ | H | H |
| 46 | 119N | $CF_3$ | $R_2 + R_3 =$ $(CH_2)_3$ | O | $CF_3O$ | H | H | H | ![epoxide] | H | H |
| 46 | 120N | $CF_3$ | $R_2 + R_3 =$ $(CH_2)_3$ | O | $CF_3O$ | H | H | H | $R_{10} + R_{11} = OCH_2O$ | | H |
| 46 | 121N | $CF_3$ | $R_2 + R_3 =$ $(CH_2)_3$ | O | $CF_3O$ | H | H | H | $R_{10} + R_{11} = OCH_2CH_2O$ | | H |
| 46 | 122N | $CF_3$ | $R_2 + R_3 =$ $(CH_2)_3$ | O | $CF_3O$ | H | H | H | $CH_3O$ | $CH_3O$ | H |
| 46 | 123N | $CF_3$ | $R_2 + R_3 =$ $(CH_2)_3$ | O | $CF_3O$ | H | H | H | ethoxy | $CH_3O$ | H |
| 46 | 124N | $CF_3$ | $R_2 + R_3 =$ $(CH_2)_3$ | O | $CF_3O$ | H | H | H | ethoxy | ethoxy | H |
| 46 | 125N | $CF_3$ | $R_2 + R_3 =$ $(CH_2)_3$ | O | $CF_3O$ | H | H | H | $CH_3CO_2$ | $CH_3CO_2$ | H |
| 46 | 126N | $CF_3$ | $R_2 + R_3 =$ $(CH_2)_3$ | O | $CF_3O$ | H | H | H | $CH_3O$ | $CH_3CO_2$ | H |
| 46 | 127N | $CF_3$ | $R_2 + R_3 =$ $(CH_2)_3$ | O | $CF_3O$ | H | H | H | n-butoxy | H | H |
| 46 | 128N | $CF_3$ | $R_2 + R_3 =$ $(CH_2)_3$ | O | $CF_3O$ | H | H | H | $CH_3O$ | H | H |
| 46 | 129N | $CF_3$ | $R_2 + R_3 =$ $(CH_2)_3$ | O | $CF_3O$ | H | H | H | H | $CH_3O$ | H |
| 46 | 130N | $CF_3$ | $R_2 + R_3 =$ $(CH_2)_3$ | O | $CH_3O$ | H | H | H | $CH_3O$ | H | H |
| 46 | 131N | $CF_3$ | $R_2 + R_3 =$ $(CH_2)_3$ | O | $CH_3O$ | H | H | H | H | $CF_3O$ | H |
| 46 | 132N | $CF_3$ | $R_2 + R_3 =$ $(CH_2)_3$ | O | $CF_3O$ | H | H | H | H | ethoxy | H |
| 46 | 133N | $CF_3$ | $R_2 + R_3 =$ $(CH_2)_3$ | O | $CF_3O$ | H | H | H | H | n-propoxy | H |
| 46 | 134N | $CF_3$ | $R_2 + R_3 =$ $(CH_2)_3$ | O | $C_6H_5$— $CH_2O$ | H | H | H | $CF_3O$ | H | H |
| 46 | 135N | $CF_3$ | $R_2 + R_3 =$ $(CH_2)_3$ | O | $C_6H_5$— $CH_2O$ | H | H | H | $C_6H_5O$ | H | H |
| 46 | 136N | $CF_3$ | $R_2 + R_3 =$ $(CH_2)_3$ | O | ethoxy | H | H | H | $CF_3O$ | H | H |
| 46 | 137N | $CF_3$ | $R_2 + R_3 =$ $(CH_2)_3$ | O | $R_5 + R_6 = OCH_2O$ | | H | H | $CF_3O$ | H | H |
| 46 | 138N | $CF_3$ | $R_2 + R_3 =$ $(CH_2)_3$ | O | $R_5 + R_6 = OCH_2O$ | | H | H | $C_6H_5O$ | H | H |
| 46 | 139N | $CF_3$ | $R_2 + R_3 =$ $(CH_2)_3$ | O | $R_5 + R_6 = OCH_2CH_2O$ | | H | H | $CF_3O$ | H | H |
| 46 | 140N | $CF_3$ | $R_2 + R_3 =$ $(CH_2)_3$ | O | $CH_3O$ | $CH_3O$ | H | H | $CF_3O$ | H | H |
| 46 | 141N | $CF_3$ | $R_2 + R_3 =$ $(CH_2)_3$ | O | $R_5 + R_6 =$ $OCH_2CH_2CH_2O$ | | H | H | $CF_3O$ | H | H |
| 46 | 142N | $CF_3$ | $R_2 + R_3 =$ $(CH_2)_3$ | O | cyclo pentoxy | $CH_3O$ | H | H | $CF_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

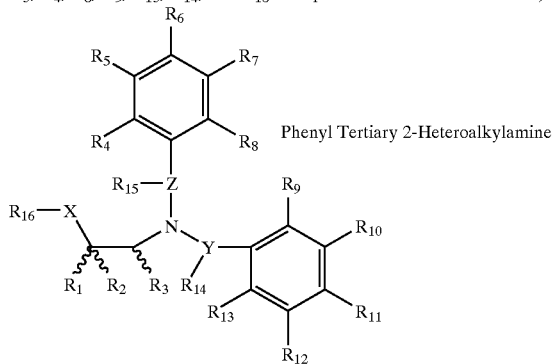

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 46 | 143N | $CF_3$ | $R_2 + R_3 = (CH_2)_3$ | O | H | $C_6H_5O$ | H | H | $CF_3O$ | H | H |
| 46 | 144N | $CF_3$ | $R_2 + R_3 = (CH_2)_3$ | O | $CH_3O$ | $CH_3O$ | $CH_3O$ | H | $CF_3O$ | H | H |
| 46 | 145N | $CF_3$ | $R_2 + R_3 = (CH_2)_3$ | O | H | $CF_3O$ | H | H | $CF_3O$ | H | H |
| 46 | 146N | $CF_3$ | $R_2 + R_3 = (CH_2)_3$ | O | H | $C_6H_5$—$CH_2$ | H | H | $CF_3O$ | H | H |
| 46 | 147N | $CF_3$ | $R_2 + R_3 = (CH_2)_3$ | O | $C_6H_5O$ | H | H | H | $R_{10} + R_{11} = OCH_2CH_2O$ | | H |
| 46 | 148N | $CF_3$ | $R_2 + R_3 = (CH_2)_3$ | O | H | $CF_3O$ | H | H | $CF_3$ | H | H |
| 46 | 149N | $CF_3$ | $R_2 + R_3 = (CH_2)_3$ | O | $C_6H_5O$ | H | H | H | $CF_3$ | H | H |
| 46 | 150N | $CF_3$ | $R_2 + R_3 = (CH_2)_3$ | O | $C_6H_5$ | H | H | H | $CF_3$ | H | H |
| 46 | 151N | $CF_3$ | $R_2 + R_3 = (CH_2)_3$ | O | H | $C_6H_5$ | H | H | $CF_3$ | H | H |
| 46 | 152N | $CF_3$ | $R_2 + R_3 = (CH_2)_3$ | O | CN | H | H | H | $CF_3$ | H | H |
| 46 | 153N | $CF_3$ | $R_2 + R_3 = (CH_2)_3$ | O | H | $OCF_3$ | H | H | $CF_3$ | H | H |
| 46 | 154N | $CF_3$ | $R_2 + R_3 = (CH_2)_3$ | O | $OCF_3$ | H | H | H | H | $CF_3$ | H |
| 46 | 155N | $CF_3$ | $R_2 + R_3 = (CH_2)_3$ | O | $C_6H_5O$ | H | H | H | H | $CF_3$ | H |
| 46 | 156N | $CF_3$ | $R_2 + R_3 = (CH_2)_3$ | O | $C_6H_5$ | H | H | H | H | $CF_3$ | H |
| 46 | 157N | $CF_3$ | $R_2 + R_3 = (CH_2)_3$ | O | H | $C_6H_5$ | H | H | H | $CF_3$ | H |
| 46 | 158N | $CF_3$ | $R_2 + R_3 = (CH_2)_3$ | O | CN | H | H | H | H | $CF_3$ | H |
| 46 | 159N | $CF_3$ | $R_2 + R_3 = (CH_2)_3$ | O | $OCF_3$ | H | H | H | H | $CF_3$ | H |
| 46 | 160N | $CF_3$ | $R_2 + R_3 = (CH_2)_3$ | O | $CF_3$ | H | H | H | H | $C_6H_5$ | H |
| 46 | 161N | $CF_3$ | $R_2 + R_3 = (CH_2)_3$ | O | $CF_3$ | H | H | H | 3-$CF_3$—$C_6H_5O$ | H | H |
| 46 | 162N | $CF_3$ | $R_2 + R_3 = (CH_2)_3$ | O | $CF_3$ | H | H | H | $C_6H_5O$ | H | H |
| 46 | 163N | $CF_3$ | $R_2 + R_3 = (CH_2)_3$ | O | $CF_3$ | H | H | H | $CF_3O$ | H | H |
| 46 | 164N | $CF_3$ | $R_2 + R_3 = (CH_2)_3$ | O | H | $CF_3$ | H | H | H | $C_6H_5$ | H |
| 46 | 165N | $CF_3$ | $R_2 + R_3 = (CH_2)_3$ | O | H | $CF_3$ | H | H | 3-$CF_3$—$C_6H_5O$ | H | H |
| 46 | 166N | $CF_3$ | $R_2 + R_3 = (CH_2)_3$ | O | H | $CF_3$ | H | H | $CF_3O$ | H | H |
| 46 | 167N | $CF_3$ | $R_2 + R_3 = (CH_2)_3$ | O | H | $CF_3$ | H | H | $C_6H_5O$ | H | H |
| 46 | 168N | $CF_3$ | $R_2 + R_3 = (CH_2)_3$ | O | $CF_3$ | H | $CF_3$ | H | $CF_3O$ | H | H |
| 46 | 169N | $CF_3$ | $R_2 + R_3 = (CH_2)_3$ | O | $CF_3$ | H | $CF_3$ | H | $C_6H_5O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

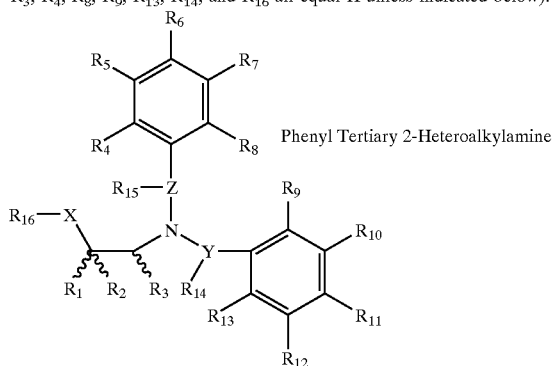

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 46 | 170N | $CF_3$ | $R_2 + R_3 =$ $(CH_2)_3$ | O | $CF_3O$ | H | H | H | $CF_3$ | H | $CF_3$ |
| 46 | 171N | $CF_3$ | $R_2 + R_3 =$ $(CH_2)_3$ | O | $C_6H_5O$ | H | H | H | $CF_3$ | H | $CF_3$ |
| 46 | 172N | $CF_3$ | $R_2 + R_3 =$ $(CH_2)_3$ | O | H | $C_6H_5O$ | H | H | $C_6H_5O$ | H | H |
| 46 | 173N | $CF_3$ | $R_2 + R_3 =$ $(CH_2)_3$ | O | H | $CF_3O$ | H | H | $CF_3O$ | H | H |
| 46 | 174N | $CF_3$ | $R_2 + R_3 =$ $(CH_2)_3$ | O | H | $CF_3O$ | H | H | H | $C_6H_5O$ | H |
| 46 | 175N | $CF_3$ | $R_2 + R_3 =$ $(CH_2)_3$ | O | $C_6H_5O$ | H | H | H | H | $C_6H_5O$ | H |
| 46 | 176N | $CF_3$ | $R_2 + R_3 =$ $(CH_2)_3$ | O | H | $C_6H_5O$ | H | H | H | $OCF_3$ | H |
| 46 | 177N | $CF_3$ | $R_2 + R_3 =$ $(CH_2)_3$ | O | H | $C_6H_5O$ | H | H | H | $C_6H_5O$ | H |
| 46 | 178N | $CF_3$ | $R_2 + R_3 =$ $(CH_2)_3$ | O | $C_6H_5O$ | H | H | H | H | CN | H |
| 46 | 179N | $CF_3$ | $R_2 + R_3 =$ $(CH_2)_3$ | O | $C_6H_5O$ | H | H | H | CN | H | H |
| 46 | 180N | $CF_3$ | $R_2 + R_3 =$ $(CH_2)_3$ | O | $C_6H_5O$ | H | H | H | $NO_2$ | H | H |
| 46 | 181N | $CF_3$ | $R_2 + R_3 =$ $(CH_2)_3$ | O | $C_6H_5O$ | H | H | H | H | $NO_2$ | H |
| 46 | 182N | $CF_3$ | $R_2 + R_3 =$ $(CH_2)_3$ | O | $C_6H_5O$ | H | H | H | H | $SO_2CH_3$ | H |
| 46 | 183N | $CF_3$ | $R_2 + R_3 =$ $(CH_2)_3$ | O | $C_6H_5O$ | H | H | H | H | 2-$NO_2$-4-Cl—$C_6H_3O$ | H |
| 46 | 184N | $CF_3$ | $R_2 + R_3 =$ $(CH_2)_3$ | O | $C_6H_5O$ | H | H | H | 4-Cl—$C_6H_4O$ | H | H |
| 46 | 185N | $CF_3$ | $R_2 + R_3 =$ $(CH_2)_3$ | O | $C_6H_5O$ | H | H | H | 3,4-Cl—$C_6H_3O$ | H | H |
| 46 | 186N | $CF_3$ | $R_2 + R_3 =$ $(CH_2)_3$ | O | $C_6H_5O$ | H | H | H | 3-$CF_3$—$C_6H_3O$ | H | H |
| 46 | 187N | $CF_3$ | $R_2 + R_3 =$ $(CH_2)_3$ | O | $C_6H_5O$ | H | H | H | 3,5-Cl—$C_6H_3O$ | H | H |
| 46 | 188N | $CF_3$ | $R_2 + R_3 =$ $(CH_2)_3$ | O | $C_6H_5O$ | H | H | H | H | $CH_3O$ | H |
| 46 | 189N | $CF_3$ | $R_2 + R_3 =$ $(CH_2)_3$ | O | $C_6H_5O$ | H | H | H | H | $CO_2CH_3$ | H |
| 46 | 190N | $CF_3$ | $R_2 + R_3 =$ $(CH_2)_3$ | O | $C_6H_5O$ | H | H | H | 3-$CH_3O$ $C_6H_5O$ | H | H |
| 46 | 191N | $CF_3$ | $R_2 + R_3 =$ $(CH_2)_3$ | O | $C_6H_5O$ | H | H | H | 4-$CH_3O$ $C_6H_5O$ | H | H |
| 46 | 193N | $CF_3$ | $R_2 + R_3 =$ $(CH_2)_3$ | O | $C_6H_5O$ | H | H | H | $CO_2CH_3$ | H | H |
| 46 | 194N | $CF_3$ | $R_2 + R_3 =$ $(CH_2)_3$ | O | CN | H | H | H | $OCF_3$ | H | H |
| 46 | 195N | $CF_3$ | $R_2 + R_3 =$ $(CH_2)_3$ | O | $NO_2$ | H | H | H | $OCF_3$ | H | H |
| 46 | 196N | $CF_3$ | $R_2 + R_3 =$ $(CH_2)_3$ | O | H | CN | H | H | $OCF_3$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

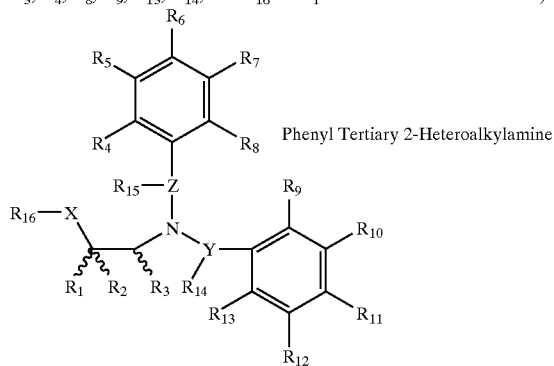

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 46 | 197N | $CF_3$ | $R_2 + R_3 =$ $(CH_2)_3$ | O | H | $NO_2$ | H | H | $OCF_3$ | H | H |
| 46 | 198N | $CF_3$ | $R_2 + R_3 =$ $(CH_2)_3$ | O | $SO_2CH_3$ | H | H | H | $OCF_3$ | H | H |
| 46 | 199N | $CF_3$ | $R_2 + R_3 =$ $(CH_2)_3$ | O | H | $SO_2CH_3$ | H | H | $OCF_3$ | H | H |
| 46 | 200N | $CF_3$ | $R_2 + R_3 =$ $(CH_2)_3$ | O | H | 4-F—$C_6H_5$ $SO_2$ | H | H | $OCF_3$ | H | H |
| 46 | 201N | $CF_3$ | $R_2 + R_3 =$ $(CH_2)_3$ | O | $SO_2N$ $(CH_3)_2$ | H | H | H | $OCF_3$ | H | H |
| 46 | 202N | $CF_3$ | $R_2 + R_3 =$ $(CH_2)_3$ | O | H | $SO_2N$ $(CH_3)_2$ | H | H | $OCF_3$ | H | H |
| 46 | 203N | $CF_3$ | $R_2 + R_3 =$ $(CH_2)_3$ | O | H | $CONH_2$ | H | H | $OCF_3$ | H | H |
| 46 | 204N | $CF_3$ | $R_2 + R_3 =$ $(CH_2)_3$ | O | H | CONH— $C_6H_5$ | H | H | $OCF_3$ | H | H |
| 46 | 205N | $CF_3$ | $R_2 + R_3 =$ $(CH_2)_3$ | O | H | $CO_2CH_3$ | H | H | $OCF_3$ | H | H |
| 46 | 206N | $CF_3$ | $R_2 + R_3 =$ $(CH_2)_3$ | O | H | $CO_2C_4H_9$ | H | H | $OCF_3$ | H | H |
| 46 | 207N | $CF_3$ | $R_2 + R_3 =$ $(CH_2)_3$ | O | H | 4-Cl—$C_6H_5$ | H | H | $C_6H_5O$ | H | H |
| 46 | 208N | $CF_3$ | $R_2 + R_3 =$ $(CH_2)_3$ | O | H | 4-$CF_3$O— $C_6H_5$ | H | H | $CF_3O$ | H | H |
| 46 | 209N | $CF_3$ | $R_2 + R_3 =$ $(CH_2)_3$ | O | 4-F— $C_6H_4O$ | H | H | H | $CF_3O$ | H | H |
| 46 | 210N | $CF_3$ | $R_2 + R_3 =$ $(CH_2)_3$ | O | $C_6H_5O$ | H | H | H | $CF_3O$ | H | H |
| 46 | 211N | $CF_3$ | $R_2 + R_3 =$ $(CH_2)_3$ | O | H | 4-F—$C_6H_5$ | H | H | $CF_3O$ | H | H |
| 46 | 212N | $CF_3$ | $R_2 + R_3 =$ $(CH_2)_3$ | O | H | 4-CN— $C_6H_5$ | H | H | $CF_3O$ | H | H |
| 46 | 213N | $CF_3$ | $R_2 + R_3 =$ $(CH_2)_3$ | O | H | 4-$C_6H_5$— | H | H | $CF_3O$ | H | H |
| 46 | 214N | $CF_3$ | $R_2 + R_3 =$ $(CH_2)_3$ | O | $C_6H_5O$ | H | H | $CH_3$ | $CF_3O$ | H | H |
| 46 | 215N | $CF_3$ | $R_2 + R_3 =$ $(CH_2)_3$ | O | $C_6H_5O$ | H | H | $CH_3$ | $NO_2$ | H | H |
| 46 | 216N | $CF_3$ | $R_2 + R_3 =$ $(CH_2)_3$ | O | $C_6H_5O$ | H | H | $CH_3$ | H | CN | H |
| 46 | 217N | $CF_3$ | $R_2 + R_3 =$ $(CH_2)_3$ | O | $C_6H_5O$ | H | H | 3-$CF_3$ $C_6H_5$ | $CF_3$ | H | H |
| 46 | 218N | $CF_3$ | $R_2 + R_3 =$ $(CH_2)_3$ | O | $C_6H_5O$ | H | H | $C_6H_5$ | H | $C_6H_5$ | H |
| 46 | 219N | $CF_3$ | $R_2 + R_3 =$ $(CH_2)_3$ | O | $C_6H_5O$ | H | H | $C_6H_5$ | $CF_3$ | H | H |
| 46 | 220N | $CF_3$ | $R_2 + R_3 =$ $(CH_2)_3$ | O | $C_6H_5O$ | H | H | $CH_3$ | F | H | H |
| 46 | 221N | $CF_3$ | $R_2 + R_3 =$ $(CH_2)_3$ | O | $C_6H_5O$ | H | H | $CF_3$ | H | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

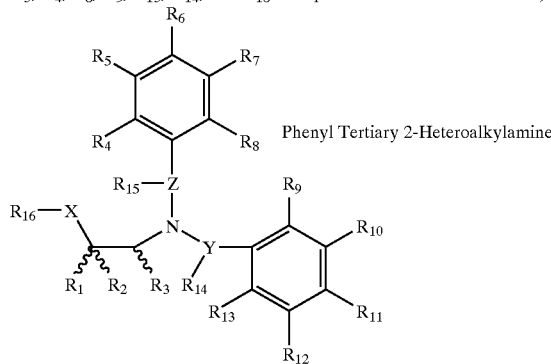

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 46 | 222N | $CF_3$ | $R_2 + R_3 =$ $(CH_2)_3$ | O | bond to —O— of $R_6$ aryl group | (2-methylphenoxy) | H | H | $CF_3O$ | H | H |
| 46 | 223N | $CF_3$ | $R_2 + R_3 =$ $(CH_2)_3$ | O | to $CH_2$ of $R_6$ aryl group | (2-bromo-4-ethyl-5-methylphenyl) | H | H | $CF_3O$ | H | H |
| 57 | 96N | $HCF_2CF_2$ $OCH_2$ | H | O | OH | OH | H | H | $C_6H_5O$ | H | H |
| 57 | 97N | $HCF_2CF_2$ $OCH_2$ | H | O | $C_6H_5O$ | H | H | H | OH | OH | H |
| 57 | 98N | $HCF_2CF_2$ $OCH_2$ | H | O | 3-pyridyl | H | H | H | $CF_3$ | H | H |
| 57 | 99N | $HCF_2CF_2$ $OCH_2$ | H | O | $SO_2N$ $(CH_3)_2$ | H | H | H | $OCF_3$ | H | H |
| 57 | 100N | $HCF_2CF_2$ $OCH_2$ | H | O | $SO_2CH_3$ | H | H | H | $OCF_3$ | H | H |
| 57 | 101N | $HCF_2CF_2$ $OCH_2$ | H | O | $C_6H_5O$ | H | H | H | $C_6H_5O$ | H | H |
| 57 | 102N | $HCF_2CF_2$ $OCH_2$ | H | O | $CF_3O$ | H | H | H | $C_6H_5O$ | H | H |
| 57 | 103N | $HCF_2CF_2$ $OCH_2$ | H | O | $C_6H_5$ | H | H | H | $C_6H_5O$ | H | H |
| 57 | 104N | $HCF_2CF_2$ $OCH_2$ | H | O | H | $C_6H_5$ | H | H | $C_6H_5O$ | H | H |
| 57 | 105N | $HCF_2CF_2$ $OCH_2$ | H | O | $C_6H_5O$ | H | H | H | 4-Cl—$C_6H_4O$ | H | H |
| 57 | 106N | $HCF_2CF_2$ $OCH_2$ | H | O | $CF_3O$ | H | H | H | 4-Cl—$C_6H_4O$ | H | H |
| 57 | 107N | $HCF_2CF_2$ $OCH_2$ | H | O | $C_6H_5O$ | H | H | H | 3,4-Cl—$C_6H_3O$ | H | H |
| 57 | 108N | $HCF_2CF_2$ $OCH_2$ | H | O | $CF_3O$ | H | H | H | 3,4-Cl—$C_6H_3O$ | H | H |
| 57 | 109N | $HCF_2CF_2$ $OCH_2$ | H | O | $CF_3O$ | H | H | H | 3,5-Cl—$C_6H_3O$ | H | H |
| 57 | 110N | $HCF_2CF_2$ $OCH_2$ | H | O | $CF_3O$ | H | H | H | 3-$CH_3O$—$C_6H_4O$ | H | H |
| 57 | 111N | $HCF_2CF_2$ $OCH_2$ | H | O | $CF_3O$ | H | H | H | H | 3-$CH_3O$—$C_6H_4O$ | H |
| 57 | 112N | $HCF_2CF_2$ $OCH_2$ | H | O | $CF_3O$ | H | H | H | 3-$CF_3$—$C_6H_4O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

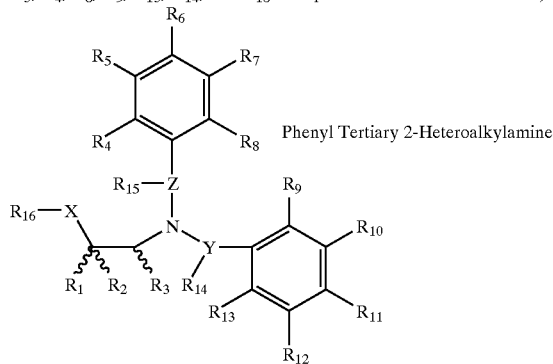

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 57 | 113N | HCF$_2$CF$_2$OCH$_2$ | H | O | CF$_3$O | H | H | H | C$_6$H$_5$—CH$_2$O | H | H |
| 57 | 114N | HCF$_2$CF$_2$OCH$_2$ | H | O | CF$_3$O | H | H | H | C$_6$H$_5$—CH$_2$O | CH$_3$O | H |
| 57 | 115N | HCF$_2$CF$_2$OCH$_2$ | H | O | CF$_3$O | H | H | H | C$_6$H$_5$—CH$_2$O | C$_6$H$_5$—CH$_2$O | H |
| 57 | 116N | HCF$_2$CF$_2$OCH$_2$ | H | O | CF$_3$O | H | H | H | ethoxy | H | H |
| 57 | 117N | HCF$_2$CF$_2$OCH$_2$ | H | O | CF$_3$O | H | H | H | CH$_3$CO$_2$ | H | H |
| 57 | 118N | HCF$_2$CF$_2$OCH$_2$ | H | O | CF$_3$O | H | H | H | HOCH$_2$—CH$_2$O | H | H |
| 57 | 119N | HCF$_2$CF$_2$OCH$_2$ | H | O | CF$_3$O | H | H | H | (epoxide) | H | H |
| 57 | 120N | HCF$_2$CF$_2$OCH$_2$ | H | O | CF$_3$O | H | H | H | $R_{10} + R_{11}$ = OCH$_2$O | | H |
| 57 | 121N | HCF$_2$CF$_2$OCH$_2$ | H | O | CF$_3$O | H | H | H | $R_{10} + R_{11}$ = OCH$_2$CH$_2$O | | H |
| 57 | 122N | HCF$_2$CF$_2$OCH$_2$ | H | O | CF$_3$O | H | H | H | CH$_3$O | CH$_3$O | H |
| 57 | 123N | HCF$_2$CF$_2$OCH$_2$ | H | O | CF$_3$O | H | H | H | ethoxy | CH$_3$O | H |
| 57 | 124N | HCF$_2$CF$_2$OCH$_2$ | H | O | CF$_3$O | H | H | H | ethoxy | ethoxy | H |
| 57 | 125N | HCF$_2$CF$_2$OCH$_2$ | H | O | CF$_3$O | H | H | H | CH$_3$CO$_2$ | CH$_3$CO$_2$ | H |
| 57 | 126N | HCF$_2$CF$_2$OCH$_2$ | H | O | CF$_3$O | H | H | H | CH$_3$O | CH$_3$CO$_2$ | H |
| 57 | 127N | HCF$_2$CF$_2$OCH$_2$ | H | O | CF$_3$O | H | H | H | n-butoxy | H | H |
| 57 | 128N | HCF$_2$CF$_2$OCH$_2$ | H | O | CF$_3$O | H | H | H | CH$_3$O | H | H |
| 57 | 129N | HCF$_2$CF$_2$OCH$_2$ | H | O | CF$_3$O | H | H | H | H | CH$_3$O | H |
| 57 | 130N | HCF$_2$CF$_2$OCH$_2$ | H | O | CF$_3$O | H | H | H | CH$_3$O | H | H |
| 57 | 131N | HCF$_2$CF$_2$OCH$_2$ | H | O | CF$_3$O | H | H | H | H | CF$_3$O | H |
| 57 | 132N | HCF$_2$CF$_2$OCH$_2$ | H | O | CF$_3$O | H | H | H | H | ethoxy | H |
| 57 | 133N | HCF$_2$CF$_2$OCH$_2$ | H | O | CF$_3$O | H | H | H | H | n-propoxy | H |
| 57 | 134N | HCF$_2$CF$_2$OCH$_2$ | H | O | C$_6$H$_5$—CH$_2$O | H | H | H | CF$_3$O | H | H |
| 57 | 135N | HCF$_2$CF$_2$OCH$_2$ | H | O | C$_6$H$_5$—CH$_2$O | H | H | H | C$_6$H$_5$O | H | H |
| 57 | 136N | HCF$_2$CF$_2$OCH$_2$ | H | O | ethoxy | H | H | H | CF$_3$O | H | H |
| 57 | 137N | HCF$_2$CF$_2$OCH$_2$ | H | O | $R_5 + R_6$ = OCH$_2$O | | H | H | CF$_3$O | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

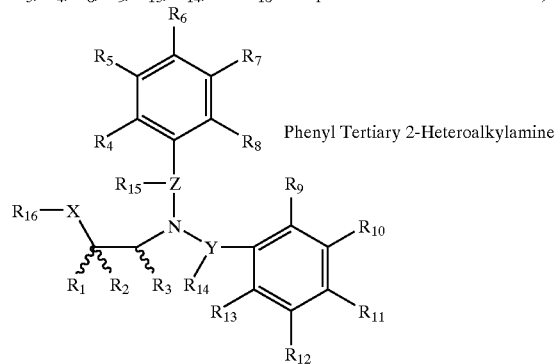

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 57 | 138N | $HCF_2CF_2OCH_2$ | H | O | $R_5 + R_6 = OCH_2O$ | | H | H | $C_6H_5O$ | H | H |
| 57 | 139N | $HCF_2CF_2OCH_2$ | H | O | $R_5 + R_6 = OCH_2CH_2O$ | | H | H | $CF_3O$ | H | H |
| 57 | 140N | $HCF_2CF_2OCH_2$ | H | O | $CH_3O$ | $CH_3O$ | H | H | $CF_3O$ | H | H |
| 57 | 141N | $HCF_2CF_2OCH_2$ | H | O | $R_5 + R_6 = OCH_2CH_2CH_2O$ | | H | H | $CF_3O$ | H | H |
| 57 | 142N | $HCF_2CF_2OCH_2$ | H | O | cyclo pentoxy | $CH_3O$ | H | H | $CF_3O$ | H | H |
| 57 | 143N | $HCF_2CF_2OCH_2$ | H | O | H | $C_6H_5O$ | H | H | $CF_3O$ | H | H |
| 57 | 144N | $HCF_2CF_2OCH_2$ | H | O | $CH_3O$ | $CH_3O$ | $CH_3O$ | H | $CF_3O$ | H | H |
| 57 | 145N | $HCF_2CF_2OCH_2$ | H | O | H | $CF_3O$ | H | H | $CF_3O$ | H | H |
| 57 | 146N | $HCF_2CF_2OCH_2$ | H | O | H | $C_6H_5$—$CH_2$ | H | H | $CF_3O$ | H | H |
| 57 | 147N | $HCF_2CF_2OCH_2$ | H | O | $C_6H_5O$ | H | H | H | $R_{10} + R_{11} = OCH_2CH_2O$ | | H |
| 57 | 148N | $HCF_2CF_2OCH_2$ | H | O | H | $CF_3O$ | H | H | $CF_3$ | H | H |
| 57 | 149N | $HCF_2CF_2OCH_2$ | H | O | $C_6H_5O$ | H | H | H | $CF_3$ | H | H |
| 57 | 150N | $HCF_2CF_2OCH_2$ | H | O | $C_6H_5$ | H | H | H | $CF_3$ | H | H |
| 57 | 151N | $HCF_2CF_2OCH_2$ | H | O | H | $C_6H_5$ | H | H | $CF_3$ | H | H |
| 57 | 152N | $HCF_2CF_2OCH_2$ | H | O | CN | H | H | H | $CF_3$ | H | H |
| 57 | 153N | $HCF_2CF_2OCH_2$ | H | O | H | $OCF_3$ | H | H | $CF_3$ | H | H |
| 57 | 154N | $HCF_2CF_2OCH_2$ | H | O | $OCF_3$ | H | H | H | H | $CF_3$ | H |
| 57 | 155N | $HCF_2CF_2OCH_2$ | H | O | $C_6H_5O$ | H | H | H | H | $CF_3$ | H |
| 57 | 156N | $HCF_2CF_2OCH_2$ | H | O | $C_6H_5$ | H | H | H | H | $CF_3$ | H |
| 57 | 157N | $HCF_2CF_2OCH_2$ | H | O | H | $C_6H_5$ | H | H | H | $CF_3$ | H |
| 57 | 158N | $HCF_2CF_2OCH_2$ | H | O | CN | H | H | H | H | $CF_3$ | H |
| 57 | 159N | $HCF_2CF_2OCH_2$ | H | O | $OCF_3$ | H | H | H | H | $CF_3$ | H |
| 57 | 160N | $HCF_2CF_2OCH_2$ | H | O | $CF_3$ | H | H | H | H | $C_6H_5$ | H |
| 57 | 161N | $HCF_2CF_2OCH_2$ | H | O | $CF_3$ | H | H | H | 3-$CF_3$—$C_6H_5O$ | H | H |
| 57 | 162N | $HCF_2CF_2OCH_2$ | H | O | $CF_3$ | H | H | H | $C_6H_5O$ | H | H |
| 57 | 163N | $HCF_2CF_2OCH_2$ | H | O | $CF_3$ | H | H | H | $CF_3O$ | H | H |
| 57 | 164N | $HCF_2CF_2OCH_2$ | H | O | H | $CF_3$ | H | H | H | $C_6H_5$ | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

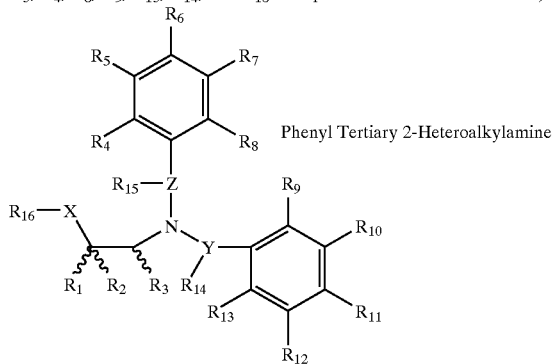

Phenyl Tertiary 2-Heteroalkylamine

| Inhibitor Number Column 1 + Column 2 | | | | | | | | | | | |
|---|---|---|---|---|---|---|---|---|---|---|---|
| Reagent | Reagent | $R_1$ | $R_2$ | X | $R_5$ | $R_6$ | $R_7$ | $R_{14}$ | $R_{10}$ | $R_{11}$ | $R_{12}$ |
| 57 | 165N | $HCF_2CF_2OCH_2$ | H | O | H | $CF_3$ | H | H | 3-$CF_3$—$C_6H_5O$ | H | H |
| 57 | 166N | $HCF_2CF_2OCH_2$ | H | O | H | $CF_3$ | H | H | $CF_3O$ | H | H |
| 57 | 167N | $HCF_2CF_2OCH_2$ | H | O | H | $CF_3$ | H | H | $C_6H_5O$ | H | H |
| 57 | 168N | $HCF_2CF_2OCH_2$ | H | O | $CF_3$ | H | $CF_3$ | H | $CF_3O$ | H | H |
| 57 | 169N | $HCF_2CF_2OCH_2$ | H | O | $CF_3$ | H | $CF_3$ | H | $C_6H_5O$ | H | H |
| 57 | 170N | $HCF_2CF_2OCH_2$ | H | O | $CF_3O$ | H | H | H | $CF_3$ | H | $CF_3$ |
| 57 | 171N | $HCF_2CF_2OCH_2$ | H | O | $C_6H_5O$ | H | H | H | $CF_3$ | H | $CF_3$ |
| 57 | 172N | $HCF_2CF_2OCH_2$ | H | O | H | $C_6H_5O$ | H | H | $C_6H_5O$ | H | H |
| 57 | 173N | $HCF_2CF_2OCH_2$ | H | O | H | $CF_3O$ | H | H | $CF_3O$ | H | H |
| 57 | 174N | $HCF_2CF_2OCH_2$ | H | O | H | $CF_3O$ | H | H | H | $C_6H_5O$ | H |
| 57 | 175N | $HCF_2CF_2OCH_2$ | H | O | $C_6H_5O$ | H | H | H | H | $C_6H_5O$ | H |
| 57 | 176N | $HCF_2CF_2OCH_2$ | H | O | H | $C_6H_5O$ | H | H | H | $OCF_3$ | H |
| 57 | 177N | $HCF_2CF_2OCH_2$ | H | O | H | $C_6H_5O$ | H | H | H | $C_6H_5O$ | H |
| 57 | 178N | $HCF_2CF_2OCH_2$ | H | O | $C_6H_5O$ | H | H | H | H | CN | H |
| 57 | 179N | $HCF_2CF_2OCH_2$ | H | O | $C_6H_5O$ | H | H | H | CN | H | H |
| 57 | 180N | $HCF_2CF_2OCH_2$ | H | O | $C_6H_5O$ | H | H | H | $NO_2$ | H | H |
| 57 | 181N | $HCF_2CF_2OCH_2$ | H | O | $C_6H_5O$ | H | H | H | H | $NO_2$ | H |
| 57 | 182N | $HCF_2CF_2OCH_2$ | H | O | $C_6H_5O$ | H | H | H | H | $SO_2CH_3$ | H |
| 57 | 183N | $HCF_2CF_2OCH_2$ | H | O | $C_6H_5O$ | H | H | H | H | 2-$NO_2$-4-Cl—$C_6H_3O$ | H |
| 57 | 184N | $HCF_2CF_2OCH_2$ | H | O | $C_6H_5O$ | H | H | H | 4-Cl—$C_6H_4O$ | H | H |
| 57 | 185N | $HCF_2CF_2OCH_2$ | H | O | $C_6H_5O$ | H | H | H | 3,4-Cl—$C_6H_3O$ | H | H |
| 57 | 186N | $HCF_2CF_2OCH_2$ | H | O | $C_6H_5O$ | H | H | H | 3-$CF_3$—$C_6H_3O$ | H | H |
| 57 | 187N | $HCF_2CF_2OCH_2$ | H | O | $C_6H_5O$ | H | H | H | 3,5-Cl—$C_6H_3O$ | H | H |
| 57 | 188N | $HCF_2CF_2OCH_2$ | H | O | $C_6H_5O$ | H | H | H | H | $CH_3O$ | H |
| 57 | 189N | $HCF_2CF_2OCH_2$ | H | O | $C_6H_5O$ | H | H | H | H | $CO_2CH_3$ | H |
| 57 | 190N | $HCF_2CF_2OCH_2$ | H | O | $C_6H_5O$ | H | H | H | 3-$CH_3O$ $C_6H_5O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

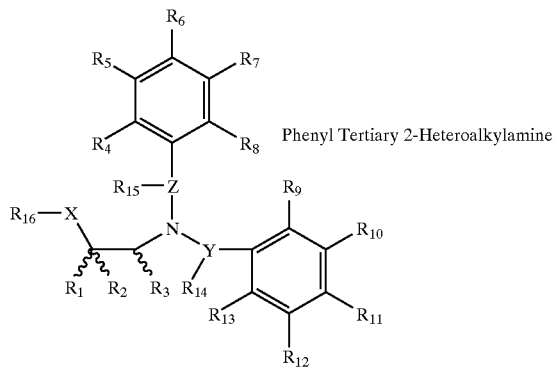

Phenyl Tertiary 2-Heteroalkylamine

Inhibitor Number
Column 1 + Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 57 | 191N | $HCF_2CF_2OCH_2$ | H | O | $C_6H_5O$ | H | H | H | 4-$CH_3O$ $C_6H_5O$ | H | H |
| 57 | 193N | $HCF_2CF_2OCH_2$ | H | O | $C_6H_5O$ | H | H | H | $CO_2CH_3$ | H | H |
| 57 | 194N | $HCF_2CF_2OCH_2$ | H | O | CN | H | H | H | $OCF_3$ | H | H |
| 57 | 195N | $HCF_2CF_2OCH_2$ | H | O | $NO_2$ | H | H | H | $OCF_3$ | H | H |
| 57 | 196N | $HCF_2CF_2OCH_2$ | H | O | H | CN | H | H | $OCF_3$ | H | H |
| 57 | 197N | $HCF_2CF_2OCH_2$ | H | O | H | $NO_2$ | H | H | $OCF_3$ | H | H |
| 57 | 198N | $HCF_2CF_2OCH_2$ | H | O | $SO_2CH_3$ | H | H | H | $OCF_3$ | H | H |
| 57 | 199N | $HCF_2CF_2OCH_2$ | H | O | H | $SO_2CH_3$ | H | H | $OCF_3$ | H | H |
| 57 | 200N | $HCF_2CF_2OCH_2$ | H | O | H | 4-F—$C_6H_5$ $SO_2$ | H | H | $OCF_3$ | H | H |
| 57 | 201N | $HCF_2CF_2OCH_2$ | H | O | $SO_2N(CH_3)_2$ | H | H | H | $OCF_3$ | H | H |
| 57 | 202N | $HCF_2CF_2OCH_2$ | H | O | H | $SO_2N(CH_3)_2$ | H | H | $OCF_3$ | H | H |
| 57 | 203N | $HCF_2CF_2OCH_2$ | H | O | H | $CONH_2$ | H | H | $OCF_3$ | H | H |
| 57 | 204N | $HCF_2CF_2OCH_2$ | H | O | H | CONH—$C_6H_5$ | H | H | $OCF_3$ | H | H |
| 57 | 205N | $HCF_2CF_2OCH_2$ | H | O | H | $CO_2CH_3$ | H | H | $OCF_3$ | H | H |
| 57 | 206N | $HCF_2CF_2OCH_2$ | H | O | H | $CO_2C_4H_9$ | H | H | $OCF_3$ | H | H |
| 57 | 207N | $HCF_2CF_2OCH_2$ | H | O | H | 4-Cl—$C_6H_5$ | H | H | $C_6H_5O$ | H | H |
| 57 | 208N | $HCF_2CF_2OCH_2$ | H | O | H | 4-$CF_3O$—$C_6H_5$ | H | H | $CF_3O$ | H | H |
| 57 | 209N | $HCF_2CF_2OCH_2$ | H | O | 4-F—$C_6H_4O$ | H | H | H | $CF_3O$ | H | H |
| 57 | 210N | $HCF_2CF_2OCH_2$ | H | O | $C_6F_5O$ | H | H | H | $CF_3O$ | H | H |

TABLE 8-continued

Structure of Substituted Phenyltertiary-2-Heteroalkylamines (Y = CH; Z is covalent bond; there is no $R_{15}$ substituent; $R_3$, $R_4$, $R_8$, $R_9$, $R_{13}$, $R_{14}$, and $R_{16}$ all equal H unless indicated below).

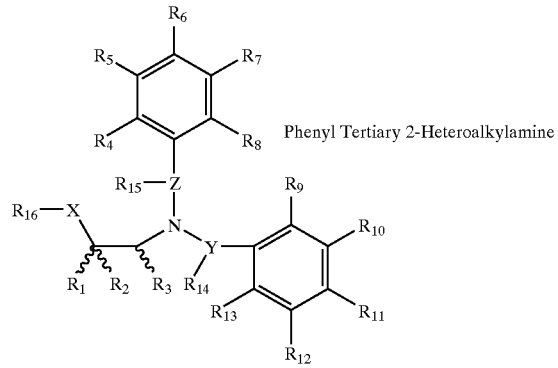

Phenyl Tertiary 2-Heteroalkylamine

Inhibitor Number
Column 1 + Column 2

| Reagent | Reagent | $R_1$ | $R_2$ | X | $R_5$ | $R_6$ | $R_7$ | $R_{14}$ | $R_{10}$ | $R_{11}$ | $R_{12}$ |
|---|---|---|---|---|---|---|---|---|---|---|---|
| 57 | 211N | $HCF_2CF_2OCH_2$ | H | O | H | 4-F—$C_6H_5$ | H | H | $CF_3O$ | H | H |
| 57 | 212N | $HCF_2CF_2OCH_2$ | H | O | H | 4-CN—$C_6H_5$ | H | H | $CF_3O$ | H | H |
| 57 | 213N | $HCF_2CF_2OCH_2$ | H | O | H | 4-$C_6H_5$—$C_6H_5$ | H | H | $CF_3O$ | H | H |
| 57 | 214N | $HCF_2CF_2OCH_2$ | H | O | $C_6H_5O$ | H | H | $CH_3$ | $CF_3O$ | H | H |
| 57 | 215N | $HCF_2CF_2OCH_2$ | H | O | $C_6H_5O$ | H | H | $CH_3$ | $NO_2$ | H | H |
| 57 | 216N | $HCF_2CF_2OCH_2$ | H | O | $C_6H_5O$ | H | H | $CH_3$ | H | CN | H |
| 57 | 217N | $HCF_2CF_2OCH_2$ | H | O | $C_6H_5O$ | H | H | 3-$CF_3$ $C_6H_5$ | $CF_3$ | H | H |
| 57 | 218N | $HCF_2CF_2OCH_2$ | H | O | $C_6H_5O$ | H | H | $C_6H_5$ | H | $C_6H_5$ | H |
| 57 | 219N | $HCF_2CF_2OCH_2$ | H | O | $C_6H_5O$ | H | H | $C_6H_5$ | $CF_3$ | H | H |
| 57 | 220N | $HCF_2CF_2OCH_2$ | H | O | $C_6H_5O$ | H | H | $CH_3$ | F | H | H |
| 57 | 221N | $HCF_2CF_2OCH_2$ | H | O | $C_6H_5O$ | H | H | $CF_3$ | H | H | H |
| 57 | 222N | $HCF_2CF_2OCH_2$ | H | O | bond to —O— of $R_6$ aryl group | 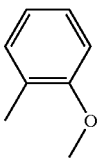 | H | H | $CF_3O$ | H | H |
| 57 | 223N | $HCF_2CF_2OCH_2$ | H | O | to $CH_2$ of $R_6$ aryl group | 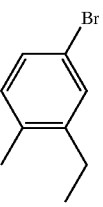 | H | H | $CF_3O$ | H | H |

TABLE 9

Structure of Substituted Polycyclictertiary-2-Heteroalkylamines (Substituents are as defined below and for Reagents 93N, 94N, and 95N).

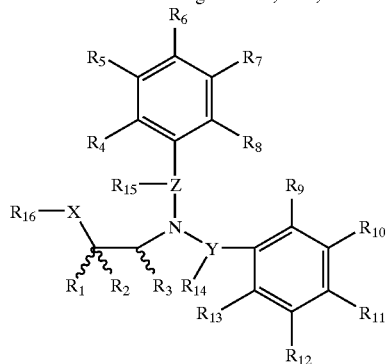

Inhibitor Number
Column 1 and
Column 2

| Reagent | Reagent | $R_1$ | $R_2$ | $R_3$ | $R_{16}$ | X |
|---|---|---|---|---|---|---|
| 93N | 1 | $CF_3$ | H | H | nothing | O |
| 93N | 2 | $CCl_3$ | H | H | nothing | O |
| 93N | 3 | $CF_3$ | $CH_3$ | H | nothing | O |
| 93N | 4 | $CF_3CF_2$ | H | H | nothing | O |
| 93N | 5 | $CF_3CF_2CF_2$ | H | H | nothing | O |
| 93N | 6 | $CF_3OCF_2CF_2$ | H | H | nothing | O |
| 93N | 7 | $CF_3CH_2$ | H | H | nothing | O |
| 93N | 8 | $CF_3$ | $CHF_2$ | H | nothing | O |
| 93N | 9 | $CF_3$ | H | $CF_3$ | nothing | O |
| 93N | 10 | $CF_3$ | $CF_3$ | H | nothing | O |
| 93N | 11 | $CF_3$ | $C_6H_5$ | H | nothing | O |
| 93N | 12 | $CCl_3$ | $C_6H_5$ | H | nothing | O |
| 93N | 13 | $CCl_3$ | Cyclopropyl | H | nothing | O |
| 93N | 14 | $CCl_3$ | $CH_3$ | H | nothing | O |
| 93N | 15 | $CCl_3$ | $(CH_3)_2CH$ | H | nothing | O |
| 93N | 16 | $CHCl_2$ | H | H | nothing | O |
| 93N | 17 | $CHCl_2$ | Cl | H | nothing | O |
| 93N | 18 | $CF_3$ | H | $CH_3$ | nothing | O |
| 93N | 19 | $CF_3$ | $CF_3$ | H | H | N |
| 93N | 20 | $CF_3$ | H | H | H | N |
| 93N | 21 | $CF_3$ | H | H | Benzyl | N |
| 93N | 22 | $CF_3$ | H | H | $CH_3O$ | N |
| 93N | 23 | $CF_3$ | H | H | $CH_3$ | N |
| 93N | 24 | $CF_3$ | H | H | Benzyloxy | N |
| 93N | 25 | $CF_3$ | H | H | nothing | S |
| 93N | 26 | $CF_3CF_2$ | H | H | nothing | S |
| 93N | 27 | $CCl_3CH_2$ | H | H | nothing | O |
| 93N | 28 | $CBr_3CH_2$ | H | H | nothing | O |
| 93N | 29 | $CHBr_2CH_2$ | H | H | nothing | O |
| 93N | 30 | $CBrCl_2$ | H | H | nothing | O |
| 93N | 31 | $CClF_2$ | H | H | nothing | O |
| 93N | 32 | $CCl_2F$ | H | H | nothing | O |
| 93N | 33 | $CCl_3CCl_2$ | H | H | nothing | O |
| 93N | 34 | $CH_3$ | H | H | nothing | O |
| 93N | 35 | $CH_3$ | $CH_3$ | H | nothing | O |
| 93N | 36 | $CH_3CH_2$ | H | H | nothing | O |
| 93N | 37 | $CH_3$=CH | H | H | nothing | O |
| 93N | 38 | $CH_3CH_2CH_2$ | H | H | nothing | O |
| 93N | 39 | $CH_2$=$CHCH_2CH_2$ | H | H | nothing | O |
| 93N | 40 | $CH_3(CH_2)_4CH_2$ | H | H | nothing | O |
| 93N | 41 | $CH_2$=$CH(CH_2)_3CH_2$ | H | H | nothing | O |
| 93N | 42 | $HOCH_2$ | H | H | nothing | O |
| 93N | 43 | $FCH_2$ | H | H | nothing | O |
| 93N | 44 | $(CH_3)_3COCH_2$ | H | H | nothing | O |
| 93N | 45 | $R_1 + R_2 = (CH_2)_5$ | | H | nothing | O |
| 93N | 46 | $CF_3$ | $R_2 + R_3 = (CH_2)_3$ | | nothing | O |
| 93N | 47 | $CF_3$ | $R_2 + R_3 = (CH_2)_4$ | | nothing | O |
| 93N | 48 | $CHF_2$ | $R_2 + R_3 = (CH_2)_4$ | | nothing | O |
| 93N | 49 | H | $R_2 + R_3 = (CF_3)CH(CH_2)_3$ | | nothing | O |
| 93N | 50 | H | $R_2 + R_3 = (CF_3)CH(CH_2)_2$ | | nothing | O |
| 93N | 51 | H | $R_2 + R_3 = CH_2(CF_3)CHCH_2$ | | nothing | O |
| 93N | 52 | $R_1 + R_2 = (CH_2)_6$ | | H | nothing | O |

TABLE 9-continued

Structure of Substituted Polycyclictertiary-2-Heteroalkylamines (Substituents are as defined below and for Reagents 93N, 94N, and 95N).

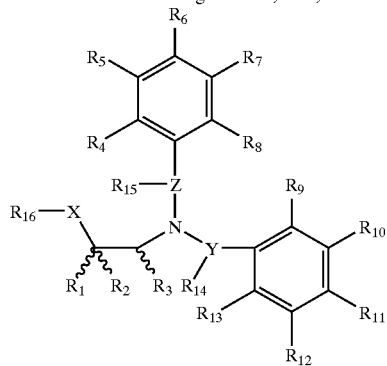

Inhibitor Number
Column 1 and
Column 2

| Reagent | Reagent | $R_1$ | $R_2$ | $R_3$ | $R_{16}$ | X |
|---|---|---|---|---|---|---|
| 93N | 53 | $CH_3CH_2O_2C$ | H | H | nothing | O |
| 93N | 54 | $CH_3CH_2CH_2$ | H | H | nothing | O |
| 93N | 55 | $CH_3OCH_2$ | H | H | nothing | O |
| 93N | 56 | $CBrF_2CClFCH_2$ | H | H | nothing | O |
| 93N | 57 | $HCF_2CF_2OCH_2$ | H | H | nothing | O |
| 93N | 58 | $[(CH_3CH_2O)]_2POCH_2$ | H | H | nothing | O |
| 93N | 59 | H | $R_2 + R_3 = (CH_2)_2SO_2$ | | nothing | O |
| 93N | 60 | $Cl^-(CH_3)_3N^{\oplus}CH_2$ | H | H | nothing | O |
| 93N | 61 | N-piperidinyl-$CH_2$ | H | H | nothing | O |
| 93N | 62 | N-phthalimido-$CH_2$ | H | H | nothing | O |
| 93N | 63 | $C_6H_5$ | H | H | nothing | O |
| 93N | 64 | $C_6H_5$ | H | $CH_3$ | nothing | O |
| 93N | 65 | $C_6F_5$ | H | H | nothing | O |
| 93N | 66 | $C_6F_5$ | $CH_3$ | H | nothing | O |
| 93N | 67 | $C_6F_5$ | $CClH_2$ | H | nothing | O |
| 93N | 68 | 2-$CH_3C_6H_4$ | H | H | nothing | O |
| 93N | 69 | 3-$CH_3C_6H_4$ | H | H | nothing | O |
| 93N | 70 | 4-$CH_3C_6H_4$ | H | H | nothing | O |
| 93N | 71 | 2-$BrC_6H_4$ | H | H | nothing | O |
| 93N | 72 | 4-$BrC_6H_4$ | H | H | nothing | O |
| 93N | 73 | 2-$ClC_6H_4$ | H | H | nothing | O |
| 93N | 74 | 3-$ClC_6H_4$ | H | H | nothing | O |
| 93N | 75 | 4-$ClC_6H_4$ | H | H | nothing | O |
| 93N | 76 | 2-$CH_3OC_6H_4$ | H | H | nothing | O |
| 93N | 77 | 3-$CH_3OC_6H_4$ | H | H | nothing | O |
| 93N | 78 | 4-$CH_3OC_6H_4$ | H | H | nothing | O |
| 93N | 79 | 3-$CF_3C_6H_4$ | H | H | nothing | O |
| 93N | 80 | $C_6H_5CH_2$ | H | H | nothing | O |
| 93N | 81 | 4F-$C_6H_4$ | H | H | nothing | O |
| 93N | 82 | 4F-$C_6H_4$ | H | 4F-$C_6H_4$ | nothing | O |
| 93N | 83 | 2-$CH_3O$-4-$CH_3OC_6H_3$ | H | H | nothing | O |
| 93N | 84 | 3,4-$OCH_2O$—$C_6H_3$ | H | H | nothing | O |
| 93N | 85 | 3-Cl-4-Cl—$C_6H_3$ | H | H | nothing | O |
| 93N | 86 | 3-Cl-5-Cl—$C_6H_3$ | H | H | nothing | O |
| 93N | 87 | $C_6H_5OCH_2$ | H | H | nothing | O |
| 93N | 88 | 4Cl—$C_6H_4OCH_2$ | H | H | nothing | O |
| 93N | 89 | $CH_3OC_6H_4OCH_2$ | H | H | nothing | O |
| 93N | 90 | $C_6H_5$ | H | $CO_2C_2H_5$ | nothing | O |
| 93N | 91 | 2-Pyridyl | H | H | nothing | O |
| 94N | 1 | $CF_3$ | H | H | nothing | O |
| 94N | 2 | $CCl_3$ | H | H | nothing | O |
| 94N | 3 | $CF_3$ | $CH_3$ | H | nothing | O |
| 94N | 4 | $CF_3CF_2$ | H | H | nothing | O |
| 94N | 5 | $CF_3CF_2CF_2$ | H | H | nothing | O |
| 94N | 6 | $CF_3OCF_2CF_2$ | H | H | nothing | O |
| 94N | 7 | $CF_3CH_2$ | H | H | nothing | O |
| 94N | 8 | $CF_3$ | $CHF_2$ | H | nothing | O |
| 94N | 9 | $CF_3$ | H | $CF_3$ | nothing | O |
| 94N | 10 | $CF_3$ | $CF_3$ | H | nothing | O |
| 94N | 11 | $CF_3$ | $C_6H_5$ | H | nothing | O |
| 94N | 12 | $CCl_3$ | $C_6H_5$ | H | nothing | O |
| 94N | 13 | $CCl_3$ | Cyclopropyl | H | nothing | O |

TABLE 9-continued

Structure of Substituted Polycyclictertiary-2-Heteroalkylamines (Substituents are as defined below and for Reagents 93N, 94N, and 95N).

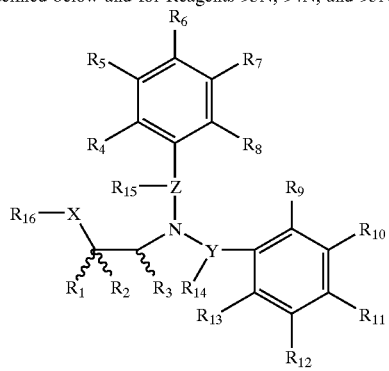

Inhibitor Number
Column 1 and
Column 2

| Reagent | Reagent | $R_1$ | $R_2$ | $R_3$ | $R_{16}$ | X |
|---|---|---|---|---|---|---|
| 94N | 14 | $CCl_3$ | $CH_3$ | H | nothing | O |
| 94N | 15 | $CCl_3$ | $(CH_3)_2CH$ | H | nothing | O |
| 94N | 16 | $CHCl_2$ | H | H | nothing | O |
| 94N | 17 | $CHCl_2$ | Cl | H | nothing | O |
| 94N | 18 | $CF_3$ | H | $CH_3$ | nothing | O |
| 94N | 19 | $CF_3$ | $CF_3$ | H | H | N |
| 94N | 20 | $CF_3$ | H | H | H | N |
| 94N | 21 | $CF_3$ | H | H | Benzyl | N |
| 94N | 22 | $CF_3$ | H | H | $CH_3O$ | N |
| 94N | 23 | $CF_3$ | H | H | $CH_3$ | N |
| 94N | 24 | $CF_3$ | H | H | Benzyloxy | N |
| 94N | 25 | $CF_3$ | H | H | nothing | S |
| 94N | 26 | $CF_3CF_2$ | H | H | nothing | S |
| 94N | 27 | $CCl_3CH_2$ | H | H | nothing | O |
| 94N | 28 | $CBr_3CH_2$ | H | H | nothing | O |
| 94N | 29 | $CHBr_2CH_2$ | H | H | nothing | O |
| 94N | 30 | $CBrCl_2$ | H | H | nothing | O |
| 94N | 31 | $CClF_2$ | H | H | nothing | O |
| 94N | 32 | $CCl_2F$ | H | H | nothing | O |
| 94N | 33 | $CCl_3CCl_2$ | H | H | nothing | O |
| 94N | 34 | $CH_3$ | H | H | nothing | O |
| 94N | 35 | $CH_3$ | $CH_3$ | H | nothing | O |
| 94N | 36 | $CH_3CH_2$ | H | H | nothing | O |
| 94N | 37 | $CH_2=CH$ | H | H | nothing | O |
| 94N | 38 | $CH_3CH_2CH_2$ | H | H | nothing | O |
| 94N | 39 | $CH_2=CHCH_2CH_2$ | H | H | nothing | O |
| 94N | 40 | $CH_3(CH_2)_4CH_2$ | H | H | nothing | O |
| 94N | 41 | $CH_2=CH(CH_2)_3CH_2$ | H | H | nothing | O |
| 94N | 42 | $HOCH_2$ | H | H | nothing | O |
| 94N | 43 | $FCH_2$ | H | H | nothing | O |
| 94N | 44 | $(CH_3)_3COCH_2$ | H | H | nothing | O |
| 94N | 45 | $R_1 + R_2 = (CH_2)_5$ | | H | nothing | O |
| 94N | 46 | $CF_3$ | $R_2 + R_3 = (CH_2)_3$ | | nothing | O |
| 94N | 47 | $CF_3$ | $R_2 + R_3 = (CH_2)_4$ | | nothing | O |
| 94N | 48 | $CHF_2$ | $R_2 + R_3 = (CH_2)_4$ | | nothing | O |
| 94N | 49 | H | $R_2 + R_3 = (CF_3)CH(CH_2)_3$ | | nothing | O |
| 94N | 50 | H | $R_2 + R_3 = (CF_3)CH(CH_2)_2$ | | nothing | O |
| 94N | 51 | H | $R_2 + R_3 = CH_2(CF_3)CHCH_2$ | | nothing | O |
| 94N | 52 | $R_1 + R_2 = (CH_2)_6$ | | H | nothing | O |
| 94N | 53 | $CH_3CH_2O_2C$ | H | H | nothing | O |
| 94N | 54 | $CH_3CH_2CH_2$ | H | H | nothing | O |
| 94N | 55 | $CH_3OCH_2$ | H | H | nothing | O |
| 94N | 56 | $CBrF_2CClFCH_2$ | H | H | nothing | O |
| 94N | 57 | $HCF_2CF_2OCH_2$ | H | H | nothing | O |
| 94N | 58 | $[(CH_3CH_2O)]_2POCH_2$ | H | H | nothing | O |
| 94N | 59 | H | $R_2 + R_3 = (CH_2)_2SO_2$ | | O | |
| 94N | 60 | $Cl^-(CH_3)_3N^{\oplus}CH_2$ | H | H | nothing | O |
| 94N | 61 | N-piperidinyl-$CH_2$ | H | H | nothing | O |
| 94N | 62 | N-phthalimido-$CH_2$ | H | H | nothing | O |
| 94N | 63 | $C_6H_5$ | H | H | nothing | O |
| 94N | 64 | $C_6H_5$ | H | $CH_3$ | nothing | O |
| 94N | 65 | $C_6F_5$ | H | H | nothing | O |

TABLE 9-continued

Structure of Substituted Polycyclictertiary-2-Heteroalkylamines (Substituents are as defined below and for Reagents 93N, 94N, and 95N).

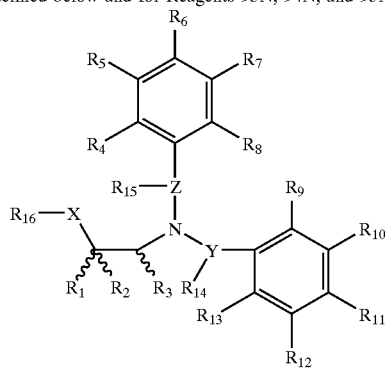

Inhibitor Number
Column 1 and
Column 2

| Reagent | Reagent | $R_1$ | $R_2$ | $R_3$ | $R_{16}$ | X |
|---|---|---|---|---|---|---|
| 94N | 66 | $C_6F_5$ | $CH_3$ | H | nothing | O |
| 94N | 67 | $C_6F_5$ | $CClH_2$ | H | nothing | O |
| 94N | 68 | 2-$CH_3C_6H_4$ | H | H | nothing | O |
| 94N | 69 | 3-$CH_3C_6H_4$ | H | H | nothing | O |
| 94N | 70 | 4-$CH_3C_6H_4$ | H | H | nothing | O |
| 94N | 71 | 2-$BrC_6H_4$ | H | H | nothing | O |
| 94N | 72 | 4-$BrC_6H_4$ | H | H | nothing | O |
| 94N | 73 | 2-$ClC_6H_4$ | H | H | nothing | O |
| 94N | 74 | 3-$ClC_6H_4$ | H | H | nothing | O |
| 94N | 75 | 4-$ClC_6H_4$ | H | H | nothing | O |
| 94N | 76 | 2-$CH_3OC_6H_4$ | H | H | nothing | O |
| 94N | 77 | 3-$CH_3OC_6H_4$ | H | H | nothing | O |
| 94N | 78 | 4-$CH_3OC_6H_4$ | H | H | nothing | O |
| 94N | 79 | 3-$CF_3C_6H_4$ | H | H | nothing | O |
| 94N | 80 | $C_6H_5CH_2$ | H | H | nothing | O |
| 94N | 81 | 4F—$C_6H_4$ | H | H | nothing | O |
| 94N | 82 | 4F—$C_6H_4$ | H | 4F—$C_6H_4$ | nothing | O |
| 94N | 83 | 2-$CH_3O$-4-$CH_3OC_6H_3$ | H | H | nothing | O |
| 94N | 84 | 3,4-$OCH_2O$-$C_6H_3$ | H | H | nothing | O |
| 94N | 85 | 3-Cl-4-Cl—$C_6H_3$ | H | H | nothing | O |
| 94N | 86 | 3-Cl-5-Cl-$C_6H_3$ | H | H | nothing | O |
| 94N | 87 | $C_6H_5OCH_2$ | H | H | nothing | O |
| 94N | 88 | 4Cl—$C_6H_4OCH_2$ | H | H | nothing | O |
| 94N | 89 | $CH_3OC_6H_4OCH_2$ | H | H | nothing | O |
| 94N | 90 | $C_6H_5$ | H | $CO_2C_2H_5$ | nothing | O |
| 94N | 91 | 2-Pyridyl | H | H | nothing | O |
| 95N | 1 | $CF_3$ | H | H | nothing | O |
| 95N | 2 | $CCl_3$ | H | H | nothing | O |
| 95N | 3 | $CF_3$ | $CH_3$ | H | nothing | O |
| 95N | 4 | $CF_3CF_2$ | H | H | nothing | O |
| 95N | 5 | $CF_3CF_2CF_2$ | H | H | nothing | O |
| 95N | 6 | $CF_3OCF_2CF_2$ | H | H | nothing | O |
| 95N | 7 | $CF_3CH_2$ | H | H | nothing | O |
| 95N | 8 | $CF_3$ | $CHF_2$ | H | nothing | O |
| 95N | 9 | $CF_3$ | H | $CF_3$ | nothing | O |
| 95N | 10 | $CF_3$ | $CF_3$ | H | nothing | O |
| 95N | 11 | $CF_3$ | $C_6H_5$ | H | nothing | O |
| 95N | 12 | $CCl_3$ | $C_6H_5$ | H | nothing | O |
| 95N | 13 | $CCl_3$ | Cyclopropyl | H | nothing | O |
| 95N | 14 | $CCl_3$ | $CH_3$ | H | nothing | O |
| 95N | 15 | $CCl_3$ | $(CH_3)_2CH$ | H | nothing | O |
| 95N | 16 | $CHCl_2$ | H | H | nothing | O |
| 95N | 17 | $CHCl_2$ | Cl | H | nothing | O |
| 95N | 18 | $CF_3$ | H | $CH_3$ | nothing | O |
| 95N | 19 | $CF_3$ | $CF_3$ | H | H | N |
| 95N | 20 | $CF_3$ | H | H | H | N |
| 95N | 21 | $CF_3$ | H | H | Benzyl | N |
| 95N | 22 | $CF_3$ | H | H | $CH_3O$ | N |
| 95N | 23 | $CF_3$ | H | H | $CH_3$ | N |
| 95N | 24 | $CF_3$ | H | H | Benzyloxy | N |
| 95N | 25 | $CF_3$ | H | H | nothing | S |
| 95N | 26 | $CF_3CF_2$ | H | H | nothing | S |

TABLE 9-continued

Structure of Substituted Polycyclictertiary-2-Heteroalkylamines (Substituents are as defined below and for Reagents 93N, 94N, and 95N).

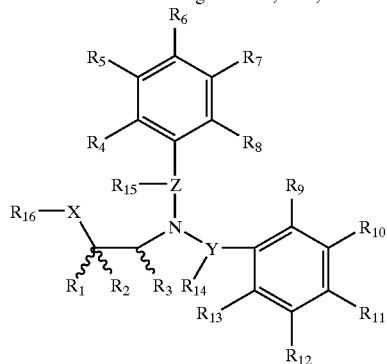

Inhibitor Number
Column 1 and
Column 2

| Reagent | Reagent | $R_1$ | $R_2$ | $R_3$ | $R_{16}$ | X |
|---|---|---|---|---|---|---|
| 95N | 27 | $CCl_3CH_2$ | H | H | nothing | O |
| 95N | 28 | $CBr_3CH_2$ | H | H | nothing | O |
| 95N | 29 | $CHBr_2CH_2$ | H | H | nothing | O |
| 95N | 30 | $CBrCl_2$ | H | H | nothing | O |
| 95N | 31 | $CClF_2$ | H | H | nothing | O |
| 95N | 32 | $CCl_2F$ | H | H | nothing | O |
| 95N | 33 | $CCl_3CCl_2$ | H | H | nothing | O |
| 95N | 34 | $CH_3$ | H | H | nothing | O |
| 95N | 35 | $CH_3$ | $CH_3$ | H | nothing | O |
| 95N | 36 | $CH_3CH_2$ | H | H | nothing | O |
| 95N | 37 | $CH_2=CH$ | H | H | nothing | O |
| 95N | 38 | $CH_3CH_2CH_2$ | H | H | nothing | O |
| 95N | 39 | $CH_2=CHCH_2CH_2$ | H | H | nothing | O |
| 95N | 40 | $CH_3(CH_2)_4CH_2$ | H | H | nothing | O |
| 95N | 41 | $CH_2=CH(CH_2)_3CH_2$ | H | H | nothing | O |
| 95N | 42 | $HOCH_2$ | H | H | nothing | O |
| 95N | 43 | $FCH_2$ | H | H | nothing | O |
| 95N | 44 | $(CH_3)_3COCH_2$ | H | H | nothing | O |
| 95N | 45 | $R_1 + R_2 = (CH_2)_5$ | | H | nothing | O |
| 95N | 46 | $CF_3$ | $R_2 + R_3 = (CH_2)_3$ | | nothing | O |
| 95N | 47 | $CF_3$ | $R_2 + R_3 = (CH_2)_4$ | | nothing | O |
| 95N | 48 | $CHF_2$ | $R_2 + R_3 = (CH_2)_4$ | | nothing | O |
| 95N | 49 | H | $R_2 + R_3 = (CF_3)CH(CH_2)_3$ | | nothing | O |
| 95N | 50 | H | $R_2 + R_3 = (CF_3)CH(CH_2)_2$ | | nothing | O |
| 95N | 51 | H | $R_2 + R_3 = {}_{CH2}(CF_3)CHCH_2$ | | nothing | O |
| 95N | 52 | $R_1 + R_2 = (CH_2)_6$ | | H | nothing | O |
| 95N | 53 | $CH_3CH_2O_2C$ | H | H | nothing | O |
| 95N | 54 | $CH_3CH_2CH_2$ | H | H | nothing | O |
| 95N | 55 | $CH_3OCH_2$ | H | H | nothing | O |
| 95N | 56 | $CBrF_2CClFCH_2$ | H | H | nothing | O |
| 95N | 57 | $HCF_2CF_2OCH_2$ | H | H | nothing | O |
| 95N | 58 | $[(CH_3CH_2O)_2POCH_2$ | H | H | nothing | O |
| 95N | 59 | H | $R_2 + R_3 = (CH_2)_2SO_2$ | | O | |
| 95N | 60 | $Cl^-(CH_3)_3N^{\oplus}CH_2$ | H | H | nothing | O |
| 95N | 61 | N-piperidinyl-$CH_2$ | H | H | nothing | O |
| 95N | 62 | N-phthalimido-$CH_2$ | H | H | nothing | O |
| 95N | 63 | $C_6H_5$ | H | H | nothing | O |
| 95N | 64 | $C_6H_5$ | H | $CH_3$ | nothing | O |
| 95N | 65 | $C_6F_5$ | H | H | nothing | O |
| 95N | 66 | $C_6F_5$ | $CH_3$ | H | nothing | O |
| 95N | 67 | $C_6F_5$ | $CClH_2$ | H | nothing | O |
| 95N | 68 | 2-$CH_3C_6H_4$ | H | H | nothing | O |
| 95N | 69 | 3-$CH_3C_6H_4$ | H | H | nothing | O |
| 95N | 70 | 4-$CH_3C_6H_4$ | H | H | nothing | O |
| 95N | 71 | 2-$BrC_6H_4$ | H | H | nothing | O |
| 95N | 72 | 4-$BrC_6H_4$ | H | H | nothing | O |
| 95N | 73 | 2-$ClC_6H_4$ | H | H | nothing | O |
| 95N | 74 | 3-$ClC_6H_4$ | H | H | nothing | O |
| 95N | 75 | 4-$ClC_6H_4$ | H | H | nothing | O |
| 95N | 76 | 2-$CH_3OC_6H_4$ | H | H | nothing | O |
| 95N | 77 | 3-$CH_3OC_6H_4$ | H | H | nothing | O |
| 95N | 78 | 4-$CH_3OC_6H_4$ | H | H | nothing | O |

TABLE 9-continued

Structure of Substituted Polycyclictertiary-2-Heteroalkylamines (Substituents are as defined below and for Reagents 93N, 94N, and 95N).

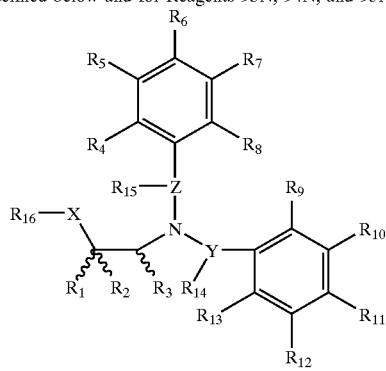

Inhibitor Number Column 1 and Column 2

| Reagent | Reagent | $R_1$ | $R_2$ | $R_3$ | $R_{16}$ | X |
|---|---|---|---|---|---|---|
| 95N | 79 | 3-$CF_3C_6H_4$ | H | H | nothing | O |
| 95N | 80 | $C_6H_5CH_2$ | H | H | nothing | O |
| 95N | 81 | 4F—$C_6H_4$ | H | H | nothing | O |
| 95N | 82 | 4F—$C_6H_4$ | H | 4F—$C_6H_4$ | nothing | O |
| 95N | 83 | 2-$CH_3$O-4-$CH_3OC_6H_3$ | H | H | nothing | O |
| 95N | 84 | 3,4-$OCH_2O$—$C_6H_3$ | H | H | nothing | O |
| 95N | 85 | 3-Cl-4-Cl—$C_6H_3$ | H | H | nothing | O |
| 95N | 86 | 3-Cl-5-Cl—$C_6H_3$ | H | H | nothing | O |
| 95N | 87 | $C_6H_5OCH_2$ | H | H | nothing | O |
| 95N | 88 | 4Cl—$C_6H_4OCH_2$ | H | H | nothing | O |
| 95N | 89 | $CH_3OC_6H_4OCH_2$ | H | H | nothing | O |
| 95N | 90 | $C_6H_5$ | H | $CO_2C_2H_5$ | nothing | O |
| 95N | 91 | 2-Pyridyl | H | H | nothing | O |

TABLE 10

$IC_{50}$ Values for CETP Inhibitors. Values from the CEPT activity assay and from the whole serum CETP activity assay are given.

| Inhibitor Number | CEPT Activity Assay $IC_{50}$ ($\mu M$) | Serum Activity Assay $IC_{50}$ ($\mu M$) |
|---|---|---|
| 1-1N | 0.15 | 6.9 |
| 1-2N | 1.2 | 36 |
| 1-5N | 0.8 | 45 |
| 1-6N | 1.5 | 47 |
| 1-1BN | 1.5 | 55 |
| 1-7N | 1.5 | 60 |
| 1-3N | 2.0 | 65 |
| 1-9N | 3.0 | 100 |
| 1-57N | 3.5 | 120 |
| 1-4N | 4.0 | 110 |
| 1-8N | 4.0 | 120 |
| 1-10N | 4.0 | >200 |
| 1-59N | 5.5 | 120 |
| 1-2BN | 6.0 | >200 |
| 1-58N | 7.0 | 100 |
| 1-60N | 7.0 | 200 |
| 1-2DB | 7.0 | NT |
| 1-11N | 7.0 | NT |
| 1-3DB | 7.0 | NT |
| 1-154N | 8.0 | NT |
| 1-12N | 10.0 | NT |
| 1-13N | 10.0 | NT |
| 1-336N | 10.0 | NT |
| 1-14N | 10.0 | NT |
| 1-15N | 10.0 | NT |
| 1-4DB | 10.0 | NT |
| 1-19N | 12.0 | NT |
| 1-17N | 12.0 | NT |
| 1-18N | 12.0 | NT |
| 1-22N | 12.5 | NT |
| 1-20N | 14.2 | NT |
| 1-21N | 15.0 | NT |
| 1-61N | 15.0 | NT |
| 1-5DB | 15.0 | NT |
| 1-6DB | 15.0 | NT |
| 1-62N | 15.0 | NT |
| 1-10BN | 15.0 | NT |
| 1-4BN | 15.0 | NT |
| 1-63N | 15.0 | NT |
| 1-92N | 15.0 | NT |
| 1-64N | 15.0 | NT |
| 1-65N | 15.0 | NT |
| 1-25N | 15.0 | NT |
| 1-23N | 15.0 | NT |
| 1-14BN | 15.0 | NT |
| 1-337N | 15.0 | >200 |
| 1-24N | 15.0 | NT |
| 1-66N | 15.0 | NT |
| 1-26N | 15.7 | NT |
| 1-67N | 18.0 | NT |
| 1-8DB | 20.0 | NT |
| 1-28N | 20.0 | NT |

TABLE 10-continued

IC$_{50}$ Values for CETP Inhibitors. Values from the CEPT activity assay and from the whole serum CETP activity assay are given.

| Inhibitor Number | CEPT Activity Assay IC$_{50}$ ($\mu$M) | Serum Activity Assay IC$_{50}$ ($\mu$M) |
|---|---|---|
| 1-68N | 20.0 | NT |
| 1-69N | 20.0 | NT |
| 1-70N | 20.0 | NT |
| 1-27N | 20.0 | NT |
| 1-76N | 20.0 | NT |
|  | 20.020 |  |
| 1-5BN | 20.0 | NT |
| 1-16N | 20.7 | NT |
| 1-71N | 22.5 | NT |
| 1-20N | 37.5 | NT |
| 1-29N | 45.0 | NT |
| 1-72N | 50.0 | NT |
| 1-73N | 50.0 | NT |
| 1-13BN | 50.0 | NT |
| 1-30N | 60.0 | NT |
| 1-74N | 60.0 | NT |
| 1-31N | 60.0 | NT |
| 1-32N | 60.0 | NT |
| 1-33N | 60.0 | NT |
| 1-75N | 65.0 | NT |
| 1-76N | 70.0 | NT |
| 1-20N (Acetylated) | 70.0 | NT |
| 1-34N | 75.0 | NT |
| 41-4N | 80.0 | NT |
| 1-35N | 100 | NT |
| 1-88N | 100 | NT |
| 1-90N | 100 | NT |
| 1-3BN | 100 | NT |
| 1-12BN | 100 | NT |
| 1-78N | >100 | NT |
| 1-37N | >100 | NT |
| 1-79N | >100 | NT |
| 1-45N | >100 | NT |
| 1-41N | >100 | NT |
| 1-46N | >100 | NT |
| 1-80N | >100 | NT |
| 1-81N | >100 | NT |
| 1-47N | >100 | NT |
| 1-48N | >100 | NT |
| 1-49N | >100 | NT |
| 1-82N | >100 | NT |
| 1-50N | >100 | NT |
| 1-83N | >100 | NT |
| 1-9DB | >100 | NT |
| 1-10DB | >100 | NT |
| 1-11DB | >100 | NT |
| 1-12DB | >100 | NT |
| 1-13DB | >100 | NT |
| 1-14DB | >100 | NT |
| 1-16DB | >100 | NT |
| 1-17DB | >100 | NT |
| 1-19DB | >100 | NT |
| 1-21DB | >100 | NT |
| 1-22DB | >100 | NT |
| 1-23DB | >100 | NT |
| 1-24DB | >100 | NT |
| 1-25DB | >100 | NT |
| 1-86N | >100 | NT |
| 1-87N | >100 | NT |
| 1-51N | >100 | NT |
| 1-26DB | >100 | NT |
| 1-52N | >100 | NT |
| 1-54N | >100 | NT |
| 1-42N | >100 | NT |
| 1-43N | >100 | NT |
| 1-89N | >100 | NT |
| 1-55N | >100 | NT |
| 1-91N | >100 | NT |
| 1-38N | >100 | NT |
| 1-39N | >100 | NT |
| 1-36N | >100 | NT |
| 1-40N1 |  |  |
| 1-40N | >100 | NT |
| 1-11BN | >100 | NT |
| 1-44N | >100 | NT |
| 1-85N | >100 | NT |
| 1-53N | >100 | NT |
| 1-84N | >100 | NT |
| 1-6BN | >100 | NT |
| 1-7BN | >100 | NT |
| 1-8BN | >100 | NT |
| 1-1DB | >100 | NT |

TABLE 11

Structure of "Secondary Phenyl Amine" Reagents
(Y and Z each equal CH; $R_8$, $R_{13}$, $R_{14}$, and $R_{15}$ each equal H).

(XIII-A)

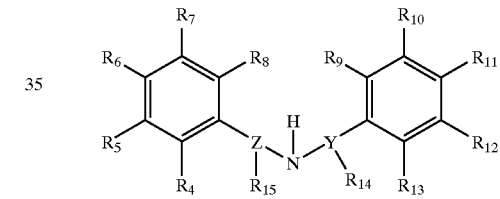

Secondary Phenyl Amine

| Reagent Number | $R_4$ | $R_5$ | $R_6$ | $R_7$ | $R_9$ | $R_{10}$ | $R_{11}$ | $R_{12}$ |
|---|---|---|---|---|---|---|---|---|
| 1DB | H | OCF$_3$ | H | H | H | OCF$_3$ | H | H |
| 2DB | H | Cl | H | H | H | H | CF$_3$ | H |
| 3DB | H | Br | H | H | H | OCF$_3$ | H | H |
| 4DB | H | Cl | H | H | H | OCF$_3$ | H | H |
| 5DB | H | Cl | H | H | H | CF$_3$ | H | H |
| 6DB | H | H | Cl | H | H | CF$_3$ | H | H |
| 7DB | H | F | H | H | H | OCF$_3$ | H | H |
| 8DB | H | H | Cl | H | H | H | CF$_3$ | H |
| 9DB | H | F | H | H | H | H | CF$_3$ | H |
| 10DB | H | H | F | H | H | H | CF$_3$ | H |
| 11DB | F | H | H | H | H | H | CF$_3$ | H |
| 12DB | H | Cl | H | H | CF$_3$ | H | H | H |
| 13DB | H | H | Cl | H | CF$_3$ | H | H | H |
| 14DB | Cl | H | H | H | CF$_3$ | H | H | H |
| 15DB | H | F | H | H | CH$_3$ | H | H | H |
| 16DB | H | H | F | H | H | H | CH$_3$ | H |
| 17DB | H | F | H | H | H | CH$_3$ | H | H |
| 18DB | F | H | H | H | CH$_3$ | H | H | H |
| 19DB | H | H | F | H | H | CH$_3$ | H | H |
| 20DB | F | H | H | H | H | H | CH$_3$ | H |
| 21DB | F | H | H | H | H | CF$_3$ | H | H |
| 22DB | Cl | H | H | H | H | CF$_3$ | H | H |
| 23DB | H | F | H | H | CF$_3$ | H | H | H |
| 24DB | H | H | F | H | CF$_3$ | H | H | H |
| 25DB | H | F | H | H | H | CF$_3$ | H | H |
| 26DB | H | H | F | H | H | CF$_3$ | H | H |
| 27DB | H | OCF$_3$ | H | H | H | H | OCF$_3$ | H |

TABLE 12

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

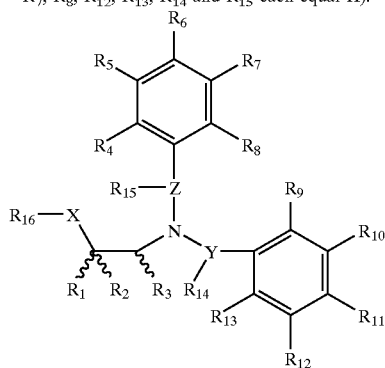

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 1 | 1DB | CF$_3$ | H | H | H | O | H | OCF$_3$ | H | H | OCF$_3$ | H |
| 1 | 2DB | CF$_3$ | H | H | H | O | H | Cl | H | H | H | CF$_3$ |
| 1 | 3DB | CF$_3$ | H | H | H | O | H | Br | H | H | OCF$_3$ | H |
| 1 | 4DB | CF$_3$ | H | H | H | O | H | Cl | H | H | OCF$_3$ | H |
| 1 | 5DB | CF$_3$ | H | H | H | O | H | Cl | H | H | CF$_3$ | H |
| 1 | 6DB | CF$_3$ | H | H | H | O | H | H | Cl | H | CF$_3$ | H |
| 1 | 7DB | CF$_3$ | H | H | H | O | H | F | H | H | OCF$_3$ | H |
| 1 | 8DB | CF$_3$ | H | H | H | O | H | H | Cl | H | H | CF$_3$ |
| 1 | 9DB | CF$_3$ | H | H | H | O | H | F | H | H | H | CF$_3$ |
| 1 | 10DB | CF$_3$ | H | H | H | O | H | H | F | H | H | CF$_3$ |
| 1 | 11DB | CF$_3$ | H | H | H | O | F | H | H | H | H | CF$_3$ |
| 1 | 12DB | CF$_3$ | H | H | H | O | H | Cl | H | CF$_3$ | H | H |
| 1 | 13DB | CF$_3$ | H | H | H | O | H | H | Cl | CF$_3$ | H | H |
| 1 | 14DB | CF$_3$ | H | H | H | O | Cl | H | H | CF$_3$ | H | H |
| 1 | 15DB | CF$_3$ | H | H | H | O | H | F | H | CH$_3$ | H | H |
| 1 | 16DB | CF$_3$ | H | H | H | O | H | H | F | H | H | CH$_3$ |
| 1 | 17DB | CF$_3$ | H | H | H | O | H | F | H | H | CH$_3$ | H |
| 1 | 18DB | CF$_3$ | H | H | H | O | F | H | H | CH$_3$ | H | H |
| 1 | 19DB | CF$_3$ | H | H | H | O | H | H | F | H | CH$_3$ | H |
| 1 | 20DB | CF$_3$ | H | H | H | O | F | H | H | H | H | CH$_3$ |
| 1 | 21DB | CF$_3$ | H | H | H | O | F | H | H | H | CF$_3$ | H |
| 1 | 22DB | CF$_3$ | H | H | H | O | Cl | H | H | H | CF$_3$ | H |
| 1 | 23DB | CF$_3$ | H | H | H | O | H | F | H | CF$_3$ | H | H |
| 1 | 24DB | CF$_3$ | H | H | H | O | H | H | F | CF$_3$ | H | H |
| 1 | 25DB | CF$_3$ | H | H | H | O | H | F | H | H | CF$_3$ | H |
| 1 | 26DB | CF$_3$ | H | H | H | O | H | H | F | H | CF$_3$ | H |
| 1 | 27DB | CF$_3$ | H | H | H | O | H | OCF$_3$ | H | H | H | OCF$_3$ |
| 2 | 1DB | CCl$_3$ | H | H | H | O | H | OCF$_3$ | H | H | OCF$_3$ | H |
| 2 | 2DB | CCl$_3$ | H | H | H | O | H | Cl | H | H | H | CF$_3$ |
| 2 | 3DB | CCl$_3$ | H | H | H | O | H | Br | H | H | OCF$_3$ | H |
| 2 | 4DB | CCl$_3$ | H | H | H | O | H | Cl | H | H | OCF$_3$ | H |
| 2 | 5DB | CCl$_3$ | H | H | H | O | H | Cl | H | H | CF$_3$ | H |
| 2 | 6DB | CCl$_3$ | H | H | H | O | H | H | Cl | H | CF$_3$ | H |
| 2 | 7DB | CCl$_3$ | H | H | H | O | H | F | H | H | OCF$_3$ | H |
| 2 | 8DB | CCl$_3$ | H | H | H | O | H | H | Cl | H | H | CF$_3$ |
| 2 | 9DB | CCl$_3$ | H | H | H | O | H | F | H | H | H | CF$_3$ |
| 2 | 10DB | CCl$_3$ | H | H | H | O | H | H | F | H | H | CF$_3$ |
| 2 | 11DB | CCl$_3$ | H | H | H | O | F | H | H | H | H | CF$_3$ |
| 2 | 12DB | CCl$_3$ | H | H | H | O | H | Cl | H | CF$_3$ | H | H |
| 2 | 13DB | CCl$_3$ | H | H | H | O | H | H | Cl | CF$_3$ | H | H |
| 2 | 14DB | CCl$_3$ | H | H | H | O | Cl | H | H | CF$_3$ | H | H |
| 2 | 15DB | CCl$_3$ | H | H | H | O | H | F | H | CH$_3$ | H | H |
| 2 | 16DB | CCl$_3$ | H | H | H | O | H | H | F | H | H | CH$_3$ |
| 2 | 17DB | CCl$_3$ | H | H | H | O | H | F | H | H | CH$_3$ | H |
| 2 | 18DB | CCl$_3$ | H | H | H | O | F | H | H | CH$_3$ | H | H |
| 2 | 19DB | CCl$_3$ | H | H | H | O | H | H | F | H | CH$_3$ | H |
| 2 | 20DB | CCl$_3$ | H | H | H | O | F | H | H | H | H | CH$_3$ |
| 2 | 21DB | CCl$_3$ | H | H | H | O | F | H | H | H | CF$_3$ | H |
| 2 | 22DB | CCl$_3$ | H | H | H | O | Cl | H | H | H | CF$_3$ | H |
| 2 | 23DB | CCl$_3$ | H | H | H | O | H | F | H | CF$_3$ | H | H |
| 2 | 24DB | CCl$_3$ | H | H | H | O | H | H | F | CF$_3$ | H | H |
| 2 | 25DB | CCl$_3$ | H | H | H | O | H | F | H | H | CF$_3$ | H |
| 2 | 26DB | CCl$_3$ | H | H | H | O | H | H | F | H | CF$_3$ | H |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

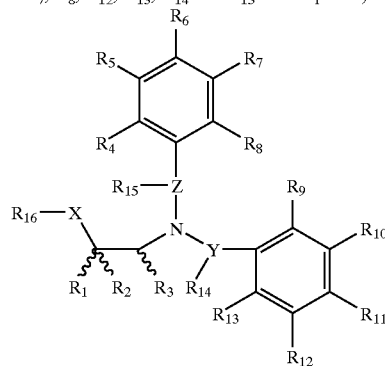

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 2 | 27DB | CCl$_3$ | H | H | H | O | H | OCF$_3$ | H | H | H | OCF$_3$ |
| 3 | 1DB | CF$_3$ | CH$_3$ | H | H | O | H | OCF$_3$ | H | H | OCF$_3$ | H |
| 3 | 2DB | CF$_3$ | CH$_3$ | H | H | O | H | Cl | H | H | H | CF$_3$ |
| 3 | 3DB | CF$_3$ | CH$_3$ | H | H | O | H | Br | H | H | OCF$_3$ | H |
| 3 | 4DB | CF$_3$ | CH$_3$ | H | H | O | H | Cl | H | H | OCF$_3$ | H |
| 3 | 5DB | CF$_3$ | CH$_3$ | H | H | O | H | Cl | H | H | CF$_3$ | H |
| 3 | 6DB | CF$_3$ | CH$_3$ | H | H | O | H | H | Cl | H | CF$_3$ | H |
| 3 | 7DB | CF$_3$ | CH$_3$ | H | H | O | H | F | H | H | OCF$_3$ | H |
| 3 | 8DB | CF$_3$ | CH$_3$ | H | H | O | H | H | Cl | H | H | CF$_3$ |
| 3 | 9DB | CF$_3$ | CH$_3$ | H | H | O | H | F | H | H | H | CF$_3$ |
| 3 | 10DB | CF$_3$ | CH$_3$ | H | H | O | H | H | F | H | H | CF$_3$ |
| 3 | 11DB | CF$_3$ | CH$_3$ | H | H | O | F | H | H | H | H | CF$_3$ |
| 3 | 12DB | CF$_3$ | CH$_3$ | H | H | O | H | Cl | H | CF$_3$ | H | H |
| 3 | 13DB | CF$_3$ | CH$_3$ | H | H | O | H | H | Cl | CF$_3$ | H | H |
| 3 | 14DB | CF$_3$ | CH$_3$ | H | H | O | Cl | H | H | CF$_3$ | H | H |
| 3 | 15DB | CF$_3$ | CH$_3$ | H | H | O | H | F | H | CH$_3$ | H | H |
| 3 | 16DB | CF$_3$ | CH$_3$ | H | H | O | H | H | F | H | H | CH$_3$ |
| 3 | 17DB | CF$_3$ | CH$_3$ | H | H | O | H | F | H | H | CH$_3$ | H |
| 3 | 18DB | CF$_3$ | CH$_3$ | H | H | O | F | H | H | CH$_3$ | H | H |
| 3 | 19DB | CF$_3$ | CH$_3$ | H | H | O | H | H | F | H | CH$_3$ | H |
| 3 | 20DB | CF$_3$ | CH$_3$ | H | H | O | F | H | H | H | H | CH$_3$ |
| 3 | 21DB | CF$_3$ | CH$_3$ | H | H | O | F | H | H | H | CF$_3$ | H |
| 3 | 22DB | CF$_3$ | CH$_3$ | H | H | O | Cl | H | H | H | CF$_3$ | H |
| 3 | 23DB | CF$_3$ | CH$_3$ | H | H | O | H | F | H | CF$_3$ | H | H |
| 3 | 24DB | CF$_3$ | CH$_3$ | H | H | O | H | H | F | CF$_3$ | H | H |
| 3 | 25DB | CF$_3$ | CH$_3$ | H | H | O | H | F | H | H | CF$_3$ | H |
| 3 | 26DB | CF$_3$ | CH$_3$ | H | H | O | H | H | F | H | CF$_3$ | H |
| 3 | 27DB | CF$_3$ | CH$_3$ | H | H | O | H | OCF$_3$ | H | H | H | OCF$_3$ |
| 4 | 1DB | CF$_3$CF$_2$ | H | H | H | O | H | OCF$_3$ | H | H | OCF$_3$ | H |
| 4 | 2DB | CF$_3$CF$_2$ | H | H | H | O | H | Cl | H | H | H | CF$_3$ |
| 4 | 3DB | CF$_3$CF$_2$ | H | H | H | O | H | Br | H | H | OCF$_3$ | H |
| 4 | 4DB | CF$_3$CF$_2$ | H | H | H | O | H | Cl | H | H | OCF$_3$ | H |
| 4 | 5DB | CF$_3$CF$_2$ | H | H | H | O | H | Cl | H | H | CF$_3$ | H |
| 4 | 6DB | CF$_3$CF$_2$ | H | H | H | O | H | H | Cl | H | CF$_3$ | H |
| 4 | 7DB | CF$_3$CF$_2$ | H | H | H | O | H | F | H | H | OCF$_3$ | H |
| 4 | 8DB | CF$_3$CF$_2$ | H | H | H | O | H | H | Cl | H | H | CF$_3$ |
| 4 | 9DB | CF$_3$CF$_2$ | H | H | H | O | H | F | H | H | H | CF$_3$ |
| 4 | 10DB | CF$_3$CF$_2$ | H | H | H | O | H | H | F | H | H | CF$_3$ |
| 4 | 11DB | CF$_3$CF$_2$ | H | H | H | O | F | H | H | H | H | CF$_3$ |
| 4 | 12DB | CF$_3$CF$_2$ | H | H | H | O | H | Cl | H | CF$_3$ | H | H |
| 4 | 13DB | CF$_3$CF$_2$ | H | H | H | O | H | H | Cl | CF$_3$ | H | H |
| 4 | 14DB | CF$_3$CF$_2$ | H | H | H | O | Cl | H | H | CF$_3$ | H | H |
| 4 | 15DB | CF$_3$CF$_2$ | H | H | H | O | H | F | H | CH$_3$ | H | H |
| 4 | 16DB | CF$_3$CF$_2$ | H | H | H | O | H | H | F | H | H | CH$_3$ |
| 4 | 17DB | CF$_3$CF$_2$ | H | H | H | O | H | F | H | H | CH$_3$ | H |
| 4 | 18DB | CF$_3$CF$_2$ | H | H | H | O | F | H | H | CH$_3$ | H | H |
| 4 | 19DB | CF$_3$CF$_2$ | H | H | H | O | H | H | F | H | CH$_3$ | H |
| 4 | 20DB | CF$_3$CF$_2$ | H | H | H | O | F | H | H | H | H | CH$_3$ |
| 4 | 21DB | CF$_3$CF$_2$ | H | H | H | O | F | H | H | H | CF$_3$ | H |
| 4 | 22DB | CF$_3$CF$_2$ | H | H | H | O | Cl | H | H | H | CF$_3$ | H |
| 4 | 23DB | CF$_3$CF$_2$ | H | H | H | O | H | F | H | CF$_3$ | H | H |
| 4 | 24DB | CF$_3$CF$_2$ | H | H | H | O | H | H | F | CF$_3$ | H | H |
| 4 | 25DB | CF$_3$CF$_2$ | H | H | H | O | H | F | H | H | CF$_3$ | H |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

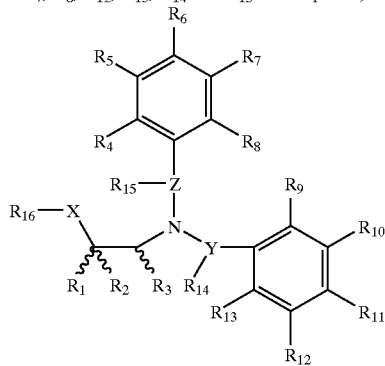

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 4 | 26DB | $CF_3CF_2$ | H | H | H | O | H | H | F | H | $CF_3$ | H |
| 4 | 27DB | $CF_3CF_2$ | H | H | H | O | H | $OCF_3$ | H | H | H | $OCF_3$ |
| 5 | 1DB | $CF_3CF_2CF_2$ | H | H | H | O | H | $OCF_3$ | H | H | $OCF_3$ | H |
| 5 | 2DB | $CF_3CF_2CF_2$ | H | H | H | O | H | Cl | H | H | H | $CF_3$ |
| 5 | 3DB | $CF_3CF_2CF_2$ | H | H | H | O | H | Br | H | H | $OCF_3$ | H |
| 5 | 4DB | $CF_3CF_2CF_2$ | H | H | H | O | H | Cl | H | H | $OCF_3$ | H |
| 5 | 5DB | $CF_3CF_2CF_2$ | H | H | H | O | H | Cl | H | H | $CF_3$ | H |
| 5 | 6DB | $CF_3CF_2CF_2$ | H | H | H | O | H | H | Cl | H | $CF_3$ | H |
| 5 | 7DB | $CF_3CF_2CF_2$ | H | H | H | O | H | F | H | H | $OCF_3$ | H |
| 5 | 8DB | $CF_3CF_2CF_2$ | H | H | H | O | H | H | Cl | H | H | $CF_3$ |
| 5 | 9DB | $CF_3CF_2CF_2$ | H | H | H | O | H | F | H | H | H | $CF_3$ |
| 5 | 10DB | $CF_3CF_2CF_2$ | H | H | H | O | H | H | F | H | H | $CF_3$ |
| 5 | 11DB | $CF_3CF_2CF_2$ | H | H | H | O | F | H | H | H | H | $CF_3$ |
| 5 | 12DB | $CF_3CF_2CF_2$ | H | H | H | O | H | Cl | H | $CF_3$ | H | H |
| 5 | 13DB | $CF_3CF_2CF_2$ | H | H | H | O | H | H | Cl | $CF_3$ | H | H |
| 5 | 14DB | $CF_3CF_2CF_2$ | H | H | H | O | Cl | H | H | $CF_3$ | H | H |
| 5 | 15DB | $CF_3CF_2CF_2$ | H | H | H | O | H | F | H | $CH_3$ | H | H |
| 5 | 16DB | $CF_3CF_2CF_2$ | H | H | H | O | H | H | F | H | H | $CH_3$ |
| 5 | 17DB | $CF_3CF_2CF_2$ | H | H | H | O | H | F | H | H | $CH_3$ | H |
| 5 | 18DB | $CF_3CF_2CF_2$ | H | H | H | O | F | H | H | $CH_3$ | H | H |
| 5 | 19DB | $CF_3CF_2CF_2$ | H | H | H | O | H | H | F | H | $CH_3$ | H |
| 5 | 20DB | $CF_3CF_2CF_2$ | H | H | H | O | F | H | H | H | H | $CH_3$ |
| 5 | 21DB | $CF_3CF_2CF_2$ | H | H | H | O | F | H | H | H | $CF_3$ | H |
| 5 | 22DB | $CF_3CF_2CF_2$ | H | H | H | O | Cl | H | H | H | $CF_3$ | H |
| 5 | 23DB | $CF_3CF_2CF_2$ | H | H | H | O | H | F | H | $CF_3$ | H | H |
| 5 | 24DB | $CF_3CF_2CF_2$ | H | H | H | O | H | H | F | $CF_3$ | H | H |
| 5 | 25DB | $CF_3CF_2CF_2$ | H | H | H | O | H | F | H | H | $CF_3$ | H |
| 5 | 26DB | $CF_3CF_2CF_2$ | H | H | H | O | H | H | F | H | $CF_3$ | H |
| 5 | 27DB | $CF_3CF_2CF_2$ | H | H | H | O | H | $OCF_3$ | H | H | H | $OCF_3$ |
| 6 | 1DB | $CF_3OCF_2CF_2$ | H | H | H | O | H | $OCF_3$ | H | H | $OCF_3$ | H |
| 6 | 2DB | $CF_3OCF_2CF_2$ | H | H | H | O | H | Cl | H | H | H | $CF_3$ |
| 6 | 3DB | $CF_3OCF_2CF_2$ | H | H | H | O | H | Br | H | H | $OCF_3$ | H |
| 6 | 4DB | $CF_3OCF_2CF_2$ | H | H | H | O | H | Cl | H | H | $OCF_3$ | H |
| 6 | 5DB | $CF_3OCF_2CF_2$ | H | H | H | O | H | Cl | H | H | $CF_3$ | H |
| 6 | 6DB | $CF_3OCF_2CF_2$ | H | H | H | O | H | H | Cl | H | $CF_3$ | H |
| 6 | 7DB | $CF_3OCF_2CF_2$ | H | H | H | O | H | F | H | H | $OCF_3$ | H |
| 6 | 8DB | $CF_3OCF_2CF_2$ | H | H | H | O | H | H | Cl | H | H | $CF_3$ |
| 6 | 9DB | $CF_3OCF_2CF_2$ | H | H | H | O | H | F | H | H | H | $CF_3$ |
| 6 | 10DB | $CF_3OCF_2CF_2$ | H | H | H | O | H | H | F | H | H | $CF_3$ |
| 6 | 11DB | $CF_3OCF_2CF_2$ | H | H | H | O | F | H | H | H | H | $CF_3$ |
| 6 | 12DB | $CF_3OCF_2CF_2$ | H | H | H | O | H | Cl | H | $CF_3$ | H | H |
| 6 | 13DB | $CF_3OCF_2CF_2$ | H | H | H | O | H | H | Cl | $CF_3$ | H | H |
| 6 | 14DB | $CF_3OCF_2CF_2$ | H | H | H | O | Cl | H | H | $CF_3$ | H | H |
| 6 | 15DB | $CF_3OCF_2CF_2$ | H | H | H | O | H | F | H | $CH_3$ | H | H |
| 6 | 16DB | $CF_3OCF_2CF_2$ | H | H | H | O | H | H | F | H | H | $CH_3$ |
| 6 | 17DB | $CF_3OCF_2CF_2$ | H | H | H | O | H | F | H | H | $CH_3$ | H |
| 6 | 18DB | $CF_3OCF_2CF_2$ | H | H | H | O | F | H | H | $CH_3$ | H | H |
| 6 | 19DB | $CF_3OCF_2CF_2$ | H | H | H | O | H | H | F | H | $CH_3$ | H |
| 6 | 20DB | $CF_3OCF_2CF_2$ | H | H | H | O | F | H | H | H | H | $CH_3$ |
| 6 | 21DB | $CF_3OCF_2CF_2$ | H | H | H | O | F | H | H | H | $CF_3$ | H |
| 6 | 22DB | $CF_3OCF_2CF_2$ | H | H | H | O | Cl | H | H | H | $CF_3$ | H |
| 6 | 23DB | $CF_3OCF_2CF_2$ | H | H | H | O | H | F | H | $CF_3$ | H | H |
| 6 | 24DB | $CF_3OCF_2CF_2$ | H | H | H | O | H | H | F | $CF_3$ | H | H |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

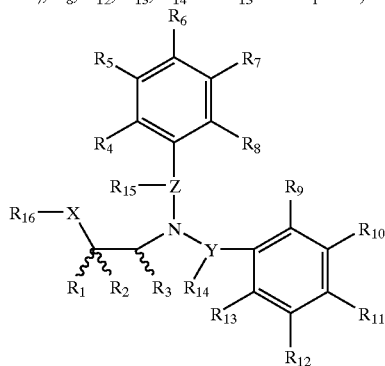

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 6 | 25DB | $CF_3OCF_2CF_2$ | H | H | H | O | H | F | H | H | $CF_3$ | H |
| 6 | 26DB | $CF_3OCF_2CF_2$ | H | H | H | O | H | H | F | H | $CF_3$ | H |
| 6 | 27DB | $CF_3OCF_2CF_2$ | H | H | H | O | H | $OCF_3$ | H | H | H | $OCF_3$ |
| 7 | 1DB | $CF_3CH_2$ | H | H | H | O | H | $OCF_3$ | H | H | $OCF_3$ | H |
| 7 | 2DB | $CF_3CH_2$ | H | H | H | O | H | Cl | H | H | H | $CF_3$ |
| 7 | 3DB | $CF_3CH_2$ | H | H | H | O | H | Br | H | H | $OCF_3$ | H |
| 7 | 4DB | $CF_3CH_2$ | H | H | H | O | H | Cl | H | H | $OCF_3$ | H |
| 7 | 5DB | $CF_3CH_2$ | H | H | H | O | H | Cl | H | H | $CF_3$ | H |
| 7 | 6DB | $CF_3CH_2$ | H | H | H | O | H | H | Cl | H | $CF_3$ | H |
| 7 | 7DB | $CF_3CH_2$ | H | H | H | O | H | F | H | H | $OCF_3$ | H |
| 7 | 8DB | $CF_3CH_2$ | H | H | H | O | H | H | Cl | H | H | $CF_3$ |
| 7 | 9DB | $CF_3CH_2$ | H | H | H | O | H | F | H | H | H | $CF_3$ |
| 7 | 10DB | $CF_3CH_2$ | H | H | H | O | H | H | F | H | H | $CF_3$ |
| 7 | 11DB | $CF_3CH_2$ | H | H | H | O | F | H | H | H | H | $CF_3$ |
| 7 | 12DB | $CF_3CH_2$ | H | H | H | O | H | Cl | H | $CF_3$ | H | H |
| 7 | 13DB | $CF_3CH_2$ | H | H | H | O | H | H | Cl | $CF_3$ | H | H |
| 7 | 14DB | $CF_3CH_2$ | H | H | H | O | Cl | H | H | $CF_3$ | H | H |
| 7 | 15DB | $CF_3CH_2$ | H | H | H | O | H | F | H | $CH_3$ | H | H |
| 7 | 16DB | $CF_3CH_2$ | H | H | H | O | H | H | F | H | H | $CH_3$ |
| 7 | 17DB | $CF_3CH_2$ | H | H | H | O | H | F | H | H | $CH_3$ | H |
| 7 | 18DB | $CF_3CH_2$ | H | H | H | O | F | H | H | $CH_3$ | H | H |
| 7 | 19DB | $CF_3CH_2$ | H | H | H | O | H | H | F | H | $CH_3$ | H |
| 7 | 20DB | $CF_3CH_2$ | H | H | H | O | F | H | H | H | H | $CH_3$ |
| 7 | 21DB | $CF_3CH_2$ | H | H | H | O | F | H | H | H | $CF_3$ | H |
| 7 | 22DB | $CF_3CH_2$ | H | H | H | O | Cl | H | H | H | $CF_3$ | H |
| 7 | 23DB | $CF_3CH_2$ | H | H | H | O | H | F | H | $CF_3$ | H | H |
| 7 | 24DB | $CF_3CH_2$ | H | H | H | O | H | H | F | $CF_3$ | H | H |
| 7 | 25DB | $CF_3CH_2$ | H | H | H | O | H | F | H | H | $CF_3$ | H |
| 7 | 26DB | $CF_3CH_2$ | H | H | H | O | H | H | F | H | $CF_3$ | H |
| 7 | 27DB | $CF_3CH_2$ | H | H | H | O | H | $OCF_3$ | H | H | H | $OCF_3$ |
| 8 | 1DB | $CF_3$ | $CHF_2$ | H | H | O | H | $OCF_3$ | H | H | $OCF_3$ | H |
| 8 | 2DB | $CF_3$ | $CHF_2$ | H | H | O | H | Cl | H | H | H | $CF_3$ |
| 8 | 3DB | $CF_3$ | $CHF_2$ | H | H | O | H | Br | H | H | $OCF_3$ | H |
| 8 | 4DB | $CF_3$ | $CHF_2$ | H | H | O | H | Cl | H | H | $OCF_3$ | H |
| 8 | 5DB | $CF_3$ | $CHF_2$ | H | H | O | H | Cl | H | H | $CF_3$ | H |
| 8 | 6DB | $CF_3$ | $CHF_2$ | H | H | O | H | H | Cl | H | $CF_3$ | H |
| 8 | 7DB | $CF_3$ | $CHF_2$ | H | H | O | H | F | H | H | $OCF_3$ | H |
| 8 | 8DB | $CF_3$ | $CHF_2$ | H | H | O | H | H | Cl | H | H | $CF_3$ |
| 8 | 9DB | $CF_3$ | $CHF_2$ | H | H | O | H | F | H | H | H | $CF_3$ |
| 8 | 10DB | $CF_3$ | $CHF_2$ | H | H | O | H | H | F | H | H | $CF_3$ |
| 8 | 11DB | $CF_3$ | $CHF_2$ | H | H | O | F | H | H | H | H | $CF_3$ |
| 8 | 12DB | $CF_3$ | $CHF_2$ | H | H | O | H | Cl | H | $CF_3$ | H | H |
| 8 | 13DB | $CF_3$ | $CHF_2$ | H | H | O | H | H | Cl | $CF_3$ | H | H |
| 8 | 14DB | $CF_3$ | $CHF_2$ | H | H | O | Cl | H | H | $CF_3$ | H | H |
| 8 | 15DB | $CF_3$ | $CHF_2$ | H | H | O | H | F | H | $CH_3$ | H | H |
| 8 | 16DB | $CF_3$ | $CHF_2$ | H | H | O | H | H | F | H | H | $CH_3$ |
| 8 | 17DB | $CF_3$ | $CHF_2$ | H | H | O | H | F | H | H | $CH_3$ | H |
| 8 | 18DB | $CF_3$ | $CHF_2$ | H | H | O | F | H | H | $CH_3$ | H | H |
| 8 | 19DB | $CF_3$ | $CHF_2$ | H | H | O | H | H | F | H | $CH_3$ | H |
| 8 | 20DB | $CF_3$ | $CHF_2$ | H | H | O | F | H | H | H | H | $CH_3$ |
| 8 | 21DB | $CF_3$ | $CHF_2$ | H | H | O | F | H | H | H | $CF_3$ | H |
| 8 | 22DB | $CF_3$ | $CHF_2$ | H | H | O | Cl | H | H | H | $CF_3$ | H |
| 8 | 23DB | $CF_3$ | $CHF_2$ | H | H | O | H | F | H | $CF_3$ | H | H |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

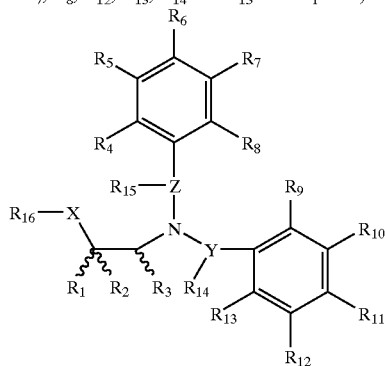

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 8 | 24DB | $CF_3$ | $CHF_2$ | H | H | O | H | H | F | $CF_3$ | H | H |
| 8 | 25DB | $CF_3$ | $CHF_2$ | H | H | O | H | F | H | H | $CF_3$ | H |
| 8 | 26DB | $CF_3$ | $CHF_2$ | H | H | O | H | H | F | H | $CF_3$ | H |
| 8 | 27DB | $CF_3$ | $CHF_2$ | H | H | O | H | $OCF_3$ | H | H | H | $OCF_3$ |
| 9 | 1DB | $CF_3$ | H | $CF_3$ | H | O | H | $OCF_3$ | H | H | $OCF_3$ | H |
| 9 | 2DB | $CF_3$ | H | $CF_3$ | H | O | H | Cl | H | H | H | $CF_3$ |
| 9 | 3DB | $CF_3$ | H | $CF_3$ | H | O | H | Br | H | H | $OCF_3$ | H |
| 9 | 4DB | $CF_3$ | H | $CF_3$ | H | O | H | Cl | H | H | $OCF_3$ | H |
| 9 | 5DB | $CF_3$ | H | $CF_3$ | H | O | H | Cl | H | H | $CF_3$ | H |
| 9 | 6DB | $CF_3$ | H | $CF_3$ | H | O | H | H | Cl | H | $CF_3$ | H |
| 9 | 7DB | $CF_3$ | H | $CF_3$ | H | O | H | F | H | H | $OCF_3$ | H |
| 9 | 8DB | $CF_3$ | H | $CF_3$ | H | O | H | H | Cl | H | H | $CF_3$ |
| 9 | 9DB | $CF_3$ | H | $CF_3$ | H | O | H | F | H | H | H | $CF_3$ |
| 9 | 10DB | $CF_3$ | H | $CF_3$ | H | O | H | H | F | H | H | $CF_3$ |
| 9 | 11DB | $CF_3$ | H | $CF_3$ | H | O | F | H | H | H | H | $CF_3$ |
| 9 | 12DB | $CF_3$ | H | $CF_3$ | H | O | H | Cl | H | $CF_3$ | H | H |
| 9 | 13DB | $CF_3$ | H | $CF_3$ | H | O | H | H | Cl | $CF_3$ | H | H |
| 9 | 14DB | $CF_3$ | H | $CF_3$ | H | O | Cl | H | H | $CF_3$ | H | H |
| 9 | 15DB | $CF_3$ | H | $CF_3$ | H | O | H | F | H | $CH_3$ | H | H |
| 9 | 16DB | $CF_3$ | H | $CF_3$ | H | O | H | H | F | H | H | $CH_3$ |
| 9 | 17DB | $CF_3$ | H | $CF_3$ | H | O | H | F | H | H | $CH_3$ | H |
| 9 | 18DB | $CF_3$ | H | $CF_3$ | H | O | F | H | H | $CH_3$ | H | H |
| 9 | 19DB | $CF_3$ | H | $CF_3$ | H | O | H | H | F | H | $CH_3$ | H |
| 9 | 20DB | $CF_3$ | H | $CF_3$ | H | O | F | H | H | H | H | $CH_3$ |
| 9 | 21DB | $CF_3$ | H | $CF_3$ | H | O | F | H | H | H | $CF_3$ | H |
| 9 | 22DB | $CF_3$ | H | $CF_3$ | H | O | Cl | H | H | H | $CF_3$ | H |
| 9 | 23DB | $CF_3$ | H | $CF_3$ | H | O | H | F | H | $CF_3$ | H | H |
| 9 | 24DB | $CF_3$ | H | $CF_3$ | H | O | H | H | F | $CF_3$ | H | H |
| 9 | 25DB | $CF_3$ | H | $CF_3$ | H | O | H | F | H | H | $CF_3$ | H |
| 9 | 26DB | $CF_3$ | H | $CF_3$ | H | O | H | H | F | H | $CF_3$ | H |
| 9 | 27DB | $CF_3$ | H | $CF_3$ | H | O | H | $OCF_3$ | H | H | H | $OCF_3$ |
| 10 | 1DB | $CF_3$ | $CF_3$ | H | H | O | H | $OCF_3$ | H | H | $OCF_3$ | H |
| 10 | 2DB | $CF_3$ | $CF_3$ | H | H | O | H | Cl | H | H | H | $CF_3$ |
| 10 | 3DB | $CF_3$ | $CF_3$ | H | H | O | H | Br | H | H | $OCF_3$ | H |
| 10 | 4DB | $CF_3$ | $CF_3$ | H | H | O | H | Cl | H | H | $OCF_3$ | H |
| 10 | 5DB | $CF_3$ | $CF_3$ | H | H | O | H | Cl | H | H | $CF_3$ | H |
| 10 | 6DB | $CF_3$ | $CF_3$ | H | H | O | H | H | Cl | H | $CF_3$ | H |
| 10 | 7DB | $CF_3$ | $CF_3$ | H | H | O | H | F | H | H | $OCF_3$ | H |
| 10 | 8DB | $CF_3$ | $CF_3$ | H | H | O | H | H | Cl | H | H | $CF_3$ |
| 10 | 9DB | $CF_3$ | $CF_3$ | H | H | O | H | F | H | H | H | $CF_3$ |
| 10 | 10DB | $CF_3$ | $CF_3$ | H | H | O | H | H | F | H | H | $CF_3$ |
| 10 | 11DB | $CF_3$ | $CF_3$ | H | H | O | F | H | H | H | H | $CF_3$ |
| 10 | 12DB | $CF_3$ | $CF_3$ | H | H | O | H | Cl | H | $CF_3$ | H | H |
| 10 | 13DB | $CF_3$ | $CF_3$ | H | H | O | H | H | Cl | $CF_3$ | H | H |
| 10 | 14DB | $CF_3$ | $CF_3$ | H | H | O | Cl | H | H | $CF_3$ | H | H |
| 10 | 15DB | $CF_3$ | $CF_3$ | H | H | O | H | F | H | $CH_3$ | H | H |
| 10 | 16DB | $CF_3$ | $CF_3$ | H | H | O | H | H | F | H | H | $CH_3$ |
| 10 | 17DB | $CF_3$ | $CF_3$ | H | H | O | H | F | H | H | $CH_3$ | H |
| 10 | 18DB | $CF_3$ | $CF_3$ | H | H | O | F | H | H | $CH_3$ | H | H |
| 10 | 19DB | $CF_3$ | $CF_3$ | H | H | O | H | H | F | H | $CH_3$ | H |
| 10 | 20DB | $CF_3$ | $CF_3$ | H | H | O | F | H | H | H | H | $CH_3$ |
| 10 | 21DB | $CF_3$ | $CF_3$ | H | H | O | F | H | H | H | $CF_3$ | H |
| 10 | 22DB | $CF_3$ | $CF_3$ | H | H | O | Cl | H | H | H | $CF_3$ | H |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

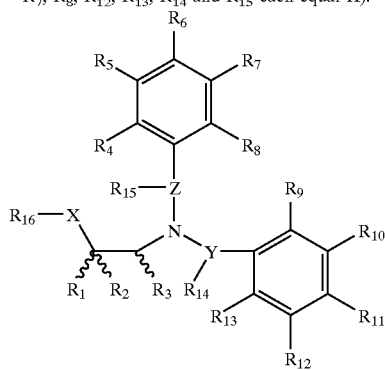

| Reagent Column 1 | Reagent Column 2 | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 10 | 23DB | $CF_3$ | $CF_3$ | H | H | O | H | F | H | $CF_3$ | H | H |
| 10 | 24DB | $CF_3$ | $CF_3$ | H | H | O | H | H | F | $CF_3$ | H | H |
| 10 | 25DB | $CF_3$ | $CF_3$ | H | H | O | H | F | H | H | $CF_3$ | H |
| 10 | 26DB | $CF_3$ | $CF_3$ | H | H | O | H | H | F | H | $CF_3$ | H |
| 10 | 27DB | $CF_3$ | $CF_3$ | H | H | O | H | $OCF_3$ | H | H | H | $OCF_3$ |
| 11 | 1DB | $CF_3$ | $C_6H_5$ | H | H | O | H | $OCF_3$ | H | H | $OCF_3$ | H |
| 11 | 2DB | $CF_3$ | $C_6H_5$ | H | H | O | H | Cl | H | H | H | $CF_3$ |
| 11 | 3DB | $CF_3$ | $C_6H_5$ | H | H | O | H | Br | H | H | $OCF_3$ | H |
| 11 | 4DB | $CF_3$ | $C_6H_5$ | H | H | O | H | Cl | H | H | $OCF_3$ | H |
| 11 | 5DB | $CF_3$ | $C_6H_5$ | H | H | O | H | Cl | H | H | $CF_3$ | H |
| 11 | 6DB | $CF_3$ | $C_6H_5$ | H | H | O | H | H | Cl | H | $CF_3$ | H |
| 11 | 7DB | $CF_3$ | $C_6H_5$ | H | H | O | H | F | H | H | $OCF_3$ | H |
| 11 | 8DB | $CF_3$ | $C_6H_5$ | H | H | O | H | H | Cl | H | H | $CF_3$ |
| 11 | 9DB | $CF_3$ | $C_6H_5$ | H | H | O | H | F | H | H | H | $CF_3$ |
| 11 | 10DB | $CF_3$ | $C_6H_5$ | H | H | O | H | H | F | H | H | $CF_3$ |
| 11 | 11DB | $CF_3$ | $C_6H_5$ | H | H | O | F | H | H | H | H | $CF_3$ |
| 11 | 12DB | $CF_3$ | $C_6H_5$ | H | H | O | H | Cl | H | $CF_3$ | H | H |
| 11 | 13DB | $CF_3$ | $C_6H_5$ | H | H | O | H | H | Cl | $CF_3$ | H | H |
| 11 | 14DB | $CF_3$ | $C_6H_5$ | H | H | O | Cl | H | H | $CF_3$ | H | H |
| 11 | 15DB | $CF_3$ | $C_6H_5$ | H | H | O | H | F | H | $CH_3$ | H | H |
| 11 | 16DB | $CF_3$ | $C_6H_5$ | H | H | O | H | H | F | H | H | $CH_3$ |
| 11 | 17DB | $CF_3$ | $C_6H_5$ | H | H | O | H | F | H | H | $CH_3$ | H |
| 11 | 18DB | $CF_3$ | $C_6H_5$ | H | H | O | F | H | H | $CH_3$ | H | H |
| 11 | 19DB | $CF_3$ | $C_6H_5$ | H | H | O | H | H | F | H | $CH_3$ | H |
| 11 | 20DB | $CF_3$ | $C_6H_5$ | H | H | O | F | H | H | H | H | $CH_3$ |
| 11 | 21DB | $CF_3$ | $C_6H_5$ | H | H | O | F | H | H | H | $CF_3$ | H |
| 11 | 22DB | $CF_3$ | $C_6H_5$ | H | H | O | Cl | H | H | H | $CF_3$ | H |
| 11 | 23DB | $CF_3$ | $C_6H_5$ | H | H | O | H | F | H | $CF_3$ | H | H |
| 11 | 24DB | $CF_3$ | $C_6H_5$ | H | H | O | H | H | F | $CF_3$ | H | H |
| 11 | 25DB | $CF_3$ | $C_6H_5$ | H | H | O | H | F | H | H | $CF_3$ | H |
| 11 | 26DB | $CF_3$ | $C_6H_5$ | H | H | O | H | H | F | H | $CF_3$ | H |
| 11 | 27DB | $CF_3$ | $C_6H_5$ | H | H | O | H | $OCF_3$ | H | H | H | $OCF_3$ |
| 12 | 1DB | $CCl_3$ | $C_6H_5$ | H | H | O | H | $OCF_3$ | H | H | $OCF_3$ | H |
| 12 | 2DB | $CCl_3$ | $C_6H_5$ | H | H | O | H | Cl | H | H | H | $CF_3$ |
| 12 | 3DB | $CCl_3$ | $C_6H_5$ | H | H | O | H | Br | H | H | $OCF_3$ | H |
| 12 | 4DB | $CCl_3$ | $C_6H_5$ | H | H | O | H | Cl | H | H | $OCF_3$ | H |
| 12 | 5DB | $CCl_3$ | $C_6H_5$ | H | H | O | H | Cl | H | H | $CF_3$ | H |
| 12 | 6DB | $CCl_3$ | $C_6H_5$ | H | H | O | H | H | Cl | H | $CF_3$ | H |
| 12 | 7DB | $CCl_3$ | $C_6H_5$ | H | H | O | H | F | H | H | $OCF_3$ | H |
| 12 | 8DB | $CCl_3$ | $C_6H_5$ | H | H | O | H | H | Cl | H | H | $CF_3$ |
| 12 | 9DB | $CCl_3$ | $C_6H_5$ | H | H | O | H | F | H | H | H | $CF_3$ |
| 12 | 10DB | $CCl_3$ | $C_6H_5$ | H | H | O | H | H | F | H | H | $CF_3$ |
| 12 | 11DB | $CCl_3$ | $C_6H_5$ | H | H | O | F | H | H | H | H | $CF_3$ |
| 12 | 12DB | $CCl_3$ | $C_6H_5$ | H | H | O | H | Cl | H | $CF_3$ | H | H |
| 12 | 13DB | $CCl_3$ | $C_6H_5$ | H | H | O | H | H | Cl | $CF_3$ | H | H |
| 12 | 14DB | $CCl_3$ | $C_6H_5$ | H | H | O | Cl | H | H | $CF_3$ | H | H |
| 12 | 15DB | $CCl_3$ | $C_6H_5$ | H | H | O | H | F | H | $CH_3$ | H | H |
| 12 | 16DB | $CCl_3$ | $C_6H_5$ | H | H | O | H | H | F | H | H | $CH_3$ |
| 12 | 17DB | $CCl_3$ | $C_6H_5$ | H | H | O | H | F | H | H | $CH_3$ | H |
| 12 | 18DB | $CCl_3$ | $C_6H_5$ | H | H | O | F | H | H | $CH_3$ | H | H |
| 12 | 19DB | $CCl_3$ | $C_6H_5$ | H | H | O | H | H | F | H | $CH_3$ | H |
| 12 | 20DB | $CCl_3$ | $C_6H_5$ | H | H | O | F | H | H | H | H | $CH_3$ |
| 12 | 21DB | $CCl_3$ | $C_6H_5$ | H | H | O | F | H | H | H | $CF_3$ | H |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

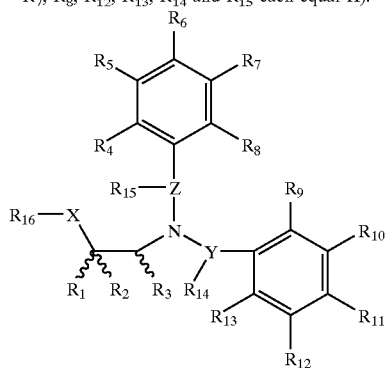

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 12 | 22DB | $CCl_3$ | $C_6H_5$ | H | H | O | Cl | H | H | H | $CF_3$ | H |
| 12 | 23DB | $CCl_3$ | $C_6H_5$ | H | H | O | H | F | H | $CF_3$ | H | H |
| 12 | 24DB | $CCl_3$ | $C_6H_5$ | H | H | O | H | H | F | $CF_3$ | H | H |
| 12 | 25DB | $CCl_3$ | $C_6H_5$ | H | H | O | H | F | H | H | $CF_3$ | H |
| 12 | 26DB | $CCl_3$ | $C_6H_5$ | H | H | O | H | H | F | H | $CF_3$ | H |
| 12 | 27DB | $CCl_3$ | $C_6H_5$ | H | H | O | H | $OCF_3$ | H | H | H | $OCF_3$ |
| 13 | 1DB | $CCl_3$ | cyclo-propyl | H | H | O | H | $OCF_3$ | H | H | $OCF_3$ | H |
| 13 | 2DB | $CCl_3$ | cyclo-propyl | H | H | O | H | Cl | H | H | H | $CF_3$ |
| 13 | 3DB | $CCl_3$ | cyclo-propyl | H | H | O | H | Br | H | H | $OCF_3$ | H |
| 13 | 4DB | $CCl_3$ | cyclo-propyl | H | H | O | H | Cl | H | H | $OCF_3$ | H |
| 13 | 5DB | $CCl_3$ | cyclo-propyl | H | H | O | H | Cl | H | H | $CF_3$ | H |
| 13 | 6DB | $CCl_3$ | cyclo-propyl | H | H | O | H | H | Cl | H | $CF_3$ | H |
| 13 | 7DB | $CCl_3$ | cyclo-propyl | H | H | O | H | F | H | H | $OCF_3$ | H |
| 13 | 8DB | $CCl_3$ | cyclo-propyl | H | H | O | H | H | Cl | H | H | $CF_3$ |
| 13 | 9DB | $CCl_3$ | cyclo-propyl | H | H | O | H | F | H | H | H | $CF_3$ |
| 13 | 10DB | $CCl_3$ | cyclo-propyl | H | H | O | H | H | F | H | H | $CF_3$ |
| 13 | 11DB | $CCl_3$ | cyclo-propyl | H | H | O | F | H | H | H | H | $CF_3$ |
| 13 | 12DB | $CCl_3$ | cyclo-propyl | H | H | O | H | Cl | H | $CF_3$ | H | H |
| 13 | 13DB | $CCl_3$ | cyclo-propyl | H | H | O | H | H | Cl | $CF_3$ | H | H |
| 13 | 14DB | $CCl_3$ | cyclo-propyl | H | H | O | Cl | H | H | $CF_3$ | H | H |
| 13 | 15DB | $CCl_3$ | cyclo-propyl | H | H | O | H | F | H | $CH_3$ | H | H |
| 13 | 16DB | $CCl_3$ | cyclo-propyl | H | H | O | H | H | F | H | H | $CH_3$ |
| 13 | 17DB | $CCl_3$ | cyclo-propyl | H | H | O | H | F | H | H | $CH_3$ | H |
| 13 | 18DB | $CCl_3$ | cyclo-propyl | H | H | O | F | H | H | $CH_3$ | H | H |
| 13 | 19DB | $CCl_3$ | cyclo-propyl | H | H | O | H | H | F | H | $CH_3$ | H |
| 13 | 20DB | $CCl_3$ | cyclo-propyl | H | H | O | F | H | H | H | H | $CH_3$ |
| 13 | 21DB | $CCl_3$ | cyclo-propyl | H | H | O | F | H | H | H | $CF_3$ | H |
| 13 | 22DB | $CCl_3$ | cyclo-propyl | H | H | O | Cl | H | H | H | $CF_3$ | H |
| 13 | 23DB | $CCl_3$ | cyclo-propyl | H | H | O | H | F | H | $CF_3$ | H | H |
| 13 | 24DB | $CCl_3$ | cyclo-propyl | H | H | O | H | H | F | $CF_3$ | H | H |
| 13 | 25DB | $CCl_3$ | cyclo-propyl | H | H | O | H | F | H | H | $CF_3$ | H |
| 13 | 26DB | $CCl_3$ | cyclo-propyl | H | H | O | H | H | F | H | $CF_3$ | H |
| 13 | 27DB | $CCl_3$ | cyclo-propyl | H | H | O | H | $OCF_3$ | H | H | H | $OCF_3$ |
| 14 | 1DB | $CCl_3$ | $CH_3$ | H | H | O | H | $OCF_3$ | H | H | $OCF_3$ | H |
| 14 | 2DB | $CCl_3$ | $CH_3$ | H | H | O | H | Cl | H | H | H | $CF_3$ |
| 14 | 3DB | $CCl_3$ | $CH_3$ | H | H | O | H | Br | H | H | $OCF_3$ | H |
| 14 | 4DB | $CCl_3$ | $CH_3$ | H | H | O | H | Cl | H | H | $OCF_3$ | H |
| 14 | 5DB | $CCl_3$ | $CH_3$ | H | H | O | H | Cl | H | H | $CF_3$ | H |
| 14 | 6DB | $CCl_3$ | $CH_3$ | H | H | O | H | H | Cl | H | $CF_3$ | H |
| 14 | 7DB | $CCl_3$ | $CH_3$ | H | H | O | H | F | H | H | $OCF_3$ | H |
| 14 | 8DB | $CCl_3$ | $CH_3$ | H | H | O | H | H | Cl | H | H | $CF_3$ |
| 14 | 9DB | $CCl_3$ | $CH_3$ | H | H | O | H | F | H | H | H | $CF_3$ |
| 14 | 10DB | $CCl_3$ | $CH_3$ | H | H | O | H | H | F | H | H | $CF_3$ |
| 14 | 11DB | $CCl_3$ | $CH_3$ | H | H | O | F | H | H | H | H | $CF_3$ |
| 14 | 12DB | $CCl_3$ | $CH_3$ | H | H | O | H | Cl | H | $CF_3$ | H | H |
| 14 | 13DB | $CCl_3$ | $CH_3$ | H | H | O | H | H | Cl | $CF_3$ | H | H |
| 14 | 14DB | $CCl_3$ | $CH_3$ | H | H | O | Cl | H | H | $CF_3$ | H | H |
| 14 | 15DB | $CCl_3$ | $CH_3$ | H | H | O | H | F | H | $CH_3$ | H | H |
| 14 | 16DB | $CCl_3$ | $CH_3$ | H | H | O | H | H | F | H | H | $CH_3$ |
| 14 | 17DB | $CCl_3$ | $CH_3$ | H | H | O | H | F | H | H | $CH_3$ | H |
| 14 | 18DB | $CCl_3$ | $CH_3$ | H | H | O | F | H | H | $CH_3$ | H | H |
| 14 | 19DB | $CCl_3$ | $CH_3$ | H | H | O | H | H | F | H | $CH_3$ | H |
| 14 | 20DB | $CCl_3$ | $CH_3$ | H | H | O | F | H | H | H | H | $CH_3$ |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

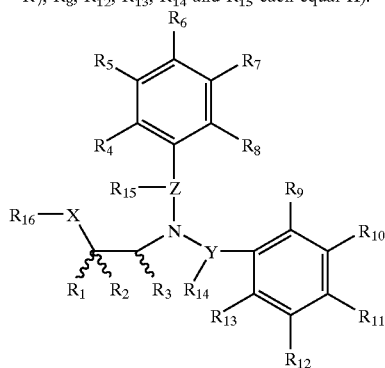

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 14 | 21DB | $CCl_3$ | $CH_3$ | H | H | O | F | H | H | H | $CF_3$ | H |
| 14 | 22DB | $CCl_3$ | $CH_3$ | H | H | O | Cl | H | H | H | $CF_3$ | H |
| 14 | 23DB | $CCl_3$ | $CH_3$ | H | H | O | H | F | H | $CF_3$ | H | H |
| 14 | 24DB | $CCl_3$ | $CH_3$ | H | H | O | H | H | F | $CF_3$ | H | H |
| 14 | 25DB | $CCl_3$ | $CH_3$ | H | H | O | H | F | H | H | $CF_3$ | H |
| 14 | 26DB | $CCl_3$ | $CH_3$ | H | H | O | H | H | F | H | $CF_3$ | H |
| 14 | 27DB | $CCl_3$ | $CH_3$ | H | H | O | H | $OCF_3$ | H | H | H | $OCF_3$ |
| 15 | 1DB | $CCl_3$ | $(CH_3)_2CH$ | H | H | O | H | $OCF_3$ | H | H | $OCF_3$ | H |
| 15 | 2DB | $CCl_3$ | $(CH_3)_2CH$ | H | H | O | H | Cl | H | H | H | $CF_3$ |
| 15 | 3DB | $CCl_3$ | $(CH_3)_2CH$ | H | H | O | H | Br | H | H | $OCF_3$ | H |
| 15 | 4DB | $CCl_3$ | $(CH_3)_2CH$ | H | H | O | H | Cl | H | H | $OCF_3$ | H |
| 15 | 5DB | $CCl_3$ | $(CH_3)_2CH$ | H | H | O | H | Cl | H | H | $CF_3$ | H |
| 15 | 6DB | $CCl_3$ | $(CH_3)_2CH$ | H | H | O | H | H | Cl | H | $CF_3$ | H |
| 15 | 7DB | $CCl_3$ | $(CH_3)_2CH$ | H | H | O | H | F | H | H | $OCF_3$ | H |
| 15 | 8DB | $CCl_3$ | $(CH_3)_2CH$ | H | H | O | H | H | Cl | H | H | $CF_3$ |
| 15 | 9DB | $CCl_3$ | $(CH_3)_2CH$ | H | H | O | H | F | H | H | H | $CF_3$ |
| 15 | 10DB | $CCl_3$ | $(CH_3)_2CH$ | H | H | O | H | H | F | H | H | $CF_3$ |
| 15 | 11DB | $CCl_3$ | $(CH_3)_2CH$ | H | H | O | F | H | H | H | H | $CF_3$ |
| 15 | 12DB | $CCl_3$ | $(CH_3)_2CH$ | H | H | O | H | Cl | H | $CF_3$ | H | H |
| 15 | 13DB | $CCl_3$ | $(CH_3)_2CH$ | H | H | O | H | H | Cl | $CF_3$ | H | H |
| 15 | 14DB | $CCl_3$ | $(CH_3)_2CH$ | H | H | O | Cl | H | H | $CF_3$ | H | H |
| 15 | 15DB | $CCl_3$ | $(CH_3)_2CH$ | H | H | O | H | F | H | $CH_3$ | H | H |
| 15 | 16DB | $CCl_3$ | $(CH_3)_2CH$ | H | H | O | H | H | F | H | H | $CH_3$ |
| 15 | 17DB | $CCl_3$ | $(CH_3)_2CH$ | H | H | O | H | F | H | H | $CH_3$ | H |
| 15 | 18DB | $CCl_3$ | $(CH_3)_2CH$ | H | H | O | F | H | H | $CH_3$ | H | H |
| 15 | 19DB | $CCl_3$ | $(CH_3)_2CH$ | H | H | O | H | H | F | H | $CH_3$ | H |
| 15 | 20DB | $CCl_3$ | $(CH_3)_2CH$ | H | H | O | F | H | H | H | H | $CH_3$ |
| 15 | 21DB | $CCl_3$ | $(CH_3)_2CH$ | H | H | O | F | H | H | H | $CF_3$ | H |
| 15 | 22DB | $CCl_3$ | $(CH_3)_2CH$ | H | H | O | Cl | H | H | H | $CF_3$ | H |
| 15 | 23DB | $CCl_3$ | $(CH_3)_2CH$ | H | H | O | H | F | H | $CF_3$ | H | H |
| 15 | 24DB | $CCl_3$ | $(CH_3)_2CH$ | H | H | O | H | H | F | $CF_3$ | H | H |
| 15 | 25DB | $CCl_3$ | $(CH_3)_2CH$ | H | H | O | H | F | H | H | $CF_3$ | H |
| 15 | 26DB | $CCl_3$ | $(CH_3)_2CH$ | H | H | O | H | H | F | H | $CF_3$ | H |
| 15 | 27DB | $CCl_3$ | $(CH_3)_2CH$ | H | H | O | H | $OCF_3$ | H | H | H | $OCF_3$ |
| 16 | 1DB | $CHCl_2$ | H | H | H | O | H | $OCF_3$ | H | H | $OCF_3$ | H |
| 16 | 2DB | $CHCl_2$ | H | H | H | O | H | Cl | H | H | H | $CF_3$ |
| 16 | 3DB | $CHCl_2$ | H | H | H | O | H | Br | H | H | $OCF_3$ | H |
| 16 | 4DB | $CHCl_2$ | H | H | H | O | H | Cl | H | H | $OCF_3$ | H |
| 16 | 5DB | $CHCl_2$ | H | H | H | O | H | Cl | H | H | $CF_3$ | H |
| 16 | 6DB | $CHCl_2$ | H | H | H | O | H | H | Cl | H | $CF_3$ | H |
| 16 | 7DB | $CHCl_2$ | H | H | H | O | H | F | H | H | $OCF_3$ | H |
| 16 | 8DB | $CHCl_2$ | H | H | H | O | H | H | Cl | H | H | $CF_3$ |
| 16 | 9DB | $CHCl_2$ | H | H | H | O | H | F | H | H | H | $CF_3$ |
| 16 | 10DB | $CHCl_2$ | H | H | H | O | H | H | F | H | H | $CF_3$ |
| 16 | 11DB | $CHCl_2$ | H | H | H | O | F | H | H | H | H | $CF_3$ |
| 16 | 12DB | $CHCl_2$ | H | H | H | O | H | Cl | H | $CF_3$ | H | H |
| 16 | 13DB | $CHCl_2$ | H | H | H | O | H | H | Cl | $CF_3$ | H | H |
| 16 | 14DB | $CHCl_2$ | H | H | H | O | Cl | H | H | $CF_3$ | H | H |
| 16 | 15DB | $CHCl_2$ | H | H | H | O | H | F | H | $CH_3$ | H | H |
| 16 | 16DB | $CHCl_2$ | H | H | H | O | H | H | F | H | H | $CH_3$ |
| 16 | 17DB | $CHCl_2$ | H | H | H | O | H | F | H | H | $CH_3$ | H |
| 16 | 18DB | $CHCl_2$ | H | H | H | O | F | H | H | $CH_3$ | H | H |
| 16 | 19DB | $CHCl_2$ | H | H | H | O | H | H | F | H | $CH_3$ | H |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

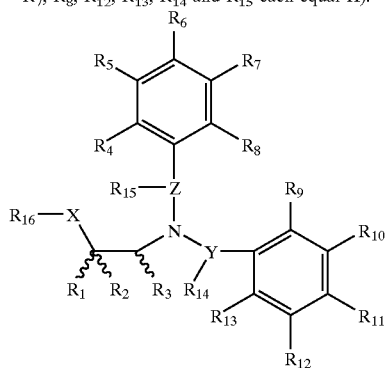

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 16 | 20DB | CHCl$_2$ | H | H | H | O | F | H | H | H | H | CH$_3$ |
| 16 | 21DB | CHCl$_2$ | H | H | H | O | F | H | H | H | CF$_3$ | H |
| 16 | 22DB | CHCl$_2$ | H | H | H | O | Cl | H | H | H | CF$_3$ | H |
| 16 | 23DB | CHCl$_2$ | H | H | H | O | H | F | H | CF$_3$ | H | H |
| 16 | 24DB | CHCl$_2$ | H | H | H | O | H | H | F | CF$_3$ | H | H |
| 16 | 25DB | CHCl$_2$ | H | H | H | O | H | F | H | H | CF$_3$ | H |
| 16 | 26DB | CHCl$_2$ | H | H | H | O | H | H | F | H | CF$_3$ | H |
| 16 | 27DB | CHCl$_2$ | H | H | H | O | H | OCF$_3$ | H | H | H | OCF$_3$ |
| 18 | 1DB | CF$_3$ | H | CH$_3$ | H | O | H | OCF$_3$ | H | H | OCF$_3$ | H |
| 18 | 2DB | CF$_3$ | H | CH$_3$ | H | O | H | Cl | H | H | H | CF$_3$ |
| 18 | 3DB | CF$_3$ | H | CH$_3$ | H | O | H | Br | H | H | OCF$_3$ | H |
| 18 | 4DB | CF$_3$ | H | CH$_3$ | H | O | H | Cl | H | H | OCF$_3$ | H |
| 18 | 5DB | CF$_3$ | H | CH$_3$ | H | O | H | Cl | H | H | CF$_3$ | H |
| 18 | 6DB | CF$_3$ | H | CH$_3$ | H | O | H | H | Cl | H | CF$_3$ | H |
| 18 | 7DB | CF$_3$ | H | CH$_3$ | H | O | H | F | H | H | OCF$_3$ | H |
| 18 | 8DB | CF$_3$ | H | CH$_3$ | H | O | H | H | Cl | H | H | CF$_3$ |
| 18 | 9DB | CF$_3$ | H | CH$_3$ | H | O | H | F | H | H | H | CF$_3$ |
| 18 | 10DB | CF$_3$ | H | CH$_3$ | H | O | H | H | F | H | H | CF$_3$ |
| 18 | 11DB | CF$_3$ | H | CH$_3$ | H | O | F | H | H | H | H | CF$_3$ |
| 18 | 12DB | CF$_3$ | H | CH$_3$ | H | O | H | Cl | H | CF$_3$ | H | H |
| 18 | 13DB | CF$_3$ | H | CH$_3$ | H | O | H | H | Cl | CF$_3$ | H | H |
| 18 | 14DB | CF$_3$ | H | CH$_3$ | H | O | Cl | H | H | CF$_3$ | H | H |
| 18 | 15DB | CF$_3$ | H | CH$_3$ | H | O | H | F | H | CH$_3$ | H | H |
| 18 | 16DB | CF$_3$ | H | CH$_3$ | H | O | H | H | F | H | H | CH$_3$ |
| 18 | 17DB | CF$_3$ | H | CH$_3$ | H | O | H | F | H | H | CH$_3$ | H |
| 18 | 18DB | CF$_3$ | H | CH$_3$ | H | O | F | H | H | CH$_3$ | H | H |
| 18 | 19DB | CF$_3$ | H | CH$_3$ | H | O | H | H | F | H | CH$_3$ | H |
| 18 | 20DB | CF$_3$ | H | CH$_3$ | H | O | F | H | H | H | H | CH$_3$ |
| 18 | 21DB | CF$_3$ | H | CH$_3$ | H | O | F | H | H | H | CF$_3$ | H |
| 18 | 22DB | CF$_3$ | H | CH$_3$ | H | O | Cl | H | H | H | CF$_3$ | H |
| 18 | 23DB | CF$_3$ | H | CH$_3$ | H | O | H | F | H | CF$_3$ | H | H |
| 18 | 24DB | CF$_3$ | H | CH$_3$ | H | O | H | H | F | CF$_3$ | H | H |
| 18 | 25DB | CF$_3$ | H | CH$_3$ | H | O | H | F | H | H | CF$_3$ | H |
| 18 | 26DB | CF$_3$ | H | CH$_3$ | H | O | H | H | F | H | CF$_3$ | H |
| 18 | 27DB | CF$_3$ | H | CH$_3$ | H | O | H | OCF$_3$ | H | H | H | OCF$_3$ |
| 19 | 1DB | CF$_3$ | CF$_3$ | H | H | N | H | OCF$_3$ | H | H | OCF$_3$ | H |
| 19 | 2DB | CF$_3$ | CF$_3$ | H | H | N | H | Cl | H | H | H | CF$_3$ |
| 19 | 3DB | CF$_3$ | CF$_3$ | H | H | N | H | Br | H | H | OCF$_3$ | H |
| 19 | 4DB | CF$_3$ | CF$_3$ | H | H | N | H | Cl | H | H | OCF$_3$ | H |
| 19 | 5DB | CF$_3$ | CF$_3$ | H | H | N | H | Cl | H | H | CF$_3$ | H |
| 19 | 6DB | CF$_3$ | CF$_3$ | H | H | N | H | H | Cl | H | CF$_3$ | H |
| 19 | 7DB | CF$_3$ | CF$_3$ | H | H | N | H | F | H | H | OCF$_3$ | H |
| 19 | 8DB | CF$_3$ | CF$_3$ | H | H | N | H | H | Cl | H | H | CF$_3$ |
| 19 | 9DB | CF$_3$ | CF$_3$ | H | H | N | H | F | H | H | H | CF$_3$ |
| 19 | 10DB | CF$_3$ | CF$_3$ | H | H | N | H | H | F | H | H | CF$_3$ |
| 19 | 11DB | CF$_3$ | CF$_3$ | H | H | N | F | H | H | H | H | CF$_3$ |
| 19 | 12DB | CF$_3$ | CF$_3$ | H | H | N | H | Cl | H | CF$_3$ | H | H |
| 19 | 13DB | CF$_3$ | CF$_3$ | H | H | N | H | H | Cl | CF$_3$ | H | H |
| 19 | 14DB | CF$_3$ | CF$_3$ | H | H | N | Cl | H | H | CF$_3$ | H | H |
| 19 | 15DB | CF$_3$ | CF$_3$ | H | H | N | H | F | H | CH$_3$ | H | H |
| 19 | 16DB | CF$_3$ | CF$_3$ | H | H | N | H | H | F | H | H | CH$_3$ |
| 19 | 17DB | CF$_3$ | CF$_3$ | H | H | N | H | F | H | H | CH$_3$ | H |
| 19 | 18DB | CF$_3$ | CF$_3$ | H | H | N | F | H | H | CH$_3$ | H | H |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

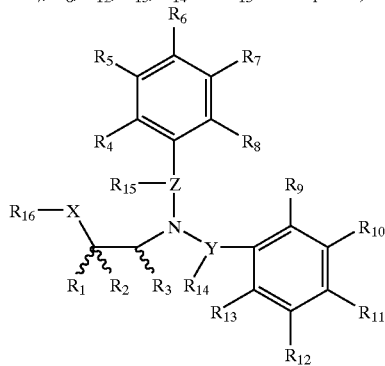

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 19 | 19DB | $CF_3$ | $CF_3$ | H | H | N | H | H | F | H | $CH_3$ | H |
| 19 | 20DB | $CF_3$ | $CF_3$ | H | H | N | F | H | H | H | H | $CH_3$ |
| 19 | 21DB | $CF_3$ | $CF_3$ | H | H | N | F | H | H | H | $CF_3$ | H |
| 19 | 22DB | $CF_3$ | $CF_3$ | H | H | N | Cl | H | H | H | $CF_3$ | H |
| 19 | 23DB | $CF_3$ | $CF_3$ | H | H | N | H | F | H | $CF_3$ | H | H |
| 19 | 24DB | $CF_3$ | $CF_3$ | H | H | N | H | H | F | $CF_3$ | H | H |
| 19 | 25DB | $CF_3$ | $CF_3$ | H | H | N | H | F | H | H | $CF_3$ | H |
| 19 | 26DB | $CF_3$ | $CF_3$ | H | H | N | H | H | F | H | $CF_3$ | H |
| 19 | 27DB | $CF_3$ | $CF_3$ | H | H | N | H | $OCF_3$ | H | H | H | $OCF_3$ |
| 20 | 1DB | $CF_3$ | H | H | H | N | H | $OCF_3$ | H | H | $OCF_3$ | H |
| 20 | 2DB | $CF_3$ | H | H | H | N | H | Cl | H | H | H | $CF_3$ |
| 20 | 3DB | $CF_3$ | H | H | H | N | H | Br | H | H | $OCF_3$ | H |
| 20 | 4DB | $CF_3$ | H | H | H | N | H | Cl | H | H | $OCF_3$ | H |
| 20 | 5DB | $CF_3$ | H | H | H | N | H | Cl | H | H | $CF_3$ | H |
| 20 | 6DB | $CF_3$ | H | H | H | N | H | H | Cl | H | $CF_3$ | H |
| 20 | 7DB | $CF_3$ | H | H | H | N | H | F | H | H | $OCF_3$ | H |
| 20 | 8DB | $CF_3$ | H | H | H | N | H | H | Cl | H | H | $CF_3$ |
| 20 | 9DB | $CF_3$ | H | H | H | N | H | F | H | H | H | $CF_3$ |
| 20 | 10DB | $CF_3$ | H | H | H | N | H | H | F | H | H | $CF_3$ |
| 20 | 11DB | $CF_3$ | H | H | H | N | F | H | H | H | H | $CF_3$ |
| 20 | 12DB | $CF_3$ | H | H | H | N | H | Cl | H | $CF_3$ | H | H |
| 20 | 13DB | $CF_3$ | H | H | H | N | H | H | Cl | $CF_3$ | H | H |
| 20 | 14DB | $CF_3$ | H | H | H | N | Cl | H | H | $CF_3$ | H | H |
| 20 | 15DB | $CF_3$ | H | H | H | N | H | F | H | $CH_3$ | H | H |
| 20 | 16DB | $CF_3$ | H | H | H | N | H | H | F | H | H | $CH_3$ |
| 20 | 17DB | $CF_3$ | H | H | H | N | H | F | H | H | $CH_3$ | H |
| 20 | 18DB | $CF_3$ | H | H | H | N | F | H | H | $CH_3$ | H | H |
| 20 | 19DB | $CF_3$ | H | H | H | N | H | H | F | H | $CH_3$ | H |
| 20 | 20DB | $CF_3$ | H | H | H | N | F | H | H | H | H | $CH_3$ |
| 20 | 21DB | $CF_3$ | H | H | H | N | F | H | H | H | $CF_3$ | H |
| 20 | 22DB | $CF_3$ | H | H | H | N | Cl | H | H | H | $CF_3$ | H |
| 20 | 23DB | $CF_3$ | H | H | H | N | H | F | H | $CF_3$ | H | H |
| 20 | 24DB | $CF_3$ | H | H | H | N | H | H | F | $CF_3$ | H | H |
| 20 | 25DB | $CF_3$ | H | H | H | N | H | F | H | H | $CF_3$ | H |
| 20 | 26DB | $CF_3$ | H | H | H | N | H | H | F | H | $CF_3$ | H |
| 20 | 27DB | $CF_3$ | H | H | H | N | H | $OCF_3$ | H | H | H | $OCF_3$ |
| 23 | 1DB | $CF_3$ | H | H | $CH_3$ | N | H | $OCF_3$ | H | H | $OCF_3$ | H |
| 23 | 2DB | $CF_3$ | H | H | $CH_3$ | N | H | Cl | H | H | H | $CF_3$ |
| 23 | 3DB | $CF_3$ | H | H | $CH_3$ | N | H | Br | H | H | $OCF_3$ | H |
| 23 | 4DB | $CF_3$ | H | H | $CH_3$ | N | H | Cl | H | H | $OCF_3$ | H |
| 23 | 5DB | $CF_3$ | H | H | $CH_3$ | N | H | Cl | H | H | $CF_3$ | H |
| 23 | 6DB | $CF_3$ | H | H | $CH_3$ | N | H | H | Cl | H | $CF_3$ | H |
| 23 | 7DB | $CF_3$ | H | H | $CH_3$ | N | H | F | H | H | $OCF_3$ | H |
| 23 | 8DB | $CF_3$ | H | H | $CH_3$ | N | H | H | Cl | H | H | $CF_3$ |
| 23 | 9DB | $CF_3$ | H | H | $CH_3$ | N | H | F | H | H | H | $CF_3$ |
| 23 | 10DB | $CF_3$ | H | H | $CH_3$ | N | H | H | F | H | H | $CF_3$ |
| 24 | 11DB | $CF_3$ | H | H | $CH_3$ | N | F | H | H | H | H | $CF_3$ |
| 24 | 12DB | $CF_3$ | H | H | $CH_3$ | N | H | Cl | H | $CF_3$ | H | H |
| 24 | 13DB | $CF_3$ | H | H | $CH_3$ | N | H | H | Cl | $CF_3$ | H | H |
| 24 | 14DB | $CF_3$ | H | H | $CH_3$ | N | Cl | H | H | $CF_3$ | H | H |
| 24 | 15DB | $CF_3$ | H | H | $CH_3$ | N | H | F | H | $CH_3$ | H | H |
| 24 | 16DB | $CF_3$ | H | H | $CH_3$ | N | H | H | F | H | H | $CH_3$ |
| 24 | 17DB | $CF_3$ | H | H | $CH_3$ | N | H | F | H | H | $CH_3$ | H |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

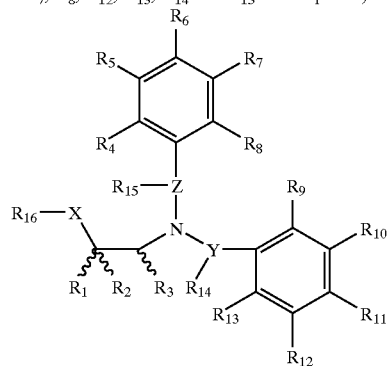

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 24 | 18DB | CF$_3$ | H | H | CH$_3$ | N | F | H | H | CH$_3$ | H | H |
| 23 | 19DB | CF$_3$ | H | H | CH$_3$ | N | H | H | F | H | CH$_3$ | H |
| 23 | 20DB | CF$_3$ | H | H | CH$_3$ | N | F | H | H | H | H | CH$_3$ |
| 23 | 21DB | CF$_3$ | H | H | CH$_3$ | N | F | H | H | H | CF$_3$ | H |
| 23 | 22DB | CF$_3$ | H | H | CH$_3$ | N | Cl | H | H | H | CF$_3$ | H |
| 23 | 23DB | CF$_3$ | H | H | CH$_3$ | N | H | F | H | CF$_3$ | H | H |
| 23 | 24DB | CF$_3$ | H | H | CH$_3$ | N | H | H | F | CF$_3$ | H | H |
| 23 | 25DB | CF$_3$ | H | H | CH$_3$ | N | H | F | H | H | CF$_3$ | H |
| 23 | 26DB | CF$_3$ | H | H | CH$_3$ | N | H | H | F | H | CF$_3$ | H |
| 23 | 27DB | CF$_3$ | H | H | CH$_3$ | N | H | OCF$_3$ | H | H | H | OCF$_3$ |
| 25 | 1DB | CF$_3$ | H | H | H | S | H | OCF$_3$ | H | H | OCF$_3$ | H |
| 25 | 2DB | CF$_3$ | H | H | H | S | H | Cl | H | H | H | CF$_3$ |
| 25 | 3DB | CF$_3$ | H | H | H | S | H | Br | H | H | OCF$_3$ | H |
| 25 | 4DB | CF$_3$ | H | H | H | S | H | Cl | H | H | OCF$_3$ | H |
| 25 | 5DB | CF$_3$ | H | H | H | S | H | Cl | H | H | CF$_3$ | H |
| 25 | 6DB | CF$_3$ | H | H | H | S | H | H | Cl | H | CF$_3$ | H |
| 25 | 7DB | CF$_3$ | H | H | H | S | H | F | H | H | OCF$_3$ | H |
| 25 | 8DB | CF$_3$ | H | H | H | S | H | H | Cl | H | H | CF$_3$ |
| 25 | 9DB | CF$_3$ | H | H | H | S | H | F | H | H | H | CF$_3$ |
| 25 | 10DB | CF$_3$ | H | H | H | S | H | H | F | H | H | CF$_3$ |
| 25 | 11DB | CF$_3$ | H | H | H | S | F | H | H | H | H | CF$_3$ |
| 25 | 12DB | CF$_3$ | H | H | H | S | H | Cl | H | CF$_3$ | H | H |
| 25 | 13DB | CF$_3$ | H | H | H | S | H | H | Cl | CF$_3$ | H | H |
| 25 | 14DB | CF$_3$ | H | H | H | S | Cl | H | H | CF$_3$ | H | H |
| 25 | 15DB | CF$_3$ | H | H | H | S | H | F | H | CH$_3$ | H | H |
| 25 | 16DB | CF$_3$ | H | H | H | S | H | H | F | H | H | CH$_3$ |
| 25 | 17DB | CF$_3$ | H | H | H | S | H | F | H | H | CH$_3$ | H |
| 25 | 18DB | CF$_3$ | H | H | H | S | F | H | H | CH$_3$ | H | H |
| 25 | 19DB | CF$_3$ | H | H | H | S | H | H | F | H | CH$_3$ | H |
| 25 | 20DB | CF$_3$ | H | H | H | S | F | H | H | H | H | CH$_3$ |
| 25 | 21DB | CF$_3$ | H | H | H | S | F | H | H | H | CF$_3$ | H |
| 25 | 22DB | CF$_3$ | H | H | H | S | Cl | H | H | H | CF$_3$ | H |
| 25 | 23DB | CF$_3$ | H | H | H | S | H | F | H | CF$_3$ | H | H |
| 25 | 24DB | CF$_3$ | H | H | H | S | H | H | F | CF$_3$ | H | H |
| 25 | 25DB | CF$_3$ | H | H | H | S | H | F | H | H | CF$_3$ | H |
| 25 | 26DB | CF$_3$ | H | H | H | S | H | H | F | H | CF$_3$ | H |
| 25 | 27DB | CF$_3$ | H | H | H | S | H | OCF$_3$ | H | H | H | OCF$_3$ |
| 26 | 1DB | CF$_3$CF$_2$ | H | H | H | S | H | OCF$_3$ | H | H | OCF$_3$ | H |
| 26 | 2DB | CF$_3$CF$_2$ | H | H | H | S | H | Cl | H | H | H | CF$_3$ |
| 26 | 3DB | CF$_3$CF$_2$ | H | H | H | S | H | Br | H | H | OCF$_3$ | H |
| 26 | 4DB | CF$_3$CF$_2$ | H | H | H | S | H | Cl | H | H | OCF$_3$ | H |
| 26 | 5DB | CF$_3$CF$_2$ | H | H | H | S | H | Cl | H | H | CF$_3$ | H |
| 26 | 6DB | CF$_3$CF$_2$ | H | H | H | S | H | H | Cl | H | CF$_3$ | H |
| 26 | 7DB | CF$_3$CF$_2$ | H | H | H | S | H | F | H | H | OCF$_3$ | H |
| 26 | 8DB | CF$_3$CF$_2$ | H | H | H | S | H | H | Cl | H | H | CF$_3$ |
| 26 | 9DB | CF$_3$CF$_2$ | H | H | H | S | H | F | H | H | H | CF$_3$ |
| 26 | 10DB | CF$_3$CF$_2$ | H | H | H | S | H | H | F | H | H | CF$_3$ |
| 26 | 11DB | CF$_3$CF$_2$ | H | H | H | S | F | H | H | H | H | CF$_3$ |
| 26 | 12DB | CF$_3$CF$_2$ | H | H | H | S | H | Cl | H | CF$_3$ | H | H |
| 26 | 13DB | CF$_3$CF$_2$ | H | H | H | S | H | H | Cl | CF$_3$ | H | H |
| 26 | 14DB | CF$_3$CF$_2$ | H | H | H | S | Cl | H | H | CF$_3$ | H | H |
| 26 | 15DB | CF$_3$CF$_2$ | H | H | H | S | H | F | H | CH$_3$ | H | H |
| 26 | 16DB | CF$_3$CF$_2$ | H | H | H | S | H | H | F | H | H | CH$_3$ |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

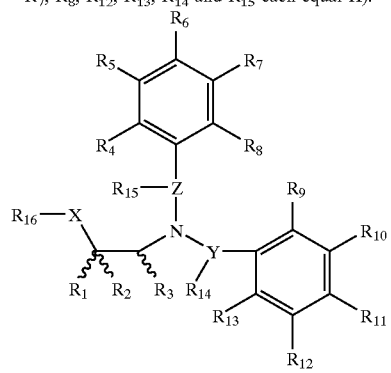

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 26 | 17DB | CF$_3$CF$_2$ | H | H | H | S | H | F | H | H | CH$_3$ | H |
| 26 | 18DB | CF$_3$CF$_2$ | H | H | H | S | F | H | H | CH$_3$ | H | H |
| 26 | 19DB | CF$_3$CF$_2$ | H | H | H | S | H | H | F | H | CH$_3$ | H |
| 26 | 20DB | CF$_3$CF$_2$ | H | H | H | S | F | H | H | H | H | CH$_3$ |
| 26 | 21DB | CF$_3$CF$_2$ | H | H | H | S | F | H | H | H | CF$_3$ | H |
| 26 | 22DB | CF$_3$CF$_2$ | H | H | H | S | Cl | H | H | H | CF$_3$ | H |
| 26 | 23DB | CF$_3$CF$_2$ | H | H | H | S | H | F | H | CF$_3$ | H | H |
| 26 | 24DB | CF$_3$CF$_2$ | H | H | H | S | H | H | F | CF$_3$ | H | H |
| 26 | 25DB | CF$_3$CF$_2$ | H | H | H | S | H | F | H | H | CF$_3$ | H |
| 26 | 26DB | CF$_3$CF$_2$ | H | H | H | S | H | H | F | H | CF$_3$ | H |
| 26 | 27DB | CF$_3$CF$_2$ | H | H | H | S | H | OCF$_3$ | H | H | H | OCF$_3$ |
| 27 | 1DB | CCl$_3$CH$_2$ | H | H | H | O | H | OCF$_3$ | H | H | OCF$_3$ | H |
| 27 | 2DB | CCl$_3$CH$_2$ | H | H | H | O | H | Cl | H | H | H | CF$_3$ |
| 27 | 3DB | CCl$_3$CH$_2$ | H | H | H | O | H | Br | H | H | OCF$_3$ | H |
| 27 | 4DB | CCl$_3$CH$_2$ | H | H | H | O | H | Cl | H | H | OCF$_3$ | H |
| 27 | 5DB | CCl$_3$CH$_2$ | H | H | H | O | H | Cl | H | H | CF$_3$ | H |
| 27 | 6DB | CCl$_3$CH$_2$ | H | H | H | O | H | H | Cl | H | CF$_3$ | H |
| 27 | 7DB | CCl$_3$CH$_2$ | H | H | H | O | H | F | H | H | OCF$_3$ | H |
| 27 | 8DB | CCl$_3$CH$_2$ | H | H | H | O | H | H | Cl | H | H | CF$_3$ |
| 27 | 9DB | CCl$_3$CH$_2$ | H | H | H | O | H | F | H | H | H | CF$_3$ |
| 27 | 10DB | CCl$_3$CH$_2$ | H | H | H | O | H | H | F | H | H | CF$_3$ |
| 27 | 11DB | CCl$_3$CH$_2$ | H | H | H | O | F | H | H | H | H | CF$_3$ |
| 27 | 12DB | CCl$_3$CH$_2$ | H | H | H | O | H | Cl | H | CF$_3$ | H | H |
| 27 | 13DB | CCl$_3$CH$_2$ | H | H | H | O | H | H | Cl | CF$_3$ | H | H |
| 27 | 14DB | CCl$_3$CH$_2$ | H | H | H | O | Cl | H | H | CF$_3$ | H | H |
| 27 | 15DB | CCl$_3$CH$_2$ | H | H | H | O | H | F | H | CH$_3$ | H | H |
| 27 | 16DB | CCl$_3$CH$_2$ | H | H | H | O | H | H | F | H | H | CH$_3$ |
| 27 | 17DB | CCl$_3$CH$_2$ | H | H | H | O | H | F | H | H | CH$_3$ | H |
| 27 | 18DB | CCl$_3$CH$_2$ | H | H | H | O | F | H | H | CH$_3$ | H | H |
| 27 | 19DB | CCl$_3$CH$_2$ | H | H | H | O | H | H | F | H | CH$_3$ | H |
| 27 | 20DB | CCl$_3$CH$_2$ | H | H | H | O | F | H | H | H | H | CH$_3$ |
| 27 | 21DB | CCl$_3$CH$_2$ | H | H | H | O | F | H | H | H | CF$_3$ | H |
| 27 | 22DB | CCl$_3$CH$_2$ | H | H | H | O | Cl | H | H | H | CF$_3$ | H |
| 27 | 23DB | CCl$_3$CH$_2$ | H | H | H | O | H | F | H | CF$_3$ | H | H |
| 27 | 24DB | CCl$_3$CH$_2$ | H | H | H | O | H | H | F | CF$_3$ | H | H |
| 27 | 25DB | CCl$_3$CH$_2$ | H | H | H | O | H | F | H | H | CF$_3$ | H |
| 27 | 26DB | CCl$_3$CH$_2$ | H | H | H | O | H | H | F | H | CF$_3$ | H |
| 27 | 27DB | CCl$_3$CH$_2$ | H | H | H | O | H | OCF$_3$ | H | H | H | OCF$_3$ |
| 28 | 1DB | CBr$_3$CH$_2$ | H | H | H | O | H | OCF$_3$ | H | H | OCF$_3$ | H |
| 28 | 2DB | CBr$_3$CH$_2$ | H | H | H | O | H | Cl | H | H | H | CF$_3$ |
| 28 | 3DB | CBr$_3$CH$_2$ | H | H | H | O | H | Br | H | H | OCF$_3$ | H |
| 28 | 4DB | CBr$_3$CH$_2$ | H | H | H | O | H | Cl | H | H | OCF$_3$ | H |
| 28 | 5DB | CBr$_3$CH$_2$ | H | H | H | O | H | Cl | H | H | CF$_3$ | H |
| 28 | 6DB | CBr$_3$CH$_2$ | H | H | H | O | H | H | Cl | H | CF$_3$ | H |
| 28 | 7DB | CBr$_3$CH$_2$ | H | H | H | O | H | F | H | H | OCF$_3$ | H |
| 28 | 8DB | CBr$_3$CH$_2$ | H | H | H | O | H | H | Cl | H | H | CF$_3$ |
| 28 | 9DB | CBr$_3$CH$_2$ | H | H | H | O | H | F | H | H | H | CF$_3$ |
| 28 | 10DB | CBr$_3$CH$_2$ | H | H | H | O | H | H | F | H | H | CF$_3$ |
| 28 | 11DB | CBr$_3$CH$_2$ | H | H | H | O | F | H | H | H | H | CF$_3$ |
| 28 | 12DB | CBr$_3$CH$_2$ | H | H | H | O | H | Cl | H | CF$_3$ | H | H |
| 28 | 13DB | CBr$_3$CH$_2$ | H | H | H | O | H | H | Cl | CF$_3$ | H | H |
| 28 | 14DB | CBr$_3$CH$_2$ | H | H | H | O | Cl | H | H | CF$_3$ | H | H |
| 28 | 15DB | CBr$_3$CH$_2$ | H | H | H | O | H | F | H | CH$_3$ | H | H |

TABLE 12-continued

Structure of Substituted Phenyltertiary-2-Heteroalkylamines (Z and Y are each CH; $R_7$, $R_8$, $R_{12}$, $R_{13}$, $R_{14}$ and $R_{15}$ each equal H).

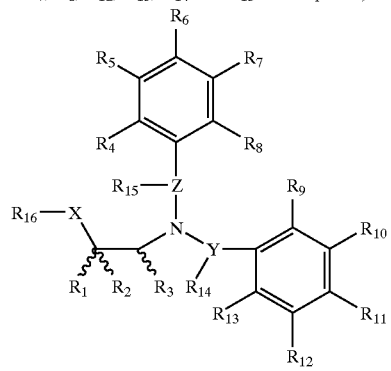

Inhibitor Number
Column 1 + Column 2

| Reagent | Reagent | $R_1$ | $R_2$ | $R_3$ | $R_{16}$ | X | $R_4$ | $R_5$ | $R_6$ | $R_9$ | $R_{10}$ | $R_{11}$ |
|---|---|---|---|---|---|---|---|---|---|---|---|---|
| 28 | 16DB | $CBr_3CH_2$ | H | H | H | O | H | H | F | H | H | $CH_3$ |
| 28 | 17DB | $CBr_3CH_2$ | H | H | H | O | H | F | H | H | $CH_3$ | H |
| 28 | 18DB | $CBr_3CH_2$ | H | H | H | O | F | H | H | $CH_3$ | H | H |
| 28 | 19DB | $CBr_3CH_2$ | H | H | H | O | H | H | F | H | $CH_3$ | H |
| 28 | 20DB | $CBr_3CH_2$ | H | H | H | O | F | H | H | H | H | $CH_3$ |
| 28 | 21DB | $CBr_3CH_2$ | H | H | H | O | F | H | H | H | $CF_3$ | H |
| 28 | 22DB | $CBr_3CH_2$ | H | H | H | O | Cl | H | H | H | $CF_3$ | H |
| 28 | 23DB | $CBr_3CH_2$ | H | H | H | O | H | F | H | $CF_3$ | H | H |
| 28 | 24DB | $CBr_3CH_2$ | H | H | H | O | H | H | F | $CF_3$ | H | H |
| 28 | 25DB | $CBr_3CH_2$ | H | H | H | O | H | F | H | H | $CF_3$ | H |
| 28 | 26DB | $CBr_3CH_2$ | H | H | H | O | H | H | F | H | $CF_3$ | H |
| 28 | 27DB | $CBr_3CH_2$ | H | H | H | O | H | $OCF_3$ | H | H | H | $OCF_3$ |

TABLE 13

Structure of "Generic Secondary Amine" Reagents ($R_{13}$ is H; $R_{14}$ is H or not present when Y = covalent bond (XIII)

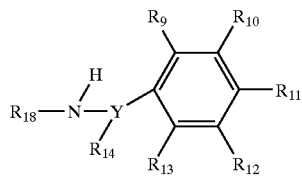

| Reagent Number | $R_{18}$ | $R_9$ | $R_{10}$ | $R_{11}$ | $R_{12}$ | Y |
|---|---|---|---|---|---|---|
| 1BN | ![fluorene] | H | $OCF_3$ | H | H | CH |
| 2BN | ![naphthyl] | H | $OCF_3$ | H | H | CH |
| 3BN | ![dibenzofuran] | H | $OCF_3$ | H | H | CH |

TABLE 13-continued

Structure of "Generic Secondary Amine" Reagents ($R_{13}$ is H; $R_{14}$ is H or not present when Y = covalent bond (XIII)

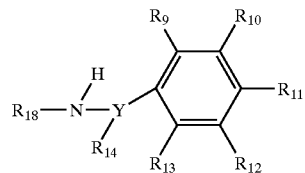

| Reagent Number | $R_{18}$ | $R_9$ | $R_{10}$ | $R_{11}$ | $R_{12}$ | Y |
|---|---|---|---|---|---|---|
| 4BN | 4-methylcyclohexyl | H | $CF_3$ | H | H | CH |
| 5BN | cyclopropyl | H | $OCF_3$ | H | H | CH |
| 6BN | isopropyl | H | $OCF_3$ | H | H | CH |
| 7BN | propyl | H | $OCF_3$ | H | H | CH |
| 8BN | cyclopentyl | H | $OCF_3$ | H | H | CH |
| 9BN | 2-(3-fluorophenyl)ethyl | H | $OCF_3$ | H | H | CH |
| 10BN | 2-(3-fluorophenyl)ethyl | H | $OCF_2CF_2H$ | H | H | CH |
| 11BN | cyclopropyl | H | H | $OCF_3$ | H | CH |
| 12BN | 1-(3-trifluoromethylphenyl)ethyl (with C=O) | H | F | H | H | covalent bond |
| 13BN | 1-(3-trifluoromethylphenyl)ethyl (with C=O) | H | F | H | H | covalent bond |
| 14BN | 4-methyl-1-methoxynaphthyl | H | F | H | H | covalent bond |

TABLE 14

Structure of Substituted tertiary-2-Heteroalkylamines ($R_9$, $R_{12}$, and $R_{13}$ are each H; $R_{14}$ is H or not present when Y = covalent bond).

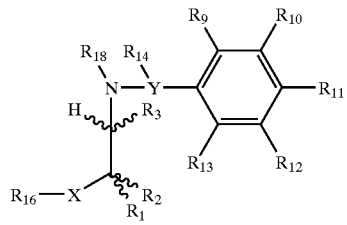

| Inhibitor Number Column1 + Column2 | | | | | | | | | | | |
|---|---|---|---|---|---|---|---|---|---|---|---|
| Reagent | Reagent | $R_1$ | $R_2$ | $R_3$ | $R_{16}$ | X | $R_{18}$ | $R_{10}$ | $R_{11}$ | Y | |
| 1 | 1BN | $CF_3$ | H | H | H | O | 2-fluorenyl | $OCF_3$ | H | CH | |
| 1 | 2BN | $CF_3$ | H | H | H | O | 2-naphthyl | $OCF_3$ | H | CH | |
| 1 | 3BN | $CF_3$ | H | H | H | O | dibenzofuranyl | $OCF_3$ | H | CH | |
| 1 | 4BN | $CF_3$ | H | H | H | O | 4-methylcyclohexyl | $CF_3$ | H | CH | |
| 1 | 5BN | $CF_3$ | H | H | H | O | cyclopropyl | $OCF_3$ | H | CH | |
| 1 | 6BN | $CF_3$ | H | H | H | O | isopropyl | $OCF_3$ | H | CH | |
| 1 | 7BN | $CF_3$ | H | H | H | O | propyl | $OCF_3$ | H | CH | |
| 1 | 8BN | $CF_3$ | H | H | H | O | cyclopentyl | $OCF_3$ | H | CH | |
| 1 | 9BN | $CF_3$ | H | H | H | O | 2-(3-fluorophenyl)ethyl | $OCF_3$ | H | CH | |
| 1 | 10BN | $CF_3$ | H | H | Acetyl | O | 2-(3-fluorophenyl)ethyl | $OCF_2CF_2H$ | H | CH | |
| 1 | 11BN | $CF_3$ | H | H | H | O | cyclopropyl | H | $OCF_3$ | CH | |
| 1 | 12BN | $CF_3$ | H | H | H | O | 3-(trifluoromethyl)benzoyl | F | H | covalent bond | |

TABLE 14-continued

Structure of Substituted tertiary-2-Heteroalkylamines ($R_9$, $R_{12}$, and $R_{13}$ are each H; $R_{14}$ is H or not present when Y = covalent bond).

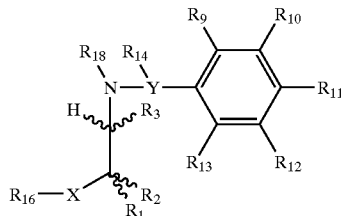

| Inhibitor Number Column1 + Column2 | | | | | | | | | | |
|---|---|---|---|---|---|---|---|---|---|---|
| Reagent | Reagent | $R_1$ | $R_2$ | $R_3$ | $R_{16}$ | X | $R_{18}$ | $R_{10}$ | $R_{11}$ | Y |
| 1 | 13BN | $CF_3$ | H | H | m-$CF_3$Benzoyl | O | m-$CF_3$-benzoyl group | F | H | covalent bond |
| 1 | 14BN | $CF_3$ | H | H | H | O | 4-methyl-1-methoxynaphthyl | F | H | covalent bond |
| 2 | 1BN | $CCl_3$ | H | H | H | O | 2-fluorenyl | $OCF_3$ | H | CH |
| 2 | 2BN | $CCl_3$ | H | H | H | O | 2-naphthyl | $OCF_3$ | H | CH |
| 2 | 3BN | $CCl_3$ | H | H | H | O | dibenzofuranyl | $OCF_3$ | H | CH |
| 2 | 4BN | $CCl_3$ | H | H | H | O | 4-methylcyclohexyl | $CF_3$ | H | CH |
| 2 | 5BN | $CCl_3$ | H | H | H | O | cyclopropylmethyl | $OCF_3$ | H | CH |
| 2 | 6BN | $CCl_3$ | H | H | H | O | isopropyl | $OCF_3$ | H | CH |
| 2 | 7BN | $CCl_3$ | H | H | H | O | propyl | $OCF_3$ | H | CH |
| 2 | 8BN | $CCl_3$ | H | H | H | O | cyclopentyl | $OCF_3$ | H | CH |
| 2 | 9BN | $CCl_3$ | H | H | H | O | 3-fluorophenethyl | $OCF_3$ | H | CH |
| 2 | 10BN | $CCl_3$ | H | H | Acetyl | O | 3-fluorophenethyl | $OCF_2CF_2H$ | H | CH |

TABLE 14-continued

Structure of Substituted tertiary-2-Heteroalkylamines ($R_9$, $R_{12}$, and $R_{13}$ are each H; $R_{14}$ is H or not present when Y = covalent bond).

| Inhibitor Number Column1 + Column2 | | | | | | | | | | | |
|---|---|---|---|---|---|---|---|---|---|---|---|
| Reagent | Reagent | $R_1$ | $R_2$ | $R_3$ | $R_{16}$ | X | $R_{18}$ | $R_{10}$ | $R_{11}$ | Y |
| 2 | 11BN | $CCl_3$ | H | H | H | O | 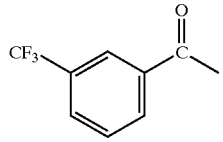 | H | $OCF_3$ | CH |
| 2 | 12BN | $CCl_3$ | H | H | H | O | 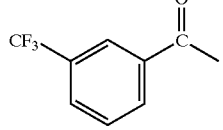 | F | H | covalent bond |
| 2 | 13BN | $CCl_3$ | H | H | m-$CF_3$Benzoyl | O | 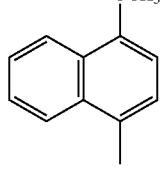 | F | H | covalent bond |
| 2 | 14BN | $CCl_3$ | H | H | H | O | 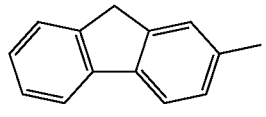 | F | H | covalent bond |
| 3 | 1BN | $CH_3$ | H | H | H | O | 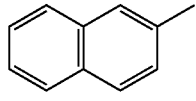 | $OCF_3$ | H | CH |
| 3 | 2BN | $CH_3$ | H | H | H | O | 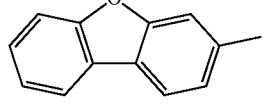 | $OCF_3$ | H | CH |
| 3 | 3BN | $CH_3$ | H | H | H | O | 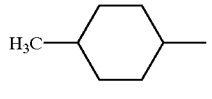 | $OCF_3$ | H | CH |
| 3 | 4BN | $CH_3$ | H | H | H | O |  | $CF_3$ | H | CH |
| 3 | 5BN | $CH_3$ | H | H | H | O |  | $OCF_3$ | H | CH |
| 3 | 6BN | $CH_3$ | H | H | H | O | isopropyl | $OCF_3$ | H | CH |
| 3 | 7BN | $CH_3$ | H | H | H | O | propyl | $OCF_3$ | H | CH |

TABLE 14-continued

Structure of Substituted tertiary-2-Heteroalkylamines ($R_9$, $R_{12}$, and $R_{13}$ are each H; $R_{14}$ is H or not present when Y = covalent bond).

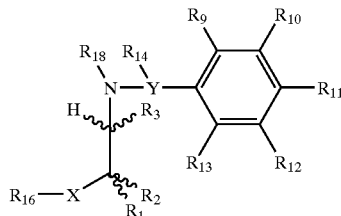

| Inhibitor Number Column1 + Column2 | | | | | | | | | | | |
|---|---|---|---|---|---|---|---|---|---|---|---|
| Reagent | Reagent | $R_1$ | $R_2$ | $R_3$ | $R_{16}$ | X | $R_{18}$ | $R_{10}$ | $R_{11}$ | Y |
| 3 | 8BN | $CH_3$ | H | H | H | O | cyclopentyl | $OCF_3$ | H | CH |
| 3 | 9BN | $CH_3$ | H | H | H | O | 3-fluorophenethyl | $OCF_3$ | H | CH |
| 3 | 10BN | $CH_3$ | H | H | Acetyl | O | 3-fluorophenethyl | $OCF_2CF_2H$ | H | CH |
| 3 | 11BN | $CH_3$ | H | H | H | O | cyclopropyl | H | $OCF_3$ | CH |
| 3 | 12BN | $CH_3$ | H | H | H | O | m-$CF_3$-benzoyl | F | H | covalent bond |
| 3 | 13BN | $CH_3$ | H | H | m-$CF_3$Benzoyl | O | m-$CF_3$-benzoyl | F | H | covalent bond |
| 3 | 14BN | $CH_3$ | H | H | H | O | 1-methoxy-4-methylnaphthyl | F | H | covalent bond |
| 4 | 1BN | $CF_3CF_2$ | H | H | H | O | 2-methylfluoren-2-yl | $OCF_3$ | H | CH |
| 4 | 2BN | $CF_3CF_2$ | H | H | H | O | 2-methylnaphthyl | $OCF_3$ | H | CH |

TABLE 14-continued

Structure of Substituted tertiary-2-Heteroalkylamines ($R_9$, $R_{12}$, and $R_{13}$ are each H; $R_{14}$ is H or not present when Y = covalent bond).

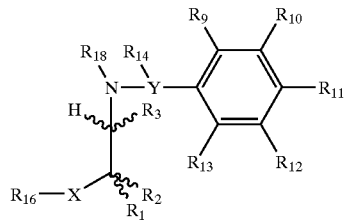

| Inhibitor Number Column1 + Column2 | | | | | | | | | | | |
|---|---|---|---|---|---|---|---|---|---|---|---|
| Reagent | Reagent | $R_1$ | $R_2$ | $R_3$ | $R_{16}$ | X | $R_{18}$ | $R_{10}$ | $R_{11}$ | Y |
| 4 | 3BN | $CF_3CF_2$ | H | H | H | O | dibenzofuranyl-methyl | $OCF_3$ | H | CH |
| 4 | 4BN | $CF_3CF_2$ | H | H | H | O | 4-methylcyclohexyl | $CF_3$ | H | CH |
| 4 | 5BN | $CF_3CF_2$ | H | H | H | O | cyclopropylmethyl | $OCF_3$ | H | CH |
| 4 | 6BN | $CF_3CF_2$ | H | H | H | O | isopropyl | $OCF_3$ | H | CH |
| 4 | 7BN | $CF_3CF_2$ | H | H | H | O | propyl | $OCF_3$ | H | CH |
| 4 | 8BN | $CF_3CF_2$ | H | H | H | O | cyclopentyl | $OCF_3$ | H | CH |
| 4 | 9BN | $CF_3CF_2$ | H | H | H | O | 3-fluorophenethyl | $OCF_3$ | H | CH |
| 4 | 10BN | $CF_3CF_2$ | H | H | Acetyl | O | 3-fluorophenethyl | $OCF_2CF_2H$ | H | CH |
| 4 | 11BN | $CF_3CF_2$ | H | H | H | O | cyclopropylmethyl | H | $OCF_3$ | CH |
| 4 | 12BN | $CF_3CF_2$ | H | H | H | O | 3-($CF_3$)benzoyl | F | H | covalent bond |
| 4 | 13BN | $CF_3CF_2$ | H | H | m-$CF_3$Benzoyl | O | 3-($CF_3$)benzoyl | F | H | covalent bond |
| 4 | 14BN | $CF_3CF_2$ | H | H | H | O | 4-methyl-1-methoxynaphthyl | F | H | covalent bond |

TABLE 14-continued

Structure of Substituted tertiary-2-Heteroalkylamines ($R_9$, $R_{12}$, and $R_{13}$ are each H; $R_{14}$ is H or not present when Y = covalent bond).

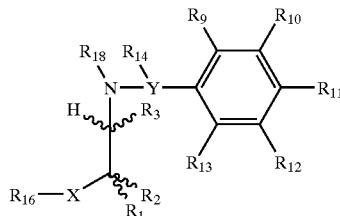

Inhibitor Number
Column1 +
Column2

| Reagent | Reagent | $R_1$ | $R_2$ | $R_3$ | $R_{16}$ | X | $R_{18}$ | $R_{10}$ | $R_{11}$ | Y |
|---|---|---|---|---|---|---|---|---|---|---|
| 5 | 1BN | $CF_3CF_2CF_2$ | H | H | H | O | fluorenyl | $OCF_3$ | H | CH |
| 5 | 2BN | $CF_3CF_2CF_2$ | H | H | H | O | naphthyl | $OCF_3$ | H | CH |
| 5 | 3BN | $CF_3CF_2CF_2$ | H | H | H | O | dibenzofuranyl | $OCF_3$ | H | CH |
| 5 | 4BN | $CF_3CF_2CF_2$ | H | H | H | O | $H_3C$-cyclohexyl | $CF_3$ | H | CH |
| 5 | 5BN | $CF_3CF_2CF_2$ | H | H | H | O | cyclopropyl | $OCF_3$ | H | CH |
| 5 | 6BN | $CF_3CF_2CF_2$ | H | H | H | O | isopropyl | $OCF_3$ | H | CH |
| 5 | 7BN | $CF_3CF_2CF_2$ | H | H | H | O | propyl | $OCF_3$ | H | CH |
| 5 | 8BN | $CF_3CF_2CF_2$ | H | H | H | O | cyclopentyl | $OCF_3$ | H | CH |
| 5 | 9BN | $CF_3CF_2CF_2$ | H | H | H | O | F-phenylethyl | $OCF_3$ | H | CH |
| 5 | 10BN | $CF_3CF_2CF_2$ | H | H | Acetyl | O | F-phenylethyl | $OCF_2CF_2H$ | H | CH |
| 5 | 11BN | $CF_3CF_2CF_2$ | H | H | H | O | cyclopropyl | H | $OCF_3$ | CH |
| 5 | 12BN | $CF_3CF_2CF_2$ | H | H | H | O | $CF_3$-phenyl-C(O)- | F | H | covalent bond |

TABLE 14-continued

Structure of Substituted tertiary-2-Heteroalkylamines ($R_9$, $R_{12}$, and $R_{13}$ are each H; $R_{14}$ is H or not present when Y = covalent bond).

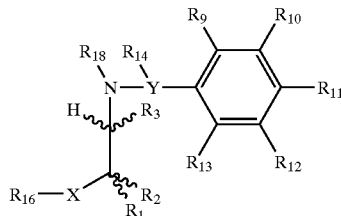

| Inhibitor Number Column1 + Column2 | | | | | | | | | | |
|---|---|---|---|---|---|---|---|---|---|---|
| Reagent | Reagent | $R_1$ | $R_2$ | $R_3$ | $R_{16}$ | X | $R_{18}$ | $R_{10}$ | $R_{11}$ | Y |
| 5 | 13BN | $CF_3CF_2CF_2$ | H | H | m-$CF_3$Benzoyl | O | 3-CF3-benzoyl group | F | H | covalent bond |
| 5 | 14BN | $CF_3CF_2CF_2$ | H | H | H | O | 4-methoxy-1-methylnaphthyl | F | H | covalent bond |
| 6 | 1BN | $CF_3OCF_2CF_2$ | H | H | H | O | 2-fluorenyl | $OCF_3$ | H | CH |
| 6 | 2BN | $CF_3OCF_2CF_2$ | H | H | H | O | 2-naphthyl | $OCF_3$ | H | CH |
| 6 | 3BN | $CF_3OCF_2CF_2$ | H | H | H | O | dibenzofuranyl | $OCF_3$ | H | CH |
| 6 | 4BN | $CF_3OCF_2CF_2$ | H | H | H | O | 4-methylcyclohexyl | $CF_3$ | H | CH |
| 6 | 5BN | $CF_3OCF_2CF_2$ | H | H | H | O | cyclopropyl | $OCF_3$ | H | CH |
| 6 | 6BN | $CF_3OCF_2CF_2$ | H | H | H | O | isopropyl | $OCF_3$ | H | CH |
| 6 | 7BN | $CF_3OCF_2CF_2$ | H | H | H | O | propyl | $OCF_3$ | H | CH |
| 6 | 8BN | $CF_3OCF_2CF_2$ | H | H | H | O | cyclopentyl | $OCF_3$ | H | CH |
| 6 | 9BN | $CF_3OCF_2CF_2$ | H | H | H | O | 2-(3-fluorophenyl)ethyl | $OCF_3$ | H | CH |
| 6 | 10BN | $CF_3OCF_2CF_2$ | H | H | Acetyl | O | 2-(3-fluorophenyl)ethyl | $OCF_2CF_2H$ | H | CH |

TABLE 14-continued

Structure of Substituted tertiary-2-Heteroalkylamines ($R_9$, $R_{12}$, and $R_{13}$ are each H; $R_{14}$ is H or not present when Y = covalent bond).

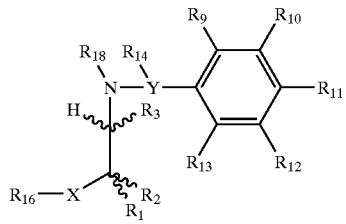

| Inhibitor Number Column1 + Column2 | | | | | | | | | | | |
|---|---|---|---|---|---|---|---|---|---|---|---|
| Reagent | Reagent | $R_1$ | $R_2$ | $R_3$ | $R_{16}$ | X | $R_{18}$ | $R_{10}$ | $R_{11}$ | Y |
| 6 | 11BN | $CF_3OCF_2CF_2$ | H | H | H | O | cyclopropyl | H | $OCF_3$ | CH |
| 6 | 12BN | $CF_3OCF_2CF_2$ | H | H | H | O | m-$CF_3$-benzoyl | F | H | covalent bond |
| 6 | 13BN | $CF_3OCF_2CF_2$ | H | H | m-$CF_3$Benzoyl | O | m-$CF_3$-benzoyl | F | H | covalent bond |
| 6 | 14BN | $CF_3OCF_2CF_2$ | H | H | H | O | 4-methyl-1-methoxynaphthyl | F | H | covalent bond |
| 7 | 1BN | $CF_3CH_2$ | H | H | H | O | 2-methylfluorenyl | $OCF_3$ | H | CH |
| 7 | 2BN | $CF_3CH_2$ | H | H | H | O | 2-methylnaphthyl | $OCF_3$ | H | CH |
| 7 | 3BN | $CF_3CH_2$ | H | H | H | O | methyldibenzofuranyl | $OCF_3$ | H | CH |
| 7 | 4BN | $CF_3CH_2$ | H | H | H | O | 4-methylcyclohexylmethyl | $CF_3$ | H | CH |
| 7 | 5BN | $CF_3CH_2$ | H | H | H | O | cyclopropyl | $OCF_3$ | H | CH |
| 7 | 6BN | $CF_3CH_2$ | H | H | H | O | isopropyl | $OCF_3$ | H | CH |
| 7 | 7BN | $CF_3CH_2$ | H | H | H | O | propyl | $OCF_3$ | H | CH |

TABLE 14-continued

Structure of Substituted tertiary-2-Heteroalkylamines ($R_9$, $R_{12}$, and $R_{13}$ are each H; $R_{14}$ is H or not present when Y = covalent bond).

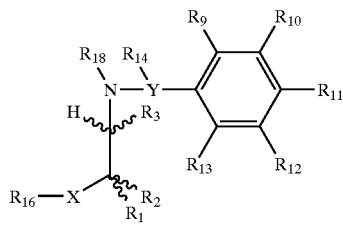

Inhibitor Number
Column1 +
Column2

| Reagent | Reagent | $R_1$ | $R_2$ | $R_3$ | $R_{16}$ | X | $R_{18}$ | $R_{10}$ | $R_{11}$ | Y |
|---|---|---|---|---|---|---|---|---|---|---|
| 7 | 8BN | $CF_3CH_2$ | H | H | H | O | cyclopentyl | $OCF_3$ | H | CH |
| 7 | 9BN | $CF_3CH_2$ | H | H | H | O | 3-F-phenylpropyl | $OCF_3$ | H | CH |
| 7 | 10BN | $CF_3CH_2$ | H | H | Acetyl | O | 3-F-phenylpropyl | $OCF_2CF_2H$ | H | CH |
| 7 | 11BN | $CF_3CH_2$ | H | H | H | O | cyclopropylmethyl | H | $OCF_3$ | CH |
| 7 | 12BN | $CF_3CH_2$ | H | H | H | O | m-$CF_3$Benzoyl | F | H | covalent bond |
| 7 | 13BN | $CF_3CH_2$ | H | H | m-$CF_3$Benzoyl | O | m-$CF_3$Benzoyl | F | H | covalent bond |
| 7 | 14BN | $CF_3CH_2$ | H | H | H | O | 4-methyl-1-methoxynaphthyl | F | H | covalent bond |

TABLE 15

Structure of Substituted Phenyl tertiary-omega-Heteroalkylamines (Y is CH; $R_8$, $R_9$, $R_{12}$, $R_{13}$, and $R_{14}$ are each H; Z is covalent bond and $R_{15}$ is absent).

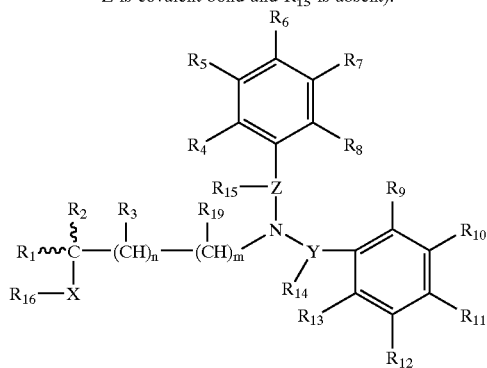

Inhibitor Number
Column1 + Column2

| Reagent | Reagent | $R_1$ | n | m | $R_2$ | $R_3$ | $XR_{16}$ | $R_4$ | $R_5$ | $R_6$ | $R_7$ | $R_{10}$ | $R_{11}$ |
|---|---|---|---|---|---|---|---|---|---|---|---|---|---|
| 1A | 1N | $CF_3$ | 1 | 1 | H | H | $CH_2OH$ | H | $C_6H_5O$ | H | H | $OCF_2CF_2H$ | H |
| 1A | 2N | $CF_3$ | 1 | 1 | H | H | $CH_2OH$ | H | $OCF_3$ | H | H | $OCF_2CF_2H$ | H |
| 1A | 3N | $CF_3$ | 1 | 1 | H | H | $CH_2OH$ | F | H | H | F | $OCF_2CF_2H$ | H |
| 1A | 4N | $CF_3$ | 1 | 1 | H | H | $CH_2OH$ | H | F | H | H | $OCF_2CF_2H$ | H |
| 1A | 5N | $CF_3$ | 1 | 1 | H | H | $CH_2OH$ | H | $C_6H_5O$ | H | H | $OCF_3$ | H |
| 1A | 6N | $CF_3$ | 1 | 1 | H | H | $CH_2OH$ | H | $OCF_3$ | H | H | $OCF_3$ | H |
| 1A | 7N | $CF_3$ | 1 | 1 | H | H | $CH_2OH$ | H | H | phenyl | H | $OCF_3$ | H |
| 1A | 8N | $CF_3$ | 1 | 1 | H | H | $CH_2OH$ | H | phenyl | H | H | $OCF_3$ | H |
| 1A | 9N | $CF_3$ | 1 | 1 | H | H | $CH_2OH$ | H | H | H | H | $OCF_3$ | H |
| 1A | 10N | $CF_3$ | 1 | 1 | H | H | $CH_2OH$ | H | Br | H | H | $OCF_3$ | H |
| 1A | 11N | $CF_3$ | 1 | 1 | H | H | $CH_2OH$ | H | $CF_3$ | F | H | $CF_3$ | H |
| 1A | 12N | $CF_3$ | 1 | 1 | H | H | $CH_2OH$ | H | $CH_3$ | H | H | $CF_3$ | H |
| 1A | 13N | $CF_3$ | 1 | 1 | H | H | $CH_2OH$ | H | $CF_3$ | H | H | $CF_3$ | H |
| 1A | 14N | $CF_3$ | 1 | 1 | H | H | $CH_2OH$ | H | $CH_3$ | H | H | $OCF_3$ | H |
| 1A | 15N | $CF_3$ | 1 | 1 | H | H | $CH_2OH$ | H | F | F | H | $OCF_3$ | H |
| 1A | 16N | $CF_3$ | 1 | 1 | H | H | $CH_2OH$ | H | Br | H | H | $CF_3$ | H |
| 1A | 17N | $CF_3$ | 1 | 1 | H | H | $CH_2OH$ | H | $CF_3$ | F | H | $OCF_3$ | H |
| 1A | 18N | $CF_3$ | 1 | 1 | H | H | $CH_2OH$ | H | F | H | H | $OCF_3$ | H |
| 1A | 19N | $CF_3$ | 1 | 1 | H | H | $CH_2OH$ | H | Cl | H | H | $OCF_3$ | H |
| 1A | 20N | $CF_3$ | 1 | 1 | H | H | $CH_2OH$ | H | F | H | H | $CF_3$ | H |
| 1A | 21N | $CF_3$ | 1 | 1 | H | H | $CH_2OH$ | H | F | F | H | $CF_3$ | H |
| 1A | 22N | $CF_3$ | 1 | 1 | H | H | $CH_2OH$ | H | Cl | H | H | $CF_3$ | H |
| 1A | 23N | $CF_3$ | 1 | 1 | H | H | $CH_2OH$ | H | F | H | H | phenoxy | H |
| 1A | 24N | $CF_3$ | 1 | 1 | H | H | $CH_2OH$ | H | $CF_3$ | Cl | H | $CH_3$ | H |
| 1A | 25N | $CF_3$ | 1 | 1 | H | H | $CH_2OH$ | H | $CF_3$ | F | H | $CH_3$ | H |
| 1A | 26N | $CF_3$ | 1 | 1 | H | H | $CH_2OH$ | H | H | H | H | $CF_3$ | H |
| 1A | 27N | $CF_3$ | 1 | 1 | H | H | $CH_2OH$ | F | F | H | H | $CF_3$ | H |
| 1A | 28N | $CF_3$ | 1 | 1 | H | H | $CH_2OH$ | H | H | $OCH_3$ | H | $CF_3$ | H |
| 1A | 29N | $CF_3$ | 1 | 1 | H | H | $CH_2OH$ | H | F | F | H | $CH_3$ | H |
| 1A | 30N | $CF_3$ | 1 | 1 | H | H | $CH_2OH$ | H | $OCH_3$ | H | H | $CH_3$ | H |
| 1A | 31N | $CF_3$ | 1 | 1 | H | H | $CH_2OH$ | H | H | $CH_3$ | H | H | H |
| 1A | 32N | $CF_3$ | 1 | 1 | H | H | $CH_2OH$ | H | Cl | H | H | H | H |
| 1A | 33N | $CF_3$ | 1 | 1 | H | H | $CH_2OH$ | H | F | H | H | F | H |
| 1A | 34N | $CF_3$ | 1 | 1 | H | H | $CH_2OH$ | H | H | $OCH_3$ | H | $CH_3$ | H |
| 1A | 35N | $CF_3$ | 1 | 1 | H | H | $CH_2OH$ | H | H | H | H | H | H |
| 1A | 36N | $CF_3$ | 1 | 1 | H | H | $CH_2OH$ | H | H | $CH_3$ | H | $CH_3$ | H |
| 1A | 37N | $CF_3$ | 1 | 1 | H | H | $CH_2OH$ | H | H | Cl | H | H | H |
| 1A | 38N | $CF_3$ | 1 | 1 | H | H | $CH_2OH$ | H | F | H | H | 3-$CF_3$-phenoxy | H |
| 1A | 39N | $CF_3$ | 1 | 1 | H | H | $CH_2OH$ | H | F | H | H | 4-$CH_3O$-phenoxy | H |
| 1A | 40N | $CF_3$ | 1 | 1 | H | H | $CH_2OH$ | H | F | H | H | 4-Cl-phenoxy | H |
| 1A | 41N | $CF_3$ | 1 | 1 | H | H | $CH_2OH$ | H | F | H | H | H | H |
| 1A | 42N | $CF_3$ | 1 | 1 | H | H | $CH_2OH$ | H | F | H | H | $CH_3$ | H |
| 1A | 43N | $CF_3$ | 1 | 1 | H | H | $CH_2OH$ | H | F | H | F | $CH_3$ | H |
| 1A | 44N | $CF_3$ | 1 | 1 | H | H | $CH_2OH$ | F | F | H | H | $CH_3$ | H |
| 1A | 45N | $CF_3$ | 1 | 1 | H | H | $CH_2OH$ | H | Cl | H | H | $CH_3$ | H |
| 1A | 46N | $CF_3$ | 1 | 1 | H | H | $CH_2OH$ | H | $CH_3$ | H | H | $CH_3$ | H |
| 1A | 47N | $CF_3$ | 1 | 1 | H | H | $CH_2OH$ | $CH_3$ | H | H | H | H | H |
| 1A | 48N | $CF_3$ | 1 | 1 | H | H | $CH_2OH$ | H | H | $CH_3$ | H | $CF_3$ | H |
| 1A | 49N | $CF_3$ | 1 | 1 | H | H | $CH_2OH$ | $CH_3$ | H | H | H | $CF_3$ | H |
| 1A | 50N | $CF_3$ | 1 | 1 | H | H | $CH_2OH$ | $CH_3$ | H | H | H | $CH_3$ | H |
| 1A | 51N | $CF_3$ | 1 | 1 | H | H | $CH_2OH$ | H | H | $CH_3$ | H | F | H |
| 1A | 52N | $CF_3$ | 1 | 1 | H | H | $CH_2OH$ | H | $CF_3$ | H | H | F | H |
| 1A | 53N | $CF_3$ | 1 | 1 | H | H | $CH_2OH$ | H | $CF_3$ | H | H | $CH_3$ | H |

TABLE 15-continued

Structure of Substituted Phenyl tertiary-omega-Heteroalkylamines (Y is CH; $R_8$, $R_9$, $R_{12}$, $R_{13}$, and $R_{14}$ are each H; Z is covalent bond and $R_{15}$ is absent).

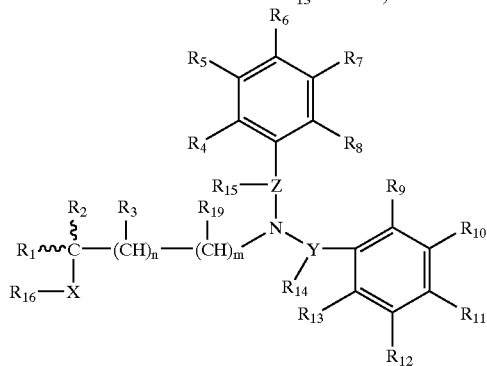

Inhibitor Number
Column1 + Column2

| Reagent | Reagent | $R_1$ | n | m | $R_2$ | $R_3$ | $XR_{16}$ | $R_4$ | $R_5$ | $R_6$ | $R_7$ | $R_{10}$ | $R_{11}$ |
|---|---|---|---|---|---|---|---|---|---|---|---|---|---|
| 1A | 54N | $CF_3$ | 1 | 1 | H | H | $CH_2OH$ | H | $OCH_3$ | H | H | $CF_3$ | H |
| 1A | 55N | $CF_3$ | 1 | 1 | H | H | $CH_2OH$ | $OCH_3$ | H | H | H | $CH_3$ | H |
| 1A | 56N | $CF_3$ | 1 | 1 | H | H | $CH_2OH$ | H | H | $CH_3$ | H | $CF_3$ | H |
| 1A | 57N | $CF_3$ | 1 | 1 | H | H | $CH_2OH$ | H | $C_6H_5O$ | H | H | H | $OCF_3$ |
| 1A | 58N | $CF_3$ | 1 | 1 | H | H | $CH_2OH$ | H | H | H | H | H | $OCF_3$ |
| 1A | 59N | $CF_3$ | 1 | 1 | H | H | $CH_2OH$ | H | $OCF_3$ | H | H | H | $OCF_3$ |
| 1A | 60N | $CF_3$ | 1 | 1 | H | H | $CH_2OH$ | H | $CF_3$ | F | H | H | $CF_3$ |
| 1A | 61N | $CF_3$ | 1 | 1 | H | H | $CH_2OH$ | H | H | $OCH_3$ | H | H | $CF_3$ |
| 1A | 62N | $CF_3$ | 1 | 1 | H | H | $CH_2OH$ | H | $CH_3$ | H | H | H | $CF_3$ |
| 1A | 63N | $CF_3$ | 1 | 1 | H | H | $CH_2OH$ | H | Cl | H | H | H | $CF_3$ |
| 1A | 64N | $CF_3$ | 1 | 1 | H | H | $CH_2OH$ | H | $CF_3$ | H | H | H | $OCF_3$ |
| 1A | 65N | $CF_3$ | 1 | 1 | H | H | $CH_2OH$ | H | F | H | H | H | $OCF_3$ |
| 1A | 66N | $CF_3$ | 1 | 1 | H | H | $CH_2OH$ | H | F | H | F | H | $OCF_3$ |
| 1A | 67N | $CF_3$ | 1 | 1 | H | H | $CH_2OH$ | H | Br | H | H | H | $OCF_3$ |
| 1A | 68N | $CF_3$ | 1 | 1 | H | H | $CH_2OH$ | H | Cl | H | H | H | $OCF_3$ |
| 1A | 69N | $CF_3$ | 1 | 1 | H | H | $CH_2OH$ | H | F | F | H | H | $OCF_3$ |
| 1A | 70N | $CF_3$ | 1 | 1 | H | H | $CH_2OH$ | H | F | H | H | H | phenyl |
| 1A | 71N | $CF_3$ | 1 | 1 | H | H | $CH_2OH$ | H | $CH_3$ | H | H | H | $OCF_3$ |
| 1A | 72N | $CF_3$ | 1 | 1 | H | H | $CH_2OH$ | H | F | F | H | H | $CF_3$ |
| 1A | 73N | $CF_3$ | 1 | 1 | H | H | $CH_2OH$ | H | Cl | H | H | H | $CH_3$ |
| 1A | 74N | $CF_3$ | 1 | 1 | H | H | $CH_2OH$ | H | $OCH_3$ | H | H | H | $CH_3$ |
| 1A | 75N | $CF_3$ | 1 | 1 | H | H | $CH_2OH$ | H | F | H | H | H | $CH_3$ |
| 1A | 76N | $CF_3$ | 1 | 1 | H | H | $CH_2OH$ | F | F | H | H | H | $OCF_3$ |
| 1A | 77N | $CF_3$ | 1 | 1 | H | H | $CH_2OH$ | $OCH_3$ | H | H | H | H | $CF_3$ |
| 1A | 78N | $CF_3$ | 1 | 1 | H | H | $CH_2OH$ | H | H | $OCH_3$ | H | H | $CH_3$ |
| 1A | 79N | $CF_3$ | 1 | 1 | H | H | $CH_2OH$ | H | H | $CH_3$ | H | H | $CH_3$ |
| 1A | 80N | $CF_3$ | 1 | 1 | H | H | $CH_2OH$ | H | $CH_3$ | H | H | H | $CH_3$ |
| 1A | 81N | $CF_3$ | 1 | 1 | H | H | $CH_2OH$ | $CH_3$ | H | H | H | H | $CH_3$ |
| 1A | 82N | $CF_3$ | 1 | 1 | H | H | $CH_2OH$ | H | F | F | H | H | $CH_3$ |
| 1A | 83N | $CF_3$ | 1 | 1 | H | H | $CH_2OH$ | H | F | H | F | H | $CH_3$ |
| 1A | 84N | $CF_3$ | 1 | 1 | H | H | $CH_2OH$ | F | F | H | H | H | $CH_3$ |
| 1A | 85N | $CF_3$ | 1 | 1 | H | H | $CH_2OH$ | F | $CF_3$ | H | H | H | $CH_3$ |
| 1A | 86N | $CF_3$ | 1 | 1 | H | H | $CH_2OH$ | H | H | $CH_3$ | H | H | $CF_3$ |
| 1A | 87N | $CF_3$ | 1 | 1 | H | H | $CH_2OH$ | $CH_3$ | H | H | H | H | $CF_3$ |
| 1A | 88N | $CF_3$ | 1 | 1 | H | H | $CH_2OH$ | H | $CF_3$ | H | H | H | $CH_3$ |
| 1A | 89N | $CF_3$ | 1 | 1 | H | H | $CH_2OH$ | $OCH_3$ | H | H | H | H | $CH_3$ |
| 1A | 90N | $CF_3$ | 1 | 1 | H | H | $CH_2OH$ | H | H | $CF_3$ | H | H | $CH_3$ |
| 1A | 91N | $CF_3$ | 1 | 1 | H | H | $CH_2OH$ | $CF_3$ | H | H | H | H | $CH_3$ |
| 1A | 92N | $CF_3$ | 1 | 1 | H | H | $CH_2OH$ | H | $CF_3$ | F | H | H | $CH_3$ |
| 2A | 1N | $CF_3$ | 1 | 2 | H | H | OH | H | $C_6H_5O$ | H | H | $OCF_2CF_2H$ | H |
| 2A | 2N | $CF_3$ | 1 | 2 | H | H | OH | H | $OCF_3$ | H | H | $OCF_2CF_2H$ | H |
| 2A | 3N | $CF_3$ | 1 | 2 | H | H | OH | F | H | H | F | $OCF_2CF_2H$ | H |
| 2A | 4N | $CF_3$ | 1 | 2 | H | H | OH | H | F | H | H | $OCF_2CF_2H$ | H |
| 2A | 5N | $CF_3$ | 1 | 2 | H | H | OH | H | $C_6H_5O$ | H | H | $OCF_3$ | H |
| 2A | 6N | $CF_3$ | 1 | 2 | H | H | OH | H | $OCF_3$ | H | H | $OCF_3$ | H |
| 2A | 7N | $CF_3$ | 1 | 2 | H | H | OH | H | H | phenyl | H | $OCF_3$ | H |
| 2A | 8N | $CF_3$ | 1 | 2 | H | H | OH | H | phenyl | H | H | $OCF_3$ | H |
| 2A | 9N | $CF_3$ | 1 | 2 | H | H | OH | H | H | H | H | $OCF_3$ | H |
| 2A | 10N | $CF_3$ | 1 | 2 | H | H | OH | H | Br | H | H | $OCF_3$ | H |
| 2A | 11N | $CF_3$ | 1 | 2 | H | H | OH | H | $CF_3$ | F | H | $CF_3$ | H |
| 2A | 12N | $CF_3$ | 1 | 2 | H | H | OH | H | $CH_3$ | H | H | $CF_3$ | H |
| 2A | 13N | $CF_3$ | 1 | 2 | H | H | OH | H | $CF_3$ | H | H | $CF_3$ | H |
| 2A | 14N | $CF_3$ | 1 | 2 | H | H | OH | H | $CH_3$ | H | H | $OCF_3$ | H |

TABLE 15-continued

Structure of Substituted Phenyl tertiary-omega-Heteroalkylamines (Y is CH; $R_8$, $R_9$, $R_{12}$, $R_{13}$, and $R_{14}$ are each H; Z is covalent bond and $R_{15}$ is absent).

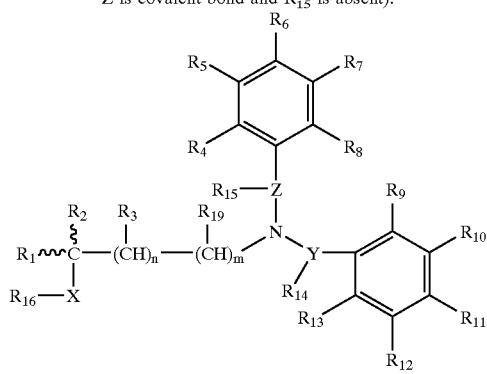

Inhibitor Number
Column1 + Column2

| Reagent | Reagent | $R_1$ | n | m | $R_2$ | $R_3$ | $XR_{16}$ | $R_4$ | $R_5$ | $R_6$ | $R_7$ | $R_{10}$ | $R_{11}$ |
|---|---|---|---|---|---|---|---|---|---|---|---|---|---|
| 2A | 15N | $CF_3$ | 1 | 2 | H | H | OH | H | F | F | H | $OCF_3$ | H |
| 2A | 16N | $CF_3$ | 1 | 2 | H | H | OH | H | Br | H | H | $CF_3$ | H |
| 2A | 17N | $CF_3$ | 1 | 2 | H | H | OH | H | $CF_3$ | F | H | $OCF_3$ | H |
| 2A | 18N | $CF_3$ | 1 | 2 | H | H | OH | H | F | H | H | $OCF_3$ | H |
| 2A | 19N | $CF_3$ | 1 | 2 | H | H | OH | H | Cl | H | H | $OCF_3$ | H |
| 2A | 20N | $CF_3$ | 1 | 2 | H | H | OH | H | F | H | H | $CF_3$ | H |
| 2A | 21N | $CF_3$ | 1 | 2 | H | H | OH | H | F | F | H | $CF_3$ | H |
| 2A | 22N | $CF_3$ | 1 | 2 | H | H | OH | H | Cl | H | H | $CF_3$ | H |
| 2A | 23N | $CF_3$ | 1 | 2 | H | H | OH | H | F | H | H | phenoxy | H |
| 2A | 24N | $CF_3$ | 1 | 2 | H | H | OH | H | $CF_3$ | Cl | H | $CH_3$ | H |
| 2A | 25N | $CF_3$ | 1 | 2 | H | H | OH | H | $CF_3$ | F | H | $CH_3$ | H |
| 2A | 26N | $CF_3$ | 1 | 2 | H | H | OH | H | H | H | H | $CF_3$ | H |
| 2A | 27N | $CF_3$ | 1 | 2 | H | H | OH | F | F | H | H | $CF_3$ | H |
| 2A | 28N | $CF_3$ | 1 | 2 | H | H | OH | H | H | $OCH_3$ | H | $CF_3$ | H |
| 2A | 29N | $CF_3$ | 1 | 2 | H | H | OH | H | F | F | H | $CH_3$ | H |
| 2A | 30N | $CF_3$ | 1 | 2 | H | H | OH | H | $OCH_3$ | H | H | $CH_3$ | H |
| 2A | 31N | $CF_3$ | 1 | 2 | H | H | OH | H | H | $CH_3$ | H | H | H |
| 2A | 32N | $CF_3$ | 1 | 2 | H | H | OH | H | Cl | H | H | H | H |
| 2A | 33N | $CF_3$ | 1 | 2 | H | H | OH | H | F | H | H | F | H |
| 2A | 34N | $CF_3$ | 1 | 2 | H | H | OH | H | H | $OCH_3$ | H | $CH_3$ | H |
| 2A | 35N | $CF_3$ | 1 | 2 | H | H | OH | H | H | H | H | H | H |
| 2A | 36N | $CF_3$ | 1 | 2 | H | H | OH | H | H | $CH_3$ | H | $CH_3$ | H |
| 2A | 37N | $CF_3$ | 1 | 2 | H | H | OH | H | H | Cl | H | H | H |
| 2A | 38N | $CF_3$ | 1 | 2 | H | H | OH | H | F | H | H | 3-$CF_3$-phenoxy | H |
| 2A | 39N | $CF_3$ | 1 | 2 | H | H | OH | H | F | H | H | 4-$CH_3$O-phenoxy | H |
| 2A | 40N | $CF_3$ | 1 | 2 | H | H | OH | H | F | H | H | 4-Cl-phenoxy | H |
| 2A | 41N | $CF_3$ | 1 | 2 | H | H | OH | H | F | H | H | H | H |
| 2A | 42N | $CF_3$ | 1 | 2 | H | H | OH | H | F | H | H | $CH_3$ | H |
| 2A | 43N | $CF_3$ | 1 | 2 | H | H | OH | H | F | H | F | $CH_3$ | H |
| 2A | 44N | $CF_3$ | 1 | 2 | H | H | OH | F | F | H | H | $CH_3$ | H |
| 2A | 45N | $CF_3$ | 1 | 2 | H | H | OH | H | Cl | H | H | $CH_3$ | H |
| 2A | 46N | $CF_3$ | 1 | 2 | H | H | OH | H | $CH_3$ | H | H | $CH_3$ | H |
| 2A | 47N | $CF_3$ | 1 | 2 | H | H | OH | $CH_3$ | H | H | H | H | H |
| 2A | 48N | $CF_3$ | 1 | 2 | H | H | OH | H | H | $CH_3$ | H | $CF_3$ | H |
| 2A | 49N | $CF_3$ | 1 | 2 | H | H | OH | $CH_3$ | H | H | H | $CF_3$ | H |
| 2A | 50N | $CF_3$ | 1 | 2 | H | H | OH | $CH_3$ | H | H | H | $CH_3$ | H |
| 2A | 51N | $CF_3$ | 1 | 2 | H | H | OH | H | H | $CH_3$ | H | F | H |
| 2A | 52N | $CF_3$ | 1 | 2 | H | H | OH | H | $CF_3$ | H | H | F | H |
| 2A | 53N | $CF_3$ | 1 | 2 | H | H | OH | H | $CF_3$ | H | H | $CH_3$ | H |
| 2A | 54N | $CF_3$ | 1 | 2 | H | H | OH | H | $OCH_3$ | H | H | $CF_3$ | H |
| 2A | 55N | $CF_3$ | 1 | 2 | H | H | OH | $OCH_3$ | H | H | H | $CH_3$ | H |
| 2A | 56N | $CF_3$ | 1 | 2 | H | H | OH | H | H | $CH_3$ | H | $CF_3$ | H |
| 2A | 57N | $CF_3$ | 1 | 2 | H | H | OH | H | $C_6H_5O$ | H | H | H | $OCF_3$ |
| 2A | 58N | $CF_3$ | 1 | 2 | H | H | OH | H | H | H | H | H | $OCF_3$ |
| 2A | 59N | $CF_3$ | 1 | 2 | H | H | OH | H | $OCF_3$ | H | H | H | $OCF_3$ |
| 2A | 60N | $CF_3$ | 1 | 2 | H | H | OH | H | $CF_3$ | F | H | H | $CF_3$ |
| 2A | 61N | $CF_3$ | 1 | 2 | H | H | OH | H | H | $OCH_3$ | H | H | $CF_3$ |
| 2A | 62N | $CF_3$ | 1 | 2 | H | H | OH | H | $CH_3$ | H | H | H | $CF_3$ |
| 2A | 63N | $CF_3$ | 1 | 2 | H | H | OH | H | Cl | H | H | H | $CF_3$ |
| 2A | 64N | $CF_3$ | 1 | 2 | H | H | OH | H | $CF_3$ | H | H | H | $OCF_3$ |
| 2A | 65N | $CF_3$ | 1 | 2 | H | H | OH | H | F | H | H | H | $OCF_3$ |
| 2A | 66N | $CF_3$ | 1 | 2 | H | H | OH | H | F | H | F | H | $OCF_3$ |
| 2A | 67N | $CF_3$ | 1 | 2 | H | H | OH | H | Br | H | H | H | $OCF_3$ |

TABLE 15-continued

Structure of Substituted Phenyl tertiary-omega-Heteroalkylamines (Y is CH; $R_8$, $R_9$, $R_{12}$, $R_{13}$, and $R_{14}$ are each H; Z is covalent bond and $R_{15}$ is absent).

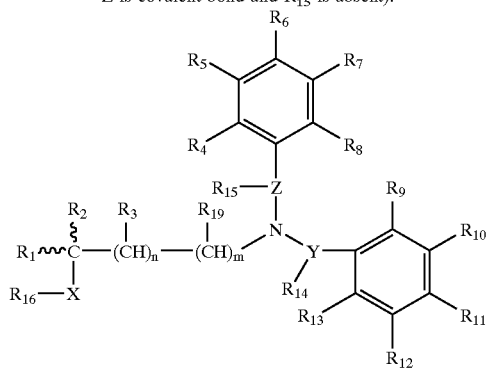

| Inhibitor Number Column1 + Column2 | | | | | | | | | | | |
|---|---|---|---|---|---|---|---|---|---|---|---|
| Reagent | Reagent | $R_1$ | n | m | $R_2$ | $R_3$ | $XR_{16}$ | $R_4$ | $R_5$ | $R_6$ | $R_7$ $R_{10}$ | $R_{11}$ |
| 2A | 68N | $CF_3$ | 1 | 2 | H | H | OH | H | Cl | H | H H | $OCF_3$ |
| 2A | 69N | $CF_3$ | 1 | 2 | H | H | OH | H | F | F | H H | $OCF_3$ |
| 2A | 70N | $CF_3$ | 1 | 2 | H | H | OH | H | F | H | H H | phenyl |
| 2A | 71N | $CF_3$ | 1 | 2 | H | H | OH | H | $CH_3$ | H | H H | $OCF_3$ |
| 2A | 72N | $CF_3$ | 1 | 2 | H | H | OH | H | F | F | H H | $CF_3$ |
| 2A | 73N | $CF_3$ | 1 | 2 | H | H | OH | H | Cl | H | H H | $CH_3$ |
| 2A | 74N | $CF_3$ | 1 | 2 | H | H | OH | H | $OCH_3$ | H | H H | $CH_3$ |
| 2A | 75N | $CF_3$ | 1 | 2 | H | H | OH | H | F | H | H H | $CH_3$ |
| 2A | 76N | $CF_3$ | 1 | 2 | H | H | OH | F | F | H | H H | $OCF_3$ |
| 2A | 77N | $CF_3$ | 1 | 2 | H | H | OH | $OCH_3$ | H | H | H H | $CF_3$ |
| 2A | 78N | $CF_3$ | 1 | 2 | H | H | OH | H | H | $OCH_3$ | H H | $CH_3$ |
| 2A | 79N | $CF_3$ | 1 | 2 | H | H | OH | H | H | $CH_3$ | H H | $CH_3$ |
| 2A | 80N | $CF_3$ | 1 | 2 | H | H | OH | H | $CH_3$ | H | H H | $CH_3$ |
| 2A | 81N | $CF_3$ | 1 | 2 | H | H | OH | $CH_3$ | H | H | H H | $CH_3$ |
| 2A | 82N | $CF_3$ | 1 | 2 | H | H | OH | H | F | F | H H | $CH_3$ |
| 2A | 83N | $CF_3$ | 1 | 2 | H | H | OH | H | F | H | F H | $CH_3$ |
| 2A | 84N | $CF_3$ | 1 | 2 | H | H | OH | F | F | H | H H | $CH_3$ |
| 2A | 85N | $CF_3$ | 1 | 2 | H | H | OH | F | $CF_3$ | H | H H | $CH_3$ |
| 2A | 86N | $CF_3$ | 1 | 2 | H | H | OH | H | H | $CH_3$ | H H | $CF_3$ |
| 2A | 87N | $CF_3$ | 1 | 2 | H | H | OH | $CH_3$ | H | H | H H | $CF_3$ |
| 2A | 88N | $CF_3$ | 1 | 2 | H | H | OH | H | $CF_3$ | H | H H | $CH_3$ |
| 2A | 89N | $CF_3$ | 1 | 2 | H | H | OH | $OCH_3$ | H | H | H H | $CH_3$ |
| 2A | 90N | $CF_3$ | 1 | 2 | H | H | OH | H | H | $CF_3$ | H H | $CH_3$ |
| 2A | 91N | $CF_3$ | 1 | 2 | H | H | OH | $CF_3$ | H | H | H H | $CH_3$ |
| 2A | 92N | $CF_3$ | 1 | 2 | H | H | OH | H | $CF_3$ | F | H H | $CH_3$ |
| 3A | 1N | $CF_3CH_2CH_2$ | 1 | 1 | H | H | OH | H | $C_6H_5O$ | H | H $OCF_2CF_2H$ | H |
| 3A | 2N | $CF_3CH_2CH_2$ | 1 | 1 | H | H | OH | H | $OCF_3$ | H | H $OCF_2CF_2H$ | H |
| 3A | 3N | $CF_3CH_2CH_2$ | 1 | 1 | H | H | OH | F | H | H | F $OCF_2CF_2H$ | H |
| 3A | 4N | $CF_3CH_2CH_2$ | 1 | 1 | H | H | OH | H | F | H | H $OCF_2CF_2H$ | H |
| 3A | 5N | $CF_3CH_2CH_2$ | 1 | 1 | H | H | OH | H | $C_6H_5O$ | H | H $OCF_3$ | H |
| 3A | 6N | $CF_3CH_2CH_2$ | 1 | 1 | H | H | OH | H | $OCF_3$ | H | H $OCF_3$ | H |
| 3A | 7N | $CF_3CH_2CH_2$ | 1 | 1 | H | H | OH | H | H | phenyl | H $OCF_3$ | H |
| 3A | 8N | $CF_3CH_2CH_2$ | 1 | 1 | H | H | OH | H | phenyl | H | H $OCF_3$ | H |
| 3A | 9N | $CF_3CH_2CH_2$ | 1 | 1 | H | H | OH | H | H | H | H $OCF_3$ | H |
| 3A | 10N | $CF_3CH_2CH_2$ | 1 | 1 | H | H | OH | H | Br | H | H $OCF_3$ | H |
| 3A | 11N | $CF_3CH_2CH_2$ | 1 | 1 | H | H | OH | H | $CF_3$ | F | H $CF_3$ | H |
| 3A | 12N | $CF_3CH_2CH_2$ | 1 | 1 | H | H | OH | H | $CH_3$ | H | H $CF_3$ | H |
| 3A | 13N | $CF_3CH_2CH_2$ | 1 | 1 | H | H | OH | H | $CF_3$ | H | H $CF_3$ | H |
| 3A | 14N | $CF_3CH_2CH_2$ | 1 | 1 | H | H | OH | H | $CH_3$ | H | H $OCF_3$ | H |
| 3A | 15N | $CF_3CH_2CH_2$ | 1 | 1 | H | H | OH | H | F | F | H $OCF_3$ | H |
| 3A | 16N | $CF_3CH_2CH_2$ | 1 | 1 | H | H | OH | H | Br | H | H $CF_3$ | H |
| 3A | 17N | $CF_3CH_2CH_2$ | 1 | 1 | H | H | OH | H | $CF_3$ | F | H $OCF_3$ | H |
| 3A | 18N | $CF_3CH_2CH_2$ | 1 | 1 | H | H | OH | H | F | H | H $OCF_3$ | H |
| 3A | 19N | $CF_3CH_2CH_2$ | 1 | 1 | H | H | OH | H | Cl | H | H $OCF_3$ | H |
| 3A | 20N | $CF_3CH_2CH_2$ | 1 | 1 | H | H | OH | H | F | H | H $CF_3$ | H |
| 3A | 21N | $CF_3CH_2CH_2$ | 1 | 1 | H | H | OH | H | F | F | H $CF_3$ | H |
| 3A | 22N | $CF_3CH_2CH_2$ | 1 | 1 | H | H | OH | H | Cl | H | H $CF_3$ | H |
| 3A | 23N | $CF_3CH_2CH_2$ | 1 | 1 | H | H | OH | H | F | H | H phenoxy | H |
| 3A | 24N | $CF_3CH_2CH_2$ | 1 | 1 | H | H | OH | H | $CF_3$ | Cl | H $CH_3$ | H |
| 3A | 25N | $CF_3CH_2CH_2$ | 1 | 1 | H | H | OH | H | $CF_3$ | F | H $CH_3$ | H |
| 3A | 26N | $CF_3CH_2CH_2$ | 1 | 1 | H | H | OH | H | H | H | H $CF_3$ | H |
| 3A | 27N | $CF_3CH_2CH_2$ | 1 | 1 | H | H | OH | F | F | H | H $CF_3$ | H |
| 3A | 28N | $CF_3CH_2CH_2$ | 1 | 1 | H | H | OH | H | H | $OCH_3$ | H $CF_3$ | H |

TABLE 15-continued

Structure of Substituted Phenyl tertiary-omega-Heteroalkylamines (Y is CH; $R_8$, $R_9$, $R_{12}$, $R_{13}$, and $R_{14}$ are each H; Z is covalent bond and $R_{15}$ is absent).

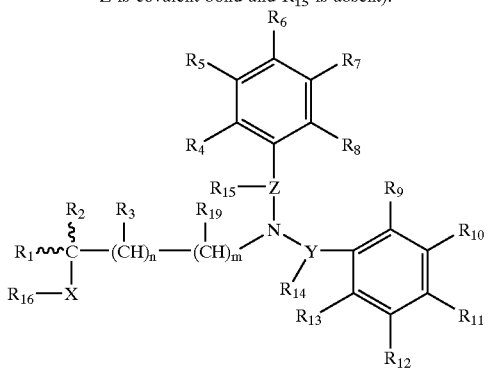

Inhibitor Number
Column1 + Column2

| Reagent | Reagent | $R_1$ | n | m | $R_2$ | $R_3$ | $XR_{16}$ | $R_4$ | $R_5$ | $R_6$ | $R_7$ | $R_{10}$ | $R_{11}$ |
|---|---|---|---|---|---|---|---|---|---|---|---|---|---|
| 3A | 29N | $CF_3CH_2CH_2$ | 1 | 1 | H | H | OH | H | F | F | H | $CH_3$ | H |
| 3A | 30N | $CF_3CH_2CH_2$ | 1 | 1 | H | H | OH | H | $OCH_3$ | H | H | $CH_3$ | H |
| 3A | 31N | $CF_3CH_2CH_2$ | 1 | 1 | H | H | OH | H | H | $CH_3$ | H | H | H |
| 3A | 32N | $CF_3CH_2CH_2$ | 1 | 1 | H | H | OH | H | Cl | H | H | H | H |
| 3A | 33N | $CF_3CH_2CH_2$ | 1 | 1 | H | H | OH | H | F | H | H | F | H |
| 3A | 34N | $CF_3CH_2CH_2$ | 1 | 1 | H | H | OH | H | H | $OCH_3$ | H | $CH_3$ | H |
| 3A | 35N | $CF_3CH_2CH_2$ | 1 | 1 | H | H | OH | H | H | H | H | H | H |
| 3A | 36N | $CF_3CH_2CH_2$ | 1 | 1 | H | H | OH | H | H | $CH_3$ | H | $CH_3$ | H |
| 3A | 37N | $CF_3CH_2CH_2$ | 1 | 1 | H | H | OH | H | H | Cl | H | H | H |
| 3A | 38N | $CF_3CH_2CH_2$ | 1 | 1 | H | H | OH | H | F | H | H | 3-$CF_3$-phenoxy | H |
| 3A | 39N | $CF_3CH_2CH_2$ | 1 | 1 | H | H | OH | H | F | H | H | 4-$CH_3$O-phenoxy | H |
| 3A | 40N | $CF_3CH_2CH_2$ | 1 | 1 | H | H | OH | H | F | H | H | 4-Cl-phenoxy | H |
| 3A | 41N | $CF_3CH_2CH_2$ | 1 | 1 | H | H | OH | H | F | H | H | H | H |
| 3A | 42N | $CF_3CH_2CH_2$ | 1 | 1 | H | H | OH | H | F | H | H | $CH_3$ | H |
| 3A | 43N | $CF_3CH_2CH_2$ | 1 | 1 | H | H | OH | H | F | H | F | $CH_3$ | H |
| 3A | 44N | $CF_3CH_2CH_2$ | 1 | 1 | H | H | OH | F | F | H | H | $CH_3$ | H |
| 3A | 45N | $CF_3CH_2CH_2$ | 1 | 1 | H | H | OH | H | Cl | H | H | $CH_3$ | H |
| 3A | 46N | $CF_3CH_2CH_2$ | 1 | 1 | H | H | OH | H | $CH_3$ | H | H | $CH_3$ | H |
| 3A | 47N | $CF_3CH_2CH_2$ | 1 | 1 | H | H | OH | $CH_3$ | H | H | H | H | H |
| 3A | 48N | $CF_3CH_2CH_2$ | 1 | 1 | H | H | OH | H | H | $CH_3$ | H | $CF_3$ | H |
| 3A | 49N | $CF_3CH_2CH_2$ | 1 | 1 | H | H | OH | $CH_3$ | H | H | H | $CF_3$ | H |
| 3A | 50N | $CF_3CH_2CH_2$ | 1 | 1 | H | H | OH | $CH_3$ | H | H | H | $CH_3$ | H |
| 3A | 51N | $CF_3CH_2CH_2$ | 1 | 1 | H | H | OH | H | H | $CH_3$ | H | F | H |
| 3A | 52N | $CF_3CH_2CH_2$ | 1 | 1 | H | H | OH | H | $CF_3$ | H | H | F | H |
| 3A | 53N | $CF_3CH_2CH_2$ | 1 | 1 | H | H | OH | H | $CF_3$ | H | H | $CH_3$ | H |
| 3A | 54N | $CF_3CH_2CH_2$ | 1 | 1 | H | H | OH | H | $OCH_3$ | H | H | $CF_3$ | H |
| 3A | 55N | $CF_3CH_2CH_2$ | 1 | 1 | H | H | OH | $OCH_3$ | H | H | H | $CH_3$ | H |
| 3A | 56N | $CF_3CH_2CH_2$ | 1 | 1 | H | H | OH | H | H | $CH_3$ | H | $CF_3$ | H |
| 3A | 57N | $CF_3CH_2CH_2$ | 1 | 1 | H | H | OH | H | $C_6H_5O$ | H | H | H | $OCF_3$ |
| 3A | 58N | $CF_3CH_2CH_2$ | 1 | 1 | H | H | OH | H | H | H | H | H | $OCF_3$ |
| 3A | 59N | $CF_3CH_2CH_2$ | 1 | 1 | H | H | OH | H | $OCF_3$ | H | H | H | $OCF_3$ |
| 3A | 60N | $CF_3CH_2CH_2$ | 1 | 1 | H | H | OH | H | $CF_3$ | F | H | H | $CF_3$ |
| 3A | 61N | $CF_3CH_2CH_2$ | 1 | 1 | H | H | OH | H | H | $OCH_3$ | H | H | $CF_3$ |
| 3A | 62N | $CF_3CH_2CH_2$ | 1 | 1 | H | H | OH | H | $CH_3$ | H | H | H | $CF_3$ |
| 3A | 63N | $CF_3CH_2CH_2$ | 1 | 1 | H | H | OH | H | Cl | H | H | H | $CF_3$ |
| 3A | 64N | $CF_3CH_2CH_2$ | 1 | 1 | H | H | OH | H | $CF_3$ | H | H | H | $OCF_3$ |
| 3A | 65N | $CF_3CH_2CH_2$ | 1 | 1 | H | H | OH | H | F | H | H | H | $OCF_3$ |
| 3A | 66N | $CF_3CH_2CH_2$ | 1 | 1 | H | H | OH | H | F | H | F | H | $OCF_3$ |
| 3A | 67N | $CF_3CH_2CH_2$ | 1 | 1 | H | H | OH | H | Br | H | H | H | $OCF_3$ |
| 3A | 68N | $CF_3CH_2CH_2$ | 1 | 1 | H | H | OH | H | Cl | H | H | H | $OCF_3$ |
| 3A | 69N | $CF_3CH_2CH_2$ | 1 | 1 | H | H | OH | H | F | F | H | H | $OCF_3$ |
| 3A | 70N | $CF_3CH_2CH_2$ | 1 | 1 | H | H | OH | H | F | H | H | H | phenyl |
| 3A | 71N | $CF_3CH_2CH_2$ | 1 | 1 | H | H | OH | H | $CH_3$ | H | H | H | $OCF_3$ |
| 3A | 72N | $CF_3CH_2CH_2$ | 1 | 1 | H | H | OH | H | F | F | H | H | $CF_3$ |
| 3A | 73N | $CF_3CH_2CH_2$ | 1 | 1 | H | H | OH | H | Cl | H | H | H | $CH_3$ |
| 3A | 74N | $CF_3CH_2CH_2$ | 1 | 1 | H | H | OH | H | $OCH_3$ | H | H | H | $CH_3$ |
| 3A | 75N | $CF_3CH_2CH_2$ | 1 | 1 | H | H | OH | H | F | H | H | H | $CH_3$ |
| 3A | 76N | $CF_3CH_2CH_2$ | 1 | 1 | H | H | OH | F | F | H | H | H | $OCF_3$ |
| 3A | 77N | $CF_3CH_2CH_2$ | 1 | 1 | H | H | OH | $OCH_3$ | H | H | H | H | $CF_3$ |
| 3A | 78N | $CF_3CH_2CH_2$ | 1 | 1 | H | H | OH | H | H | $OCH_3$ | H | H | $CH_3$ |
| 3A | 79N | $CF_3CH_2CH_2$ | 1 | 1 | H | H | OH | H | H | $CH_3$ | H | H | $CH_3$ |
| 3A | 80N | $CF_3CH_2CH_2$ | 1 | 1 | H | H | OH | H | $CH_3$ | H | H | H | $CH_3$ |
| 3A | 81N | $CF_3CH_2CH_2$ | 1 | 1 | H | H | OH | $CH_3$ | H | H | H | H | $CH_3$ |

TABLE 15-continued

Structure of Substituted Phenyl tertiary-omega-Heteroalkylamines (Y is CH; $R_8$, $R_9$, $R_{12}$, $R_{13}$, and $R_{14}$ are each H; Z is covalent bond and $R_{15}$ is absent).

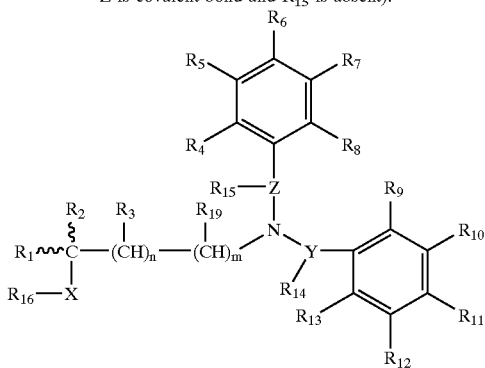

Inhibitor Number
Column1 + Column2

| Reagent | Reagent | $R_1$ | n | m | $R_2$ | $R_3$ | $XR_{16}$ | $R_4$ | $R_5$ | $R_6$ | $R_7$ | $R_{10}$ | $R_{11}$ |
|---|---|---|---|---|---|---|---|---|---|---|---|---|---|
| 3A | 82N | $CF_3CH_2CH_2$ | 1 | 1 | H | H | OH | H | F | F | H | H | $CH_3$ |
| 3A | 83N | $CF_3CH_2CH_2$ | 1 | 1 | H | H | OH | H | F | H | F | H | $CH_3$ |
| 3A | 84N | $CF_3CH_2CH_2$ | 1 | 1 | H | H | OH | F | F | H | H | H | $CH_3$ |
| 3A | 85N | $CF_3CH_2CH_2$ | 1 | 1 | H | H | OH | F | $CF_3$ | H | H | H | $CH_3$ |
| 3A | 86N | $CF_3CH_2CH_2$ | 1 | 1 | H | H | OH | H | H | $CH_3$ | H | H | $CF_3$ |
| 3A | 87N | $CF_3CH_2CH_2$ | 1 | 1 | H | H | OH | $CH_3$ | H | H | H | H | $CF_3$ |
| 3A | 88N | $CF_3CH_2CH_2$ | 1 | 1 | H | H | OH | H | $CF_3$ | H | H | H | $CH_3$ |
| 3A | 89N | $CF_3CH_2CH_2$ | 1 | 1 | H | H | OH | $OCH_3$ | H | H | H | H | $CH_3$ |
| 3A | 90N | $CF_3CH_2CH_2$ | 1 | 1 | H | H | OH | H | H | $CF_3$ | H | H | $CH_3$ |
| 3A | 91N | $CF_3CH_2CH_2$ | 1 | 1 | H | H | OH | $CF_3$ | H | H | H | H | $CH_3$ |
| 3A | 92N | $CF_3CH_2CH_2$ | 1 | 1 | H | H | OH | H | $CF_3$ | F | H | H | $CH_3$ |
| 4A | 1N | $CF_3$ | 1 | 1 | H | H | OH | H | $C_6H_5O$ | H | H | $OCF_2CF_2H$ | H |
| 4A | 2N | $CF_3$ | 1 | 1 | H | H | OH | H | $OCF_3$ | H | H | $OCF_2CF_2H$ | H |
| 4A | 3N | $CF_3$ | 1 | 1 | H | H | OH | F | H | H | F | $OCF_2CF_2H$ | H |
| 4A | 4N | $CF_3$ | 1 | 1 | H | H | OH | H | F | H | H | $OCF_2CF_2H$ | H |
| 4A | 5N | $CF_3$ | 1 | 1 | H | H | OH | H | $C_6H_5O$ | H | H | $OCF_3$ | H |
| 4A | 6N | $CF_3$ | 1 | 1 | H | H | OH | H | $OCF_3$ | H | H | $OCF_3$ | H |
| 4A | 7N | $CF_3$ | 1 | 1 | H | H | OH | H | H | phenyl | H | $OCF_3$ | H |
| 4A | 8N | $CF_3$ | 1 | 1 | H | H | OH | H | phenyl | H | H | $OCF_3$ | H |
| 4A | 9N | $CF_3$ | 1 | 1 | H | H | OH | H | H | H | H | $OCF_3$ | H |
| 4A | 10N | $CF_3$ | 1 | 1 | H | H | OH | H | Br | H | H | $OCF_3$ | H |
| 4A | 11N | $CF_3$ | 1 | 1 | H | H | OH | H | $CF_3$ | F | H | $CF_3$ | H |
| 4A | 12N | $CF_3$ | 1 | 1 | H | H | OH | H | $CH_3$ | H | H | $CF_3$ | H |
| 4A | 13N | $CF_3$ | 1 | 1 | H | H | OH | H | $CF_3$ | H | H | $CF_3$ | H |
| 4A | 14N | $CF_3$ | 1 | 1 | H | H | OH | H | $CH_3$ | H | H | $OCF_3$ | H |
| 4A | 15N | $CF_3$ | 1 | 1 | H | H | OH | H | F | F | H | $OCF_3$ | H |
| 4A | 16N | $CF_3$ | 1 | 1 | H | H | OH | H | Br | H | H | $CF_3$ | H |
| 4A | 17N | $CF_3$ | 1 | 1 | H | H | OH | H | $CF_3$ | F | H | $OCF_3$ | H |
| 4A | 18N | $CF_3$ | 1 | 1 | H | H | OH | H | F | H | H | $OCF_3$ | H |
| 4A | 19N | $CF_3$ | 1 | 1 | H | H | OH | H | Cl | H | H | $OCF_3$ | H |
| 4A | 20N | $CF_3$ | 1 | 1 | H | H | OH | H | F | H | H | $CF_3$ | H |
| 4A | 21N | $CF_3$ | 1 | 1 | H | H | OH | H | F | F | H | $CF_3$ | H |
| 4A | 22N | $CF_3$ | 1 | 1 | H | H | OH | H | Cl | H | H | $CF_3$ | H |
| 4A | 23N | $CF_3$ | 1 | 1 | H | H | OH | H | F | H | H | phenoxy | H |
| 4A | 24N | $CF_3$ | 1 | 1 | H | H | OH | H | $CF_3$ | Cl | H | $CH_3$ | H |
| 4A | 25N | $CF_3$ | 1 | 1 | H | H | OH | H | $CF_3$ | F | H | $CH_3$ | H |
| 4A | 26N | $CF_3$ | 1 | 1 | H | H | OH | H | H | H | H | $CF_3$ | H |
| 4A | 27N | $CF_3$ | 1 | 1 | H | H | OH | F | F | H | H | $CF_3$ | H |
| 4A | 28N | $CF_3$ | 1 | 1 | H | H | OH | H | H | $OCH_3$ | H | $CF_3$ | H |
| 4A | 29N | $CF_3$ | 1 | 1 | H | H | OH | H | F | F | H | $CH_3$ | H |
| 4A | 30N | $CF_3$ | 1 | 1 | H | H | OH | H | $OCH_3$ | H | H | $CH_3$ | H |
| 4A | 31N | $CF_3$ | 1 | 1 | H | H | OH | H | H | $CH_3$ | H | H | H |
| 4A | 32N | $CF_3$ | 1 | 1 | H | H | OH | H | Cl | H | H | H | H |
| 4A | 33N | $CF_3$ | 1 | 1 | H | H | OH | H | F | H | H | F | H |
| 4A | 34N | $CF_3$ | 1 | 1 | H | H | OH | H | H | $OCH_3$ | H | $CH_3$ | H |
| 4A | 35N | $CF_3$ | 1 | 1 | H | H | OH | H | H | H | H | H | H |
| 4A | 36N | $CF_3$ | 1 | 1 | H | H | OH | H | H | $CH_3$ | H | $CH_3$ | H |
| 4A | 37N | $CF_3$ | 1 | 1 | H | H | OH | H | H | Cl | H | H | H |
| 4A | 38N | $CF_3$ | 1 | 1 | H | H | OH | H | F | H | H | 3-$CF_3$-phenoxy | H |
| 4A | 39N | $CF_3$ | 1 | 1 | H | H | OH | H | F | H | H | 4-$CH_3$O-phenoxy | H |
| 4A | 40N | $CF_3$ | 1 | 1 | H | H | OH | H | F | H | H | 4-Cl-phenoxy | H |
| 4A | 41N | $CF_3$ | 1 | 1 | H | H | OH | H | F | H | H | H | H |
| 4A | 42N | $CF_3$ | 1 | 1 | H | H | OH | H | F | H | H | $CH_3$ | H |

TABLE 15-continued

Structure of Substituted Phenyl tertiary-omega-Heteroalkylamines (Y is CH; $R_8$, $R_9$, $R_{12}$, $R_{13}$, and $R_{14}$ are each H; Z is covalent bond and $R_{15}$ is absent).

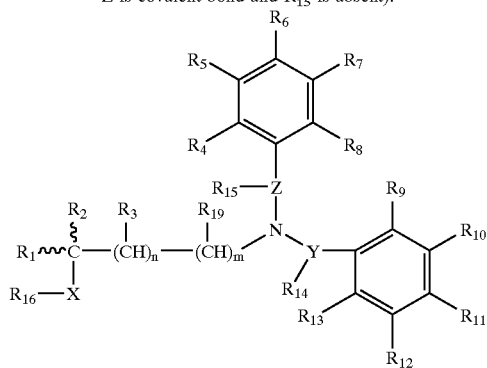

Inhibitor Number
Column1 + Column2

| Reagent | Reagent | $R_1$ | n | m | $R_2$ | $R_3$ | $XR_{16}$ | $R_4$ | $R_5$ | $R_6$ | $R_7$ | $R_{10}$ | $R_{11}$ |
|---|---|---|---|---|---|---|---|---|---|---|---|---|---|
| 4A | 43N | $CF_3$ | 1 | 1 | H | H | OH | H | F | H | F | $CH_3$ | H |
| 4A | 44N | $CF_3$ | 1 | 1 | H | H | OH | F | F | H | H | $CH_3$ | H |
| 4A | 45N | $CF_3$ | 1 | 1 | H | H | OH | H | Cl | H | H | $CH_3$ | H |
| 4A | 46N | $CF_3$ | 1 | 1 | H | H | OH | H | $CH_3$ | H | H | $CH_3$ | H |
| 4A | 47N | $CF_3$ | 1 | 1 | H | H | OH | $CH_3$ | H | H | H | H | H |
| 4A | 48N | $CF_3$ | 1 | 1 | H | H | OH | H | H | $CH_3$ | H | $CF_3$ | H |
| 4A | 49N | $CF_3$ | 1 | 1 | H | H | OH | $CH_3$ | H | H | H | $CF_3$ | H |
| 4A | 50N | $CF_3$ | 1 | 1 | H | H | OH | $CH_3$ | H | H | H | $CH_3$ | H |
| 4A | 51N | $CF_3$ | 1 | 1 | H | H | OH | H | H | $CH_3$ | H | F | H |
| 4A | 52N | $CF_3$ | 1 | 1 | H | H | OH | H | $CF_3$ | H | H | F | H |
| 4A | 53N | $CF_3$ | 1 | 1 | H | H | OH | H | $CF_3$ | H | H | $CH_3$ | H |
| 4A | 54N | $CF_3$ | 1 | 1 | H | H | OH | H | $OCH_3$ | H | H | $CF_3$ | H |
| 4A | 55N | $CF_3$ | 1 | 1 | H | H | OH | $OCH_3$ | H | H | H | $CH_3$ | H |
| 4A | 56N | $CF_3$ | 1 | 1 | H | H | OH | H | H | $CH_3$ | H | $CF_3$ | H |
| 4A | 57N | $CF_3$ | 1 | 1 | H | H | OH | H | $C_6H_5O$ | H | H H | | $OCF_3$ |
| 4A | 58N | $CF_3$ | 1 | 1 | H | H | OH | H | H | H | H H | | $OCF_3$ |
| 4A | 59N | $CF_3$ | 1 | 1 | H | H | OH | H | $OCF_3$ | H | H H | | $OCF_3$ |
| 4A | 60N | $CF_3$ | 1 | 1 | H | H | OH | H | $CF_3$ | F | H H | | $CF_3$ |
| 4A | 61N | $CF_3$ | 1 | 1 | H | H | OH | H | H | $OCH_3$ | H H | | $CF_3$ |
| 4A | 62N | $CF_3$ | 1 | 1 | H | H | OH | H | $CH_3$ | H | H H | | $CF_3$ |
| 4A | 63N | $CF_3$ | 1 | 1 | H | H | OH | H | Cl | H | H H | | $CF_3$ |
| 4A | 64N | $CF_3$ | 1 | 1 | H | H | OH | H | $CF_3$ | H | H H | | $OCF_3$ |
| 4A | 65N | $CF_3$ | 1 | 1 | H | H | OH | H | F | H | H H | | $OCF_3$ |
| 4A | 66N | $CF_3$ | 1 | 1 | H | H | OH | H | F | H | F H | | $OCF_3$ |
| 4A | 67N | $CF_3$ | 1 | 1 | H | H | OH | H | Br | H | H H | | $OCF_3$ |
| 4A | 68N | $CF_3$ | 1 | 1 | H | H | OH | H | Cl | H | H H | | $OCF_3$ |
| 4A | 69N | $CF_3$ | 1 | 1 | H | H | OH | H | F | F | H H | | $OCF_3$ |
| 4A | 70N | $CF_3$ | 1 | 1 | H | H | OH | H | F | H | H H | | phenyl |
| 4A | 71N | $CF_3$ | 1 | 1 | H | H | OH | H | $CH_3$ | H | H H | | $OCF_3$ |
| 4A | 72N | $CF_3$ | 1 | 1 | H | H | OH | H | F | F | H H | | $CF_3$ |
| 4A | 73N | $CF_3$ | 1 | 1 | H | H | OH | H | Cl | H | H H | | $CH_3$ |
| 4A | 74N | $CF_3$ | 1 | 1 | H | H | OH | H | $OCH_3$ | H | H H | | $CH_3$ |
| 4A | 75N | $CF_3$ | 1 | 1 | H | H | OH | H | F | H | H H | | $CH_3$ |
| 4A | 76N | $CF_3$ | 1 | 1 | H | H | OH | F | F | H | H H | | $OCF_3$ |
| 4A | 77N | $CF_3$ | 1 | 1 | H | H | OH | $OCH_3$ | H | H | H H | | $CF_3$ |
| 4A | 78N | $CF_3$ | 1 | 1 | H | H | OH | H | H | $OCH_3$ | H H | | $CH_3$ |
| 4A | 79N | $CF_3$ | 1 | 1 | H | H | OH | H | H | $CH_3$ | H H | | $CH_3$ |
| 4A | 80N | $CF_3$ | 1 | 1 | H | H | OH | H | $CH_3$ | H | H H | | $CH_3$ |
| 4A | 81N | $CF_3$ | 1 | 1 | H | H | OH | $CH_3$ | H | H | H H | | $CH_3$ |
| 4A | 82N | $CF_3$ | 1 | 1 | H | H | OH | H | F | F | H H | | $CH_3$ |
| 4A | 83N | $CF_3$ | 1 | 1 | H | H | OH | H | F | H | F H | | $CH_3$ |
| 4A | 84N | $CF_3$ | 1 | 1 | H | H | OH | F | F | H | H H | | $CH_3$ |
| 4A | 85N | $CF_3$ | 1 | 1 | H | H | OH | F | $CF_3$ | H | H H | | $CH_3$ |
| 4A | 86N | $CF_3$ | 1 | 1 | H | H | OH | H | H | $CH_3$ | H H | | $CF_3$ |
| 4A | 87N | $CF_3$ | 1 | 1 | H | H | OH | $CH_3$ | H | H | H H | | $CF_3$ |
| 4A | 88N | $CF_3$ | 1 | 1 | H | H | OH | H | $CF_3$ | H | H H | | $CH_3$ |
| 4A | 89N | $CF_3$ | 1 | 1 | H | H | OH | $OCH_3$ | H | H | H H | | $CH_3$ |
| 4A | 90N | $CF_3$ | 1 | 1 | H | H | OH | H | H | $CF_3$ | H H | | $CH_3$ |
| 4A | 91N | $CF_3$ | 1 | 1 | H | H | OH | $CF_3$ | H | H | H H | | $CH_3$ |
| 4A | 92N | $CF_3$ | 1 | 1 | H | H | OH | H | $CF_3$ | F | H H | | $CH_3$ |

TABLE 16

Structure of Substituted Phenyltertiary-omega-Heteroalkylamines
(Z and Y are each CH; $R_7$, $R_8$, $R_{12}$, $R_{13}$, $R_{14}$ and $R_{15}$ are each H).

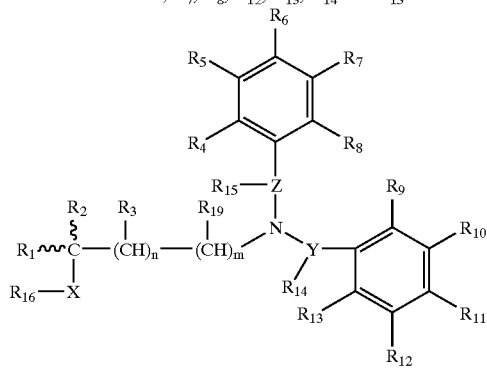

Inhibitor Number
Column 1 + Column 2

| Reagent | Reagent | $R_1$ | n | m | $R_2$ | $R_3$ | $XR_{16}$ | $R_4$ | $R_5$ | $R_6$ | $R_9$ | $R_{10}$ | $R_{11}$ |
|---|---|---|---|---|---|---|---|---|---|---|---|---|---|
| 1A | 1DB | $CF_3$ | 1 | 1 | H | H | $CH_2OH$ | H | $OCF_3$ | H | H | $OCF_3$ | H |
| 1A | 2DB | $CF_3$ | 1 | 1 | H | H | $CH_2OH$ | H | Cl | H | H | H | $CF_3$ |
| 1A | 3DB | $CF_3$ | 1 | 1 | H | H | $CH_2OH$ | H | Br | H | H | $OCF_3$ | H |
| 1A | 4DB | $CF_3$ | 1 | 1 | H | H | $CH_2OH$ | H | Cl | H | H | $OCF_3$ | H |
| 1A | 5DB | $CF_3$ | 1 | 1 | H | H | $CH_2OH$ | H | Cl | H | H | $CF_3$ | H |
| 1A | 6DB | $CF_3$ | 1 | 1 | H | H | $CH_2OH$ | H | H | Cl | H | $CF_3$ | H |
| 1A | 7DB | $CF_3$ | 1 | 1 | H | H | $CH_2OH$ | H | F | H | H | $OCF_3$ | H |
| 1A | 8DB | $CF_3$ | 1 | 1 | H | H | $CH_2OH$ | H | H | Cl | H | H | $CF_3$ |
| 1A | 9DB | $CF_3$ | 1 | 1 | H | H | $CH_2OH$ | H | F | H | H | H | $CF_3$ |
| 1A | 10DB | $CF_3$ | 1 | 1 | H | H | $CH_2OH$ | H | H | F | H | H | $CF_3$ |
| 1A | 11DB | $CF_3$ | 1 | 1 | H | H | $CH_2OH$ | F | H | H | H | H | $CF_3$ |
| 1A | 12DB | $CF_3$ | 1 | 1 | H | H | $CH_2OH$ | H | Cl | H | $CF_3$ | H | H |
| 1A | 13DB | $CF_3$ | 1 | 1 | H | H | $CH_2OH$ | H | H | Cl | $CF_3$ | H | H |
| 1A | 14DB | $CF_3$ | 1 | 1 | H | H | $CH_2OH$ | Cl | H | H | $CF_3$ | H | H |
| 1A | 15DB | $CF_3$ | 1 | 1 | H | H | $CH_2OH$ | H | F | H | $CH_3$ | H | H |
| 1A | 16DB | $CF_3$ | 1 | 1 | H | H | $CH_2OH$ | H | H | F | H | H | $CH_3$ |
| 1A | 17DB | $CF_3$ | 1 | 1 | H | H | $CH_2OH$ | H | F | H | H | $CH_3$ | H |
| 1A | 18DB | $CF_3$ | 1 | 1 | H | H | $CH_2OH$ | F | H | H | $CH_3$ | H | H |
| 1A | 19DB | $CF_3$ | 1 | 1 | H | H | $CH_2OH$ | H | H | F | H | $CH_3$ | H |
| 1A | 20DB | $CF_3$ | 1 | 1 | H | H | $CH_2OH$ | F | H | H | H | H | $CH_3$ |
| 1A | 21DB | $CF_3$ | 1 | 1 | H | H | $CH_2OH$ | F | H | H | H | $CF_3$ | H |
| 1A | 22DB | $CF_3$ | 1 | 1 | H | H | $CH_2OH$ | Cl | H | H | H | $CF_3$ | H |
| 1A | 23DB | $CF_3$ | 1 | 1 | H | H | $CH_2OH$ | H | F | H | $CF_3$ | H | H |
| 1A | 24DB | $CF_3$ | 1 | 1 | H | H | $CH_2OH$ | H | H | F | $CF_3$ | H | H |
| 1A | 25DB | $CF_3$ | 1 | 1 | H | H | $CH_2OH$ | H | F | H | H | $CF_3$ | H |
| 1A | 26DB | $CF_3$ | 1 | 1 | H | H | $CH_2OH$ | H | H | F | H | $CF_3$ | H |
| 1A | 27DB | $CF_3$ | 1 | 1 | H | H | $CH_2OH$ | H | $OCF_3$ | H | H | H | $OCF_3$ |
| 2A | 1DB | $CF_3$ | 1 | 2 | H | H | OH | H | $OCF_3$ | H | H | $OCF_3$ | H |
| 2A | 2DB | $CF_3$ | 1 | 2 | H | H | OH | H | Cl | H | H | H | $CF_3$ |
| 2A | 3DB | $CF_3$ | 1 | 2 | H | H | OH | H | Br | H | H | $OCF_3$ | H |
| 2A | 4DB | $CF_3$ | 1 | 2 | H | H | OH | H | Cl | H | H | $OCF_3$ | H |
| 2A | 5DB | $CF_3$ | 1 | 2 | H | H | OH | H | Cl | H | H | $CF_3$ | H |
| 2A | 6DB | $CF_3$ | 1 | 2 | H | H | OH | H | H | Cl | H | $CF_3$ | H |
| 2A | 7DB | $CF_3$ | 1 | 2 | H | H | OH | H | F | H | H | $OCF_3$ | H |
| 2A | 8DB | $CF_3$ | 1 | 2 | H | H | OH | H | H | Cl | H | H | $CF_3$ |
| 2A | 9DB | $CF_3$ | 1 | 2 | H | H | OH | H | F | H | H | H | $CF_3$ |
| 2A | 10DB | $CF_3$ | 1 | 2 | H | H | OH | H | H | F | H | H | $CF_3$ |
| 2A | 11DB | $CF_3$ | 1 | 2 | H | H | OH | F | H | H | H | H | $CF_3$ |
| 2A | 12DB | $CF_3$ | 1 | 2 | H | H | OH | H | Cl | H | $CF_3$ | H | H |
| 2A | 13DB | $CF_3$ | 1 | 2 | H | H | OH | H | H | Cl | $CF_3$ | H | H |
| 2A | 14DB | $CF_3$ | 1 | 2 | H | H | OH | Cl | H | H | $CF_3$ | H | H |
| 2A | 15DB | $CF_3$ | 1 | 2 | H | H | OH | H | F | H | $CH_3$ | H | H |
| 2A | 16DB | $CF_3$ | 1 | 2 | H | H | OH | H | H | F | H | H | $CH_3$ |
| 2A | 17DB | $CF_3$ | 1 | 2 | H | H | OH | H | F | H | H | $CH_3$ | H |
| 2A | 18DB | $CF_3$ | 1 | 2 | H | H | OH | F | H | H | $CH_3$ | H | H |
| 2A | 19DB | $CF_3$ | 1 | 2 | H | H | OH | H | H | F | H | $CH_3$ | H |
| 2A | 20DB | $CF_3$ | 1 | 2 | H | H | OH | F | H | H | H | H | $CH_3$ |
| 2A | 21DB | $CF_3$ | 1 | 2 | H | H | OH | F | H | H | H | $CF_3$ | H |
| 2A | 22DB | $CF_3$ | 1 | 2 | H | H | OH | Cl | H | H | H | $CF_3$ | H |
| 2A | 23DB | $CF_3$ | 1 | 2 | H | H | OH | H | F | H | $CF_3$ | H | H |
| 2A | 24DB | $CF_3$ | 1 | 2 | H | H | OH | H | H | F | $CF_3$ | H | H |
| 2A | 25DB | $CF_3$ | 1 | 2 | H | H | OH | H | F | H | H | $CF_3$ | H |
| 2A | 26DB | $CF_3$ | 1 | 2 | H | H | OH | H | H | F | H | $CF_3$ | H |

TABLE 16-continued

Structure of Substituted Phenyltertiary-omega-Heteroalkylamines
(Z and Y are each CH; $R_7$, $R_8$, $R_{12}$, $R_{13}$, $R_{14}$ and $R_{15}$ are each H).

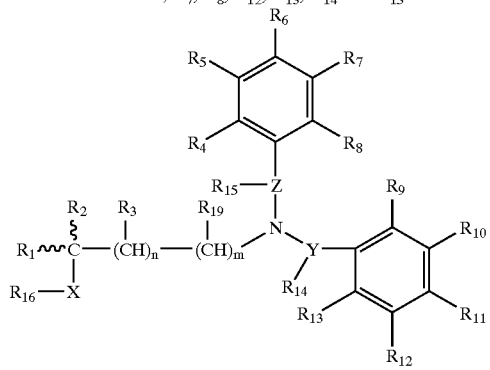

Inhibitor Number
Column 1 + Column 2

| Reagent | Reagent | $R_1$ | n | m | $R_2$ | $R_3$ | $XR_{16}$ | $R_4$ | $R_5$ | $R_6$ | $R_9$ | $R_{10}$ | $R_{11}$ |
|---|---|---|---|---|---|---|---|---|---|---|---|---|---|
| 2A | 27DB | $CF_3$ | 1 | 2 | H | H | OH | H | $OCF_3$ | H | H | H | $OCF_3$ |
| 3A | 1DB | $CF_3CH_2CH_2$ | 1 | 1 | H | H | OH | H | $OCF_3$ | H | H | $OCF_3$ | H |
| 3A | 2DB | $CF_3CH_2CH_2$ | 1 | 1 | H | H | OH | H | Cl | H | H | H | $CF_3$ |
| 3A | 3DB | $CF_3CH_2CH_2$ | 1 | 1 | H | H | OH | H | Br | H | H | $OCF_3$ | H |
| 3A | 4DB | $CF_3CH_2CH_2$ | 1 | 1 | H | H | OH | H | Cl | H | H | $OCF_3$ | H |
| 3A | 5DB | $CF_3CH_2CH_2$ | 1 | 1 | H | H | OH | H | Cl | H | H | $CF_3$ | H |
| 3A | 6DB | $CF_3CH_2CH_2$ | 1 | 1 | H | H | OH | H | H | Cl | H | $CF_3$ | H |
| 3A | 7DB | $CF_3CH_2CH_2$ | 1 | 1 | H | H | OH | H | F | H | H | $OCF_3$ | H |
| 3A | 8DB | $CF_3CH_2CH_2$ | 1 | 1 | H | H | OH | H | H | Cl | H | H | $CF_3$ |
| 3A | 9DB | $CF_3CH_2CH_2$ | 1 | 1 | H | H | OH | H | F | H | H | H | $CF_3$ |
| 3A | 10DB | $CF_3CH_2CH_2$ | 1 | 1 | H | H | OH | H | H | F | H | H | $CF_3$ |
| 3A | 11DB | $CF_3CH_2CH_2$ | 1 | 1 | H | H | OH | F | H | H | H | H | $CF_3$ |
| 3A | 12DB | $CF_3CH_2CH_2$ | 1 | 1 | H | H | OH | H | Cl | H | $CF_3$ | H | H |
| 3A | 13DB | $CF_3CH_2CH_2$ | 1 | 1 | H | H | OH | H | H | Cl | $CF_3$ | H | H |
| 3A | 14DB | $CF_3CH_2CH_2$ | 1 | 1 | H | H | OH | Cl | H | H | $CF_3$ | H | H |
| 3A | 15DB | $CF_3CH_2CH_2$ | 1 | 1 | H | H | OH | H | F | H | $CH_3$ | H | H |
| 3A | 16DB | $CF_3CH_2CH_2$ | 1 | 1 | H | H | OH | H | H | F | H | H | $CH_3$ |
| 3A | 17DB | $CF_3CH_2CH_2$ | 1 | 1 | H | H | OH | H | F | H | H | $CH_3$ | H |
| 3A | 18DB | $CF_3CH_2CH_2$ | 1 | 1 | H | H | OH | F | H | H | $CH_3$ | H | H |
| 3A | 19DB | $CF_3CH_2CH_2$ | 1 | 1 | H | H | OH | H | H | F | H | $CH_3$ | H |
| 3A | 20DB | $CF_3CH_2CH_2$ | 1 | 1 | H | H | OH | F | H | H | H | H | $CH_3$ |
| 3A | 21DB | $CF_3CH_2CH_2$ | 1 | 1 | H | H | OH | F | H | H | H | $CF_3$ | H |
| 3A | 22DB | $CF_3CH_2CH_2$ | 1 | 1 | H | H | OH | Cl | H | H | H | $CF_3$ | H |
| 3A | 23DB | $CF_3CH_2CH_2$ | 1 | 1 | H | H | OH | H | F | H | $CF_3$ | H | H |
| 3A | 24DB | $CF_3CH_2CH_2$ | 1 | 1 | H | H | OH | H | H | F | $CF_3$ | H | H |
| 3A | 25DB | $CF_3CH_2CH_2$ | 1 | 1 | H | H | OH | H | F | H | H | $CF_3$ | H |
| 3A | 26DB | $CF_3CH_2CH_2$ | 1 | 1 | H | H | OH | H | H | F | H | $CF_3$ | H |
| 3A | 27DB | $CF_3CH_2CH_2$ | 1 | 1 | H | H | OH | H | $OCF_3$ | H | H | H | $OCF_3$ |
| 4A | 1DB | $CF_3$ | 1 | 1 | H | H | OH | H | $OCF_3$ | H | H | $OCF_3$ | H |
| 4A | 2DB | $CF_3$ | 1 | 1 | H | H | OH | H | Cl | H | H | H | $CF_3$ |
| 4A | 3DB | $CF_3$ | 1 | 1 | H | H | OH | H | Br | H | H | $OCF_3$ | H |
| 4A | 4DB | $CF_3$ | 1 | 1 | H | H | OH | H | Cl | H | H | $OCF_3$ | H |
| 4A | 5DB | $CF_3$ | 1 | 1 | H | H | OH | H | Cl | H | H | $CF_3$ | H |
| 4A | 6DB | $CF_3$ | 1 | 1 | H | H | OH | H | H | Cl | H | $CF_3$ | H |
| 4A | 7DB | $CF_3$ | 1 | 1 | H | H | OH | H | F | H | H | $OCF_3$ | H |
| 4A | 8DB | $CF_3$ | 1 | 1 | H | H | OH | H | H | Cl | H | H | $CF_3$ |
| 4A | 9DB | $CF_3$ | 1 | 1 | H | H | OH | H | F | H | H | H | $CF_3$ |
| 4A | 10DB | $CF_3$ | 1 | 1 | H | H | OH | H | H | F | H | H | $CF_3$ |
| 4A | 11DB | $CF_3$ | 1 | 1 | H | H | OH | F | H | H | H | H | $CF_3$ |
| 4A | 12DB | $CF_3$ | 1 | 1 | H | H | OH | H | Cl | H | $CF_3$ | H | H |
| 4A | 13DB | $CF_3$ | 1 | 1 | H | H | OH | H | H | Cl | $CF_3$ | H | H |
| 4A | 14DB | $CF_3$ | 1 | 1 | H | H | OH | Cl | H | H | $CF_3$ | H | H |
| 4A | 15DB | $CF_3$ | 1 | 1 | H | H | OH | H | F | H | $CH_3$ | H | H |
| 4A | 16DB | $CF_3$ | 1 | 1 | H | H | OH | H | H | F | H | H | $CH_3$ |
| 4A | 17DB | $CF_3$ | 1 | 1 | H | H | OH | H | F | H | H | $CH_3$ | H |
| 4A | 18DB | $CF_3$ | 1 | 1 | H | H | OH | F | H | H | $CH_3$ | H | H |
| 4A | 19DB | $CF_3$ | 1 | 1 | H | H | OH | H | H | F | H | $CH_3$ | H |
| 4A | 20DB | $CF_3$ | 1 | 1 | H | H | OH | F | H | H | H | H | $CH_3$ |
| 4A | 21DB | $CF_3$ | 1 | 1 | H | H | OH | F | H | H | H | $CF_3$ | H |
| 4A | 22DB | $CF_3$ | 1 | 1 | H | H | OH | Cl | H | H | H | $CF_3$ | H |
| 4A | 23DB | $CF_3$ | 1 | 1 | H | H | OH | H | F | H | $CF_3$ | H | H |
| 4A | 24DB | $CF_3$ | 1 | 1 | H | H | OH | H | H | F | $CF_3$ | H | H |
| 4A | 25DB | $CF_3$ | 1 | 1 | H | H | OH | H | F | H | H | $CF_3$ | H |

TABLE 16-continued

Structure of Substituted Phenyltertiary-omega-Heteroalkylamines
(Z and Y are each CH; $R_7$, $R_8$, $R_{12}$, $R_{13}$, $R_{14}$ and $R_{15}$ are each H).

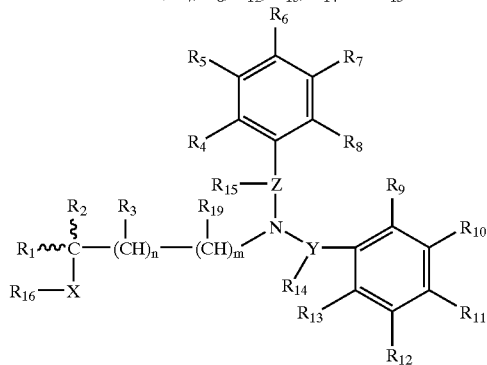

Inhibitor Number
Column 1 + Column 2

| Reagent | Reagent | $R_1$ | n | m | $R_2$ | $R_3$ | $XR_{16}$ | $R_4$ | $R_5$ | $R_6$ | $R_9$ | $R_{10}$ | $R_{11}$ |
|---|---|---|---|---|---|---|---|---|---|---|---|---|---|
| 4A | 26DB | $CF_3$ | 1 | 1 | H | H | OH | H | H | F | H | $CF_3$ | H |
| 4A | 27DB | $CF_3$ | 1 | 1 | H | H | OH | H | $OCF_3$ | H | H | H | $OCF_3$ |

TABLE 17

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

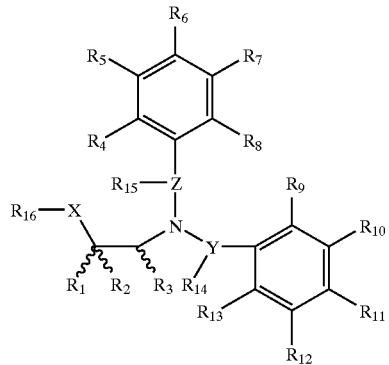

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 1 | 224N | $CF_3$ | H | O | $C_6H_5O$ | H | $OCF_2CF_2H$ | H |
| 1 | 225N | $CF_3$ | H | O | 4-Cl—$C_6H_5O$ | H | $OCF_2CF_2H$ | H |
| 1 | 226N | $CF_3$ | H | O | 4-F—$C_6H_5O$ | H | $OCF_2CF_2H$ | H |
| 1 | 227N | $CF_3$ | H | O | 3,4-Cl—$C_6H_5O$ | H | $OCF_2CF_2H$ | H |
| 1 | 228N | $CF_3$ | H | O | H | $C_6H_5$ | $OCF_2CF_2H$ | H |
| 1 | 229N | $CF_3$ | H | O | H | 4-Cl—$C_6H_5$ | $OCF_2CF_2H$ | H |
| 1 | 230N | $CF_3$ | H | O | H | 4-F—$C_6H_5$ | $OCF_2CF_2H$ | H |
| 1 | 231N | $CF_3$ | H | O | H | 4-Br—$C_6H_5$ | $OCF_2CF_2H$ | H |
| 1 | 232N | $CF_3$ | H | O | 4-Br—$C_6H_5O$ | H | $OCF_2CF_2H$ | H |
| 1 | 233N | $CF_3$ | H | O | $C_6H_5O$ | H | $OCF_2CF_3$ | H |
| 1 | 234N | $CF_3$ | H | O | 4-Cl—$C_6H_5O$ | H | $OCF_2CF_3$ | H |
| 1 | 235N | $CF_3$ | H | O | 4-F—$C_6H_5O$ | H | $OCF_2CF_3$ | H |
| 1 | 236N | $CF_3$ | H | O | 3,4-Cl—$C_6H_5O$ | H | $OCF_2CF_3$ | H |
| 1 | 237N | $CF_3$ | H | O | H | $C_6H_5$ | $OCF_2CF_3$ | H |
| 1 | 238N | $CF_3$ | H | O | H | 4-Cl—$C_6H_5$ | $OCF_2CF_3$ | H |
| 1 | 239N | $CF_3$ | H | O | H | 4-F—$C_6H_5$ | $CCF_2CF_3$ | H |
| 1 | 240N | $CF_3$ | H | O | H | 4-Br—$C_6H_5$ | $OCF_2CF_3$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

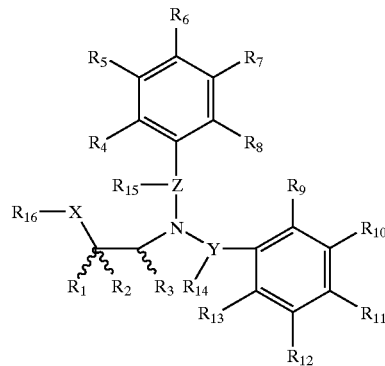

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 1 | 241N | $CF_3$ | H | O | 4-Br—$C_6H_5O$ | H | $OCF_2CF_3$ | H |
| 1 | 242N | $CF_3$ | H | O | $C_6H_5O$ | H | $OCCl_2CCl_2H$ | H |
| 1 | 243N | $CF_3$ | H | O | 4-Cl—$C_6H_5O$ | H | $OCCl_2CCl_2H$ | H |
| 1 | 244N | $CF_3$ | H | O | 4-F—$C_6H_5O$ | H | $OCCl_2CCl_2H$ | H |
| 1 | 245N | $CF_3$ | H | O | 3,4-Cl—$C_6H_5O$ | H | $OCCl_2CCl_2H$ | H |
| 1 | 246N | $CF_3$ | H | O | H | $C_6H_5$ | $OCCl_2CCl_2H$ | H |
| 1 | 247N | $CF_3$ | H | O | H | 4-Cl—$C_6H_5$ | $OCCl_2CCl_2H$ | H |
| 1 | 248N | $CF_3$ | H | O | H | 4-F—$C_6H_5$ | $OCCl_2CCl_2H$ | H |
| 1 | 249N | $CF_3$ | H | O | H | 4-Br—$C_6H_5$ | $OCCl_2CCl_2H$ | H |
| 1 | 250N | $CF_3$ | H | O | 4-Br—$C_6H_5O$ | H | $OCCl_2CCl_2H$ | H |
| 1 | 251N | $CF_3$ | H | O | $C_6H_5O$ | H | $OCCl_2CCl_3$ | H |
| 1 | 252N | $CF_3$ | H | O | 4-Cl—$C_6H_5O$ | H | $OCCl_2CCl_3$ | H |
| 1 | 253N | $CF_3$ | H | O | 4-F—$C_6H_5O$ | H | $OCCl_2CCl_3$ | H |
| 1 | 254N | $CF_3$ | H | O | 3,4-Cl—$C_6H_5O$ | H | $OCCl_2CCl_3$ | H |
| 1 | 255N | $CF_3$ | H | O | H | $C_6H_5$ | $OCCl_2CCl_3$ | H |
| 1 | 256N | $CF_3$ | H | O | H | 4-Cl—$C_6H_5$ | $OCCl_2CCl_3$ | H |
| 1 | 257N | $CF_3$ | H | O | H | 4-F—$C_6H_5$ | $OCCl_2CCl_3$ | H |
| 1 | 258N | $CF_3$ | H | O | H | 4-Br—$C_6H_5$ | $OCCl_2CCl_3$ | H |
| 1 | 259N | $CF_3$ | H | O | 4-Br—$C_6H_5O$ | H | $OCCl_2CCl_3$ | H |
| 1 | 260N | $CF_3$ | H | O | $C_6H_5O$ | H | $OCCl_2CF_3$ | H |
| 1 | 261N | $CF_3$ | H | O | 4-Cl—$C_6H_5O$ | H | $OCCl_2CF_3$ | H |
| 1 | 262N | $CF_3$ | H | O | 4-F—$C_6H_5O$ | H | $OCCl_2CF_3$ | H |
| 1 | 263N | $CF_3$ | H | O | 3,4-Cl—$C_6H_5O$ | H | $OCCl_2CF_3$ | H |
| 1 | 264N | $CF_3$ | H | O | H | $C_6H_5$ | $OCCl_2CF_3$ | H |
| 1 | 265N | $CF_3$ | H | O | H | 4-Cl—$C_6H_5$ | $OCCl_2CF_3$ | H |
| 1 | 266N | $CF_3$ | H | O | H | 4-F—$C_6H_5$ | $OCCl_2CF_3$ | H |
| 1 | 267N | $CF_3$ | H | O | H | 4-Br—$C_6H_5$ | $OCCl_2CF_3$ | H |
| 1 | 268N | $CF_3$ | H | O | 4-Br—$C_6H_5O$ | H | $OCCl_2CF_3$ | H |
| 1 | 269N | $CF_3$ | H | O | $C_6H_5O$ | H | $OCF_2CCl_3$ | H |
| 1 | 270N | $CF_3$ | H | O | 4-Cl—$C_6H_5O$ | H | $OCF_2CCl_3$ | H |
| 1 | 271N | $CF_3$ | H | O | 4-F—$C_6H_5O$ | H | $OCF_2CCl_3$ | H |
| 1 | 272N | $CF_3$ | H | O | 3,4-Cl—$C_6H_5O$ | H | $OCF_2CCl_3$ | H |
| 1 | 273N | $CF_3$ | H | O | H | $C_6H_5$ | $OCF_2CCl_3$ | H |
| 1 | 274N | $CF_3$ | H | O | H | 4-Cl—$C_6H_5$ | $OCF_2CCl_3$ | H |
| 1 | 275N | $CF_3$ | H | O | H | 4-F—$C_6H_5$ | $OCF_2CCl_3$ | H |
| 1 | 276N | $CF_3$ | H | O | H | 4-Br—$C_6H_5$ | $OCF_2CCl_3$ | H |
| 1 | 277N | $CF_3$ | H | O | 4-Br—$C_6H_5O$ | H | $OCF_2CCl_3$ | H |
| 1 | 278N | $CF_3$ | H | O | $C_6H_5O$ | H | $OCF_2CF_2H$ | $OCF_2CF_2H$ |
| 1 | 279N | $CF_3$ | H | O | 4-Cl—$C_6H_5O$ | H | $OCF_2CF_2H$ | $OCF_2CF_2H$ |
| 1 | 280N | $CF_3$ | H | O | 4-F—$C_6H_5O$ | H | $OCF_2CF_2H$ | $OCF_2CF_2H$ |
| 1 | 281N | $CF_3$ | H | O | 3,4-Cl—$C_6H_5O$ | H | $OCF_2CF_2H$ | $OCF_2CF_2H$ |
| 1 | 282N | $CF_3$ | H | O | H | $C_6H_5$ | $OCF_2CF_2H$ | $OCF_2CF_2H$ |
| 1 | 283N | $CF_3$ | H | O | H | 4-Cl—$C_6H_5$ | $OCF_2CF_2H$ | $OCF_2CF_2H$ |
| 1 | 284N | $CF_3$ | H | O | H | 4-F—$C_6H_5$ | $OCF_2CF_2H$ | $OCF_2CF_2H$ |
| 1 | 285N | $CF_3$ | H | O | H | 4-Br—$C_6H_5$ | $OCF_2CF_2H$ | $OCF_2CF_2H$ |
| 1 | 286N | $CF_3$ | H | O | 4-Br—$C_6H_5O$ | H | $OCF_2CF_2H$ | $OCF_2CF_2H$ |
| 1 | 287N | $CF_3$ | H | O | $C_6H_5O$ | H | $OCF_3$ | $OCF_3$ |
| 1 | 288N | $CF_3$ | H | O | 4-Cl—$C_6H_5O$ | H | $OCF_3$ | $OCF_3$ |
| 1 | 289N | $CF_3$ | H | O | 4-F—$C_6H_5O$ | H | $OCF_3$ | $OCF_3$ |
| 1 | 290N | $CF_3$ | H | O | 3,4-Cl—$C_6H_5O$ | H | $OCF_3$ | $OCF_3$ |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

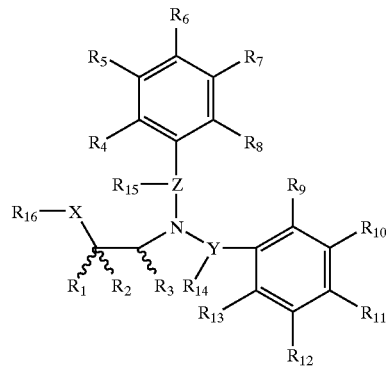

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 1 | 291N | $CF_3$ | H | O | H | $C_6H_5$ | $OCF_3$ | $OCF_3$ |
| 1 | 292N | $CF_3$ | H | O | H | 4-Cl—$C_6H_5$ | $OCF_3$ | $OCF_3$ |
| 1 | 293N | $CF_3$ | H | O | H | 4-F—$C_6H_5$ | $OCF_3$ | $OCF_3$ |
| 1 | 294N | $CF_3$ | H | O | H | 4-Br—$C_6H_5$ | $OCF_3$ | $OCF_3$ |
| 1 | 295N | $CF_3$ | H | O | 4-Br—$C_6H_5O$ | H | $OCF_3$ | $OCF_3$ |
| 1 | 296N | $CF_3$ | H | O | $C_6H_5O$ | H | $OCF_2H$ | $OCF_2H$ |
| 1 | 297N | $CF_3$ | H | O | 4-Cl—$C_6H_5O$ | H | $OCF_2H$ | $OCF_2H$ |
| 1 | 298N | $CF_3$ | H | O | 4-F—$C_6H_5O$ | H | $OCF_2H$ | $OCF_2H$ |
| 1 | 299N | $CF_3$ | H | O | 3,4-Cl—$C_6H_5O$ | H | $OCF_2H$ | $OCF_2H$ |
| 1 | 300N | $CF_3$ | H | O | H | $C_6H_5$ | $OCF_2H$ | $OCF_2H$ |
| 1 | 301N | $CF_3$ | H | O | H | 4-Cl—$C_6H_5$ | $OCF_2H$ | $OCF_2H$ |
| 1 | 302N | $CF_3$ | H | O | H | 4-F—$C_6H_5$ | $OCF_2H$ | $OCF_2H$ |
| 1 | 303N | $CF_3$ | H | O | H | 4-Br—$C_6H_5$ | $OCF_2H$ | $OCF_2H$ |
| 1 | 304N | $CF_3$ | H | O | 4-Br—$C_6H_5O$ | H | $OCF_2H$ | $OCF_2H$ |
| 1 | 305N | $CF_3$ | H | O | $C_6H_5O$ | H | $R_{10} + R_{11} = OCF_2CF_2O$ | |
| 1 | 306N | $CF_3$ | H | O | 4-Cl—$C_6H_5O$ | H | $R_{10} + R_{11} = OCF_2CF_2O$ | |
| 1 | 307N | $CF_3$ | H | O | 4-F—$C_6H_5O$ | H | $R_{10} + R_{11} = OCF_2CF_2O$ | |
| 1 | 308N | $CF_3$ | H | O | 3,4-Cl—$C_6H_5O$ | H | $R_{10} + R_{11} = OCF_2CF_2O$ | |
| 1 | 309N | $CF_3$ | H | O | H | $C_6H_5$ | $R_{10} + R_{11} = OCF_2CF_2O$ | |
| 1 | 310N | $CF_3$ | H | O | H | 4-Cl—$C_6H_5$ | $R_{10} + R_{11} = OCF_2CF_2O$ | |
| 1 | 311N | $CF_3$ | H | O | H | 4-F—$C_6H_5$ | $R_{10} + R_{11} = OCF_2CF_2O$ | |
| 1 | 312N | $CF_3$ | H | O | H | 4-Br—$C_6H_5$ | $R_{10} + R_{11} = OCF_2CF_2O$ | |
| 1 | 313N | $CF_3$ | H | O | 4-Br—$C_6H_5O$ | H | $R_{10} + R_{11} = OCF_2CF_2O$ | |
| 1 | 314N | $CF_3$ | H | O | $C_6H_5O$ | H | $R_{10} + R_{11} = OCCl_2CCl_2O$ | |
| 1 | 315N | $CF_3$ | H | O | 4-Cl—$C_6H_5O$ | H | $R_{10} + R_{11} = OCCl_2CCl_2O$ | |
| 1 | 316N | $CF_3$ | H | O | 4-F—$C_6H_5O$ | H | $R_{10} + R_{11} = OCCl_2CCl_2O$ | |
| 1 | 317N | $CF_3$ | H | O | 3,4-Cl—$C_6H_5O$ | H | $R_{10} + R_{11} = OCCl_2CCl_2O$ | |
| 1 | 318N | $CF_3$ | H | O | H | $C_6H_5$ | $R_{10} + R_{11} = OCCl_2CCl_2O$ | |
| 1 | 319N | $CF_3$ | H | O | H | 4-Cl—$C_6H_5$ | $R_{10} + R_{11} = OCCl_2CCl_2O$ | |
| 1 | 320N | $CF_3$ | H | O | H | 4-F—$C_6H_5$ | $R_{10} + R_{11} = OCCl_2CCl_2O$ | |
| 1 | 321N | $CF_3$ | H | O | H | 4-Br—$C_6H_5$ | $R_{10} + R_{11} = OCCl_2CCl_2O$ | |
| 1 | 322N | $CF_3$ | H | O | 4-Br—$C_6H_5O$ | H | $R_{10} + R_{11} = OCCl_2CCl_2O$ | |
| 1 | 323N | $CF_3$ | H | O | H | H | OH | H |
| 1 | 324N | $CF_3$ | H | O | H | H | OH | OH |
| 1 | 325N | $CF_3$ | H | O | H | H | H | OH |
| 1 | 326N | $CF_3$ | H | O | H | H | $OCH_2CF_3$ | H |
| 1 | 327N | $CF_3$ | H | O | H | H | H | $OCH_2CF_3$ |
| 1 | 328N | $CF_3$ | H | O | H | H | $OCH_2CF_2CF_3$ | H |
| 1 | 329N | $CF_3$ | H | O | H | H | $OCH_2CH_2CF_3$ | H |
| 1 | 330N | $CF_3$ | H | O | H | H | $OCH(CF_3)_3$ | H |
| 1 | 331N | $CF_3$ | H | O | H | 4-F—$C_6H_5O$ | H | H |
| 1 | 332N | $CF_3$ | H | O | 4-F—$C_6H_5O$ | H | H | H |
| 1 | 333N | $CF_3$ | H | O | H | cyclohexoxy | H | H |
| 1 | 334N | $CF_3$ | H | O | cyclohexoxy | H | H | H |
| 1 | 335N | $CF_3$ | H | O | H | $CH(CH_3)_3$ | H | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

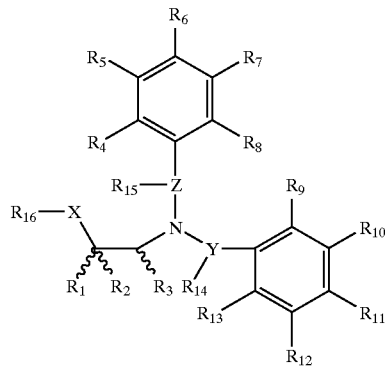

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 1 | 336N | $CF_3$ | H | O | F | H |  | bond to indicated phenyl carbon of $R_{10}$ substituent |
| 2 | 224N | $CCl_3$ | H | O | $C_6H_5O$ | H | $OCF_2CF_2H$ | H |
| 2 | 225N | $CCl_3$ | H | O | 4-Cl—$C_6H_5O$ | H | $OCF_2CF_2H$ | H |
| 2 | 226N | $CCl_3$ | H | O | 4-F—$C_6H_5O$ | H | $OCF_2CF_2H$ | H |
| 2 | 227N | $CCl_3$ | H | O | 3,4-Cl—$C_6H_5O$ | H | $OCF_2CF_2H$ | H |
| 2 | 228N | $CCl_3$ | H | O | H | $C_6H_5$ | $OCF_2CF_2H$ | H |
| 2 | 229N | $CCl_3$ | H | O | H | 4-Cl—$C_6H_5$ | $OCF_2CF_2H$ | H |
| 2 | 230N | $CCl_3$ | H | O | H | 4-F—$C_6H_5$ | $OCF_2CF_2H$ | H |
| 2 | 231N | $CCl_3$ | H | O | H | 4-Br—$C_6H_5$ | $OCF_2CF_2H$ | H |
| 2 | 232N | $CCl_3$ | H | O | 4-Br—$C_6H_5O$ | H | $OCF_2CF_2H$ | H |
| 2 | 233N | $CCl_3$ | H | O | $C_6H_5O$ | H | $OCF_2CF_3$ | H |
| 2 | 234N | $CCl_3$ | H | O | 4-Cl—$C_6H_5O$ | H | $OCF_2CF_3$ | H |
| 2 | 235N | $CCl_3$ | H | O | 4-F—$C_6H_5O$ | H | $OCF_2CF_3$ | H |
| 2 | 236N | $CCl_3$ | H | O | 3,4-Cl—$C_6H_5O$ | H | $OCF_2CF_3$ | H |
| 2 | 237N | $CCl_3$ | H | O | H | $C_6H_5$ | $OCF_2CF_3$ | H |
| 2 | 238N | $CCl_3$ | H | O | H | 4-Cl—$C_6H_5$ | $OCF_2CF_3$ | H |
| 2 | 239N | $CCl_3$ | H | O | H | 4-F—$C_6H_5$ | $OCF_2CF_3$ | H |
| 2 | 240N | $CCl_3$ | H | O | H | 4-Br—$C_6H_5$ | $OCF_2CF_3$ | H |
| 2 | 241N | $CCl_3$ | H | O | 4-Br—$C_6H_5O$ | H | $OCF_2CF_3$ | H |
| 2 | 242N | $CCl_3$ | H | O | $C_6H_5O$ | H | $OCCl_2CCl_2H$ | H |
| 2 | 243N | $CCl_3$ | H | O | 4-Cl—$C_6H_5O$ | H | $OCCl_2CCl_2H$ | H |
| 2 | 244N | $CCl_3$ | H | O | 4-F—$C_6H_5O$ | H | $OCCl_2CCl_2H$ | H |
| 2 | 245N | $CCl_3$ | H | O | 3,4-Cl—$C_6H_5O$ | H | $OCCl_2CCl_2H$ | H |
| 2 | 246N | $CCl_3$ | H | O | H | $C_6H_5$ | $OCCl_2CCl_2H$ | H |
| 2 | 247N | $CCl_3$ | H | O | H | 4-Cl—$C_6H_5$ | $OCCl_2CCl_2H$ | H |
| 2 | 248N | $CCl_3$ | H | O | H | 4-F—$C_6H_5$ | $OCCl_2CCl_2H$ | H |
| 2 | 249N | $CCl_3$ | H | O | H | 4-Br—$C_6H_5$ | $OCCl_2CCl_2H$ | H |
| 2 | 250N | $CCl_3$ | H | O | 4-Br—$C_6H_5O$ | H | $OCCl_2CCl_2H$ | H |
| 2 | 251N | $CCl_3$ | H | O | $C_6H_5O$ | H | $OCCl_2CCl_3$ | H |
| 2 | 252N | $CCl_3$ | H | O | 4-Cl—$C_6H_5O$ | H | $OCCl_2CCl_3$ | H |
| 2 | 253N | $CCl_3$ | H | O | 4-F—$C_6H_5O$ | H | $OCCl_2CCl_3$ | H |
| 2 | 254N | $CCl_3$ | H | O | 3,4-Cl—$C_6H_5O$ | H | $OCCl_2CCl_3$ | H |
| 2 | 255N | $CCl_3$ | H | O | H | $C_6H_5$ | $OCCl_2CCl_3$ | H |
| 2 | 256N | $CCl_3$ | H | O | H | 4-Cl—$C_6H_5$ | $OCCl_2CCl_3$ | H |
| 2 | 257N | $CCl_3$ | H | O | H | 4-F—$C_6H_5$ | $OCCl_2CCl_3$ | H |
| 2 | 258N | $CCl_3$ | H | O | H | 4-Br—$C_6H_5$ | $OCCl_2CCl_3$ | H |
| 2 | 259N | $CCl_3$ | H | O | 4-Br—$C_6H_5O$ | H | $OCCl_2CCl_3$ | H |
| 2 | 260N | $CCl_3$ | H | O | $C_6H_5O$ | H | $OCCl_2CF_3$ | H |
| 2 | 261N | $CCl_3$ | H | O | 4-Cl—$C_6H_5O$ | H | $OCCl_2CF_3$ | H |
| 2 | 262N | $CCl_3$ | H | O | 4-F—$C_6H_5O$ | H | $OCCl_2CF_3$ | H |
| 2 | 263N | $CCl_3$ | H | O | 3,4-Cl—$C_6H_5O$ | H | $OCCl_2CF_3$ | H |
| 2 | 264N | $CCl_3$ | H | O | H | $C_6H_5$ | $OCCl_2CF_3$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

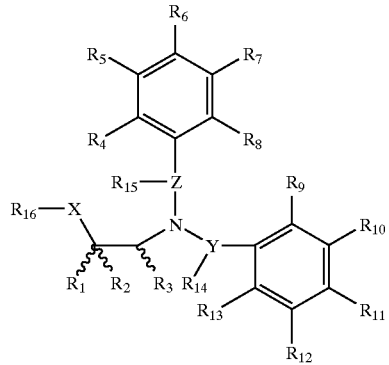

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 2 | 265N | $CCl_3$ | H | O | H | 4-Cl—$C_6H_5$ | $OCCl_2CF_3$ | H |
| 2 | 266N | $CCl_3$ | H | O | H | 4-F—$C_6H_5$ | $OCCl_2CF_3$ | H |
| 2 | 267N | $CCl_3$ | H | O | H | 4-Br—$C_6H_5$ | $OCCl_2CF_3$ | H |
| 2 | 268N | $CCl_3$ | H | O | 4-Br—$C_6H_5O$ | H | $OCCl_2CF_3$ | H |
| 2 | 269N | $CCl_3$ | H | O | $C_6H_5O$ | H | $OCF_2CCl_3$ | H |
| 2 | 270N | $CCl_3$ | H | O | 4-Cl—$C_6H_5O$ | H | $OCF_2CCl_3$ | H |
| 2 | 271N | $CCl_3$ | H | O | 4-F—$C_6H_5O$ | H | $OCF_2CCl_3$ | H |
| 2 | 272N | $CCl_3$ | H | O | 3,4-Cl—$C_6H_5O$ | H | $OCF_2CCl_3$ | H |
| 2 | 273N | $CCl_3$ | H | O | H | $C_6H_5$ | $OCF_2CCl_3$ | H |
| 2 | 274N | $CCl_3$ | H | O | H | 4-Cl—$C_6H_5$ | $OCF_2CCl_3$ | H |
| 2 | 275N | $CCl_3$ | H | O | H | 4-F—$C_6H_5$ | $OCF_2CCl_3$ | H |
| 2 | 276N | $CCl_3$ | H | O | H | 4-Br—$C_6H_5$ | $OCF_2CCl_3$ | H |
| 2 | 277N | $CCl_3$ | H | O | 4-Br—$C_6H_5O$ | H | $OCF_2CCl_3$ | H |
| 2 | 278N | $CCl_3$ | H | O | $C_6H_5O$ | H | $OCF_2CF_2H$ | $OCF_2CF_2H$ |
| 2 | 279N | $CCl_3$ | H | O | 4-Cl—$C_6H_5O$ | H | $OCF_2CF_2H$ | $OCF_2CF_2H$ |
| 2 | 280N | $CCl_3$ | H | O | 4-F—$C_6H_5O$ | H | $OCF_2CF_2H$ | $OCF_2CF_2H$ |
| 2 | 281N | $CCl_3$ | H | O | 3,4-Cl—$C_6H_5O$ | H | $OCF_2CF_2H$ | $OCF_2CF_2H$ |
| 2 | 282N | $CCl_3$ | H | O | H | $C_6H_5$ | $OCF_2CF_2H$ | $OCF_2CF_2H$ |
| 2 | 283N | $CCl_3$ | H | O | H | 4-Cl—$C_6H_5$ | $OCF_2CF_2H$ | $OCF_2CF_2H$ |
| 2 | 284N | $CCl_3$ | H | O | H | 4-F—$C_6H_5$ | $OCF_2CF_2H$ | $OCF_2CF_2H$ |
| 2 | 285N | $CCl_3$ | H | O | H | 4-Br—$C_6H_5$ | $OCF_2CF_2H$ | $OCF_2CF_2H$ |
| 2 | 286N | $CCl_3$ | H | O | 4-Br—$C_6H_5O$ | H | $OCF_2CF_2H$ | $OCF_2CF_2H$ |
| 2 | 287N | $CCl_3$ | H | O | $C_6H_5O$ | H | $OCF_3$ | $OCF_3$ |
| 2 | 288N | $CCl_3$ | H | O | 4-Cl—$C_6H_5O$ | H | $OCF_3$ | $OCF_3$ |
| 2 | 289N | $CCl_3$ | H | O | 4-F—$C_6H_5O$ | H | $OCF_3$ | $OCF_3$ |
| 2 | 290N | $CCl_3$ | H | O | 3,4-Cl—$C_6H_5O$ | H | $OCF_3$ | $OCF_3$ |
| 2 | 291N | $CCl_3$ | H | O | H | $C_6H_5$ | $OCF_3$ | $OCF_3$ |
| 2 | 292N | $CCl_3$ | H | O | H | 4-Cl—$C_6H_5$ | $OCF_3$ | $OCF_3$ |
| 2 | 293N | $CCl_3$ | H | O | H | 4-F—$C_6H_5$ | $OCF_3$ | $OCF_3$ |
| 2 | 294N | $CCl_3$ | H | O | H | 4-Br—$C_6H_5$ | $OCF_3$ | $OCF_3$ |
| 2 | 295N | $CCl_3$ | H | O | 4-Br—$C_6H_5O$ | H | $OCF_3$ | $OCF_3$ |
| 2 | 296N | $CCl_3$ | H | O | $C_6H_5O$ | H | $OCF_2H$ | $OCF_2H$ |
| 2 | 297N | $CCl_3$ | H | O | 4-Cl—$C_6H_5O$ | H | $OCF_2H$ | $OCF_2H$ |
| 2 | 298N | $CCl_3$ | H | O | 4-F—$C_6H_5O$ | H | $OCF_2H$ | $OCF_2H$ |
| 2 | 299N | $CCl_3$ | H | O | 3,4-Cl—$C_6H_5O$ | H | $OCF_2H$ | $OCF_2H$ |
| 2 | 300N | $CCl_3$ | H | O | H | $C_6H_5$ | $OCF_2H$ | $OCF_2H$ |
| 2 | 301N | $CCl_3$ | H | O | H | 4-Cl—$C_6H_5$ | $OCF_2H$ | $OCF_2H$ |
| 2 | 302N | $CCl_3$ | H | O | H | 4-F—$C_6H_5$ | $OCF_2H$ | $OCF_2H$ |
| 2 | 303N | $CCl_3$ | H | O | H | 4-Br—$C_6H_5$ | $OCF_2H$ | $OCF_2H$ |
| 2 | 304N | $CCl_3$ | H | O | 4-Br—$C_6H_5O$ | H | $OCF_2H$ | $OCF_2H$ |
| 2 | 305N | $CCl_3$ | H | O | $C_6H_5O$ | H | $R_{10} + R_{11} = OCF_2CF_2O$ | |
| 2 | 306N | $CCl_3$ | H | O | 4-Cl—$C_6H_5O$ | H | $R_{10} + R_{11} = OCF_2CF_2O$ | |
| 2 | 307N | $CCl_3$ | H | O | 4-F—$C_6H_5O$ | H | $R_{10} + R_{11} = OCF_2CF_2O$ | |
| 2 | 308N | $CCl_3$ | H | O | 3,4-Cl—$C_6H_5O$ | H | $R_{10} + R_{11} = OCF_2CF_2O$ | |
| 2 | 309N | $CCl_3$ | H | O | H | $C_6H_5$ | $R_{10} + R_{11} = OCF_2CF_2O$ | |
| 2 | 310N | $CCl_3$ | H | O | H | 4-Cl—$C_6H_5$ | $R_{10} + R_{11} = OCF_2CF_2O$ | |
| 2 | 311N | $CCl_3$ | H | O | H | 4-F—$C_6H_5$ | $R_{10} + R_{11} = OCF_2CF_2O$ | |
| 2 | 312N | $CCl_3$ | H | O | H | 4-Br—$C_6H_5$ | $R_{10} + R_{11} = OCF_2CF_2O$ | |
| 2 | 313N | $CCl_3$ | H | O | 4-Br—$C_6H_5O$ | H | $R_{10} + R_{11} = OCF_2CF_2O$ | |
| 2 | 314N | $CCl_3$ | H | O | $C_6H_5O$ | H | $R_{10} + R_{11} = OCCl_2CCl_2O$ | |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

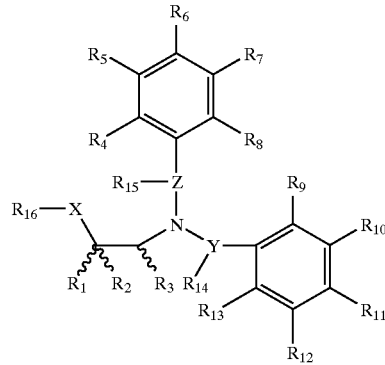

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 2 | 315N | CCl$_3$ | H | O | 4-Cl—C$_6$H$_5$O | H | $R_{10}$ + $R_{11}$ = OCCl$_2$CCl$_2$O | |
| 2 | 316N | CCl$_3$ | H | O | 4-F—C$_6$H$_5$O | H | $R_{10}$ + $R_{11}$ = OCCl$_2$CCl$_2$O | |
| 2 | 317N | CCl$_3$ | H | O | 3,4-Cl—C$_6$H$_5$O | H | $R_{10}$ + $R_{11}$ = OCCl$_2$CCl$_2$O | |
| 2 | 318N | CCl$_3$ | H | O | H | C$_6$H$_5$ | $R_{10}$ + $R_{11}$ = OCCl$_2$CCl$_2$O | |
| 2 | 319N | CCl$_3$ | H | O | H | 4-Cl—C$_6$H$_5$ | $R_{10}$ + $R_{11}$ = OCCl$_2$CCl$_2$O | |
| 2 | 320N | CCl$_3$ | H | O | H | 4-F—C$_6$H$_5$ | $R_{10}$ + $R_{11}$ = OCCl$_2$CCl$_2$O | |
| 2 | 321N | CCl$_3$ | H | O | H | 4-Br—C$_6$H$_5$ | $R_{10}$ + $R_{11}$ = OCCl$_2$CCl$_2$O | |
| 2 | 322N | CCl$_3$ | H | O | 4-Br—C$_6$H$_5$O | H | $R_{10}$ + $R_{11}$ = OCCl$_2$CCl$_2$O | |
| 2 | 323N | CCl$_3$ | H | O | H | H | OH | H |
| 2 | 324N | CCl$_3$ | H | O | H | H | OH | OH |
| 2 | 325N | CCl$_3$ | H | O | H | H | H | OH |
| 2 | 326N | CCl$_3$ | H | O | H | H | OCH$_2$CF$_3$ | H |
| 2 | 327N | CCl$_3$ | H | O | H | H | H | OCH$_2$CF$_3$ |
| 2 | 328N | CCl$_3$ | H | O | H | H | OCH$_2$CF$_2$CF$_3$ | H |
| 2 | 329N | CCl$_3$ | H | O | H | H | OCH$_2$CH$_2$CF$_3$ | H |
| 2 | 330N | CCl$_3$ | H | O | H | H | OCH(CF$_3$)$_3$ | H |
| 2 | 331N | CCl$_3$ | H | O | H | 4-F—C$_6$H$_5$O | H | H |
| 2 | 332N | CCl$_3$ | H | O | 4-F—C$_6$H$_5$O | H | H | H |
| 2 | 333N | CCl$_3$ | H | O | H | cyclohexoxy | H | H |
| 2 | 334N | CCl$_3$ | H | O | cyclohexoxy | H | H | H |
| 2 | 335N | CCl$_3$ | H | O | H | CH(CH$_3$)$_3$ | H | H |
| 2 | 336N | CCl$_3$ | H | O | F | H | 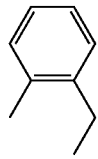 | bond to indicated phenyl carbon of $R_{10}$ substituent |
| 3 | 224N | CF$_3$ | CH$_3$ | O | C$_6$H$_5$O | H | OCF$_2$CF$_2$H | H |
| 3 | 225N | CF$_3$ | CH$_3$ | O | 4-Cl—C$_6$H$_5$O | H | OCF$_2$CF$_2$H | H |
| 3 | 226N | CF$_3$ | CH$_3$ | O | 4-F—C$_6$H$_5$O | H | OCF$_2$CF$_2$H | H |
| 3 | 227N | CF$_3$ | CH$_3$ | O | 3,4-Cl—C$_6$H$_5$O | H | OCF$_2$CF$_2$H | H |
| 3 | 228N | CF$_3$ | CH$_3$ | O | H | C$_6$H$_5$ | OCF$_2$CF$_2$H | H |
| 3 | 229N | CF$_3$ | CH$_3$ | O | H | 4-Cl—C$_6$H$_5$ | OCF$_2$CF$_2$H | H |
| 3 | 230N | CF$_3$ | CH$_3$ | O | H | 4-F—C$_6$H$_5$ | OCF$_2$CF$_2$H | H |
| 3 | 231N | CF$_3$ | CH$_3$ | O | H | 4-Br—C$_6$H$_5$ | OCF$_2$CF$_2$H | H |
| 3 | 232N | CF$_3$ | CH$_3$ | O | 4-Br—C$_6$H$_5$O | H | OCF$_2$CF$_2$H | H |
| 3 | 233N | CF$_3$ | CH$_3$ | O | C$_6$H$_5$O | H | OCF$_2$CF$_3$ | H |
| 3 | 234N | CF$_3$ | CH$_3$ | O | 4-Cl—C$_6$H$_5$O | H | OCF$_2$CF$_3$ | H |
| 3 | 235N | CF$_3$ | CH$_3$ | O | 4-F—C$_6$H$_5$O | H | OCF$_2$CF$_3$ | H |
| 3 | 236N | CF$_3$ | CH$_3$ | O | 3,4-Cl—C$_6$H$_5$O | H | OCF$_2$CF$_3$ | H |
| 3 | 237N | CF$_3$ | CH$_3$ | O | H | C$_6$H$_5$ | OCF$_2$CF$_3$ | H |
| 3 | 238N | CF$_3$ | CH$_3$ | O | H | 4-Cl—C$_6$H$_5$ | OCF$_2$CF$_3$ | H |
| 3 | 239N | CF$_3$ | CH$_3$ | O | H | 4-F—C$_6$H$_5$ | OCF$_2$CF$_3$ | H |
| 3 | 240N | CF$_3$ | CH$_3$ | O | H | 4-Br—C$_6$H$_5$ | OCF$_2$CF$_3$ | H |
| 3 | 241N | CF$_3$ | CH$_3$ | O | 4-Br—C$_6$H$_5$O | H | OCF$_2$CF$_3$ | H |
| 3 | 242N | CF$_3$ | CH$_3$ | O | C$_6$H$_5$O | H | OCCl$_2$CCl$_2$H | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

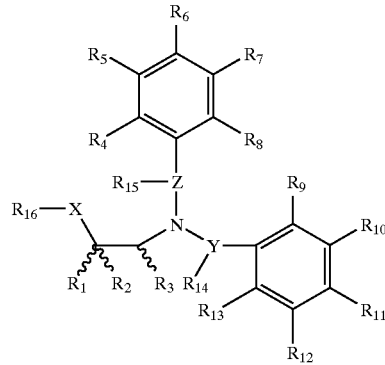

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 3 | 243N | $CF_3$ | $CH_3$ | O | 4-Cl—$C_6H_5$O | H | $OCCl_2CCl_2H$ | H |
| 3 | 244N | $CF_3$ | $CH_3$ | O | 4-F—$C_6H_5$O | H | $OCCl_2CCl_2H$ | H |
| 3 | 245N | $CF_3$ | $CH_3$ | O | 3,4-Cl—$C_6H_5$O | H | $OCCl_2CCl_2H$ | H |
| 3 | 246N | $CF_3$ | $CH_3$ | O | H | $C_6H_5$ | $OCCl_2CCl_2H$ | H |
| 3 | 247N | $CF_3$ | $CH_3$ | O | H | 4-Cl—$C_6H_5$ | $OCCl_2CCl_2H$ | H |
| 3 | 248N | $CF_3$ | $CH_3$ | O | H | 4-F—$C_6H_5$ | $OCCl_2CCl_2H$ | H |
| 3 | 249N | $CF_3$ | $CH_3$ | O | H | 4-Br—$C_6H_5$ | $OCCl_2CCl_2H$ | H |
| 3 | 250N | $CF_3$ | $CH_3$ | O | 4-Br—$C_6H_5$O | H | $OCCl_2CCl_2H$ | H |
| 3 | 251N | $CF_3$ | $CH_3$ | O | $C_6H_5$O | H | $OCCl_2CCl_3$ | H |
| 3 | 252N | $CF_3$ | $CH_3$ | O | 4-Cl—$C_6H_5$O | H | $OCCl_2CCl_3$ | H |
| 3 | 253N | $CF_3$ | $CH_3$ | O | 4-F—$C_6H_5$O | H | $OCCl_2CCl_3$ | H |
| 3 | 254N | $CF_3$ | $CH_3$ | O | 3,4-Cl—$C_6H_5$O | H | $OCCl_2CCl_3$ | R |
| 3 | 255N | $CF_3$ | $CH_3$ | O | H | $C_6H_5$ | $OCCl_2CCl_3$ | H |
| 3 | 256N | $CF_3$ | $CH_3$ | O | H | 4-Cl—$C_6H_5$ | $OCCl_2CCl_3$ | H |
| 3 | 257N | $CF_3$ | $CH_3$ | O | H | 4-F—$C_6H_5$ | $OCCl_2CCl_3$ | H |
| 3 | 258N | $CF_3$ | $CH_3$ | O | H | 4-Br—$C_6H_5$ | $OCCl_2CCl_3$ | H |
| 3 | 259N | $CF_3$ | $CH_3$ | O | 4-Br—$C_6H_5$O | H | $OCCl_2CCl_3$ | H |
| 3 | 260N | $CF_3$ | $CH_3$ | O | $C_6H_5$O | H | $OCCl_2CF_3$ | H |
| 3 | 261N | $CF_3$ | $CH_3$ | O | 4-Cl—$C_6H_5$O | H | $OCCl_2CF_3$ | H |
| 3 | 262N | $CF_3$ | $CH_3$ | O | 4-F—$C_6H_5$O | H | $OCCl_2CF_3$ | H |
| 3 | 263N | $CF_3$ | $CH_3$ | O | 3,4-Cl—$C_6H_5$O | H | $OCCl_2CF_3$ | H |
| 3 | 264N | $CF_3$ | $CH_3$ | O | H | $C_6H_5$ | $OCCl_2CF_3$ | H |
| 3 | 265N | $CF_3$ | $CH_3$ | O | H | 4-Cl—$C_6H_5$ | $OCCl_2CF_3$ | H |
| 3 | 266N | $CF_3$ | $CH_3$ | O | H | 4-F—$C_6H_5$ | $OCCl_2CF_3$ | H |
| 3 | 267N | $CF_3$ | $CH_3$ | O | H | 4-Br—$C_6H_5$ | $OCCl_2CF_3$ | H |
| 3 | 268N | $CF_3$ | $CH_3$ | O | 4-Br—$C_6H_5$O | H | $OCCl_2CF_3$ | H |
| 3 | 269N | $CF_3$ | $CH_3$ | O | $C_6H_5$O | H | $OCF_2CCl_3$ | H |
| 3 | 270N | $CF_3$ | $CH_3$ | O | 4-Cl—$C_6H_5$O | H | $OCF_2CCl_3$ | H |
| 3 | 271N | $CF_3$ | $CH_3$ | O | 4-F—$C_6H_5$O | H | $OCF_2CCl_3$ | H |
| 3 | 272N | $CF_3$ | $CH_3$ | O | 3,4-Cl—$C_6H_5$O | H | $OCF_2CCl_3$ | H |
| 3 | 273N | $CF_3$ | $CH_3$ | O | H | $C_6H_5$ | $OCF_2CCl_3$ | H |
| 3 | 274N | $CF_3$ | $CH_3$ | O | H | 4-Cl—$C_6H_5$ | $OCF_2CCl_3$ | H |
| 3 | 275N | $CF_3$ | $CH_3$ | O | H | 4-F—$C_6H_5$ | $OCF_2CCl_3$ | H |
| 3 | 276N | $CF_3$ | $CH_3$ | O | H | 4-Br—$C_6H_5$ | $OCF_2CCl_3$ | H |
| 3 | 277N | $CF_3$ | $CH_3$ | O | 4-Br—$C_6H_5$O | H | $OCF_2CCl_3$ | H |
| 3 | 278N | $CF_3$ | $CH_3$ | O | $C_6H_5$O | H | $OCF_2CF_2H$ | $OCF_2CF_2H$ |
| 3 | 279N | $CF_3$ | $CH_3$ | O | 4-Cl—$C_6H_5$O | H | $OCF_2CF_2H$ | $OCF_2CF_2H$ |
| 3 | 280N | $CF_3$ | $CH_3$ | O | 4-F—$C_6H_5$O | H | $OCF_2CF_2H$ | $OCF_2CF_2H$ |
| 3 | 281N | $CF_3$ | $CH_3$ | O | 3,4-Cl—$C_6H_5$O | H | $OCF_2CF_2H$ | $OCF_2CF_2H$ |
| 3 | 282N | $CF_3$ | $CH_3$ | O | H | $C_6H_5$ | $OCF_2CF_2H$ | $OCF_2CF_2H$ |
| 3 | 283N | $CF_3$ | $CH_3$ | O | H | 4-Cl—$C_6H_5$ | $OCF_2CF_2H$ | $OCF_2CF_2H$ |
| 3 | 284N | $CF_3$ | $CH_3$ | O | H | 4-F—$C_6H_5$ | $OCF_2CF_2H$ | $OCF_2CF_2H$ |
| 3 | 285N | $CF_3$ | $CH_3$ | O | H | 4-Br—$C_6H_5$ | $OCF_2CF_2H$ | $OCF_2CF_2H$ |
| 3 | 286N | $CF_3$ | $CH_3$ | O | 4-Br—$C_6H_5$O | H | $OCF_2CF_2H$ | $OCF_2CF_2H$ |
| 3 | 287N | $CF_3$ | $CH_3$ | O | $C_6H_5$O | H | $OCF_3$ | $OCF_3$ |
| 3 | 288N | $CF_3$ | $CH_3$ | O | 4-Cl—$C_6H_5$O | H | $OCF_3$ | $OCF_3$ |
| 3 | 289N | $CF_3$ | $CH_3$ | O | 4-F—$C_6H_5$O | H | $OCF_3$ | $OCF_3$ |
| 3 | 290N | $CF_3$ | $CH_3$ | O | 3,4-Cl—$C_6H_5$O | H | $OCF_3$ | $OCF_3$ |
| 3 | 291N | $CF_3$ | $CH_3$ | O | H | $C_6H_5$ | $OCF_3$ | $OCF_3$ |
| 3 | 292N | $CF_3$ | $CH_3$ | O | H | 4-Cl—$C_6H_5$ | $OCF_3$ | $OCF_3$ |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

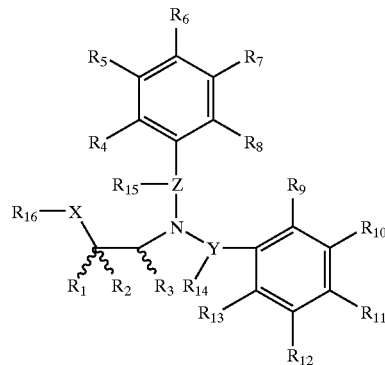

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 3 | 293N | $CF_3$ | $CH_3$ | O | H | 4-F—$C_6H_5$ | $OCF_3$ | $OCF_3$ |
| 3 | 294N | $CF_3$ | $CH_3$ | O | H | 4-Br—$C_6H_5$ | $OCF_3$ | $OCF_3$ |
| 3 | 295N | $CF_3$ | $CH_3$ | O | 4-Br—$C_6H_5O$ | H | $OCF_3$ | $OCF_3$ |
| 3 | 296N | $CF_3$ | $CH_3$ | O | $C_6H_5O$ | H | $OCF_2H$ | $OCF_2H$ |
| 3 | 297N | $CF_3$ | $CH_3$ | O | 4-Cl—$C_6H_5O$ | H | $OCF_2H$ | $OCF_2H$ |
| 3 | 298N | $CF_3$ | $CH_3$ | O | 4-F—$C_6H_5O$ | H | $OCF_2H$ | $OCF_2H$ |
| 3 | 299N | $CF_3$ | $CH_3$ | O | 3,4-Cl—$C_6H_5O$ | H | $OCF_2H$ | $OCF_2H$ |
| 3 | 300N | $CF_3$ | $CH_3$ | O | H | $C_6H_5$ | $OCF_2H$ | $OCF_2H$ |
| 3 | 301N | $CF_3$ | $CH_3$ | O | H | 4-Cl—$C_6H_5$ | $OCF_2H$ | $OCF_2H$ |
| 3 | 302N | $CF_3$ | $CH_3$ | O | H | 4-F—$C_6H_5$ | $OCF_2H$ | $OCF_2H$ |
| 3 | 303N | $CF_3$ | $CH_3$ | O | H | 4-Br—$C_6H_5$ | $OCF_2H$ | $OCF_2H$ |
| 3 | 304N | $CF_3$ | $CH_3$ | O | 4-Br—$C_6H_5O$ | H | $OCF_2H$ | $OCF_2H$ |
| 3 | 305N | $CF_3$ | $CH_3$ | O | $C_6H_5O$ | H | $R_{10} + R_{11} = OCF_2CF_2O$ | |
| 3 | 306N | $CF_3$ | $CH_3$ | O | 4-Cl—$C_6H_5O$ | H | $R_{10} + R_{11} = OCF_2CF_2O$ | |
| 3 | 307N | $CF_3$ | $CH_3$ | O | 4-F—$C_6H_5O$ | H | $R_{10} + R_{11} = OCF_2CF_2O$ | |
| 3 | 308N | $CF_3$ | $CH_3$ | O | 3,4-Cl—$C_6H_5O$ | H | $R_{10} + R_{11} = OCF_2CF_2O$ | |
| 3 | 309N | $CF_3$ | $CH_3$ | O | H | $C_6H_5$ | $R_{10} + R_{11} = OCF_2CF_2O$ | |
| 3 | 310N | $CF_3$ | $CH_3$ | O | H | 4-Cl—$C_6H_5$ | $R_{10} + R_{11} = OCF_2CF_2O$ | |
| 3 | 311N | $CF_3$ | $CH_3$ | O | H | 4-F—$C_6H_5$ | $R_{10} + R_{11} = OCF_2CF_2O$ | |
| 3 | 312N | $CF_3$ | $CH_3$ | O | H | 4-Br—$C_6H_5$ | $R_{10} + R_{11} = OCF_2CF_2O$ | |
| 3 | 313N | $CF_3$ | $CH_3$ | O | 4-Br—$C_6H_5O$ | H | $R_{10} + R_{11} = OCF_2CF_2O$ | |
| 3 | 314N | $CF_3$ | $CH_3$ | O | $C_6H_5O$ | H | $R_{10} + R_{11} = OCCl_2CCl_2O$ | |
| 3 | 315N | $CF_3$ | $CH_3$ | O | 4-Cl—$C_6H_5O$ | H | $R_{10} + R_{11} = OCCl_2CCl_2O$ | |
| 3 | 316N | $CF_3$ | $CH_3$ | O | 4-F—$C_6H_5O$ | H | $R_{10} + R_{11} = OCCl_2CCl_2O$ | |
| 3 | 317N | $CF_3$ | $CH_3$ | O | 3,4-Cl—$C_6H_5O$ | H | $R_{10} + R_{11} = OCCl_2CCl_2O$ | |
| 3 | 318N | $CF_3$ | $CH_3$ | O | H | $C_6H_5$ | $R_{10} + R_{11} = OCCl_2CCl_2O$ | |
| 3 | 319N | $CF_3$ | $CH_3$ | O | H | 4-Cl—$C_6H_5$ | $R_{10} + R_{11} = OCCl_2CCl_2O$ | |
| 3 | 320N | $CF_3$ | $CH_3$ | O | H | 4-F—$C_6H_5$ | $R_{10} + R_{11} = OCCl_2CCl_2O$ | |
| 3 | 321N | $CF_3$ | $CH_3$ | O | H | 4-Br—$C_6H_5$ | $R_{10} + R_{11} = OCCl_2CCl_2O$ | |
| 3 | 322N | $CF_3$ | $CH_3$ | O | 4-Br—$C_6H_5O$ | H | $R_{10} + R_{11} = OCCl_2CCl_2O$ | |
| 3 | 323N | $CF_3$ | $CH_3$ | O | H | H | OH | H |
| 3 | 324N | $CF_3$ | $CH_3$ | O | H | H | OH | OH |
| 3 | 325N | $CF_3$ | $CH_3$ | O | H | H | H | OH |
| 3 | 326N | $CF_3$ | $CH_3$ | O | H | H | $OCH_2CF_3$ | H |
| 3 | 327N | $CF_3$ | $CH_3$ | O | H | H | H | $OCH_2CF_3$ |
| 3 | 328N | $CF_3$ | $CH_3$ | O | H | H | $OCH_2CF_2CF_3$ | H |
| 3 | 329N | $CF_3$ | $CH_3$ | O | H | H | $OCH_2CH_2CF_3$ | H |
| 3 | 330N | $CF_3$ | $CH_3$ | O | H | H | $OCH(CF_3)_3$ | H |
| 3 | 331N | $CF_3$ | $CH_3$ | O | H | 4-F—$C_6H_5O$ | H | H |
| 3 | 332N | $CF_3$ | $CH_3$ | O | 4-F—$C_6H_5O$ | H | H | H |
| 3 | 333N | $CF_3$ | $CH_3$ | O | H | cyclohexoxy | H | H |
| 3 | 334N | $CF_3$ | $CH_3$ | O | cyclohexoxy | H | H | H |
| 3 | 335N | $CF_3$ | $CH_3$ | O | H | $CH(CH_3)_3$ | H | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

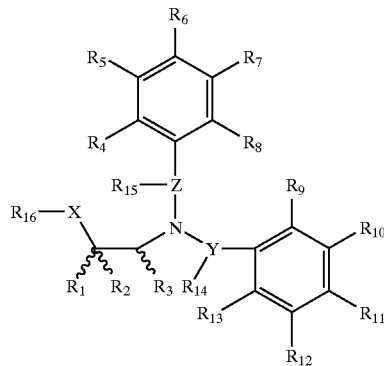

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 3 | 336N | $CF_3$ | $CH_3$ | O | F | H | (2-ethylphenyl) | bond to indicated phenyl carbon of $R_{10}$ substituent |
| 4 | 224N | $CF_3CF_2$ | H | O | $C_6H_5O$ | H | $OCF_2CF_2H$ | H |
| 4 | 225N | $CF_3CF_2$ | H | O | 4-Cl—$C_6H_5O$ | H | $OCF_2CF_2H$ | H |
| 4 | 226N | $CF_3CF_2$ | H | O | 4-F—$C_6H_5O$ | H | $OCF_2CF_2H$ | H |
| 4 | 227N | $CF_3CF_2$ | H | O | 3,4-Cl—$C_6H_5O$ | H | $OCF_2CF_2H$ | H |
| 4 | 228N | $CF_3CF_2$ | H | O | H | $C_6H_5$ | $OCF_2CF_2H$ | H |
| 4 | 229N | $CF_3CF_2$ | H | O | H | 4-Cl—$C_6H_5$ | $OCF_2CF_2H$ | H |
| 4 | 230N | $CF_3CF_2$ | H | O | H | 4-F—$C_6H_5$ | $OCF_2CF_2H$ | H |
| 4 | 231N | $CF_3CF_2$ | H | O | H | 4-Br—$C_6H_5$ | $OCF_2CF_2H$ | H |
| 4 | 232N | $CF_3CF_2$ | H | O | 4-Br—$C_6H_5O$ | H | $OCF_2CF_2H$ | H |
| 4 | 233N | $CF_3CF_2$ | H | O | $C_6H_5O$ | H | $OCF_2CF_3$ | H |
| 4 | 234N | $CF_3CF_2$ | H | O | 4-Cl—$C_6H_5O$ | H | $OCF_2CF_3$ | H |
| 4 | 235N | $CF_3CF_2$ | H | O | 4-F—$C_6H_5O$ | H | $OCF_2CF_3$ | H |
| 4 | 236N | $CF_3CF_2$ | H | O | 3,4-Cl—$C_6H_5O$ | H | $OCF_2CF_3$ | H |
| 4 | 237N | $CF_3CF_2$ | H | O | H | $C_6H_5$ | $OCF_2CF_3$ | H |
| 4 | 238N | $CF_3CF_2$ | H | O | H | 4-Cl—$C_6H_5$ | $OCF_2CF_3$ | H |
| 4 | 239N | $CF_3CF_2$ | H | O | H | 4-F—$C_6H_5$ | $OCF_2CF_3$ | H |
| 4 | 240N | $CF_3CF_2$ | H | O | H | 4-Br—$C_6H_5$ | $OCF_2CF_3$ | H |
| 4 | 241N | $CF_3CF_2$ | H | O | 4-Br—$C_6H_5O$ | H | $OCF_2CF_3$ | H |
| 4 | 242N | $CF_3CF_2$ | H | O | $C_6H_5O$ | H | $OCCl_2CCl_2H$ | H |
| 4 | 243N | $CF_3CF_2$ | H | O | 4-Cl—$C_6H_5O$ | H | $OCCl_2CCl_2H$ | H |
| 4 | 244N | $CF_3CF_2$ | H | O | 4-F—$C_6H_5O$ | H | $OCCl_2CCl_2H$ | H |
| 4 | 245N | $CF_3CF_2$ | H | O | 3,4-Cl—$C_6H_5O$ | H | $OCCl_2CCl_2H$ | H |
| 4 | 246N | $CF_3CF_2$ | H | O | H | $C_6H_5$ | $OCCl_2CCl_2H$ | H |
| 4 | 247N | $CF_3CF_2$ | H | O | H | 4-Cl—$C_6H_5$ | $OCCl_2CCl_2H$ | H |
| 4 | 248N | $CF_3CF_2$ | H | O | H | 4-F—$C_6H_5$ | $OCCl_2CCl_2H$ | H |
| 4 | 249N | $CF_3CF_2$ | H | O | H | 4-Br—$C_6H_5$ | $OCCl_2CCl_2H$ | H |
| 4 | 250N | $CF_3CF_2$ | H | O | 4-Br—$C_6H_5O$ | H | $OCCl_2CCl_2H$ | H |
| 4 | 251N | $CF_3CF_2$ | H | O | $C_6H_5O$ | H | $OCCl_2CCl_3$ | H |
| 4 | 252N | $CF_3CF_2$ | H | O | 4-Cl—$C_6H_5O$ | H | $OCCl_2CCl_3$ | H |
| 4 | 253N | $CF_3CF_2$ | H | O | 4-F—$C_6H_5O$ | H | $OCCl_2CCl_3$ | H |
| 4 | 254N | $CF_3CF_2$ | H | O | 3,4-Cl—$C_6H_5O$ | H | $OCCl_2CCl_3$ | H |
| 4 | 255N | $CF_3CF_2$ | H | O | H | $C_6H_5$ | $OCCl_2CCl_3$ | H |
| 4 | 256N | $CF_3CF_2$ | H | O | H | 4-Cl—$C_6H_5$ | $OCCl_2CCl_3$ | H |
| 4 | 257N | $CF_3CF_2$ | H | O | H | 4-F—$C_6H_5$ | $OCCl_2CCl_3$ | H |
| 4 | 258N | $CF_3CF_2$ | H | O | H | 4-Br—$C_6H_5$ | $OCCl_2CCl_3$ | H |
| 4 | 259N | $CF_3CF_2$ | H | O | 4-Br—$C_6H_5O$ | H | $OCCl_2CCl_3$ | H |
| 4 | 260N | $CF_3CF_2$ | H | O | $C_6H_5O$ | H | $OCCl_2CF_3$ | H |
| 4 | 261N | $CF_3CF_2$ | H | O | 4-Cl—$C_6H_5O$ | H | $OCCl_2CF_3$ | H |
| 4 | 262N | $CF_3CF_2$ | H | O | 4-F—$C_6H_5O$ | H | $OCCl_2CF_3$ | H |
| 4 | 263N | $CF_3CF_2$ | H | O | 3,4-Cl—$C_6H_5O$ | H | $OCCl_2CF_3$ | H |
| 4 | 264N | $CF_3CF_2$ | H | O | H | $C_6H_5$ | $OCCl_2CF_3$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

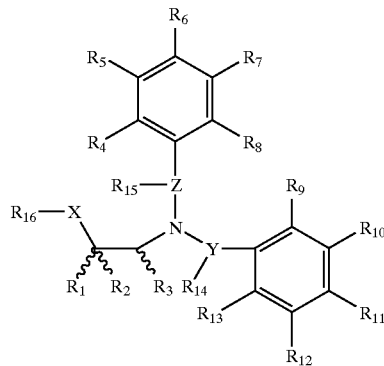

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 4 | 265N | $CF_3CF_2$ | H | O | H | 4-Cl—$C_6H_5$ | $OCCl_2CF_3$ | H |
| 4 | 266N | $CF_3CF_2$ | H | O | H | 4-F—$C_6H_5$ | $OCCl_2CF_3$ | H |
| 4 | 267N | $CF_3CF_2$ | H | O | H | 4-Br—$C_6H_5$ | $OCCl_2CF_3$ | H |
| 4 | 268N | $CF_3CF_2$ | H | O | 4-Br—$C_6H_5O$ | H | $OCCl_2CF_3$ | H |
| 4 | 269N | $CF_3CF_2$ | H | O | $C_6H_5O$ | H | $OCF_2CCl_3$ | H |
| 4 | 270N | $CF_3CF_2$ | H | O | 4-Cl—$C_6H_5O$ | H | $OCF_2CCl_3$ | H |
| 4 | 271N | $CF_3CF_2$ | H | O | 4-F—$C_6H_5O$ | H | $OCF_2CCl_3$ | H |
| 4 | 272N | $CF_3CF_2$ | H | O | 3,4-Cl—$C_6H_5O$ | H | $OCF_2CCl_3$ | H |
| 4 | 273N | $CF_3CF_2$ | H | O | H | $C_6H_5$ | $OCF_2CCl_3$ | H |
| 4 | 274N | $CF_3CF_2$ | H | O | H | 4-Cl—$C_6H_5$ | $OCF_2CCl_3$ | H |
| 4 | 275N | $CF_3CF_2$ | H | O | H | 4-F—$C_6H_5$ | $OCF_2CCl_3$ | H |
| 4 | 276N | $CF_3CF_2$ | H | O | H | 4-Br—$C_6H_5$ | $OCF_2CCl_3$ | H |
| 4 | 277N | $CF_3CF_2$ | H | O | 4-Br—$C_6H_5O$ | H | $OCF_2CCl_3$ | H |
| 4 | 278N | $CF_3CF_2$ | H | O | $C_6H_5O$ | H | $OCF_2CF_2H$ | $OCF_2CF_2H$ |
| 4 | 279N | $CF_3CF_2$ | H | O | 4-Cl—$C_6H_5O$ | H | $OCF_2CF_2H$ | $OCF_2CF_2H$ |
| 4 | 280N | $CF_3CF_2$ | H | O | 4-F—$C_6H_5O$ | H | $OCF_2CF_2H$ | $OCF_2CF_2H$ |
| 4 | 281N | $CF_3CF_2$ | H | O | 3,4-Cl—$C_6H_5O$ | H | $OCF_2CF_2H$ | $OCF_2CF_2H$ |
| 4 | 282N | $CF_3CF_2$ | H | O | H | $C_6H_5$ | $OCF_2CF_2H$ | $OCF_2CF_2H$ |
| 4 | 283N | $CF_3CF_2$ | H | O | H | 4-Cl—$C_6H_5$ | $OCF_2CF_2H$ | $OCF_2CF_2H$ |
| 4 | 284N | $CF_3CF_2$ | H | O | H | 4-F—$C_6H_5$ | $OCF_2CF_2H$ | $OCF_2CF_2H$ |
| 4 | 285N | $CF_3CF_2$ | H | O | H | 4-Br—$C_6H_5$ | $OCF_2CF_2H$ | $OCF_2CF_2H$ |
| 4 | 286N | $CF_3CF_2$ | H | O | 4-Br—$C_6H_5O$ | H | $OCF_2CF_2H$ | $OCF_2CF_2H$ |
| 4 | 287N | $CF_3CF_2$ | H | O | $C_6H_5O$ | H | $OCF_3$ | $OCF_3$ |
| 4 | 288N | $CF_3CF_2$ | H | O | 4-Cl—$C_6H_5O$ | H | $OCF_3$ | $OCF_3$ |
| 4 | 289N | $CF_3CF_2$ | H | O | 4-F—$C_6H_5O$ | H | $OCF_3$ | $OCF_3$ |
| 4 | 290N | $CF_3CF_2$ | H | O | 3,4-Cl—$C_6H_5O$ | H | $OCF_3$ | $OCF_3$ |
| 4 | 291N | $CF_3CF_2$ | H | O | H | $C_6H_5$ | $OCF_3$ | $OCF_3$ |
| 4 | 292N | $CF_3CF_2$ | H | O | H | 4-Cl—$C_6H_5$ | $OCF_3$ | $OCF_3$ |
| 4 | 293N | $CF_3CF_2$ | H | O | H | 4-F—$C_6H_5$ | $OCF_3$ | $OCF_3$ |
| 4 | 294N | $CF_3CF_2$ | H | O | H | 4-Br—$C_6H_5$ | $OCF_3$ | $OCF_3$ |
| 4 | 295N | $CF_3CF_2$ | H | O |  | H | $OCF_3$ | $OCF_3$ |
| 4 | 296N | $CF_3CF_2$ | H | O | $C_6H_5O$ | H | $OCF_2H$ | $OCF_2H$ |
| 4 | 297N | $CF_3CF_2$ | H | O | 4-Cl—$C_6H_5O$ | H | $OCF_2H$ | $OCF_2H$ |
| 4 | 298N | $CF_3CF_2$ | H | O | 4-F—$C_6H_5O$ | H | $OCF_2H$ | $OCF_2H$ |
| 4 | 299N | $CF_3CF_2$ | H | O | 3,4-Cl—$C_6H_5O$ | H | $OCF_2H$ | $OCF_2H$ |
| 4 | 300N | $CF_3CF_2$ | H | O | H | $C_6H_5$ | $OCF_2H$ | $OCF_2H$ |
| 4 | 301N | $CF_3CF_2$ | H | O | H | 4-Cl—$C_6H_5$ | $OCF_2H$ | $OCF_2H$ |
| 4 | 302N | $CF_3CF_2$ | H | O | H | 4-F—$C_6H_5$ | $OCF_2H$ | $OCF_2H$ |
| 4 | 303N | $CF_3CF_2$ | H | O | H | 4-Br—$C_6H_5$ | $OCF_2H$ | $OCF_2H$ |
| 4 | 304N | $CF_3CF_2$ | H | O | 4-Br—$C_6H_5O$ | H | $OCF_2H$ | $OCF_2H$ |
| 4 | 305N | $CF_3CF_2$ | H | O | $C_6H_5O$ | H | $R_{10} + R_{11} = OCF_2CF_2O$ | |
| 4 | 306N | $CF_3CF_2$ | H | O | 4-Cl—$C_6H_5O$ | H | $R_{10} + R_{11} = OCF_2CF_2O$ | |
| 4 | 307N | $CF_3CF_2$ | H | O | 4-F—$C_6H_5O$ | H | $R_{10} + R_{11} = OCF_2CF_2O$ | |
| 4 | 308N | $CF_3CF_2$ | H | O | 3,4-Cl—$C_6H_5O$ | H | $R_{10} + R_{11} = OCF_2CF_2O$ | |
| 4 | 309N | $CF_3CF_2$ | H | O | H | $C_6H_5$ | $R_{10} + R_{11} = OCF_2CF_2O$ | |
| 4 | 310N | $CF_3CF_2$ | H | O | H | 4-Cl—$C_6H_5$ | $R_{10} + R_{11} = OCF_2CF_2O$ | |
| 4 | 311N | $CF_3CF_2$ | H | O | H | 4-F—$C_6H_5$ | $R_{10} + R_{11} = OCF_2CF_2O$ | |
| 4 | 312N | $CF_3CF_2$ | H | O | H | 4-Br—$C_6H_5$ | $R_{10} + R_{11} = OCF_2CF_2O$ | |
| 4 | 313N | $CF_3CF_2$ | H | O | 4-Br—$C_6H_5O$ | H | $R_{10} + R_{11} = OCF_2CF_2O$ | |
| 4 | 314N | $CF_3CF_2$ | H | O | $C_6H_5O$ | H | $R_{10} + R_{11} = OCCl_2CCl_2O$ | |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

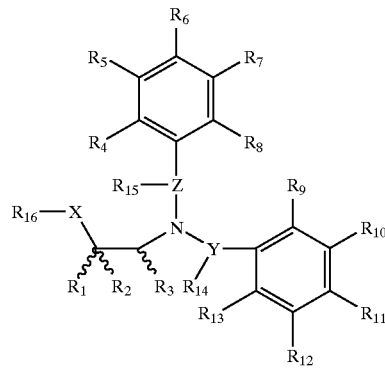

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 4 | 315N | $CF_3CF_2$ | H | O | 4-Cl—$C_6H_5O$ | H | $R_{10} + R_{11} = OCCl_2CCl_2O$ | |
| 4 | 316N | $CF_3CF_2$ | H | O | 4-F—$C_6H_5O$ | H | $R_{10} + R_{11} = OCCl_2CCl_2O$ | |
| 4 | 317N | $CF_3CF_2$ | H | O | 3,4-Cl—$C_6H_5O$ | H | $R_{10} + R_{11} = OCCl_2CCl_2O$ | |
| 4 | 318N | $CF_3CF_2$ | H | O | H | $C_6H_5$ | $R_{10} + R_{11} = OCCl_2CCl_2O$ | |
| 4 | 319N | $CF_3CF_2$ | H | O | H | 4-Cl—$C_6H_5$ | $R_{10} + R_{11} = OCCl_2CCl_2O$ | |
| 4 | 320N | $CF_3CF_2$ | H | O | H | 4-F—$C_6H_5$ | $R_{10} + R_{11} = OCCl_2CCl_2O$ | |
| 4 | 321N | $CF_3CF_2$ | H | O | H | 4-Br—$C_6H_5$ | $R_{10} + R_{11} = OCCl_2CCl_2O$ | |
| 4 | 322N | $CF_3CF_2$ | H | O | 4-Br—$C_6H_5O$ | H | $R_{10} + R_{11} = OCCl_2CCl_2O$ | |
| 4 | 323N | $CF_3CF_2$ | H | O | H | H | OH | H |
| 4 | 324N | $CF_3CF_2$ | H | O | H | H | OH | OH |
| 4 | 325N | $CF_3CF_2$ | H | O | H | H | H | OH |
| 4 | 326N | $CF_3CF_2$ | H | O | H | H | $OCH_2CF_3$ | H |
| 4 | 327N | $CF_3CF_2$ | H | O | H | H | H | $OCH_2CF_3$ |
| 4 | 328N | $CF_3CF_2$ | H | O | H | H | $OCH_2CF_2CF_3$ | H |
| 4 | 329N | $CF_3CF_2$ | H | O | H | H | $OCH_2CH_2CF_3$ | H |
| 4 | 330N | $CF_3CF_2$ | H | O | H | H | $OCH(CF_3)_3$ | H |
| 4 | 331N | $CF_3CF_2$ | H | O | H | 4-F—$C_6H_5O$ | H | H |
| 4 | 332N | $CF_3CF_2$ | H | O | 4-F—$C_6H_5O$ | H | H | H |
| 4 | 333N | $CF_3CF_2$ | H | O | H | cyclohexoxy | H | H |
| 4 | 334N | $CF_3CF_2$ | H | O | cyclohexoxy | H | H | H |
| 4 | 335N | $CF_3CF_2$ | H | O | H | $CH(CH_3)_3$ | H | H |
| 4 | 336N | $CF_3CF_2$ | H | O | F | H | 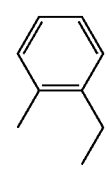 | bond to indicated phenyl carbon of $R_{10}$ substituent |
| 5 | 224N | $CF_3CF_2CF_2$ | H | O | $C_6H_5O$ | H | $OCF_2CF_2H$ | H |
| 5 | 225N | $CF_3CF_2CF_2$ | H | O | 4-Cl—$C_6H_5O$ | H | $OCF_2CF_2H$ | H |
| 5 | 226N | $CF_3CF_2CF_2$ | H | O | 4-F—$C_6H_5O$ | H | $OCF_2CF_2H$ | H |
| 5 | 227N | $CF_3CF_2CF_2$ | H | O | 3,4-Cl—$C_6H_5O$ | H | $OCF_2CF_2H$ | H |
| 5 | 228N | $CF_3CF_2CF_2$ | H | O | H | $C_6H_5$ | $OCF_2CF_2H$ | H |
| 5 | 229N | $CF_3CF_2CF_2$ | H | O | H | 4-Cl—$C_6H_5$ | $OCF_2CF_2H$ | H |
| 5 | 230N | $CF_3CF_2CF_2$ | H | O | H | 4-F—$C_6H_5$ | $OCF_2CF_2H$ | H |
| 5 | 231N | $CF_3CF_2CF_2$ | H | O | H | 4-Br—$C_6H_5$ | $OCF_2CF_2H$ | H |
| 5 | 232N | $CF_3CF_2CF_2$ | H | O | 4-Br—$C_6H_5O$ | H | $OCF_2CF_2H$ | H |
| 5 | 233N | $CF_3CF_2CF_2$ | H | O | $C_6H_5O$ | H | $OCF_2CF_3$ | H |
| 5 | 234N | $CF_3CF_2CF_2$ | H | O | 4-Cl—$C_6H_5O$ | H | $OCF_2CF_3$ | H |
| 5 | 235N | $CF_3CF_2CF_2$ | H | O | 4-F—$C_6H_5O$ | H | $OCF_2CF_3$ | H |
| 5 | 236N | $CF_3CF_2CF_2$ | H | O | 3,4-Cl—$C_6H_5O$ | H | $OCF_2CF_3$ | H |
| 5 | 237N | $CF_3CF_2CF_2$ | H | O | H | $C_6H_5$ | $OCF_2CF_3$ | H |
| 5 | 238N | $CF_3CF_2CF_2$ | H | O | H | 4-Cl-$C_6H_5$ | $OCF_2CF_3$ | H |
| 5 | 239N | $CF_3CF_2CF_2$ | H | O | H | 4-F—$C_6H_5$ | $OCF_2CF_3$ | H |
| 5 | 240N | $CF_3CF_2CF_2$ | H | O | H | 4-Br—$C_6H_5$ | $OCF_2CF_3$ | H |
| 5 | 241N | $CF_3CF_2CF_2$ | H | O | 4-Br—$C_6H_5O$ | H | $OCF_2CF_3$ | H |
| 5 | 242N | $CF_3CF_2CF_2$ | H | O | $C_6H_5O$ | H | $OCCl_2CCl_2H$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

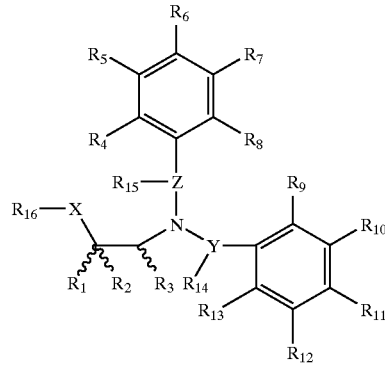

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 5 | 243N | $CF_3CF_2CF_2$ | H | O | 4-Cl—$C_6H_5$O | H | $OCCl_2CCl_2H$ | H |
| 5 | 244N | $CF_3CF_2CF_2$ | H | O | 4-F—$C_6H_5$O | H | $OCCl_2CCl_2H$ | H |
| 5 | 245N | $CF_3CF_2CF_2$ | H | O | 3,4-Cl—$C_6H_5$O | H | $OCCl_2CCl_2H$ | H |
| 5 | 246N | $CF_3CF_2CF_2$ | H | O | H | $C_6H_5$ | $OCCl_2CCl_2H$ | H |
| 5 | 247N | $CF_3CF_2CF_2$ | H | O | H | 4-Cl—$C_6H_5$ | $OCCl_2CCl_2H$ | H |
| 5 | 248N | $CF_3CF_2CF_2$ | H | O | H | 4-F—$C_6H_5$ | $OCCl_2CCl_2H$ | H |
| 5 | 249N | $CF_3CF_2CF_2$ | H | O | H | 4-Br—$C_6H_5$ | $OCCl_2CCl_2H$ | H |
| 5 | 250N | $CF_3CF_2CF_2$ | H | O | 4-Br—$C_6H_5$O | H | $OCCl_2CCl_2H$ | H |
| 5 | 251N | $CF_3CF_2CF_2$ | H | O | $C_6H_5$O | H | $OCCl_2CCl_3$ | H |
| 5 | 252N | $CF_3CF_2CF_2$ | H | O | 4-Cl—$C_6H_5$O | H | $OCCl_2CCl_3$ | H |
| 5 | 253N | $CF_3CF_2CF_2$ | H | O | 4-F—$C_6H_5$O | H | $OCCl_2CCl_3$ | H |
| 5 | 254N | $CF_3CF_2CF_2$ | H | O | 3,4-Cl—$C_6H_5$O | H | $OCCl_2CCl_3$ | H |
| 5 | 255N | $CF_3CF_2CF_2$ | H | O | H | $C_6H_5$ | $OCCl_2CCl_3$ | H |
| 5 | 256N | $CF_3CF_2CF_2$ | H | O | H | 4-Cl—$C_6H_5$ | $OCCl_2CCl_3$ | H |
| 5 | 257N | $CF_3CF_2CF_2$ | H | O | H | 4-F—$C_6H_5$ | $OCCl_2CCl_3$ | H |
| 5 | 258N | $CF_3CF_2CF_2$ | H | O | H | 4-Br—$C_6H_5$ | $OCCl_2CCl_3$ | H |
| 5 | 259N | $CF_3CF_2CF_2$ | H | O | 4-Br—$C_6H_5$O | H | $OCCl_2CCl_3$ | H |
| 5 | 260N | $CF_3CF_2CF_2$ | H | O | $C_6H_5$O | H | $OCCl_2CF_3$ | H |
| 5 | 261N | $CF_3CF_2CF_2$ | H | O | 4-Cl—$C_6H_5$O | H | $OCCl_2CF_3$ | H |
| 5 | 262N | $CF_3CF_2CF_2$ | H | O | 4-F—$C_6H_5$O | H | $OCCl_2CF_3$ | H |
| 5 | 263N | $CF_3CF_2CF_2$ | H | O | 3,4-Cl—$C_6H_5$O | H | $OCCl_2CF_3$ | H |
| 5 | 264N | $CF_3CF_2CF_2$ | H | O | H | $C_6H_5$ | $OCCl_2CF_3$ | H |
| 5 | 265N | $CF_3CF_2CF_2$ | H | O | H | 4-Cl—$C_6H_5$ | $OCCl_2CF_3$ | H |
| 5 | 266N | $CF_3CF_2CF_2$ | H | O | H | 4-F—$C_6H_5$ | $OCCl_2CF_3$ | H |
| 5 | 267N | $CF_3CF_2CF_2$ | H | O | H | 4-Br—$C_6H_5$ | $OCCl_2CF_3$ | H |
| 5 | 268N | $CF_3CF_2CF_2$ | H | O | 4-Br—$C_6H_5$O | H | $OCCl_2CF_3$ | H |
| 5 | 269N | $CF_3CF_2CF_2$ | H | O | $C_6H_5$O | H | $OCF_2CCl_3$ | H |
| 5 | 270N | $CF_3CF_2CF_2$ | H | O | 4-Cl—$C_6H_5$O | H | $OCF_2CCl_3$ | H |
| 5 | 271N | $CF_3CF_2CF_2$ | H | O | 4-F—$C_6H_5$O | H | $OCF_2CCl_3$ | H |
| 5 | 272N | $CF_3CF_2CF_2$ | H | O | 3,4-Cl—$C_6H_5$O | H | $OCF_2CCl_3$ | H |
| 5 | 273N | $CF_3CF_2CF_2$ | H | O | H | $C_6H_5$ | $OCF_2CCl_3$ | H |
| 5 | 274N | $CF_3CF_2CF_2$ | H | O | H | 4-Cl—$C_6H_5$ | $OCF_2CCl_3$ | H |
| 5 | 275N | $CF_3CF_2CF_2$ | H | O | H | 4-F—$C_6H_5$ | $OCF_2CCl_3$ | H |
| 5 | 276N | $CF_3CF_2CF_2$ | H | O | H | 4-Br—$C_6H_5$ | $OCF_2CCl_3$ | H |
| 5 | 277N | $CF_3CF_2CF_2$ | H | O | 4-Br—$C_6H_5$O | H | $OCF_2CCl_3$ | H |
| 5 | 278N | $CF_3CF_2CF_2$ | H | O | $C_6H_5$O | H | $OCF_2CF_2H$ | $OCF_2CF_2H$ |
| 5 | 279N | $CF_3CF_2CF_2$ | H | O | 4-Cl—$C_6H_5$O | H | $OCF_2CF_2H$ | $OCF_2CF_2H$ |
| 5 | 280N | $CF_3CF_2CF_2$ | H | O | 4-F—$C_6H_5$O | H | $OCF_2CF_2H$ | $OCF_2CF_2H$ |
| 5 | 281N | $CF_3CF_2CF_2$ | H | O | 3,4-Cl—$C_6H_5$O | H | $OCF_2CF_2H$ | $OCF_2CF_2H$ |
| 5 | 282N | $CF_3CF_2CF_2$ | H | O | H | $C_6H_5$ | $OCF_2CF_2H$ | $OCF_2CF_2H$ |
| 5 | 283N | $CF_3CF_2CF_2$ | H | O | H | 4-Cl—$C_6H_5$ | $OCF_2CF_2H$ | $OCF_2CF_2H$ |
| 5 | 284N | $CF_3CF_2CF_2$ | H | O | H | 4-F—$C_6H_5$ | $OCF_2CF_2H$ | $OCF_2CF_2H$ |
| 5 | 285N | $CF_3CF_2CF_2$ | H | O | H | 4-Br—$C_6H_5$ | $OCF_2CF_2H$ | $OCF_2CF_2H$ |
| 5 | 286N | $CF_3CF_2CF_2$ | H | O | 4-Br—$C_6H_5$O | H | $OCF_2CF_2H$ | $OCF_2CF_2H$ |
| 5 | 287N | $CF_3CF_2CF_2$ | H | O | $C_6H_5$O | H | $OCF_3$ | $OCF_3$ |
| 5 | 288N | $CF_3CF_2CF_2$ | H | O | 4-Cl—$C_6H_5$O | H | $OCF_3$ | $OCF_3$ |
| 5 | 289N | $CF_3CF_2CF_2$ | H | O | 4-F—$C_6H_5$O | H | $OCF_3$ | $OCF_3$ |
| 5 | 290N | $CF_3CF_2CF_2$ | H | O | 3,4-Cl—$C_6H_5$O | H | $OCF_3$ | $OCF_3$ |
| 5 | 291N | $CF_3CF_2CF_2$ | H | O | H | $C_6H_5$ | $OCF_3$ | $OCF_3$ |
| 5 | 292N | $CF_3CF_2CF_2$ | H | O | H | 4-Cl—$C_6H_5$ | $OCF_3$ | $OCF_3$ |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

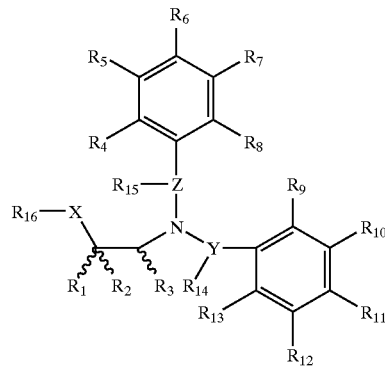

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 5 | 293N | $CF_3CF_2CF_2$ | H | O | H | 4-F—$C_6H_5$ | $OCF_3$ | $OCF_3$ |
| 5 | 294N | $CF_3CF_2CF_2$ | H | O | H | 4-Br—$C_6H_5$ | $OCF_3$ | $OCF_3$ |
| 5 | 295N | $CF_3CF_2CF_2$ | H | O | 4-Br—$C_6H_5O$ | H | $OCF_3$ | $OCF_3$ |
| 5 | 296N | $CF_3CF_2CF_2$ | H | O | $C_6H_5O$ | H | $OCF_2H$ | $OCF_2H$ |
| 5 | 297N | $CF_3CF_2CF_2$ | H | O | 4-Cl—$C_6H_5O$ | H | $OCF_2H$ | $OCF_2H$ |
| 5 | 298N | $CF_3CF_2CF_2$ | H | O | 4-F—$C_6H_5O$ | H | $OCF_2H$ | $OCF_2H$ |
| 5 | 299N | $CF_3CF_2CF_2$ | H | O | 3,4-Cl—$C_6H_5O$ | H | $OCF_2H$ | $OCF_2H$ |
| 5 | 300N | $CF_3CF_2CF_2$ | H | O | H | $C_6H_5$ | $OCF_2H$ | $OCF_2H$ |
| 5 | 301N | $CF_3CF_2CF_2$ | H | O | H | 4-Cl—$C_6H_5$ | $OCF_2H$ | $OCF_2H$ |
| 5 | 302N | $CF_3CF_2CF_2$ | H | O | H | 4-F—$C_6H_5$ | $OCF_2H$ | $OCF_2H$ |
| 5 | 303N | $CF_3CF_2CF_2$ | H | O | H | 4-Br—$C_6H_5$ | $OCF_2H$ | $OCF_2H$ |
| 5 | 304N | $CF_3CF_2CF_2$ | H | O | 4-Br—$C_6H_5O$ | H | $OCF_2H$ | $OCF_2H$ |
| 5 | 305N | $CF_3CF_2CF_2$ | H | O | $C_6H_5O$ | H | $R_{10} + R_{11} = OCF_2CF_2O$ | |
| 5 | 306N | $CF_3CF_2CF_2$ | H | O | 4-Cl—$C_6H_5O$ | H | $R_{10} + R_{11} = OCF_2CF_2O$ | |
| 5 | 307N | $CF_3CF_2CF_2$ | H | O | 4-F—$C_6H_5O$ | H | $R_{10} + R_{11} = OCF_2CF_2O$ | |
| 5 | 308N | $CF_3CF_2CF_2$ | H | O | 3,4-Cl—$C_6H_5O$ | H | $R_{10} + R_{11} = OCF_2CF_2O$ | |
| 5 | 309N | $CF_3CF_2CF_2$ | H | O | H | $C_6H_5$ | $R_{10} + R_{11} = OCF_2CF_2O$ | |
| 5 | 310N | $CF_3CF_2CF_2$ | H | O | H | 4-Cl—$C_6H_5$ | $R_{10} + R_{11} = OCF_2CF_2O$ | |
| 5 | 311N | $CF_3CF_2CF_2$ | H | O | H | 4-F—$C_6H_5$ | $R_{10} + R_{11} = OCF_2CF_2O$ | |
| 5 | 312N | $CF_3CF_2CF_2$ | H | O | H | 4-Br—$C_6H_5$ | $R_{10} + R_{11} = OCF_2CF_2O$ | |
| 5 | 313N | $CF_3CF_2CF_2$ | H | O | 4-Br—$C_6H_5O$ | H | $R_{10} + R_{11} = OCF_2CF_2O$ | |
| 5 | 314N | $CF_3CF_2CF_2$ | H | O | $C_6H_5O$ | H | $R_{10} + R_{11} = OCCl_2CCl_2O$ | |
| 5 | 315N | $CF_3CF_2CF_2$ | H | O | 4-Cl—$C_6H_5O$ | H | $R_{10} + R_{11} = OCCl_2CCl_2O$ | |
| 5 | 316N | $CF_3CF_2CF_2$ | H | O | 4-F—$C_6H_5O$ | H | $R_{10} + R_{11} = OCCl_2CCl_2O$ | |
| 5 | 317N | $CF_3CF_2CF_2$ | H | O | 3,4-Cl—$C_6H_5O$ | H | $R_{10} + R_{11} = OCCl_2CCl_2O$ | |
| 5 | 318N | $CF_3CF_2CF_2$ | H | O | H | $C_6H_5$ | $R_{10} + R_{11} = OCCl_2CCl_2O$ | |
| 5 | 319N | $CF_3CF_2CF_2$ | H | O | H | 4-Cl—$C_6H_5$ | $R_{10} + R_{11} = OCCl_2CCl_2O$ | |
| 5 | 320N | $CF_3CF_2CF_2$ | H | O | H | 4-F—$C_6H_5$ | $R_{10} + R_{11} = OCCl_2CCl_2O$ | |
| 5 | 321N | $CF_3CF_2CF_2$ | H | O | H | 4-Br—$C_6H_5$ | $R_{10} + R_{11} = OCCl_2CCl_2O$ | |
| 5 | 322N | $CF_3CF_2CF_2$ | H | O | 4-Br—$C_6H_5O$ | H | $R_{10} + R_{11} = OCCl_2CCl_2O$ | |
| 5 | 323N | $CF_3CF_2CF_2$ | H | O | H | H | OH | H |
| 5 | 324N | $CF_3CF_2CF_2$ | H | O | H | H | OH | OH |
| 5 | 325N | $CF_3CF_2CF_2$ | H | O | H | H | H | OH |
| 5 | 326N | $CF_3CF_2CF_2$ | H | O | H | H | $OCH_2CF_3$ | H |
| 5 | 327N | $CF_3CF_2CF_2$ | H | O | H | H | H | $OCH_2CF_3$ |
| 5 | 328N | $CF_3CF_2CF_2$ | H | O | H | H | $OCH_2CF_2CF_3$ | H |
| 5 | 329N | $CF_3CF_2CF_2$ | H | O | H | H | $OCH_2CH_2CF_3$ | H |
| 5 | 330N | $CF_3CF_2CF_2$ | H | O | H | H | $OCH(CF_3)_3$ | H |
| 5 | 331N | $CF_3CF_2CF_2$ | H | O | H | 4-F—$C_6H_5O$ | H | H |
| 5 | 332N | $CF_3CF_2CF_2$ | H | O | 4-F—$C_6H_5O$ | H | H | H |
| 5 | 333N | $CF_3CF_2CF_2$ | H | O | H | cyclohexoxy | H | H |
| 5 | 334N | $CF_3CF_2CF_2$ | H | O | cyclohexoxy | H | H | H |
| 5 | 335N | $CF_3CF_2CF_2$ | H | O | H | $CH(CH_3)_3$ | H | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

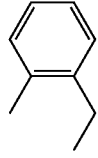

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 5 | 336N | $CF_3CF_2CF_2$ | H | O | F | H | 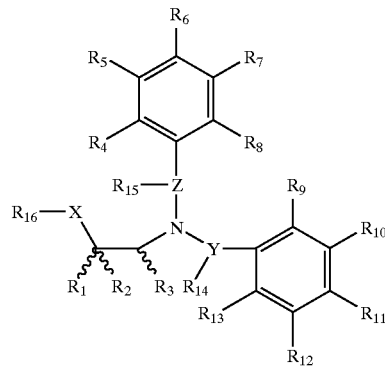 | bond to indicated phenyl carbon of $R_{10}$ substituent |
| 6 | 224N | $CF_3OCF_2CF_2$ | H | O | $C_6H_5O$ | H | $OCF_2CF_2H$ | H |
| 6 | 225N | $CF_3OCF_2CF_2$ | H | O | 4-Cl—$C_6H_5O$ | H | $OCF_2CF_2H$ | H |
| 6 | 226N | $CF_3OCF_2CF_2$ | H | O | 4-F—$C_6H_5O$ | H | $OCF_2CF_2H$ | H |
| 6 | 227N | $CF_3OCF_2CF_2$ | H | O | 3,4-Cl—$C_6H_5O$ | H | $OCF_2CF_2H$ | H |
| 6 | 228N | $CF_3OCF_2CF_2$ | H | O | H | $C_6H_5$ | $OCF_2CF_2H$ | H |
| 6 | 229N | $CF_3OCF_2CF_2$ | H | O | H | 4-Cl—$C_6H_5$ | $OCF_2CF_2H$ | H |
| 6 | 230N | $CF_3OCF_2CF_2$ | H | O | H | 4-F—$C_6H_5$ | $OCF_2CF_2H$ | H |
| 6 | 231N | $CF_3OCF_2CF_2$ | H | O | H | 4-Br—$C_6H_5$ | $OCF_2CF_2H$ | H |
| 6 | 232N | $CF_3OCF_2CF_2$ | H | O | 4-Br—$C_6H_5O$ | H | $OCF_2CF_2H$ | H |
| 6 | 233N | $CF_3OCF_2CF_2$ | H | O | $C_6H_5O$ | H | $OCF_2CF_3$ | H |
| 6 | 234N | $CF_3OCF_2CF_2$ | H | O | 4-Cl—$C_6H_5O$ | H | $OCF_2CF_3$ | H |
| 6 | 235N | $CF_3OCF_2CF_2$ | H | O | 4-F—$C_6H_5O$ | H | $OCF_2CF_3$ | H |
| 6 | 236N | $CF_3OCF_2CF_2$ | H | O | 3,4-Cl—$C_6H_5O$ | H | $OCF_2CF_3$ | H |
| 6 | 237N | $CF_3OCF_2CF_2$ | H | O | H | $C_6H_5$ | $OCF_2CF_3$ | H |
| 6 | 238N | $CF_3OCF_2CF_2$ | H | O | H | 4-Cl—$C_6H_5$ | $OCF_2CF_3$ | H |
| 6 | 239N | $CF_3OCF_2CF_2$ | H | O | H | 4-F—$C_6H_5$ | $OCF_2CF_3$ | H |
| 6 | 240N | $CF_3OCF_2CF_2$ | H | O | H | 4-Br—$C_6H_5$ | $OCF_2CF_3$ | H |
| 6 | 241N | $CF_3OCF_2CF_2$ | H | O | 4-Br—$C_6H_5O$ | H | $OCF_2CF_3$ | H |
| 6 | 242N | $CF_3OCF_2CF_2$ | H | O | $C_6H_5O$ | H | $OCCl_2CCl_2H$ | H |
| 6 | 243N | $CF_3OCF_2CF_2$ | H | O | 4-Cl—$C_6H_5O$ | H | $OCCl_2CCl_2H$ | H |
| 6 | 244N | $CF_3OCF_2CF_2$ | H | O | 4-F—$C_6H_5O$ | H | $OCCl_2CCl_2H$ | H |
| 6 | 245N | $CF_3OCF_2CF_2$ | H | O | 3,4-Cl—$C_6H_5O$ | H | $OCCl_2CCl_2H$ | H |
| 6 | 246N | $CF_3OCF_2CF_2$ | H | O | H | $C_6H_5$ | $OCCl_2CCl_2H$ | H |
| 6 | 247N | $CF_3OCF_2CF_2$ | H | O | H | 4-Cl—$C_6H_5$ | $OCCl_2CCl_2H$ | H |
| 6 | 248N | $CF_3OCF_2CF_2$ | H | O | H | 4-F—$C_6H_5$ | $OCCl_2CCl_2H$ | H |
| 6 | 249N | $CF_3OCF_2CF_2$ | H | O | H | 4-Br—$C_6H_5$ | $OCCl_2CCl_2H$ | H |
| 6 | 250N | $CF_3OCF_2CF_2$ | H | O | 4-Br—$C_6H_5O$ | H | $OCCl_2CCl_2H$ | H |
| 6 | 251N | $CF_3OCF_2CF_2$ | H | O | $C_6H_5O$ | H | $OCCl_2CCl_3$ | H |
| 6 | 252N | $CF_3OCF_2CF_2$ | H | O | 4-Cl—$C_6H_5O$ | H | $OCCl_2CCl_3$ | H |
| 6 | 253N | $CF_3OCF_2CF_2$ | H | O | 4-F—$C_6H_5O$ | H | $OCCl_2CCl_3$ | H |
| 6 | 254N | $CF_3OCF_2CF_2$ | H | O | 3,4-Cl—$C_6H_5O$ | H | $OCCl_2CCl_3$ | H |
| 6 | 255N | $CF_3OCF_2CF_2$ | H | O | H | $C_6H_5$ | $OCCl_2CCl_3$ | H |
| 6 | 256N | $CF_3OCF_2CF_2$ | H | O | H | 4-Cl—$C_6H_5$ | $OCCl_2CCl_3$ | H |
| 6 | 257N | $CF_3OCF_2CF_2$ | H | O | H | 4-F—$C_6H_5$ | $OCCl_2CCl_3$ | H |
| 6 | 258N | $CF_3OCF_2CF_2$ | H | O | H | 4-Br—$C_6H_5$ | $OCCl_2CCl_3$ | H |
| 6 | 259N | $CF_3OCF_2CF_2$ | H | O | 4-Br—$C_6H_5O$ | H | $OCCl_2CCl_3$ | H |
| 6 | 260N | $CF_3OCF_2CF_2$ | H | O | $C_6H_5O$ | H | $OCCl_2CF_3$ | H |
| 6 | 261N | $CF_3OCF_2CF_2$ | H | O | 4-Cl—$C_6H_5O$ | H | $OCCl_2CF_3$ | H |
| 6 | 262N | $CF_3OCF_2CF_2$ | H | O | 4-F—$C_6H_5O$ | H | $OCCl_2CF_3$ | H |
| 6 | 263N | $CF_3OCF_2CF_2$ | H | O | 3,4-Cl—$C_6H_5O$ | H | $OCCl_2CF_3$ | H |
| 6 | 264N | $CF_3OCF_2CF_2$ | H | O | H | $C_6H_5$ | $OCCl_2CF_3$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

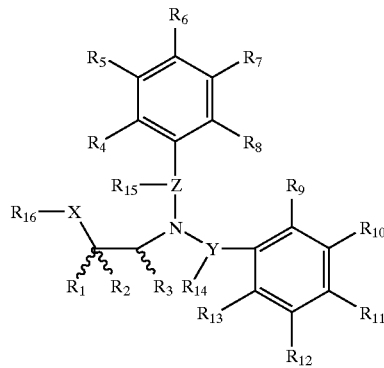

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 6 | 265N | $CF_3OCF_2CF_2$ | H | O | H | 4-Cl—$C_6H_5$ | $OCCl_2CF_3$ | H |
| 6 | 266N | $CF_3OCF_2CF_2$ | H | O | H | 4-F—$C_6H_5$ | $OCCl_2CF_3$ | H |
| 6 | 267N | $CF_3OCF_2CF_2$ | H | O | H | 4-Br—$C_6H_5$ | $OCCl_2CF_3$ | H |
| 6 | 268N | $CF_3OCF_2CF_2$ | H | O | 4-Br—$C_6H_5O$ | H | $OCCl_2CF_3$ | H |
| 6 | 269N | $CF_3OCF_2CF_2$ | H | O | $C_6H_5O$ | H | $OCF_2CCl_3$ | H |
| 6 | 270N | $CF_3OCF_2CF_2$ | H | O | 4-Cl—$C_6H_5O$ | H | $OCF_2CCl_3$ | H |
| 6 | 271N | $CF_3OCF_2CF_2$ | H | O | 4-F—$C_6H_5O$ | H | $OCF_2CCl_3$ | H |
| 6 | 272N | $CF_3OCF_2CF_2$ | H | O | 3,4-Cl—$C_6H_5O$ | H | $OCF_2CCl_3$ | H |
| 6 | 273N | $CF_3OCF_2CF_2$ | H | O | H | $C_6H_5$ | $OCF_2CCl_3$ | H |
| 6 | 274N | $CF_3OCF_2CF_2$ | H | O | H | 4-Cl—$C_6H_5$ | $OCF_2CCl_3$ | H |
| 6 | 275N | $CF_3OCF_2CF_2$ | H | O | H | 4-F—$C_6H_5$ | $OCF_2CCl_3$ | H |
| 6 | 276N | $CF_3OCF_2CF_2$ | H | O | H | 4-Br—$C_6H_5$ | $OCF_2CCl_3$ | H |
| 6 | 277N | $CF_3OCF_2CF_2$ | H | O | 4-Br—$C_6H_5O$ | H | $OCF_2CCl_3$ | H |
| 6 | 278N | $CF_3OCF_2CF_2$ | H | O | $C_6H_5O$ | H | $OCF_2CF_2H$ | $OCF_2CF_2H$ |
| 6 | 279N | $CF_3OCF_2CF_2$ | H | O | 4-Cl—$C_6H_5O$ | H | $OCF_2CF_2H$ | $OCF_2CF_2H$ |
| 6 | 280N | $CF_3OCF_2CF_2$ | H | O | 4-F—$C_6H_5O$ | H | $OCF_2CF_2H$ | $OCF_2CF_2H$ |
| 6 | 281N | $CF_3OCF_2CF_2$ | H | O | 3,4-Cl—$C_6H_5O$ | H | $OCF_2CF_2H$ | $OCF_2CF_2H$ |
| 6 | 282N | $CF_3OCF_2CF_2$ | H | O | H | $C_6H_5$ | $OCF_2CF_2H$ | $OCF_2CF_2H$ |
| 6 | 283N | $CF_3OCF_2CF_2$ | H | O | H | 4-Cl—$C_6H_5$ | $OCF_2CF_2H$ | $OCF_2CF_2H$ |
| 6 | 284N | $CF_3OCF_2CF_2$ | H | O | H | 4-F—$C_6H_5$ | $OCF_2CF_2H$ | $OCF_2CF_2H$ |
| 6 | 285N | $CF_3OCF_2CF_2$ | H | O | H | 4-Br—$C_6H_5$ | $OCF_2CF_2H$ | $OCF_2CF_2H$ |
| 6 | 286N | $CF_3OCF_2CF_2$ | H | O | 4-Br—$C_6H_5O$ | H | $OCF_2CF_2H$ | $OCF_2CF_2H$ |
| 6 | 287N | $CF_3OCF_2CF_2$ | H | O | $C_6H_5O$ | H | $OCF_3$ | $OCF_3$ |
| 6 | 288N | $CF_3OCF_2CF_2$ | H | O | 4-Cl—$C_6H_5O$ | H | $OCF_3$ | $OCF_3$ |
| 6 | 289N | $CF_3OCF_2CF_2$ | H | O | 4-F—$C_6H_5O$ | H | $OCF_3$ | $OCF_3$ |
| 6 | 290N | $CF_3OCF_2CF_2$ | H | O | 3,4-Cl—$C_6H_5O$ | H | $OCF_3$ | $OCF_3$ |
| 6 | 291N | $CF_3OCF_2CF_2$ | H | O | H | $C_6H_5$ | $OCF_3$ | $OCF_3$ |
| 6 | 292N | $CF_3OCF_2CF_2$ | H | O | H | 4-Cl—$C_6H_5$ | $OCF_3$ | $OCF_3$ |
| 6 | 293N | $CF_3OCF_2CF_2$ | H | O | H | 4-F—$C_6H_5$ | $OCF_3$ | $OCF_3$ |
| 6 | 294N | $CF_3OCF_2CF_2$ | H | O | H | 4-Br—$C_6H_5$ | $OCF_3$ | $OCF_3$ |
| 6 | 295N | $CF_3OCF_2CF_2$ | H | O | 4-Br—$C_6H_5O$ | H | $OCF_3$ | $OCF_3$ |
| 6 | 296N | $CF_3OCF_2CF_2$ | H | O | $C_6H_5O$ | H | $OCF_2H$ | $OCF_2H$ |
| 6 | 297N | $CF_3OCF_2CF_2$ | H | O | 4-Cl—$C_6H_5O$ | H | $OCF_2H$ | $OCF_2H$ |
| 6 | 298N | $CF_3OCF_2CF_2$ | H | O | 4-F—$C_6H_5O$ | H | $OCF_2H$ | $OCF_2H$ |
| 6 | 299N | $CF_3OCF_2CF_2$ | H | O | 3,4-Cl—$C_6H_5O$ | H | $OCF_2H$ | $OCF_2H$ |
| 6 | 300N | $CF_3OCF_2CF_2$ | H | O | H | $C_6H_5$ | $OCF_2H$ | $OCF_2H$ |
| 6 | 301N | $CF_3OCF_2CF_2$ | H | O | H | 4-Cl—$C_6H_5$ | $OCF_2H$ | $OCF_2H$ |
| 6 | 302N | $CF_3OCF_2CF_2$ | H | O | H | 4-F—$C_6H_5$ | $OCF_2H$ | $OCF_2H$ |
| 6 | 303N | $CF_3OCF_2CF_2$ | H | O | H | 4-Br—$C_6H_5$ | $OCF_2H$ | $OCF_2H$ |
| 6 | 304N | $CF_3OCF_2CF_2$ | H | O | 4-Br—$C_6H_5O$ | H | $OCF_2H$ | $OCF_2H$ |
| 6 | 305N | $CF_3OCF_2CF_2$ | H | O | $C_6H_5O$ | H | $R_{10} + R_{11} = OCF_2CF_2O$ | |
| 6 | 306N | $CF_3OCF_2CF_2$ | H | O | 4-Cl—$C_6H_5O$ | H | $R_{10} + R_{11} = OCF_2CF_2O$ | |
| 6 | 307N | $CF_3OCF_2CF_2$ | H | O | 4-F—$C_6H_5O$ | H | $R_{10} + R_{11} = OCF_2CF_2O$ | |
| 6 | 308N | $CF_3OCF_2CF_2$ | H | o | 3,4-Cl—$C_6H_5O$ | H | $R_{10} + R_{11} = OCF_2CF_2O$ | |
| 6 | 309N | $CF_3OCF_2CF_2$ | H | O | H | $C_6H_5$ | $R_{10} + R_{11} = OCF_2CF_2O$ | |
| 6 | 310N | $CF_3OCF_2CF_2$ | H | O | H | 4-Cl—$C_6H_5$ | $R_{10} + R_{11} = OCF_2CF_2O$ | |
| 6 | 311N | $CF_3OCF_2CF_2$ | H | O | H | 4-F—$C_6H_5$ | $R_{10} + R_{11} = OCF_2CF_2O$ | |
| 6 | 312N | $CF_3OCF_2CF_2$ | H | O | H | 4-Br—$C_6H_5$ | $R_{10} + R_{11} = OCF_2CF_2O$ | |
| 6 | 313N | $CF_3OCF_2CF_2$ | H | O | 4-Br—$C_6H_5O$ | H | $R_{10} + R_{11} = OCF_2CF_2O$ | |
| 6 | 314N | $CF_3OCF_2CF_2$ | H | O | $C_6H_5O$ | H | $R_{10} + R_{11} = OCCl_2CCl_2O$ | |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

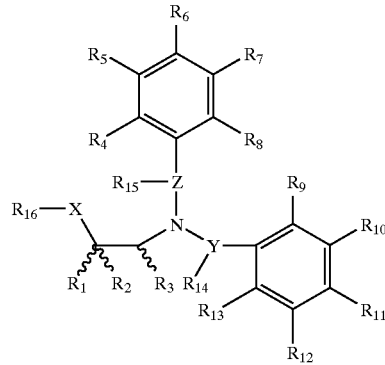

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 6 | 315N | $CF_3OCF_2CF_2$ | H | O | 4-Cl—$C_6H_5O$ | H | $R_{10} + R_{11} = OCCl_2CCl_2O$ | |
| 6 | 316N | $CF_3OCF_2CF_2$ | H | O | 4-F—$C_6H_5O$ | H | $R_{10} + R_{11} = OCCl_2CCl_2O$ | |
| 6 | 317N | $CF_3OCF_2CF_2$ | H | O | 3,4-Cl—$C_6H_5O$ | H | $R_{10} + R_{11} = OCCl_2CCl_2O$ | |
| 6 | 318N | $CF_3OCF_2CF_2$ | H | O | H | $C_6H_5$ | $R_{10} + R_{11} = OCCl_2CCl_2O$ | |
| 6 | 319N | $CF_3OCF_2CF_2$ | H | O | H | 4-Cl—$C_6H_5$ | $R_{10} + R_{11} = OCCl_2CCl_2O$ | |
| 6 | 320N | $CF_3OCF_2CF_2$ | H | O | H | 4-F—$C_6H_5$ | $R_{10} + R_{11} = OCCl_2CCl_2O$ | |
| 6 | 321N | $CF_3OCF_2CF_2$ | H | O | H | 4-Br—$C_6H_5$ | $R_{10} + R_{11} = OCCl_2CCl_2O$ | |
| 6 | 322N | $CF_3OCF_2CF_2$ | H | O | 4-Br—$C_6H_5O$ | H | $R_{10} + R_{11} = OCCl_2CCl_2O$ | |
| 6 | 323N | $CF_3OCF_2CF_2$ | H | O | H | H | OH | H |
| 6 | 324N | $CF_3OCF_2CF_2$ | H | O | H | H | OH | OH |
| 6 | 325N | $CF_3OCF_2CF_2$ | H | O | H | H | H | OH |
| 6 | 326N | $CF_3OCF_2CF_2$ | H | O | H | H | $OCH_2CF_3$ | H |
| 6 | 327N | $CF_3OCF_2CF_2$ | H | O | H | H | H | $OCH_2CF_3$ |
| 6 | 328N | $CF_3OCF_2CF_2$ | H | O | H | H | $OCH_2CF_2CF_3$ | H |
| 6 | 329N | $CF_3OCF_2CF_2$ | H | O | H | H | $OCH_2CH_2CF_3$ | H |
| 6 | 330N | $CF_3OCF_2CF_2$ | H | O | H | H | $OCH(CF_3)_3$ | H |
| 6 | 331N | $CF_3OCF_2CF_2$ | H | O | H | 4-F—$C_6H_5O$ | H | H |
| 6 | 332N | $CF_3OCF_2CF_2$ | H | O | 4-F—$C_6H_5O$ | H | H | H |
| 6 | 333N | $CF_3OCF_2CF_2$ | H | O | H | cyclohexoxy | H | H |
| 6 | 334N | $CF_3OCF_2CF_2$ | H | O | cyclohexoxy | H | H | H |
| 6 | 335N | $CF_3OCF_2CF_2$ | H | O | H | $CH(CH_3)_3$ | H | H |
| 6 | 336N | $CF_3OCF_2CF_2$ | H | O | F | H | 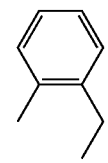 | bond to indicated phenyl carbon of $R_{10}$ substituent |
| 7 | 224N | $CF_3CH_2$ | $CH_3$ | O | $C_6H_5O$ | H | $OCF_2CF_2H$ | H |
| 7 | 225N | $CF_3CH_2$ | $CH_3$ | O | 4-Cl—$C_6H_5O$ | H | $OCF_2CF_2H$ | H |
| 7 | 226N | $CF_3CH_2$ | $CH_3$ | O | 4-F—$C_6H_5O$ | H | $OCF_2CF_2H$ | H |
| 7 | 227N | $CF_3CH_2$ | $CH_3$ | O | 3,4-Cl—$C_6H_5O$ | H | $OCF_2CF_2H$ | H |
| 7 | 228N | $CF_3CH_2$ | $CH_3$ | O | H | $C_6H_5$ | $OCF_2CF_2H$ | H |
| 7 | 229N | $CF_3CH_2$ | $CH_3$ | O | H | 4-Cl—$C_6H_5$ | $OCF_2CF_2H$ | H |
| 7 | 230N | $CF_3CH_2$ | $CH_3$ | O | H | 4-F—$C_6H_5$ | $OCF_2CF_2H$ | H |
| 7 | 231N | $CF_3CH_2$ | $CH_3$ | O | H | 4-Br—$C_6H_5$ | $OCF_2CF_2H$ | H |
| 7 | 232N | $CF_3CH_2$ | $CH_3$ | O | 4-Br—$C_6H_5O$ | H | $OCF_2CF_2H$ | H |
| 7 | 233N | $CF_3CH_2$ | $CH_3$ | O | $C_6H_5O$ | H | $OCF_2CF_3$ | H |
| 7 | 234N | $CF_3CH_2$ | $CH_3$ | O | 4-Cl—$C_6H_5O$ | H | $OCF_2CF_3$ | H |
| 7 | 235N | $CF_3CH_2$ | $CH_3$ | O | 4-F—$C_6H_5O$ | H | $OCF_2CF_3$ | H |
| 7 | 236N | $CF_3CH_2$ | $CH_3$ | O | 3,4-Cl—$C_6H_5O$ | H | $OCF_2CF_3$ | H |
| 7 | 237N | $CF_3CH_2$ | $CH_3$ | O | H | $C_6H_5$ | $OCF_2CF_3$ | H |
| 7 | 238N | $CF_3CH_2$ | $CH_3$ | O | H | 4-Cl—$C_6H_5$ | $OCF_2CF_3$ | H |
| 7 | 239N | $CF_3CH_2$ | $CH_3$ | O | H | 4-F—$C_6H_5$ | $OCF_2CF_3$ | H |
| 7 | 240N | $CF_3CH_2$ | $CH_3$ | O | H | 4-Br—$C_6H_5$ | $OCF_2CF_3$ | H |
| 7 | 241N | $CF_3CH_2$ | $CH_3$ | O | 4-Br—$C_6H_5O$ | H | $OCF_2CF_3$ | H |
| 7 | 242N | $CF_3CH_2$ | $CH_3$ | O | $C_6H_5O$ | H | $OCCl_2CCl_2H$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

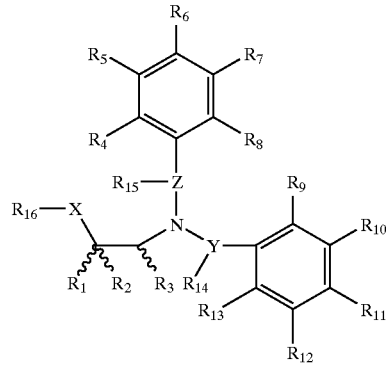

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 7 | 243N | $CF_3CH_2$ | $CH_3$ | O | 4-Cl—$C_6H_5O$ | H | $OCCl_2CCl_2H$ | H |
| 7 | 244N | $CF_3CH_2$ | $CH_3$ | O | 4-F—$C_6H_5O$ | H | $OCCl_2CCl_2H$ | H |
| 7 | 245N | $CF_3CH_2$ | $CH_3$ | O | 3,4-Cl—$C_6H_5O$ | H | $OCCl_2CCl_2H$ | H |
| 7 | 246N | $CF_3CH_2$ | $CH_3$ | O | H | $C_6H_5$ | $OCCl_2CCl_2H$ | H |
| 7 | 247N | $CF_3CH_2$ | $CH_3$ | O | H | 4-Cl—$C_6H_5$ | $OCCl_2CCl_2H$ | H |
| 7 | 248N | $CF_3CH_2$ | $CH_3$ | O | H | 4-F—$C_6H_5$ | $OCCl_2CCl_2H$ | H |
| 7 | 249N | $CF_3CH_2$ | $CH_3$ | O | H | 4-Br—$C_6H_5$ | $OCCl_2CCl_2H$ | H |
| 7 | 250N | $CF_3CH_2$ | $CH_3$ | O | 4-Br—$C_6H_5O$ | H | $OCCl_2CCl_2H$ | H |
| 7 | 251N | $CF_3CH_2$ | $CH_3$ | O | $C_6H_5O$ | H | $OCCl_2CCl_3$ | H |
| 7 | 252N | $CF_3CH_2$ | $CH_3$ | O | 4-Cl—$C_6H_5O$ | H | $OCCl_2CCl_3$ | H |
| 7 | 253N | $CF_3CH_2$ | $CH_3$ | O | 4-F—$C_6H_5O$ | H | $OCCl_2CCl_3$ | H |
| 7 | 254N | $CF_3CH_2$ | $CH_3$ | O | 3,4-Cl—$C_6H_5O$ | H | $OCCl_2CCl_3$ | H |
| 7 | 255N | $CF_3CH_2$ | $CH_3$ | O | H | $C_6H_5$ | $OCCl_2CCl_3$ | H |
| 7 | 256N | $CF_3CH_2$ | $CH_3$ | O | H | 4-Cl—$C_6H_5$ | $OCCl_2CCl_3$ | H |
| 7 | 257N | $CF_3CH_2$ | $CH_3$ | O | H | 4-F—$C_6H_5$ | $OCCl_2CCl_3$ | H |
| 7 | 258N | $CF_3CH_2$ | $CH_3$ | O | H | 4-Br—$C_6H_5$ | $OCCl_2CCl_3$ | H |
| 7 | 259N | $CF_3CH_2$ | $CH_3$ | O | 4-Br—$C_6H_5O$ | H | $OCCl_2CCl_3$ | H |
| 7 | 260N | $CF_3CH_2$ | $CH_3$ | O | $C_6H_5O$ | H | $OCCl_2CF_3$ | H |
| 7 | 261N | $CF_3CH_2$ | $CH_3$ | O | 4-Cl—$C_6H_5O$ | H | $OCCl_2CF_3$ | H |
| 7 | 262N | $CF_3CH_2$ | $CH_3$ | O | 4-F—$C_6H_5O$ | H | $OCCl_2CF_3$ | H |
| 7 | 263N | $CF_3CH_2$ | $CH_3$ | O | 3,4-Cl—$C_6H_5O$ | H | $OCCl_2CF_3$ | H |
| 7 | 264N | $CF_3CH_2$ | $CH_3$ | O | H | $C_6H_5$ | $OCCl_2CF_3$ | H |
| 7 | 265N | $CF_3CH_2$ | $CH_3$ | O | H | 4-Cl—$C_6H_5$ | $OCCl_2CF_3$ | H |
| 7 | 266N | $CF_3CH_2$ | $CH_3$ | O | H | 4-F—$C_6H_5$ | $OCCl_2CF_3$ | H |
| 7 | 267N | $CF_3CH_2$ | $CH_3$ | O | H | 4-Br—$C_6H_5$ | $OCCl_2CF_3$ | H |
| 7 | 268N | $CF_3CH_2$ | $CH_3$ | O | 4-Br—$C_6H_5O$ | H | $OCCl_2CF_3$ | H |
| 7 | 269N | $CF_3CH_2$ | $CH_3$ | O | $C_6H_5O$ | H | $OCF_2CCl_3$ | H |
| 7 | 270N | $CF_3CH_2$ | $CH_3$ | O | 4-Cl—$C_6H_5O$ | H | $OCF_2CCl_3$ | H |
| 7 | 271N | $CF_3CH_2$ | $CH_3$ | O | 4-F—$C_6H_5O$ | H | $OCF_2CCl_3$ | H |
| 7 | 272N | $CF_3CH_2$ | $CH_3$ | O | 3,4-Cl—$C_6H_5O$ | H | $OCF_2CCl_3$ | H |
| 7 | 273N | $CF_3CH_2$ | $CH_3$ | O | H | $C_6H_5$ | $OCF_2CCl_3$ | H |
| 7 | 274N | $CF_3CH_2$ | $CH_3$ | O | H | 4-Cl—$C_6H_5$ | $OCF_2CCl_3$ | H |
| 7 | 275N | $CF_3CH_2$ | $CH_3$ | O | H | 4-F—$C_6H_5$ | $OCF_2CCl_3$ | H |
| 7 | 276N | $CF_3CH_2$ | $CH_3$ | O | H | 4-Br—$C_6H_5$ | $OCF_2CCl_3$ | H |
| 7 | 277N | $CF_3CH_2$ | $CH_3$ | O | 4-Br—$C_6H_5O$ | H | $OCF_2CCl_3$ | H |
| 7 | 278N | $CF_3CH_2$ | $CH_3$ | O | $C_6H_5O$ | H | $OCF_2CF_2H$ | $OCF_2CF_2H$ |
| 7 | 279N | $CF_3CH_2$ | $CH_3$ | O | 4-Cl—$C_6H_5O$ | H | $OCF_2CF_2H$ | $OCF_2CF_2H$ |
| 7 | 280N | $CF_3CH_2$ | $CH_3$ | O | 4-F—$C_6H_5O$ | H | $OCF_2CF_2H$ | $OCF_2CF_2H$ |
| 7 | 281N | $CF_3CH_2$ | $CH_3$ | O | 3,4-Cl—$C_6H_5O$ | H | $OCF_2CF_2H$ | $OCF_2CF_2H$ |
| 7 | 282N | $CF_3CH_2$ | $CH_3$ | O | H | $C_6H_5$ | $OCF_2CF_2H$ | $OCF_2CF_2H$ |
| 7 | 283N | $CF_3CH_2$ | $CH_3$ | O | H | 4-Cl—$C_6H_5$ | $OCF_2CF_2H$ | $OCF_2CF_2H$ |
| 7 | 284N | $CF_3CH_2$ | $CH_3$ | O | H | 4-F—$C_6H_5$ | $OCF_2CF_2H$ | $OCF_2CF_2H$ |
| 7 | 285N | $CF_3CH_2$ | $CH_3$ | O | H | 4-Br—$C_6H_5$ | $OCF_2CF_2H$ | $OCF_2CF_2H$ |
| 7 | 286N | $CF_3CH_2$ | $CH_3$ | O | 4-Br—$C_6H_5O$ | H | $OCF_2CF_2H$ | $OCF_2CF_2H$ |
| 7 | 287N | $CF_3CH_2$ | $CH_3$ | O | $C_6H_5O$ | H | $OCF_3$ | $OCF_3$ |
| 7 | 288N | $CF_3CH_2$ | $CH_3$ | O | 4-Cl—$C_6H_5O$ | H | $OCF_3$ | $OCF_3$ |
| 7 | 289N | $CF_3CH_2$ | $CH_3$ | O | 4-F—$C_6H_5O$ | H | $OCF_3$ | $OCF_3$ |
| 7 | 290N | $CF_3CH_2$ | $CH_3$ | O | 3,4-Cl—$C_6H_5O$ | H | $OCF_3$ | $OCF_3$ |
| 7 | 291N | $CF_3CH_2$ | $CH_3$ | O | H | $C_6H_5$ | $OCF_3$ | $OCF_3$ |
| 7 | 292N | $CF_3CH_2$ | $CH_3$ | O | H | 4-Cl—$C_6H_5$ | $OCF_3$ | $OCF_3$ |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

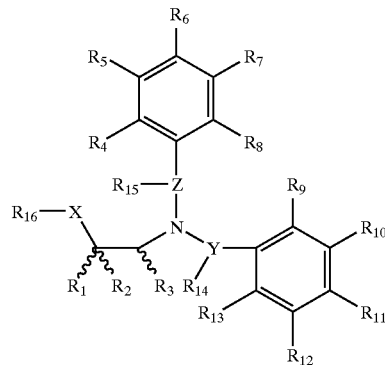

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 7 | 293N | $CF_3CH_2$ | $CH_3$ | O | H | 4-F—$C_6H_5$ | $OCF_3$ | $OCF_3$ |
| 7 | 294N | $CF_3CH_2$ | $CH_3$ | O | H | 4-Br—$C_6H_5$ | $OCF_3$ | $OCF_3$ |
| 7 | 295N | $CF_3CH_2$ | $CH_3$ | O | 4-Br—$C_6H_5O$ | H | $OCF_3$ | $OCF_3$ |
| 7 | 296N | $CF_3CH_2$ | $CH_3$ | O | $C_6H_5O$ | H | $OCF_2H$ | $OCF_2H$ |
| 7 | 297N | $CF_3CH_2$ | $CH_3$ | O | 4-Cl—$C_6H_5O$ | H | $OCF_2H$ | $OCF_2H$ |
| 7 | 298N | $CF_3CH_2$ | $CH_3$ | O | 4-F—$C_6H_5O$ | H | $OCF_2H$ | $OCF_2H$ |
| 7 | 299N | $CF_3CH_2$ | $CH_3$ | O | 3,4-Cl—$C_6H_5O$ | H | $OCF_2H$ | $OCF_2H$ |
| 7 | 300N | $CF_3CH_2$ | $CH_3$ | O | H | $C_6H_5$ | $OCF_2H$ | $OCF_2H$ |
| 7 | 301N | $CF_3CH_2$ | $CH_3$ | O | H | 4-Cl—$C_6H_5$ | $OCF_2H$ | $OCF_2H$ |
| 7 | 302N | $CF_3CH_2$ | $CH_3$ | O | H | 4-F—$C_6H_5$ | $OCF_2H$ | $OCF_2H$ |
| 7 | 303N | $CF_3CH_2$ | $CH_3$ | O | H | 4-Br—$C_6H_5$ | $OCF_2H$ | $OCF_2H$ |
| 7 | 304N | $CF_3CH_2$ | $CH_3$ | O | 4-Br—$C_6H_5O$ | H | $OCF_2H$ | $OCF_2H$ |
| 7 | 305N | $CF_3CH_2$ | $CH_3$ | O | $C_6H_5O$ | H | $R_{10} + R_{11} = OCF_2CF_2O$ | |
| 7 | 306N | $CF_3CH_2$ | $CH_3$ | O | 4-Cl—$C_6H_5O$ | H | $R_{10} + R_{11} = OCF_2CF_2O$ | |
| 7 | 307N | $CF_3CH_2$ | $CH_3$ | O | 4-F—$C_6H_5O$ | H | $R_{10} + R_{11} = OCF_2CF_2O$ | |
| 7 | 308N | $CF_3CH_2$ | $CH_3$ | O | 3,4-Cl—$C_6H_5O$ | H | $R_{10} + R_{11} = OCF_2CF_2O$ | |
| 7 | 309N | $CF_3CH_2$ | $CH_3$ | O | H | $C_6H_5$ | $R_{10} + R_{11} = OCF_2CF_2O$ | |
| 7 | 310N | $CF_3CH_2$ | $CH_3$ | O | H | 4-Cl—$C_6H_5$ | $R_{10} + R_{11} = OCF_2CF_2O$ | |
| 7 | 311N | $CF_3CH_2$ | $CH_3$ | O | H | 4-F—$C_6H_5$ | $R_{10} + R_{11} = OCF_2CF_2O$ | |
| 7 | 312N | $CF_3CH_2$ | $CH_3$ | O | H | 4-Br—$C_6H_5$ | $R_{10} + R_{11} = OCF_2CF_2O$ | |
| 7 | 313N | $CF_3CH_2$ | $CH_3$ | O | 4-Br—$C_6H_5O$ | H | $R_{10} + R_{11} = OCF_2CF_2O$ | |
| 7 | 314N | $CF_3CH_2$ | $CH_3$ | O | $C_6H_5O$ | H | $R_{10} + R_{11} = OCCl_2CCl_2O$ | |
| 7 | 315N | $CF_3CH_2$ | $CH_3$ | O | 4-Cl—$C_6H_5O$ | H | $R_{10} + R_{11} = OCCl_2CCl_2O$ | |
| 7 | 316N | $CF_3CH_2$ | $CH_3$ | O | 4-F—$C_6H_5O$ | H | $R_{10} + R_{11} = OCCl_2CCl_2O$ | |
| 7 | 317N | $CF_3CH_2$ | $CH_3$ | O | 3,4-Cl—$C_6H_5O$ | H | $R_{10} + R_{11} = OCCl_2CCl_2O$ | |
| 7 | 318N | $CF_3CH_2$ | $CH_3$ | O | H | $C_6H_5$ | $R_{10} + R_{11} = OCCl_2CCl_2O$ | |
| 7 | 319N | $CF_3CH_2$ | $CH_3$ | O | H | 4-Cl—$C_6H_5$ | $R_{10} + R_{11} = OCCl_2CCl2O$ | |
| 7 | 320N | $CF_3CH_2$ | $CH_3$ | O | H | 4-F—$C_6H_5$ | $R_{10} + R_{11} = OCCl_2CCl_2O$ | |
| 7 | 321N | $CF_3CH_2$ | $CH_3$ | O | H | 4-Br—$C_6H_5$ | $R_{10} + R_{11} = OCCl_2CCl_2O$ | |
| 7 | 322N | $CF_3CH_2$ | $CH_3$ | O | 4-Br—$C_6H_5O$ | H | $R_{10} + R_{11} = OCCl_2CCl_2O$ | |
| 7 | 323N | $CF_3CH_2$ | $CH_3$ | O | H | H | OH | H |
| 7 | 324N | $CF_3CH_2$ | $CH_3$ | O | H | H | OH | OH |
| 7 | 325N | $CF_3CH_2$ | $CH_3$ | O | H | H | H | OH |
| 7 | 326N | $CF_3CH_2$ | $CH_3$ | O | H | H | $OCH_2CF_3$ | H |
| 7 | 327N | $CF_3CH_2$ | $CH_3$ | O | H | H | H | $OCH_2CF_3$ |
| 7 | 328N | $CF_3CH_2$ | $CH_3$ | O | H | H | $OCH_2CF_2CF_3$ | H |
| 7 | 329N | $CF_3CH_2$ | $CH_3$ | O | H | H | $OCH_2CH_2CF_3$ | H |
| 7 | 330N | $CF_3CH_2$ | $CH_3$ | O | H | H | $OCH(CF_3)_3$ | H |
| 7 | 331N | $CF_3CH_2$ | $CH_3$ | O | H | 4-F—$C_6H_5O$ | H | H |
| 7 | 332N | $CF_3CH_2$ | $CH_3$ | O | 4-F—$C_6H_5O$ | H | H | H |
| 7 | 333N | $CF_3CH_2$ | $CH_3$ | O | H | cyclohexoxy | H | H |
| 7 | 334N | $CF_3CH_2$ | $CH_3$ | O | cyclohexoxy | H | H | H |
| 7 | 335N | $CF_3CH_2$ | $CH_3$ | O | H | $CH(CH_3)_3$ | H | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

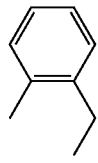

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 7 | 336N | $CF_3CH_2$ | $CH_3$ | O | F | H | 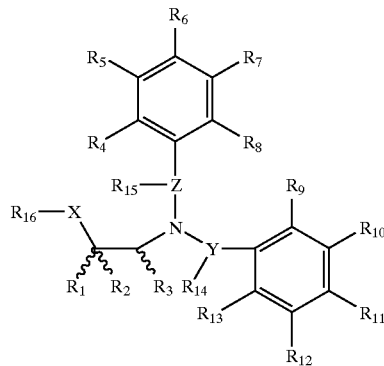 | bond to indicated phenyl carbon of $R_{10}$ substituent |
| 10 | 224N | $CF_3$ | $CF_3$ | O | $C_6H_5O$ | H | $OCF_2CF_2H$ | H |
| 10 | 225N | $CF_3$ | $CF_3$ | O | 4-Cl—$C_6H_5O$ | H | $OCF_2CF_2H$ | H |
| 10 | 226N | $CF_3$ | $CF_3$ | O | 4-F—$C_6H_5O$ | H | $OCF_2CF_2H$ | H |
| 10 | 227N | $CF_3$ | $CF_3$ | O | 3,4-Cl—$C_6H_5O$ | H | $OCF_2CF_2H$ | H |
| 10 | 228N | $CF_3$ | $CF_3$ | O | H | $C_6H_5$ | $OCF_2CF_2H$ | H |
| 10 | 229N | $CF_3$ | $CF_3$ | O | H | 4-Cl—$C_6H_5$ | $OCF_2CF_2H$ | H |
| 10 | 230N | $CF_3$ | $CF_3$ | O | H | 4-F—$C_6H_5$ | $OCF_2CF_2H$ | H |
| 10 | 231N | $CF_3$ | $CF_3$ | O | H | 4-Br—$C_6H_5$ | $OCF_2CF_2H$ | H |
| 10 | 232N | $CF_3$ | $CF_3$ | O | 4-Br—$C_6H_5O$ | H | $OCF_2CF_2H$ | H |
| 10 | 233N | $CF_3$ | $CF_3$ | O | $C_6H_5O$ | H | $OCF_2CF_3$ | H |
| 10 | 234N | $CF_3$ | $CF_3$ | O | 4-Cl—$C_6H_5O$ | H | $OCF_2CF_3$ | H |
| 10 | 235N | $CF_3$ | $CF_3$ | O | 4-F—$C_6H_5O$ | H | $OCF_2CF_3$ | H |
| 10 | 236N | $CF_3$ | $CF_3$ | O | 3,4-Cl—$C_6H_5O$ | H | $OCF_2CF_3$ | H |
| 10 | 237N | $CF_3$ | $CF_3$ | O | H | $C_6H_5$ | $OCF_2CF_3$ | H |
| 10 | 238N | $CF_3$ | $CF_3$ | O | H | 4-Cl—$C_6H_5$ | $OCF_2CF_3$ | H |
| 10 | 239N | $CF_3$ | $CF_3$ | O | H | 4-F—$C_6H_5$ | $OCF_2CF_3$ | H |
| 10 | 240N | $CF_3$ | $CF_3$ | O | H | 4-Br—$C_6H_5$ | $OCF_2CF_3$ | H |
| 10 | 241N | $CF_3$ | $CF_3$ | O | 4-Br—$C_6H_5O$ | H | $OCF_2CF_3$ | H |
| 10 | 242N | $CF_3$ | $CF_3$ | O | $C_6H_5O$ | H | $OCCl_2CCl_2H$ | H |
| 10 | 243N | $CF_3$ | $CF_3$ | O | 4-Cl—$C_6H_5O$ | H | $OCCl_2CCl_2H$ | H |
| 10 | 244N | $CF_3$ | $CF_3$ | O | 4-F—$C_6H_5O$ | H | $OCCl_2CCl_2H$ | H |
| 10 | 245N | $CF_3$ | $CF_3$ | O | 3,4-Cl—$C_6H_5O$ | H | $OCCl_2CCl_2H$ | H |
| 10 | 246N | $CF_3$ | $CF_3$ | O | H | $C_6H_5$ | $OCCl_2CCl_2H$ | H |
| 10 | 247N | $CF_3$ | $CF_3$ | O | H | 4-Cl—$C_6H_5$ | $OCCl_2CCl_2H$ | H |
| 10 | 248N | $CF_3$ | $CF_3$ | O | H | 4-F—$C_6H_5$ | $OCCl_2CCl_2H$ | H |
| 10 | 249N | $CF_3$ | $CF_3$ | O | H | 4-Br—$C_6H_5$ | $OCCl_2CCl_2H$ | H |
| 10 | 250N | $CF_3$ | $CF_3$ | O | 4-Br—$C_6H_5O$ | H | $OCCl_2CCl_2H$ | H |
| 10 | 251N | $CF_3$ | $CF_3$ | O | $C_6H_5O$ | H | $OCCl_2CCl_3$ | H |
| 10 | 252N | $CF_3$ | $CF_3$ | O | 4-Cl—$C_6H_5O$ | H | $OCCl_2CCl_3$ | H |
| 10 | 253N | $CF_3$ | $CF_3$ | O | 4-F—$C_6H_5O$ | H | $OCCl_2CCl_3$ | H |
| 10 | 254N | $CF_3$ | $CF_3$ | O | 3,4-Cl—$C_6H_5O$ | H | $OCCl_2CCl_3$ | H |
| 10 | 255N | $CF_3$ | $CF_3$ | O | H | $C_6H_5$ | $OCCl_2CCl_3$ | H |
| 10 | 256N | $CF_3$ | $CF_3$ | O | H | 4-Cl—$C_6H_5$ | $OCCl_2CCl_3$ | H |
| 10 | 257N | $CF_3$ | $CF_3$ | O | H | 4-F—$C_6H_5$ | $OCCl_2CCl_3$ | H |
| 10 | 258N | $CF_3$ | $CF_3$ | O | H | 4-Br—$C_6H_5$ | $OCCl_2CCl_3$ | H |
| 10 | 259N | $CF_3$ | $CF_3$ | O | 4-Br—$C_6H_5O$ | H | $OCCl_2CCl_3$ | H |
| 10 | 260N | $CF_3$ | $CF_3$ | O | $C_6H_5O$ | H | $OCCl_2CF_3$ | H |
| 10 | 261N | $CF_3$ | $CF_3$ | O | 4-Cl—$C_6H_5O$ | H | $OCCl_2CF_3$ | H |
| 10 | 262N | $CF_3$ | $CF_3$ | O | 4-F—$C_6H_5O$ | H | $OCCl_2CF_3$ | H |
| 10 | 263N | $CF_3$ | $CF_3$ | O | 3,4-Cl—$C_6H_5O$ | H | $OCCl_2CF_3$ | H |
| 10 | 264N | $CF_3$ | $CF_3$ | O | H | $C_6H_5$ | $OCCl_2CF_3$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

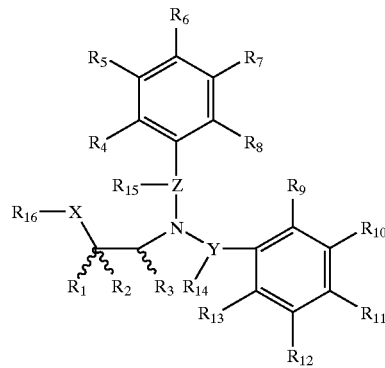

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 10 | 265N | $CF_3$ | $CF_3$ | O | H | 4-Cl—$C_6H_5$ | $OCCl_2CF_3$ | H |
| 10 | 266N | $CF_3$ | $CF_3$ | O | H | 4-F—$C_6H_5$ | $OCCl_2CF_3$ | H |
| 10 | 267N | $CF_3$ | $CF_3$ | O | H | 4-Br—$C_6H_5$ | $OCCl_2CF_3$ | H |
| 10 | 268N | $CF_3$ | $CF_3$ | O | 4-Br—$C_6H_5O$ | H | $OCCl_2CF_3$ | H |
| 10 | 269N | $CF_3$ | $CF_3$ | O | $C_6H_5O$ | H | $OCF_2CCl_3$ | H |
| 10 | 270N | $CF_3$ | $CF_3$ | O | 4-Cl—$C_6H_5O$ | H | $OCF_2CCl_3$ | H |
| 10 | 271N | $CF_3$ | $CF_3$ | O | 4-F—$C_6H_5O$ | H | $OCF_2CCl_3$ | H |
| 10 | 272N | $CF_3$ | $CF_3$ | O | 3,4-Cl—$C_6H_5O$ | H | $OCF_2CCl_3$ | H |
| 10 | 273N | $CF_3$ | $CF_3$ | O | H | $C_6H_5$ | $OCF_2CCl_3$ | H |
| 10 | 274N | $CF_3$ | $CF_3$ | O | H | 4-Cl—$C_6H_5$ | $OCF_2CCl_3$ | H |
| 10 | 275N | $CF_3$ | $CF_3$ | O | H | 4-F—$C_6H_5$ | $OCF_2CCl_3$ | H |
| 10 | 276N | $CF_3$ | $CF_3$ | O | H | 4-Br—$C_6H_5$ | $OCF_2CCl_3$ | H |
| 10 | 277N | $CF_3$ | $CF_3$ | O | 4-Br—$C_6H_5O$ | H | $OCF_2CCl_3$ | H |
| 10 | 278N | $CF_3$ | $CF_3$ | O | $C_6H_5O$ | H | $OCF_2CF_2H$ | $OCF_2CF_2H$ |
| 10 | 279N | $CF_3$ | $CF_3$ | O | 4-Cl—$C_6H_5O$ | H | $OCF_2CF_2H$ | $OCF_2CF_2H$ |
| 10 | 280N | $CF_3$ | $CF_3$ | O | 4-F—$C_6H_5O$ | H | $OCF_2CF_2H$ | $OCF_2CF_2H$ |
| 10 | 281N | $CF_3$ | $CF_3$ | O | 3,4-Cl—$C_6H_5O$ | H | $OCF_2CF_2H$ | $OCF_2CF_2H$ |
| 10 | 282N | $CF_3$ | $CF_3$ | O | H | $C_6H_5$ | $OCF_2CF_2H$ | $OCF_2CF_2H$ |
| 10 | 283N | $CF_3$ | $CF_3$ | O | H | 4-Cl—$C_6H_5$ | $OCF_2CF_2H$ | $OCF_2CF_2H$ |
| 10 | 284N | $CF_3$ | $CF_3$ | O | H | 4-F—$C_6H_5$ | $OCF_2CF_2H$ | $OCF_2CF_2H$ |
| 10 | 285N | $CF_3$ | $CF_3$ | O | H | 4-Br—$C_6H_5$ | $OCF_2CF_2H$ | $OCF_2CF_2H$ |
| 10 | 286N | $CF_3$ | $CF_3$ | O | 4-Br—$C_6H_5O$ | H | $OCF_2CF_2H$ | $OCF_2CF_2H$ |
| 10 | 287N | $CF_3$ | $CF_3$ | O | $C_6H_5O$ | H | $OCF_3$ | $OCF_3$ |
| 10 | 288N | $CF_3$ | $CF_3$ | O | 4-Cl—$C_6H_5O$ | H | $OCF_3$ | $OCF_3$ |
| 10 | 289N | $CF_3$ | $CF_3$ | O | 4-F—$C_6H_5O$ | H | $OCF_3$ | $OCF_3$ |
| 10 | 290N | $CF_3$ | $CF_3$ | O | 3,4-Cl—$C_6H_5O$ | H | $OCF_3$ | $OCF_3$ |
| 10 | 291N | $CF_3$ | $CF_3$ | O | H | $C_6H_5$ | $OCF_3$ | $OCF_3$ |
| 10 | 292N | $CF_3$ | $CF_3$ | O | H | 4-Cl—$C_6H_5$ | $OCF_3$ | $OCF_3$ |
| 10 | 293N | $CF_3$ | $CF_3$ | O | H | 4-F—$C_6H_5$ | $OCF_3$ | $OCF_3$ |
| 10 | 294N | $CF_3$ | $CF_3$ | O | H | 4-Br—$C_6H_5$ | $OCF_3$ | $OCF_3$ |
| 10 | 295N | $CF_3$ | $CF_3$ | O | 4-Br—$C_6H_5O$ | H | $OCF_3$ | $OCF_3$ |
| 10 | 296N | $CF_3$ | $CF_3$ | O | $C_6H_5O$ | H | $OCF_2H$ | $OCF_2H$ |
| 10 | 297N | $CF_3$ | $CF_3$ | O | 4-Cl—$C_6H_5O$ | H | $OCF_2H$ | $OCF_2H$ |
| 10 | 298N | $CF_3$ | $CF_3$ | O | 4-F—$C_6H_5O$ | H | $OCF_2H$ | $OCF_2H$ |
| 10 | 299N | $CF_3$ | $CF_3$ | O | 3,4-Cl—$C_6H_5O$ | H | $OCF_2H$ | $OCF_2H$ |
| 10 | 300N | $CF_3$ | $CF_3$ | O | H | $C_6H_5$ | $OCF_2H$ | $OCF_2H$ |
| 10 | 301N | $CF_3$ | $CF_3$ | O | H | 4-Cl—$C_6H_5$ | $OCF_2H$ | $OCF_2H$ |
| 10 | 302N | $CF_3$ | $CF_3$ | O | H | 4-F—$C_6H_5$ | $OCF_2H$ | $OCF_2H$ |
| 10 | 303N | $CF_3$ | $CF_3$ | O | H | 4-Br—$C_6H_5$ | $OCF_2H$ | $OCF_2H$ |
| 10 | 304N | $CF_3$ | $CF_3$ | O | 4-Br—$C_6H_5O$ | H | $OCF_2H$ | $OCF_2H$ |
| 10 | 305N | $CF_3$ | $CF_3$ | O | $C_6H_5O$ | H | $R_{10} + R_{11} = OCF_2CF_2O$ | |
| 10 | 306N | $CF_3$ | $CF_3$ | O | 4-Cl—$C_6H_5O$ | H | $R_{10} + R_{11} = OCF_2CF_2O$ | |
| 10 | 307N | $CF_3$ | $CF_3$ | O | 4-F—$C_6H_5O$ | H | $R_{10} + R_{11} = OCF_2CF_2O$ | |
| 10 | 308N | $CF_3$ | $CF_3$ | O | 3,4-Cl—$C_6H_5O$ | H | $R_{10} + R_{11} = OCF_2CF_2O$ | |
| 10 | 309N | $CF_3$ | $CF_3$ | O | H | $C_6H_5$ | $R_{10} + R_{11} = OCF_2CF_2O$ | |
| 10 | 310N | $CF_3$ | $CF_3$ | O | H | 4-Cl—$C_6H_5$ | $R_{10} + R_{11} = OCF_2CF_2O$ | |
| 10 | 311N | $CF_3$ | $CF_3$ | O | H | 4-F—$C_6H_5$ | $R_{10} + R_{11} = OCF_2CF_2O$ | |
| 10 | 312N | $CF_3$ | $CF_3$ | O | H | 4-Br—$C_6H_5$ | $R_{10} + R_{11} = OCF_2CF_2O$ | |
| 10 | 313N | $CF_3$ | $CF_3$ | O | 4-Br—$C_6H_5O$ | H | $R_{10} + R_{11} = OCF_2CF_2O$ | |
| 10 | 314N | $CF_3$ | $CF_3$ | O | $C_6H_5O$ | H | $R_{10} + R_{11} = OCCl_2CCl_2O$ | |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

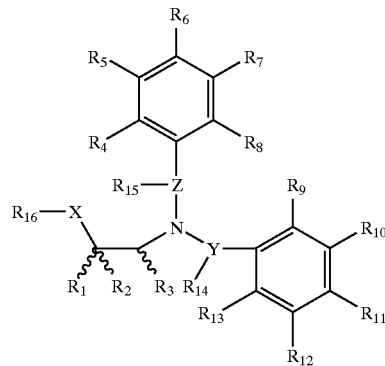

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 10 | 315N | $CF_3$ | $CF_3$ | O | 4-Cl—$C_6H_5O$ | H | $R_{10} + R_{11}$ = $OCCl_2CCl_2O$ | |
| 10 | 316N | $CF_3$ | $CF_3$ | O | 4-F—$C_6H_5O$ | H | $R_{10} + R_{11}$ = $OCCl_2CCl_2O$ | |
| 10 | 317N | $CF_3$ | $CF_3$ | O | 3,4-Cl—$C_6H_5O$ | H | $R_{10} + R_{11}$ = $OCCl_2CCl_2O$ | |
| 10 | 318N | $CF_3$ | $CF_3$ | O | H | $C_6H_5$ | $R_{10} + R_{11}$ = $OCCl_2CCl_2O$ | |
| 10 | 319N | $CF_3$ | $CF_3$ | O | H | 4-Cl—$C_6H_5$ | $R_{10} + R_{11}$ = $OCCl_2CCl_2O$ | |
| 10 | 320N | $CF_3$ | $CF_3$ | O | H | 4-F—$C_6H_5$ | $R_{10} + R_{11}$ = $OCCl_2CCl_2O$ | |
| 10 | 321N | $CF_3$ | $CF_3$ | O | H | 4-Br—$C_6H_5$ | $R_{10} + R_{11}$ = $OCCl_2CCl_2O$ | |
| 10 | 322N | $CF_3$ | $CF_3$ | O | 4-Br—$C_6H_5O$ | H | $R_{10} + R_{11}$ = $OCCl_2CCl_2O$ | |
| 10 | 323N | $CF_3$ | $CF_3$ | O | H | H | OH | H |
| 10 | 324N | $CF_3$ | $CF_3$ | O | H | H | OH | OH |
| 10 | 325N | $CF_3$ | $CF_3$ | O | H | H | H | OH |
| 10 | 326N | $CF_3$ | $CF_3$ | O | H | H | $OCH_2CF_3$ | H |
| 10 | 327N | $CF_3$ | $CF_3$ | O | H | H | H | $OCH_2CF_3$ |
| 10 | 328N | $CF_3$ | $CF_3$ | O | H | H | $OCH_2CF_2CF_3$ | H |
| 10 | 329N | $CF_3$ | $CF_3$ | O | H | H | $OCH_2CH_2CF_3$ | H |
| 10 | 330N | $CF_3$ | $CF_3$ | O | H | H | $OCH(CF_3)_3$ | H |
| 10 | 331N | $CF_3$ | $CF_3$ | O | H | 4-F—$C_6H_5O$ | H | H |
| 10 | 332N | $CF_3$ | $CF_3$ | O | 4-F—$C_6H_5O$ | H | H | H |
| 10 | 333N | $CF_3$ | $CF_3$ | O | H | cyclohexoxy | H | H |
| 10 | 334N | $CF_3$ | $CF_3$ | O | cyclohexoxy | H | H | H |
| 10 | 335N | $CF_3$ | $CF_3$ | O | H | $CH(CH_3)_3$ | H | H |
| 10 | 336N | $CF_3$ | $CF_3$ | O | F | H | 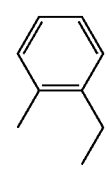 | bond to indicated phenyl carbon of $R_{10}$ substituent |
| 19 | 224N | $CF_3$ | $CF_3$ | NH | $C_6H_5O$ | H | $OCF_2CF_2H$ | H |
| 19 | 225N | $CF_3$ | $CF_3$ | NH | 4-Cl—$C_6H_5O$ | H | $OCF_2CF_2H$ | H |
| 19 | 226N | $CF_3$ | $CF_3$ | NH | 4-F—$C_6H_5O$ | H | $OCF_2CF_2H$ | H |
| 19 | 227N | $CF_3$ | $CF_3$ | NH | 3,4-Cl—$C_6H_5O$ | H | $OCF_2CF_2H$ | H |
| 19 | 228N | $CF_3$ | $CF_3$ | NH | H | $C_6H_5$ | $OCF_2CF_2H$ | H |
| 19 | 229N | $CF_3$ | $CF_3$ | NH | H | 4-Cl—$C_6H_5$ | $OCF_2CF_2H$ | H |
| 19 | 230N | $CF_3$ | $CF_3$ | NH | H | 4-F—$C_6H_5$ | $OCF_2CF_2H$ | H |
| 19 | 231N | $CF_3$ | $CF_3$ | NH | H | 4-Br—$C_6H_5$ | $OCF_2CF_2H$ | H |
| 19 | 232N | $CF_3$ | $CF_3$ | NH | 4-Br—$C_6H_5O$ | H | $OCF_2CF_2H$ | H |
| 19 | 233N | $CF_3$ | $CF_3$ | NH | $C_6H_5O$ | H | $OCF_2CF_3$ | H |
| 19 | 234N | $CF_3$ | $CF_3$ | NH | 4-Cl—$C_6H_5O$ | H | $OCF_2CF_3$ | H |
| 19 | 235N | $CF_3$ | $CF_3$ | NH | 4-F—$C_6H_5O$ | H | $OCF_2CF_3$ | H |
| 19 | 236N | $CF_3$ | $CF_3$ | NH | 3,4-Cl—$C_6H_5O$ | H | $OCF_2CF_3$ | H |
| 19 | 237N | $CF_3$ | $CF_3$ | NH | H | $C_6H_5$ | $OCF_2CF_3$ | H |
| 19 | 238N | $CF_3$ | $CF_3$ | NH | H | 4-Cl—$C_6H_5$ | $OCF_2CF_3$ | H |
| 19 | 239N | $CF_3$ | $CF_3$ | NH | H | 4-F—$C_6H_5$ | $OCF_2CF_3$ | H |
| 19 | 240N | $CF_3$ | $CF_3$ | NH | H | 4-Br—$C_6H_5$ | $OCF_2CF_3$ | H |
| 19 | 241N | $CF_3$ | $CF_3$ | NH | 4-Br—$C_6H_5O$ | H | $OCF_2CF_3$ | H |
| 19 | 242N | $CF_3$ | $CF_3$ | NH | $C_6H_5O$ | H | $OCCl_2CCl_2H$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

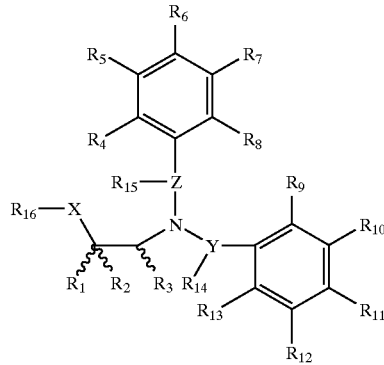

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 19 | 243N | $CF_3$ | $CF_3$ | NH | 4-Cl—$C_6H_5O$ | H | $OCCl_2CCl_2H$ | H |
| 19 | 244N | $CF_3$ | $CF_3$ | NH | 4-F—$C_6H_5O$ | H | $OCCl_2CCl_2H$ | H |
| 19 | 245N | $CF_3$ | $CF_3$ | NH | 3,4-Cl—$C_6H_5O$ | H | $OCCl_2CCl_2H$ | H |
| 19 | 246N | $CF_3$ | $CF_3$ | NH | H | $C_6H_5$ | $OCCl_2CCl_2H$ | H |
| 19 | 247N | $CF_3$ | $CF_3$ | NH | H | 4-Cl—$C_6H_5$ | $OCCl_2CCl_2H$ | H |
| 19 | 248N | $CF_3$ | $CF_3$ | NH | H | 4-F—$C_6H_5$ | $OCCl_2CCl_2H$ | H |
| 19 | 249N | $CF_3$ | $CF_3$ | NH | H | 4-Br—$C_6H_5$ | $OCCl_2CCl_2H$ | H |
| 19 | 250N | $CF_3$ | $CF_3$ | NH | 4-Br—$C_6H_5O$ | H | $OCCl_2CCl_2H$ | H |
| 19 | 251N | $CF_3$ | $CF_3$ | NH | $C_6H_5O$ | H | $OCCl_2CCl_3$ | H |
| 19 | 252N | $CF_3$ | $CF_3$ | NH | 4-Cl—$C_6H_5O$ | H | $OCCl_2CCl_3$ | H |
| 19 | 253N | $CF_3$ | $CF_3$ | NH | 4-F—$C_6H_5O$ | H | $OCCl_2CCl_3$ | H |
| 19 | 254N | $CF_3$ | $CF_3$ | NH | 3,4-Cl—$C_6H_5O$ | H | $OCCl_2CCl_3$ | H |
| 19 | 255N | $CF_3$ | $CF_3$ | NH | H | $C_6H_5$ | $OCCl_2CCl_3$ | H |
| 19 | 256N | $CF_3$ | $CF_3$ | NH | H | 4-Cl—$C_6H_5$ | $OCCl_2CCl_3$ | H |
| 19 | 257N | $CF_3$ | $CF_3$ | NH | H | 4-F—$C_6H_5$ | $OCCl_2CCl_3$ | H |
| 19 | 258N | $CF_3$ | $CF_3$ | NH | H | 4-Br—$C_6H_5$ | $OCCl_2CCl_3$ | H |
| 19 | 259N | $CF_3$ | $CF_3$ | NH | 4-Br—$C_6H_5O$ | H | $OCCl_2CCl_3$ | H |
| 19 | 260N | $CF_3$ | $CF_3$ | NH | $C_6H_5O$ | H | $OCCl_2CF_3$ | H |
| 19 | 261N | $CF_3$ | $CF_3$ | NH | 4-Cl—$C_6H_5O$ | H | $OCCl_2CF_3$ | H |
| 19 | 262N | $CF_3$ | $CF_3$ | NH | 4-F—$C_6H_5O$ | H | $OCCl_2CF_3$ | H |
| 19 | 263N | $CF_3$ | $CF_3$ | NH | 3,4-Cl—$C_6H_5O$ | H | $OCCl_2CF_3$ | H |
| 19 | 264N | $CF_3$ | $CF_3$ | NH | H | $C_6H_5$ | $OCCl_2CF_3$ | H |
| 19 | 265N | $CF_3$ | $CF_3$ | NH | H | 4-Cl—$C_6H_5$ | $OCCl_2CF_3$ | H |
| 19 | 266N | $CF_3$ | $CF_3$ | NH | H | 4-F—$C_6H_5$ | $OCCl_2CF_3$ | H |
| 19 | 267N | $CF_3$ | $CF_3$ | NH | H | 4-Br—$C_6H_5$ | $OCCl_2CF_3$ | H |
| 19 | 268N | $CF_3$ | $CF_3$ | NH | 4-Br—$C_6H_5O$ | H | $OCCl_2CF_3$ | H |
| 19 | 269N | $CF_3$ | $CF_3$ | NH | $C_6H_5O$ | H | $OCF_2CCl_3$ | H |
| 19 | 270N | $CF_3$ | $CF_3$ | NH | 4-Cl—$C_6H_5O$ | H | $OCF_2CCl_3$ | H |
| 19 | 271N | $CF_3$ | $CF_3$ | NH | 4-F—$C_6H_5O$ | H | $OCF_2CCl_3$ | H |
| 19 | 272N | $CF_3$ | $CF_3$ | NH | 3,4-Cl—$C_6H_5O$ | H | $OCF_2CCl_3$ | H |
| 19 | 273N | $CF_3$ | $CF_3$ | NH | H | $C_6H_5$ | $OCF_2CCl_3$ | H |
| 19 | 274N | $CF_3$ | $CF_3$ | NH | H | 4-Cl—$C_6H_5$ | $OCF_2CCl_3$ | H |
| 19 | 275N | $CF_3$ | $CF_3$ | NH | H | 4-F—$C_6H_5$ | $OCF_2CCl_3$ | H |
| 19 | 276N | $CF_3$ | $CF_3$ | NH | H | 4-Br—$C_6H_5$ | $OCF_2CCl_3$ | H |
| 19 | 277N | $CF_3$ | $CF_3$ | NH | 4-Br—$C_6H_5O$ | H | $OCF_2CCl_3$ | H |
| 19 | 278N | $CF_3$ | $CF_3$ | NH | $C_6H_5O$ | H | $OCF_2CF_2H$ | $OCF_2CF_2H$ |
| 19 | 279N | $CF_3$ | $CF_3$ | NH | 4-Cl—$C_6H_5O$ | H | $OCF_2CF_2H$ | $OCF_2CF_2H$ |
| 19 | 280N | $CF_3$ | $CF_3$ | NH | 4-F—$C_6H_5O$ | H | $OCF_2CF_2H$ | $OCF_2CF_2H$ |
| 19 | 281N | $CF_3$ | $CF_3$ | NH | 3,4-Cl—$C_6H_5O$ | H | $OCF_2CF_2H$ | $OCF_2CF_2H$ |
| 19 | 282N | $CF_3$ | $CF_3$ | NH | H | $C_6H_5$ | $OCF_2CF_2H$ | $OCF_2CF_2H$ |
| 19 | 283N | $CF_3$ | $CF_3$ | NH | H | 4-Cl—$C_6H_5$ | $OCF_2CF_2H$ | $OCF_2CF_2H$ |
| 19 | 284N | $CF_3$ | $CF_3$ | NH | H | 4-F—$C_6H_5$ | $OCF_2CF_2H$ | $OCF_2CF_2H$ |
| 19 | 285N | $CF_3$ | $CF_3$ | NH | H | 4-Br—$C_6H_5$ | $OCF_2CF_2H$ | $OCF_2CF_2H$ |
| 19 | 286N | $CF_3$ | $CF_3$ | NH | 4-Br—$C_6H_5O$ | H | $OCF_2CF_2H$ | $OCF_2CF_2H$ |
| 19 | 287N | $CF_3$ | $CF_3$ | NH | $C_6H_5O$ | H | $OCF_3$ | $OCF_3$ |
| 19 | 288N | $CF_3$ | $CF_3$ | NH | 4-Cl—$C_6H_5O$ | H | $OCF_3$ | $OCF_3$ |
| 19 | 289N | $CF_3$ | $CF_3$ | NH | 4-F—$C_6H_5O$ | H | $OCF_3$ | $OCF_3$ |
| 19 | 290N | $CF_3$ | $CF_3$ | NH | 3,4-Cl—$C_6H_5O$ | H | $OCF_3$ | $OCF_3$ |
| 19 | 291N | $CF_3$ | $CF_3$ | NH | H | $C_6H_5$ | $OCF_3$ | $OCF_3$ |
| 19 | 292N | $CF_3$ | $CF_3$ | NH | H | 4-Cl—$C_6H_5$ | $OCF_3$ | $OCF_3$ |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

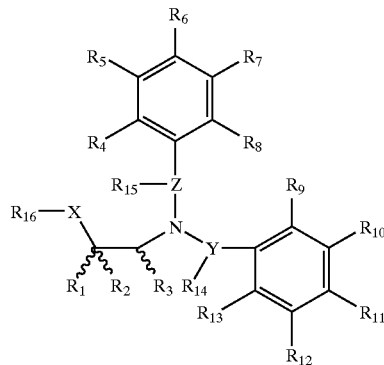

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 19 | 293N | $CF_3$ | $CF_3$ | NH | H | 4-F—$C_6H_5$ | $OCF_3$ | $OCF_3$ |
| 19 | 294N | $CF_3$ | $CF_3$ | NH | H | 4-Br—$C_6H_5$ | $OCF_3$ | $OCF_3$ |
| 19 | 295N | $CF_3$ | $CF_3$ | NH | 4-Br—$C_6H_5O$ | H | $OCF_3$ | $OCF_3$ |
| 19 | 296N | $CF_3$ | $CF_3$ | NH | $C_6H_5O$ | H | $OCF_2H$ | $OCF_2H$ |
| 19 | 297N | $CF_3$ | $CF_3$ | NH | 4-Cl—$C_6H_5O$ | H | $OCF_2H$ | $OCF_2H$ |
| 19 | 298N | $CF_3$ | $CF_3$ | NH | 4-F—$C_6H_5O$ | H | $OCF_2H$ | $OCF_2H$ |
| 19 | 299N | $CF_3$ | $CF_3$ | NH | 3,4-Cl—$C_6H_5O$ | H | $OCF_2H$ | $OCF_2H$ |
| 19 | 300N | $CF_3$ | $CF_3$ | NH | H | $C_6H_5$ | $OCF_2H$ | $OCF_2H$ |
| 19 | 301N | $CF_3$ | $CF_3$ | NH | H | 4-Cl—$C_6H_5$ | $OCF_2H$ | $OCF_2H$ |
| 19 | 302N | $CF_3$ | $CF_3$ | NH | H | 4-F—$C_6H_5$ | $OCF_2H$ | $OCF_2H$ |
| 19 | 303N | $CF_3$ | $CF_3$ | NH | H | 4-Br—$C_6H_5$ | $OCF_2H$ | $OCF_2H$ |
| 19 | 304N | $CF_3$ | $CF_3$ | NH | 4-Br—$C_6H_5O$ | H | $OCF_2H$ | $OCF_2H$ |
| 19 | 305N | $CF_3$ | $CF_3$ | NH | $C_6H_5O$ | H | $R_{10} + R_{11} = OCF_2CF_2O$ | |
| 19 | 306N | $CF_3$ | $CF_3$ | NH | 4-Cl—$C_6H_5O$ | H | $R_{10} + R_{11} = OCF_2CF_2O$ | |
| 19 | 307N | $CF_3$ | $CF_3$ | NH | 4-F—$C_6H_5O$ | H | $R_{10} + R_{11} = OCF_2CF_2O$ | |
| 19 | 308N | $CF_3$ | $CF_3$ | NH | 3,4-Cl—$C_6H_5O$ | H | $R_{10} + R_{11} = OCF_2CF_2O$ | |
| 19 | 309N | $CF_3$ | $CF_3$ | NH | H | $C_6H_5$ | $R_{10} + R_{11} = OCF_2CF_2O$ | |
| 19 | 310N | $CF_3$ | $CF_3$ | NH | H | 4-Cl—$C_6H_5$ | $R_{10} + R_{11} = OCF_2CF_2O$ | |
| 19 | 311N | $CF_3$ | $CF_3$ | NH | H | 4-F—$C_6H_5$ | $R_{10} + R_{11} = OCF_2CF_2O$ | |
| 19 | 312N | $CF_3$ | $CF_3$ | NH | H | 4-Br—$C_6H_5$ | $R_{10} + R_{11} = OCF_2CF_2O$ | |
| 19 | 313N | $CF_3$ | $CF_3$ | NH | 4-Br—$C_6H_5O$ | H | $R_{10} + R_{11} = OCF_2CF_2O$ | |
| 19 | 314N | $CF_3$ | $CF_3$ | NH | $C_6H_5O$ | H | $R_{10} + R_{11} = OCCl_2CCl_2O$ | |
| 19 | 315N | $CF_3$ | $CF_3$ | NH | 4-Cl—$C_6H_5O$ | H | $R_{10} + R_{11} = OCCl_2CCl_2O$ | |
| 19 | 316N | $CF_3$ | $CF_3$ | NH | 4-F—$C_6H_5O$ | H | $R_{10} + R_{11} = OCCl_2CCl_2O$ | |
| 19 | 317N | $CF_3$ | $CF_3$ | NH | 3,4-Cl—$C_6H_5O$ | H | $R_{10} + R_{11} = OCCl_2CCl_2O$ | |
| 19 | 318N | $CF_3$ | $CF_3$ | NH | H | $C_6H_5$ | $R_{10} + R_{11} = OCCl_2CCl_2O$ | |
| 19 | 319N | $CF_3$ | $CF_3$ | NH | H | 4-Cl—$C_6H_5$ | $R_{10} + R_{11} = OCCl_2CCl_2O$ | |
| 19 | 320N | $CF_3$ | $CF_3$ | NH | H | 4-F—$C_6H_5$ | $R_{10} + R_{11} = OCCl_2CCl_2O$ | |
| 19 | 321N | $CF_3$ | $CF_3$ | NH | H | 4-Br—$C_6H_5$ | $R_{10} + R_{11} = OCCl_2CCl_2O$ | |
| 19 | 322N | $CF_3$ | $CF_3$ | NH | 4-Br—$C_6H_5O$ | H | $R_{10} + R_{11} = OCCl_2CCl_2O$ | |
| 19 | 323N | $CF_3$ | $CF_3$ | NH | H | H | OH | H |
| 19 | 324N | $CF_3$ | $CF_3$ | NH | H | H | OH | OH |
| 19 | 325N | $CF_3$ | $CF_3$ | NH | H | H | H | OH |
| 19 | 326N | $CF_3$ | $CF_3$ | NH | H | H | $OCH_2CF_3$ | H |
| 19 | 327N | $CF_3$ | $CF_3$ | NH | H | H | H | $OCH_2CF_3$ |
| 19 | 328N | $CF_3$ | $CF_3$ | NH | H | H | $OCH_2CF_2CF_3$ | H |
| 19 | 329N | $CF_3$ | $CF_3$ | NH | H | H | $OCH_2CH_2CF_3$ | H |
| 19 | 330N | $CF_3$ | $CF_3$ | NH | H | H | $OCH(CF_3)_3$ | H |
| 19 | 331N | $CF_3$ | $CF_3$ | NH | H | 4-F—$C_6H_5O$ | H | H |
| 19 | 332N | $CF_3$ | $CF_3$ | NH | 4-F—$C_6H_5O$ | H | H | H |
| 19 | 333N | $CF_3$ | $CF_3$ | NH | H | cyclohexoxy | H | H |
| 19 | 334N | $CF_3$ | $CF_3$ | NH | cyclohexoxy | H | H | H |
| 19 | 335N | $CF_3$ | $CF_3$ | NH | H | $CH(CH_3)_3$ | H | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

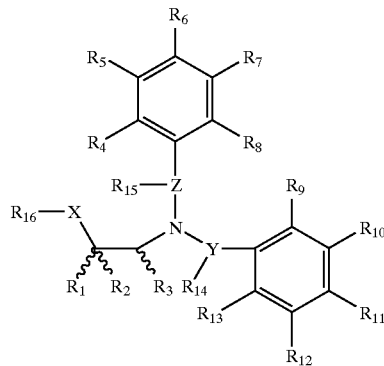

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 19 | 336N | $CF_3$ | $CF_3$ | NH | F | H | (2-ethylphenyl) | bond to indicated phenyl carbon of $R_{10}$ substituent |
| 20 | 224N | $CF_3$ | H | NH | $C_6H_5O$ | H | $OCF_2CF_2H$ | H |
| 20 | 225N | $CF_3$ | H | NH | 4-Cl—$C_6H_5O$ | H | $OCF_2CF_2H$ | H |
| 20 | 226N | $CF_3$ | H | NH | 4-F—$C_6H_5O$ | H | $OCF_2CF_2H$ | H |
| 20 | 227N | $CF_3$ | H | NH | 3,4-Cl—$C_6H_5O$ | H | $OCF_2CF_2H$ | H |
| 20 | 228N | $CF_3$ | H | NH | H | $C_6H_5$ | $OCF_2CF_2H$ | H |
| 20 | 229N | $CF_3$ | H | NH | H | 4-Cl—$C_6H_5$ | $OCF_2CF_2H$ | H |
| 20 | 230N | $CF_3$ | H | NH | H | 4-F—$C_6H_5$ | $OCF_2CF_2H$ | H |
| 20 | 231N | $CF_3$ | H | NH | H | 4-Br—$C_6H_5$ | $OCF_2CF_2H$ | H |
| 20 | 232N | $CF_3$ | H | NH | 4-Br—$C_6H_5O$ | H | $OCF_2CF_2H$ | H |
| 20 | 233N | $CF_3$ | H | NH | $C_6H_5O$ | H | $OCF_2CF_3$ | H |
| 20 | 234N | $CF_3$ | H | NH | 4-Cl—$C_6H_5O$ | H | $OCF_2CF_3$ | H |
| 20 | 235N | $CF_3$ | H | NH | 4-F—$C_6H_5O$ | H | $OCF_2CF_3$ | H |
| 20 | 236N | $CF_3$ | H | NH | 3,4-Cl—$C_6H_5O$ | H | $OCF_2CF_3$ | H |
| 20 | 237N | $CF_3$ | H | NH | H | $C_6H_5$ | $OCF_2CF_3$ | H |
| 20 | 238N | $CF_3$ | H | NH | H | 4-Cl—$C_6H_5$ | $OCF_2CF_3$ | H |
| 20 | 239N | $CF_3$ | H | NH | H | 4-F—$C_6H_5$ | $OCF_2CF_3$ | H |
| 20 | 240N | $CF_3$ | H | NH | H | 4-Br—$C_6H_5$ | $OCF_2CF_3$ | H |
| 20 | 241N | $CF_3$ | H | NH | 4-Br—$C_6H_5O$ | H | $OCF_2CF_3$ | H |
| 20 | 242N | $CF_3$ | H | NH | $C_6H_5O$ | H | $OCCl_2CCl_2H$ | H |
| 20 | 243N | $CF_3$ | H | NH | 4-Cl—$C_6H_5O$ | H | $OCCl_2CCl_2H$ | H |
| 20 | 244N | $CF_3$ | H | NH | 4-F—$C_6H_5O$ | H | $OCCl_2CCl_2H$ | H |
| 20 | 245N | $CF_3$ | H | NH | 3,4-Cl—$C_6H_5O$ | H | $OCCl_2CCl_2H$ | H |
| 20 | 246N | $CF_3$ | H | NH | H | $C_6H_5$ | $OCCl_2CCl_2H$ | H |
| 20 | 247N | $CF_3$ | H | NH | H | 4-Cl—$C_6H_5$ | $OCCl_2CCl_2H$ | H |
| 20 | 248N | $CF_3$ | H | NH | H | 4-F—$C_6H_5$ | $OCCl_2CCl_2H$ | H |
| 20 | 249N | $CF_3$ | H | NH | H | 4-Br—$C_6H_5$ | $OCCl_2CCl_2H$ | H |
| 20 | 250N | $CF_3$ | H | NH | 4-Br—$C_6H_5O$ | H | $OCCl_2CCl_2H$ | H |
| 20 | 251N | $CF_3$ | H | NH | $C_6H_5O$ | H | $OCCl_2CCl_3$ | H |
| 20 | 252N | $CF_3$ | H | NH | 4-Cl—$C_6H_5O$ | H | $OCCl_2CCl_3$ | H |
| 20 | 253N | $CF_3$ | H | NH | 4-F—$C_6H_5O$ | H | $OCCl_2CCl_3$ | H |
| 20 | 254N | $CF_3$ | H | NH | 3,4-Cl—$C_6H_5O$ | H | $OCCl_2CCl_3$ | H |
| 20 | 255N | $CF_3$ | H | NH | H | $C_6H_5$ | $OCCl_2CCl_3$ | H |
| 20 | 256N | $CF_3$ | H | NH | H | 4-Cl—$C_6H_5$ | $OCCl_2CCl_3$ | H |
| 20 | 257N | $CF_3$ | H | NH | H | 4-F—$C_6H_5$ | $OCCl_2CCl_3$ | H |
| 20 | 258N | $CF_3$ | H | NH | H | 4-Br—$C_6H_5$ | $OCCl_2CCl_3$ | H |
| 20 | 259N | $CF_3$ | H | NH | 4-Br—$C_6H_5O$ | H | $OCCl_2CCl_3$ | H |
| 20 | 260N | $CF_3$ | H | NH | $C_6H_5O$ | H | $OCCl_2CF_3$ | H |
| 20 | 261N | $CF_3$ | H | NH | 4-Cl—$C_6H_5O$ | H | $OCCl_2CF_3$ | H |
| 20 | 262N | $CF_3$ | H | NH | 4-F—$C_6H_5O$ | H | $OCCl_2CF_3$ | H |
| 20 | 263N | $CF_3$ | H | NH | 3,4-Cl—$C_6H_5O$ | H | $OCCl_2CF_3$ | H |
| 20 | 264N | $CF_3$ | H | NH | H | $C_6H_5$ | $OCCl_2CF_3$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

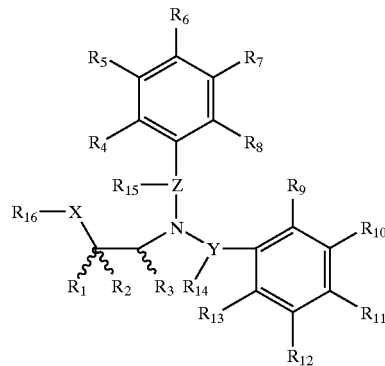

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 20 | 265N | $CF_3$ | H | NH | H | 4-Cl—$C_6H_5$ | $OCCl_2CF_3$ | H |
| 20 | 266N | $CF_3$ | H | NH | H | 4-F—$C_6H_5$ | $OCCl_2CF_3$ | H |
| 20 | 267N | $CF_3$ | H | NH | H | 4-Br—$C_6H_5$ | $OCCl_2CF_3$ | H |
| 20 | 268N | $CF_3$ | H | NH | 4-Br—$C_6H_5O$ | H | $OCCl_2CF_3$ | H |
| 20 | 269N | $CF_3$ | H | NH | $C_6H_5O$ | H | $OCF_2CCl_3$ | H |
| 20 | 270N | $CF_3$ | H | NH | 4-Cl—$C_6H_5O$ | H | $OCF_2CCl_3$ | H |
| 20 | 271N | $CF_3$ | H | NH | 4-F—$C_6H_5O$ | H | $OCF_2CCl_3$ | H |
| 20 | 272N | $CF_3$ | H | NH | 3,4-Cl—$C_6H_5O$ | H | $OCF_2CCl_3$ | H |
| 20 | 273N | $CF_3$ | H | NH | H | $C_6H_5$ | $OCF_2CCl_3$ | H |
| 20 | 274N | $CF_3$ | H | NH | H | 4-Cl—$C_6H_5$ | $OCF_2CCl_3$ | H |
| 20 | 275N | $CF_3$ | H | NH | H | 4-F—$C_6H_5$ | $OCF_2CCl_3$ | H |
| 20 | 276N | $CF_3$ | H | NH | H | 4-Br—$C_6H_5$ | $OCF_2CCl_3$ | H |
| 20 | 277N | $CF_3$ | H | NH | 4-Br—$C_6H_5O$ | H | $OCF_2CCl_3$ | H |
| 20 | 278N | $CF_3$ | H | NH | $C_6H_5O$ | H | $OCF_2CF_2H$ | $OCF_2CF_2H$ |
| 20 | 279N | $CF_3$ | H | NH | 4-Cl—$C_6H_5O$ | H | $OCF_2CF_2H$ | $OCF_2CF_2H$ |
| 20 | 280N | $CF_3$ | H | NH | 4-F—$C_6H_5O$ | H | $OCF_2CF_2H$ | $OCF_2CF_2H$ |
| 20 | 281N | $CF_3$ | H | NH | 3,4-Cl—$C_6H_5O$ | H | $OCF_2CF_2H$ | $OCF_2CF_2H$ |
| 20 | 282N | $CF_3$ | H | NH | H | $C_6H_5$ | $OCF_2CF_2H$ | $OCF_2CF_2H$ |
| 20 | 283N | $CF_3$ | H | NH | H | 4-Cl—$C_6H_5$ | $OCF_2CF_2H$ | $OCF_2CF_2H$ |
| 20 | 284N | $CF_3$ | H | NH | H | 4-F—$C_6H_5$ | $OCF_2CF_2H$ | $OCF_2CF_2H$ |
| 20 | 285N | $CF_3$ | H | NH | H | 4-Br—$C_6H_5$ | $OCF_2CF_2H$ | $OCF_2CF_2H$ |
| 20 | 286N | $CF_3$ | H | NH | 4-Br—$C_6H_5O$ | H | $OCF_2CF_2H$ | $OCF_2CF_2H$ |
| 20 | 287N | $CF_3$ | H | NH | $C_6H_5O$ | H | $OCF_3$ | $OCF_3$ |
| 20 | 288N | $CF_3$ | H | NH | 4-Cl—$C_6H_5O$ | H | $OCF_3$ | $OCF_3$ |
| 20 | 289N | $CF_3$ | H | NH | 4-F—$C_6H_5O$ | H | $OCF_3$ | $OCF_3$ |
| 20 | 290N | $CF_3$ | H | NH | 3,4-Cl—$C_6H_5O$ | H | $OCF_3$ | $OCF_3$ |
| 20 | 291N | $CF_3$ | H | NH | H | $C_6H_5$ | $OCF_3$ | $OCF_3$ |
| 20 | 292N | $CF_3$ | H | NH | H | 4-Cl—$C_6H_5$ | $OCF_3$ | $OCF_3$ |
| 20 | 293N | $CF_3$ | H | NH | H | 4-F—$C_6H_5$ | $OCF_3$ | $OCF_3$ |
| 20 | 294N | $CF_3$ | H | NH | H | 4-Br—$C_6H_5$ | $OCF_3$ | $OCF_3$ |
| 20 | 295N | $CF_3$ | H | NH | 4-Br—$C_6H_5O$ | H | $OCF_3$ | $OCF_3$ |
| 20 | 296N | $CF_3$ | H | NH | $C_6H_5O$ | H | $OCF_2H$ | $OCF_2H$ |
| 20 | 297N | $CF_3$ | H | NH | 4-Cl—$C_6H_5O$ | H | $OCF_2H$ | $OCF_2H$ |
| 20 | 298N | $CF_3$ | H | NH | 4-F—$C_6H_5O$ | H | $OCF_2H$ | $OCF_2H$ |
| 20 | 299N | $CF_3$ | H | NH | 3,4-Cl—$C_6H_5O$ | H | $OCF_2H$ | $OCF_2H$ |
| 20 | 300N | $CF_3$ | H | NH | H | $C_6H_5$ | $OCF_2H$ | $OCF_2H$ |
| 20 | 301N | $CF_3$ | H | NH | H | 4-Cl—$C_6H_5$ | $OCF_2H$ | $OCF_2H$ |
| 20 | 302N | $CF_3$ | H | NH | H | 4-F—$C_6H_5$ | $OCF_2H$ | $OCF_2H$ |
| 20 | 303N | $CF_3$ | H | NH | H | 4-Br—$C_6H_5$ | $OCF_2H$ | $OCF_2H$ |
| 20 | 304N | $CF_3$ | H | NH | 4-Br—$C_6H_5O$ | H | $OCF_2H$ | $OCF_2H$ |
| 20 | 305N | $CF_3$ | H | NH | $C_6H_5O$ | H | $R_{10} + R_{11} = OCF_2CF_2O$ | |
| 20 | 306N | $CF_3$ | H | NH | 4-Cl—$C_6H_5O$ | H | $R_{10} + R_{11} = OCF_2CF_2O$ | |
| 20 | 307N | $CF_3$ | H | NH | 4-F—$C_6H_5O$ | H | $R_{10} + R_{11} = OCF_2CF_2O$ | |
| 20 | 308N | $CF_3$ | H | NH | 3,4-Cl—$C_6H_5O$ | H | $R_{10} + R_{11} = OCF_2CF_2O$ | |
| 20 | 309N | $CF_3$ | H | NH | H | $C_6H_5$ | $R_{10} + R_{11} = OCF_2CF_2O$ | |
| 20 | 310N | $CF_3$ | H | NH | H | 4-Cl—$C_6H_5$ | $R_{10} + R_{11} = OCF_2CF_2O$ | |
| 20 | 311N | $CF_3$ | H | NH | H | 4-F—$C_6H_5$ | $R_{10} + R_{11} = OCF_2CF_2O$ | |
| 20 | 312N | $CF_3$ | H | NH | H | 4-Br—$C_6H_5$ | $R_{10} + R_{11} = OCF_2CF_2O$ | |
| 20 | 313N | $CF_3$ | H | NH | 4-Br—$C_6H_5O$ | H | $R_{10} + R_{11} = OCF_2CF_2O$ | |
| 20 | 314N | $CF_3$ | H | NH | $C_6H_5O$ | H | $R_{10} + R_{11} = OCCl_2CCl_2O$ | |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

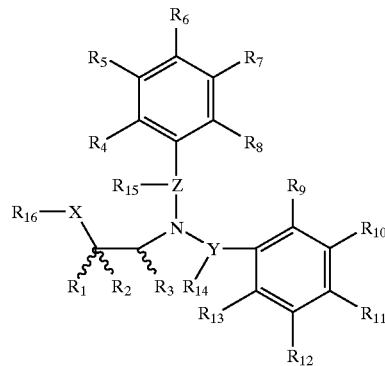

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 20 | 315N | $CF_3$ | H | NH | 4-Cl—$C_6H_5$O | H | $R_{10} + R_{11}$ = $OCCl_2CCl_2O$ | |
| 20 | 316N | $CF_3$ | H | NH | 4-F—$C_6H_5$O | H | $R_{10} + R_{11}$ = $OCCl_2CCl_2O$ | |
| 20 | 317N | $CF_3$ | H | NH | 3,4-Cl—$C_6H_5$O | H | $R_{10} + R_{11}$ = $OCCl_2CCl_2O$ | |
| 20 | 318N | $CF_3$ | H | NH | H | $C_6H_5$ | $R_{10} + R_{11}$ = $OCCl_2CCl_2O$ | |
| 20 | 319N | $CF_3$ | H | NH | H | 4-Cl—$C_6H_5$ | $R_{10} + R_{11}$ = $OCCl_2CCl_2O$ | |
| 20 | 320N | $CF_3$ | H | NH | H | 4-F—$C_6H_5$ | $R_{10} + R_{11}$ = $OCCl_2CCl_2O$ | |
| 20 | 321N | $CF_3$ | H | NH | H | 4-Br—$C_6H_5$ | $R_{10} + R_{11}$ = $OCCl_2CCl_2O$ | |
| 20 | 322N | $CF_3$ | H | NH | 4-Br—$C_6H_5$O | H | $R_{10} + R_{11}$ = $OCCl_2CCl_2O$ | |
| 20 | 323N | $CF_3$ | H | NH | H | H | OH | H |
| 20 | 324N | $CF_3$ | H | NH | H | H | OH | OH |
| 20 | 325N | $CF_3$ | H | NH | H | H | H | OH |
| 20 | 326N | $CF_3$ | H | NH | H | H | $OCH_2CF_3$ | H |
| 20 | 327N | $CF_3$ | H | NH | H | H | H | $OCH_2CF_3$ |
| 20 | 328N | $CF_3$ | H | NH | H | H | $OCH_2CF_2CF_3$ | H |
| 20 | 329N | $CF_3$ | H | NH | H | H | $OCH_2CH_2CF_3$ | H |
| 20 | 330N | $CF_3$ | H | NH | H | H | $OCH(CF_3)_3$ | H |
| 20 | 331N | $CF_3$ | H | NH | H | 4-F—$C_6H_5$O | H | H |
| 20 | 332N | $CF_3$ | H | NH | 4-F—$C_6H_5$O | H | H | H |
| 20 | 333N | $CF_3$ | H | NH | H | cyclo-hexoxy | H | H |
| 20 | 334N | $CF_3$ | H | NH | cyclo-hexoxy | H | H | H |
| 20 | 335N | $CF_3$ | H | NH | H | $CH(CH_3)_3$ | H | H |
| 20 | 336N | $CF_3$ | H | NH | F | H | 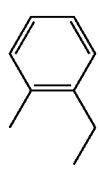 | bond to indicated phenyl carbon of $R_{10}$ substituent |
| 25 | 224N | $CF_3$ | H | S | $C_6H_5$O | H | $OCF_2CF_2H$ | H |
| 25 | 225N | $CF_3$ | H | S | 4-Cl—$C_6H_5$O | H | $OCF_2CF_2H$ | H |
| 25 | 226N | $CF_3$ | H | S | 4-F—$C_6H_5$O | H | $OCF_2CF_2H$ | H |
| 25 | 227N | $CF_3$ | H | S | 3,4-Cl—$C_6H_5$O | H | $OCF_2CF_2H$ | H |
| 25 | 228N | $CF_3$ | H | S | H | $C_6H_5$ | $OCF_2CF_2H$ | H |
| 25 | 229N | $CF_3$ | H | S | H | 4-Cl—$C_6H_5$ | $OCF_2CF_2H$ | H |
| 25 | 230N | $CF_3$ | H | S | H | 4-F—$C_6H_5$ | $OCF_2CF_2H$ | H |
| 25 | 231N | $CF_3$ | H | S | H | 4-Br—$C_6H_5$ | $OCF_2CF_2H$ | H |
| 25 | 232N | $CF_3$ | H | S | 4-Br—$C_6H_5$O | H | $OCF_2CF_2H$ | H |
| 25 | 233N | $CF_3$ | H | S | $C_6H_5$O | H | $OCF_2CF_3$ | H |
| 25 | 234N | $CF_3$ | H | S | 4-Cl—$C_6H_5$O | H | $OCF_2CF_3$ | H |
| 25 | 235N | $CF_3$ | H | S | 4-F—$C_6H_5$O | H | $OCF_2CF_3$ | H |
| 25 | 236N | $CF_3$ | H | S | 3,4-Cl—$C_6H_5$O | H | $OCF_2CF_3$ | H |
| 25 | 237N | $CF_3$ | H | S | H | $C_6H_5$ | $OCF_2CF_3$ | H |
| 25 | 238N | $CF_3$ | H | S | H | 4-Cl—$C_6H_5$ | $OCF_2CF_3$ | H |
| 25 | 239N | $CF_3$ | H | S | H | 4-F—$C_6H_5$ | $OCF_2CF_3$ | H |
| 25 | 240N | $CF_3$ | H | S | H | 4-Br—$C_6H_5$ | $OCF_2CF_3$ | H |
| 25 | 241N | $CF_3$ | H | S | 4-Br—$C_6H_5$O | H | $OCF_2CF_3$ | H |
| 25 | 242N | $CF_3$ | H | S | $C_6H_5$O | H | $OCCl_2CCl_2H$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

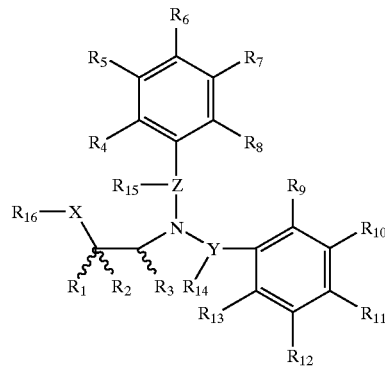

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 25 | 243N | $CF_3$ | H | S | 4-Cl—$C_6H_5O$ | H | $OCCl_2CCl_2H$ | H |
| 25 | 244N | $CF_3$ | H | S | 4-F—$C_6H_5O$ | H | $OCCl_2CCl_2H$ | H |
| 25 | 245N | $CF_3$ | H | S | 3,4-Cl—$C_6H_5O$ | H | $OCCl_2CCl_2H$ | H |
| 25 | 246N | $CF_3$ | H | S | H | $C_6H_5$ | $OCCl_2CCl_2H$ | H |
| 25 | 247N | $CF_3$ | H | s | H | 4-Cl—$C_6H_5$ | $OCCl_2CCl_2H$ | H |
| 25 | 248N | $CF_3$ | H | S | H | 4-F—$C_6H_5$ | $OCCl_2CCl_2H$ | H |
| 25 | 249N | $CF_3$ | H | S | H | 4-Br—$C_6H_5$ | $OCCl_2CCl_2H$ | H |
| 25 | 250N | $CF_3$ | H | S | 4-Br—$C_6H_5O$ | H | $OCCl_2CCl_2H$ | H |
| 25 | 251N | $CF_3$ | H | S | $C_6H_5O$ | H | $OCCl_2CCl_3$ | H |
| 25 | 252N | $CF_3$ | H | S | 4-Cl—$C_6H_5O$ | H | $OCCl_2CCl_3$ | H |
| 25 | 253N | $CF_3$ | H | S | 4-F—$C_6H_5O$ | H | $OCCl_2CCl_3$ | H |
| 25 | 254N | $CF_3$ | H | S | 3,4-Cl—$C_6H_5O$ | H | $OCCl_2CCl_3$ | H |
| 25 | 255N | $CF_3$ | H | S | H | $C_6H_5$ | $OCCl_2CCl_3$ | H |
| 25 | 256N | $CF_3$ | H | S | H | 4-Cl—$C_6H_5$ | $OCCl_2CCl_3$ | H |
| 25 | 257N | $CF_3$ | H | S | H | 4-F—$C_6H_5$ | $OCCl_2CCl_3$ | H |
| 25 | 258N | $CF_3$ | H | S | H | 4-Br—$C_6H_5$ | $OCCl_2CCl_3$ | H |
| 25 | 259N | $CF_3$ | H | S | 4-Br—$C_6H_5O$ | H | $OCCl_2CCl_3$ | H |
| 25 | 260N | $CF_3$ | H | S | $C_6H_5O$ | H | $OCCl_2CF_3$ | H |
| 25 | 261N | $CF_3$ | H | S | 4-Cl—$C_6H_5O$ | H | $OCCl_2CF_3$ | H |
| 25 | 262N | $CF_3$ | H | S | 4-F—$C_6H_5O$ | H | $OCCl_2CF_3$ | H |
| 25 | 263N | $CF_3$ | H | S | 3,4-Cl—$C_6H_5O$ | H | $OCCl_2CF_3$ | H |
| 25 | 264N | $CF_3$ | H | S | H | $C_6H_5$ | $OCCl_2CF_3$ | H |
| 25 | 265N | $CF_3$ | H | S | H | 4-Cl—$C_6H_5$ | $OCCl_2CF_3$ | H |
| 25 | 266N | $CF_3$ | H | S | H | 4-F—$C_6H_5$ | $OCCl_2CF_3$ | H |
| 25 | 267N | $CF_3$ | H | S | H | 4-Br—$C_6H_5$ | $OCCl_2CF_3$ | H |
| 25 | 268N | $CF_3$ | H | S | 4-Br—$C_6H_5O$ | H | $OCCl_2CF_3$ | H |
| 25 | 269N | $CF_3$ | H | S | $C_6H_5O$ | H | $OCF_2CCl_3$ | H |
| 25 | 270N | $CF_3$ | H | S | 4-Cl—$C_6H_5O$ | H | $OCF_2CCl_3$ | H |
| 25 | 271N | $CF_3$ | H | S | 4-F—$C_6H_5O$ | H | $OCF_2CCl_3$ | H |
| 25 | 272N | $CF_3$ | H | S | 3,4-Cl—$C_6H_5O$ | H | $OCF_2CCl_3$ | H |
| 25 | 273N | $CF_3$ | H | S | H | $C_6H_5$ | $OCF_2CCl_3$ | H |
| 25 | 274N | $CF_3$ | H | S | H | 4-Cl—$C_6H_5$ | $OCF_2CCl_3$ | H |
| 25 | 275N | $CF_3$ | H | S | H | 4-F—$C_6H_5$ | $OCF_2CCl_3$ | H |
| 25 | 276N | $CF_3$ | H | S | H | 4-Br—$C_6H_5$ | $OCF_2CCl_3$ | H |
| 25 | 277N | $CF_3$ | H | S | 4-Br—$C_6H_5O$ | H | $OCF_2CCl_3$ | H |
| 25 | 278N | $CF_3$ | H | S | $C_6H_5O$ | H | $OCF_2CF_2H$ | $OCF_2CF_2H$ |
| 25 | 279N | $CF_3$ | H | S | 4-Cl—$C_6H_5O$ | H | $OCF_2CF_2H$ | $OCF_2CF_2H$ |
| 25 | 280N | $CF_3$ | H | S | 4-F—$C_6H_5O$ | H | $OCF_2CF_2H$ | $OCF_2CF_2H$ |
| 25 | 281N | $CF_3$ | H | S | 3,4-Cl—$C_6H_5O$ | H | $OCF_2CF_2H$ | $OCF_2CF_2H$ |
| 25 | 282N | $CF_3$ | H | S | H | $C_6H_5$ | $OCF_2CF_2H$ | $OCF_2CF_2H$ |
| 25 | 283N | $CF_3$ | H | S | H | 4-Cl—$C_6H_5$ | $OCF_2CF_2H$ | $OCF_2CF_2H$ |
| 25 | 284N | $CF_3$ | H | S | H | 4-F—$C_6H_5$ | $OCF_2CF_2H$ | $OCF_2CF_2H$ |
| 25 | 285N | $CF_3$ | H | S | H | 4-Br—$C_6H_5$ | $OCF_2CF_2H$ | $OCF_2CF_2H$ |
| 25 | 286N | $CF_3$ | H | S | 4-Br—$C_6H_5O$ | H | $OCF_2CF_2H$ | $OCF_2CF_2H$ |
| 25 | 287N | $CF_3$ | H | S | $C_6H_5O$ | H | $OCF_3$ | $OCF_3$ |
| 25 | 288N | $CF_3$ | H | S | 4-Cl—$C_6H_5O$ | H | $OCF_3$ | $OCF_3$ |
| 25 | 289N | $CF_3$ | H | S | 4-F—$C_6H_5O$ | H | $OCF_3$ | $OCF_3$ |
| 25 | 290N | $CF_3$ | H | S | 3,4-Cl—$C_6H_5O$ | H | $OCF_3$ | $OCF_3$ |
| 25 | 291N | $CF_3$ | H | S | H | $C_6H_5$ | $OCF_3$ | $OCF_3$ |
| 25 | 292N | $CF_3$ | H | S | H | 4-Cl—$C_6H_5$ | $OCF_3$ | $OCF_3$ |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

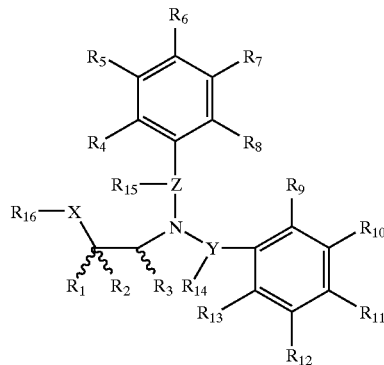

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 25 | 293N | $CF_3$ | H | S | H | 4-F—$C_6H_5$ | $OCF_3$ | $OCF_3$ |
| 25 | 294N | $CF_3$ | H | S | H | 4-Br—$C_6H_5$ | $OCF_3$ | $OCF_3$ |
| 25 | 295N | $CF_3$ | H | S | 4-Br—$C_6H_5O$ | H | $OCF_3$ | $OCF_3$ |
| 25 | 296N | $CF_3$ | H | S | $C_6H_5O$ | H | $OCF_2H$ | $OCF_2H$ |
| 25 | 297N | $CF_3$ | H | S | 4-Cl—$C_6H_5O$ | H | $OCF_2H$ | $OCF_2H$ |
| 25 | 298N | $CF_3$ | H | S | 4-F—$C_6H_5O$ | H | $OCF_2H$ | $OCF_2H$ |
| 25 | 299N | $CF_3$ | H | S | 3,4-Cl—$C_6H_5O$ | H | $OCF_2H$ | $OCF_2H$ |
| 25 | 300N | $CF_3$ | H | S | H | $C_6H_5$ | $OCF_2H$ | $OCF_2H$ |
| 25 | 301N | $CF_3$ | H | S | H | 4-Cl—$C_6H_5$ | $OCF_2H$ | $OCF_2H$ |
| 25 | 302N | $CF_3$ | H | S | H | 4-F—$C_6H_5$ | $OCF_2H$ | $OCF_2H$ |
| 25 | 303N | $CF_3$ | H | S | H | 4-Br—$C_6H_5$ | $OCF_2H$ | $OCF_2H$ |
| 25 | 304N | $CF_3$ | H | S | 4-Br—$C_6H_5O$ | H | $OCF_2H$ | $OCF_2H$ |
| 25 | 305N | $CF_3$ | H | S | $C_6H_5O$ | H | $R_{10} + R_{11} = OCF_2CF_2O$ | |
| 25 | 306N | $CF_3$ | H | S | 4-Cl—$C_6H_5O$ | H | $R_{10} + R_{11} = OCF_2CF_2O$ | |
| 25 | 307N | $CF_3$ | H | S | 4-F—$C_6H_5O$ | H | $R_{10} + R_{11} = OCF_2CF_2O$ | |
| 25 | 308N | $CF_3$ | H | S | 3,4-Cl—$C_6H_5O$ | H | $R_{10} + R_{11} = OCF_2CF_2O$ | |
| 25 | 309N | $CF_3$ | H | S | H | $C_6H_5$ | $R_{10} + R_{11} = OCF_2CF_2O$ | |
| 25 | 310N | $CF_3$ | H | S | H | 4-Cl—$C_6H_5$ | $R_{10} + R_{11} = OCF_2CF_2O$ | |
| 25 | 311N | $CF_3$ | H | S | H | 4-F—$C_6H_5$ | $R_{10} + R_{11} = OCF_2CF_2O$ | |
| 25 | 312N | $CF_3$ | H | S | H | 4-Br—$C_6H_5$ | $R_{10} + R_{11} = OCF_2CF_2O$ | |
| 25 | 313N | $CF_3$ | H | S | 4-Br—$C_6H_5O$ | H | $R_{10} + R_{11} = OCF_2CF_2O$ | |
| 25 | 314N | $CF_3$ | H | S | $C_6H_5O$ | H | $R_{10} + R_{11} = OCCl_2CCl_2O$ | |
| 25 | 315N | $CF_3$ | H | S | 4-Cl—$C_6H_5O$ | H | $R_{10} + R_{11} = OCCl_2CCl_2O$ | |
| 25 | 316N | $CF_3$ | H | S | 4-F—$C_6H_5O$ | H | $R_{10} + R_{11} = OCCl_2CCl_2O$ | |
| 25 | 317N | $CF_3$ | H | S | 3,4-Cl—$C_6H_5O$ | H | $R_{10} + R_{11} = OCCl_2CCl_2O$ | |
| 25 | 318N | $CF_3$ | H | S | H | $C_6H_5$ | $R_{10} + R_{11} = OCCl_2CCl_2O$ | |
| 25 | 319N | $CF_3$ | H | S | H | 4-Cl—$C_6H_5$ | $R_{10} + R_{11} = OCCl_2CCl_2O$ | |
| 25 | 320N | $CF_3$ | H | S | H | 4-F—$C_6H_5$ | $R_{10} + R_{11} = OCCl_2CCl_2O$ | |
| 25 | 321N | $CF_3$ | H | S | H | 4-Br—$C_6H_5$ | $R_{10} + R_{11} = OCCl_2CCl_2O$ | |
| 25 | 322N | $CF_3$ | H | S | 4-Br—$C_6H_5O$ | H | $R_{10} + R_{11} = OCCl_2CCl_2O$ | |
| 25 | 323N | $CF_3$ | H | S | H | H | OH | H |
| 25 | 324N | $CF_3$ | H | S | H | H | OH | OH |
| 25 | 325N | $CF_3$ | H | S | H | H | H | OH |
| 25 | 326N | $CF_3$ | H | S | H | H | $OCH_2CF_3$ | H |
| 25 | 327N | $CF_3$ | H | S | H | H | H | $OCH_2CF_3$ |
| 25 | 328N | $CF_3$ | H | S | H | H | $OCH_2CF_2CF_3$ | H |
| 25 | 329N | $CF_3$ | H | S | H | H | $OCH_2CH_2CF_3$ | H |
| 25 | 330N | $CF_3$ | H | S | H | H | $OCH(CF_3)_3$ | H |
| 25 | 331N | $CF_3$ | H | S | H | 4-F—$C_6H_5O$ | H | H |
| 25 | 332N | $CF_3$ | H | S | 4-F—$C_6H_5O$ | H | H | H |
| 25 | 333N | $CF_3$ | H | S | H | cyclo-hexoxy | H | H |
| 25 | 334N | $CF_3$ | H | S | cyclo-hexoxy | H | H | H |
| 25 | 335N | $CF_3$ | H | S | H | $CH(CH_3)_3$ | H | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

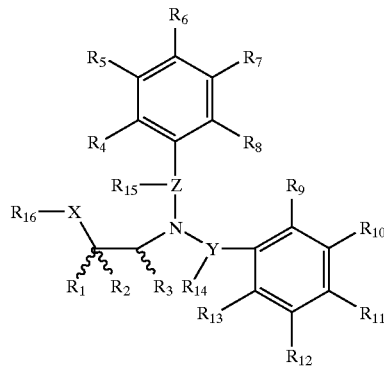

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 25 | 336N | $CF_3$ | H | S | F | H | (2-ethylphenyl) | bond to indicated phenyl carbon of $R_{10}$ substituent |
| 26 | 224N | $CF_3CF_2$ | H | S | $C_6H_5O$ | H | $OCF_2CF_2H$ | H |
| 26 | 225N | $CF_3CF_2$ | H | S | 4-Cl—$C_6H_5O$ | H | $OCF_2CF_2H$ | H |
| 26 | 226N | $CF_3CF_2$ | H | S | 4-F—$C_6H_5O$ | H | $OCF_2CF_2H$ | H |
| 26 | 227N | $CF_3CF_2$ | H | S | 3,4-Cl—$C_6H_5O$ | H | $OCF_2CF_2H$ | H |
| 26 | 228N | $CF_3CF_2$ | H | S | H | $C_6H_5$ | $OCF_2CF_2H$ | H |
| 26 | 229N | $CF_3CF_2$ | H | S | H | 4-Cl—$C_6H_5$ | $OCF_2CF_2H$ | H |
| 26 | 230N | $CF_3CF_2$ | H | S | H | 4-F—$C_6H_5$ | $OCF_2CF_2H$ | H |
| 26 | 231N | $CF_3CF_2$ | H | S | H | 4-Br—$C_6H_5$ | $OCF_2CF_2H$ | H |
| 26 | 232N | $CF_3CF_2$ | H | S | 4-Br—$C_6H_5O$ | H | $OCF_2CF_2H$ | H |
| 26 | 233N | $CF_3CF_2$ | H | S | $C_6H_5O$ | H | $OCF_2CF_3$ | H |
| 26 | 234N | $CF_3CF_2$ | H | S | 4-Cl—$C_6H_5O$ | H | $OCF_2CF_3$ | H |
| 26 | 235N | $CF_3CF_2$ | H | S | 4-F—$C_6H_5O$ | H | $OCF_2CF_3$ | H |
| 26 | 236N | $CF_3CF_2$ | H | S | 3,4-Cl—$C_6H_5O$ | H | $OCF_2CF_3$ | H |
| 26 | 237N | $CF_3CF_2$ | H | S | H | $C_6H_5$ | $OCF_2CF_3$ | H |
| 26 | 238N | $CF_3CF_2$ | H | S | H | 4-Cl—$C_6H_5$ | $OCF_2CF_3$ | H |
| 26 | 239N | $CF_3CF_2$ | H | S | H | 4-F—$C_6H_5$ | $OCF_2CF_3$ | H |
| 26 | 240N | $CF_3CF_2$ | H | S | H | 4-Br—$C_6H_5$ | $OCF_2CF_3$ | H |
| 26 | 241N | $CF_3CF_2$ | H | S | 4-Br—$C_6H_5O$ | H | $OCF_2CF_3$ | H |
| 26 | 242N | $CF_3CF_2$ | H | S | $C_6H_5O$ | H | $OCCl_2CCl_2H$ | H |
| 26 | 243N | $CF_3CF_2$ | H | S | 4-Cl—$C_6H_5O$ | H | $OCCl_2CCl_2H$ | H |
| 26 | 244N | $CF_3CF_2$ | H | S | 4-F—$C_6H_5O$ | H | $OCCl_2CCl_2H$ | H |
| 26 | 245N | $CF_3CF_2$ | H | S | 3,4-Cl—$C_6H_5O$ | H | $OCCl_2CCl_2H$ | H |
| 26 | 246N | $CF_3CF_2$ | H | S | H | $C_6H_5$ | $OCCl_2CCl_2H$ | H |
| 26 | 247N | $CF_3CF_2$ | H | S | H | 4-Cl—$C_6H_5$ | $OCCl_2CCl_2H$ | H |
| 26 | 248N | $CF_3CF_2$ | H | S | H | 4-F—$C_6H_5$ | $OCCl_2CCl_2H$ | H |
| 26 | 249N | $CF_3CF_2$ | H | S | H | 4-Br—$C_6H_5$ | $OCCl_2CCl_2H$ | H |
| 26 | 250N | $CF_3CF_2$ | H | S | 4-Br—$C_6H_5O$ | H | $OCCl_2CCl_2H$ | H |
| 26 | 251N | $CF_3CF_2$ | H | S | $C_6H_5O$ | H | $OCCl_2CCl_3$ | H |
| 26 | 252N | $CF_3CF_2$ | H | S | 4-Cl—$C_6H_5O$ | H | $OCCl_2CCl_3$ | H |
| 26 | 253N | $CF_3CF_2$ | H | S | 4-F—$C_6H_5O$ | H | $OCCl_2CCl_3$ | H |
| 26 | 254N | $CF_3CF_2$ | H | S | 3,4-Cl—$C_6H_5O$ | H | $OCCl_2CCl_3$ | H |
| 26 | 255N | $CF_3CF_2$ | H | S | H | $C_6H_5$ | $OCCl_2CCl_3$ | H |
| 26 | 256N | $CF_3CF_2$ | H | S | H | 4-Cl—$C_6H_5$ | $OCCl_2CCl_3$ | H |
| 26 | 257N | $CF_3CF_2$ | H | S | H | 4-F—$C_6H_5$ | $OCCl_2CCl_3$ | H |
| 26 | 258N | $CF_3CF_2$ | H | S | H | 4-Br—$C_6H_5$ | $OCCl_2CCl_3$ | H |
| 26 | 259N | $CF_3CF_2$ | H | S | 4-Br—$C_6H_5O$ | H | $OCCl_2CCl_3$ | H |
| 26 | 260N | $CF_3CF_2$ | H | S | $C_6H_5O$ | H | $OCCl_2CF_3$ | H |
| 26 | 261N | $CF_3CF_2$ | H | S | 4-Cl—$C_6H_5O$ | H | $OCCl_2CF_3$ | H |
| 26 | 262N | $CF_3CF_2$ | H | S | 4-F—$C_6H_5O$ | H | $OCCl_2CF_3$ | H |
| 26 | 263N | $CF_3CF_2$ | H | S | 3,4-Cl—$C_6H_5O$ | H | $OCCl_2CF_3$ | H |
| 26 | 264N | $CF_3CF_2$ | H | S | H | $C_6H_5$ | $OCCl_2CF_3$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

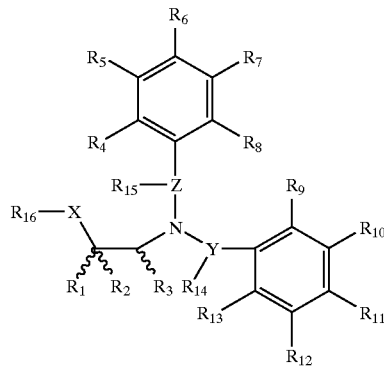

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 26 | 265N | $CF_3CF_2$ | H | S | H | 4-Cl—$C_6H_5$ | $OCCl_2CF_3$ | H |
| 26 | 266N | $CF_3CF_2$ | H | S | H | 4-F—$C_6H_5$ | $OCCl_2CF_3$ | H |
| 26 | 267N | $CF_3CF_2$ | H | S | H | 4-Br—$C_6H_5$ | $OCCl_2CF_3$ | H |
| 26 | 268N | $CF_3CF_2$ | H | S | 4-Br—$C_6H_5O$ | H | $OCCl_2CF_3$ | H |
| 26 | 269N | $CF_3CF_2$ | H | S | $C_6H_5O$ | H | $OCF_2CCl_3$ | H |
| 26 | 270N | $CF_3CF_2$ | H | S | 4-Cl—$C_6H_5O$ | H | $OCF_2CCl_3$ | H |
| 26 | 271N | $CF_3CF_2$ | H | S | 4-F—$C_6H_5O$ | H | $OCF_2CCl_3$ | H |
| 26 | 272N | $CF_3CF_2$ | H | S | 3,4-Cl—$C_6H_5O$ | H | $OCF_2CCl_3$ | H |
| 26 | 273N | $CF_3CF_2$ | H | S | H | $C_6H_5$ | $OCF_2CCl_3$ | H |
| 26 | 274N | $CF_3CF_2$ | H | S | H | 4-Cl—$C_6H_5$ | $OCF_2CCl_3$ | H |
| 26 | 275N | $CF_3CF_2$ | H | S | H | 4-F—$C_6H_5$ | $OCF_2CCl_3$ | H |
| 26 | 276N | $CF_3CF_2$ | H | S | H | 4-Br—$C_6H_5$ | $OCF_2CCl_3$ | H |
| 26 | 277N | $CF_3CF_2$ | H | S | 4-Br—$C_6H_5O$ | H | $OCF_2CCl_3$ | H |
| 26 | 278N | $CF_3CF_2$ | H | S | $C_6H_5O$ | H | $OCF_2CF_2H$ | $OCF_2CF_2H$ |
| 26 | 279N | $CF_3CF_2$ | H | S | 4-Cl—$C_6H_5O$ | H | $OCF_2CF_2H$ | $OCF_2CF_2H$ |
| 26 | 280N | $CF_3CF_2$ | H | S | 4-F—$C_6H_5O$ | H | $OCF_2CF_2H$ | $OCF_2CF_2H$ |
| 26 | 281N | $CF_3CF_2$ | H | S | 3,4-Cl—$C_6H_5O$ | H | $OCF_2CF_2H$ | $OCF_2CF_2H$ |
| 26 | 282N | $CF_3CF_2$ | H | S | H | $C_6H_5$ | $OCF_2CF_2H$ | $OCF_2CF_2H$ |
| 26 | 283N | $CF_3CF_2$ | H | S | H | 4-Cl—$C_6H_5$ | $OCF_2CF_2H$ | $OCF_2CF_2H$ |
| 26 | 284N | $CF_3CF_2$ | H | S | H | 4-F—$C_6H_5$ | $OCF_2CF_2H$ | $OCF_2CF_2H$ |
| 26 | 285N | $CF_3CF_2$ | H | S | H | 4-Br—$C_6H_5$ | $OCF_2CF_2H$ | $OCF_2CF_2H$ |
| 26 | 286N | $CF_3CF_2$ | H | S | 4-Br—$C_6H_5O$ | H | $OCF_2CF_2H$ | $OCF_2CF_2H$ |
| 26 | 287N | $CF_3CF_2$ | H | S | $C_6H_5O$ | H | $OCF_3$ | $OCF_3$ |
| 26 | 288N | $CF_3CF_2$ | H | S | 4-Cl—$C_6H_5O$ | H | $OCF_3$ | $OCF_3$ |
| 26 | 289N | $CF_3CF_2$ | H | S | 4-F—$C_6H_5O$ | H | $OCF_3$ | $OCF_3$ |
| 26 | 290N | $CF_3CF_2$ | H | S | 3,4-Cl—$C_6H_5O$ | H | $OCF_3$ | $OCF_3$ |
| 26 | 291N | $CF_3CF_2$ | H | S | H | $C_6H_5$ | $OCF_3$ | $OCF_3$ |
| 26 | 292N | $CF_3CF_2$ | H | S | H | 4-Cl—$C_6H_5$ | $OCF_3$ | $OCF_3$ |
| 26 | 293N | $CF_3CF_2$ | H | S | H | 4-F—$C_6H_5$ | $OCF_3$ | $OCF_3$ |
| 26 | 294N | $CF_3CF_2$ | H | S | H | 4-Br—$C_6H_5$ | $OCF_3$ | $OCF_3$ |
| 26 | 295N | $CF_3CF_2$ | H | S | 4-Br—$C_6H_5O$ | H | $OCF_3$ | $OCF_3$ |
| 26 | 296N | $CF_3CF_2$ | H | S | $C_6H_5O$ | H | $OCF_2H$ | $OCF_2H$ |
| 26 | 297N | $CF_3CF_2$ | H | S | 4-Cl—$C_6H_5O$ | H | $OCF_2H$ | $OCF_2H$ |
| 26 | 298N | $CF_3CF_2$ | H | S | 4-F—$C_6H_5O$ | H | $OCF_2H$ | $OCF_2H$ |
| 26 | 299N | $CF_3CF_2$ | H | S | 3,4-Cl—$C_6H_5O$ | H | $OCF_2H$ | $OCF_2H$ |
| 26 | 300N | $CF_3CF_2$ | H | S | H | $C_6H_5$ | $OCF_2H$ | $OCF_2H$ |
| 26 | 301N | $CF_3CF_2$ | H | S | H | 4-Cl—$C_6H_5$ | $OCF_2H$ | $OCF_2H$ |
| 26 | 302N | $CF_3CF_2$ | H | S | H | 4-F—$C_6H_5$ | $OCF_2H$ | $OCF_2H$ |
| 26 | 303N | $CF_3CF_2$ | H | S | H | 4-Br—$C_6H_5$ | $OCF_2H$ | $OCF_2H$ |
| 26 | 304N | $CF_3CF_2$ | H | S | 4-Br—$C_6H_5O$ | H | $OCF_2H$ | $OCF_2H$ |
| 26 | 305N | $CF_3CF_2$ | H | S | $C_6H_5O$ | H | $R_{10} + R_{11} = OCF_2CF_2O$ | |
| 26 | 306N | $CF_3CF_2$ | H | S | 4-Cl—$C_6H_5O$ | H | $R_{10} + R_{11} = OCF_2CF_2O$ | |
| 26 | 307N | $CF_3CF_2$ | H | S | 4-F—$C_6H_5O$ | H | $R_{10} + R_{11} = OCF_2CF_2O$ | |
| 26 | 308N | $CF_3CF_2$ | H | S | 3,4-Cl—$C_6H_5O$ | H | $R_{10} + R_{11} = OCF_2CF_2O$ | |
| 26 | 309N | $CF_3CF_2$ | H | S | H | $C_6H_5$ | $R_{10} + R_{11} = OCF_2CF_2O$ | |
| 26 | 310N | $CF_3CF_2$ | H | S | H | 4-Cl—$C_6H_5$ | $R_{10} + R_{11} = OCF_2CF_2O$ | |
| 26 | 311N | $CF_3CF_2$ | H | S | H | 4-F—$C_6H_5$ | $R_{10} + R_{11} = OCF_2CF_2O$ | |
| 26 | 312N | $CF_3CF_2$ | H | S | H | 4-Br—$C_6H_5$ | $R_{10} + R_{11} = OCF_2CF_2O$ | |
| 26 | 313N | $CF_3CF_2$ | H | S | 4-Br—$C_6H_5O$ | H | $R_{10} + R_{11} = OCF_2CF_2O$ | |
| 26 | 314N | $CF_3CF_2$ | H | S | $C_6H_5O$ | H | $R_{10} + R_{11} = OCCl_2CCl_2O$ | |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

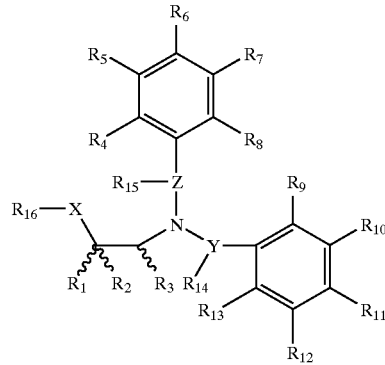

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 26 | 315N | $CF_3CF_2$ | H | S | 4-Cl—$C_6H_5O$ | H | $R_{10} + R_{11}$ = $OCCl_2CCl_2O$ | |
| 26 | 316N | $CF_3CF_2$ | H | S | 4-F—$C_6H_5O$ | H | $R_{10} + R_{11}$ = $OCCl_2CCl_2O$ | |
| 26 | 317N | $CF_3CF_2$ | H | S | 3,4-Cl—$C_6H_5O$ | H | $R_{10} + R_{11}$ = $OCCl_2CCl_2O$ | |
| 26 | 318N | $CF_3CF_2$ | H | S | H | $C_6H_5$ | $R_{10} + R_{11}$ = $OCCl_2CCl_2O$ | |
| 26 | 319N | $CF_3CF_2$ | H | S | H | 4-Cl—$C_6H_5$ | $R_{10} + R_{11}$ = $OCCl_2CCl_2O$ | |
| 26 | 320N | $CF_3CF_2$ | H | S | H | 4-F—$C_6H_5$ | $R_{10} + R_{11}$ = $OCCl_2CCl_2O$ | |
| 26 | 321N | $CF_3CF_2$ | H | S | H | 4-Br—$C_6H_5$ | $R_{10} + R_{11}$ = $OCCl_2CCl_2O$ | |
| 26 | 322N | $CF_3CF_2$ | H | S | 4-Br—$C_6H_5O$ | H | $R_{10} + R_{11}$ = $OCCl_2CCl_2O$ | |
| 26 | 323N | $CF_3CF_2$ | H | S | H | H | OH | H |
| 26 | 324N | $CF_3CF_2$ | H | S | H | H | OH | OH |
| 26 | 325N | $CF_3CF_2$ | H | S | H | H | H | OH |
| 26 | 326N | $CF_3CF_2$ | H | S | H | H | $OCH_2CF_3$ | H |
| 26 | 327N | $CF_3CF_2$ | H | S | H | H | H | $OCH_2CF_3$ |
| 26 | 328N | $CF_3CF_2$ | H | S | H | H | $OCH_2CF_2CF_3$ | H |
| 26 | 329N | $CF_3CF_2$ | H | S | H | H | $OCH_2CH_2CF_3$ | H |
| 26 | 330N | $CF_3CF_2$ | H | S | H | H | $OCH(CF_3)_3$ | H |
| 26 | 331N | $CF_3CF_2$ | H | S | H | 4-F—$C_6H_5O$ | H | H |
| 26 | 332N | $CF_3CF_2$ | H | S | 4-F—$C_6H_5O$ | H | H | H |
| 26 | 333N | $CF_3CF_2$ | H | S | H | cyclo-hexoxy | H | H |
| 26 | 334N | $CF_3CF_2$ | H | S | cyclo-hexoxy | H | H | H |
| 26 | 335N | $CF_3CF_2$ | H | S | H | $CH(CH_3)_3$ | H | H |
| 26 | 336N | $CF_3CF_2$ | H | S | F | H | | bond to indicated phenyl carbon of $R_{10}$ substituent |
| 63 | 224N | $C_6H_5$ | H | O | $C_6H_5O$ | H | $OCF_2CF_2H$ | H |
| 63 | 225N | $C_6H_5$ | H | O | 4-Cl—$C_6H_5O$ | H | $OCF_2CF_2H$ | H |
| 63 | 226N | $C_6H_5$ | H | O | 4-F—$C_6H_5O$ | H | $OCF_2CF_2H$ | H |
| 63 | 227N | $C_6H_5$ | H | O | 3,4-Cl—$C_6H_5O$ | H | $OCF_2CF_2H$ | H |
| 63 | 228N | $C_6H_5$ | H | O | H | $C_6H_5$ | $OCF_2CF_2H$ | H |
| 63 | 229N | $C_6H_5$ | H | O | H | 4-Cl—$C_6H_5$ | $OCF_2CF_2H$ | H |
| 63 | 230N | $C_6H_5$ | H | O | H | 4-F—$C_6H_5$ | $OCF_2CF_2H$ | H |
| 63 | 231N | $C_6H_5$ | H | O | H | 4-Br—$C_6H_5$ | $OCF_2CF_2H$ | H |
| 63 | 232N | $C_6H_5$ | H | O | 4-Br—$C_6H_5O$ | H | $OCF_2CF_2H$ | H |
| 63 | 233N | $C_6H_5$ | H | O | $C_6H_5O$ | H | $OCF_2CF_3$ | H |
| 63 | 234N | $C_6H_5$ | H | O | 4-Cl—$C_6H_5O$ | H | $OCF_2CF_3$ | H |
| 63 | 235N | $C_6H_5$ | H | O | 4-F—$C_6H_5O$ | H | $OCF_2CF_3$ | H |
| 63 | 236N | $C_6H_5$ | H | O | 3,4-Cl—$C_6H_5O$ | H | $OCF_2CF_3$ | H |
| 63 | 237N | $C_6H_5$ | H | O | H | $C_6H_5$ | $OCF_2CF_3$ | H |
| 63 | 238N | $C_6H_5$ | H | O | H | 4-Cl—$C_6H_5$ | $OCF_2CF_3$ | H |
| 63 | 239N | $C_6H_5$ | H | O | H | 4-F—$C_6H_5$ | $OCF_2CF_3$ | H |
| 63 | 240N | $C_6H_5$ | H | O | H | 4-Br—$C_6H_5$ | $OCF_2CF_3$ | H |
| 63 | 241N | $C_6H_5$ | H | O | 4-Br—$C_6H_5O$ | H | $OCF_2CF_3$ | H |
| 63 | 242N | $C_6H_5$ | H | O | $C_6H_5O$ | H | $OCCl_2CCl_2H$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

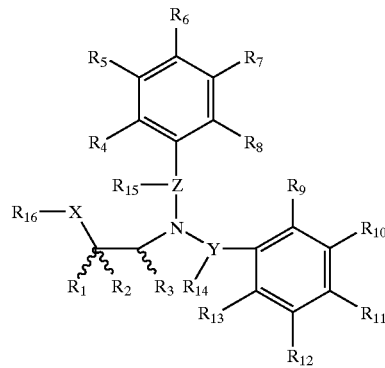

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 63 | 243N | $C_6H_5$ | H | O | 4-Cl—$C_6H_5$O | H | $OCCl_2CCl_2H$ | H |
| 63 | 244N | $C_6H_5$ | H | O | 4-F—$C_6H_5$O | H | $OCCl_2CCl_2H$ | H |
| 63 | 245N | $C_6H_5$ | H | O | 3,4-Cl—$C_6H_5$O | H | $OCCl_2CCl_2H$ | H |
| 63 | 246N | $C_6H_5$ | H | O | H | $C_6H_5$ | $OCCl_2CCl_2H$ | H |
| 63 | 247N | $C_6H_5$ | H | O | H | 4-Cl—$C_6H_5$ | $OCCl_2CCl_2H$ | H |
| 63 | 248N | $C_6H_5$ | H | O | H | 4-F—$C_6H_5$ | $OCCl_2CCl_2H$ | H |
| 63 | 249N | $C_6H_5$ | H | O | H | 4-Br—$C_6H_5$ | $OCCl_2CCl_2H$ | H |
| 63 | 250N | $C_6H_5$ | H | O | 4-Br—$C_6H_5$O | H | $OCCl_2CCl_2H$ | H |
| 63 | 251N | $C_6H_5$ | H | O | $C_6H_5$O | H | $OCCl_2CCl_3$ | H |
| 63 | 252N | $C_6H_5$ | H | O | 4-Cl—$C_6H_5$O | H | $OCCl_2CCl_3$ | H |
| 63 | 253N | $C_6H_5$ | H | O | 4-F—$C_6H_5$O | H | $OCCl_2CCl_3$ | H |
| 63 | 254N | $C_6H_5$ | H | O | 3,4-Cl—$C_6H_5$O | H | $OCCl_2CCl_3$ | H |
| 63 | 255N | $C_6H_5$ | H | O | H | $C_6H_5$ | $OCCl_2CCl_3$ | H |
| 63 | 256N | $C_6H_5$ | H | O | H | 4-Cl—$C_6H_5$ | $OCCl_2CCl_3$ | H |
| 63 | 257N | $C_6H_5$ | H | O | H | 4-F—$C_6H_5$ | $OCCl_2CCl_3$ | H |
| 63 | 258N | $C_6H_5$ | H | O | H | 4-Br—$C_6H_5$ | $OCCl_2CCl_3$ | H |
| 63 | 259N | $C_6H_5$ | H | O | 4-Br—$C_6H_5$O | H | $OCCl_2CCl_3$ | H |
| 63 | 260N | $C_6H_5$ | H | O | $C_6H_5$O | H | $OCCl_2CF_3$ | H |
| 63 | 261N | $C_6H_5$ | H | O | 4-Cl—$C_6H_5$O | H | $OCCl_2CF_3$ | H |
| 63 | 262N | $C_6H_5$ | H | O | 4-F—$C_6H_5$O | H | $OCCl_2CF_3$ | H |
| 63 | 263N | $C_6H_5$ | H | O | 3,4-Cl—$C_6H_5$O | H | $OCCl_2CF_3$ | H |
| 63 | 264N | $C_6H_5$ | H | O | H | $C_6H_5$ | $OCCl_2CF_3$ | H |
| 63 | 265N | $C_6H_5$ | H | O | H | 4-Cl—$C_6H_5$ | $OCCl_2CF_3$ | H |
| 63 | 266N | $C_6H_5$ | H | O | H | 4-F—$C_6H_5$ | $OCCl_2CF_3$ | H |
| 63 | 267N | $C_6H_5$ | H | O | H | 4-Br—$C_6H_5$ | $OCCl_2CF_3$ | H |
| 63 | 268N | $C_6H_5$ | H | O | 4-Br—$C_6H_5$O | H | $OCCl_2CF_3$ | H |
| 63 | 269N | $C_6H_5$ | H | O | $C_6H_5$O | H | $OCF_2CCl_3$ | H |
| 63 | 270N | $C_6H_5$ | H | O | 4-Cl—$C_6H_5$O | H | $OCF_2CCl_3$ | H |
| 63 | 271N | $C_6H_5$ | H | O | 4-F—$C_6H_5$O | H | $OCF_2CCl_3$ | H |
| 63 | 272N | $C_6H_5$ | H | O | 3,4-Cl—$C_6H_5$O | H | $OCF_2CCl_3$ | H |
| 63 | 273N | $C_6H_5$ | H | O | H | $C_6H_5$ | $OCF_2CCl_3$ | H |
| 63 | 274N | $C_6H_5$ | H | O | H | 4-Cl—$C_6H_5$ | $OCF_2CCl_3$ | H |
| 63 | 275N | $C_6H_5$ | H | O | H | 4-F—$C_6H_5$ | $OCF_2CCl_3$ | H |
| 63 | 276N | $C_6H_5$ | H | O | H | 4-Br—$C_6H_5$ | $OCF_2CCl_3$ | H |
| 63 | 277N | $C_6H_5$ | H | O | 4-Br—$C_6H_5$O | H | $OCF_2CCl_3$ | H |
| 63 | 278N | $C_6H_5$ | H | O | $C_6H_5$O | H | $OCF_2CF_2H$ | $OCF_2CF_2H$ |
| 63 | 279N | $C_6H_5$ | H | O | 4-Cl—$C_6H_5$O | H | $OCF_2CF_2H$ | $OCF_2CF_2H$ |
| 63 | 280N | $C_6H_5$ | H | O | 4-F—$C_6H_5$O | H | $OCF_2CF_2H$ | $OCF_2CF_2H$ |
| 63 | 281N | $C_6H_5$ | H | O | 3,4-Cl—$C_6H_5$O | H | $OCF_2CF_2H$ | $OCF_2CF_2H$ |
| 63 | 282N | $C_6H_5$ | H | O | H | $C_6H_5$ | $OCF_2CF_2H$ | $OCF_2CF_2H$ |
| 63 | 283N | $C_6H_5$ | H | O | H | 4-Cl—$C_6H_5$ | $OCF_2CF_2H$ | $OCF_2CF_2H$ |
| 63 | 284N | $C_6H_5$ | H | O | H | 4-F—$C_6H_5$ | $OCF_2CF_2H$ | $OCF_2CF_2H$ |
| 63 | 285N | $C_6H_5$ | H | O | H | 4-Br—$C_6H_5$ | $OCF_2CF_2H$ | $OCF_2CF_2H$ |
| 63 | 286N | $C_6H_5$ | H | O | 4-Br—$C_6H_5$O | H | $OCF_2CF_2H$ | $OCF_2CF_2H$ |
| 63 | 287N | $C_6H_5$ | H | O | $C_6H_5$O | H | $OCF_3$ | $OCF_3$ |
| 63 | 288N | $C_6H_5$ | H | O | 4-Cl—$C_6H_5$O | H | $OCF_3$ | $OCF_3$ |
| 63 | 289N | $C_6H_5$ | H | O | 4-F—$C_6H_5$O | H | $OCF_3$ | $OCF_3$ |
| 63 | 290N | $C_6H_5$ | H | O | 3,4-Cl—$C_6H_5$O | H | $OCF_3$ | $OCF_3$ |
| 63 | 291N | $C_6H_5$ | H | O | H | $C_6H_5$ | $OCF_3$ | $OCF_3$ |
| 63 | 292N | $C_6H_5$ | H | O | H | 4-Cl—$C_6H_5$ | $OCF_3$ | $OCF_3$ |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

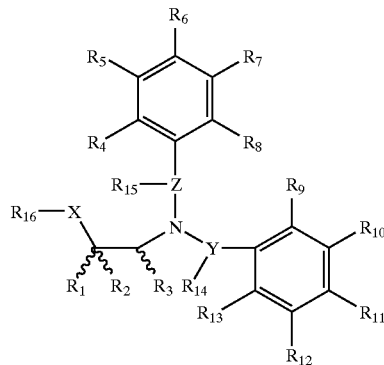

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 63 | 293N | $C_6H_5$ | H | O | H | 4-F—$C_6H_5$ | $OCF_3$ | $OCF_3$ |
| 63 | 294N | $C_6H_5$ | H | O | H | 4-Br—$C_6H_5$ | $OCF_3$ | $OCF_3$ |
| 63 | 295N | $C_6H_5$ | H | O | 4-Br—$C_6H_5O$ | H | $OCF_3$ | $OCF_3$ |
| 63 | 296N | $C_6H_5$ | H | O | $C_6H_5O$ | H | $OCF_2H$ | $OCF_2H$ |
| 63 | 297N | $C_6H_5$ | H | O | 4-Cl—$C_6H_5O$ | H | $OCF_2H$ | $OCF_2H$ |
| 63 | 298N | $C_6H_5$ | H | O | 4-F—$C_6H_5O$ | H | $OCF_2H$ | $OCF_2H$ |
| 63 | 299N | $C_6H_5$ | H | O | 3,4-Cl—$C_6H_5O$ | H | $OCF_2H$ | $OCF_2H$ |
| 63 | 300N | $C_6H_5$ | H | O | H | $C_6H_5$ | $OCF_2H$ | $OCF_2H$ |
| 63 | 301N | $C_6H_5$ | H | O | H | 4-Cl—$C_6H_5$ | $OCF_2H$ | $OCF_2H$ |
| 63 | 302N | $C_6H_5$ | H | O | H | 4-F—$C_6H_5$ | $OCF_2H$ | $OCF_2H$ |
| 63 | 303N | $C_6H_5$ | H | O | H | 4-Br—$C_6H_5$ | $OCF_2H$ | $OCF_2H$ |
| 63 | 304N | $C_6H_5$ | H | O | 4-Br—$C_6H_5O$ | H | $OCF_2H$ | $OCF_2H$ |
| 63 | 305N | $C_6H_5$ | H | O | $C_6H_5O$ | H | $R_{10} + R_{11} = OCF_2CF_2O$ | |
| 63 | 306N | $C_6H_5$ | H | O | 4-Cl—$C_6H_5O$ | H | $R_{10} + R_{11} = OCF_2CF_2O$ | |
| 63 | 307N | $C_6H_5$ | H | O | 4-F—$C_6H_5O$ | H | $R_{10} + R_{11} = OCF_2CF_2O$ | |
| 63 | 308N | $C_6H_5$ | H | O | 3,4-Cl—$C_6H_5O$ | H | $R_{10} + R_{11} = OCF_2CF_2O$ | |
| 63 | 309N | $C_6H_5$ | H | O | H | $C_6H_5$ | $R_{10} + R_{11} = OCF_2CF_2O$ | |
| 63 | 310N | $C_6H_5$ | H | O | H | 4-Cl—$C_6H_5$ | $R_{10} + R_{11} = OCF_2CF_2O$ | |
| 63 | 311N | $C_6H_5$ | H | O | H | 4-F—$C_6H_5$ | $R_{10} + R_{11} = OCF_2CF_2O$ | |
| 63 | 312N | $C_6H_5$ | H | O | H | 4-Br—$C_6H_5$ | $R_{10} + R_{11} = OCF_2CF_2O$ | |
| 63 | 313N | $C_6H_5$ | H | O | 4-Br—$C_6H_5O$ | H | $R_{10} + R_{11} = OCF_2CF_2O$ | |
| 63 | 314N | $C_6H_5$ | H | O | $C_6H_5O$ | H | $R_{10} + R_{11} = OCCl_2CCl_2O$ | |
| 63 | 315N | $C_6H_5$ | H | O | 4-Cl—$C_6H_5O$ | H | $R_{10} + R_{11} = OCCl_2CCl_2O$ | |
| 63 | 316N | $C_6H_5$ | H | O | 4-F—$C_6H_5O$ | H | $R_{10} + R_{11} = OCCl_2CCl_2O$ | |
| 63 | 317N | $C_6H_5$ | H | O | 3,4-Cl—$C_6H_5O$ | H | $R_{10} + R_{11} = OCCl_2CCl_2O$ | |
| 63 | 318N | $C_6H_5$ | H | O | H | $C_6H_5$ | $R_{10} + R_{11} = OCCl_2CCl_2O$ | |
| 63 | 319N | $C_6H_5$ | H | O | H | 4-Cl—$C_6H_5$ | $R_{10} + R_{11} = OCCl_2CCl_2O$ | |
| 63 | 320N | $C_6H_5$ | H | O | H | 4-F—$C_6H_5$ | $R_{10} + R_{11} = OCCl_2CCl_2O$ | |
| 63 | 321N | $C_6H_5$ | H | O | H | 4-Br—$C_6H_5$ | $R_{10} + R_{11} = OCCl_2CCl_2O$ | |
| 63 | 322N | $C_6H_5$ | H | O | 4-Br—$C_6H_5O$ | H | $R_{10} + R_{11} = OCCl_2CCl_2O$ | |
| 63 | 323N | $C_6H_5$ | H | O | H | H | OH | H |
| 63 | 324N | $C_6H_5$ | H | O | H | H | OH | OH |
| 63 | 325N | $C_6H_5$ | H | O | H | H | H | OH |
| 63 | 326N | $C_6H_5$ | H | O | H | H | $OCH_2CF_3$ | H |
| 63 | 327N | $C_6H_5$ | H | O | H | H | H | $OCH_2CF_3$ |
| 63 | 328N | $C_6H_5$ | H | O | H | H | $OCH_2CF_2CF_3$ | H |
| 63 | 329N | $C_6H_5$ | H | O | H | H | $OCH_2CH_2CF_3$ | H |
| 63 | 330N | $C_6H_5$ | H | O | H | H | $OCH(CF_3)_3$ | H |
| 63 | 331N | $C_6H_5$ | H | O | H | 4-F—$C_6H_5O$ | H | H |
| 63 | 332N | $C_6H_5$ | H | O | 4-F—$C_6H_5O$ | H | H | H |
| 63 | 333N | $C_6H_5$ | H | O | H | cyclo-hexoxy | H | H |
| 63 | 334N | $C_6H_5$ | H | O | cyclo-hexoxy | H | H | H |
| 63 | 335N | $C_6H_5$ | H | O | H | $CH(CH_3)_3$ | H | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

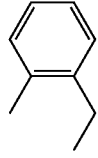

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 63 | 336N | $C_6H_5$ | H | O | F | H | 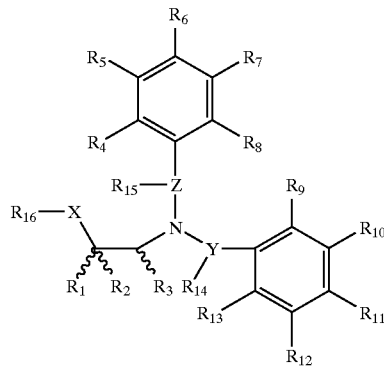 | bond to indicated phenyl carbon of $R_{10}$ substituent |
| 65 | 224N | $C_6F_5$ | H | O | $C_6H_5O$ | H | $OCF_2CF_2H$ | H |
| 65 | 225N | $C_6F_5$ | H | O | 4-Cl—$C_6H_5O$ | H | $OCF_2CF_2H$ | H |
| 65 | 226N | $C_6F_5$ | H | O | 4-F—$C_6H_5O$ | H | $OCF_2CF_2H$ | H |
| 65 | 227N | $C_6F_5$ | H | O | 3,4-Cl—$C_6H_5O$ | H | $OCF_2CF_2H$ | H |
| 65 | 228N | $C_6F_5$ | H | O | H | $C_6H_5$ | $OCF_2CF_2H$ | H |
| 65 | 229N | $C_6F_5$ | H | O | H | 4-Cl—$C_6H_5$ | $OCF_2CF_2H$ | H |
| 65 | 230N | $C_6F_5$ | H | O | H | 4-F—$C_6H_5$ | $OCF_2CF_2H$ | H |
| 65 | 231N | $C_6F_5$ | H | O | H | 4-Br—$C_6H_5$ | $OCF_2CF_2H$ | H |
| 65 | 232N | $C_6F_5$ | H | O | 4-Br—$C_6H_5O$ | H | $OCF_2CF_2H$ | H |
| 65 | 233N | $C_6F_5$ | H | O | $C_6H_5O$ | H | $OCF_2CF_3$ | H |
| 65 | 234N | $C_6F_5$ | H | O | 4-Cl—$C_6H_5O$ | H | $OCF_2CF_3$ | H |
| 65 | 235N | $C_6F_5$ | H | O | 4-F—$C_6H_5O$ | H | $OCF_2CF_3$ | H |
| 65 | 236N | $C_6F_5$ | H | O | 3,4-Cl—$C_6H_5O$ | H | $OCF_2CF_3$ | H |
| 65 | 237N | $C_6F_5$ | H | O | H | $C_6H_5$ | $OCF_2CF_3$ | H |
| 65 | 238N | $C_6F_5$ | H | O | H | 4-Cl—$C_6H_5$ | $OCF_2CF_3$ | H |
| 65 | 239N | $C_6F_5$ | H | O | H | 4-F—$C_6H_5$ | $OCF_2CF_3$ | H |
| 65 | 240N | $C_6F_5$ | H | O | H | 4-Br—$C_6H_5$ | $OCF_2CF_3$ | H |
| 65 | 241N | $C_6F_5$ | H | O | 4-Br—$C_6H_5O$ | H | $OCF_2CF_3$ | H |
| 65 | 242N | $C_6F_5$ | H | O | $C_6H_5O$ | H | $OCCl_2CCl_2H$ | H |
| 65 | 243N | $C_6F_5$ | H | O | 4-Cl—$C_6H_5O$ | H | $OCCl_2CCl_2H$ | H |
| 65 | 244N | $C_6F_5$ | H | O | 4-F—$C_6H_5O$ | H | $OCCl_2CCl_2H$ | H |
| 65 | 245N | $C_6F_5$ | H | O | 3,4-Cl—$C_6H_5O$ | H | $OCCl_2CCl_2H$ | H |
| 65 | 246N | $C_6F_5$ | H | O | H | $C_6H_5$ | $OCCl_2CCl_2H$ | H |
| 65 | 247N | $C_6F_5$ | H | O | H | 4-Cl—$C_6H_5$ | $OCCl_2CCl_2H$ | H |
| 65 | 248N | $C_6F_5$ | H | O | H | 4-F—$C_6H_5$ | $OCCl_2CCl_2H$ | H |
| 65 | 249N | $C_6F_5$ | H | O | H | 4-Br—$C_6H_5$ | $OCCl_2CCl_2H$ | H |
| 65 | 250N | $C_6F_5$ | H | O | 4-Br—$C_6H_5O$ | H | $OCCl_2CCl_2H$ | H |
| 65 | 251N | $C_6F_5$ | H | O | $C_6H_5O$ | H | $OCCl_2CCl_3$ | H |
| 65 | 252N | $C_6F_5$ | H | O | 4-Cl—$C_6H_5O$ | H | $OCCl_2CCl_3$ | H |
| 65 | 253N | $C_6F_5$ | H | O | 4-F—$C_6H_5O$ | H | $OCCl_2CCl_3$ | H |
| 65 | 254N | $C_6F_5$ | H | O | 3,4-Cl—$C_6H_5O$ | H | $OCCl_2CCl_3$ | H |
| 65 | 255N | $C_6F_5$ | H | O | H | $C_6H_5$ | $OCCl_2CCl_3$ | H |
| 65 | 256N | $C_6F_5$ | H | O | H | 4-Cl—$C_6H_5$ | $OCCl_2CCl_3$ | H |
| 65 | 257N | $C_6F_5$ | H | O | H | 4-F—$C_6H_5$ | $OCCl_2CCl_3$ | H |
| 65 | 258N | $C_6F_5$ | H | O | H | 4-Br—$C_6H_5$ | $OCCl_2CCl_3$ | H |
| 65 | 259N | $C_6F_5$ | H | O | 4-Br—$C_6H_5O$ | H | $OCCl_2CCl_3$ | H |
| 65 | 260N | $C_6F_5$ | H | O | $C_6H_5O$ | H | $OCCl_2CF_3$ | H |
| 65 | 261N | $C_6F_5$ | H | O | 4-Cl—$C_6H_5O$ | H | $OCCl_2CF_3$ | H |
| 65 | 262N | $C_6F_5$ | H | O | 4-F—$C_6H_5O$ | H | $OCCl_2CF_3$ | H |
| 65 | 263N | $C_6F_5$ | H | O | 3,4-Cl—$C_6H_5O$ | H | $OCCl_2CF_3$ | H |
| 65 | 264N | $C_6F_5$ | H | O | H | $C_6H_5$ | $OCCl_2CF_3$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

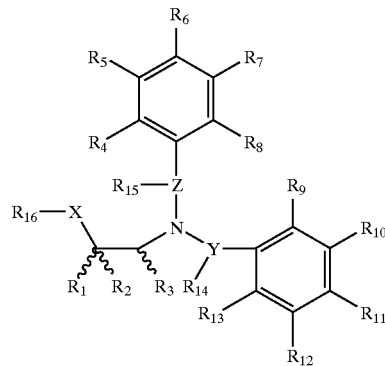

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 65 | 265N | $C_6F_5$ | H | O | H | 4-Cl—$C_6H_5$ | $OCCl_2CF_3$ | H |
| 65 | 266N | $C_6F_5$ | H | O | H | 4-F—$C_6H_5$ | $OCCl_2CF_3$ | H |
| 65 | 267N | $C_6F_5$ | H | O | H | 4-Br—$C_6H_5$ | $OCCl_2CF_3$ | H |
| 65 | 268N | $C_6F_5$ | H | O | 4-Br—$C_6H_5O$ | H | $OCCl_2CF_3$ | H |
| 65 | 269N | $C_6F_5$ | H | O | $C_6H_5O$ | H | $OCF_2CCl_3$ | H |
| 65 | 270N | $C_6F_5$ | H | O | 4-Cl—$C_6H_5O$ | H | $OCF_2CCl_3$ | H |
| 65 | 271N | $C_6F_5$ | H | O | 4-F—$C_6H_5O$ | H | $OCF_2CCl_3$ | H |
| 65 | 272N | $C_6F_5$ | H | O | 3,4-Cl—$C_6H_5O$ | H | $OCF_2CCl_3$ | H |
| 65 | 273N | $C_6F_5$ | H | O | H | $C_6H_5$ | $OCF_2CCl_3$ | H |
| 65 | 274N | $C_6F_5$ | H | O | H | 4-Cl—$C_6H_5$ | $OCF_2CCl_3$ | H |
| 65 | 275N | $C_6F_5$ | H | O | H | 4-F—$C_6H_5$ | $OCF_2CCl_3$ | H |
| 65 | 276N | $C_6F_5$ | H | O | H | 4-Br—$C_6H_5$ | $OCF_2CCl_3$ | H |
| 65 | 277N | $C_6F_5$ | H | O | 4-Br—$C_6H_5O$ | H | $OCF_2CCl_3$ | H |
| 65 | 278N | $C_6F_5$ | H | O | $C_6H_5O$ | H | $OCF_2CF_2H$ | $OCF_2CF_2H$ |
| 65 | 279N | $C_6F_5$ | H | O | 4-Cl—$C_6H_5O$ | H | $OCF_2CF_2H$ | $OCF_2CF_2H$ |
| 65 | 280N | $C_6F_5$ | H | O | 4-F—$C_6H_5O$ | H | $OCF_2CF_2H$ | $OCF_2CF_2H$ |
| 65 | 281N | $C_6F_5$ | H | O | 3,4-Cl—$C_6H_5O$ | H | $OCF_2CF_2H$ | $OCF_2CF_2H$ |
| 65 | 282N | $C_6F_5$ | H | O | H | $C_6H_5$ | $OCF_2CF_2H$ | $OCF_2CF_2H$ |
| 65 | 283N | $C_6F_5$ | H | O | H | 4-Cl—$C_6H_5$ | $OCF_2CF_2H$ | $OCF_2CF_2H$ |
| 65 | 284N | $C_6F_5$ | H | O | H | 4-F—$C_6H_5$ | $OCF_2CF_2H$ | $OCF_2CF_2H$ |
| 65 | 285N | $C_6F_5$ | H | O | H | 4-Br—$C_6H_5$ | $OCF_2CF_2H$ | $OCF_2CF_2H$ |
| 65 | 286N | $C_6F_5$ | H | O | 4-Br—$C_6H_5O$ | H | $OCF_2CF_2H$ | $OCF_2CF_2H$ |
| 65 | 287N | $C_6F_5$ | H | O | $C_6H_5O$ | H | $OCF_3$ | $OCF_3$ |
| 65 | 288N | $C_6F_5$ | H | O | 4-Cl—$C_6H_5O$ | H | $OCF_3$ | $OCF_3$ |
| 65 | 289N | $C_6F_5$ | H | O | 4-F—$C_6H_5O$ | H | $OCF_3$ | $OCF_3$ |
| 65 | 290N | $C_6F_5$ | H | O | 3,4-Cl—$C_6H_5O$ | H | $OCF_3$ | $OCF_3$ |
| 65 | 291N | $C_6F_5$ | H | O | H | $C_6H_5$ | $OCF_3$ | $OCF_3$ |
| 65 | 292N | $C_6F_5$ | H | O | H | 4-Cl—$C_6H_5$ | $OCF_3$ | $OCF_3$ |
| 65 | 293N | $C_6F_5$ | H | O | H | 4-F—$C_6H_5$ | $OCF_3$ | $OCF_3$ |
| 65 | 294N | $C_6F_5$ | H | O | H | 4-Br—$C_6H_5$ | $OCF_3$ | $OCF_3$ |
| 65 | 295N | $C_6F_5$ | H | O | 4-Br—$C_6H_5O$ | H | $OCF_3$ | $OCF_3$ |
| 65 | 296N | $C_6F_5$ | H | O | $C_6H_5O$ | H | $OCF_2H$ | $OCF_2H$ |
| 65 | 297N | $C_6F_5$ | H | O | 4-Cl—$C_6H_5O$ | H | $OCF_2H$ | $OCF_2H$ |
| 65 | 298N | $C_6F_5$ | H | O | 4-F—$C_6H_5O$ | H | $OCF_2H$ | $OCF_2H$ |
| 65 | 299N | $C_6F_5$ | H | O | 3,4-Cl—$C_6H_5O$ | H | $OCF_2H$ | $OCF_2H$ |
| 65 | 300N | $C_6F_5$ | H | O | H | $C_6H_5$ | $OCF_2H$ | $OCF_2H$ |
| 65 | 301N | $C_6F_5$ | H | O | H | 4-Cl—$C_6H_5$ | $OCF_2H$ | $OCF_2H$ |
| 65 | 302N | $C_6F_5$ | H | O | H | 4-F—$C_6H_5$ | $OCF_2H$ | $OCF_2H$ |
| 65 | 303N | $C_6F_5$ | H | O | H | 4-Br—$C_6H_5$ | $OCF_2H$ | $OCF_2H$ |
| 65 | 304N | $C_6F_5$ | H | O | 4-Br—$C_6H_5O$ | H | $OCF_2H$ | $OCF_2H$ |
| 65 | 305N | $C_6F_5$ | H | O | $C_6H_5O$ | H | $R_{10} + R_{11} = OCF_2CF_2O$ | |
| 65 | 306N | $C_6F_5$ | H | O | 4-Cl—$C_6H_5O$ | H | $R_{10} + R_{11} = OCF_2CF_2O$ | |
| 65 | 307N | $C_6F_5$ | H | O | 4-F—$C_6H_5O$ | H | $R_{10} + R_{11} = OCF_2CF_2O$ | |
| 65 | 308N | $C_6F_5$ | H | O | 3,4-Cl—$C_6H_5O$ | H | $R_{10} + R_{11} = OCF_2CF_2O$ | |
| 65 | 309N | $C_6F_5$ | H | O | H | $C_6H_5$ | $R_{10} + R_{11} = OCF_2CF_2O$ | |
| 65 | 310N | $C_6F_5$ | H | O | H | 4-Cl—$C_6H_5$ | $R_{10} + R_{11} = OCF_2CF_2O$ | |
| 65 | 311N | $C_6F_5$ | H | O | H | 4-F—$C_6H_5$ | $R_{10} + R_{11} = OCF_2CF_2O$ | |
| 65 | 312N | $C_6F_5$ | H | O | H | 4-Br—$C_6H_5$ | $R_{10} + R_{11} = OCF_2CF_2O$ | |
| 65 | 313N | $C_6F_5$ | H | O | 4-Br—$C_6H_5O$ | H | $R_{10} + R_{11} = OCF_2CF_2O$ | |
| 65 | 314N | $C_6F_5$ | H | O | $C_6H_5O$ | H | $R_{10} + R_{11} = OCCl_2CCl_2O$ | |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

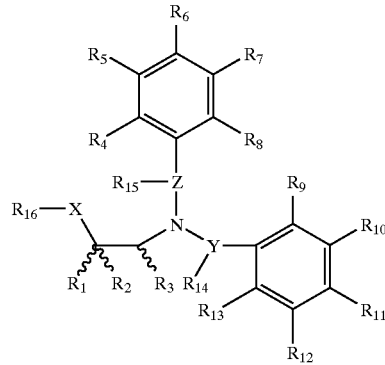

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 65 | 315N | $C_6F_5$ | H | O | 4-Cl—$C_6H_5$O | H | $R_{10} + R_{11} = OCCl_2CCl_2O$ | |
| 65 | 316N | $C_6F_5$ | H | O | 4-F—$C_6H_5$O | H | $R_{10} + R_{11} = OCCl_2CCl_2O$ | |
| 65 | 317N | $C_6F_5$ | H | O | 3,4-Cl—$C_6H_5$O | H | $R_{10} + R_{11} = OCCl_2CCl_2O$ | |
| 65 | 318N | $C_6F_5$ | H | O | H | $C_6H_5$ | $R_{10} + R_{11} = OCCl_2CCl_2O$ | |
| 65 | 319N | $C_6F_5$ | H | O | H | 4-Cl—$C_6H_5$ | $R_{10} + R_{11} = OCCl_2CCl_2O$ | |
| 65 | 320N | $C_6F_5$ | H | O | H | 4-F—$C_6H_5$ | $R_{10} + R_{11} = OCCl_2CCl_2O$ | |
| 65 | 321N | $C_6F_5$ | H | O | H | 4-Br—$C_6H_5$ | $R_{10} + R_{11} = OCCl_2CCl_2O$ | |
| 65 | 322N | $C_6F_5$ | H | O | 4-Br—$C_6H_5$O | H | $R_{10} + R_{11} = OCCl_2CCl_2O$ | |
| 65 | 323N | $C_6F_5$ | H | O | H | H | OH | H |
| 65 | 324N | $C_6F_5$ | H | O | H | H | OH | OH |
| 65 | 325N | $C_6F_5$ | H | O | H | H | H | OH |
| 65 | 326N | $C_6F_5$ | H | O | H | H | $OCH_2CF_3$ | H |
| 65 | 327N | $C_6F_5$ | H | O | H | H | H | $OCH_2CF_3$ |
| 65 | 328N | $C_6F_5$ | H | O | H | H | $OCH_2CF_2CF_3$ | H |
| 65 | 329N | $C_6F_5$ | H | O | H | H | $OCH_2CH_2CF_3$ | H |
| 65 | 330N | $C_6F_5$ | H | O | H | H | $OCH(CF_3)_3$ | H |
| 65 | 331N | $C_6F_5$ | H | O | H | 4-F—$C_6H_5$O | H | H |
| 65 | 332N | $C_6F_5$ | H | O | 4-F—$C_6H_5$O | H | H | H |
| 65 | 333N | $C_6F_5$ | H | O | H | cyclo-hexoxy | H | H |
| 65 | 334N | $C_6F_5$ | H | O | cyclo-hexoxy | H | H | H |
| 65 | 335N | $C_6F_5$ | H | O | H | $CH(CH_3)_3$ | H | H |
| 65 | 336N | $C_6F_5$ | H | O | F | H | 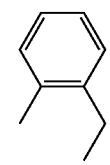 | bond to indicated phenyl carbon of $R_{10}$ substituent |
| 46 | 224N | $CF_3$ | $R_2 + R_3 = (CH_2)_3$ | O | $C_6H_5$O | H | $OCF_2CF_2H$ | H |
| 46 | 225N | $CF_3$ | $R_2 + R_3 = (CH_2)_3$ | O | 4-Cl—$C_6H_5$O | H | $OCF_2CF_2H$ | H |
| 46 | 226N | $CF_3$ | $R_2 + R_3 = (CH_2)_3$ | O | 4-F—$C_6H_5$O | H | $OCF_2CF_2H$ | H |
| 46 | 227N | $CF_3$ | $R_2 + R_3 = (CH_2)_3$ | O | 3,4-Cl—$C_6H_5$O | H | $OCF_2CF_2H$ | H |
| 46 | 228N | $CF_3$ | $R_2 + R_3 = (CH_2)_3$ | O | H | $C_6H_5$ | $OCF_2CF_2H$ | H |
| 46 | 229N | $CF_3$ | $R_2 + R_3 = (CH_2)_3$ | O | H | 4-Cl—$C_6H_5$ | $OCF_2CF_2H$ | H |
| 46 | 230N | $CF_3$ | $R_2 + R_3 = (CH_2)_3$ | O | H | 4-F—$C_6H_5$ | $OCF_2CF_2H$ | H |
| 46 | 231N | $CF_3$ | $R_2 + R_3 = (CH_2)_3$ | O | H | 4-Br—$C_6H_5$ | $OCF_2CF_2H$ | H |
| 46 | 232N | $CF_3$ | $R_2 + R_3 = (CH_2)_3$ | O | 4-Br—$C_6H_5$O | H | $OCF_2CF_2H$ | H |
| 46 | 233N | $CF_3$ | $R_2 + R_3 = (CH_2)_3$ | O | $C_6H_5$O | H | $OCF_2CF_3$ | H |
| 46 | 234N | $CF_3$ | $R_2 + R_3 = (CH_2)_3$ | O | 4-Cl—$C_6H_5$O | H | $OCF_2CF_3$ | H |
| 46 | 235N | $CF_3$ | $R_2 + R_3 = (CH_2)_3$ | O | 4-F—$C_6H_5$O | H | $OCF_2CF_3$ | H |
| 46 | 236N | $CF_3$ | $R_2 + R_3 = (CH_2)_3$ | O | 3,4-Cl—$C_6H_5$O | H | $OCF_2CF_3$ | H |
| 46 | 237N | $CF_3$ | $R_2 + R_3 = (CH_2)_3$ | O | H | $C_6H_5$ | $OCF_2CF_3$ | H |
| 46 | 238N | $CF_3$ | $R_2 + R_3 = (CH_2)_3$ | O | H | 4-Cl—$C_6H_5$ | $OCF_2CF_3$ | H |
| 46 | 239N | $CF_3$ | $R_2 + R_3 = (CH_2)_3$ | O | H | 4-F—$C_6H_5$ | $OCF_2CF_3$ | H |
| 46 | 240N | $CF_3$ | $R_2 + R_3 = (CH_2)_3$ | O | H | 4-Br—$C_6H_5$ | $OCF_2CF_3$ | H |
| 46 | 241N | $CF_3$ | $R_2 + R_3 = (CH_2)_3$ | O | 4-Br—$C_6H_5$O | H | $OCF_2CF_3$ | H |
| 46 | 242N | $CF_3$ | $R_2 + R_3 = (CH_2)_3$ | O | $C_6H_5$O | H | $OCCl_2CCl_2H$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

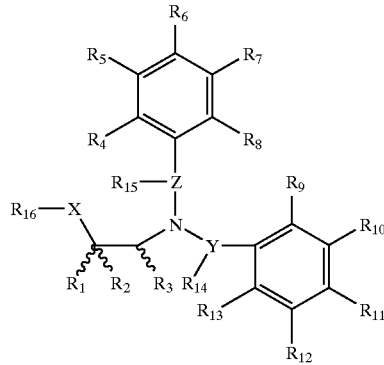

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 46 | 243N | $CF_3$ | $R_2 + R_3 = (CH_2)_3$ | O | 4-Cl—$C_6H_5O$ | H | $OCCl_2CCl_2H$ | H |
| 46 | 244N | $CF_3$ | $R_2 + R_3 = (CH_2)_3$ | O | 4-F—$C_6H_5O$ | H | $OCCl_2CCl_2H$ | H |
| 46 | 245N | $CF_3$ | $R_2 + R_3 = (CH_2)_3$ | O | 3,4-Cl—$C_6H_5O$ | H | $OCCl_2CCl_2H$ | H |
| 46 | 246N | $CF_3$ | $R_2 + R_3 = (CH_2)_3$ | O | H | $C_6H_5$ | $OCCl_2CCl_2H$ | H |
| 46 | 247N | $CF_3$ | $R_2 + R_3 = (CH_2)_3$ | O | H | 4-Cl—$C_6H_5$ | $OCCl_2CCl_2H$ | H |
| 46 | 248N | $CF_3$ | $R_2 + R_3 = (CH_2)_3$ | O | H | 4-F—$C_6H_5$ | $OCCl_2CCl_2H$ | H |
| 46 | 249N | $CF_3$ | $R_2 + R_3 = (CH_2)_3$ | O | H | 4-Br—$C_6H_5$ | $OCCl_2CCl_2H$ | H |
| 46 | 250N | $CF_3$ | $R_2 + R_3 = (CH_2)_3$ | O | 4-Br—$C_6H_5O$ | H | $OCCl_2CCl_2H$ | H |
| 46 | 251N | $CF_3$ | $R_2 + R_3 = (CH_2)_3$ | O | $C_6H_5O$ | H | $OCCl_2CCl_3$ | H |
| 46 | 252N | $CF_3$ | $R_2 + R_3 = (CH_2)_3$ | O | 4-Cl—$C_6H_5O$ | H | $OCCl_2CCl_3$ | H |
| 46 | 253N | $CF_3$ | $R_2 + R_3 = (CH_2)_3$ | O | 4-F—$C_6H_5O$ | H | $OCCl_2CCl_3$ | H |
| 46 | 254N | $CF_3$ | $R_2 + R_3 = (CH_2)_3$ | O | 3,4-Cl—$C_6H_5O$ | H | $OCCl_2CCl_3$ | H |
| 46 | 255N | $CF_3$ | $R_2 + R_3 = (CH_2)_3$ | O | H | $C_6H_5$ | $OCCl_2CCl_3$ | H |
| 46 | 256N | $CF_3$ | $R_2 + R_3 = (CH_2)_3$ | O | H | 4-Cl—$C_6H_5$ | $OCCl_2CCl_3$ | H |
| 46 | 257N | $CF_3$ | $R_2 + R_3 = (CH_2)_3$ | O | H | 4-F—$C_6H_5$ | $OCCl_2CCl_3$ | H |
| 46 | 258N | $CF_3$ | $R_2 + R_3 = (CH_2)_3$ | O | H | 4-Br—$C_6H_5$ | $OCCl_2CCl_3$ | H |
| 46 | 259N | $CF_3$ | $R_2 + R_3 = (CH_2)_3$ | O | 4-Br—$C_6H_5O$ | H | $OCCl_2CCl_3$ | H |
| 46 | 260N | $CF_3$ | $R_2 + R_3 = (CH_2)_3$ | O | $C_6H_5O$ | H | $OCCl_2CF_3$ | H |
| 46 | 261N | $CF_3$ | $R_2 + R_3 = (CH_2)_3$ | O | 4-Cl—$C_6H_5O$ | H | $OCCl_2CF_3$ | H |
| 46 | 262N | $CF_3$ | $R_2 + R_3 = (CH_2)_3$ | O | 4-F—$C_6H_5O$ | H | $OCCl_2CF_3$ | H |
| 46 | 263N | $CF_3$ | $R_2 + R_3 = (CH_2)_3$ | O | 3,4-Cl—$C_6H_5O$ | H | $OCCl_2CF_3$ | H |
| 46 | 264N | $CF_3$ | $R_2 + R_3 = (CH_2)_3$ | O | H | $C_6H_5$ | $OCCl_2CF_3$ | H |
| 46 | 265N | $CF_3$ | $R_2 + R_3 = (CH_2)_3$ | O | H | 4-Cl—$C_6H_5$ | $OCCl_2CF_3$ | H |
| 46 | 266N | $CF_3$ | $R_2 + R_3 = (CH_2)_3$ | O | H | 4-F—$C_6H_5$ | $OCCl_2CF_3$ | H |
| 46 | 267N | $CF_3$ | $R_2 + R_3 = (CH_2)_3$ | O | H | 4-Br—$C_6H_5$ | $OCCl_2CF_3$ | H |
| 46 | 268N | $CF_3$ | $R_2 + R_3 = (CH_2)_3$ | O | 4-Br—$C_6H_5O$ | H | $OCCl_2CF_3$ | H |
| 46 | 269N | $CF_3$ | $R_2 + R_3 = (CH_2)_3$ | O | $C_6H_5O$ | H | $OCF_2CCl_3$ | H |
| 46 | 270N | $CF_3$ | $R_2 + R_3 = (CH_2)_3$ | O | 4-Cl—$C_6H_5O$ | H | $OCF_2CCl_3$ | H |
| 46 | 271N | $CF_3$ | $R_2 + R_3 = (CH_2)_3$ | O | 4-F—$C_6H_5O$ | H | $OCF_2CCl_3$ | H |
| 46 | 272N | $CF_3$ | $R_2 + R_3 = (CH_2)_3$ | O | 3,4-Cl—$C_6H_5O$ | H | $OCF_2CCl_3$ | H |
| 46 | 273N | $CF_3$ | $R_2 + R_3 = (CH_2)_3$ | O | H | $C_6H_5$ | $OCF_2CCl_3$ | H |
| 46 | 274N | $CF_3$ | $R_2 + R_3 = (CH_2)_3$ | O | H | 4-Cl—$C_6H_5$ | $OCF_2CCl_3$ | H |
| 46 | 275N | $CF_3$ | $R_2 + R_3 = (CH_2)_3$ | O | H | 4-F—$C_6H_5$ | $OCF_2CCl_3$ | H |
| 46 | 276N | $CF_3$ | $R_2 + R_3 = (CH_2)_3$ | O | H | 4-Br—$C_6H_5$ | $OCF_2CCl_3$ | H |
| 46 | 277N | $CF_3$ | $R_2 + R_3 = (CH_2)_3$ | O | 4-Br—$C_6H_5O$ | H | $OCF_2CCl_3$ | H |
| 46 | 278N | $CF_3$ | $R_2 + R_3 = (CH_2)_3$ | O | $C_6H_5O$ | H | $OCF_2CF_2H$ | $OCF_2CF_2H$ |
| 46 | 279N | $CF_3$ | $R_2 + R_3 = (CH_2)_3$ | O | 4-Cl—$C_6H_5O$ | H | $OCF_2CF_2H$ | $OCF_2CF_2H$ |
| 46 | 280N | $CF_3$ | $R_2 + R_3 = (CH_2)_3$ | O | 4-F—$C_6H_5O$ | H | $OCF_2CF_2H$ | $OCF_2CF_2H$ |
| 46 | 281N | $CF_3$ | $R_2 + R_3 = (CH_2)_3$ | O | 3,4-Cl—$C_6H_5O$ | H | $OCF_2CF_2H$ | $OCF_2CF_2H$ |
| 46 | 282N | $CF_3$ | $R_2 + R_3 = (CH_2)_3$ | O | H | $C_6H_5$ | $OCF_2CF_2H$ | $OCF_2CF_2H$ |
| 46 | 283N | $CF_3$ | $R_2 + R_3 = (CH_2)_3$ | O | H | 4-Cl—$C_6H_5$ | $OCF_2CF_2H$ | $OCF_2CF_2H$ |
| 46 | 284N | $CF_3$ | $R_2 + R_3 = (CH_2)_3$ | O | H | 4-F—$C_6H_5$ | $OCF_2CF_2H$ | $OCF_2CF_2H$ |
| 46 | 285N | $CF_3$ | $R_2 + R_3 = (CH_2)_3$ | O | H | 4-Br—$C_6H_5$ | $OCF_2CF_2H$ | $OCF_2CF_2H$ |
| 46 | 286N | $CF_3$ | $R_2 + R_3 = (CH_2)_3$ | O | 4-Br—$C_6H_5O$ | H | $OCF_2CF_2H$ | $OCF_2CF_2H$ |
| 46 | 287N | $CF_3$ | $R_2 + R_3 = (CH_2)_3$ | O | $C_6H_5O$ | H | $OCF_3$ | $OCF_3$ |
| 46 | 288N | $CF_3$ | $R_2 + R_3 = (CH_2)_3$ | O | 4-Cl—$C_6H_5O$ | H | $OCF_3$ | $OCF_3$ |
| 46 | 289N | $CF_3$ | $R_2 + R_3 = (CH_2)_3$ | O | 4-F—$C_6H_5O$ | H | $OCF_3$ | $OCF_3$ |
| 46 | 290N | $CF_3$ | $R_2 + R_3 = (CH_2)_3$ | O | 3,4-Cl—$C_6H_5O$ | H | $OCF_3$ | $OCF_3$ |
| 46 | 291N | $CF_3$ | $R_2 + R_3 = (CH_2)_3$ | O | H | $C_6H_5$ | $OCF_3$ | $OCF_3$ |
| 46 | 292N | $CF_3$ | $R_2 + R_3 = (CH_2)_3$ | O | H | 4-Cl—$C_6H_5$ | $OCF_3$ | $OCF_3$ |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

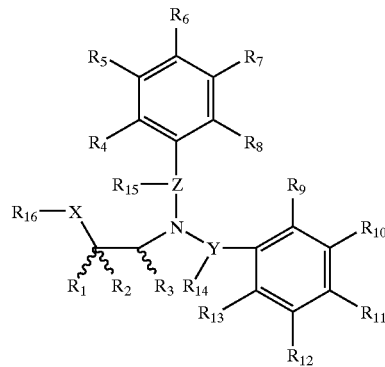

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 46 | 293N | $CF_3$ | $R_2 + R_3 = (CH_2)_3$ | O | H | 4-F—$C_6H_5$ | $OCF_3$ | $OCF_3$ |
| 46 | 294N | $CF_3$ | $R_2 + R_3 = (CH_2)_3$ | O | H | 4-Br—$C_6H_5$ | $OCF_3$ | $OCF_3$ |
| 46 | 295N | $CF_3$ | $R_2 + R_3 = (CH_2)_3$ | O | 4-Br—$C_6H_5O$ | H | $OCF_3$ | $OCF_3$ |
| 46 | 296N | $CF_3$ | $R_2 + R_3 = (CH_2)_3$ | O | $C_6H_5O$ | H | $OCF_2H$ | $OCF_2H$ |
| 46 | 297N | $CF_3$ | $R_2 + R_3 = (CH_2)_3$ | O | 4-Cl—$C_6H_5O$ | H | $OCF_2H$ | $OCF_2H$ |
| 46 | 298N | $CF_3$ | $R_2 + R_3 = (CH_2)_3$ | O | 4-F—$C_6H_5O$ | H | $OCF_2H$ | $OCF_2H$ |
| 46 | 299N | $CF_3$ | $R_2 + R_3 = (CH_2)_3$ | O | 3,4-Cl—$C_6H_5O$ | H | $OCF_2H$ | $OCF_2H$ |
| 46 | 300N | $CF_3$ | $R_2 + R_3 = (CH_2)_3$ | O | H | $C_6H_5$ | $OCF_2H$ | $OCF_2H$ |
| 46 | 301N | $CF_3$ | $R_2 + R_3 = (CH_2)_3$ | O | H | 4-Cl—$C_6H_5$ | $OCF_2H$ | $OCF_2H$ |
| 46 | 302N | $CF_3$ | $R_2 + R_3 = (CH_2)_3$ | O | H | 4-F—$C_6H_5$ | $OCF_2H$ | $OCF_2H$ |
| 46 | 303N | $CF_3$ | $R_2 + R_3 = (CH_2)_3$ | O | H | 4-Br—$C_6H_5$ | $OCF_2H$ | $OCF_2H$ |
| 46 | 304N | $CF_3$ | $R_2 + R_3 = (CH_2)_3$ | O | 4-Br—$C_6H_5O$ | H | $OCF_2H$ | $OCF_2H$ |
| 46 | 305N | $CF_3$ | $R_2 + R_3 = (CH_2)_3$ | O | $C_6H_5O$ | H | $R_{10} + R_{11} = OCF_2CF_2O$ | |
| 46 | 306N | $CF_3$ | $R_2 + R_3 = (CH_2)_3$ | O | 4-Cl—$C_6H_5O$ | H | $R_{10} + R_{11} = OCF_2CF_2O$ | |
| 46 | 307N | $CF_3$ | $R_2 + R_3 = (CH_2)_3$ | O | 4-F—$C_6H_5O$ | H | $R_{10} + R_{11} = OCF_2CF_2O$ | |
| 46 | 308N | $CF_3$ | $R_2 + R_3 = (CH_2)_3$ | O | 3,4-Cl—$C_6H_5O$ | H | $R_{10} + R_{11} = OCF_2CF_2O$ | |
| 46 | 309N | $CF_3$ | $R_2 + R_3 = (CH_2)_3$ | O | H | $C_6H_5$ | $R_{10} + R_{11} = OCF_2CF_2O$ | |
| 46 | 310N | $CF_3$ | $R_2 + R_3 = (CH_2)_3$ | O | H | 4-Cl—$C_6H_5$ | $R_{10} + R_{11} = OCF_2CF_2O$ | |
| 46 | 311N | $CF_3$ | $R_2 + R_3 = (CH_2)_3$ | O | H | 4-F—$C_6H_5$ | $R_{10} + R_{11} = OCF_2CF_2O$ | |
| 46 | 312N | $CF_3$ | $R_2 + R_3 = (CH_2)_3$ | O | H | 4-Br—$C_6H_5$ | $R_{10} + R_{11} = OCF_2CF_2O$ | |
| 46 | 313N | $CF_3$ | $R_2 + R_3 = (CH_2)_3$ | O | 4-Br—$C_6H_5O$ | H | $R_{10} + R_{11} = OCF_2CF_2O$ | |
| 46 | 314N | $CF_3$ | $R_2 + R_3 = (CH_2)_3$ | O | $C_6H_5O$ | H | $R_{10} + R_{11} = OCCl_2CCl_2O$ | |
| 46 | 315N | $CF_3$ | $R_2 + R_3 = (CH_2)_3$ | O | 4-Cl—$C_6H_5O$ | H | $R_{10} + R_{11} = OCCl_2CCl_2O$ | |
| 46 | 316N | $CF_3$ | $R_2 + R_3 = (CH_2)_3$ | O | 4-F—$C_6H_5O$ | H | $R_{10} + R_{11} = OCCl_2CCl_2O$ | |
| 46 | 317N | $CF_3$ | $R_2 + R_3 = (CH_2)_3$ | O | 3,4-Cl—$C_6H_5O$ | H | $R_{10} + R_{11} = OCCl_2CCl_2O$ | |
| 46 | 318N | $CF_3$ | $R_2 + R_3 = (CH_2)_3$ | O | H | $C_6H_5$ | $R_{10} + R_{11} = OCCl_2CCl_2O$ | |
| 46 | 319N | $CF_3$ | $R_2 + R_3 = (CH_2)_3$ | O | H | 4-Cl—$C_6H_5$ | $R_{10} + R_{11} = OCCl_2CCl_2O$ | |
| 46 | 320N | $CF_3$ | $R_2 + R_3 = (CH_2)_3$ | O | H | 4-F—$C_6H_5$ | $R_{10} + R_{11} = OCCl_2CCl_2O$ | |
| 46 | 321N | $CF_3$ | $R_2 + R_3 = (CH_2)_3$ | O | H | 4-Br—$C_6H_5$ | $R_{10} + R_{11} = OCCl_2CCl_2O$ | |
| 46 | 322N | $CF_3$ | $R_2 + R_3 = (CH_2)_3$ | O | 4-Br—$C_6H_5O$ | H | $R_{10} + R_{11} = OCCl_2CCl_2O$ | |
| 46 | 323N | $CF_3$ | $R_2 + R_3 = (CH_2)_3$ | O | H | H | OH | H |
| 46 | 324N | $CF_3$ | $R_2 + R_3 = (CH_2)_3$ | O | H | H | OH | OH |
| 46 | 325N | $CF_3$ | $R_2 + R_3 = (CH_2)_3$ | O | H | H | H | OH |
| 46 | 326N | $CF_3$ | $R_2 + R_3 = (CH_2)_3$ | O | H | H | $OCH_2CF_3$ | H |
| 46 | 327N | $CF_3$ | $R_2 + R_3 = (CH_2)_3$ | O | H | H | H | $OCH_2CF_3$ |
| 46 | 328N | $CF_3$ | $R_2 + R_3 = (CH_2)_3$ | O | H | H | $OCH_2CF_2CF_3$ | H |
| 46 | 329N | $CF_3$ | $R_2 + R_3 = (CH_2)_3$ | O | H | H | $OCH_2CH_2CF_3$ | H |
| 46 | 330N | $CF_3$ | $R_2 + R_3 = (CH_2)_3$ | O | H | H | $OCH(CF_3)_3$ | H |
| 46 | 331N | $CF_3$ | $R_2 + R_3 = (CH_2)_3$ | O | H | 4-F—$C_6H_5O$ | H | H |
| 46 | 332N | $CF_3$ | $R_2 + R_3 = (CH_2)_3$ | O | 4-F—$C_6H_5O$ | H | H | H |
| 46 | 333N | $CF_3$ | $R_2 + R_3 = (CH_2)_3$ | O | H | cyclo-hexoxy | H | H |
| 46 | 334N | $CF_3$ | $R_2 + R_3 = (CH_2)_3$ | O | cyclo-hexoxy | H | H | H |
| 46 | 335N | $CF_3$ | $R_2 + R_3 = (CH_2)_3$ | O | H | $CH(CH_3)_3$ | H | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

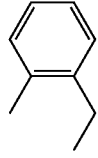

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 46 | 336N | $CF_3$ | $R_2 + R_3 = (CH_2)_3$ | O | F | H | 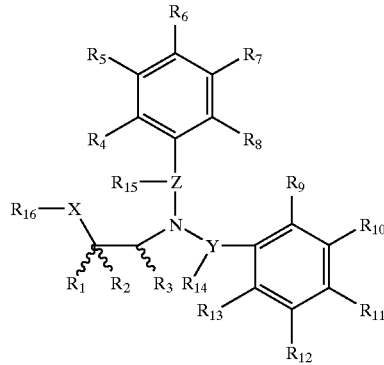 | bond to indicated phenyl carbon of $R_{10}$ substituent |
| 57 | 224N | $HCF_2CF_2OCH_2$ | H | O | $C_6H_5O$ | H | $OCF_2CF_2H$ | H |
| 57 | 225N | $HCF_2CF_2OCH_2$ | H | O | 4-Cl—$C_6H_5O$ | H | $OCF_2CF_2H$ | H |
| 57 | 226N | $HCF_2CF_2OCH_2$ | H | O | 4-F—$C_6H_5O$ | H | $OCF_2CF_2H$ | H |
| 57 | 227N | $HCF_2CF_2OCH_2$ | H | O | 3,4-Cl—$C_6H_5O$ | H | $OCF_2CF_2H$ | H |
| 57 | 228N | $HCF_2CF_2OCH_2$ | H | O | H | $C_6H_5$ | $OCF_2CF_2H$ | H |
| 57 | 229N | $HCF_2CF_2OCH_2$ | H | O | H | 4-Cl—$C_6H_5$ | $OCF_2CF_2H$ | H |
| 57 | 230N | $HCF_2CF_2OCH_2$ | H | O | H | 4-F—$C_6H_5$ | $OCF_2CF_2H$ | H |
| 57 | 231N | $HCF_2CF_2OCH_2$ | H | O | H | 4-Br—$C_6H_5$ | $OCF_2CF_2H$ | H |
| 57 | 232N | $HCF_2CF_2OCH_2$ | H | O | 4-Br—$C_6H_5O$ | H | $OCF_2CF_2H$ | H |
| 57 | 233N | $HCF_2CF_2OCH_2$ | H | O | $C_6H_5O$ | H | $OCF_2CF_3$ | H |
| 57 | 234N | $HCF_2CF_2OCH_2$ | H | O | 4-Cl—$C_6H_5O$ | H | $OCF_2CF_3$ | H |
| 57 | 235N | $HCF_2CF_2OCH_2$ | H | O | 4-F—$C_6H_5O$ | H | $OCF_2CF_3$ | H |
| 57 | 236N | $HCF_2CF_2OCH_2$ | H | O | 3,4-Cl—$C_6H_5O$ | H | $OCF_2CF_3$ | H |
| 57 | 237N | $HCF_2CF_2OCH_2$ | H | O | H | $C_6H_5$ | $OCF_2CF_3$ | H |
| 57 | 238N | $HCF_2CF_2OCH_2$ | H | O | H | 4-Cl—$C_6H_5$ | $OCF_2CF_3$ | H |
| 57 | 239N | $HCF_2CF_2OCH_2$ | H | O | H | 4-F—$C_6H_5$ | $OCF_2CF_3$ | H |
| 57 | 240N | $HCF_2CF_2OCH_2$ | H | O | H | 4-Br—$C_6H_5$ | $OCF_2CF_3$ | H |
| 57 | 241N | $HCF_2CF_2OCH_2$ | H | O | 4-Br—$C_6H_5O$ | H | $OCF_2CF_3$ | H |
| 57 | 242N | $HCF_2CF_2OCH_2$ | H | O | $C_6H_5O$ | H | $OCCl_2CCl_2H$ | H |
| 57 | 243N | $HCF_2CF_2OCH_2$ | H | O | 4-Cl—$C_6H_5O$ | H | $OCCl_2CCl_2H$ | H |
| 57 | 244N | $HCF_2CF_2OCH_2$ | H | O | 4-F—$C_6H_5O$ | H | $OCCl_2CCl_2H$ | H |
| 57 | 245N | $HCF_2CF_2OCH_2$ | H | O | 3,4-Cl—$C_6H_5O$ | H | $OCCl_2CCl_2H$ | H |
| 57 | 246N | $HCF_2CF_2OCH_2$ | H | O | H | $C_6H_5$ | $OCCl_2CCl_2H$ | H |
| 57 | 247N | $HCF_2CF_2OCH_2$ | H | O | H | 4-Cl—$C_6H_5$ | $OCCl_2CCl_2H$ | H |
| 57 | 248N | $HCF_2CF_2OCH_2$ | H | O | H | 4-F—$C_6H_5$ | $OCCl_2CCl_2H$ | H |
| 57 | 249N | $HCF_2CF_2OCH_2$ | H | O | H | 4-Br—$C_6H_5$ | $OCCl_2CCl_2H$ | H |
| 57 | 250N | $HCF_2CF_2OCH_2$ | H | O | 4-Br—$C_6H_5O$ | H | $OCCl_2CCl_2H$ | H |
| 57 | 251N | $HCF_2CF_2OCH_2$ | H | O | $C_6H_5O$ | H | $OCCl_2CCl_3$ | H |
| 57 | 252N | $HCF_2CF_2OCH_2$ | H | O | 4-Cl—$C_6H_5O$ | H | $OCCl_2CCl_3$ | H |
| 57 | 253N | $HCF_2CF_2OCH_2$ | H | O | 4-F—$C_6H_5O$ | H | $OCCl_2CCl_3$ | H |
| 57 | 254N | $HCF_2CF_2OCH_2$ | H | O | 3,4-Cl—$C_6H_5O$ | H | $OCCl_2CCl_3$ | H |
| 57 | 255N | $HCF_2CF_2OCH_2$ | H | O | H | $C_6H_5$ | $OCCl_2CCl_3$ | H |
| 57 | 256N | $HCF_2CF_2OCH_2$ | H | O | H | 4-Cl—$C_6H_5$ | $OCCl_2CCl_3$ | H |
| 57 | 257N | $HCF_2CF_2OCH_2$ | H | O | H | 4-F—$C_6H_5$ | $OCCl_2CCl_3$ | H |
| 57 | 258N | $HCF_2CF_2OCH_2$ | H | O | H | 4-Br—$C_6H_5$ | $OCCl_2CCl_3$ | H |
| 57 | 259N | $HCF_2CF_2OCH_2$ | H | O | 4-Br—$C_6H_5O$ | H | $OCCl_2CCl_3$ | H |
| 57 | 260N | $HCF_2CF_2OCH_2$ | H | O | $C_6H_5O$ | H | $OCCl_2CF_3$ | H |
| 57 | 261N | $HCF_2CF_2OCH_2$ | H | O | 4-Cl—$C_6H_5O$ | H | $OCCl_2CF_3$ | H |
| 57 | 262N | $HCF_2CF_2OCH_2$ | H | O | 4-F—$C_6H_5O$ | H | $OCCl_2CF_3$ | H |
| 57 | 263N | $HCF_2CF_2OCH_2$ | H | O | 3,4-Cl—$C_6H_5O$ | H | $OCCl_2CF_3$ | H |
| 57 | 264N | $HCF_2CF_2OCH_2$ | H | O | H | $C_6H_5$ | $OCCl_2CF_3$ | H |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

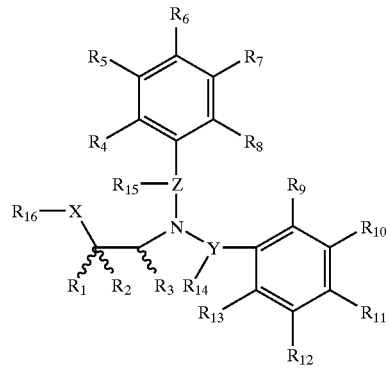

Phenyl Tertiary 2-Heteroalkylamine

Inhibitor Number
Column 1 + Column 2

| Reagent | Reagent | $R_1$ | $R_2$ | X | $R_5$ | $R_6$ | $R_{10}$ | $R_{11}$ |
|---|---|---|---|---|---|---|---|---|
| 57 | 265N | $HCF_2CF_2OCH_2$ | H | O | H | 4-Cl—$C_6H_5$ | $OCCl_2CF_3$ | H |
| 57 | 266N | $HCF_2CF_2OCH_2$ | H | O | H | 4-F—$C_6H_5$ | $OCCl_2CF_3$ | H |
| 57 | 267N | $HCF_2CF_2OCH_2$ | H | O | H | 4-Br—$C_6H_5$ | $OCCl_2CF_3$ | H |
| 57 | 268N | $HCF_2CF_2OCH_2$ | H | O | 4-Br—$C_6H_5O$ | H | $OCCl_2CF_3$ | H |
| 57 | 269N | $HCF_2CF_2OCH_2$ | H | O | $C_6H_5O$ | H | $OCF_2CCl_3$ | H |
| 57 | 270N | $HCF_2CF_2OCH_2$ | H | O | 4-Cl—$C_6H_5O$ | H | $OCF_2CCl_3$ | H |
| 57 | 271N | $HCF_2CF_2OCH_2$ | H | O | 4-F—$C_6H_5O$ | H | $OCF_2CCl_3$ | H |
| 57 | 272N | $HCF_2CF_2OCH_2$ | H | O | 3,4-Cl—$C_6H_5O$ | H | $OCF_2CCl_3$ | H |
| 57 | 273N | $HCF_2CF_2OCH_2$ | H | O | H | $C_6H_5$ | $OCF_2CCl_3$ | H |
| 57 | 274N | $HCF_2CF_2OCH_2$ | H | O | H | 4-Cl—$C_6H_5$ | $OCF_2CCl_3$ | H |
| 57 | 275N | $HCF_2CF_2OCH_2$ | H | O | H | 4-F—$C_6H_5$ | $OCF_2CCl_3$ | H |
| 57 | 276N | $HCF_2CF_2OCH_2$ | H | O | H | 4-Br—$C_6H_5$ | $OCF_2CCl_3$ | H |
| 57 | 277N | $HCF_2CF_2OCH_2$ | H | O | 4-Br—$C_6H_5O$ | H | $OCF_2CCl_3$ | H |
| 57 | 278N | $HCF_2CF_2OCH_2$ | H | O | $C_6H_5O$ | H | $OCF_2CF_2H$ | $OCF_2CF_2H$ |
| 57 | 279N | $HCF_2CF_2OCH_2$ | H | O | 4-Cl—$C_6H_5O$ | H | $OCF_2CF_2H$ | $OCF_2CF_2H$ |
| 57 | 280N | $HCF_2CF_2OCH_2$ | H | O | 4-F—$C_6H_5O$ | H | $OCF_2CF_2H$ | $OCF_2CF_2H$ |
| 57 | 281N | $HCF_2CF_2OCH_2$ | H | O | 3,4-Cl—$C_6H_5O$ | H | $OCF_2CF_2H$ | $OCF_2CF_2H$ |
| 57 | 282N | $HCF_2CF_2OCH_2$ | H | O | H | $C_6H_5$ | $OCF_2CF_2H$ | $OCF_2CF_2H$ |
| 57 | 283N | $HCF_2CF_2OCH_2$ | H | O | H | 4-Cl—$C_6H_5$ | $OCF_2CF_2H$ | $OCF_2CF_2H$ |
| 57 | 284N | $HCF_2CF_2OCH_2$ | H | O | H | 4-F—$C_6H_5$ | $OCF_2CF_2H$ | $OCF_2CF_2H$ |
| 57 | 285N | $HCF_2CF_2OCH_2$ | H | O | H | 4-Br—$C_6H_5$ | $OCF_2CF_2H$ | $OCF_2CF_2H$ |
| 57 | 286N | $HCF_2CF_2OCH_2$ | H | O | 4-Br—$C_6H_5O$ | H | $OCF_2CF_2H$ | $OCF_2CF_2H$ |
| 57 | 287N | $HCF_2CF_2OCH_2$ | H | O | $C_6H_5O$ | H | $OCF_3$ | $OCF_3$ |
| 57 | 288N | $HCF_2CF_2OCH_2$ | H | O | 4-Cl—$C_6H_5O$ | H | $OCF_3$ | $OCF_3$ |
| 57 | 289N | $HCF_2CF_2OCH_2$ | H | O | 4-F—$C_6H_5O$ | H | $OCF_3$ | $OCF_3$ |
| 57 | 290N | $HCF_2CF_2OCH_2$ | H | O | 3,4-Cl—$C_6H_5O$ | H | $OCF_3$ | $OCF_3$ |
| 57 | 291N | $HCF_2CF_2OCH_2$ | H | O | H | $C_6H_5$ | $OCF_3$ | $OCF_3$ |
| 57 | 292N | $HCF_2CF_2OCH_2$ | H | O | H | 4-Cl—$C_6H_5$ | $OCF_3$ | $OCF_3$ |
| 57 | 293N | $HCF_2CF_2OCH_2$ | H | O | H | 4-F—$C_6H_5$ | $OCF_3$ | $OCF_3$ |
| 57 | 294N | $HCF_2CF_2OCH_2$ | H | O | H | 4-Br—$C_6H_5$ | $OCF_3$ | $OCF_3$ |
| 57 | 295N | $HCF_2CF_2OCH_2$ | H | O | 4-Br—$C_6H_5O$ | H | $OCF_3$ | $OCF_3$ |
| 57 | 296N | $HCF_2CF_2OCH_2$ | H | O | $C_6H_5O$ | H | $OCF_2H$ | $OCF_2H$ |
| 57 | 297N | $HCF_2CF_2OCH_2$ | H | O | 4-Cl—$C_6H_5O$ | H | $OCF_2H$ | $OCF_2H$ |
| 57 | 298N | $HCF_2CF_2OCH_2$ | H | O | 4-F—$C_6H_5O$ | H | $OCF_2H$ | $OCF_2H$ |
| 57 | 299N | $HCF_2CF_2OCH_2$ | H | O | 3,4-Cl—$C_6H_5O$ | H | $OCF_2H$ | $OCF_2H$ |

TABLE 17-continued

Structure of Substituted Phenyltertiary-2-Heteroalkylamines (Y=CH; Z is covalent bond; there is no $R_{15}$ substituent; $R_3$, $R_4$, $R_7$, $R_8$, $R_8$, $R_9$, $R_{12}$, $R_{13}$, $R_{14}$, and $R_{16}$ all equal H unless indicated below).

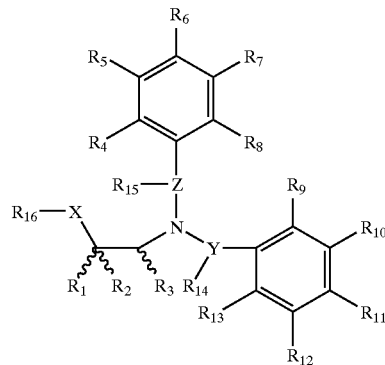

Phenyl Tertiary 2-Heteroalkylamine

| Inhibitor Number Column 1 + Column 2 | | | | | | | | |
|---|---|---|---|---|---|---|---|---|
| Reagent | Reagent | $R_1$ | $R_2$ | X | $R_5$ | $R_6$ | $R_{10}$ | $R_{11}$ |
| 57 | 300N | $HCF_2CF_2OCH_2$ | H | O | H | $C_6H_5$ | $OCF_2H$ | $OCF_2H$ |
| 57 | 301N | $HCF_2CF_2OCH_2$ | H | O | H | 4-Cl—$C_6H_5$ | $OCF_2H$ | $OCF_2H$ |
| 57 | 302N | $HCF_2CF_2OCH_2$ | H | O | H | 4-F—$C_6H_5$ | $OCF_2H$ | $OCF_2H$ |
| 57 | 303N | $HCF_2CF_2OCH_2$ | H | O | H | 4-Br—$C_6H_5$ | $OCF_2H$ | $OCF_2H$ |
| 57 | 304N | $HCF_2CF_2OCH_2$ | H | O | 4-Br—$C_6H_5O$ | H | $OCF_2H$ | $OCF_2H$ |
| 57 | 305N | $HCF_2CF_2OCH_2$ | H | O | $C_6H_5O$ | H | $R_{10} + R_{11} = OCF_2CF_2O$ | |
| 57 | 306N | $HCF_2CF_2OCH_2$ | H | O | 4-Cl—$C_6H_5O$ | H | $R_{10} + R_{11} = OCF_2CF_2O$ | |
| 57 | 307N | $HCF_2CF_2OCH_2$ | H | O | 4-F—$C_6H_5O$ | H | $R_{10} + R_{11} = OCF_2CF_2O$ | |
| 57 | 308N | $HCF_2CF_2OCH_2$ | H | O | 3,4-Cl—$C_6H_5O$ | H | $R_{10} + R_{11} = OCF_2CF_2O$ | |
| 57 | 309N | $HCF_2CF_2OCH_2$ | H | O | H | $C_6H_5$ | $R_{10} + R_{11} = OCF_2CF_2O$ | |
| 57 | 310N | $HCF_2CF_2OCH_2$ | H | O | H | 4-Cl—$C_6H_5$ | $R_{10} + R_{11} = OCF_2CF_2O$ | |
| 57 | 311N | $HCF_2CF_2OCH_2$ | H | O | H | 4-F—$C_6H_5$ | $R_{10} + R_{11} = OCF_2CF_2O$ | |
| 57 | 312N | $HCF_2CF_2OCH_2$ | H | O | H | 4-Br—$C_6H_5$ | $R_{10} + R_{11} = OCF_2CF_2O$ | |
| 57 | 313N | $HCF_2CF_2OCH_2$ | H | O | 4-Br—$C_6H_5O$ | H | $R_{10} + R_{11} = OCF_2CF_2O$ | |
| 57 | 314N | $HCF_2CF_2OCH_2$ | H | O | $C_6H_5O$ | H | $R_{10} + R_{11} = OCCl_2CCl_2O$ | |
| 57 | 315N | $HCF_2CF_2OCH_2$ | H | O | 4-Cl—$C_6H_5O$ | H | $R_{10} + R_{11} = OCCl_2CCl_2O$ | |
| 57 | 316N | $HCF_2CF_2OCH_2$ | H | O | 4-F—$C_6H_5O$ | H | $R_{10} + R_{11} = OCCl_2CCl_2O$ | |
| 57 | 317N | $HCF_2CF_2OCH_2$ | H | O | 3,4-Cl—$C_6H_5O$ | H | $R_{10} + R_{11} = OCCl_2CCl_2O$ | |
| 57 | 318N | $HCF_2CF_2OCH_2$ | H | O | H | $C_6H_5$ | $R_{10} + R_{11} = OCCl_2CCl_2O$ | |
| 57 | 319N | $HCF_2CF_2OCH_2$ | H | O | H | 4-Cl—$C_6H_5$ | $R_{10} + R_{11} = OCCl_2CCl_2O$ | |
| 57 | 320N | $HCF_2CF_2OCH_2$ | H | O | H | 4-F—$C_6H_5$ | $R_{10} + R_{11} = OCCl_2CCl_2O$ | |
| 57 | 321N | $HCF_2CF_2OCH_2$ | H | O | H | 4-Br—$C_6H_5$ | $R_{10} + R_{11} = OCCl_2CCl_2O$ | |
| 57 | 322N | $HCF_2CF_2OCH_2$ | H | O | 4-Br—$C_6H_5O$ | H | $R_{10} + R_{11} = OCCl_2CCl_2O$ | |
| 57 | 323N | $HCF_2CF_2OCH_2$ | H | O | H | H | OH | H |
| 57 | 324N | $HCF_2CF_2OCH_2$ | H | O | H | H | OH | OH |
| 57 | 325N | $HCF_2CF_2OCH_2$ | H | O | H | H | H | OH |
| 57 | 326N | $HCF_2CF_2OCH_2$ | H | O | H | H | $OCH_2CF_3$ | H |
| 57 | 327N | $HCF_2CF_2OCH_2$ | H | O | H | H | H | $OCH_2CF_3$ |
| 57 | 328N | $HCF_2CF_2OCH_2$ | H | O | H | H | $OCH_2CF_2CF_3$ | H |
| 57 | 329N | $HCF_2CF_2OCH_2$ | H | O | H | H | $OCH_2CH_2CF_3$ | H |
| 57 | 330N | $HCF_2CF_2OCH_2$ | H | O | H | H | $OCH(CF_3)_3$ | H |
| 57 | 331N | $HCF_2CF_2OCH_2$ | H | O | H | 4-F—$C_6H_5O$ | H | H |
| 57 | 332N | $HCF_2CF_2OCH_2$ | H | O | 4-F—$C_6H_5O$ | H | H | H |
| 57 | 333N | $HCF_2CF_2OCH_2$ | H | O | H | cyclo-hexoxy | H | H |
| 57 | 334N | $HCF_2CF_2OCH_2$ | H | O | cyclo-hexoxy | H | H | H |
| 57 | 335N | $HCF_2CF_2OCH_2$ | H | O | H | $CH(CH_3)_3$ | H | H |
| 57 | 336N | $HCF_2CF_2OCH_2$ | H | O | F | H | 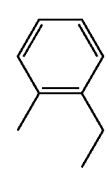 | bond to indicated phenyl carbon of $R_{10}$ substituent |

TABLE 18

Structure of Substituted Tricyclic Phenyl tertiary-2-Heteroalkylamines (Z is covalent bond; Y is CH and $R_{14}$ is H).
(Cyclo-VII)

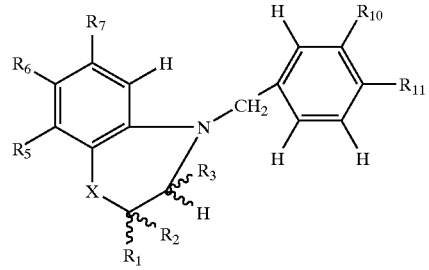

| Cyclized Compound of Inhibitor Number | Cyclized Compound Number | $R_1$ | $R_2$ | $R_3$ | X | $R_5$ | $R_6$ | $R_7$ | $R_{10}$ | $R_{11}$ |
|---|---|---|---|---|---|---|---|---|---|---|
| 1 | 3N | 1-337N | $CF_3$ | H | H | O | H | H | F | $OCF_2CF_2H$ | H |
| 1 | 27N | | $CF_3$ | H | H | O | F | H | H | $CF_3$ | H |
| 1 | 44N | | $CF_3$ | H | H | O | F | H | H | $CH_3$ | H |
| 1 | 76N | | $CF_3$ | H | H | O | F | H | H | H | $OCF_3$ |
| 1 | 84N | | $CF_3$ | H | H | O | F | H | H | H | $CH_3$ |
| 1 | 85N | | $CF_3$ | H | H | O | $CF_3$ | H | H | H | $CH_3$ |
| 2 | 3N | | $CCl_3$ | H | H | O | H | H | F | $OCF_2CF_2H$ | H |
| 2 | 27N | | $CCl_3$ | H | H | O | F | H | H | $CF_3$ | H |
| 2 | 44N | | $CCl_3$ | H | H | O | F | H | H | $CH_3$ | H |
| 2 | 76N | | $CCl_3$ | H | H | O | F | H | H | H | $OCF_3$ |
| 2 | 84N | | $CCl_3$ | H | H | O | F | H | H | H | $CH_3$ |
| 2 | 85N | | $CCl_3$ | H | H | O | $CF_3$ | H | H | H | $CH_3$ |
| 3 | 3N | | $CF_3$ | $CH_3$ | H | O | H | H | F | $OCF_2CF_2H$ | H |
| 3 | 27N | | $CF_3$ | $CH_3$ | H | O | F | H | H | $CF_3$ | H |
| 3 | 44N | | $CF_3$ | $CH_3$ | H | O | F | H | H | $CH_3$ | H |
| 3 | 76N | | $CF_3$ | $CH_3$ | H | O | F | H | H | H | $OCF_3$ |
| 3 | 84N | | $CF_3$ | $CH_3$ | H | O | F | H | H | H | $CH_3$ |
| 3 | 85N | | $CF_3$ | $CH_3$ | H | O | $CF_3$ | H | H | H | $CH_3$ |
| 4 | 3N | | $CF_3CF_2$ | H | H | O | H | H | F | $OCF_2CF_2H$ | H |
| 4 | 27N | | $CF_3CF_2$ | H | H | O | F | H | H | $CF_3$ | H |
| 4 | 44N | | $CF_3CF_2$ | H | H | O | F | H | H | $CH_3$ | H |
| 4 | 76N | | $CF_3CF_2$ | H | H | O | F | H | H | H | $OCF_3$ |
| 4 | 84N | | $CF_3CF_2$ | H | H | O | F | H | H | H | $CH_3$ |
| 4 | 85N | | $CF_3CF_2$ | H | H | O | $CF_3$ | H | H | H | $CH_3$ |
| 5 | 3N | | $CF_3CF_2CF_2$ | H | H | O | H | H | F | $OCF_2CF_2H$ | H |
| 5 | 27N | | $CF_3CF_2CF_2$ | H | H | O | F | H | H | $CF_3$ | H |
| 5 | 44N | | $CF_3CF_2CF_2$ | H | H | O | F | H | H | $CH_3$ | H |
| 5 | 76N | | $CF_3CF_2CF_2$ | H | H | O | F | H | H | H | $OCF_3$ |
| 5 | 84N | | $CF_3CF_2CF_2$ | H | H | O | F | H | H | H | $CH_3$ |
| 5 | 85N | | $CF_3CF_2CF_2$ | H | H | O | $CF_3$ | H | H | H | $CH_3$ |
| 6 | 3N | | $CF_3OCF_2CF_2$ | H | H | O | H | H | F | $OCF_2CF_2H$ | H |
| 6 | 27N | | $CF_3OCF_2CF_2$ | H | H | O | F | H | H | $CF_3$ | H |
| 6 | 44N | | $CF_3OCF_2CF_2$ | H | H | O | F | H | H | $CH_3$ | H |
| 6 | 76N | | $CF_3OCF_2CF_2$ | H | H | O | F | H | H | H | $OCF_3$ |
| 6 | 84N | | $CF_3OCF_2CF_2$ | H | H | O | F | H | H | H | $CH_3$ |
| 6 | 85N | | $CF_3OCF_2CF_2$ | H | H | O | $CF_3$ | H | H | H | $CH_3$ |
| 7 | 3N | | $CF_3CH_2$ | H | H | O | H | H | F | $OCF_2CF_2H$ | H |
| 7 | 27N | | $CF_3CH_2$ | H | H | O | F | H | H | $CF_3$ | H |
| 7 | 44N | | $CF_3CH_2$ | H | H | O | F | H | H | $CH_3$ | H |
| 7 | 76N | | $CF_3CH_2$ | H | H | O | F | H | H | H | $OCF_3$ |
| 7 | 84N | | $CF_3CH_2$ | H | H | O | F | H | H | H | $CH_3$ |
| 7 | 85N | | $CF_3CH_2$ | H | H | O | $CF_3H$ | H | H | H | $CH_3$ |
| 8 | 3N | | $CF_3$ | $CHF_2$ | H | O | H | H | F | $OCF_2CF_2H$ | H |
| 8 | 27N | | $CF_3$ | $CHF_2$ | H | O | F | H | H | $CF_3$ | H |
| 8 | 44N | | $CF_3$ | $CHF_2$ | H | O | F | H | H | $CH_3$ | H |
| 8 | 76N | | $CF_3$ | $CHF_2$ | H | O | F | H | H | H | $OCF_3$ |
| 8 | 84N | | $CF_3$ | $CHF_2$ | H | O | F | H | H | H | $CH_3$ |
| 8 | 85N | | $CF_3$ | $CHF_2$ | H | O | $CF_3$ | H | H | H | $CH_3$ |
| 9 | 3N | | $CF_3$ | H | $CF_3$ | O | H | H | F | $OCF_2CF_2H$ | H |
| 9 | 27N | | $CF_3$ | H | $CF_3$ | O | F | H | H | $CF_3$ | H |
| 9 | 44N | | $CF_3$ | H | $CF_3$ | O | F | H | H | $CH_3$ | H |
| 9 | 76N | | $CF_3$ | H | $CF_3$ | O | F | H | H | H | $OCF_3$ |
| 9 | 84N | | $CF_3$ | H | $CF_3$ | O | F | H | H | H | $CH_3$ |
| 9 | 85N | | $CF_3$ | H | $CF_3$ | O | $CF_3$ | H | H | H | $CH_3$ |
| 10 | 3N | | $CF_3$ | $CF_3$ | H | O | H | H | F | $OCF_2CF_2H$ | H |
| 10 | 27N | | $CF_3$ | $CF_3$ | H | O | F | H | H | $CF_3$ | H |
| 10 | 44N | | $CF_3$ | $CF_3$ | H | O | F | H | H | $CH_3$ | H |
| 10 | 76N | | $CF_3$ | $CF_3$ | H | O | F | H | H | H | $OCF_3$ |
| 10 | 84N | | $CF_3$ | $CF_3$ | H | O | F | H | H | H | $CH_3$ |

TABLE 18-continued

Structure of Substituted Tricyclic Phenyl tertiary-2-Heteroalkylamines (Z is covalent bond; Y is CH and $R_{14}$ is H).

(Cyclo-VII)

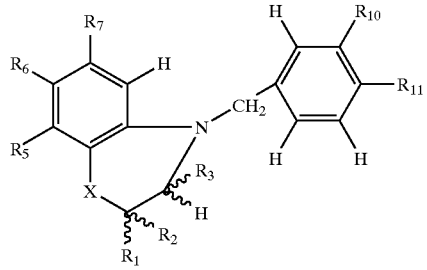

| Cyclized Compound of Inhibitor Number | Cyclized Compound Number | $R_1$ | $R_2$ | $R_3$ | X | $R_5$ | $R_6$ | $R_7$ | $R_{10}$ | $R_{11}$ |
|---|---|---|---|---|---|---|---|---|---|---|
| 10 | 85N | $CF_3$ | $CF_3$ | H | O | $CF_3$ | H | H | H | $CH_3$ |
| 11 | 3N | $CF_3$ | $C_6H_5$ | H | O | H | H | F | $OCF_2CF_2H$ | H |
| 11 | 27N | $CF_3$ | $C_6H_5$ | H | O | F | H | H | $CF_3$ | H |
| 11 | 44N | $CF_3$ | $C_6H_5$ | H | O | F | H | H | $CH_3$ | H |
| 11 | 76N | $CF_3$ | $C_6H_5$ | H | O | F | H | H | H | $OCF_3$ |
| 11 | 84N | $CF_3$ | $C_6H_5$ | H | O | F | H | H | H | $CH_3$ |
| 11 | 85N | $CF_3$ | $C_6H_5$ | H | O | $CF_3$ | H | H | H | $CH_3$ |
| 12 | 3N | $CCl_3$ | $C_6H_5$ | H | O | H | H | F | $OCF_2CF_2H$ | H |
| 12 | 27N | $CCl_3$ | $C_6H_5$ | H | O | F | H | H | $CF_3$ | H |
| 12 | 44N | $CCl_3$ | $C_6H_5$ | H | O | F | H | H | $CH_3$ | H |
| 12 | 76N | $CCl_3$ | $C_6H_5$ | H | O | F | H | H | H | $OCF_3$ |
| 12 | 84N | $CCl_3$ | $C_6H_5$ | H | O | F | H | H | H | $CH_3$ |
| 12 | 85N | $CCl_3$ | $C_6H_5$ | H | O | $CF_3$ | H | H | H | $CH_3$ |
| 19 | 3N | $CF_3$ | $CF_3$ | H | NH | H | H | F | $OCF_2CF_2H$ | H |
| 19 | 27N | $CF_3$ | $CF_3$ | H | NH | F | H | H | $CF_3$ | H |
| 19 | 44N | $CF_3$ | $CF_3$ | H | NH | F | H | H | $CH_3$ | H |
| 19 | 76N | $CF_3$ | $CF_3$ | H | NH | F | H | H | H | $OCF_3$ |
| 19 | 84N | $CF_3$ | $CF_3$ | H | NH | F | H | H | H | $CH_3$ |
| 19 | 85N | $CF_3$ | $CF_3$ | H | NH | $CF_3$ | H | H | H | $CH_3$ |
| 20 | 3N | $CF_3$ | H | H | NH | H | H | F | $OCF_2CF_2H$ | H |
| 20 | 27N | $CF_3$ | H | H | NH | F | H | H | $CF_3$ | H |
| 20 | 44N | $CF_3$ | H | H | NH | F | H | H | $CH_3$ | H |
| 20 | 76N | $CF_3$ | H | H | NH | F | H | H | H | $OCF_3$ |
| 20 | 84N | $CF_3$ | H | H | NH | F | H | H | H | $CH_3$ |
| 20 | 85N | $CF_3$ | H | H | NH | $CF_3$ | H | H | H | $CH_3$ |
| 25 | 3N | $CF_3$ | H | H | S | H | H | F | $OCF_2CF_2H$ | H |
| 25 | 27N | $CF_3$ | H | H | S | F | H | H | $CF_3$ | H |
| 25 | 44N | $CF_3$ | H | H | S | F | H | H | $CH_3$ | H |
| 25 | 76N | $CF_3$ | H | H | S | F | H | H | H | $OCF_3$ |
| 25 | 84N | $CF_3$ | H | H | S | F | H | H | H | $CH_3$ |
| 25 | 85N | $CF_3$ | H | H | S | $CF_3$ | H | H | H | $CH_3$ |

What is claimed is:

1. A method for treating coronary artery disease in a mammal comprising administering to a mammal in need of treatment thereof a therapeutically effective amount of a substituted tertiary-heteroalkylamine Compound or a pharmaceutically acceptable salt thereof.

2. A method for inhibiting CETP in a mammal comprising administering to a mammal in need of treatment thereof a therapeutically effective amount of a substituted tertiary-heteroalkylamine compound or a pharmaceutically acceptable salt thereof.

3. The method of claim 1 or 2, wherein the substituted tertiary-heteroalkylamine compound is a tertiary-omegaheteroalkylamine compound.

4. The method of claim 1 or 2, wherein the substituted tertiary-heteroalkylamine compound is an aromatic tertiary-omegaheteroalkylamine compound.

5. The method of claim 1 or 2, wherein the substituted tertiary-heteroalkylamine compound is a tertiary-2-heteroalkylamine compound.

6. The method of claim 1 or 2, wherein the substituted tertiary-heteroalkylamine compound is an aromatic tertiary-2-omegaheteroalkylamine compound.

7. The method of claim 1 or 2, wherein the substituted tertiary-heteroalkylamine compound is a heteroaryl tertiary-omegaheteroalkylamine compound.

8. The method of claim 1 or 2, wherein the substituted tertiary-heteroalkylamine compound is a phenyl tertiary-omegaheteroalkylamine compound.

* * * * *